United States Patent
Jang et al.

(10) Patent No.: US 12,242,191 B2
(45) Date of Patent: Mar. 4, 2025

(54) COMPOUND, PHOTOSENSITIVE FLUORESCENT RESIN COMPOSITION COMPRISING SAME, COLOR CONVERSION FILM, BACKLIGHT UNIT, AND DISPLAY DEVICE

(71) Applicant: LG CHEM, LTD., Seoul (KR)

(72) Inventors: Hanbit Jang, Daejeon (KR); Duy Hieu Le, Daejeon (KR); Jaemyeng Jeong, Daejeon (KR); Hoyong Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 524 days.

(21) Appl. No.: 17/621,172

(22) PCT Filed: Jul. 13, 2020

(86) PCT No.: PCT/KR2020/009176
§ 371 (c)(1),
(2) Date: Dec. 20, 2021

(87) PCT Pub. No.: WO2021/010700
PCT Pub. Date: Jan. 21, 2021

(65) Prior Publication Data
US 2022/0390841 A1 Dec. 8, 2022

(30) Foreign Application Priority Data

Jul. 18, 2019 (KR) .................. 10-2019-0087017

(51) Int. Cl.
*G03F 7/004* (2006.01)
*C08K 5/3437* (2006.01)
(Continued)

(52) U.S. Cl.
CPC .......... *G03F 7/0045* (2013.01); *C08K 5/3437* (2013.01); *C09B 5/62* (2013.01);
(Continued)

(58) Field of Classification Search
CPC ........ C09B 5/62; C09B 62/465; C09B 62/467
See application file for complete search history.

(56) References Cited

U.S. PATENT DOCUMENTS 6,312,132 B1 * 11/2001 Pavelka ............... C08K 5/0041
428/407
2019/0241801 A1 * 8/2019 Li ..................... G02F 1/133617
(Continued)

FOREIGN PATENT DOCUMENTS

KR  10-2016-0097147 A   8/2016
KR  10-2017-0084648 A   7/2017
(Continued)

OTHER PUBLICATIONS

Liu et al., "Supramolecular assembly of fluorogenic glycol-dots from perylenediimide-based glycoclusters for targeted imaging of cancer cells", 2017, Chemical Communication, vol. 53 No. 7, 11937-11940. (Year: 2017).*
(Continued)

*Primary Examiner* — Chanceity N Robinson
*Assistant Examiner* — Anna Malloy
(74) *Attorney, Agent, or Firm* — ROTHWELL, FIGG, ERNST & MANBECK, P.C.

(57) ABSTRACT

A compound represented by Chemical Formula 1:

(Continued)

wherein, in the Chemical Formula 1, X1, X2, X4 and X5 are the same as or different from each other, and each independently a direct bond, or a substituted or unsubstituted alkylene group, a photoresist fluorescent resin composition including the same, and a color conversion film, a backlight unit and a display apparatus manufactured using the same.

13 Claims, 1 Drawing Sheet

(51) Int. Cl.
*C09B 5/62* (2006.01)
*C09B 62/38* (2006.01)
*C09B 62/487* (2006.01)
*C09B 62/56* (2006.01)
*C09B 62/80* (2006.01)
*C09K 11/06* (2006.01)
*G02B 1/04* (2006.01)

(52) U.S. Cl.
CPC ............ *C09B 62/38* (2013.01); *C09B 62/487* (2013.01); *C09B 62/56* (2013.01); *C09B 62/80* (2013.01); *C09K 11/06* (2013.01); *C09K 2211/1416* (2013.01); *C09K 2211/1425* (2013.01); *C09K 2211/1433* (2013.01); *C09K 2211/1466* (2013.01); *G02B 1/04* (2013.01)

(56) References Cited

U.S. PATENT DOCUMENTS

| | | |
|---|---|---|
| 2019/0359829 A1 | 11/2019 | Koenemann et al. |
| 2020/0071531 A1 | 3/2020 | Koenemann et al. |

FOREIGN PATENT DOCUMENTS

| | | | | |
|---|---|---|---|---|
| KR | 2017084648 A | * | 7/2017 | ........... C08K 5/3437 |
| KR | 10-2019-0067184 A | | 6/2019 | |
| KR | 10-1992084 B1 | | 6/2019 | |
| TW | 201823242 A | | 7/2018 | |
| TW | 201833109 A | | 9/2018 | |

OTHER PUBLICATIONS

Donnier-Marechal et al., "Perylenediimide-based glycoclusters as high affinity ligands of bacterial lectins: synthesis, binding studies and anti-adhesive properties", 2017, Organic & Biomolecular Chemistry, vol. 5 No. 47, 10037-10043. (Year: 2017).*
Maiti et al., "Modulation of Fluorescence Resonance Energy Transfer Efficiency for White Light Emission from a Series of Stilbene-Perylene Based Donor-Acceptor Pair", 2013, The Journal of Physical Chemistry, Vo. 117 No. 44, 23178-23189. (Year: 2013).*
English translation of KR2017084648. (Year: 2017).*
Lu et al., "Helical Assembly induced by Hydrogen Bonding from Chiral Carboxylic Acids Based on Perylene Bisimides", 2011, The Journal of Physcial Chemistry, vol. 115 No. 37, 10871-10876. (Year: 2011).*
International Search Report issued for International Application No. PCT/KR2020/009176 on Oct. 14, 2020, 5 pages.
Donnier-Maréchal, et al., Perylenediimide-based glycoclusters as high affinity ligands of bacterial lectins: synthesis, binding studies and anti-adhesive properties, Org. Biomol. Chem., vol. 15, Nov. 2017, pp. 10037-10043.
Avlasevich, et al., Synthesis and applications of core-enlarged perylene dyes, J. Mater. Chem., vol. 20, Mar. 2010, pp. 3814-3826.
Maiti, et al., Modulation of Fluorescence Resonance Energy Transfer Efficiency for White Light Emission from a Series of Stilbene-Perylene Based Donor-Acceptor Pair, The Journal of Physical Chemistry C, 2013, 117(44), pp. 23178-23189.
Lu et al., Helical Assembly Induced by Hydrogen Bonding from Chiral Carboxylic Acids Based on Perylene Bisimides, The Journal of Physical Chemistry B, 2011, 115(37), pp. 10871-10876.
Donnier-Maréchal, et al, "Perylenediimide-based glycoclusters as high affinity ligands of bacterial lectins: synthesis, binding studies and anti-adhesive properties", Organic & Biomolecular Chemistry, 2017, vol. 15, No. 47, p. 10037-10043.
Liu et al., "Supramolecular assembly of fluorogenic glyco-dots from perylenediimide-based glycoclusters for targeted imaging of cancer cells," Chemical Communication, 2017, vol. 53, No. 7, p. 11937-11940.
Japanese Office Action issued for Japanese Patent Application No. 2021-571296 on Jan. 4, 2023, with English translation, 6 pages.

* cited by examiner

[FIG. 1]
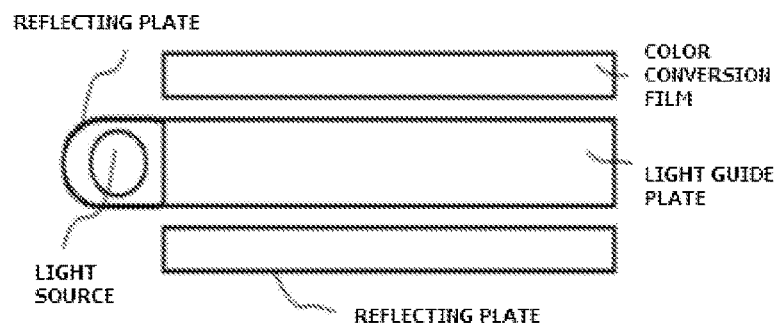
[FIG. 2]
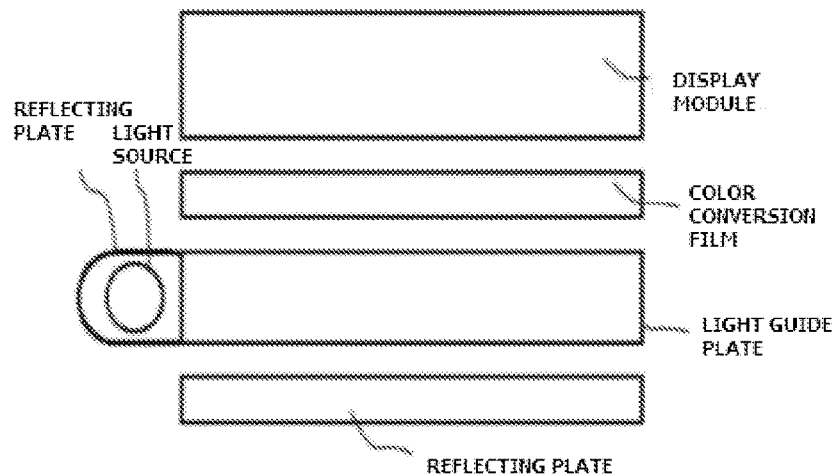

COMPOUND, PHOTOSENSITIVE FLUORESCENT RESIN COMPOSITION COMPRISING SAME, COLOR CONVERSION FILM, BACKLIGHT UNIT, AND DISPLAY DEVICE

This application is a 35 U.S.C. 371 National Phase Entry Application from PCT/KR2020/009176, filed on Jul. 13, 2020, which claims priority to and the benefits of Korean Patent Application No. 10-2019-0087017, filed with the Korean Intellectual Property Office on Jul. 18, 2019, the entire contents of which are incorporated herein by reference.

TECHNICAL FIELD

The present specification relates to a compound, a photoresist fluorescent resin composition including the same, and a color conversion film manufactured using the same, a backlight unit and a display apparatus.

BACKGROUND OF THE INVENTION

Existing light emitting diodes (LED) are obtained by mixing a green phosphorescent substance and a red phosphorescent substance to a blue light emitting diode, or mixing a yellow phosphorescent substance and a blue-green phosphorescent substance to a UV light emitting diode. However, with such a method, it is difficult to control colors, and therefore, color rendering is not favorable. Accordingly, color gamut declines.

In order to overcome such color gamut decline and to reduce production costs, methods of obtaining green and red in a manner of filming quantum dots and binding the dots to a blue LED have been recently tried. However, cadmium series quantum dots have safety problems, and other quantum dots have significantly decreased efficiency compared to cadmium series quantum dots. In addition, quantum dots have reduced stability for oxygen and water, and have a disadvantage in that the performance is significantly degraded when aggregated. Furthermore, unit costs of production are high since, when producing quantum dots, maintaining the sizes to be constant is difficult.

Existing compounds having a $BF_2$ or $B(CN)_2$-based bodipy structure provides, as a fluorescent dye having high light efficiency and a narrow full width at half maximum, excellent light properties when used in a color conversion film, but has insufficient light resistance and heat resistance to be commercialized, and development of compounds having high durability has been required.

BRIEF DESCRIPTION OF THE INVENTION

The present specification is directed to providing a compound, a photoresist fluorescent resin composition including the same, and a color conversion film manufactured using the same, a backlight unit and a display apparatus.

One embodiment of the present specification provides a compound represented by the following Chemical Formula 1.

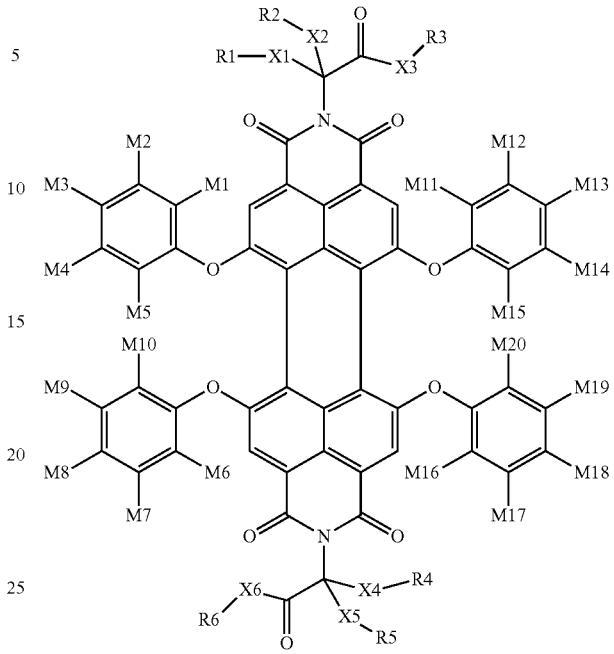

[Chemical Formula 1]

In Chemical Formula 1,
X1, X2, X4 and X5 are the same as or different from each other, and each independently a direct bond, or a substituted or unsubstituted alkylene group,
X3 and X6 are the same as or different from each other, and each independently O or NR',
R' and R1 to R6 are the same as or different from each other, and each independently hydrogen; a halogen group; a substituted or unsubstituted alkyl group; a substituted or unsubstituted cycloalkyl group; a substituted or unsubstituted aryl group; or a substituted or unsubstituted heterocyclic group, or bond to adjacent groups to form a ring, and
at least one of M1 to M5, at least one of M6 to M10, at least one of M11 to M15 and at least one of M16 to M20 are each independently a substituent represented by the following Chemical Formula 2, and the rest are hydrogen,

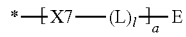

[Chemical Formula 2]

in Chemical Formula 2,
X7 is a direct bond; O; C(=O)NH; or NH,
L is a substituted or unsubstituted alkylene group; a substituted or unsubstituted cycloalkylene group; a substituted or unsubstituted arylene group; or a substituted or unsubstituted divalent heterocyclic group,
a and l are each 1 or 2,
when a and l are each 2, structures in the parentheses are the same as or different from each other,
E is a polymerizable group, and
* represents a bonding position.

Another embodiment of the present specification provides a photoresist fluorescent resin composition including a binder resin; a multifunctional monomer; and the compound described above.

Another embodiment of the present specification provides a color conversion film including the compound described above bonding to a binder resin.

Another embodiment of the present specification provides a backlight unit including the color conversion film described above.

Another embodiment of the present specification provides a display apparatus including the backlight unit described above.

Advantageous Effects

A compound according to one embodiment of the present specification is capable of high color reproduction.

A compound according to one embodiment of the present specification has high solubility.

A compound according to one embodiment of the present specification has high light resistance.

A compound according to one embodiment of the present specification has an advantage of being not dyed.

BRIEF DESCRIPTION OF DRAWINGS

FIG. 1 is a mimetic diagram of using a color conversion film according to one embodiment of the present specification in a backlight unit.

FIG. 2 is a mimetic diagram illustrating a structure of a display apparatus according to one embodiment of the present specification.

DETAILED DESCRIPTION OF THE INVENTION

Hereinafter, the present specification will be described in detail.

One embodiment of the present specification provides a compound represented by Chemical Formula 1.

Existing perylene derivatives have a limitation in high color reproduction since absorption and emission wavelengths thereof are short wavelengths. In addition, existing perylene derivatives have disadvantages of being dyed and having weak light resistance.

Meanwhile, the compound according to one embodiment of the present specification is capable of high color reproduction by absorption and emission wavelengths moving to long wavelengths compared to existing perylene derivatives. Specifically, the compound according to one embodiment of the present specification is capable of high color reproduction by absorption and emission wavelengths moving to long wavelengths and thereby accomplishing a wider range of color coordinates compared to existing perylene derivatives.

The compound according to one embodiment of the present specification has superior light resistance compared to existing perylene derivatives. Specifically, the compound according to one embodiment of the present specification has superior light resistance by having an electron withdrawing group at the imide position compared to existing perylene derivatives.

The compound according to one embodiment of the present specification has a reaction group polymerizable with a binder in the molecule and thereby has an advantage of being not dyed due to the bond with a binder.

In the present specification, a certain part "including" certain constituents means capable of further including other constituents, and does not exclude other constituents unless particularly stated on the contrary.

In the present specification, one member being placed "on" another member includes not only a case of the one member being in contact with the another member but a case of still another member being present between the two members.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a cyano group; a nitro group; a hydroxyl group; an imide group; an amide group; a substituted or unsubstituted amine group; a substituted or unsubstituted silyl group; a substituted or unsubstituted alkyl group; a substituted or unsubstituted cycloalkyl group; a substituted or unsubstituted haloalkyl group; a substituted or unsubstituted alkoxy group; a substituted or unsubstituted alkenyl group; a substituted or unsubstituted alkynyl group; a substituted or unsubstituted aryl group and a substituted or unsubstituted heterocyclic group, or being substituted with a substituent linking two or more substituents among the substituents illustrated above, or having no substituents.

In the present specification, examples of the halogen group may include fluorine, chlorine, bromine or iodine.

In the present specification, the number of carbon atoms of the imide group is not particularly limited, but is preferably from 1 to 30. Specifically, compounds having structures as below may be included, however, the imide group is not limited thereto.

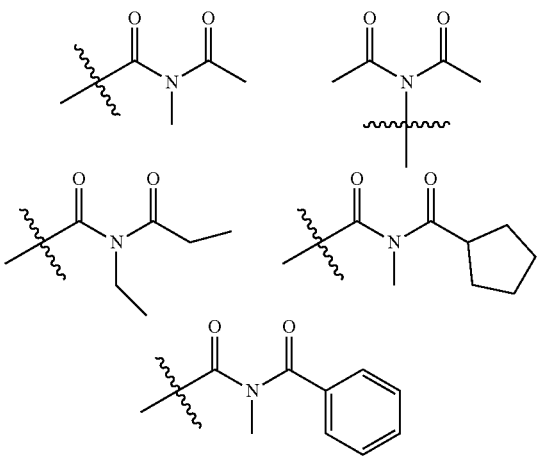

In the present specification, in the amide group, nitrogen of the amide group may be substituted with hydrogen, a linear, branched or cyclic alkyl group having 1 to 30 carbon atoms, or an aryl group having 6 to 30 carbon atoms. Specifically, compounds having the following structural formulae may be included, however, the amide group is not limited thereto.

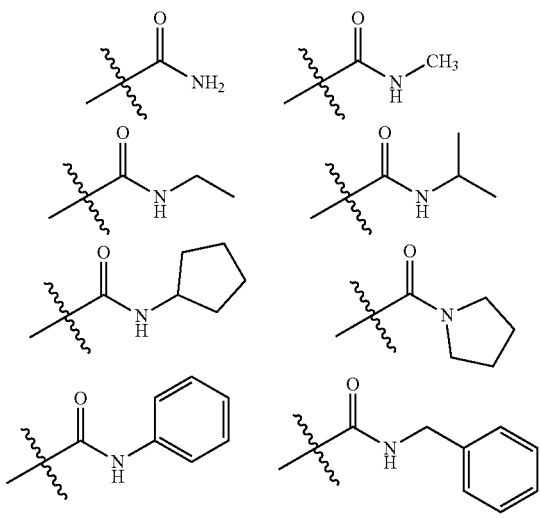

In the present specification, the amine group may be selected from the group consisting of —NH₂; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and, although not particularly limited thereto, the number of carbon atoms is preferably from 1 to 30.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, an alkyl group in the alkylamine group, the N-alkylarylamine group and the N-alkylheteroarylamine group is the same as examples of an alkyl group to describe later.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the alkyl group may be linear or branched, and although not particularly limited thereto, the number of carbon atoms is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methyl pentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the haloalkyl group represents an alkyl group in which one or more hydrogen atoms of the alkyl group are replaced by the same or a different halogen group. The haloalkyl group may be linear or branched, and although not particularly limited thereto, the number of carbon atoms is preferably from 1 to 10. Specific examples thereof may include —CH₂Cl, —CF₃, —CH₂CF₃, —CF₂CF₃ and the like, but are not limited thereto.

In the present specification, the alkoxy group may be linear, branched or cyclic. The number of carbon atoms of the alkoxy group is not particularly limited, but is preferably from 1 to 30. In the present specification, the alkenyl group may be linear or branched, and although not particularly limited thereto, the number of carbon atoms is preferably from 2 to 30.

In the present specification, the alkynyl group may be linear or branched, and although not particularly limited thereto, the number of carbon atoms is preferably from 2 to 30. Specific examples thereof may include alkynyl groups such as ethynyl, propynyl, 2-methyl-2-propynyl, 2-butynyl, 2-pentynyl and the like, but are not limited thereto.

In the present specification, the aryl group is not particularly limited, but preferably has 6 to 30 carbon atoms, and the aryl group may be monocyclic or polycyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a polycyclic aryl group, the number of carbon atoms is not particularly limited, but is preferably from 10 to 30. Specific examples of the polycyclic aryl group may include a naphthyl group, an anthracenyl group, a phenanthryl group, a triphenyl group, a pyrenyl group, a perylenyl group, a chrysenyl group, a fluorenyl group and the like, but are not limited thereto.

In the present specification, the fluorenyl group may be substituted, and adjacent groups may bond to each other to form a ring.

When the fluorenyl group is substituted,

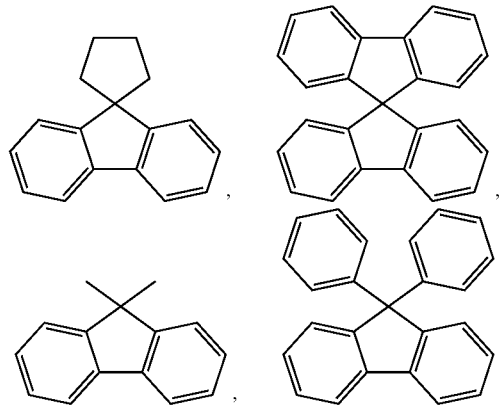

and the like may be included. However, the structure is not limited thereto.

In the present specification, the heterocyclic group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heterocyclic group may be monocyclic or polycyclic. Examples of the heterocyclic group may include a thiophene group, a furanyl group, a pyrrole group, an imidazolyl group, a thiazolyl group, an oxazolyl group, an oxadiazolyl group, a pyridyl group, a bipyridyl group, a pyrimidyl group, a triazinyl group, a triazolyl group, an acridyl group, a pyridazinyl group, a pyrazinyl group, a quinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthrolinyl group, an isoxazolyl group, a thiadiazolyl group, a phenothiazinyl group, a dibenzofuranyl group and the like, but are not limited thereto.

In the present specification, descriptions on the heterocyclic group may be applied to the heteroaryl group except that it is an aromatic heterocyclic group.

In one embodiment of the present specification, the polymerizable group may have at least one selected from the group consisting of a substituted or unsubstituted ethylenically unsaturated group, a substituted or unsubstituted siloxane group and a substituted or unsubstituted epoxy group.

The polymerizable group may be any one of the following structures.

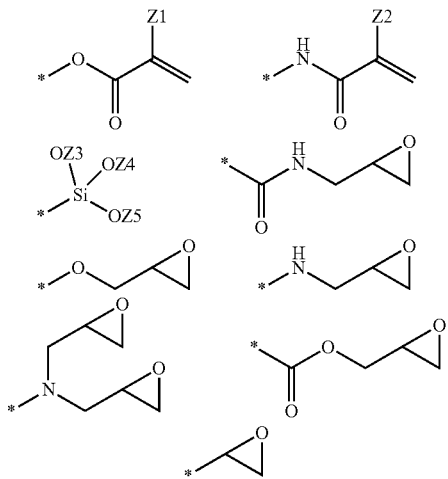

In the structures,
Z1 and Z2 are each independently hydrogen, a halogen group, or a substituted or unsubstituted alkyl group,
Z3 to Z5 are each independently a substituted or unsubstituted alkyl group, and
*represents a bonding position.

In one embodiment of the present specification, X1, X2, X4 and X5 are the same as or different from each other, and each independently a direct bond, or a substituted or unsubstituted alkylene group.

In one embodiment of the present specification, X1, X2, X4 and X5 are the same as or different from each other, and each independently a direct bond, or a linear or branched alkylene group.

In one embodiment of the present specification, X3 and X6 are the same as or different from each other, and each independently O or NR'.

In one embodiment of the present specification, X3 and X6 are O.

In one embodiment of the present specification, X3 and X6 are each NR', and herein, R' is hydrogen; a halogen group; a substituted or unsubstituted alkyl group; a substituted or unsubstituted cycloalkyl group; a substituted or unsubstituted aryl group; or a substituted or unsubstituted heterocyclic group, or bonds to adjacent groups to form a ring.

In one embodiment of the present specification, X3 and X6 are each NR', and herein, R' is hydrogen; a halogen group; a substituted or unsubstituted linear or branched alkyl group; a substituted or unsubstituted cyclohexyl group; a substituted or unsubstituted phenyl group; or a substituted or unsubstituted pyridyl group.

In one embodiment of the present specification, X3 and X6 are each NR', and herein, R' of X3 bonds to adjacent R3 to form a ring, and R' of X6 bonds to adjacent R6 to form a ring.

In one embodiment of the present specification, R1 to R6 are the same as or different from each other, and each independently hydrogen; a halogen group; a substituted or unsubstituted alkyl group; a substituted or unsubstituted cycloalkyl group; a substituted or unsubstituted aryl group; or a substituted or unsubstituted heterocyclic group, or bond to adjacent groups to form a ring.

In one embodiment of the present specification, R1, R2, R4 and R5 are the same as or different from each other, and each independently hydrogen; a halogen group; a substituted or unsubstituted alkyl group; a substituted or unsubstituted cycloalkyl group; a substituted or unsubstituted aryl group; or a substituted or unsubstituted heterocyclic group.

In one embodiment of the present specification, R1, R2, R4 and R5 are the same as or different from each other, and each independently hydrogen; a halogen group; a linear or branched alkyl group; a linear or branched haloalkyl group; a substituted or unsubstituted cyclohexyl group; a substituted or unsubstituted phenyl group; a substituted or unsubstituted naphthyl group; a substituted or unsubstituted pyridyl group; a substituted or unsubstituted thiophenyl group; or a substituted or unsubstituted furanyl group.

In one embodiment of the present specification, R1, R2, R4 and R5 are the same as or different from each other, and each independently hydrogen; a halogen group; a linear or branched alkyl group; a linear or branched haloalkyl group; a cyclohexyl group; a phenyl group unsubstituted or substituted with a hydroxyl group; a naphthyl group; a pyridyl group; a thiophenyl group; or a furanyl group.

In one embodiment of the present specification, R3 and R6 are the same as or different from each other, and each independently hydrogen; a halogen group; a substituted or unsubstituted alkyl group; a substituted or unsubstituted cycloalkyl group; a substituted or unsubstituted aryl group; or a substituted or unsubstituted heterocyclic group, or bond to adjacent groups to form a ring.

In one embodiment of the present specification, R3 and R6 are the same as or different from each other, and each independently hydrogen; a halogen group; an alkyl group unsubstituted or substituted with a group selected from the group consisting of a halogen group, an alkoxy group, an aryl group and a heterocyclic group; a substituted or unsubstituted cyclohexyl group; a phenyl group unsubstituted or substituted with a group selected from the group consisting of a halogen group, an alkoxy group and an alkyl group; a substituted or unsubstituted naphthyl group; a substituted or unsubstituted pyridyl group; a substituted or unsubstituted thiophenyl group; a substituted or unsubstituted furanyl group; or a substituted or unsubstituted dibenzofuranyl group, or bond to adjacent groups to form a ring.

In one embodiment of the present specification, L is a substituted or unsubstituted alkylene group; a substituted or unsubstituted cycloalkylene group; a substituted or unsubstituted arylene group; or a substituted or unsubstituted divalent heterocyclic group.

In one embodiment of the present specification, L is a substituted or unsubstituted linear or branched alkylene group; a substituted or unsubstituted cyclohexylene group; a substituted or unsubstituted phenylene group; or a substituted or unsubstituted divalent pyridyl group.

In one embodiment of the present specification, X7 is a direct bond; O; C(=O)NH; or NH.

In one embodiment of the present specification, X7 is a direct bond.

In one embodiment of the present specification, X7 is O.

In one embodiment of the present specification, X7 is C(=O)NH.

In one embodiment of the present specification, X7 is NH.

In one embodiment of the present specification, at least one of M1 to M5, at least one of M6 to M10, at least one of M11 to M15 and at least one of M16 to M20 are each independently a substituent represented by Chemical Formula 2, and the rest are hydrogen.

In one embodiment of the present specification, any one of M1 to M5, any one of M6 to M10, any one of M11 to M15 and any one of M16 to M20 are each independently the substituent represented by Chemical Formula 2, and the rest may be hydrogen.

In one embodiment of the present specification, Chemical Formula 1 may be represented by the following Chemical Formula 3.

[Chemical Formula 3]

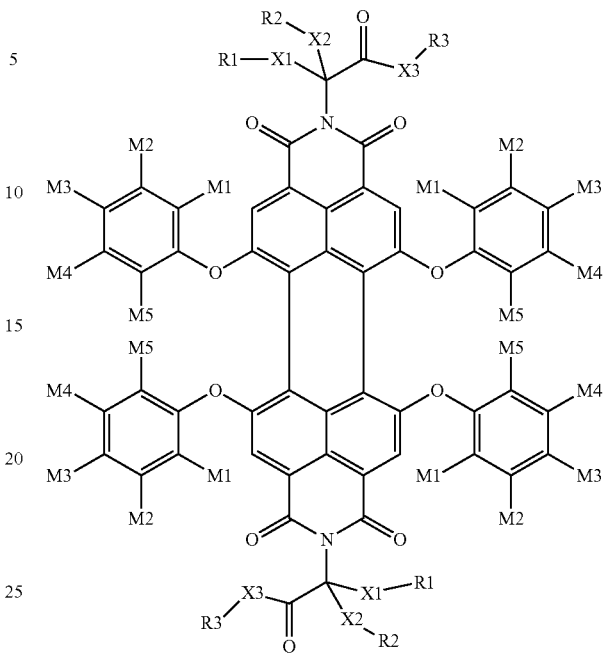

In Chemical Formula 3,
X1 to X3, R1 to R3 and M1 to M5 have the same definitions as in Chemical Formula 1.

In one embodiment of the present specification, Chemical Formula 1 may be represented by the following Chemical Formula 4 or 5.

[Chemical Formula 4]

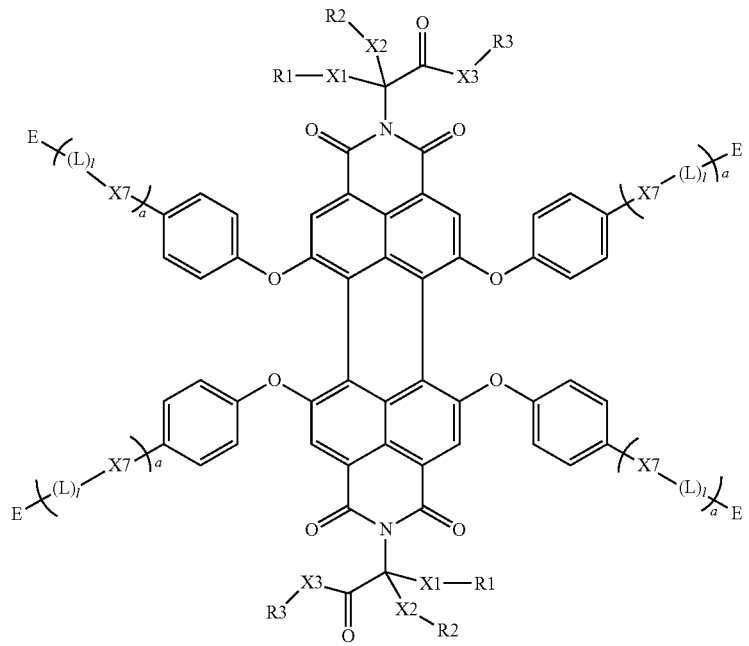

[Chemical Formula 5]

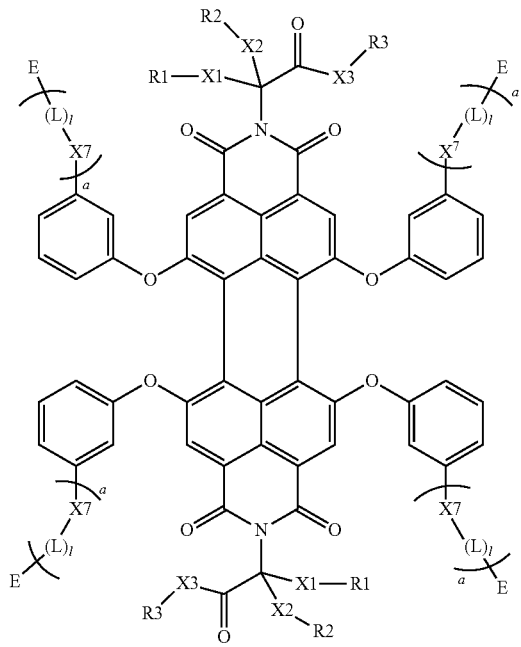

In Chemical Formulae 4 and 5,

X1 to X3 and R1 to R3 have the same definitions as in Chemical Formula 1, and X7, L, E, l and a have the same definitions as in Chemical Formula 2.

In one embodiment of the present specification, Chemical Formula 1 may be represented by the following Chemical Formula 6.

In Chemical Formula 6,

X1, X3, X4, X6, R1, R3, R4, R6 and M1 to M20 have the same definitions as in Chemical Formula 1.

In one embodiment of the present specification, Chemical Formula 1 may be represented by any one of the following Chemical Formulae 6-1 to 6-3.

[Chemical Formula 6]

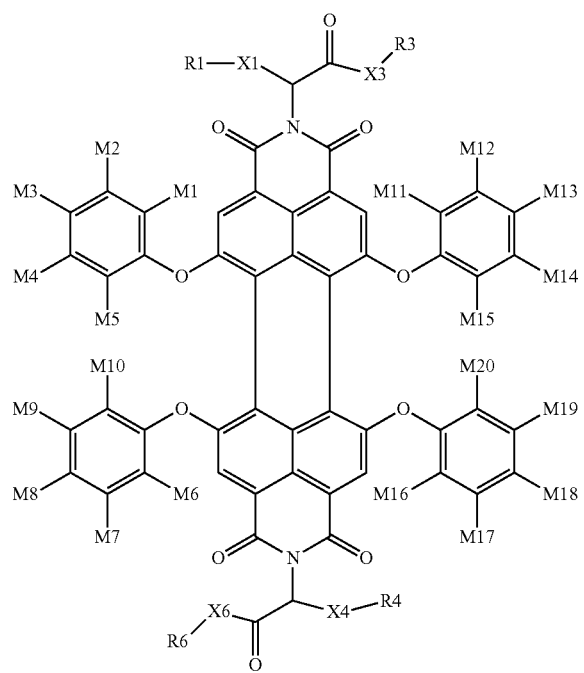

[Chemical Formula 6-1]

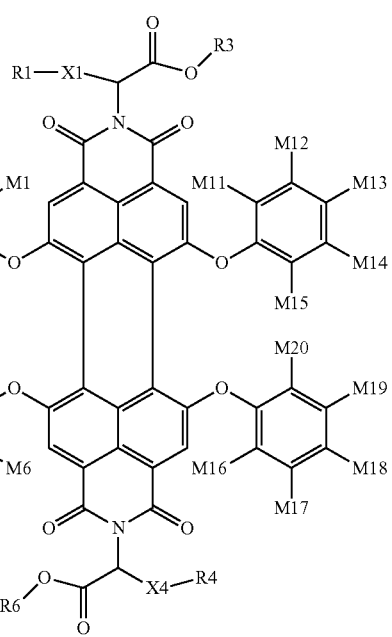

[Chemical Formula 6-2]

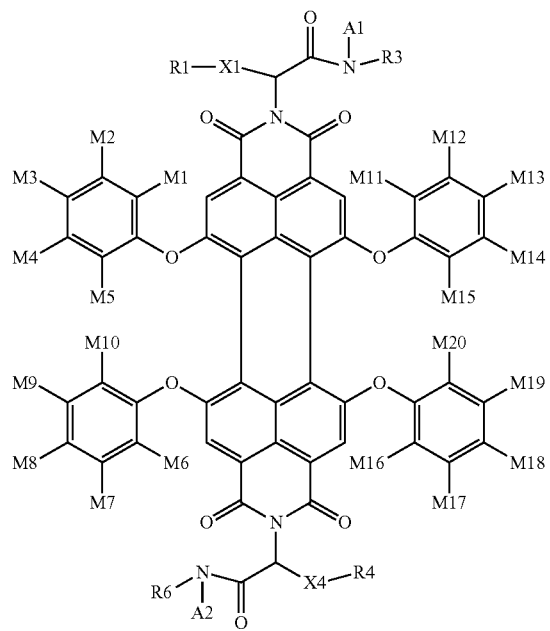

[Chemical Formula 6-3]

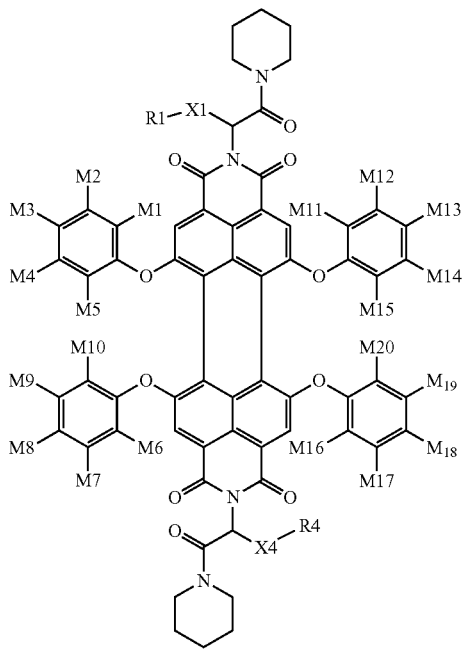

In Chemical Formulae 6-1 to 6-3,

X1, X4, R1, R3, R4, R6 and M1 to M20 have the same definitions as in Chemical Formula 1, A1 and A2 are the same as or different from each other, and each independently hydrogen; a halogen group; a substituted or unsubstituted alkyl group; a substituted or unsubstituted cycloalkyl group; a substituted or unsubstituted aryl group; or a substituted or unsubstituted heterocyclic group.

In one embodiment of the present specification, Chemical Formula 1 may be represented by any one of the following Chemical Formulae 3-1 to 3-3.

[Chemical Formula 3-1]

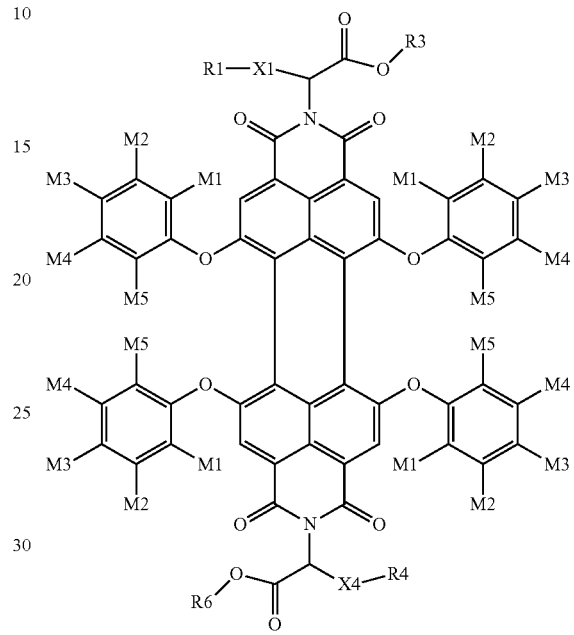

[Chemical Formula 3-2]

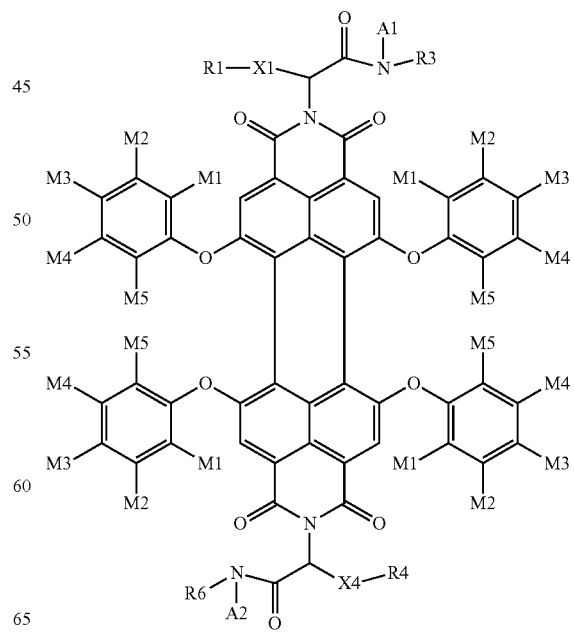

[Chemical Formula 3-3]

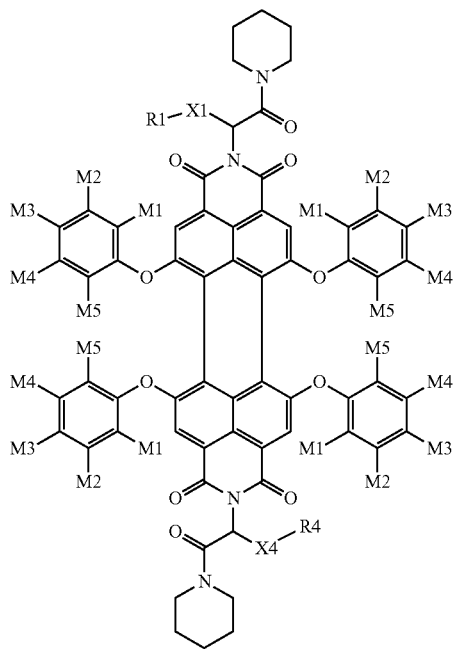

In Chemical Formulae 3-1 to 3-3,

X1, X4, R1, R3, R4 and R6 have the same definitions as in Chemical Formula 1, any one of M1 to M5 is the substituent represented by Chemical Formula 2, and the rest are hydrogen, A1 and A2 are the same as or different from each other, and each independently hydrogen; a halogen group; a substituted or unsubstituted alkyl group; a substituted or unsubstituted cycloalkyl group; a substituted or unsubstituted aryl group; or a substituted or unsubstituted heterocyclic group.

In one embodiment of the present specification, the compound represented by Chemical Formula 1 is point symmetric, line symmetric or surface symmetric.

In one embodiment of the present specification, the compound represented by Chemical Formula 1 may be represented by any one of the following compounds.

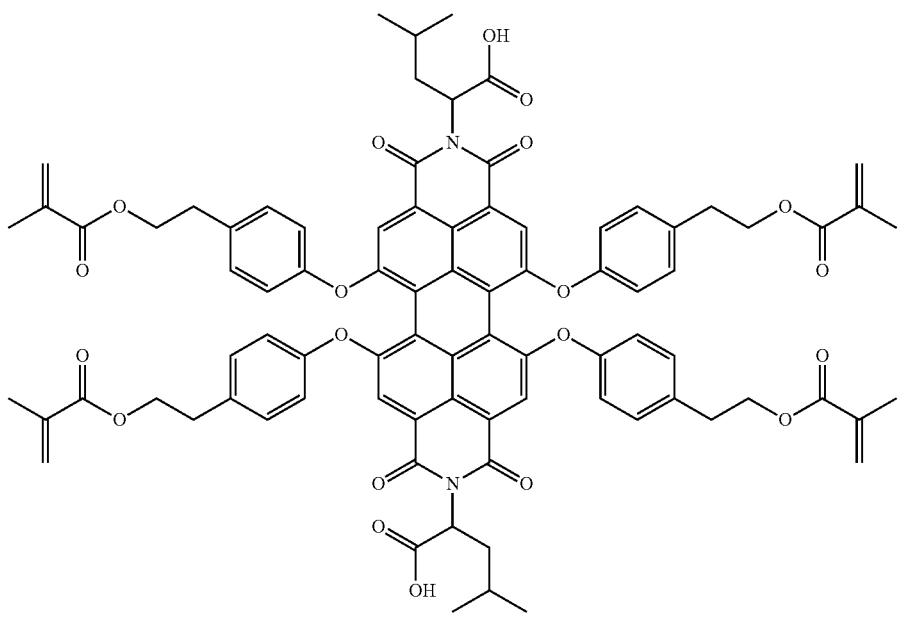

-continued
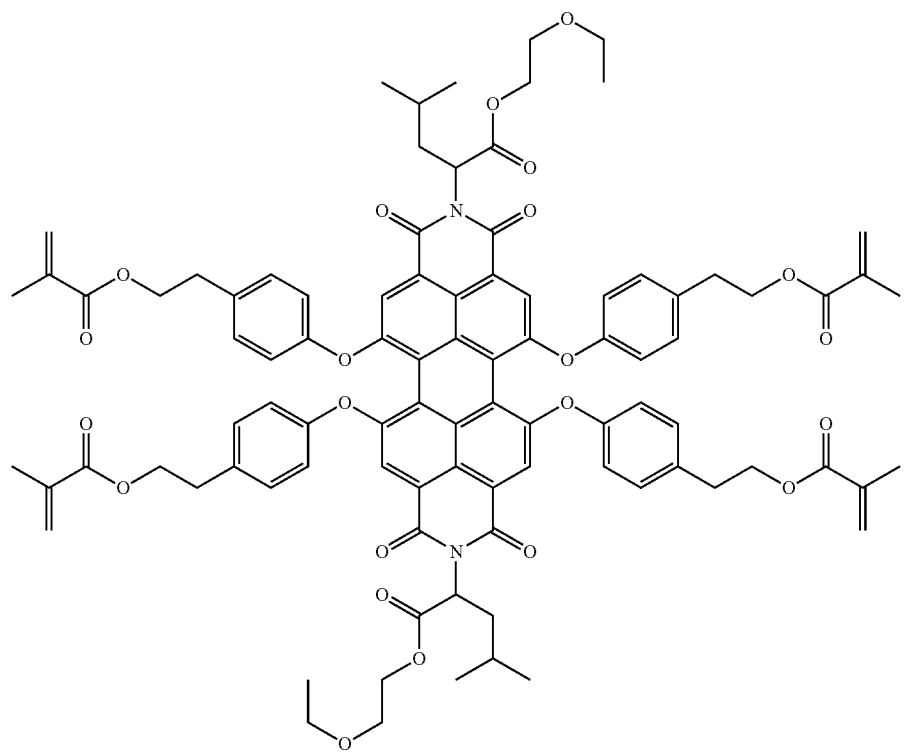
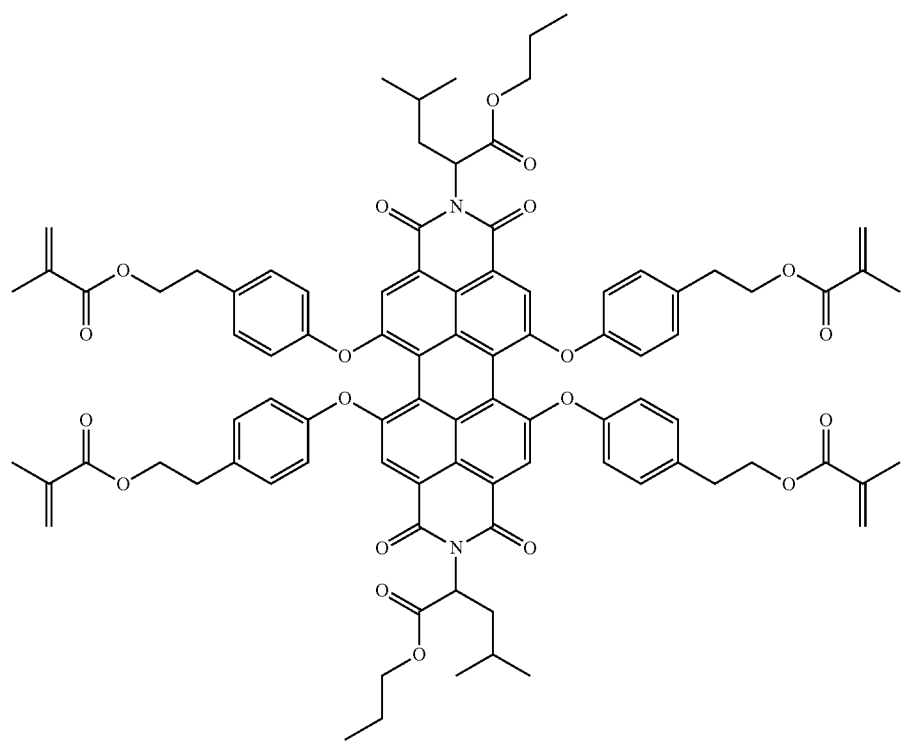

-continued
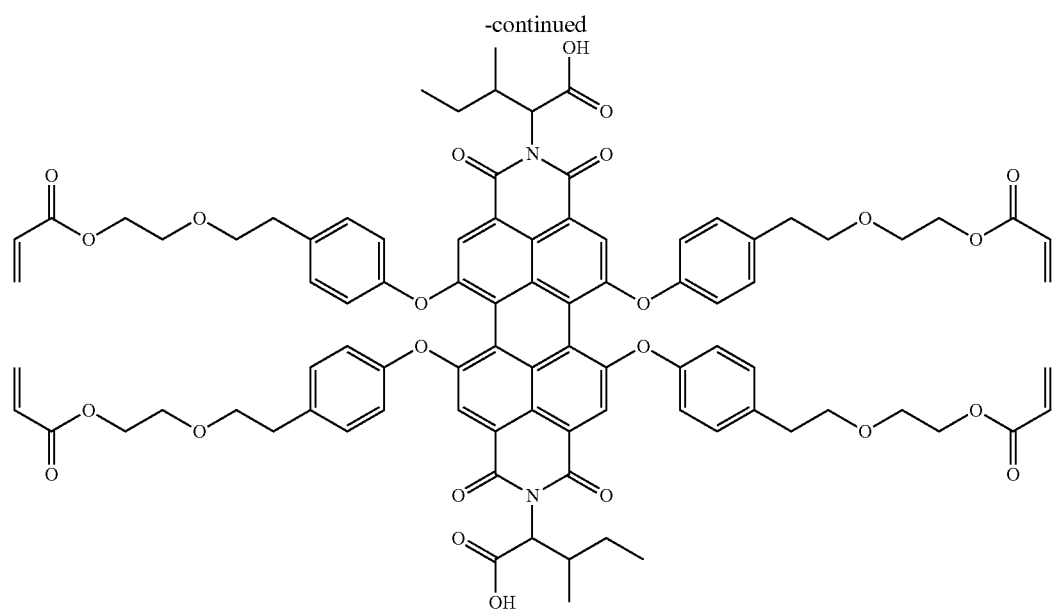
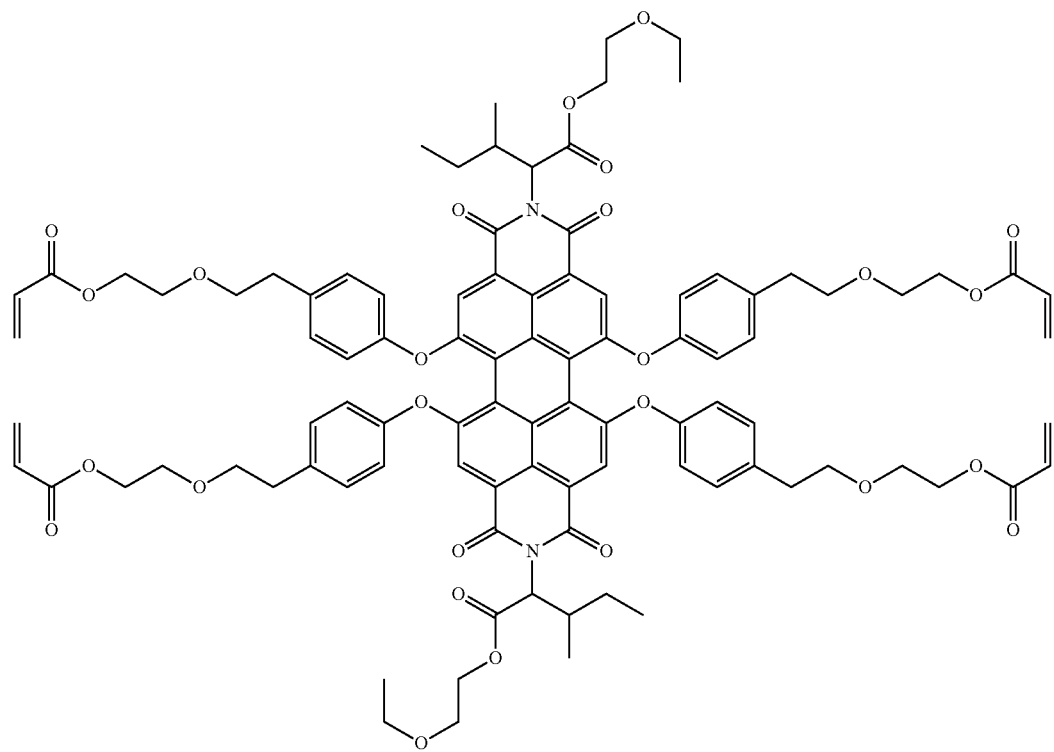

-continued
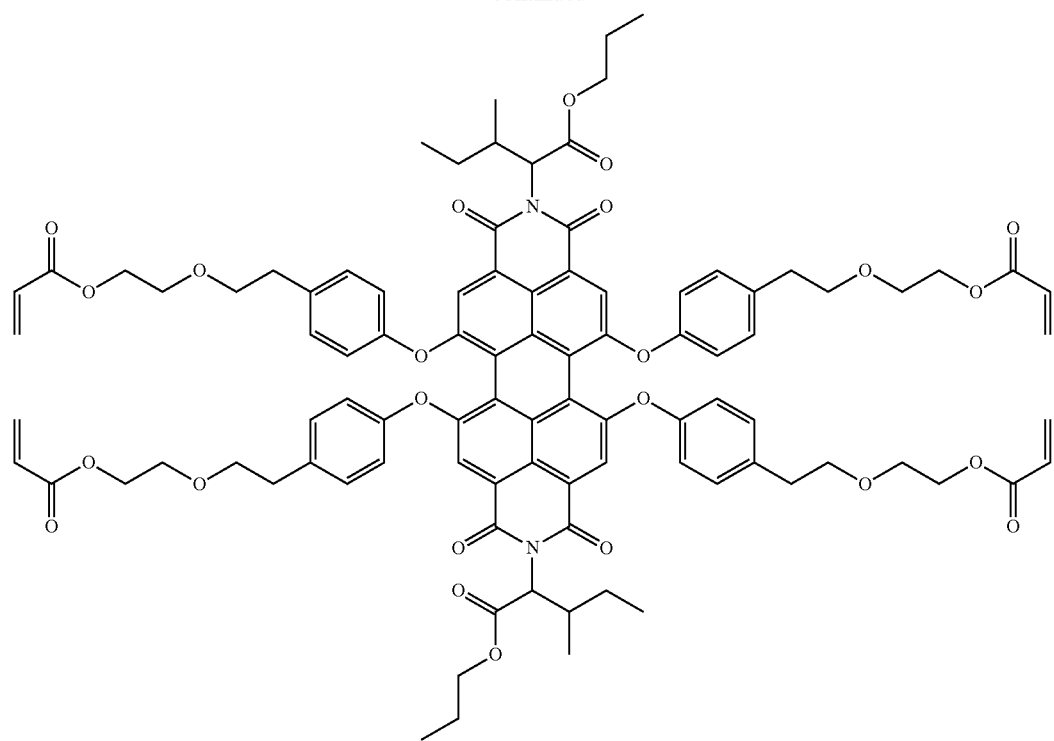
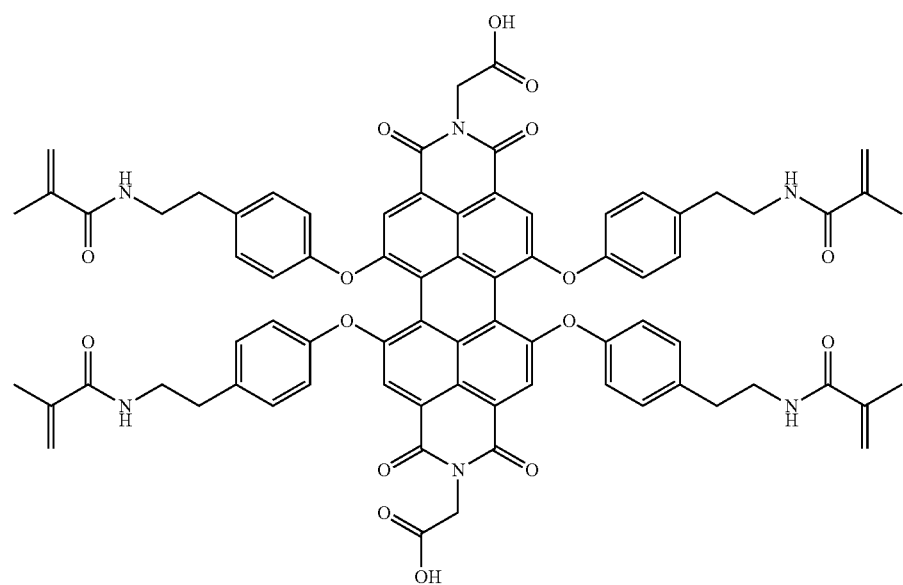

-continued
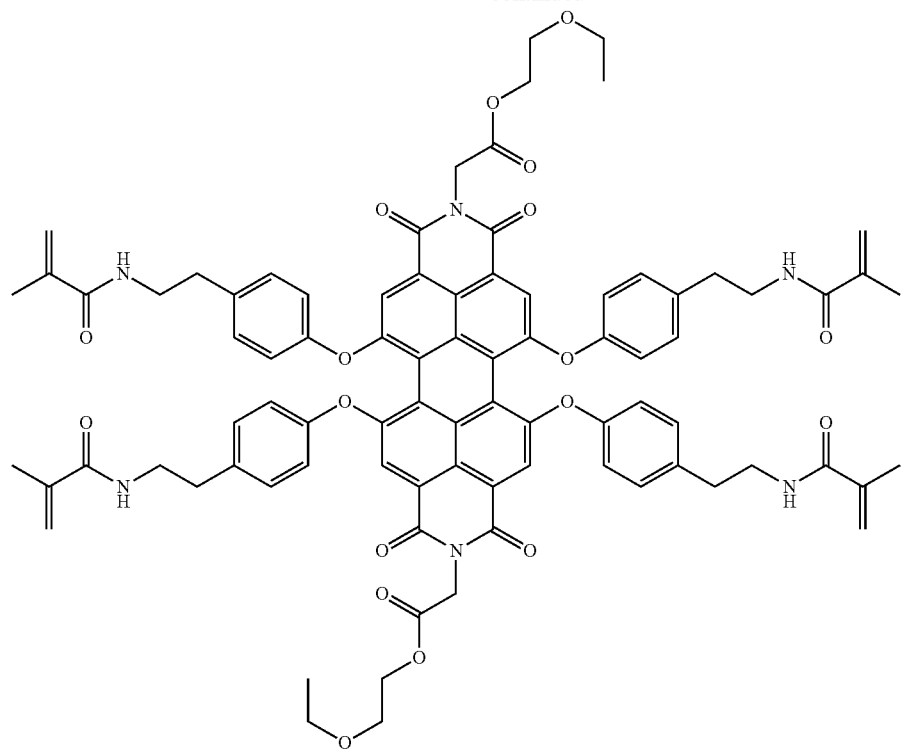
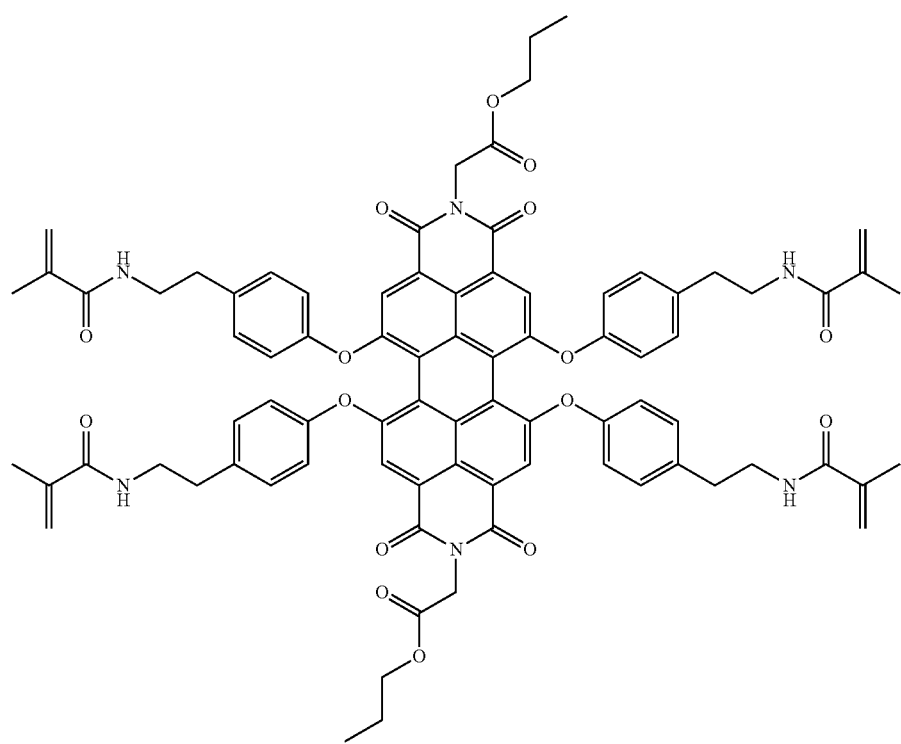

-continued
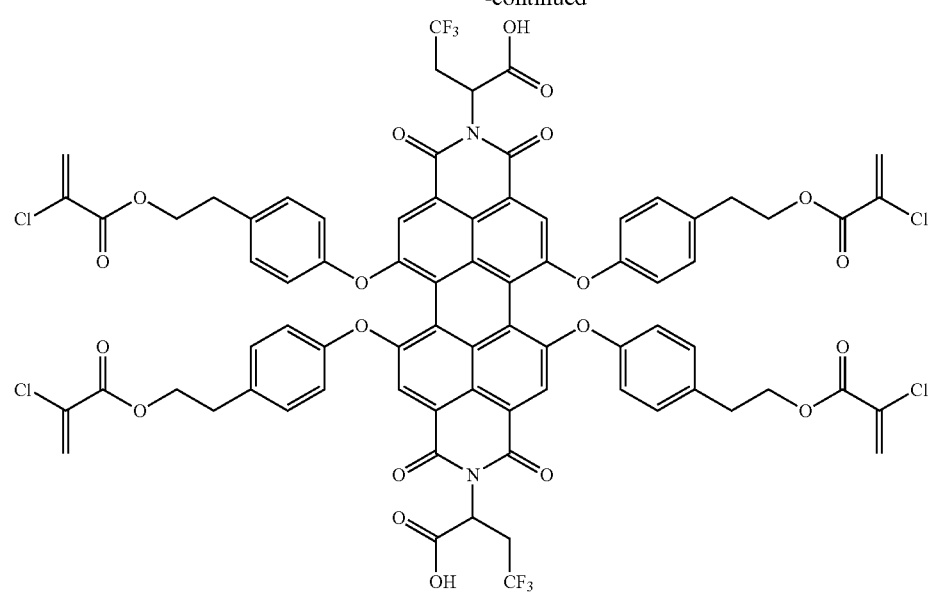
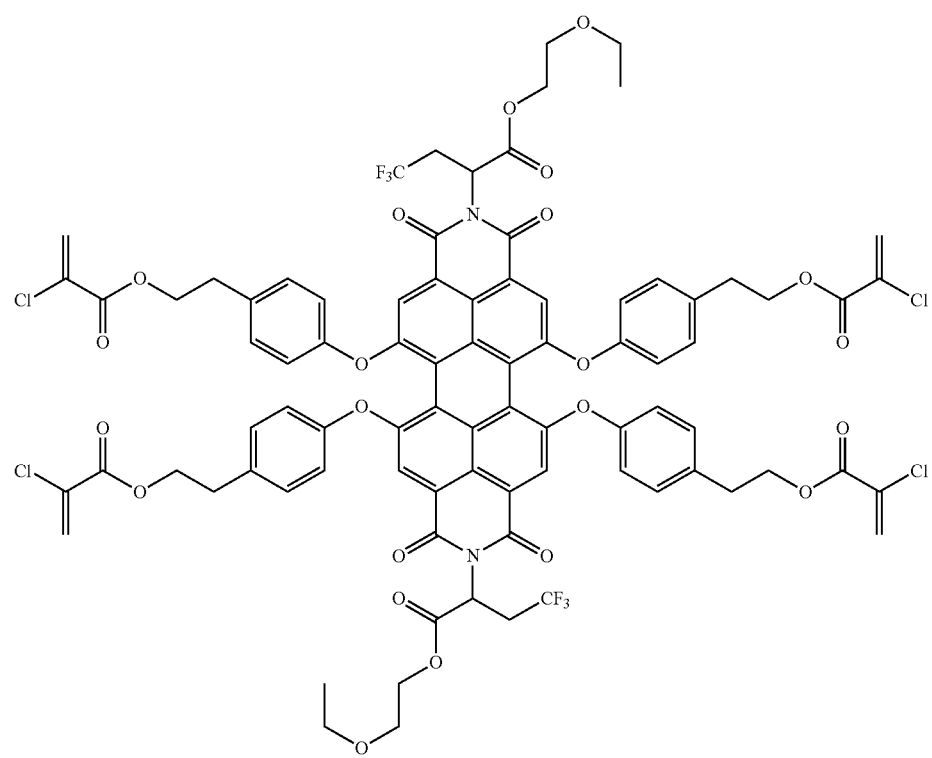

-continued
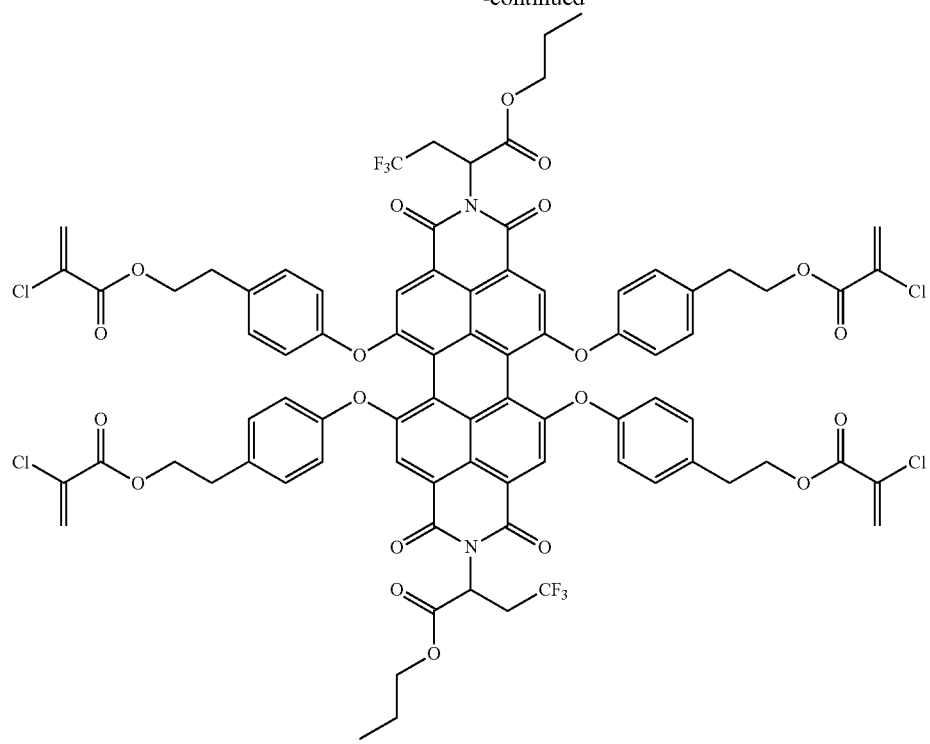
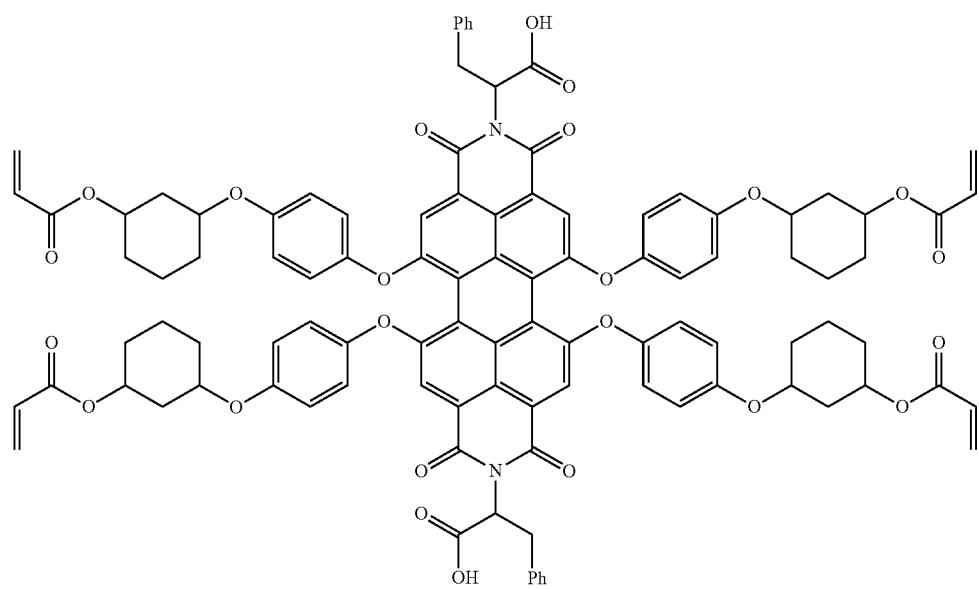

-continued
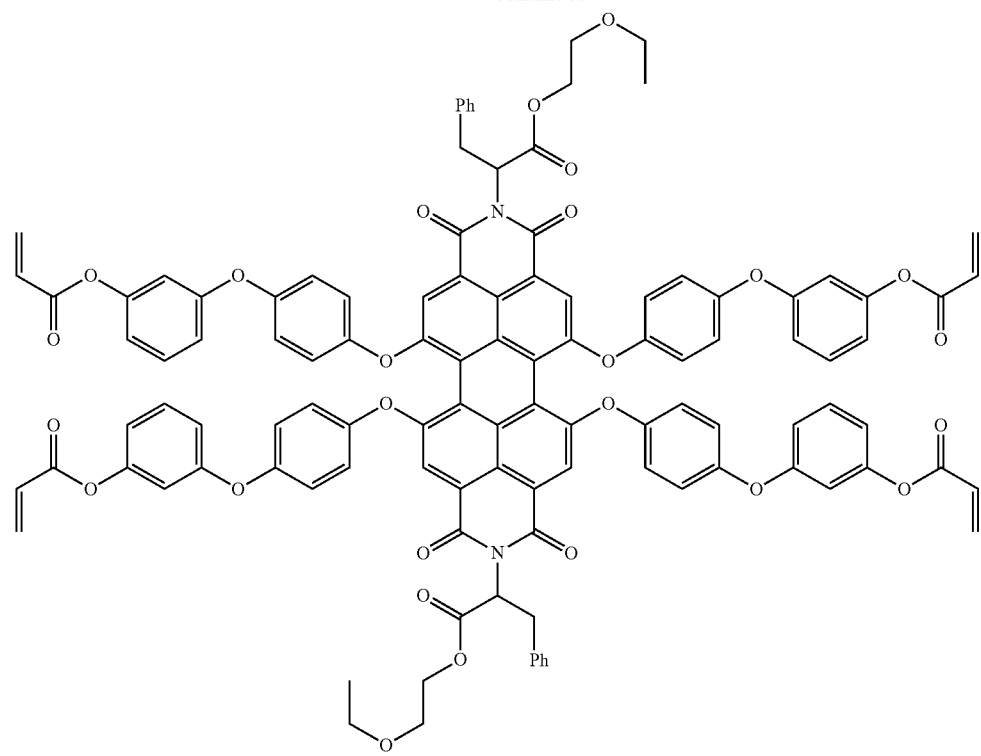
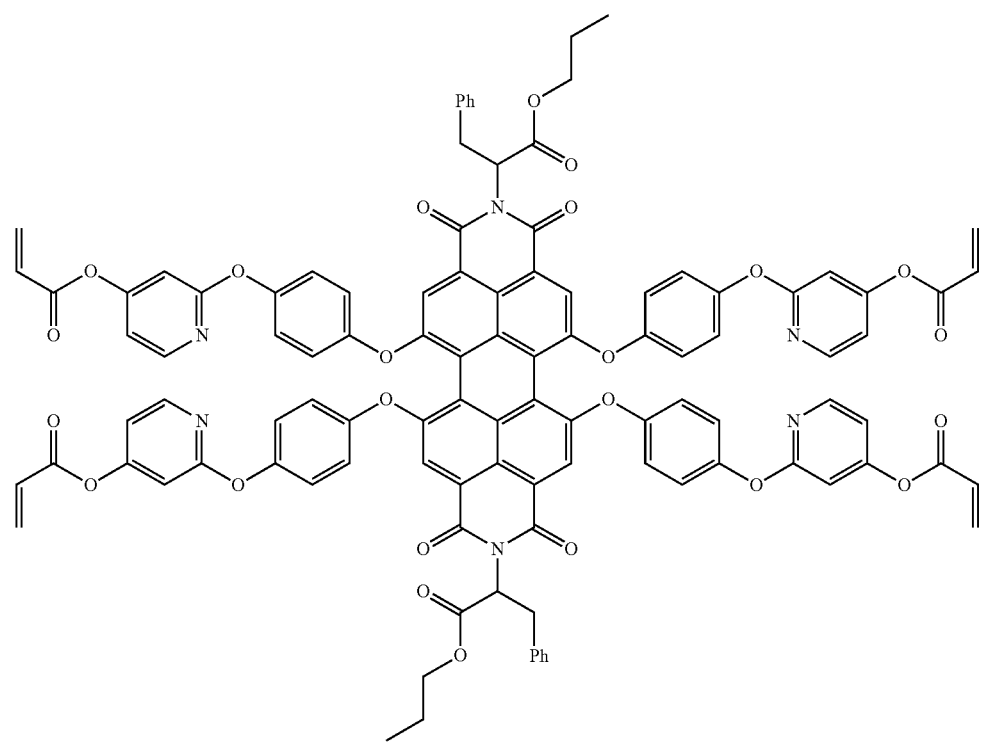

-continued
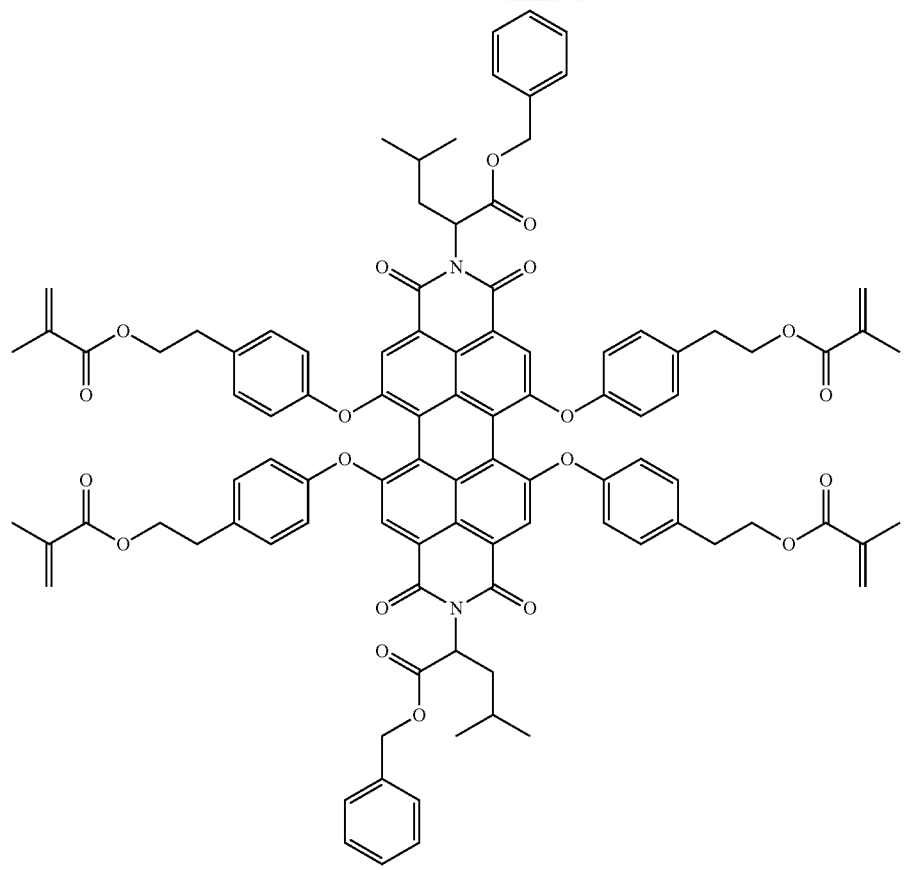
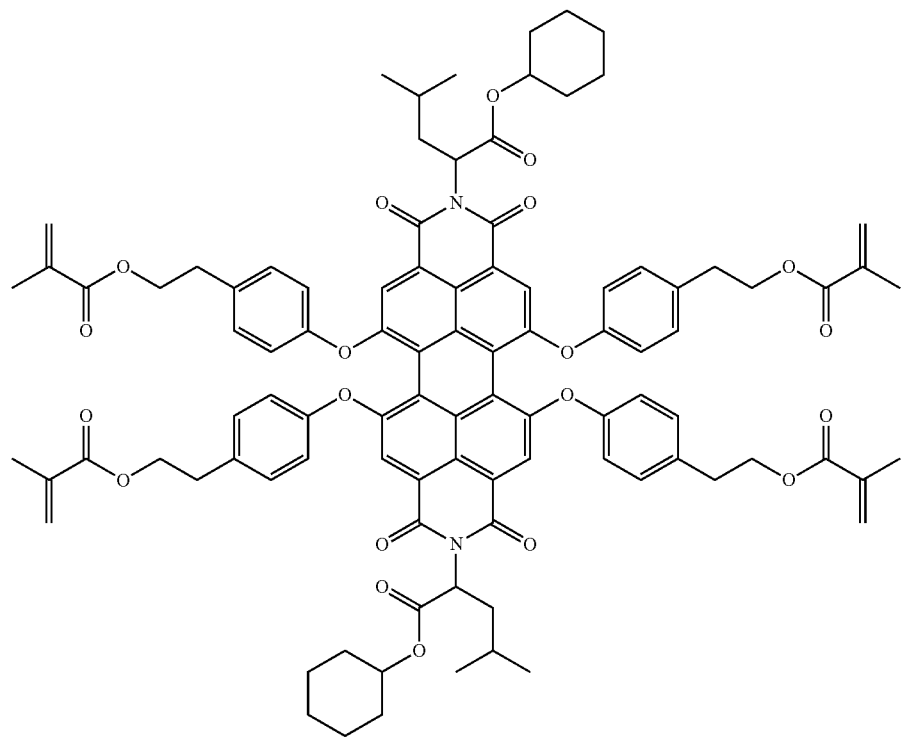

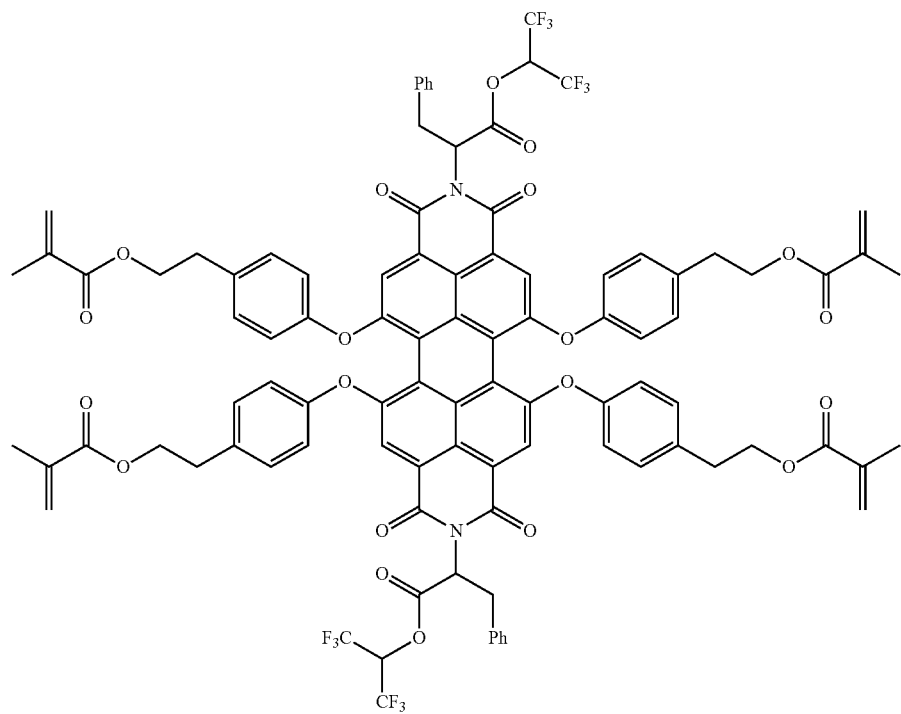
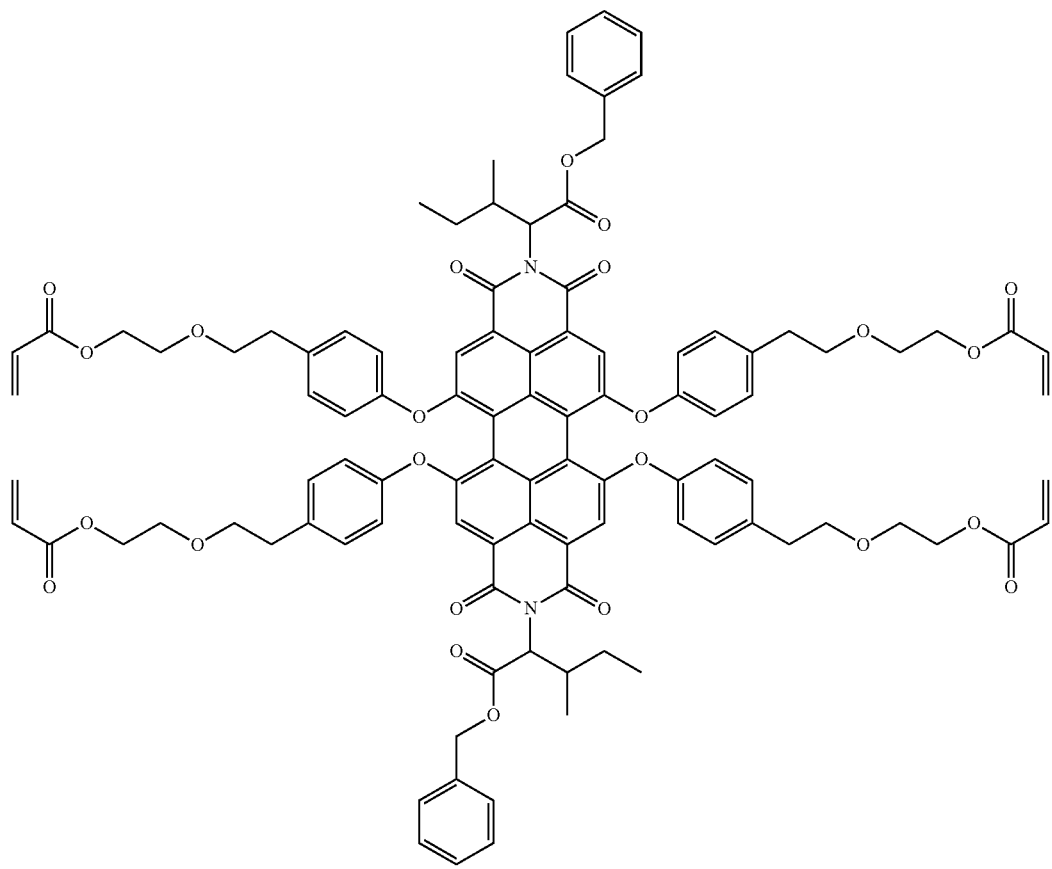

-continued
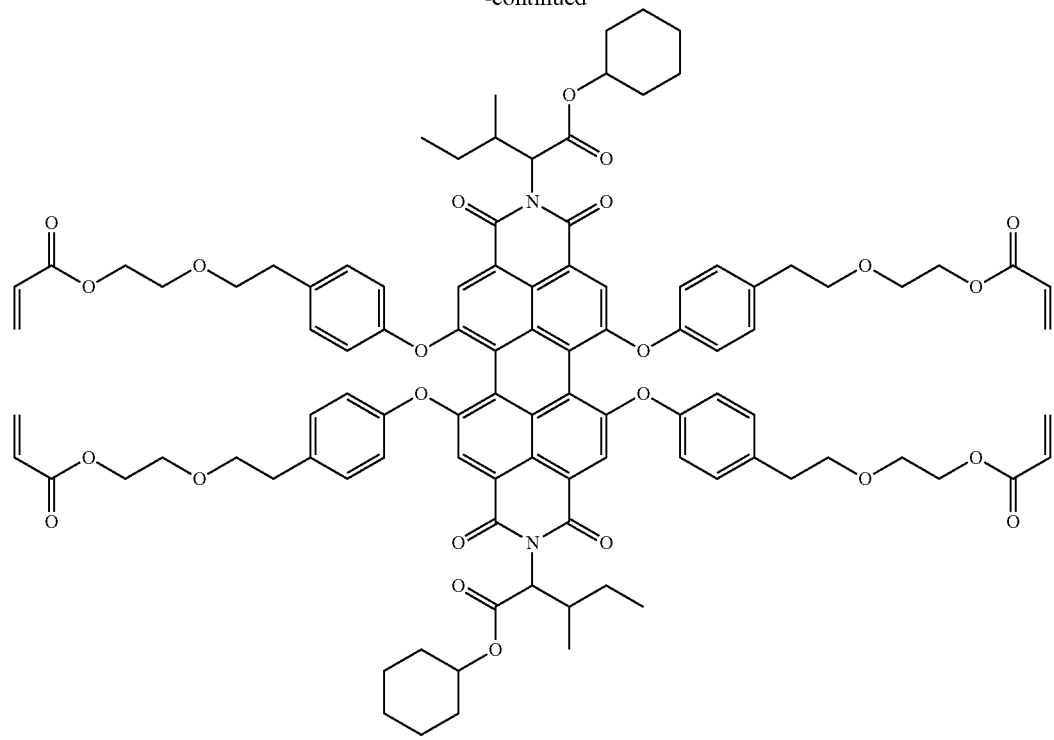
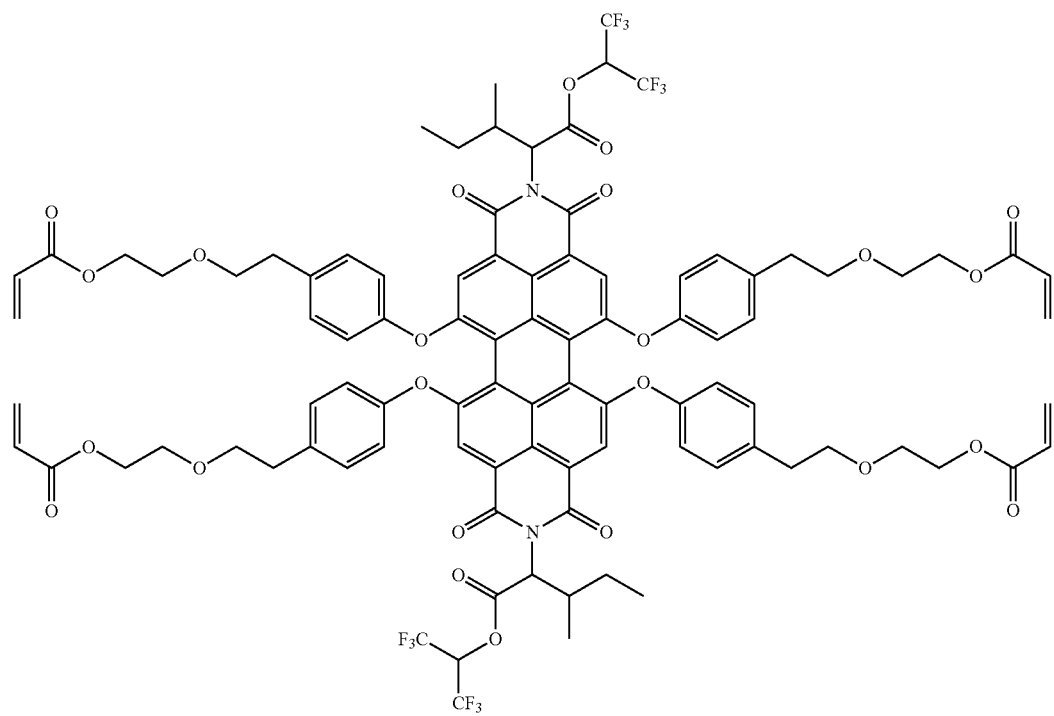

-continued
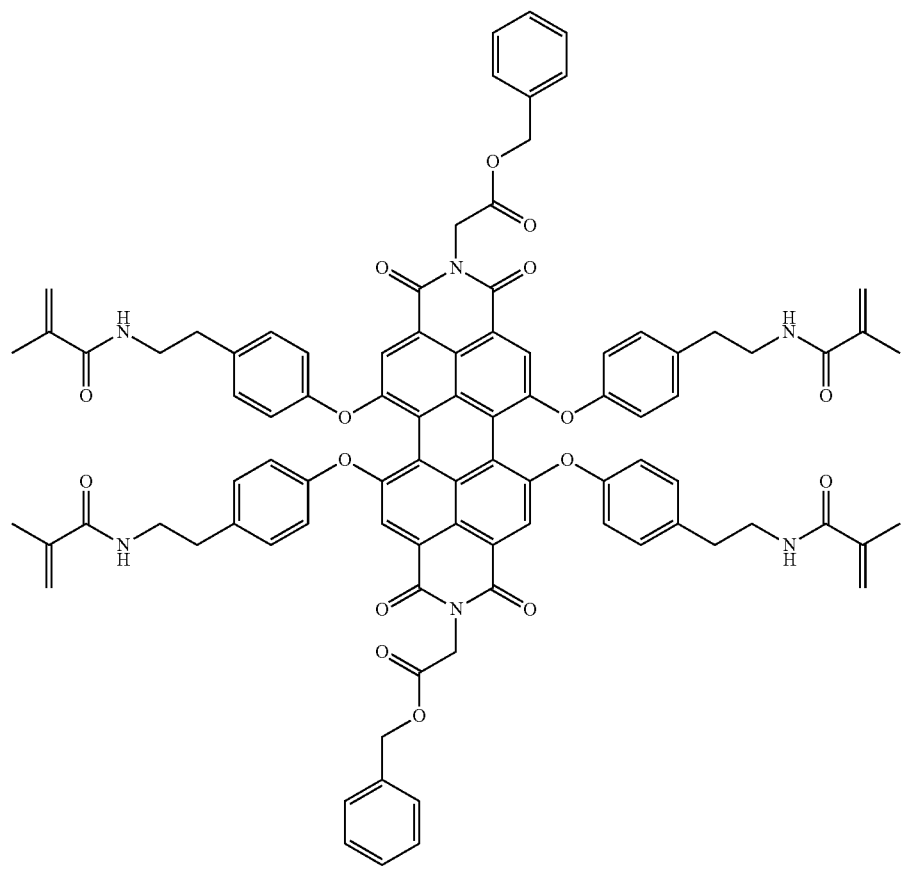
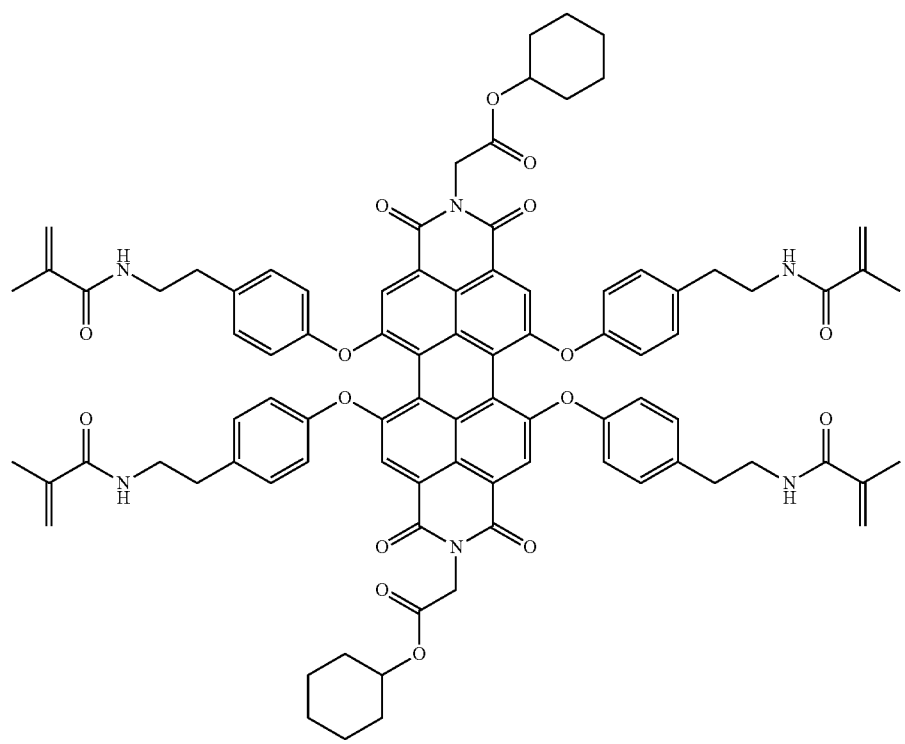

-continued
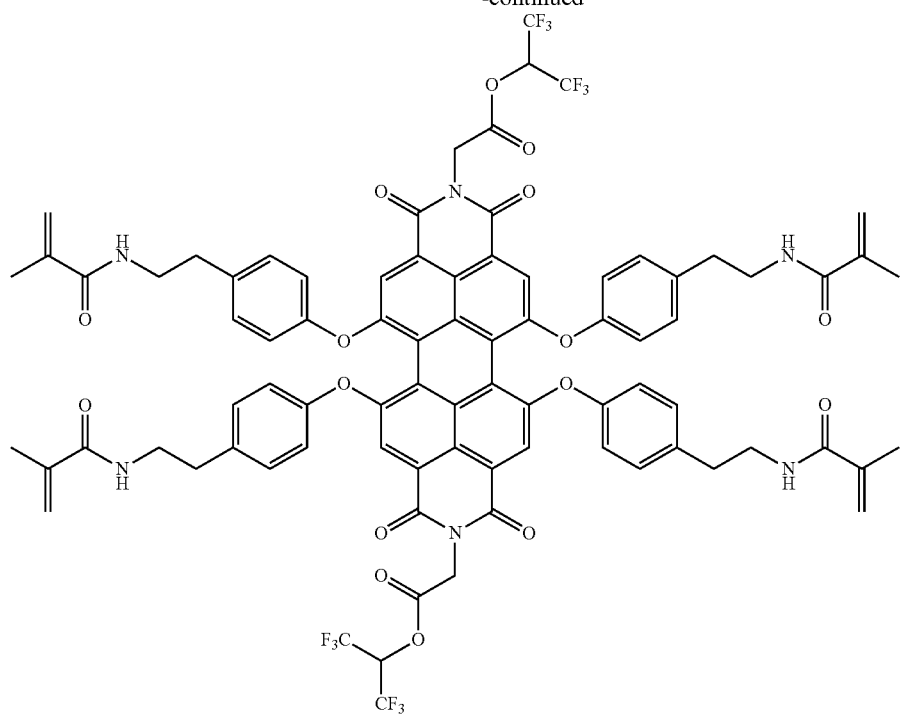
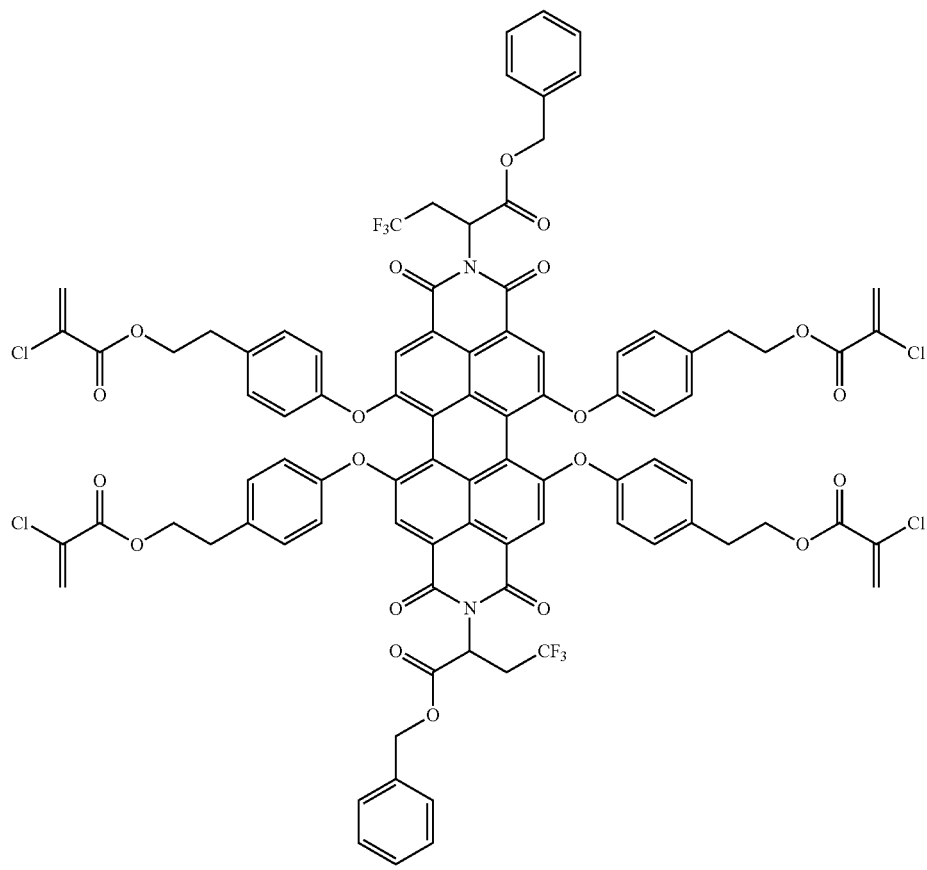

-continued
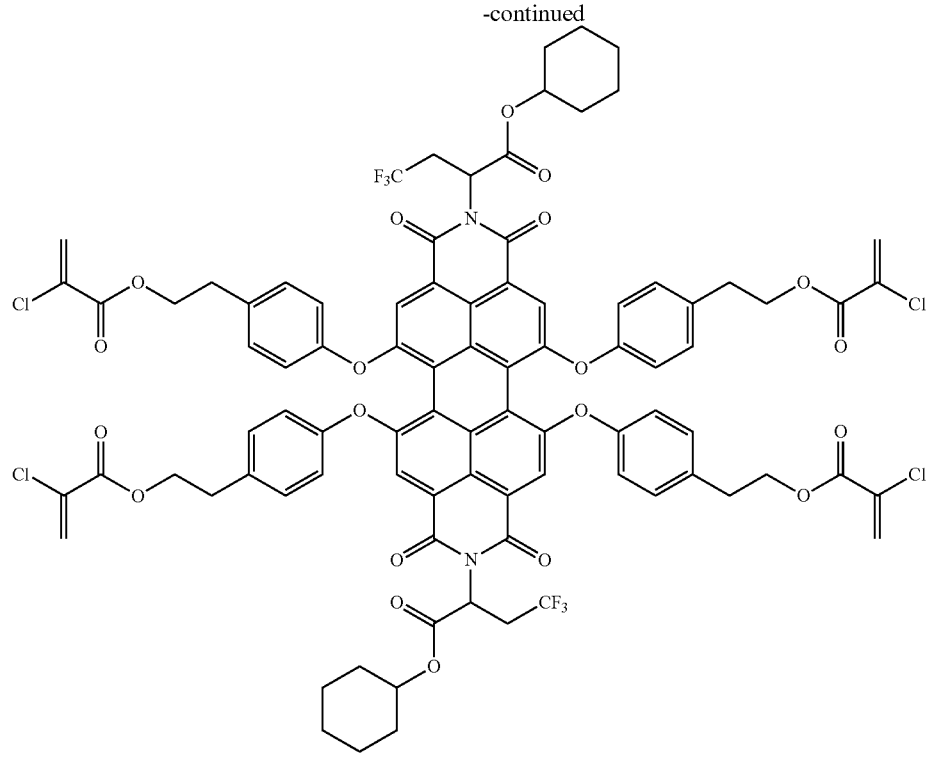
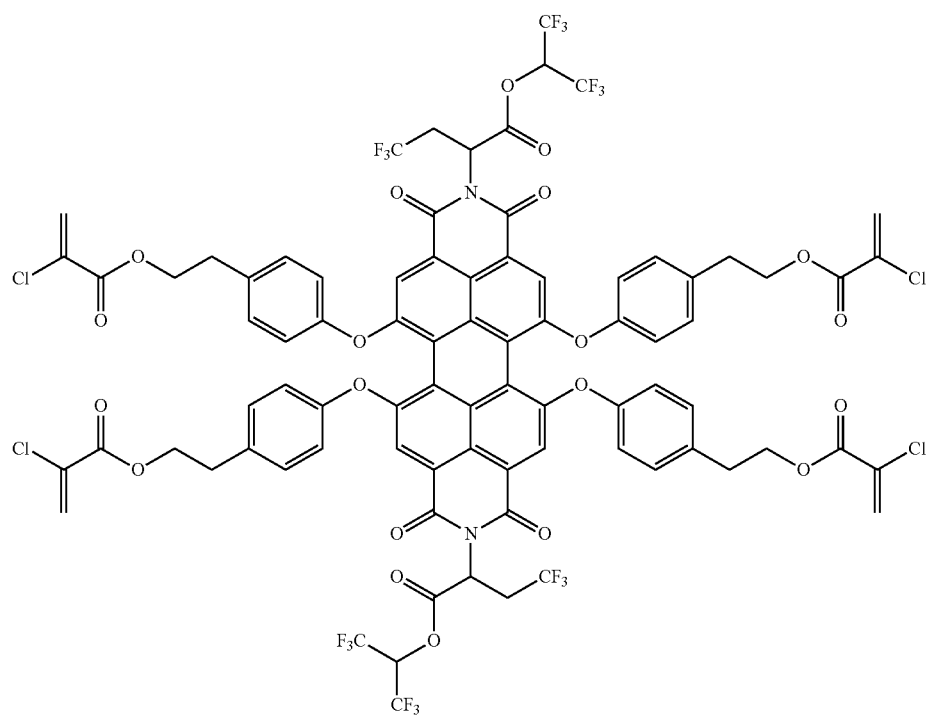

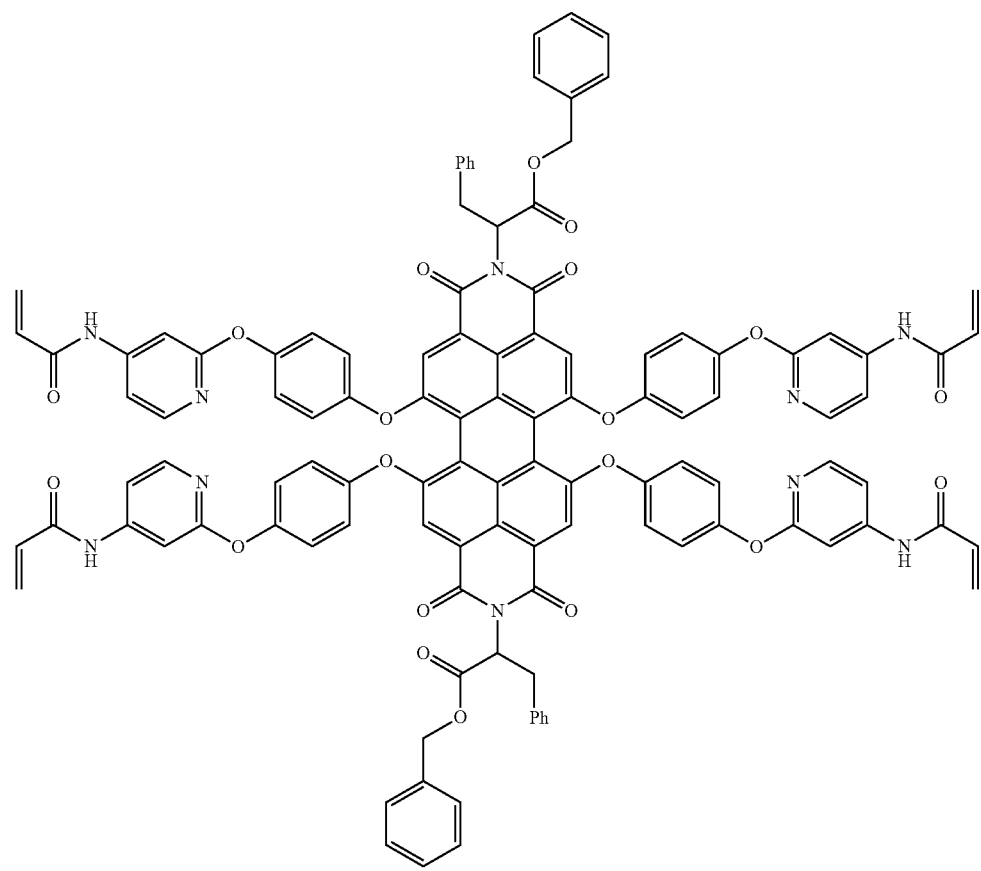
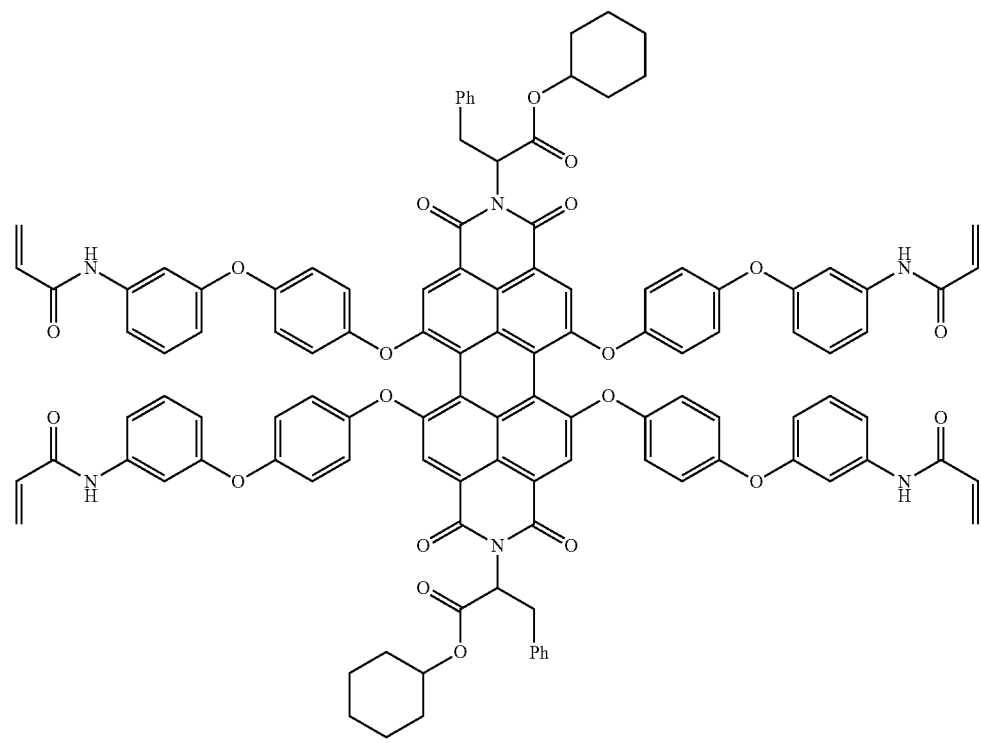

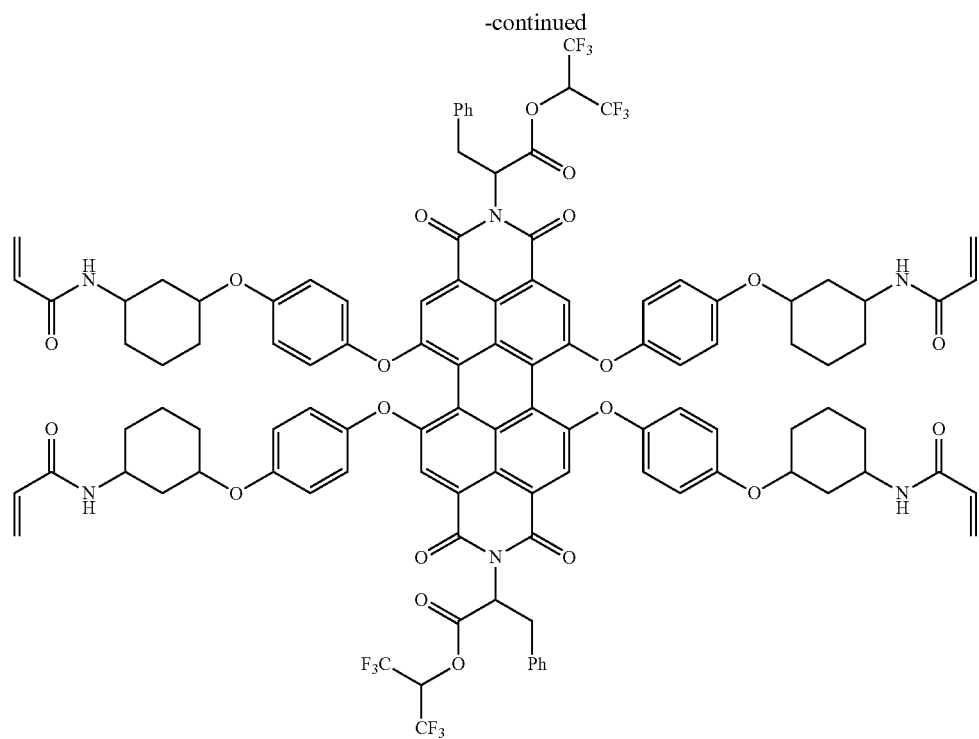
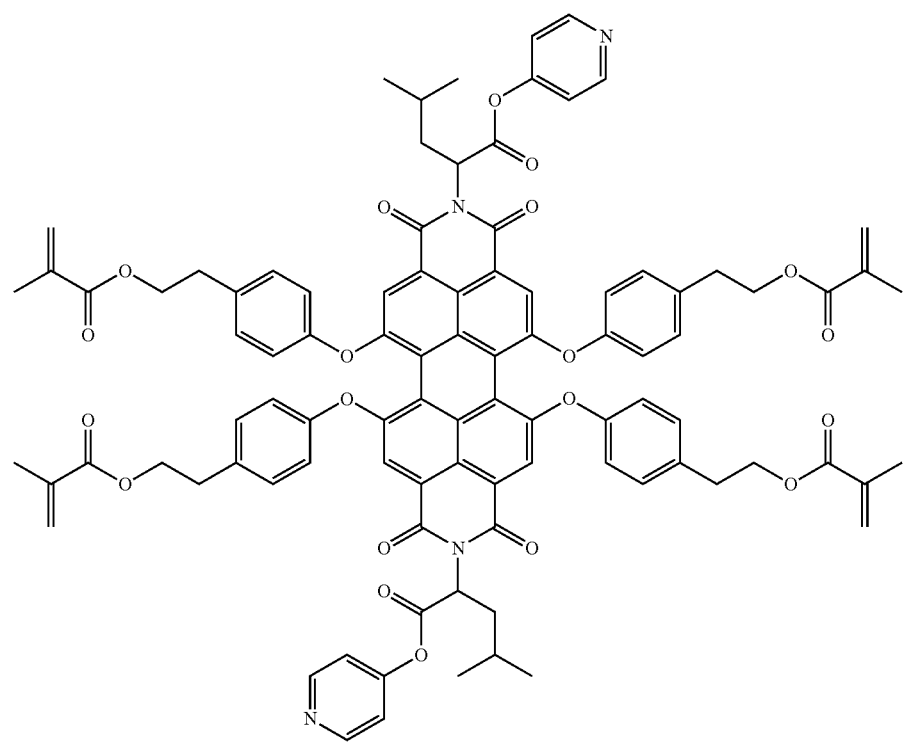

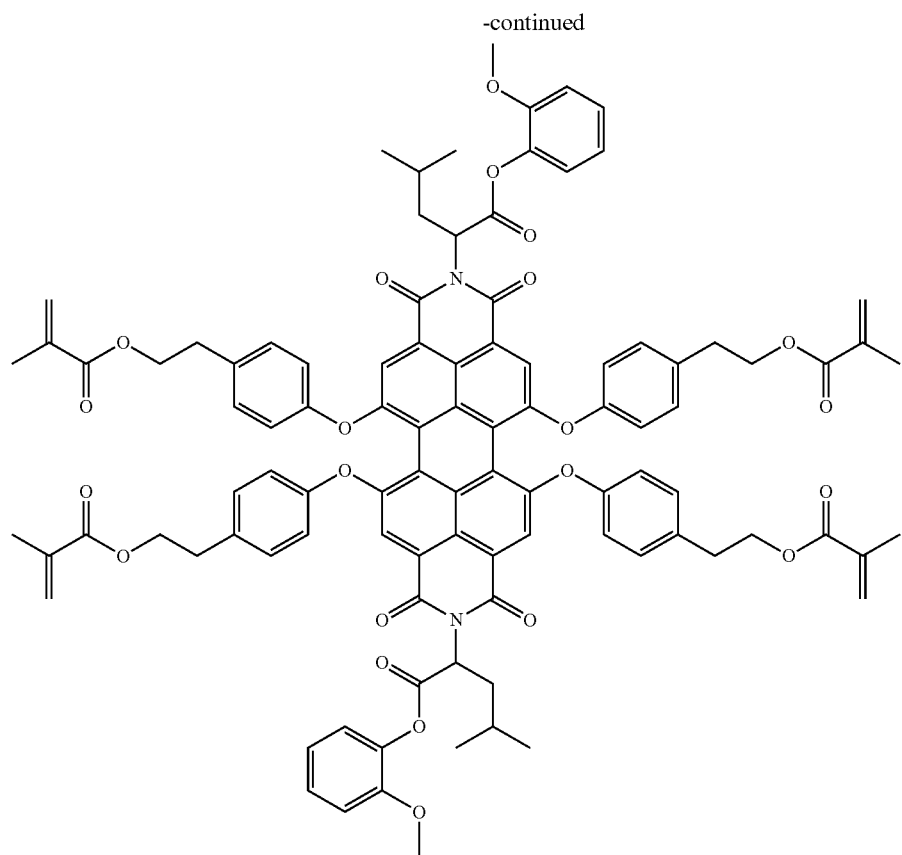

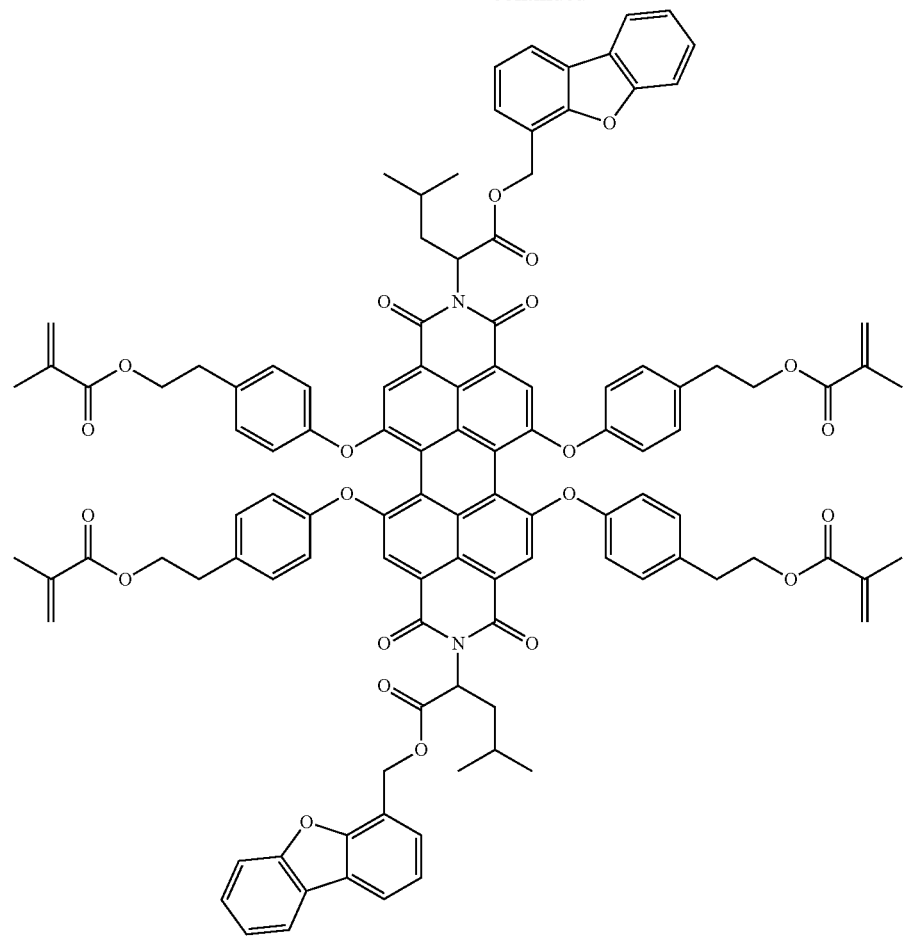
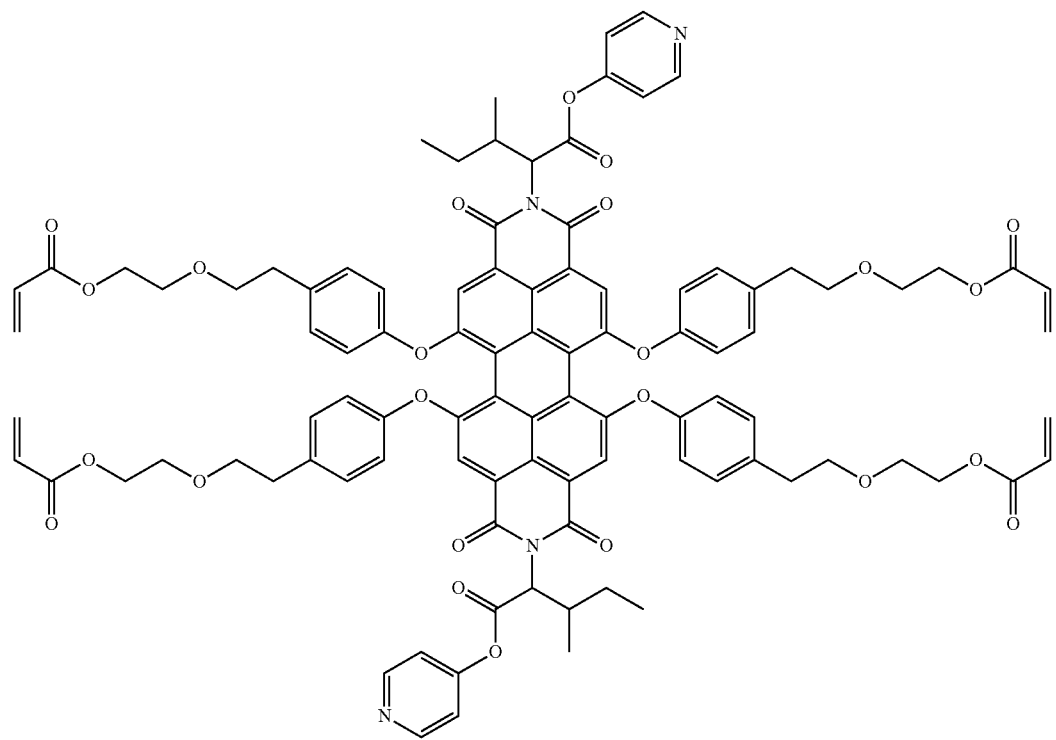

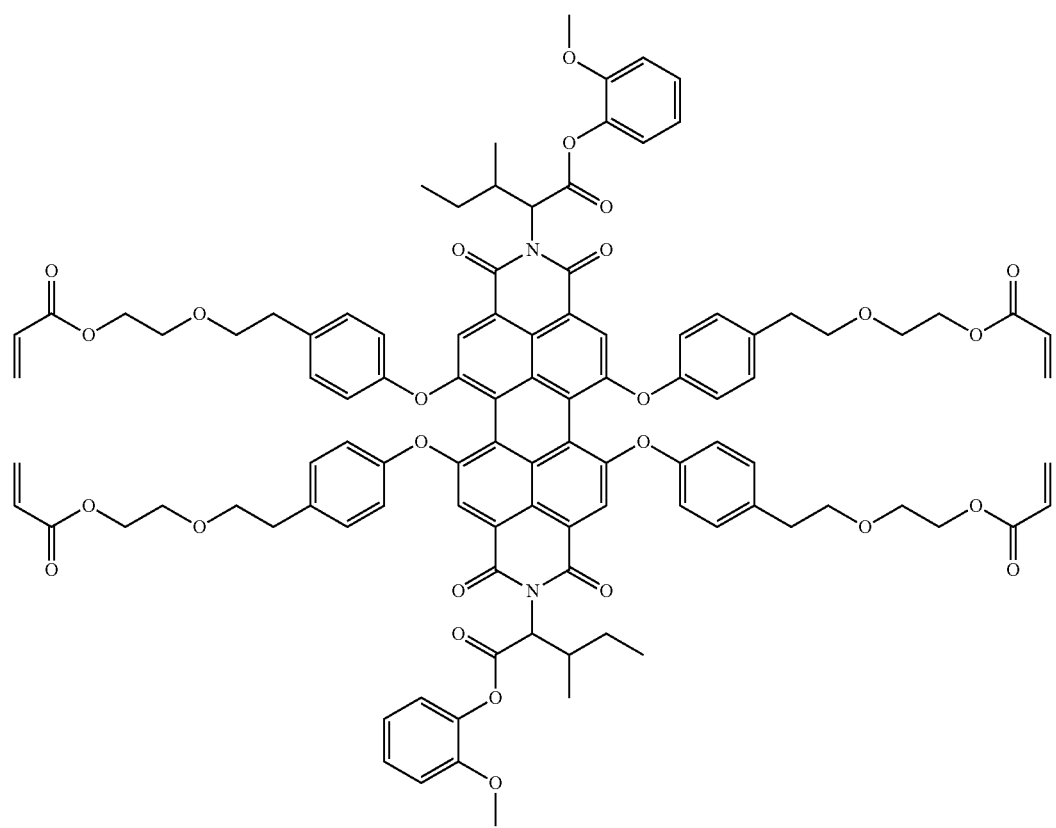

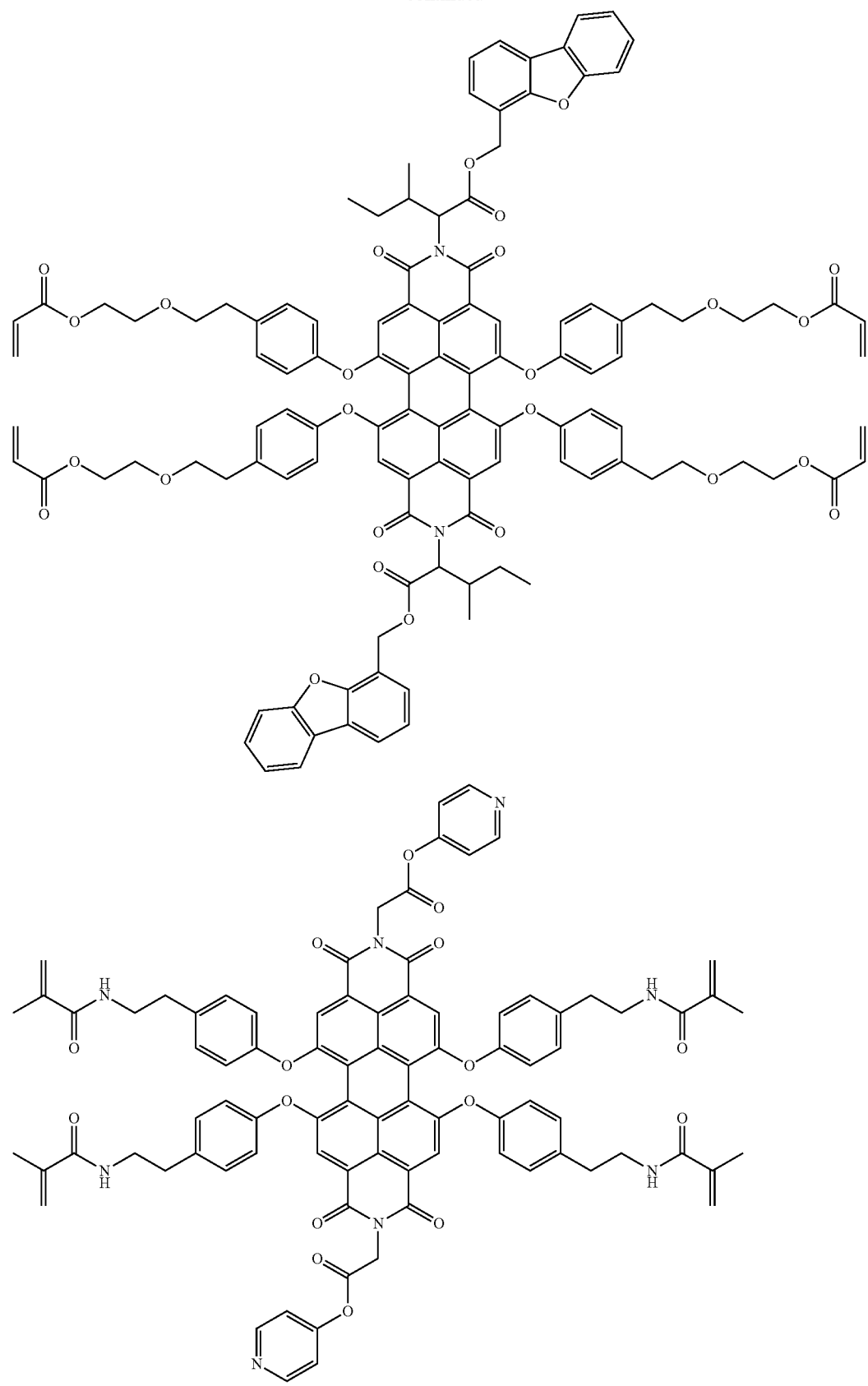

-continued
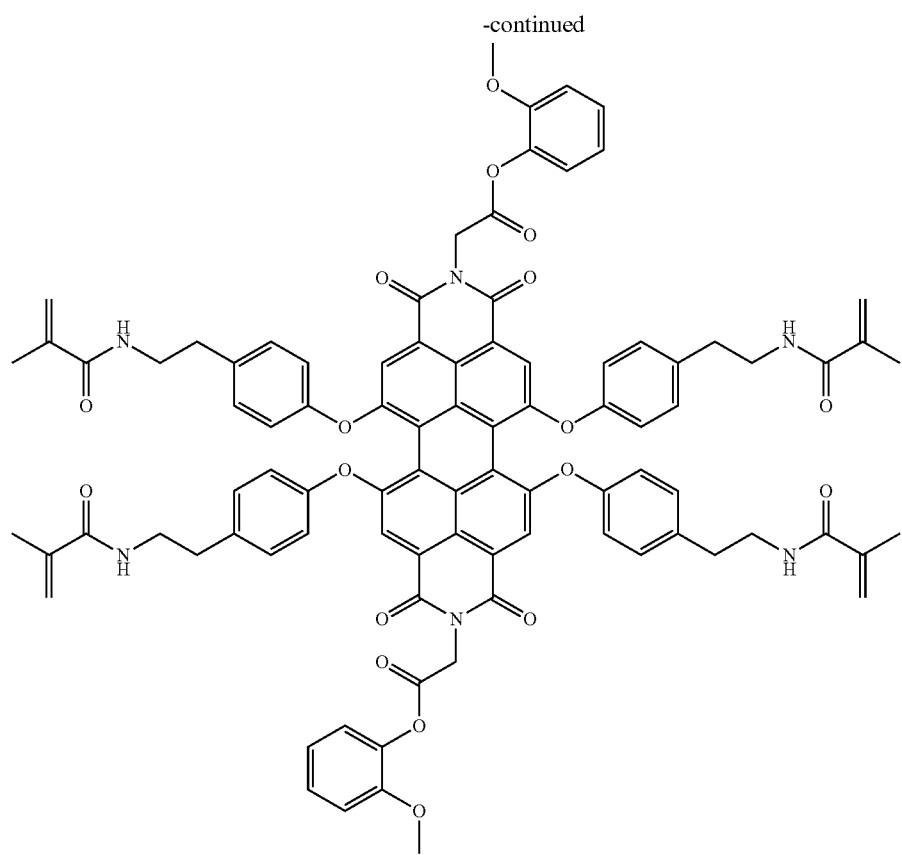

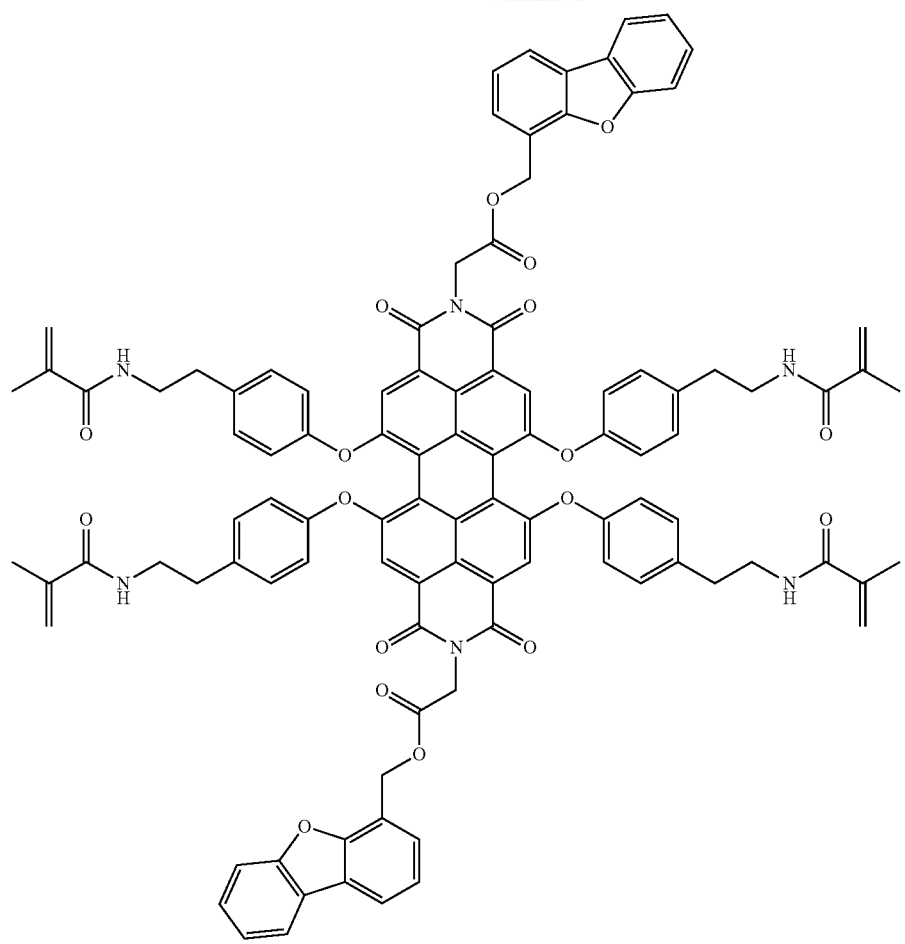
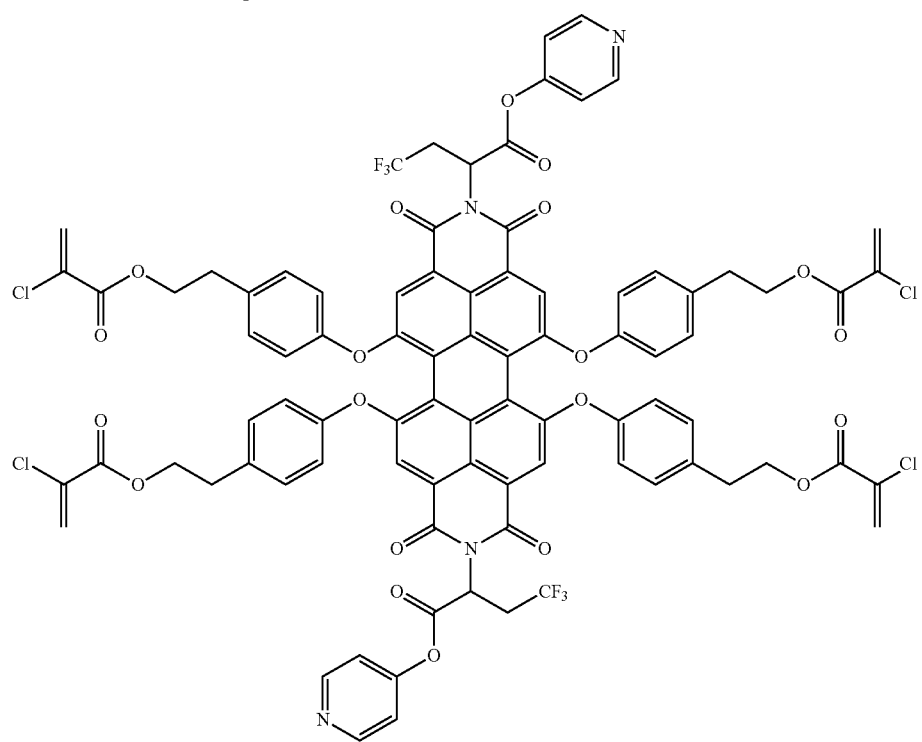

-continued
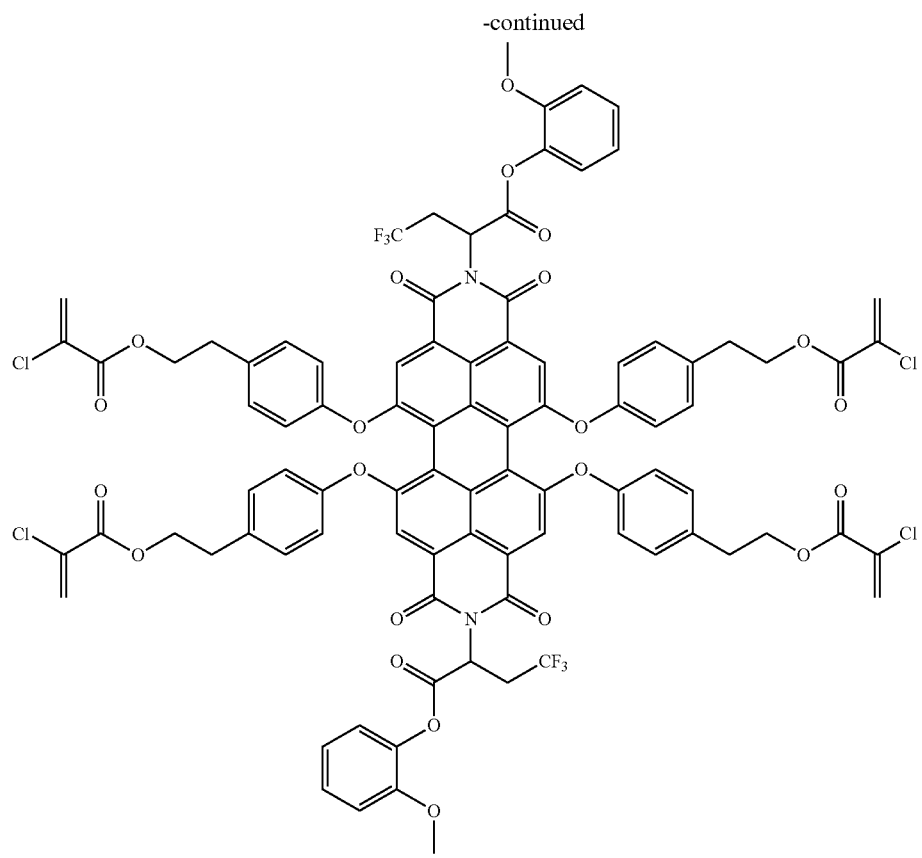

-continued
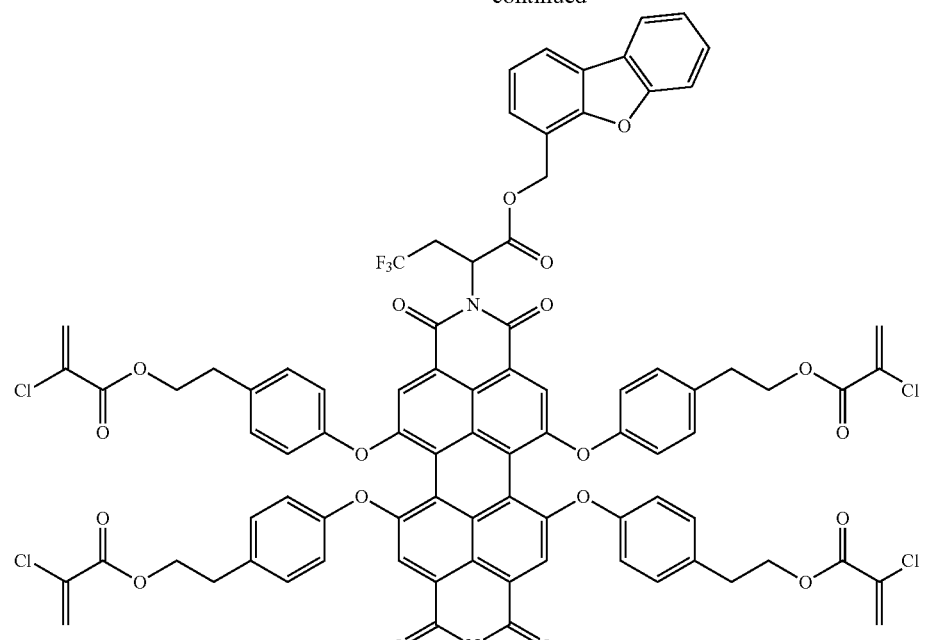
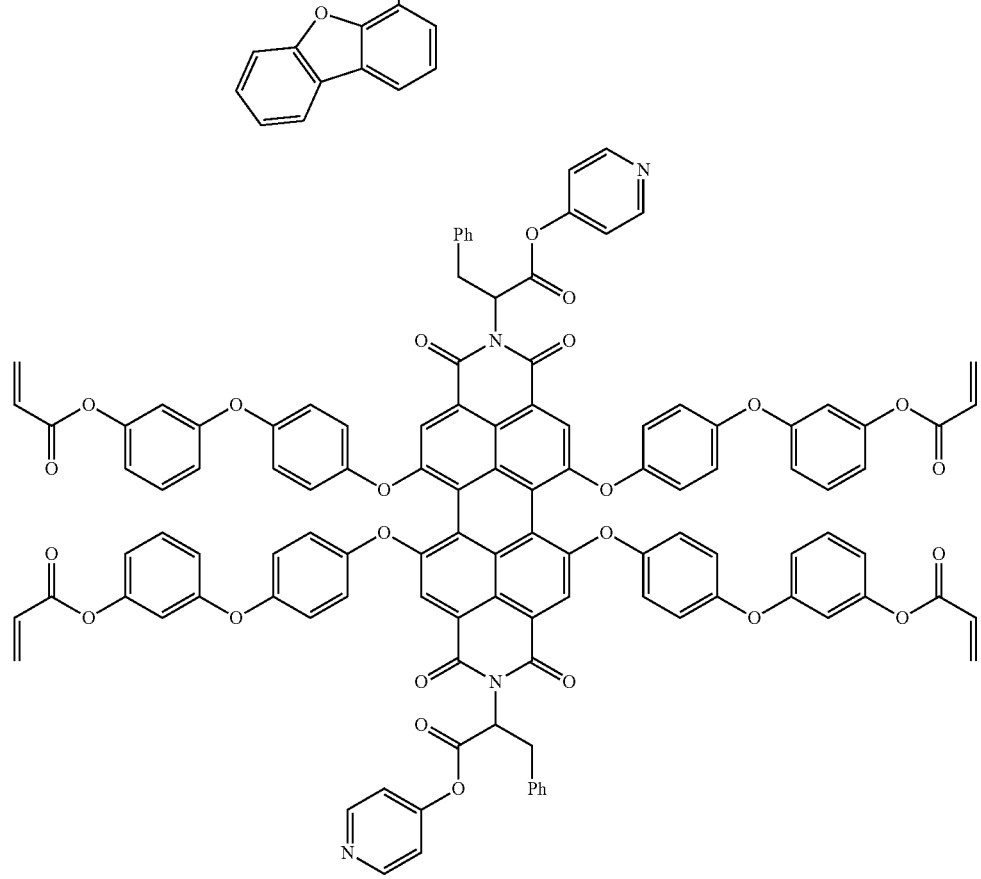

-continued
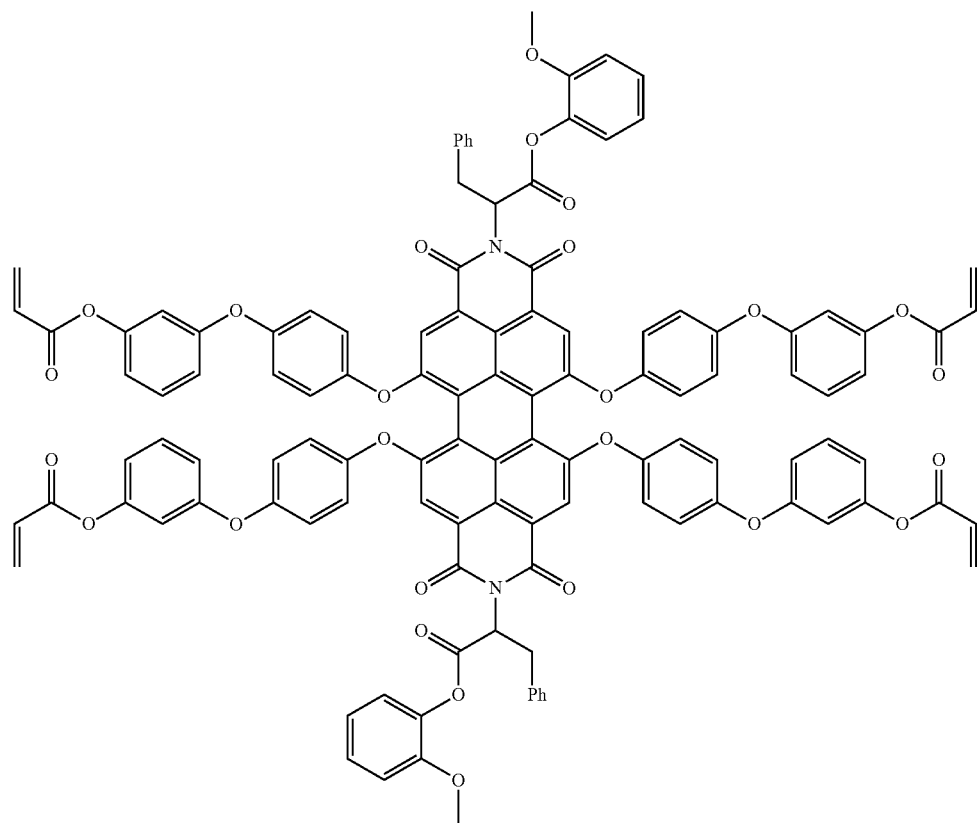

-continued
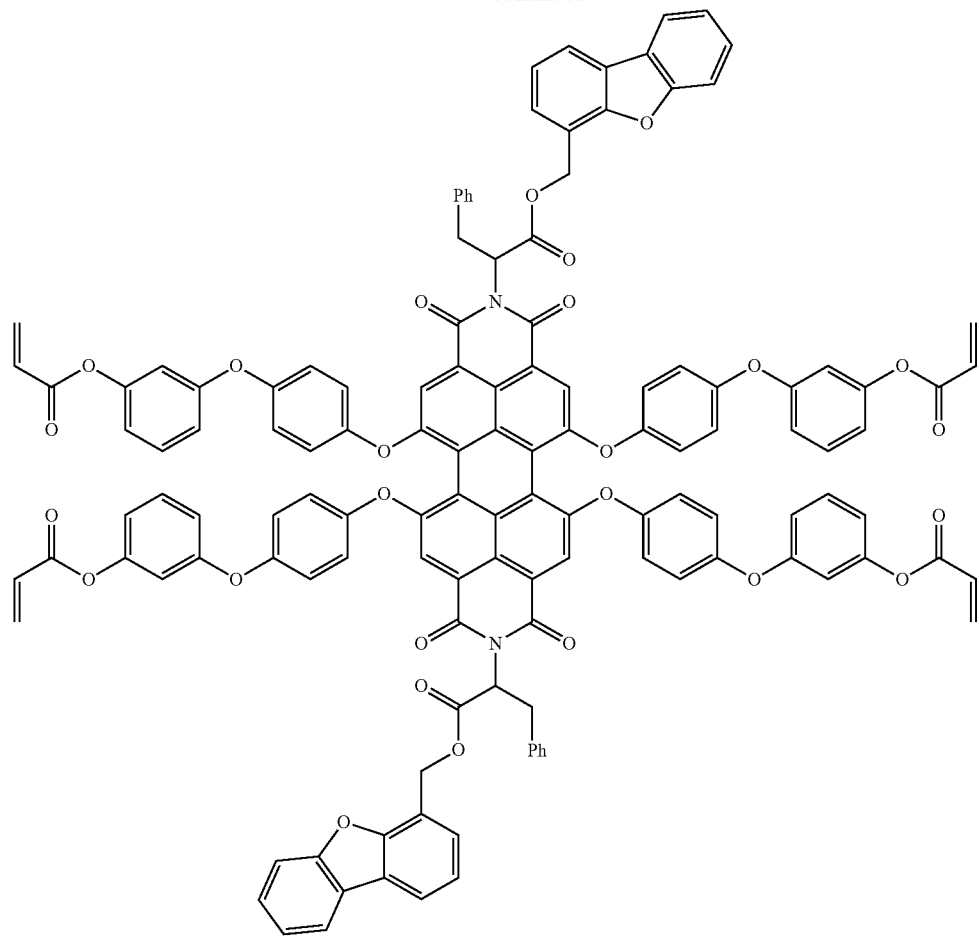

-continued
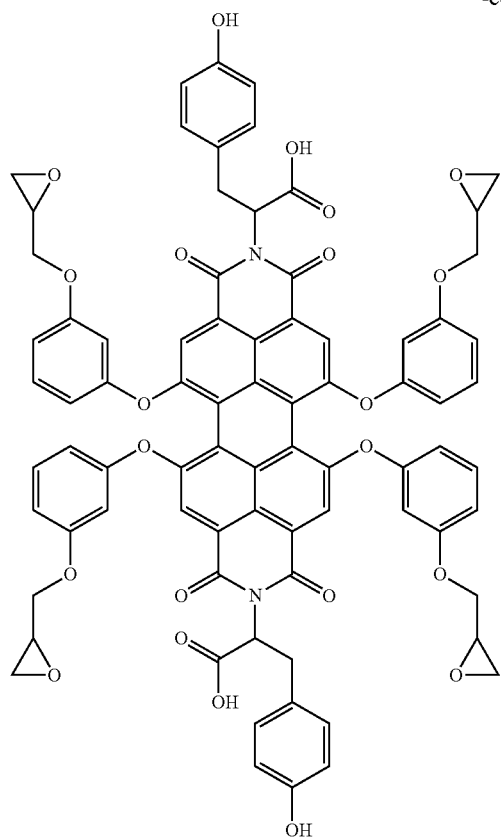
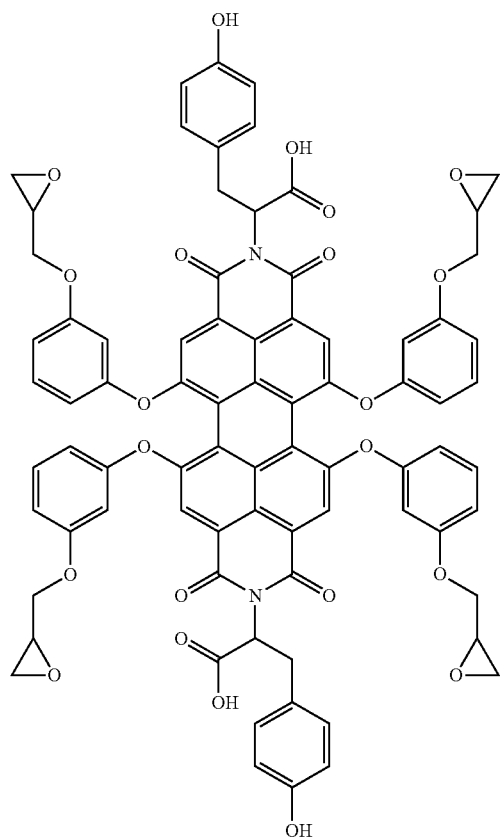

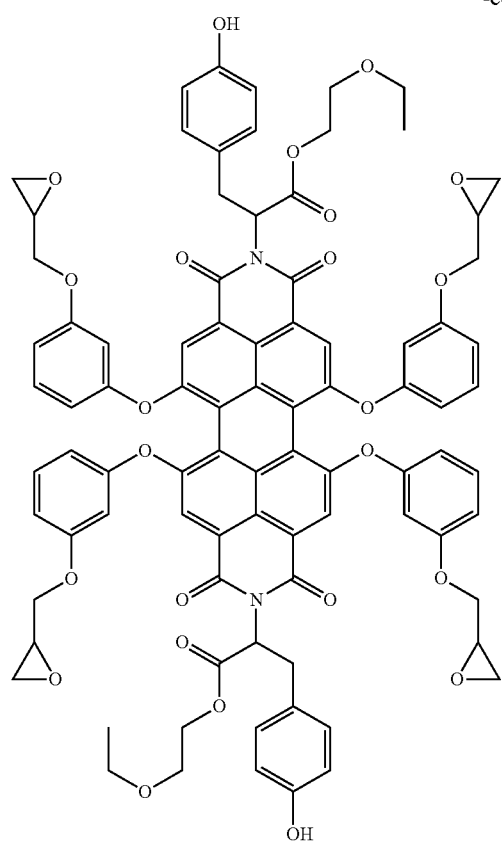
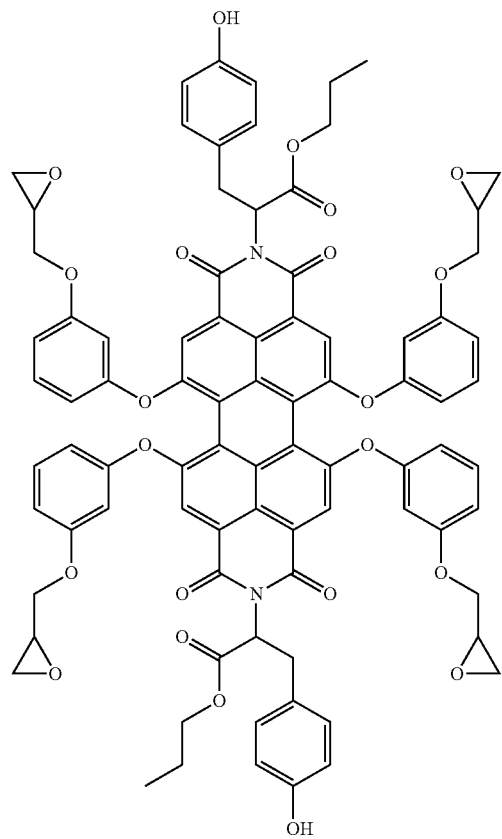

-continued
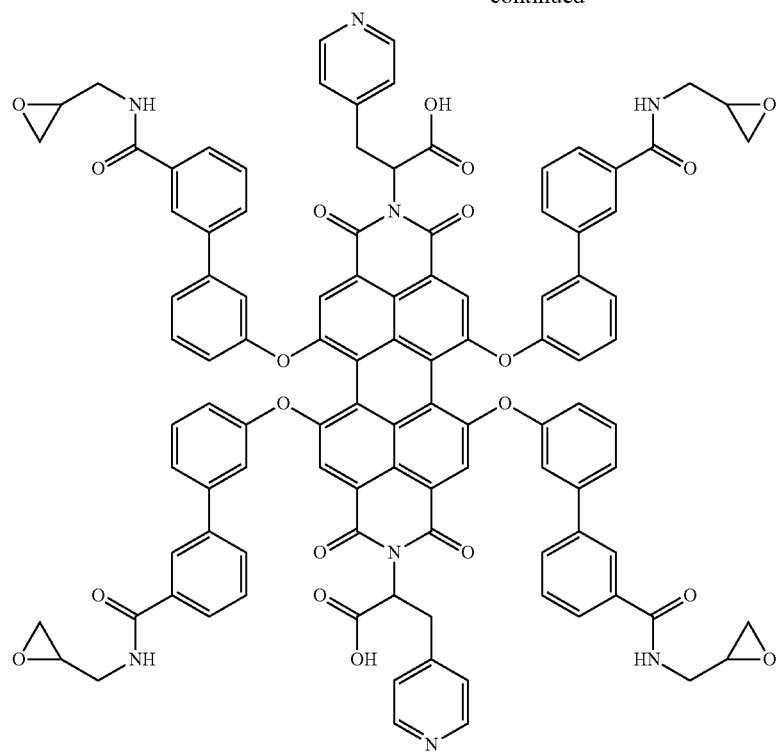
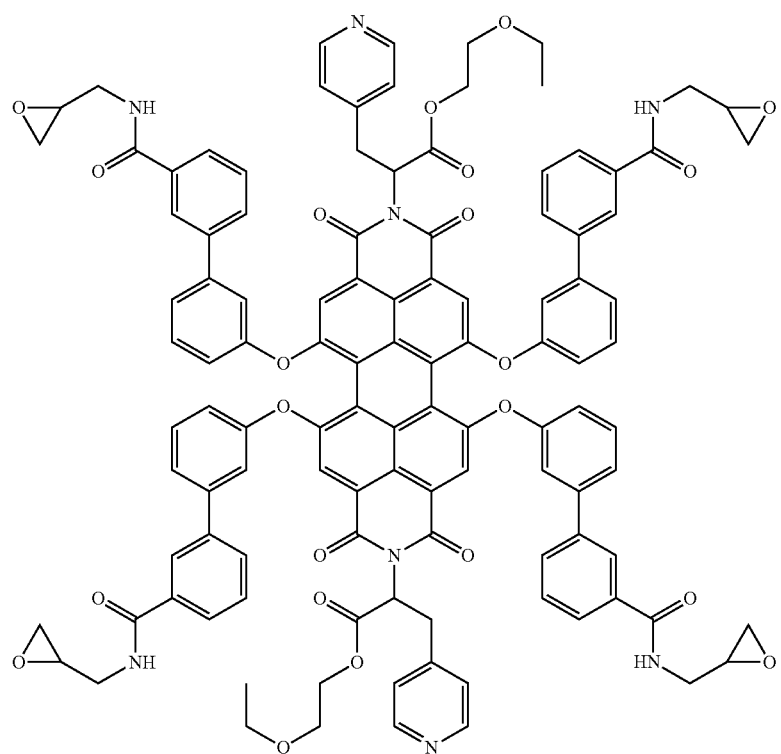

-continued
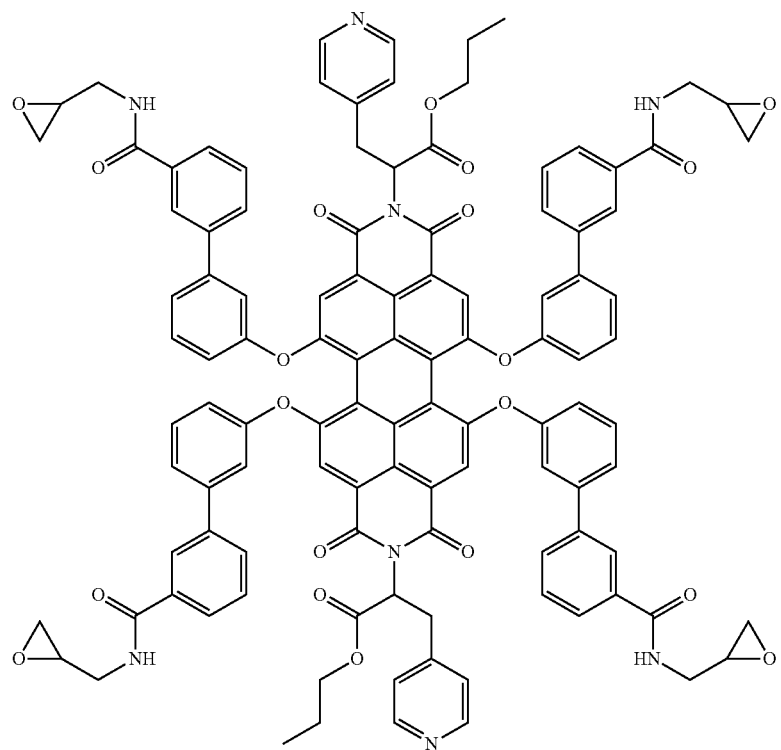
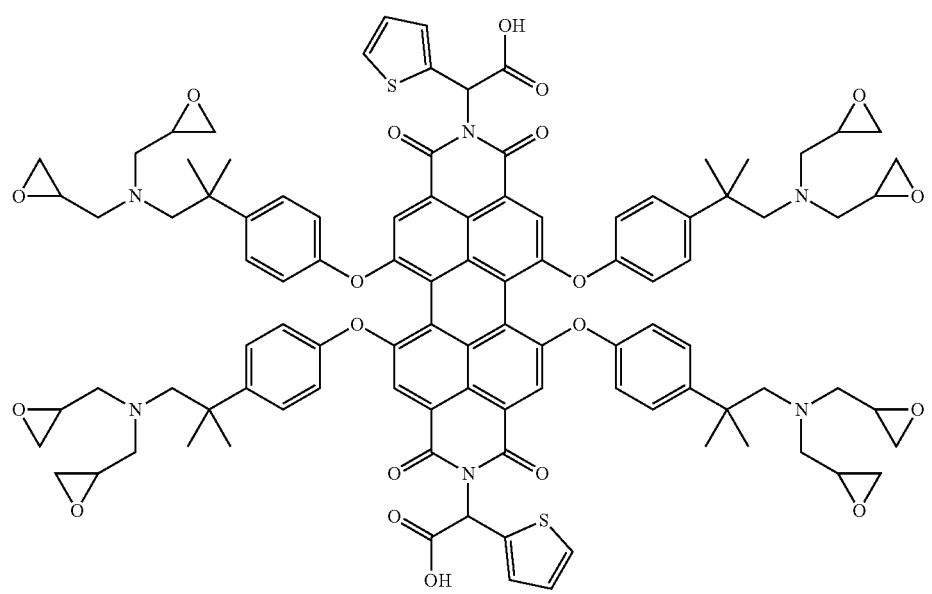

-continued
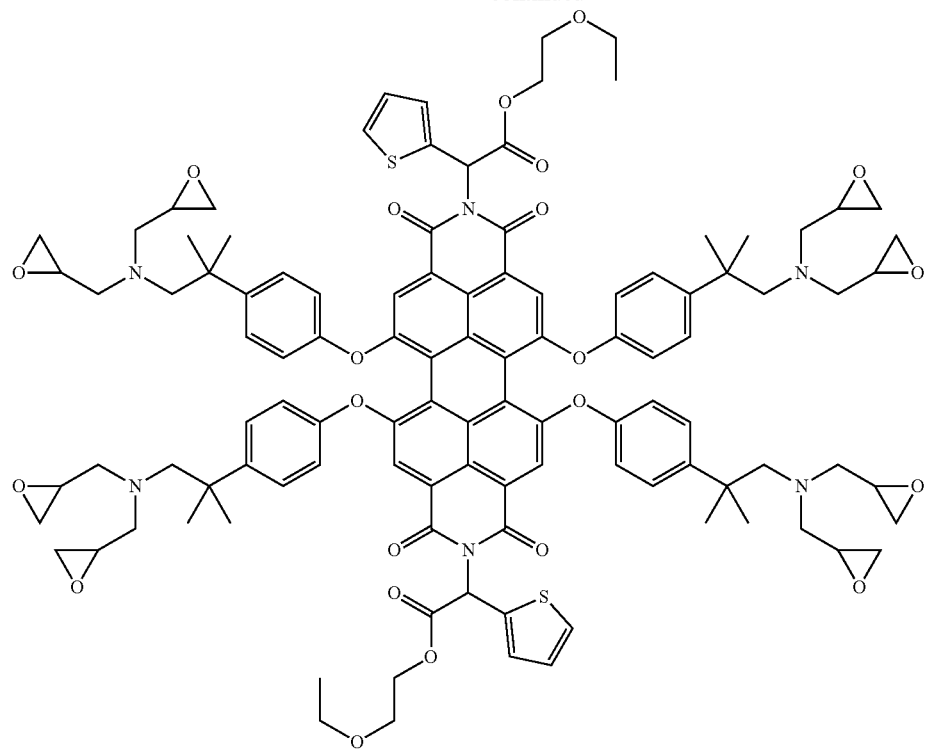
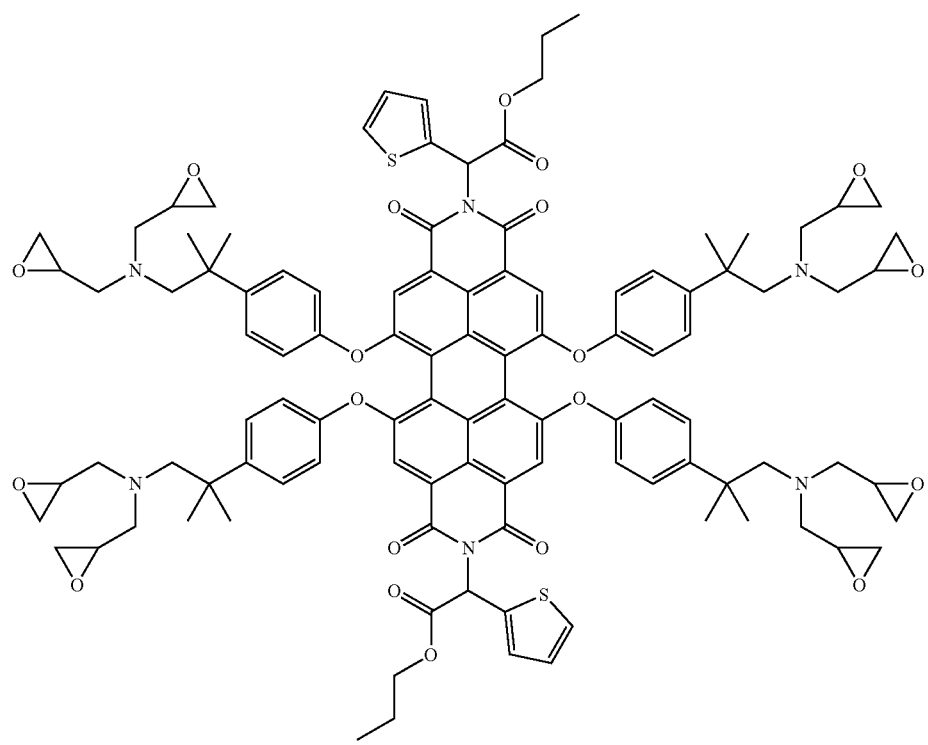

-continued
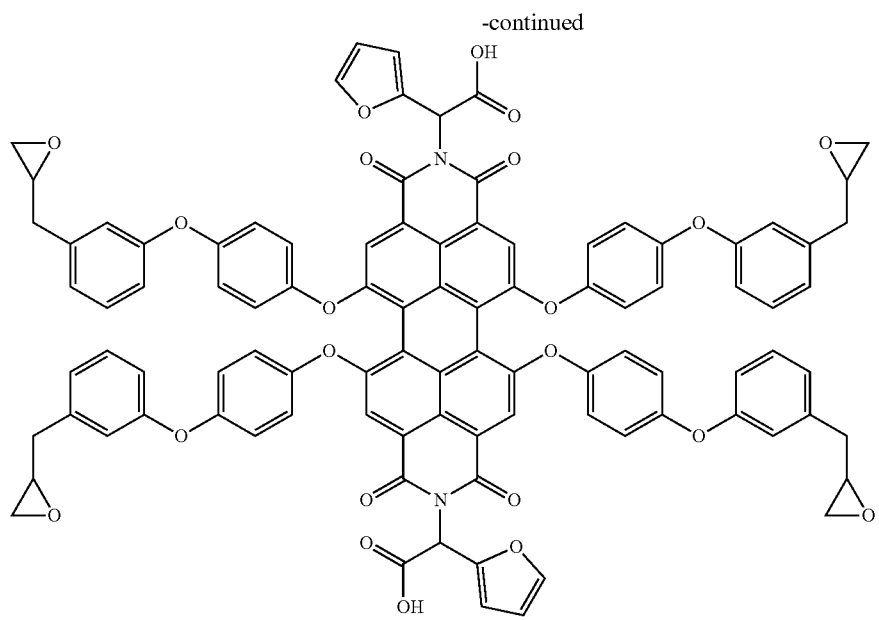
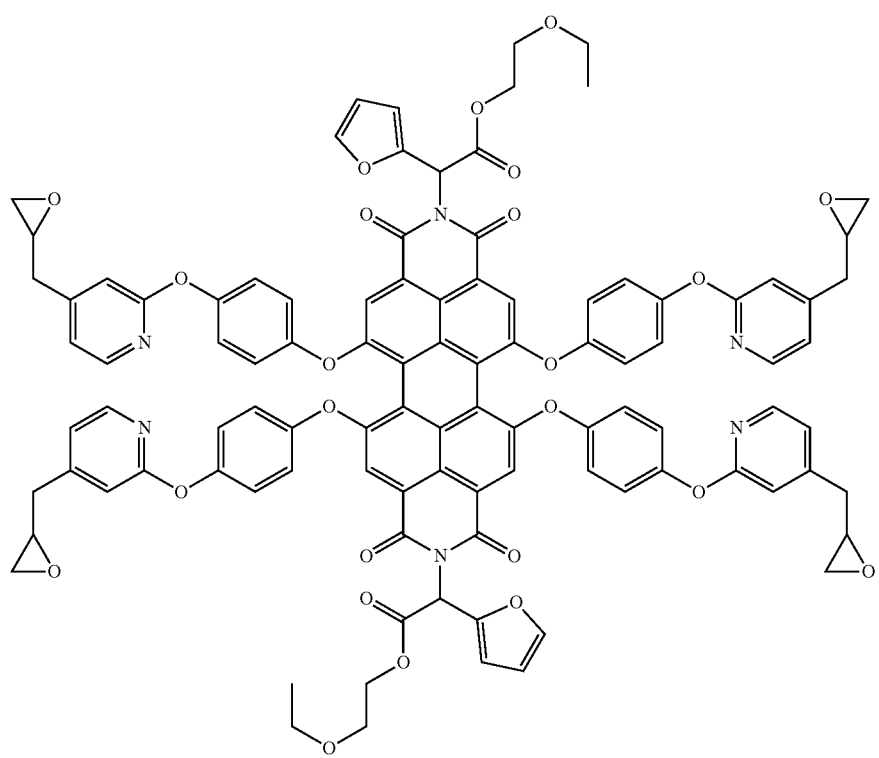

-continued
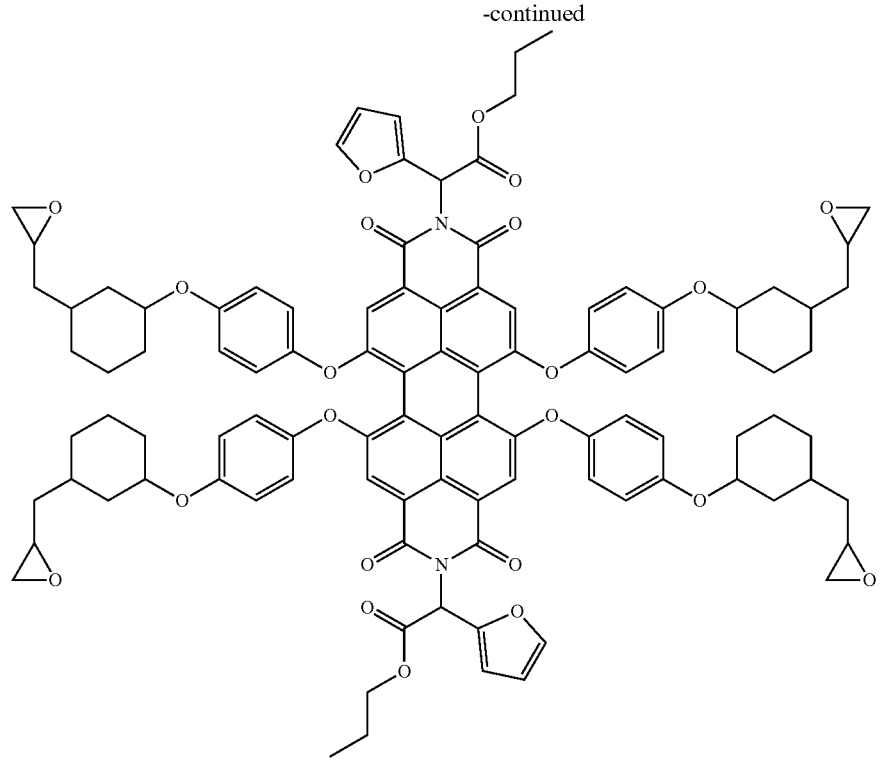
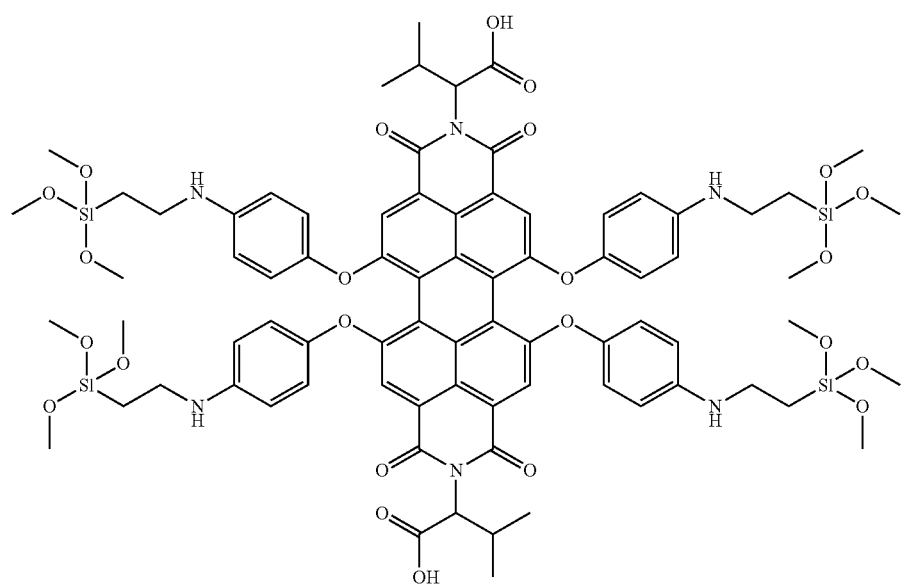

-continued
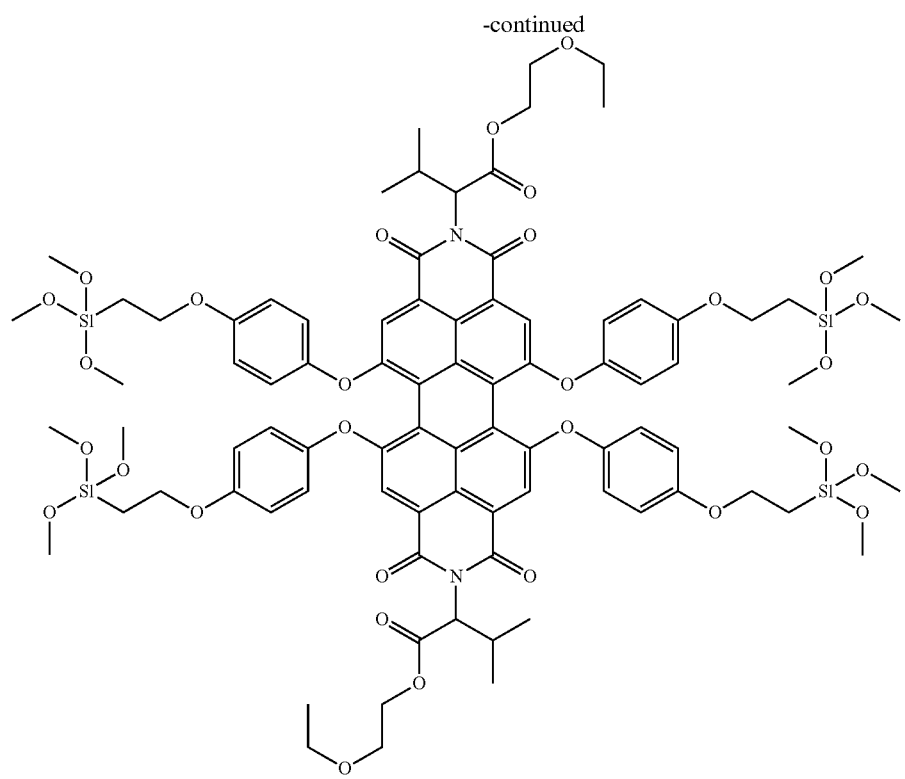
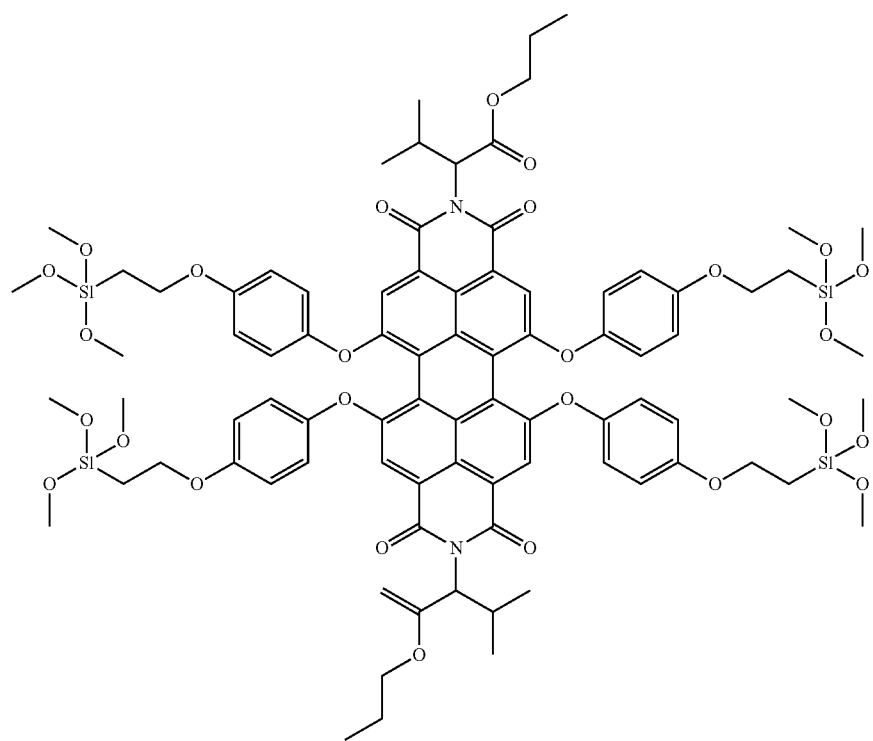

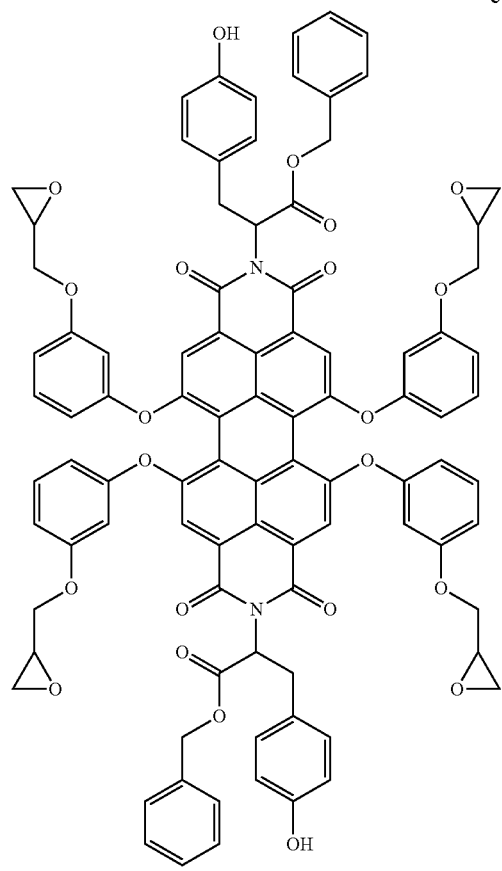
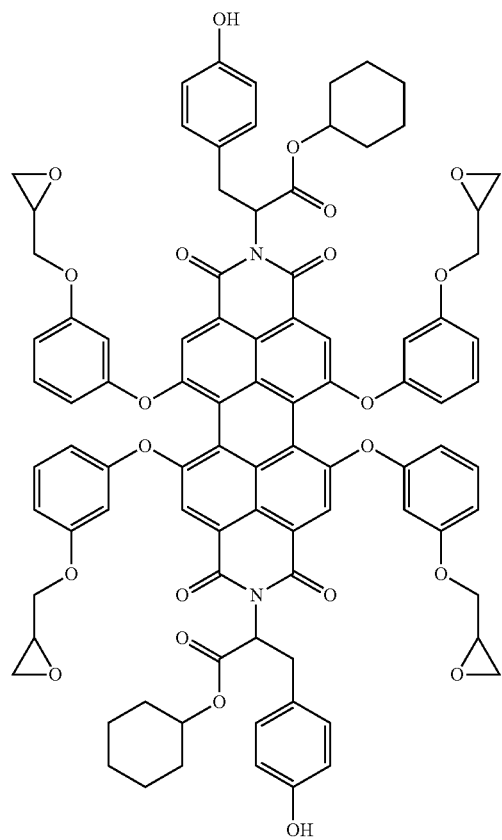

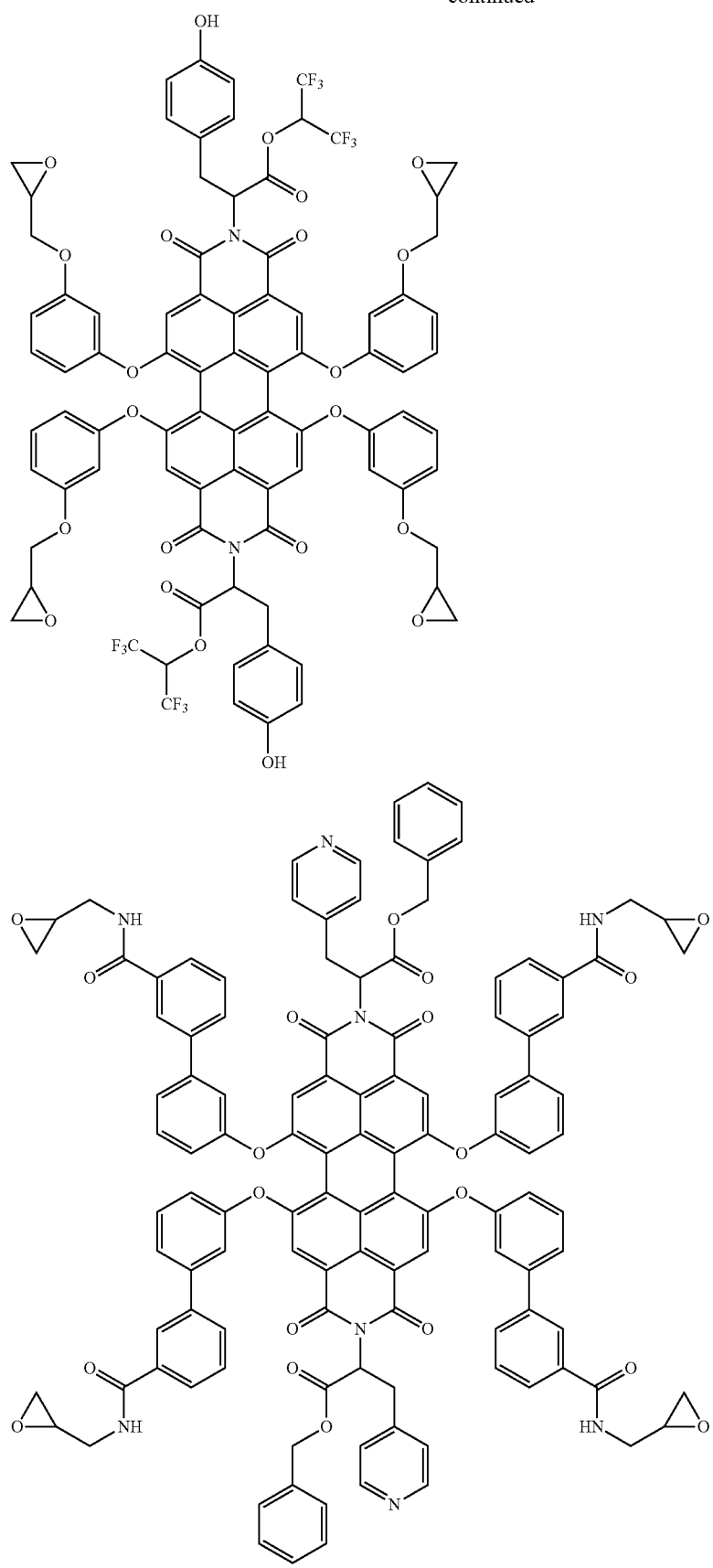

-continued
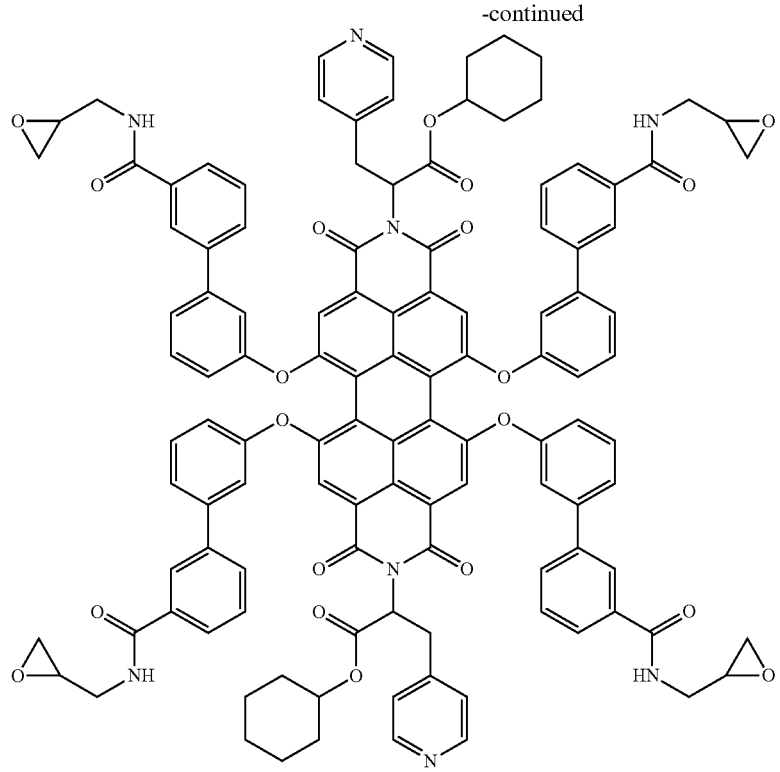
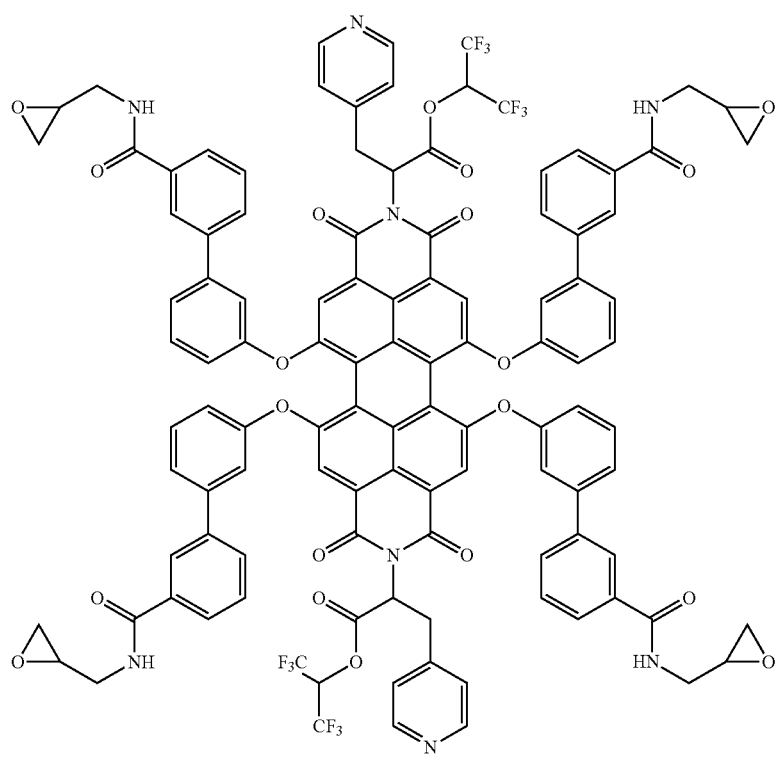

-continued
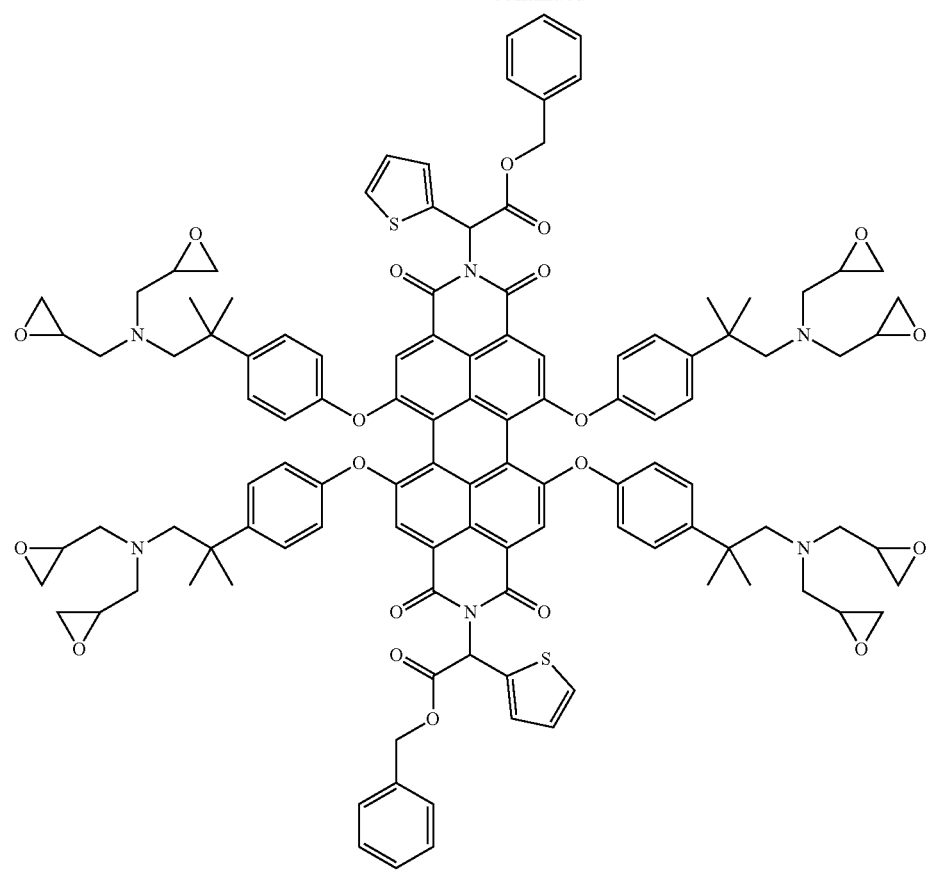
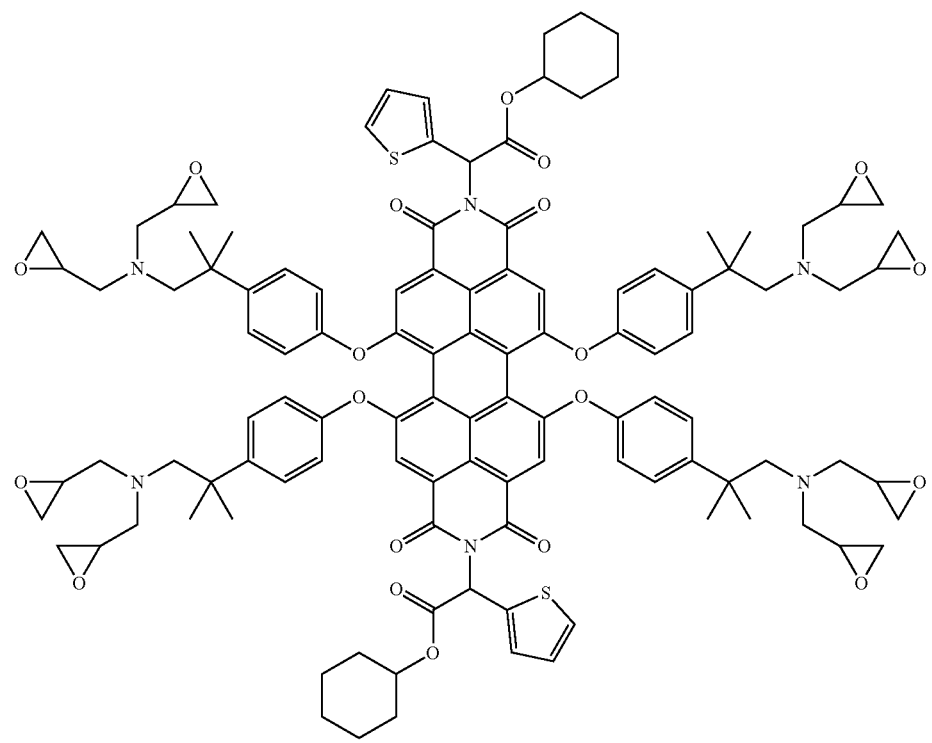

-continued
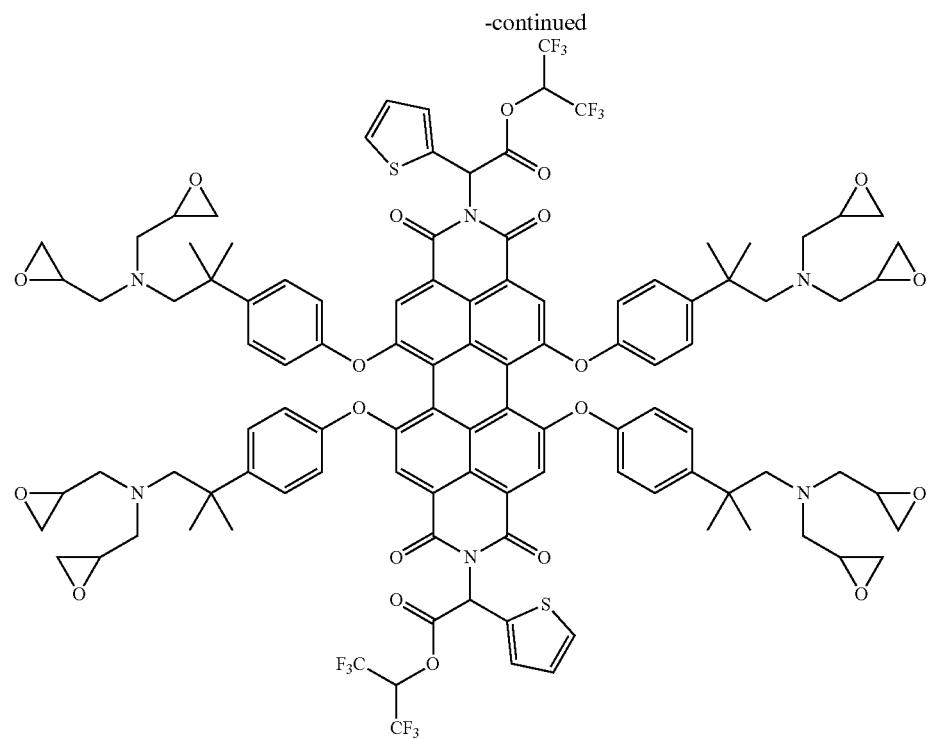
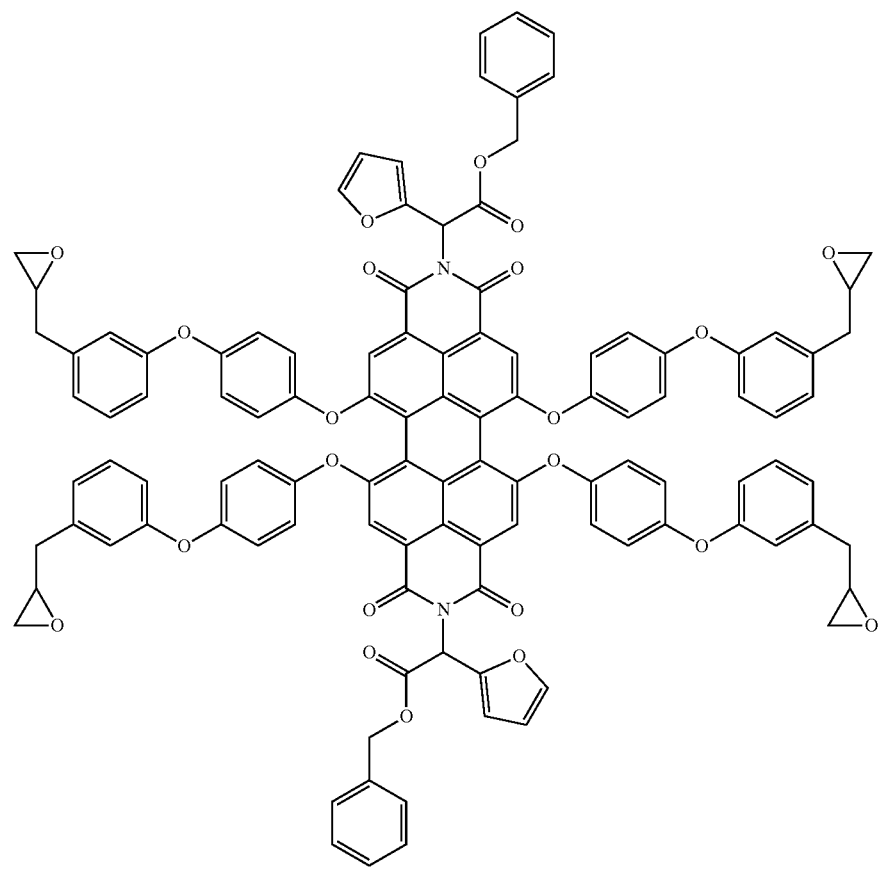

-continued
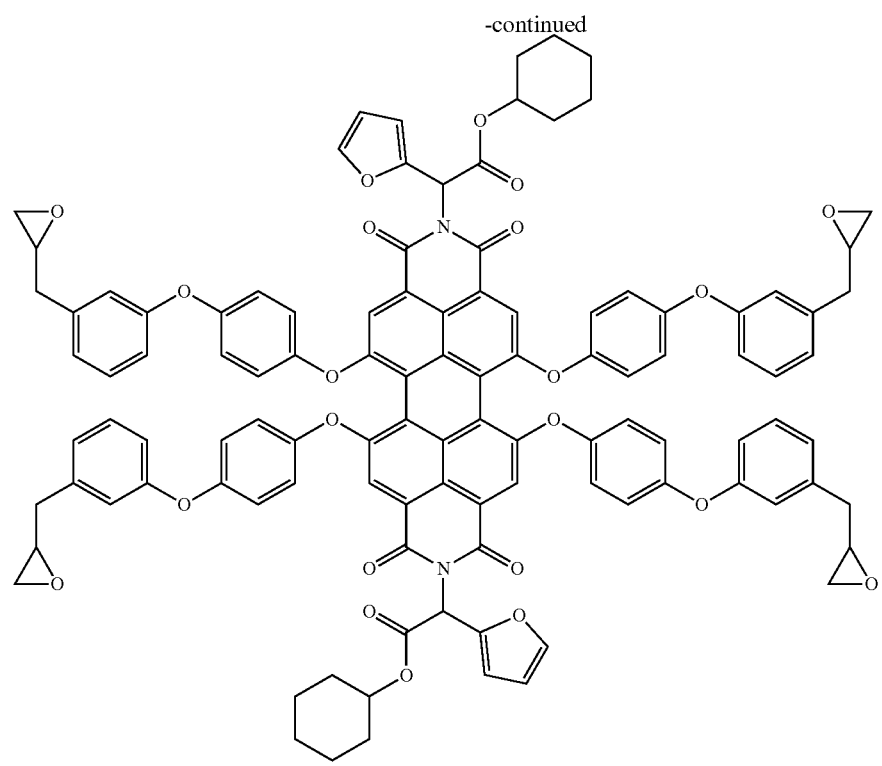
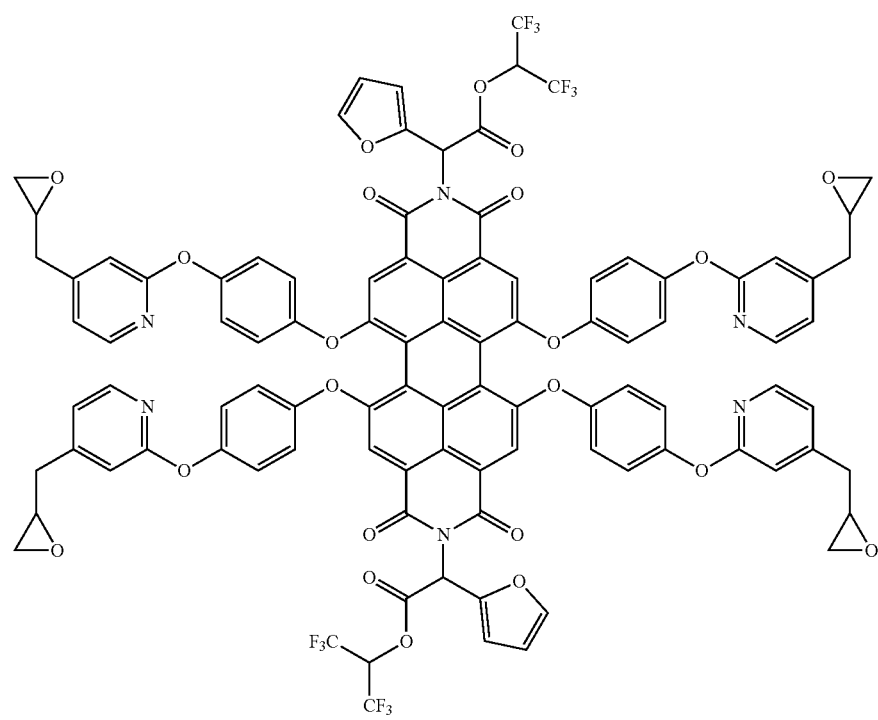

-continued
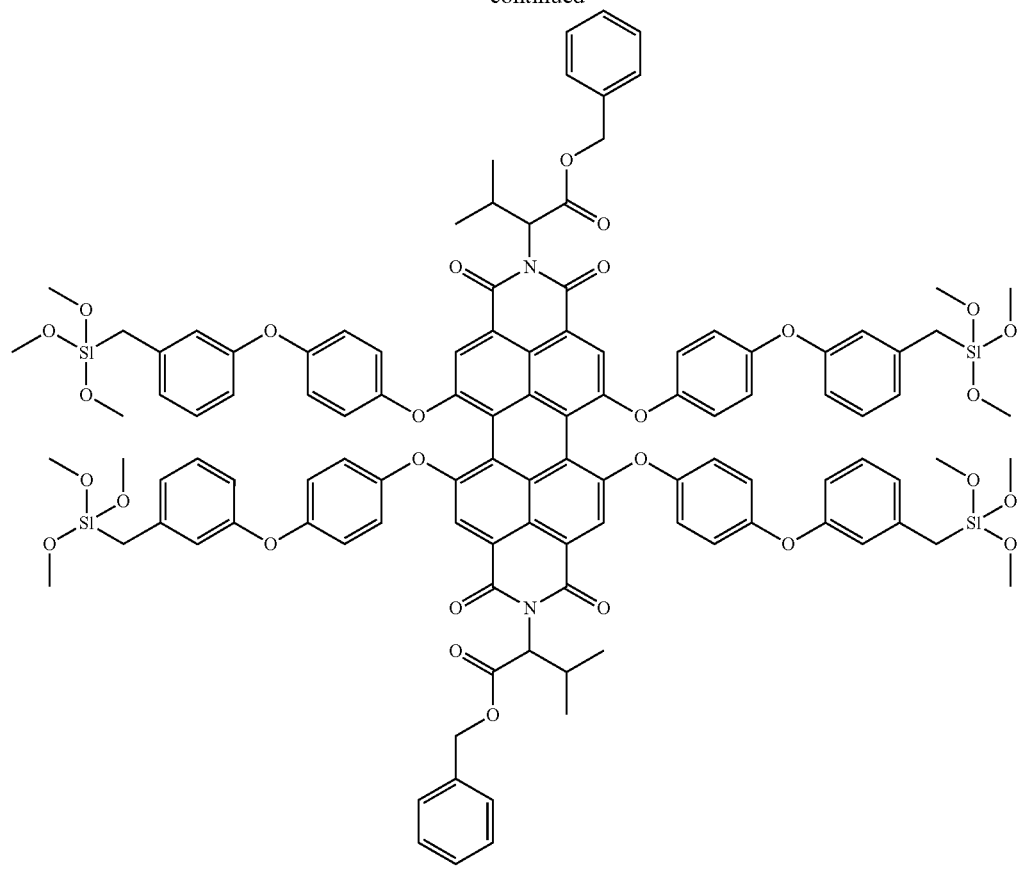
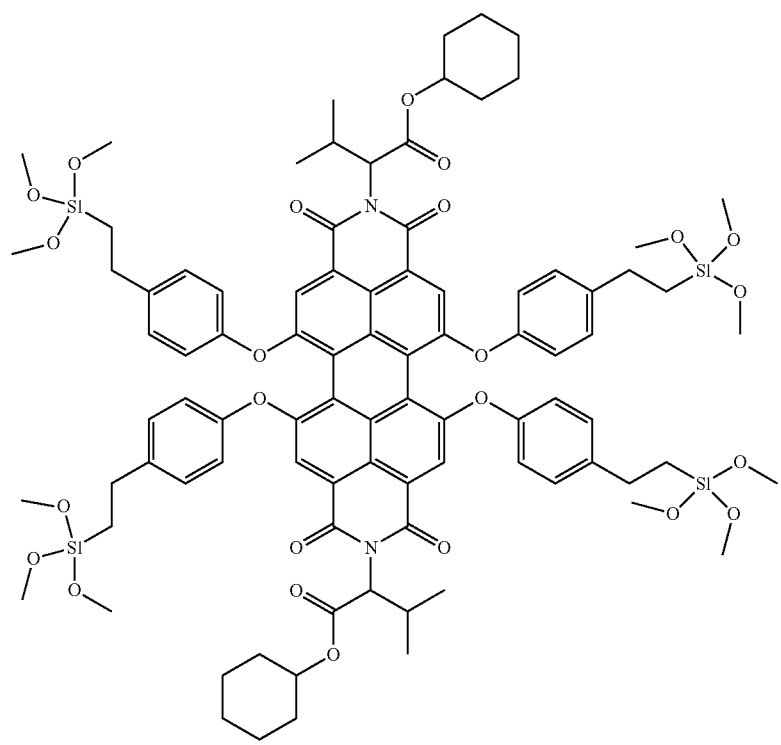

-continued
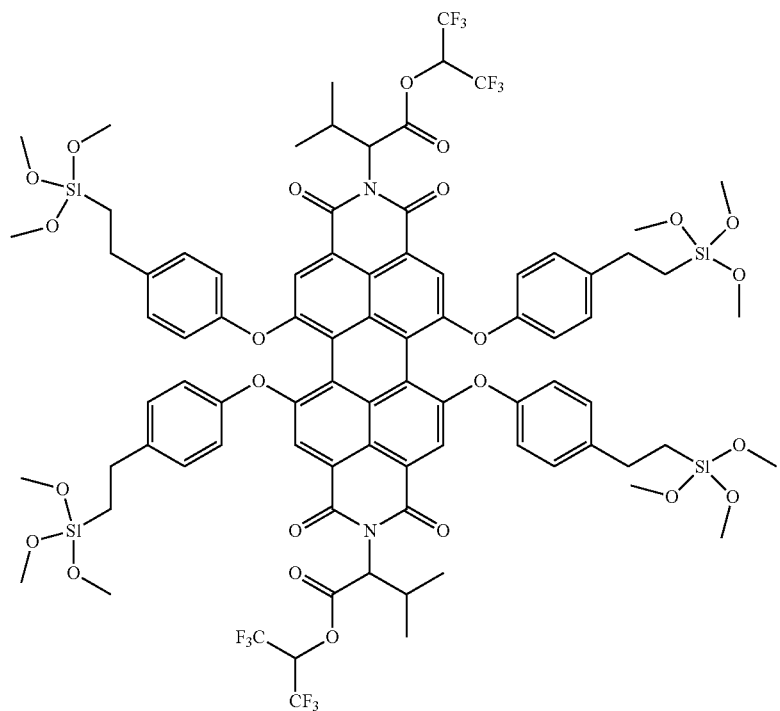
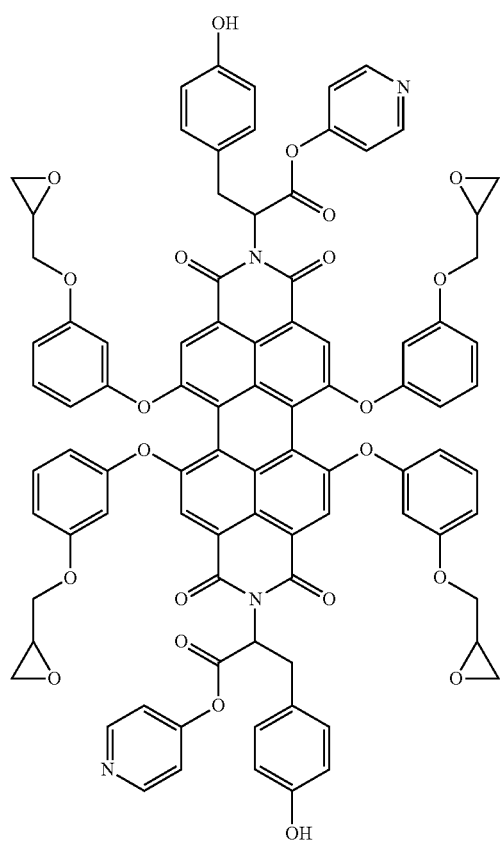

-continued
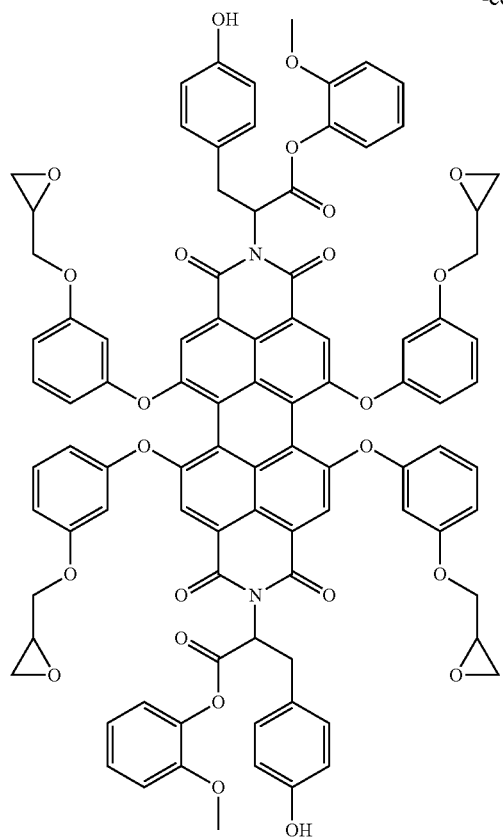

-continued
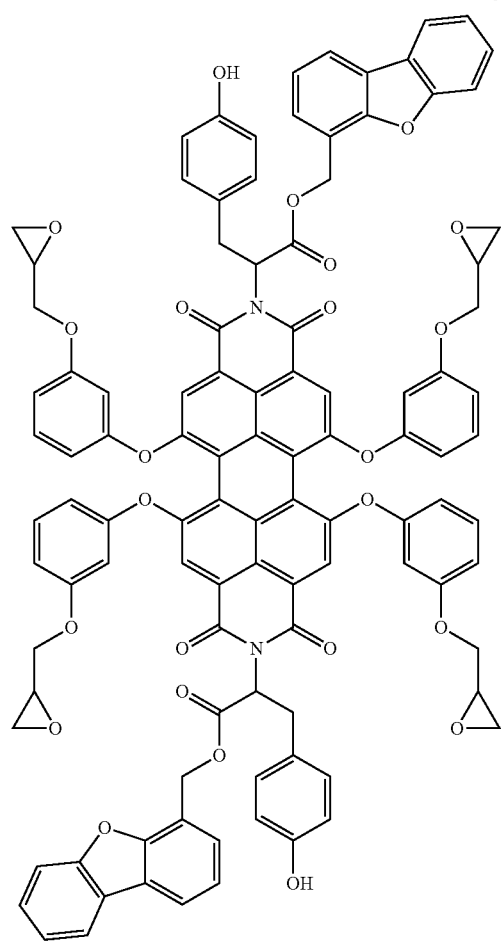
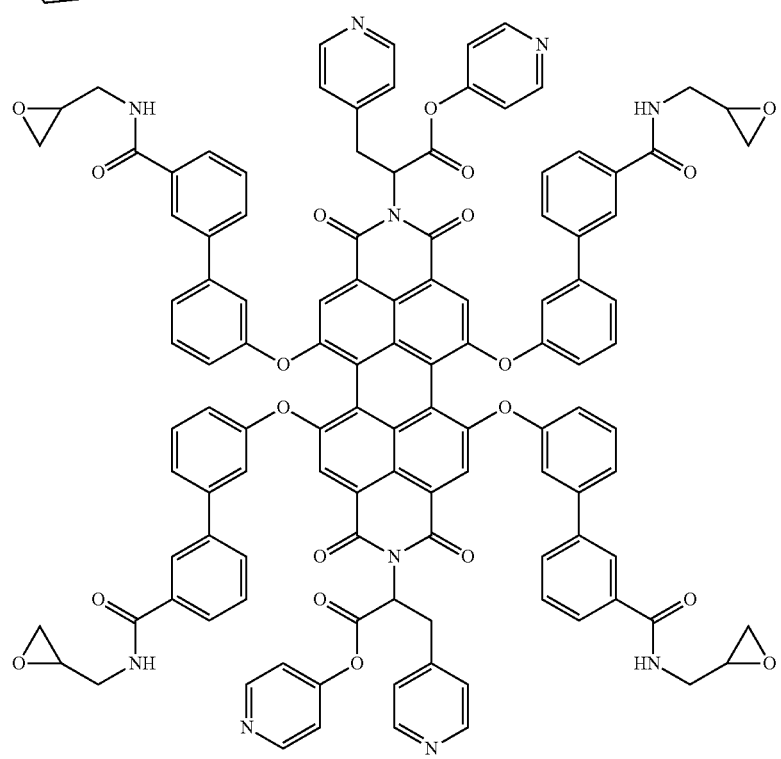

-continued
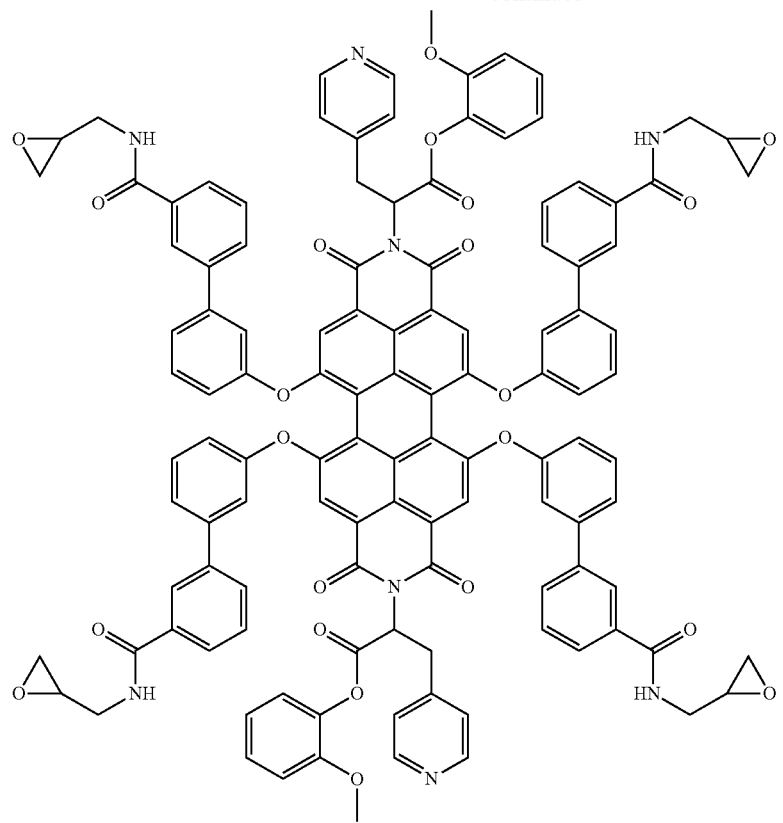

-continued
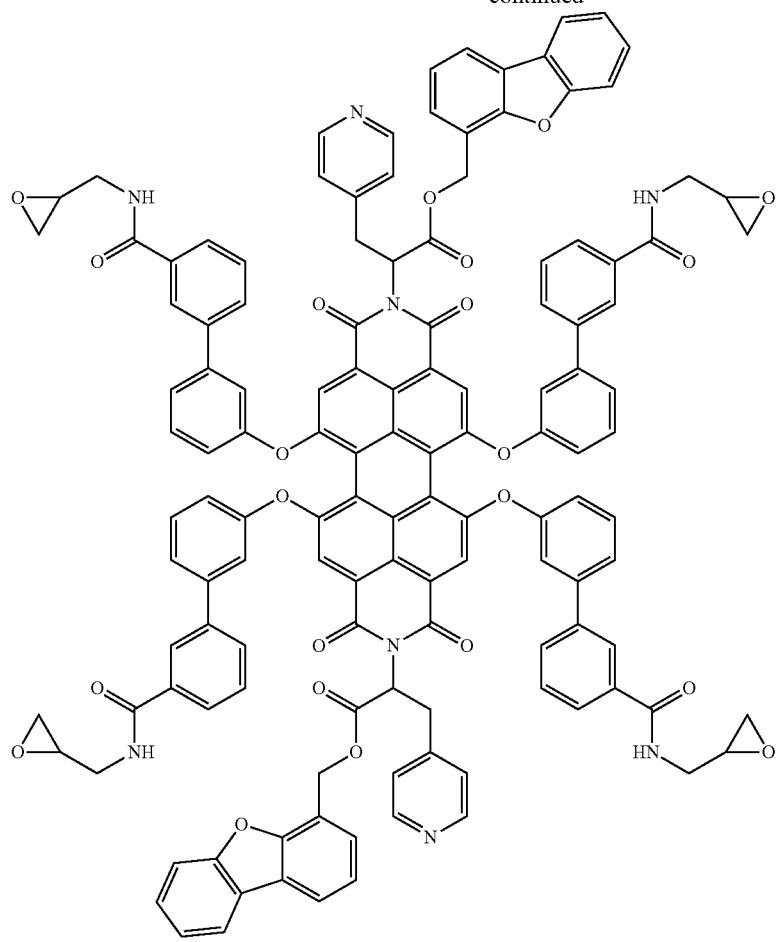
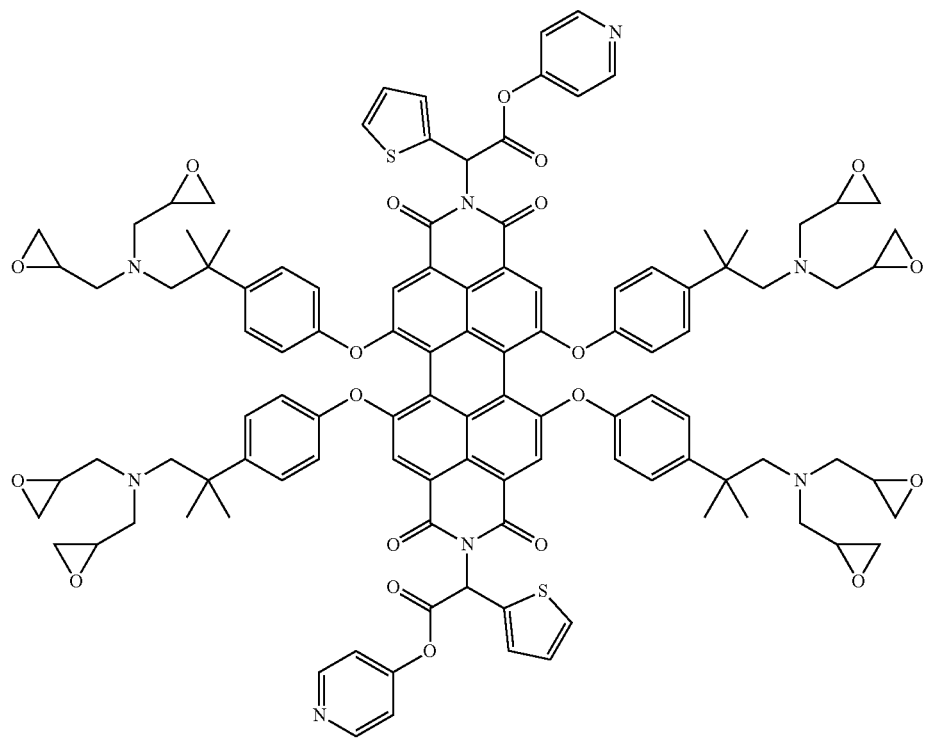

-continued
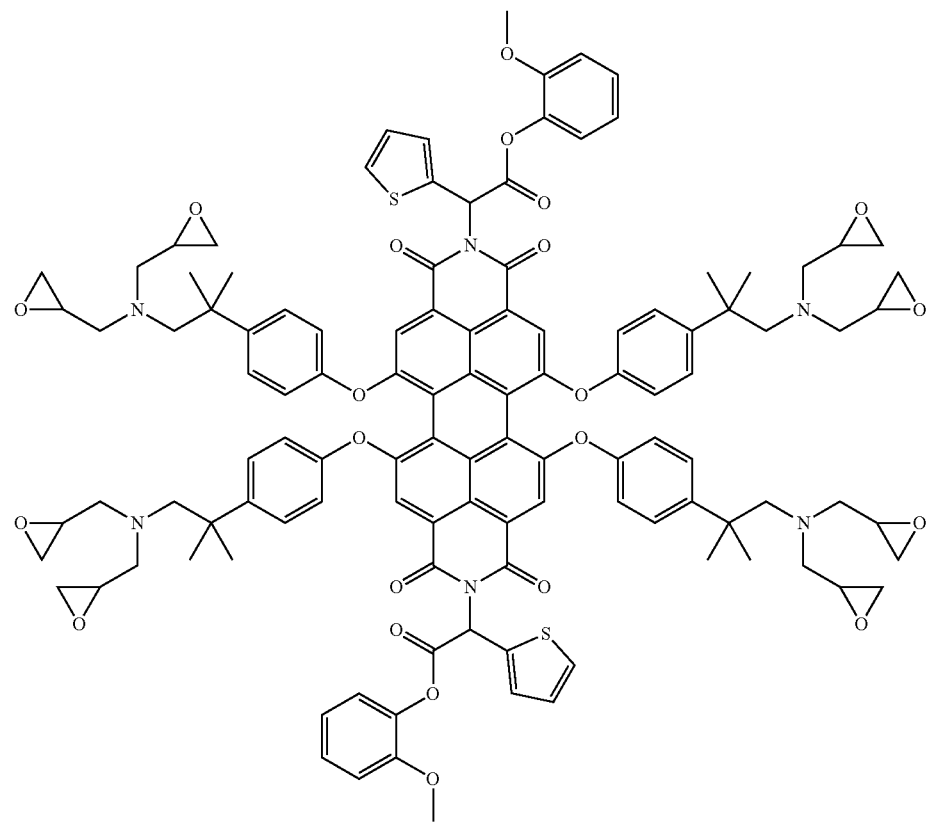

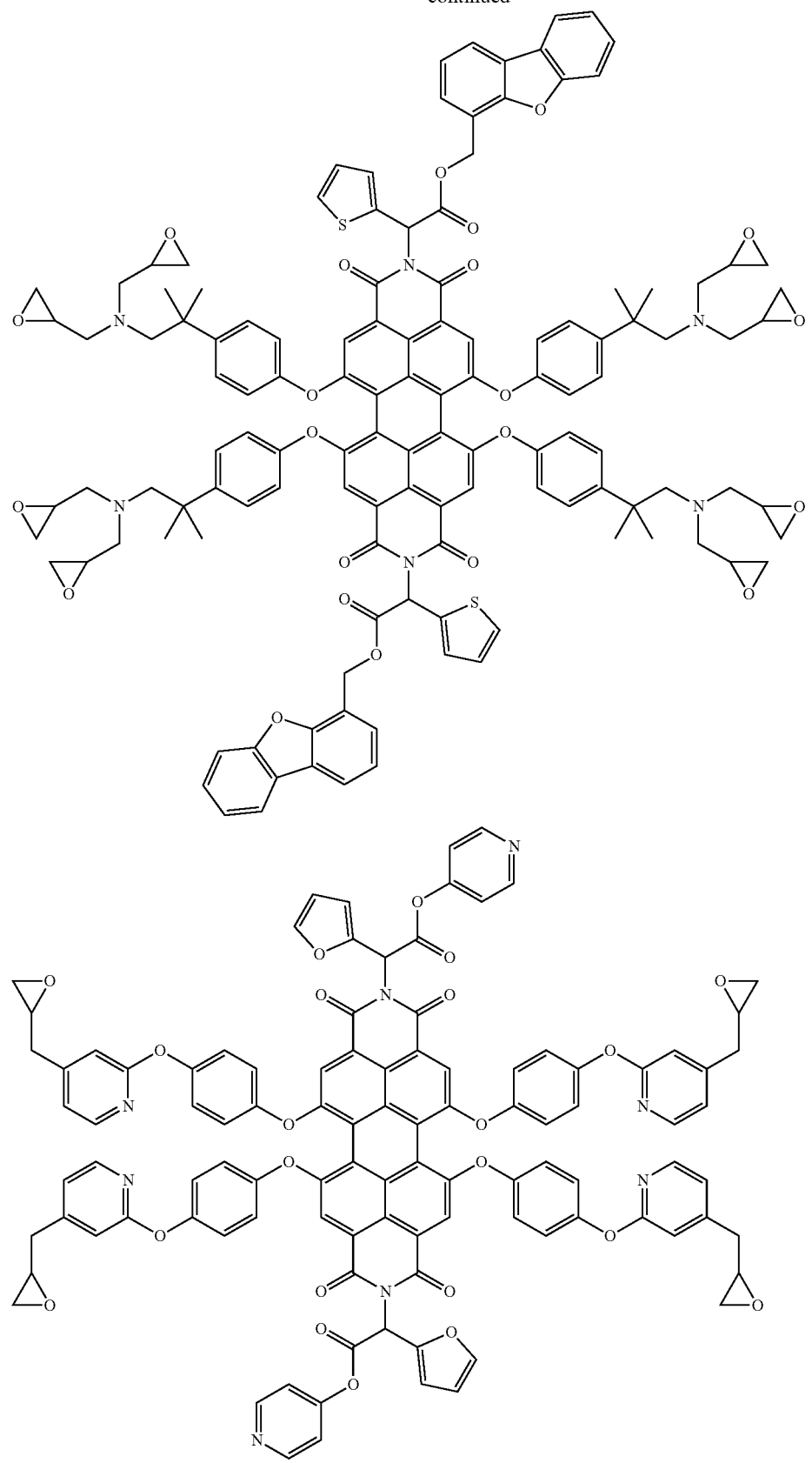

-continued
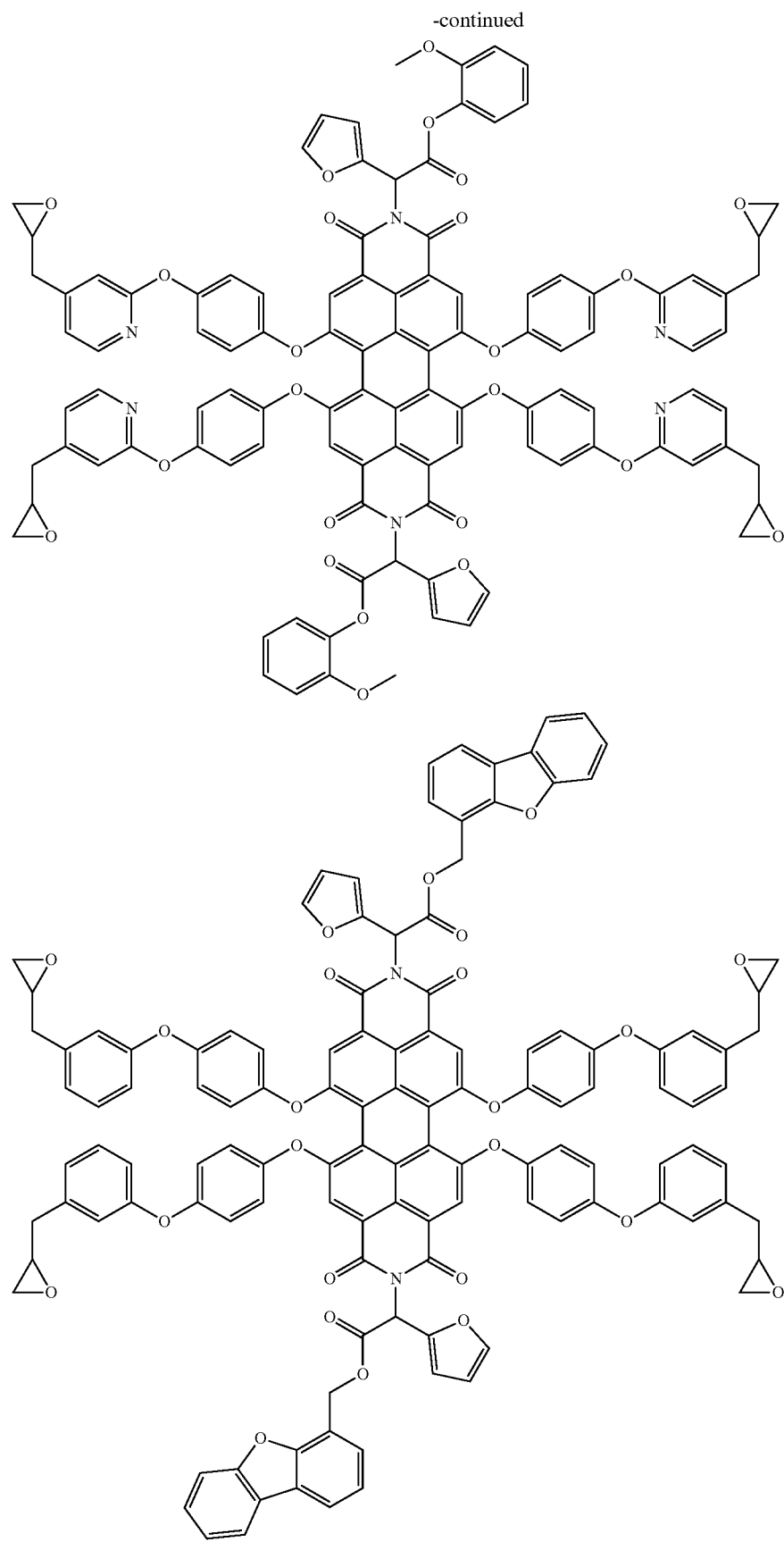

-continued
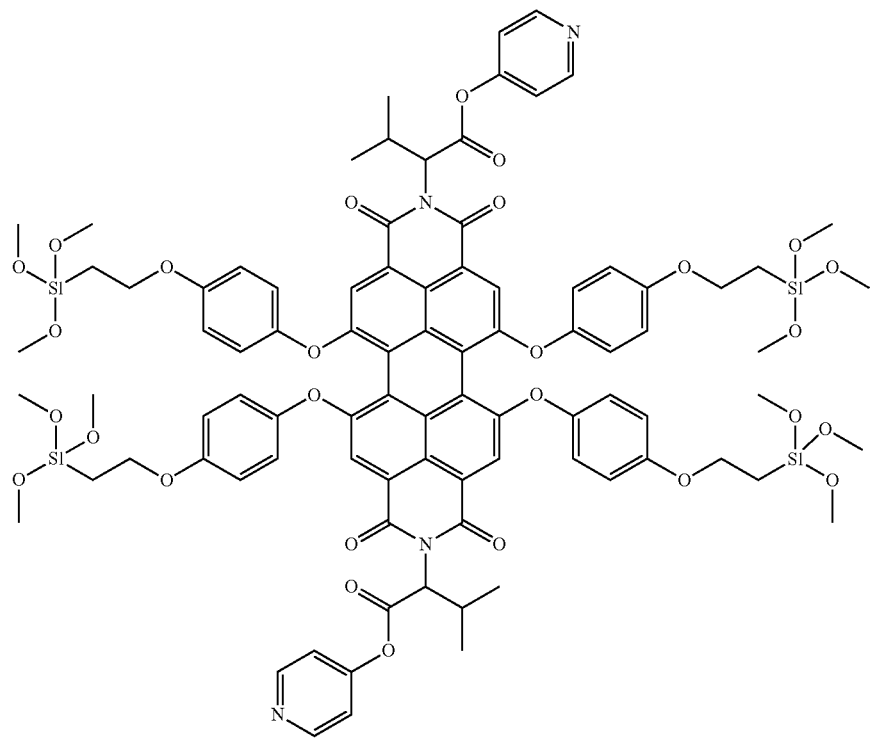
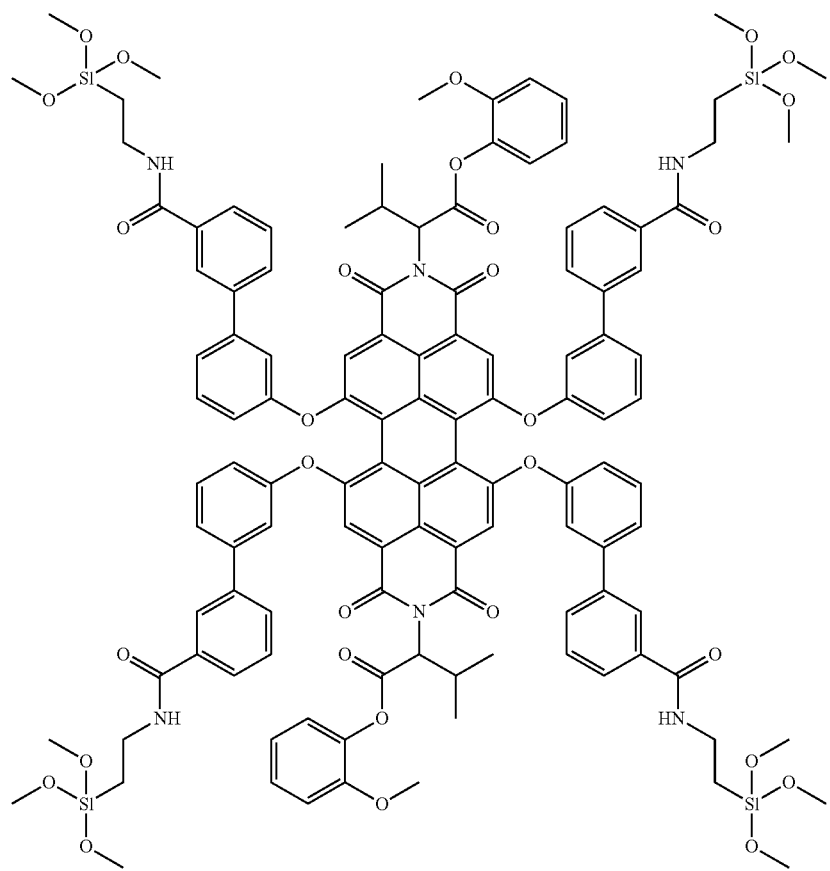

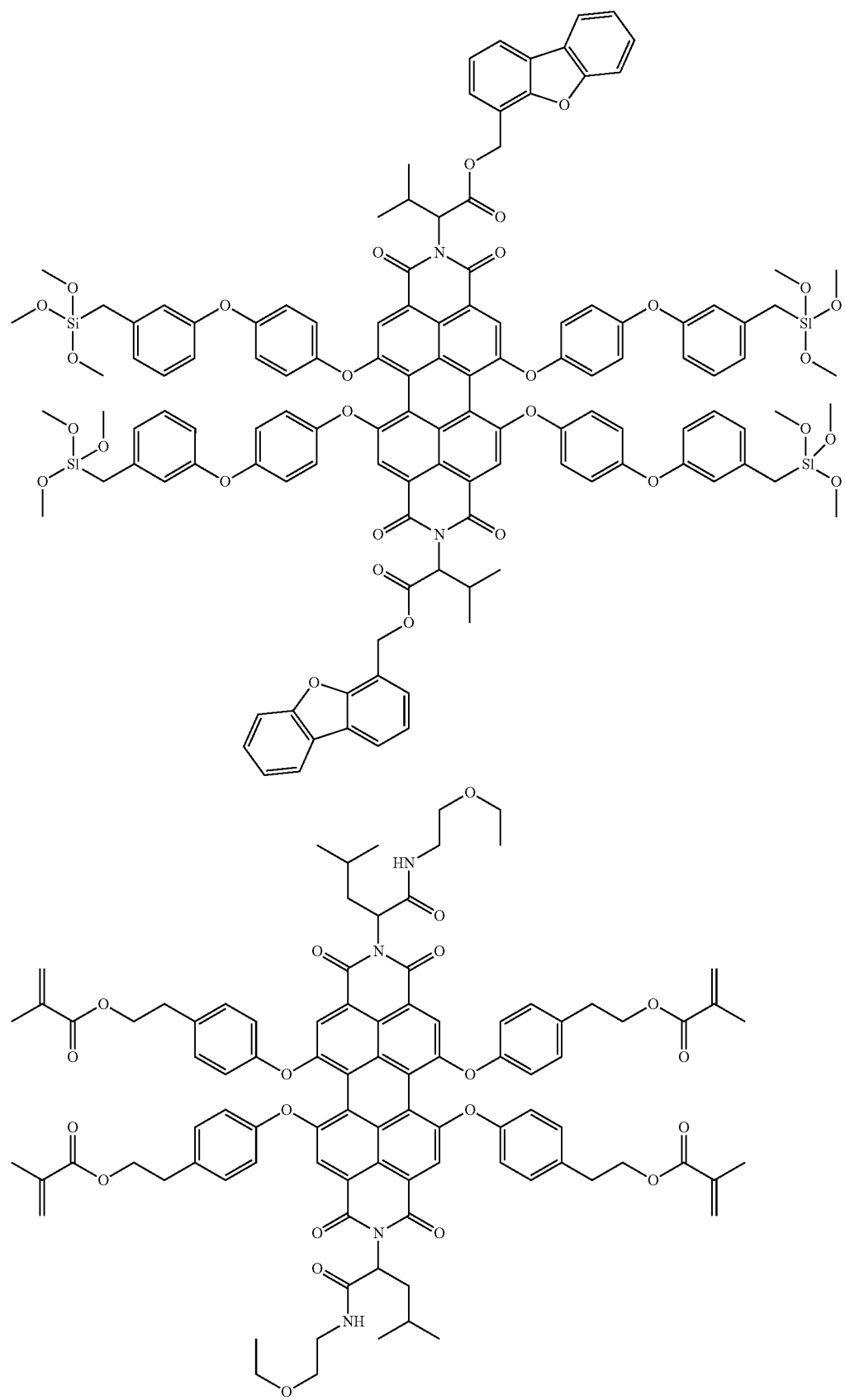

-continued
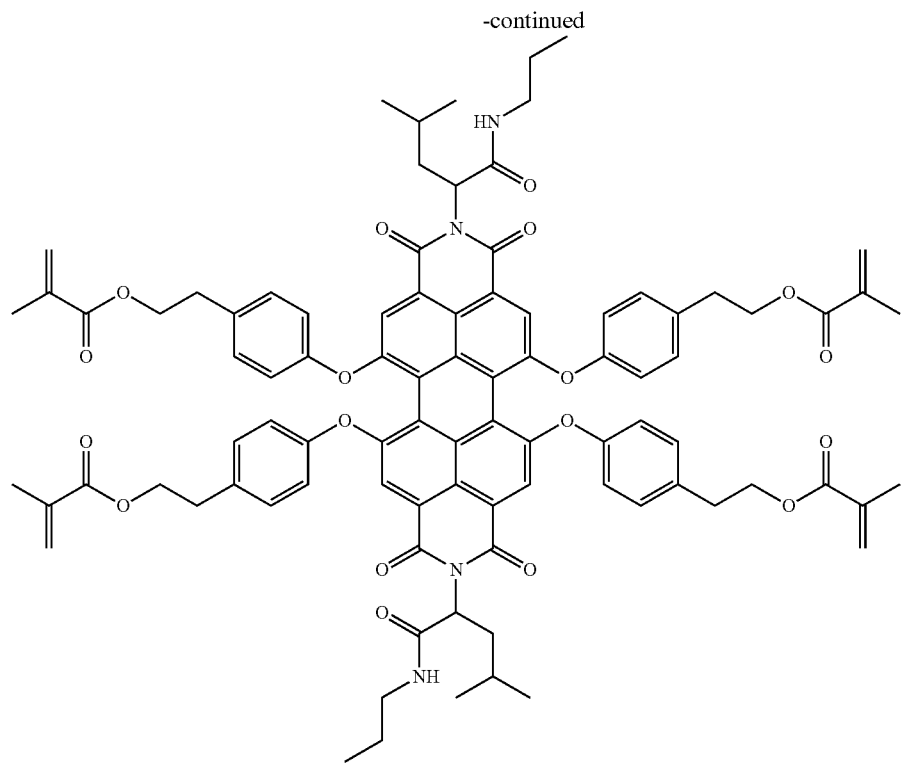
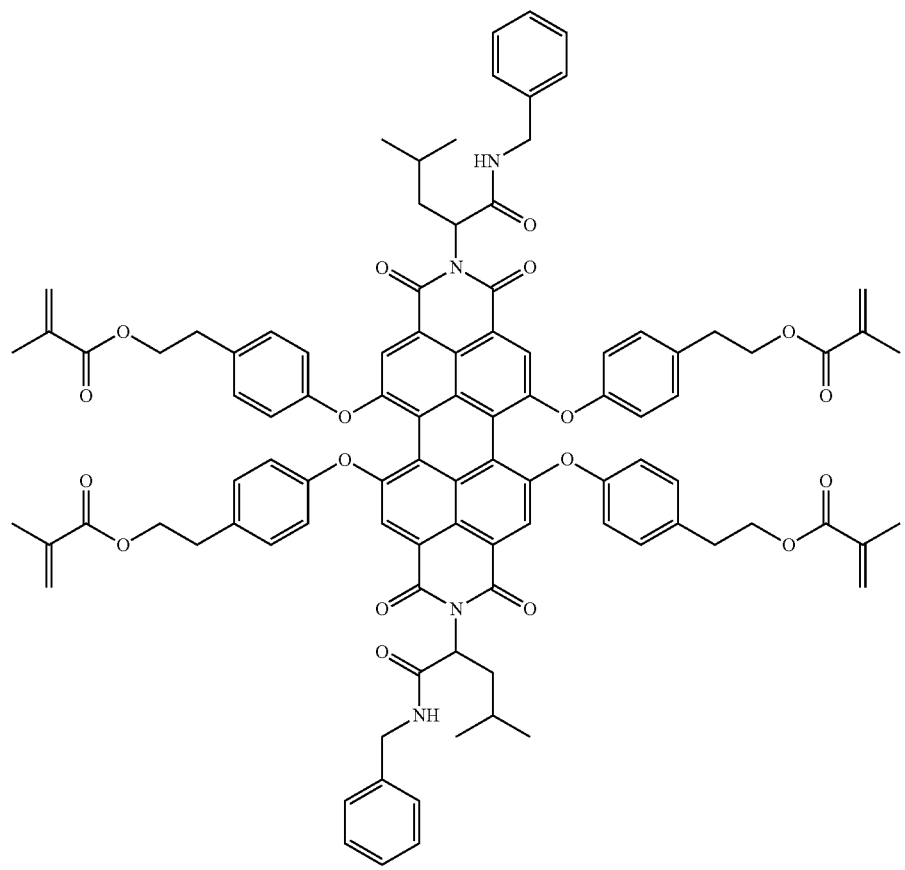

119 120
-continued
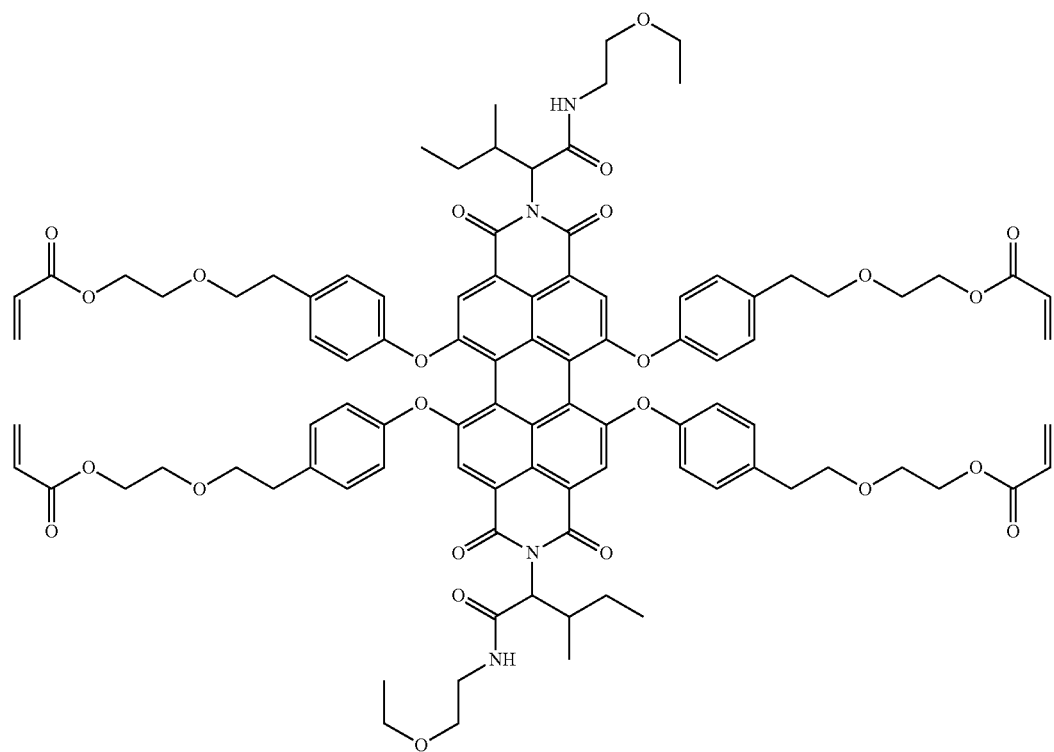
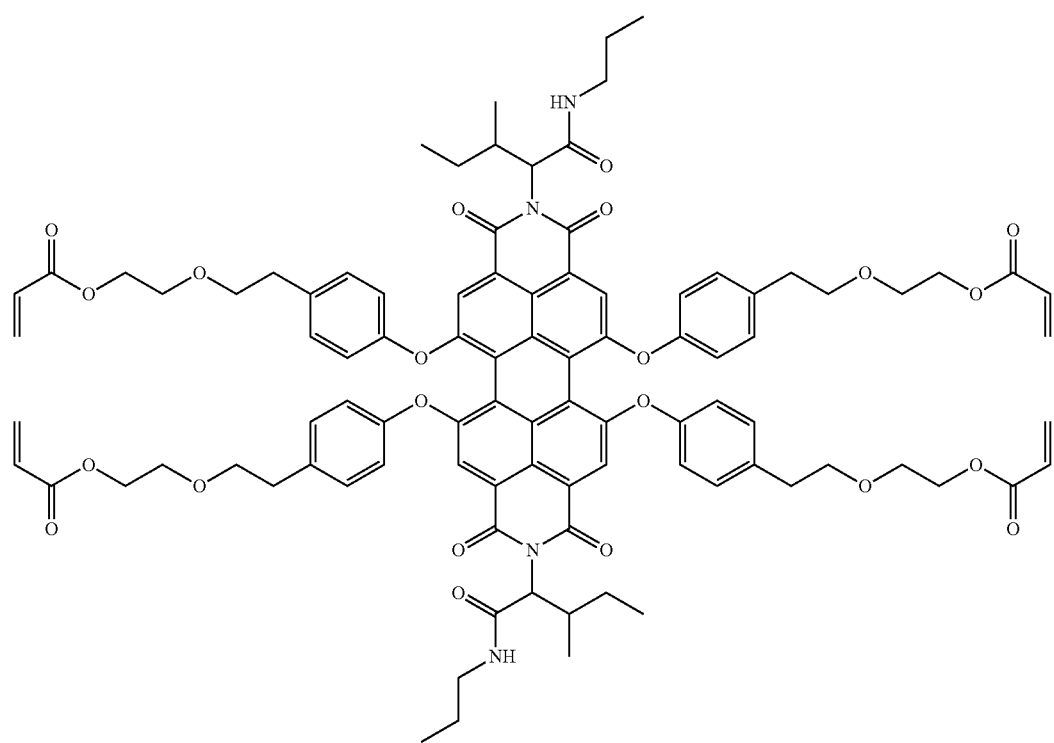

-continued
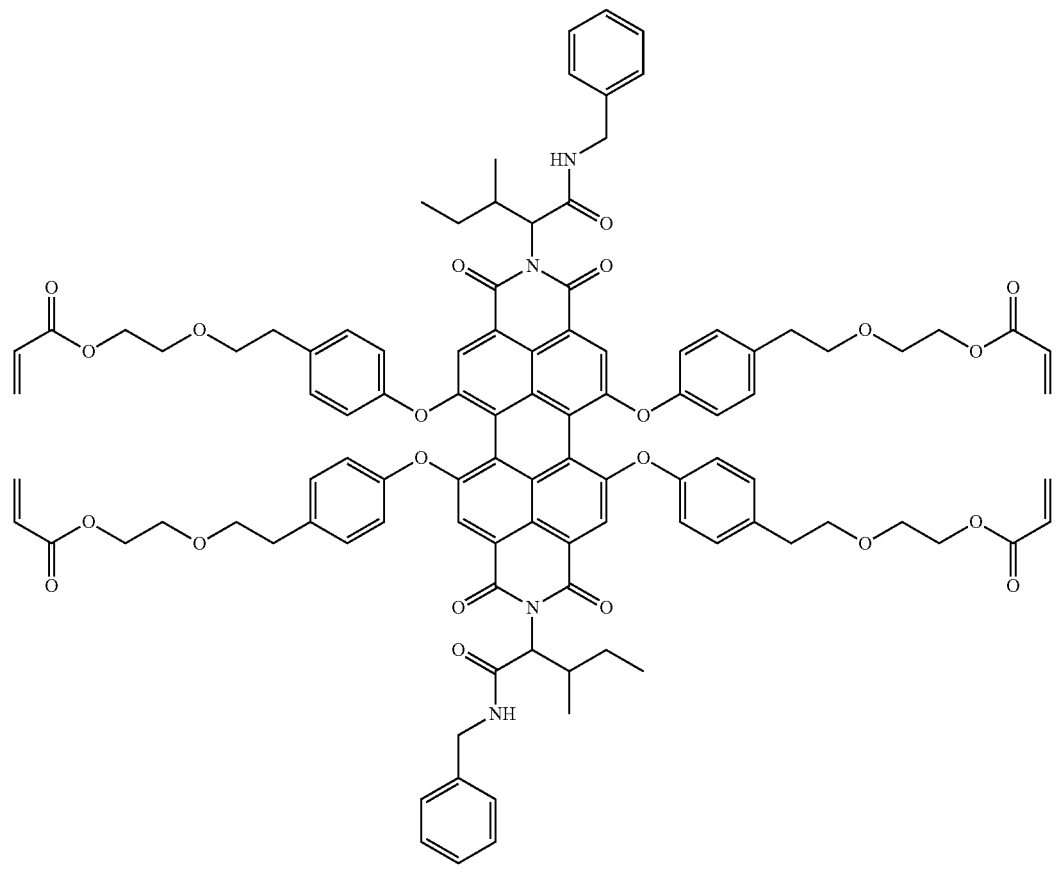
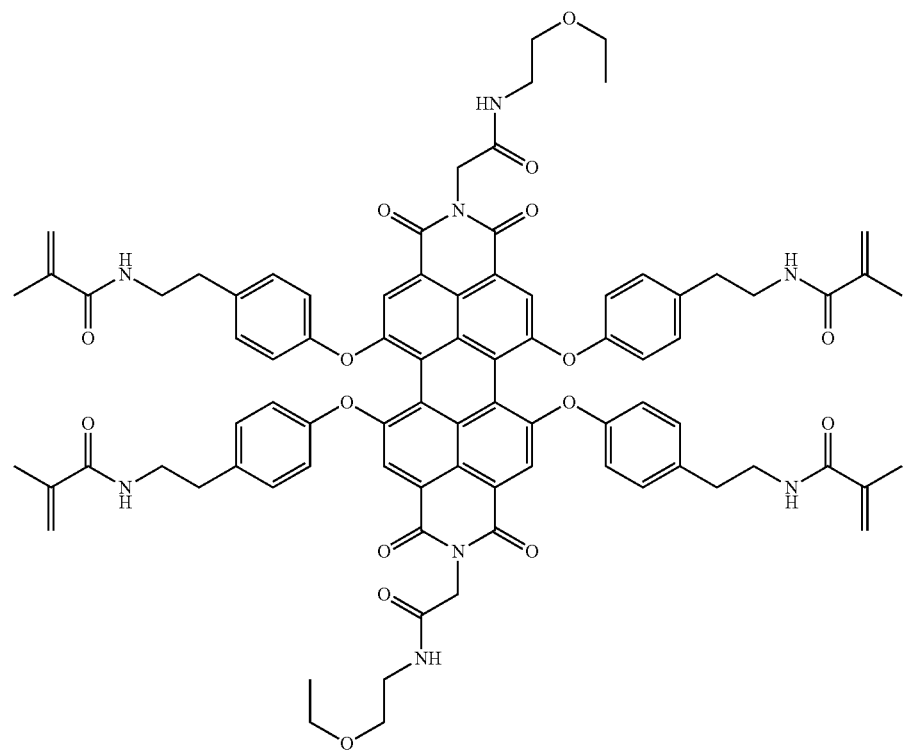

-continued
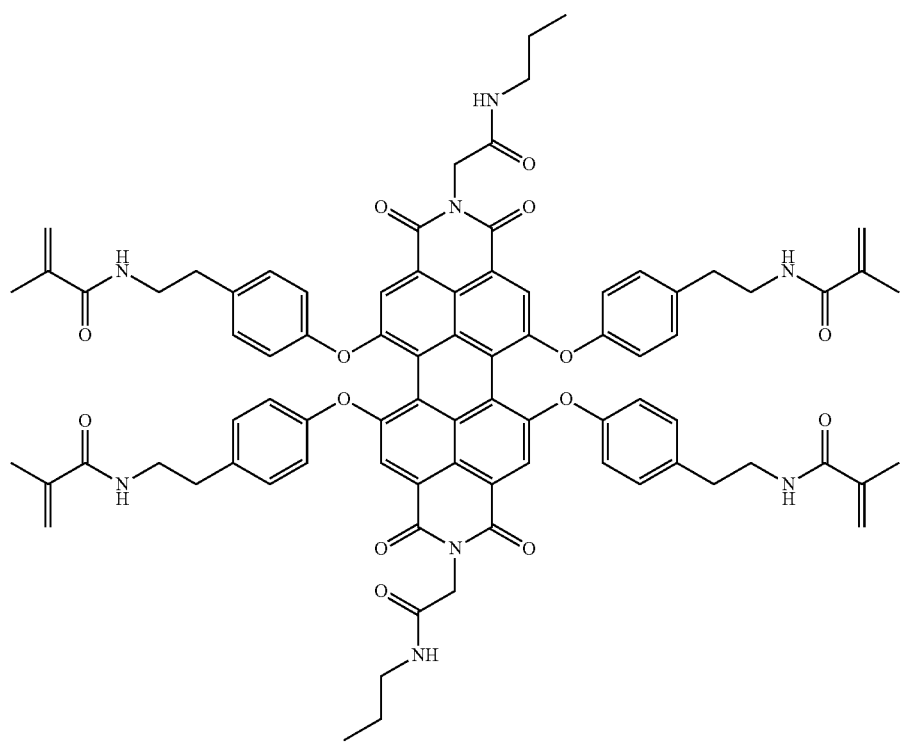
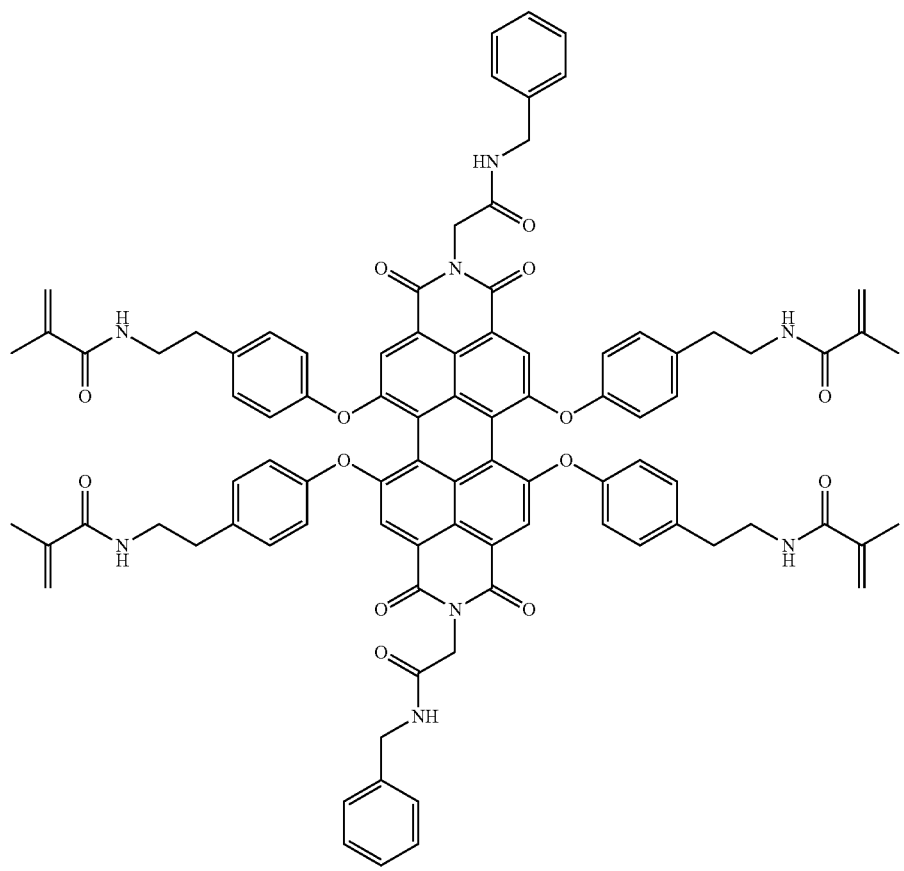

-continued
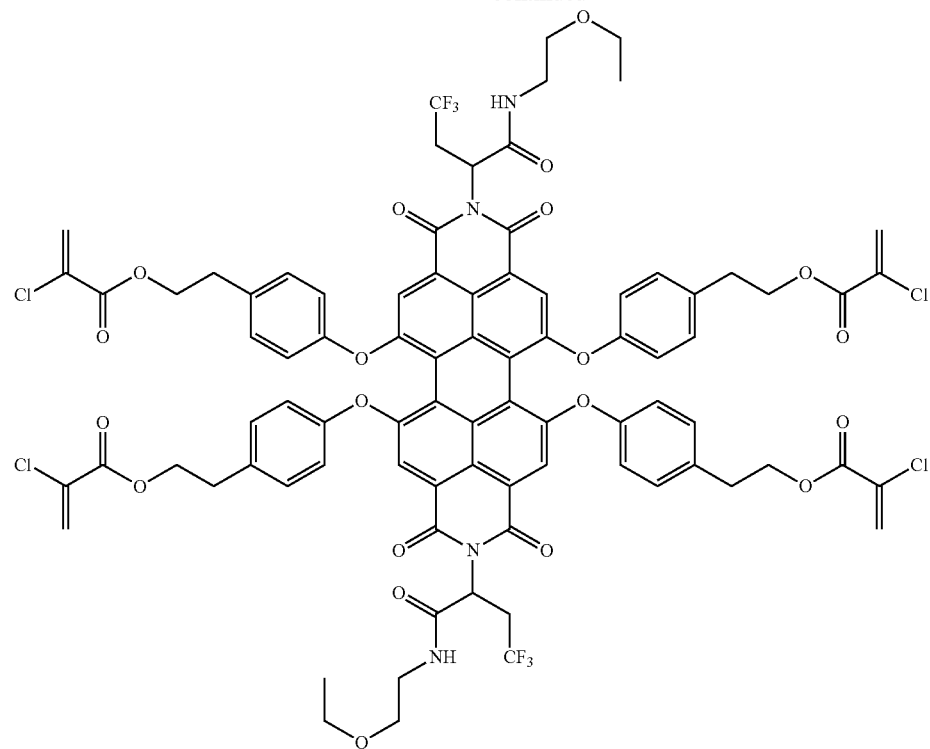
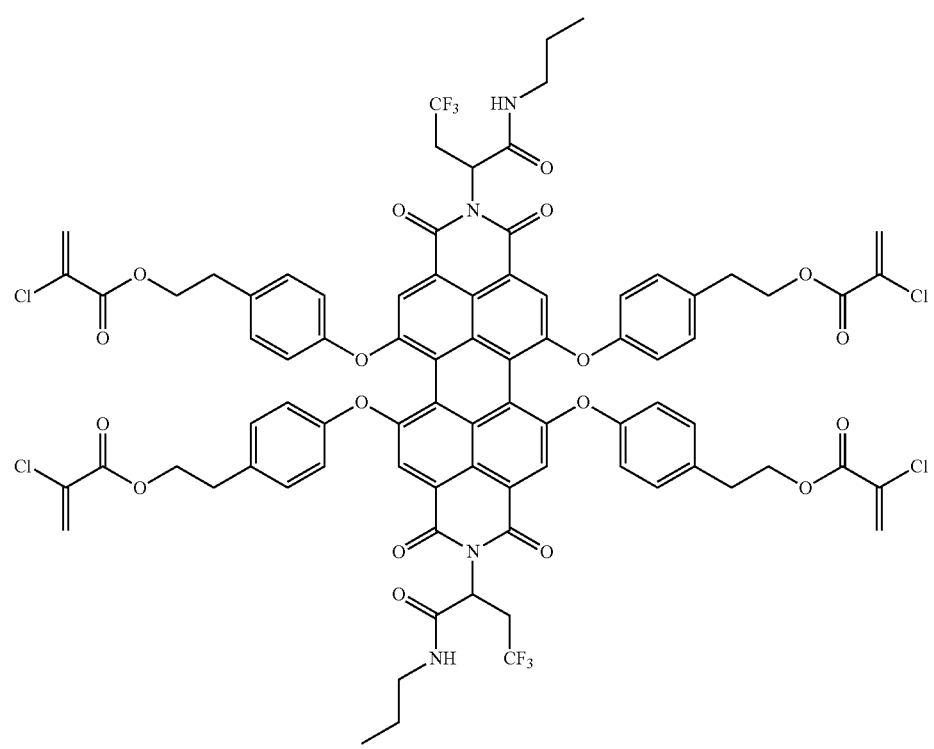

-continued
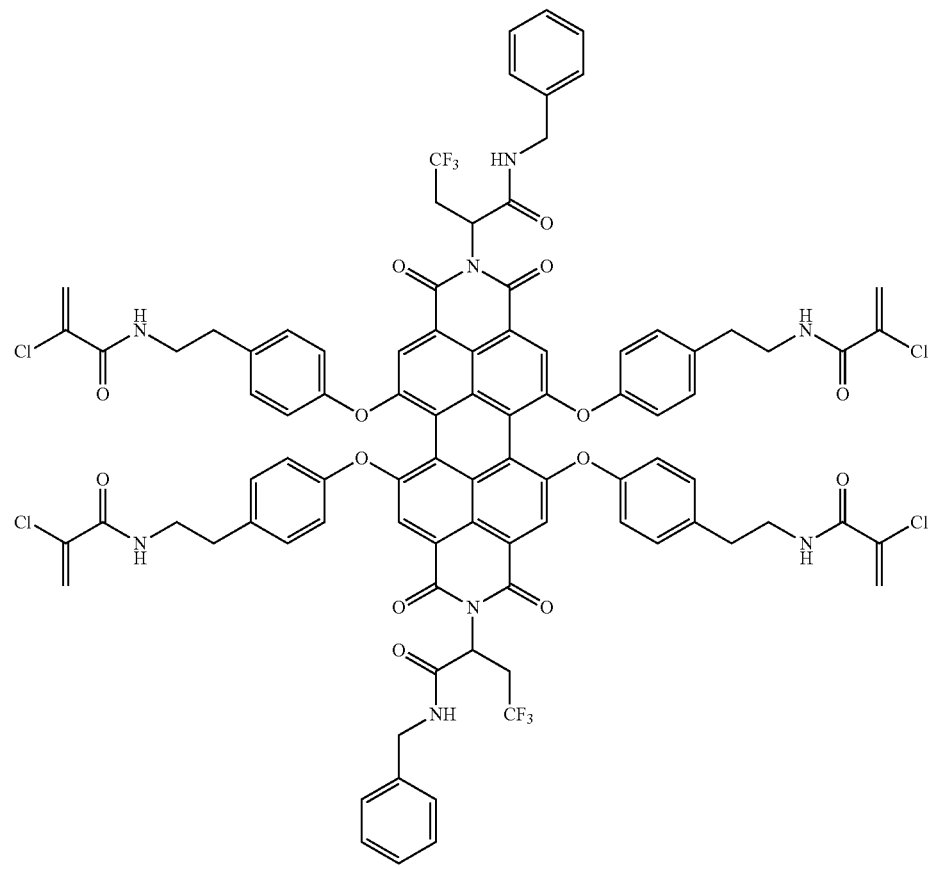
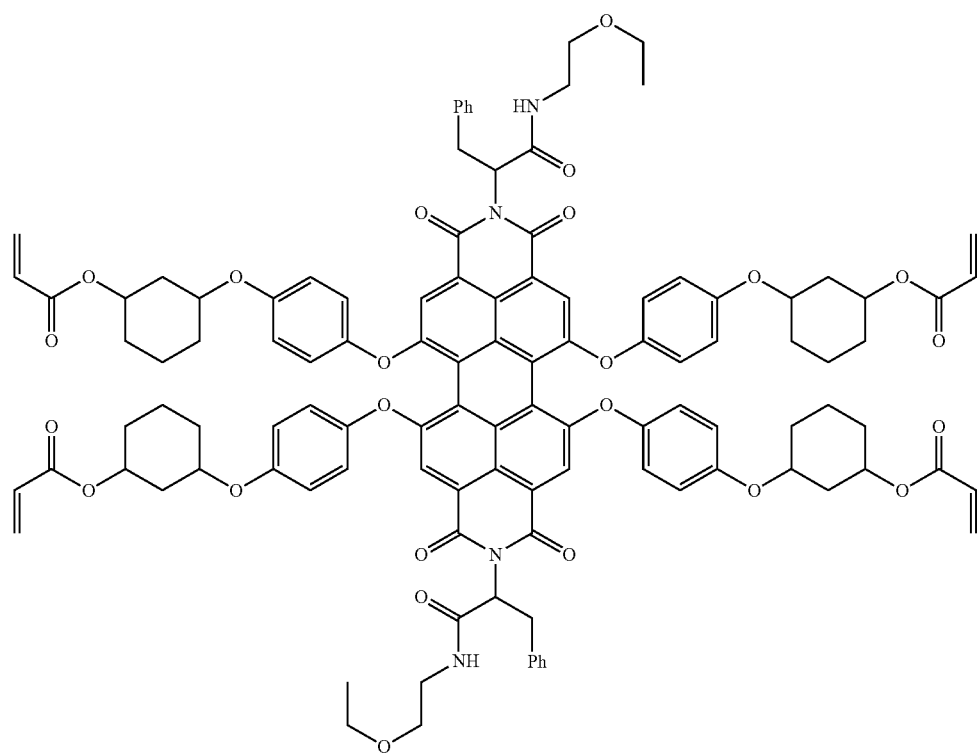

-continued
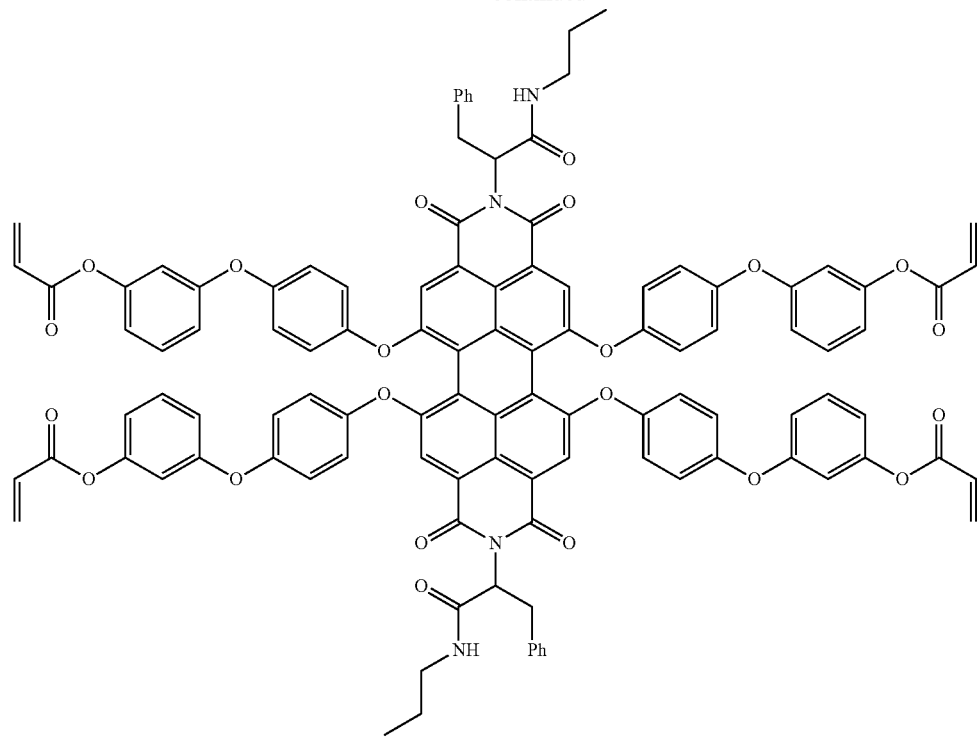
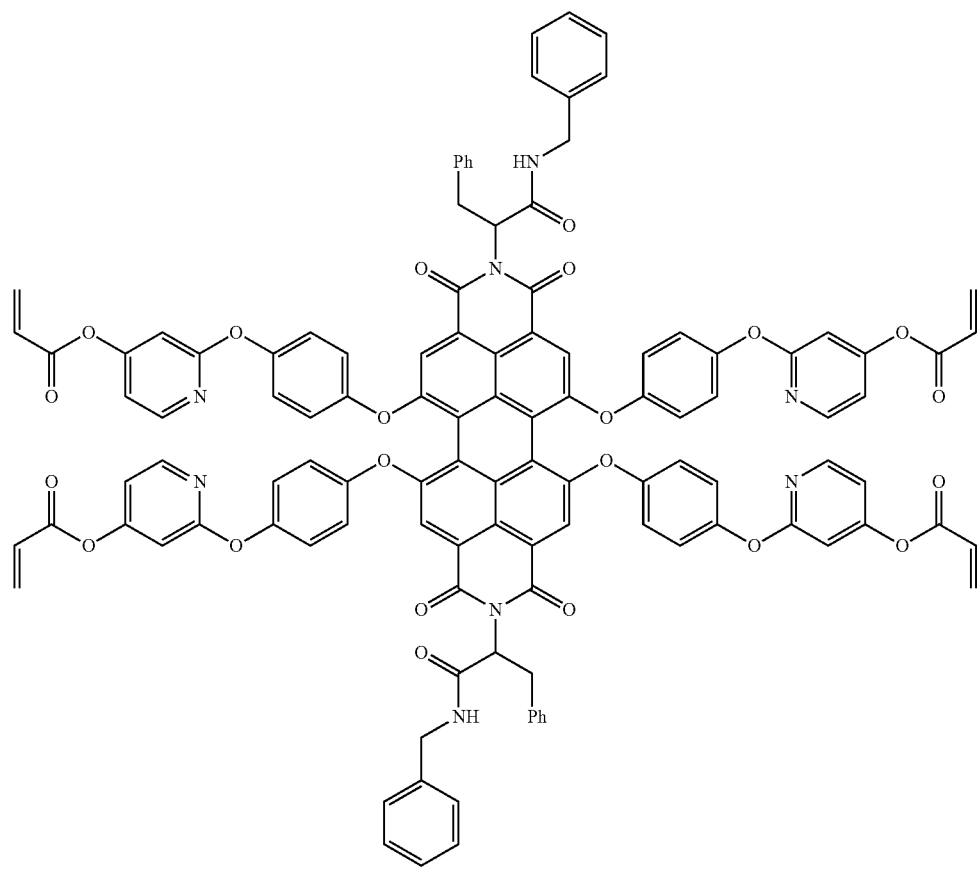

-continued
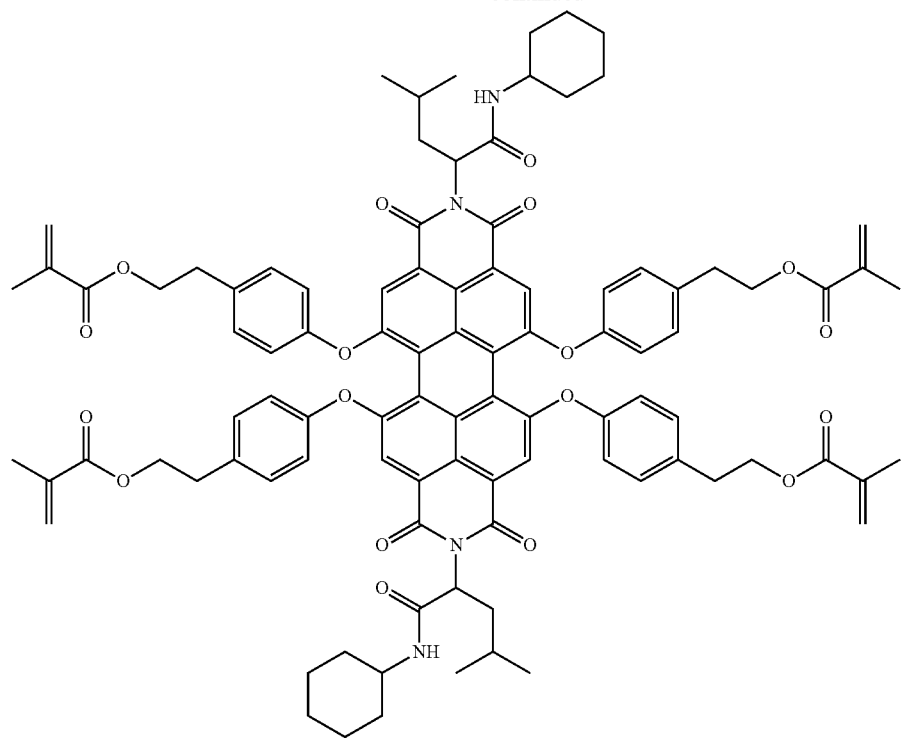
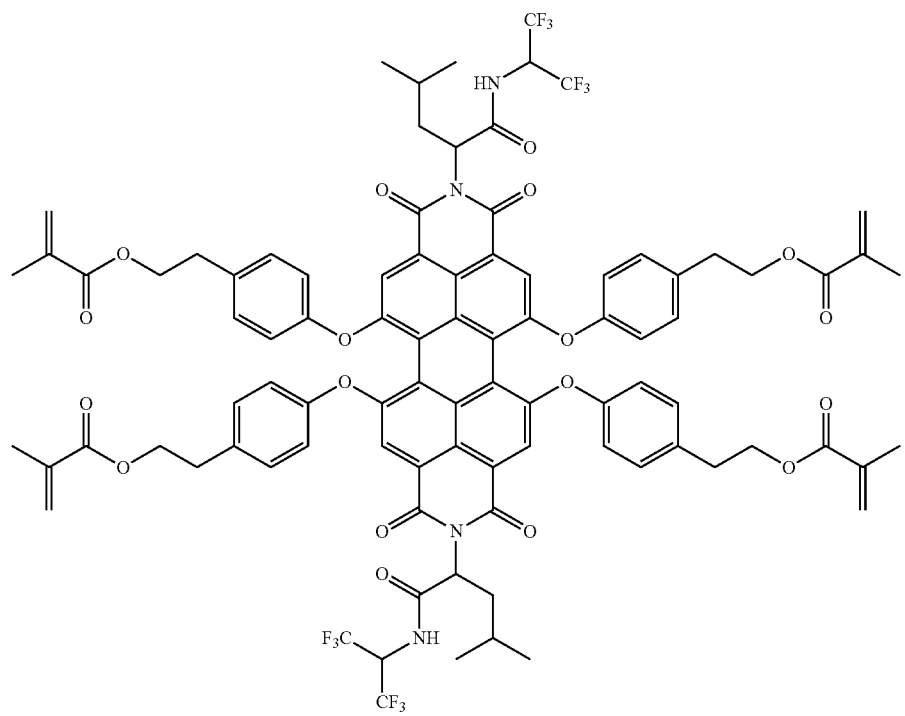

-continued
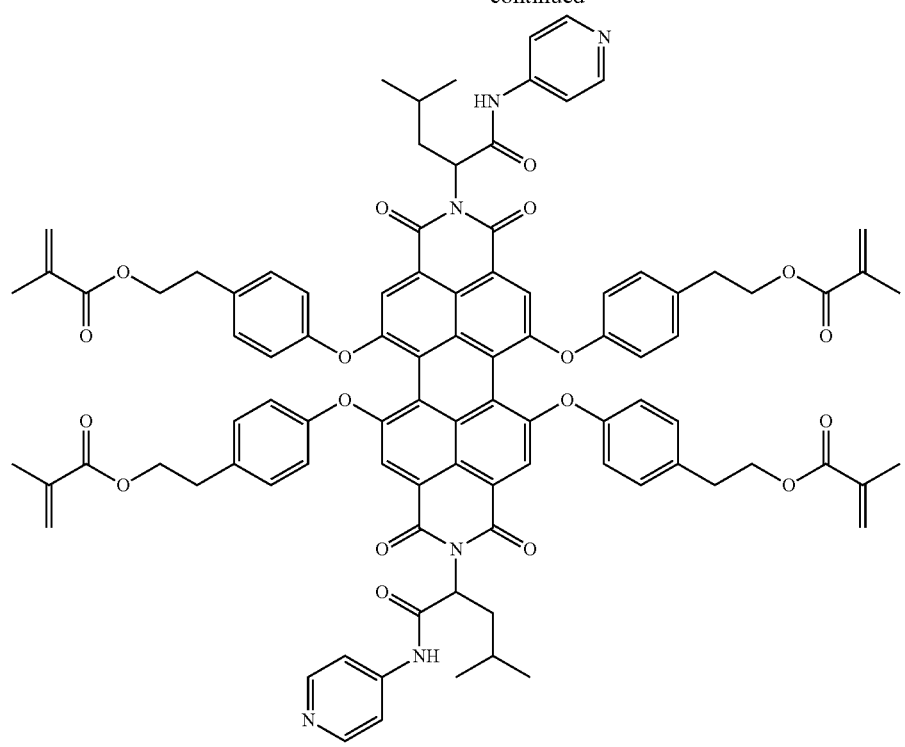
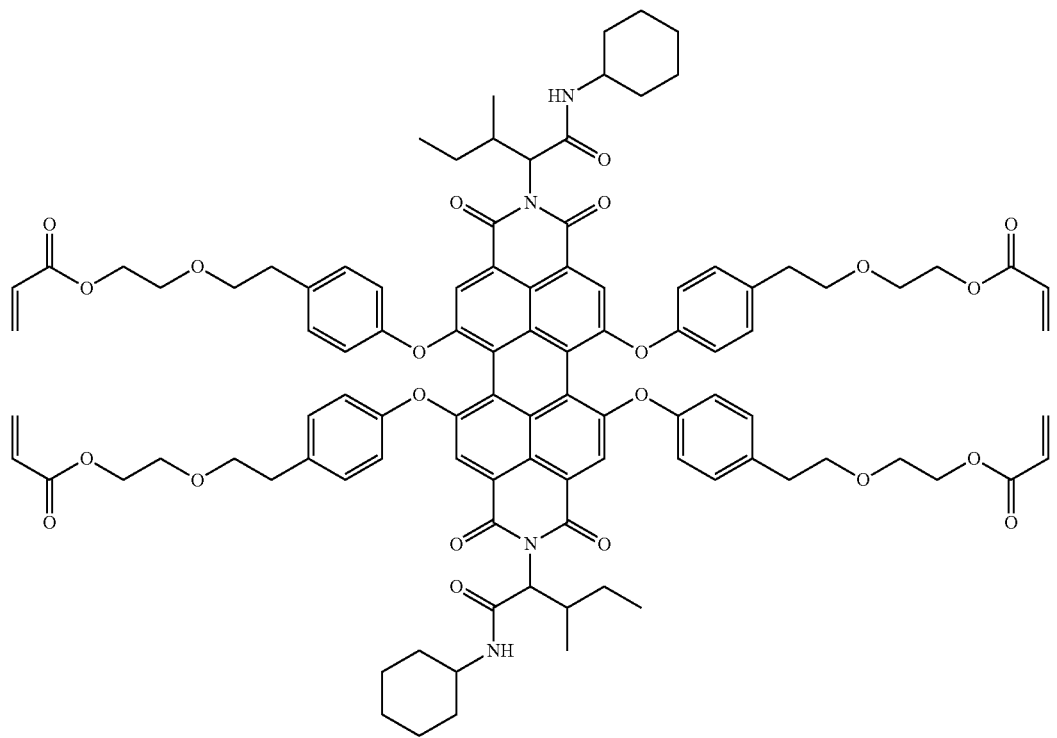

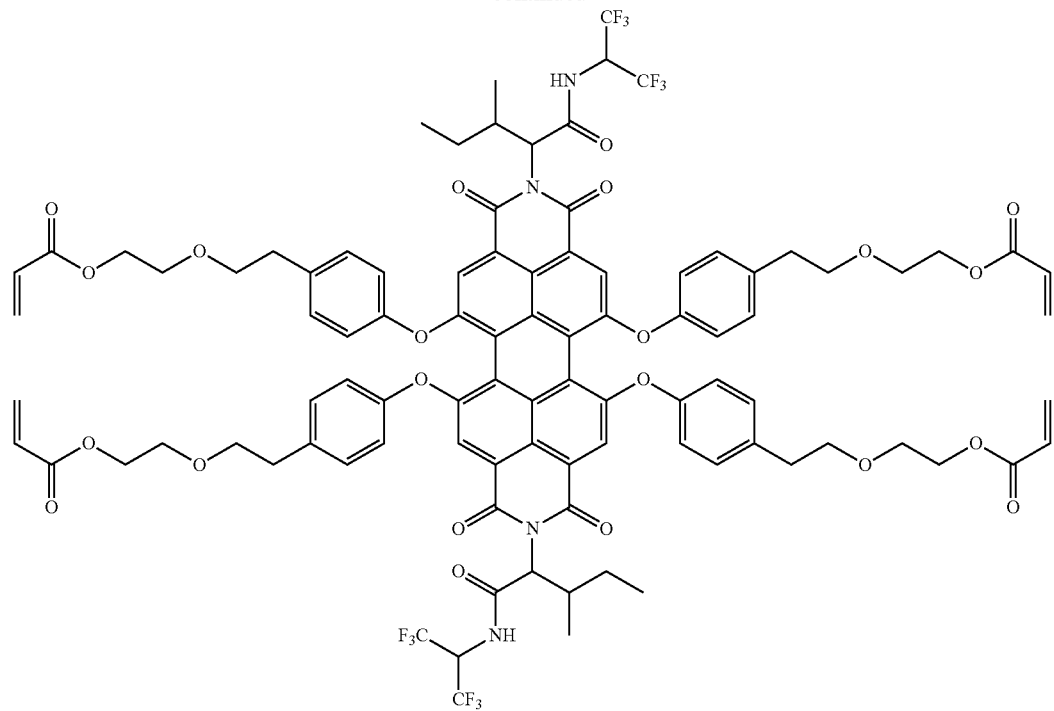
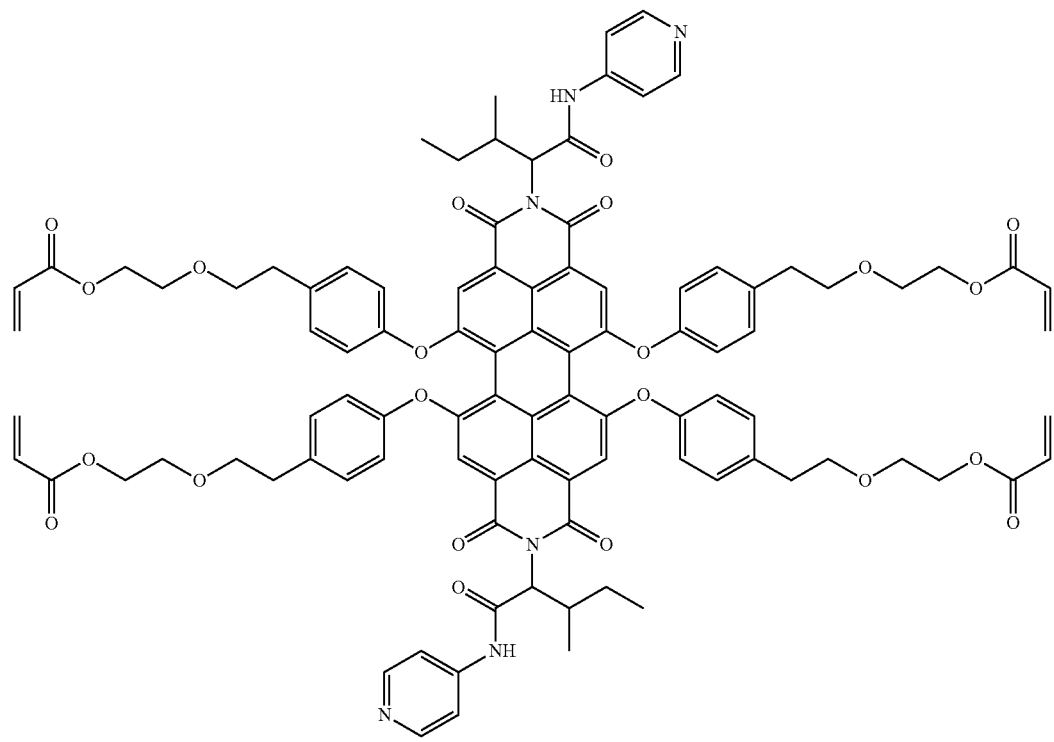

-continued
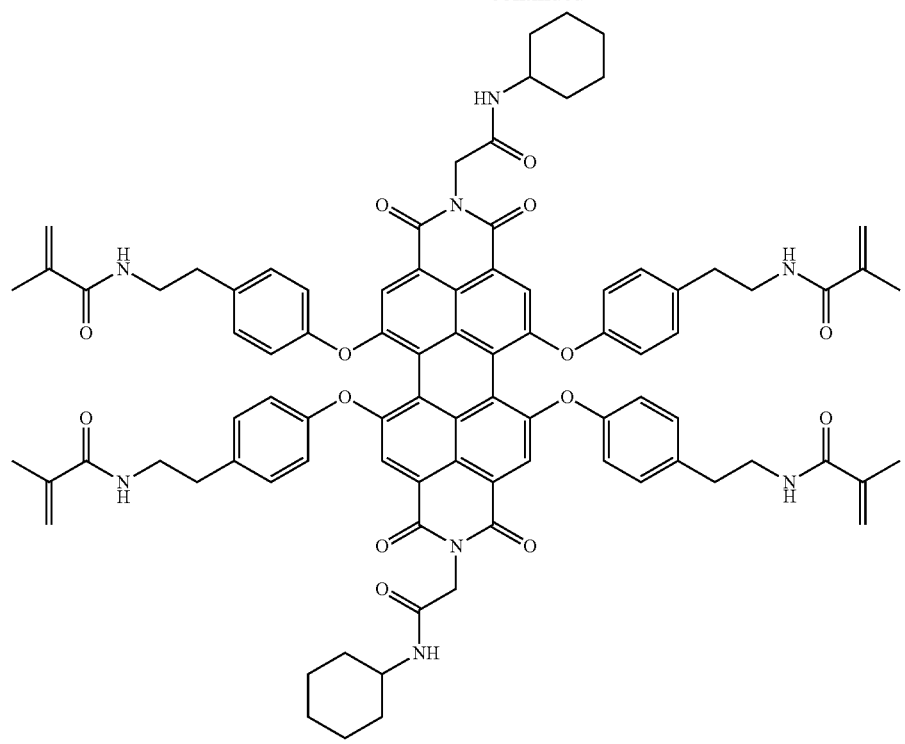
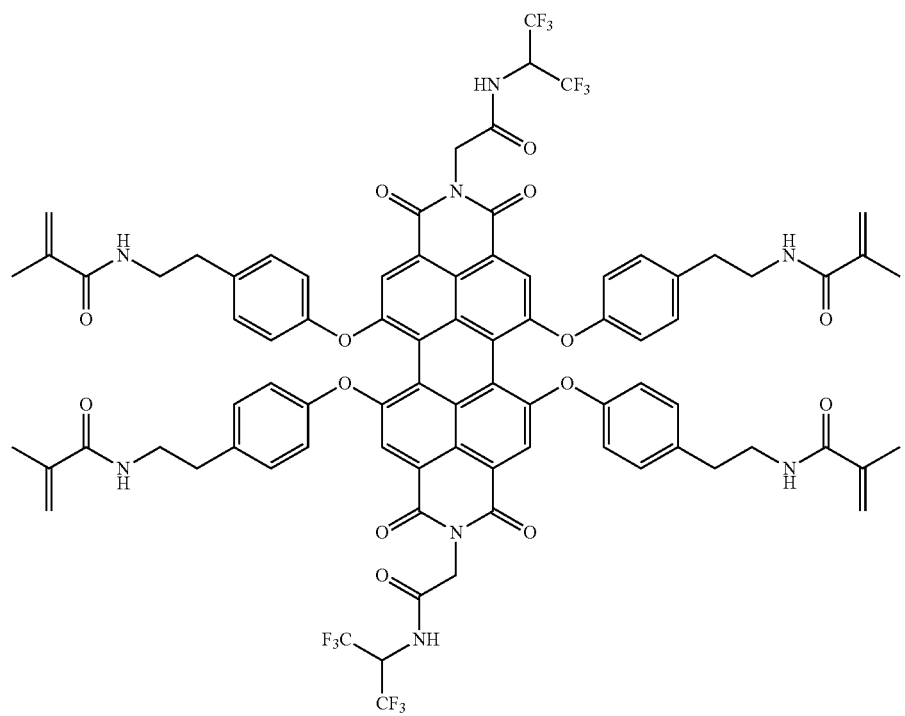

-continued
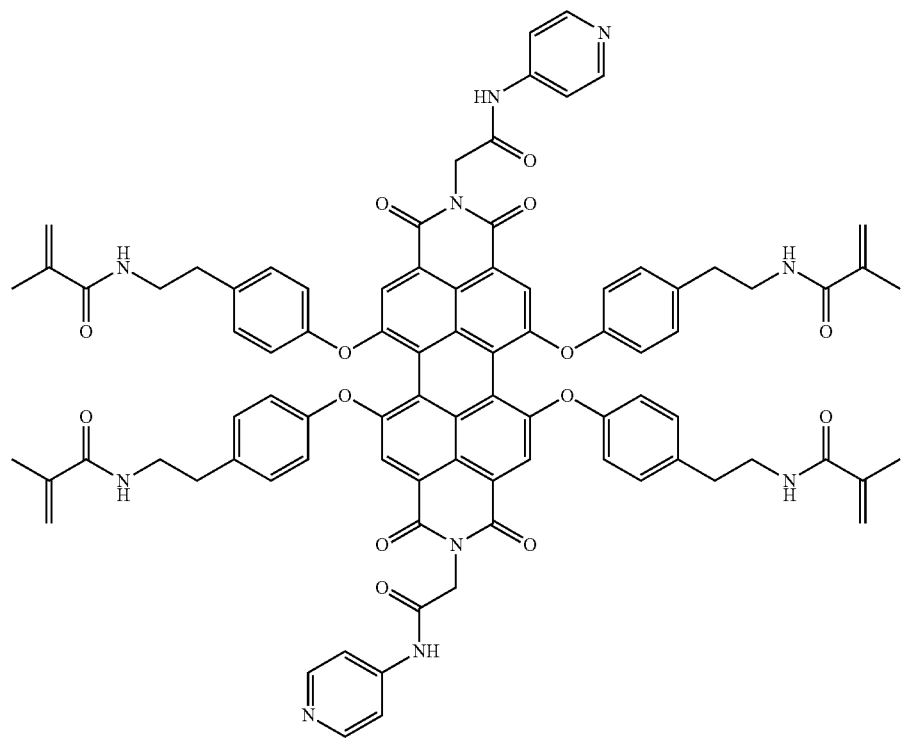
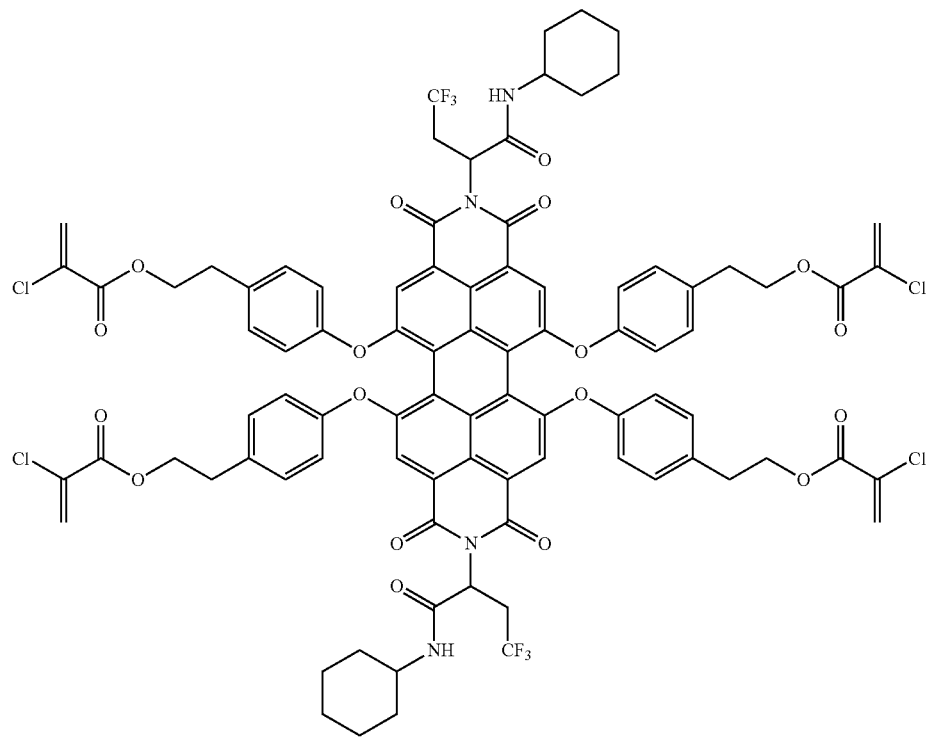

-continued
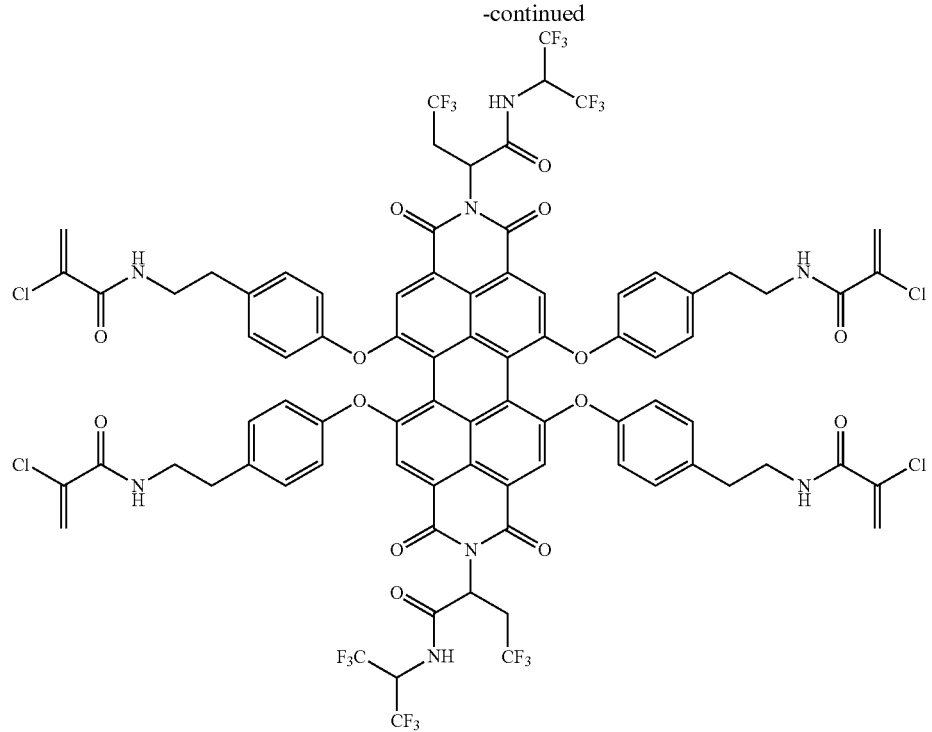
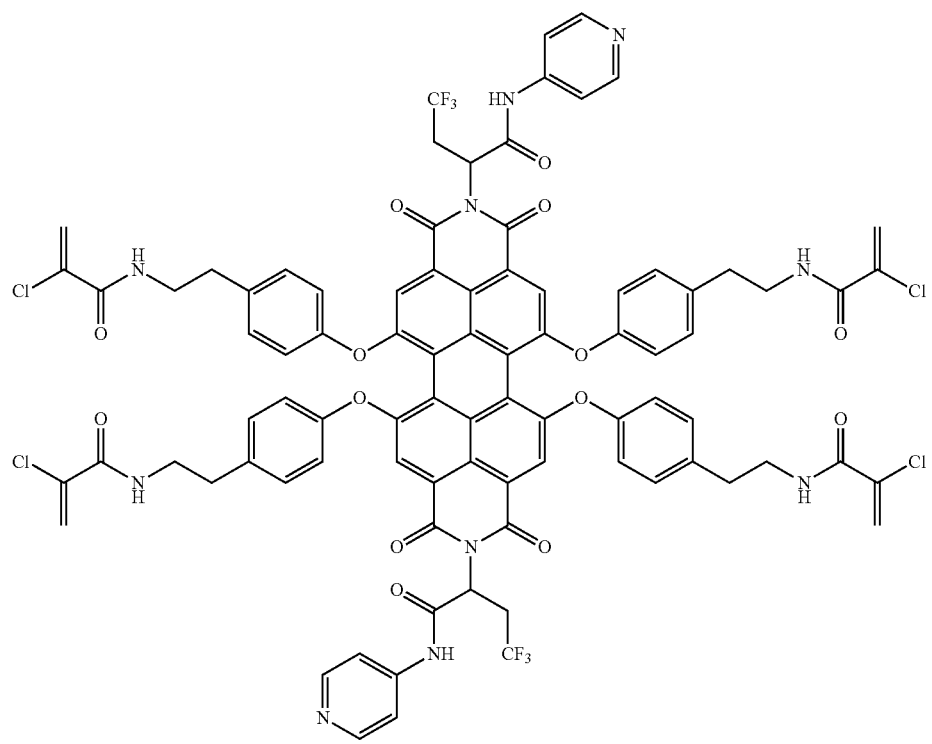

-continued
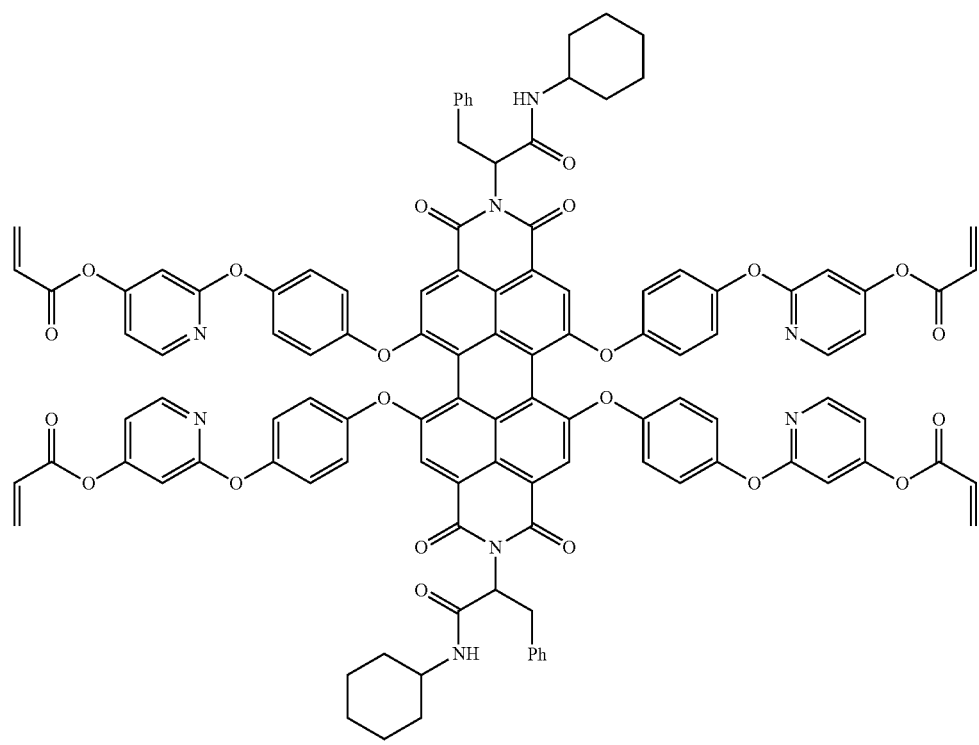
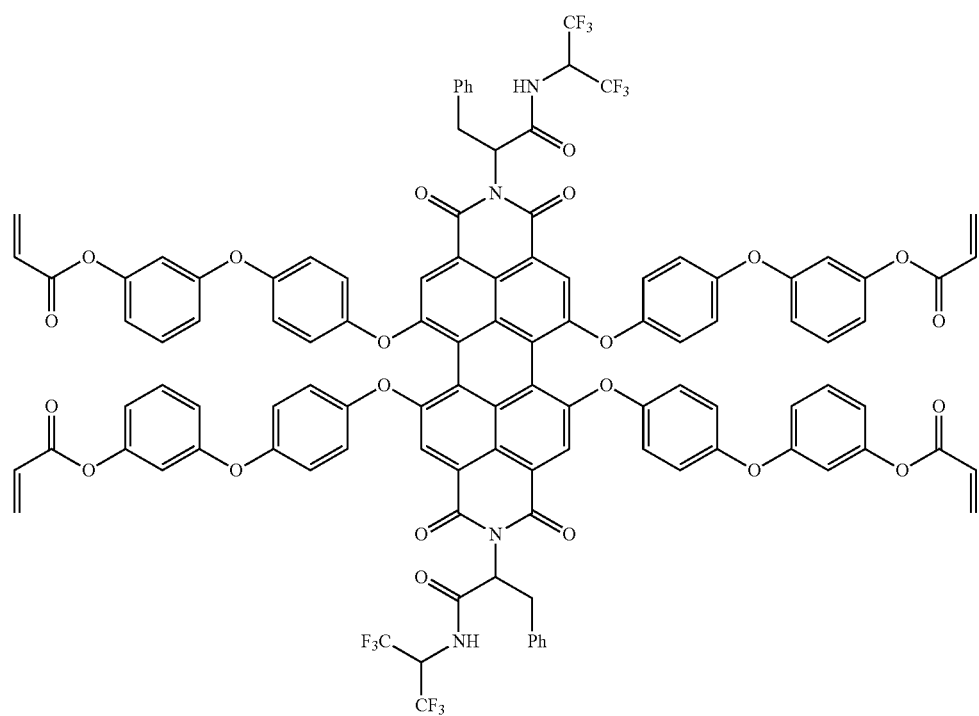

-continued
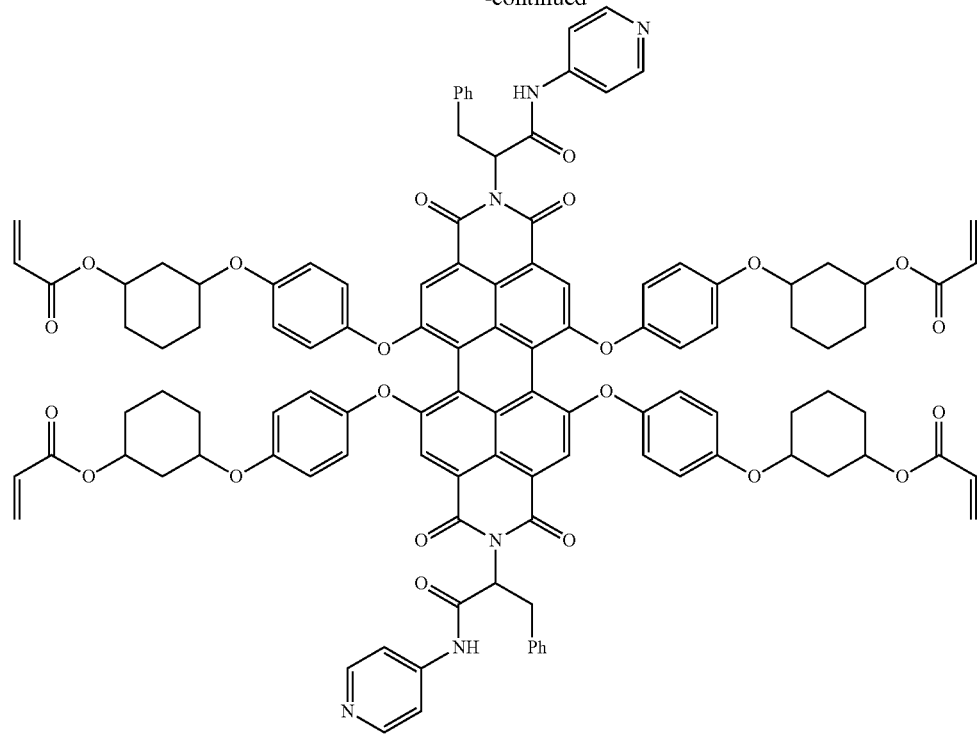
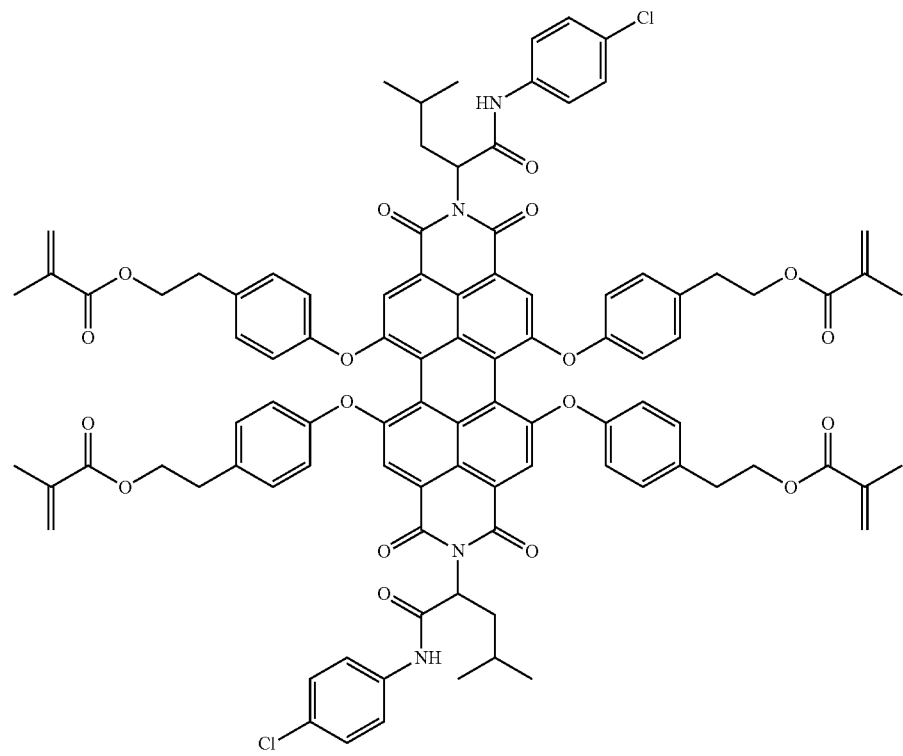

-continued
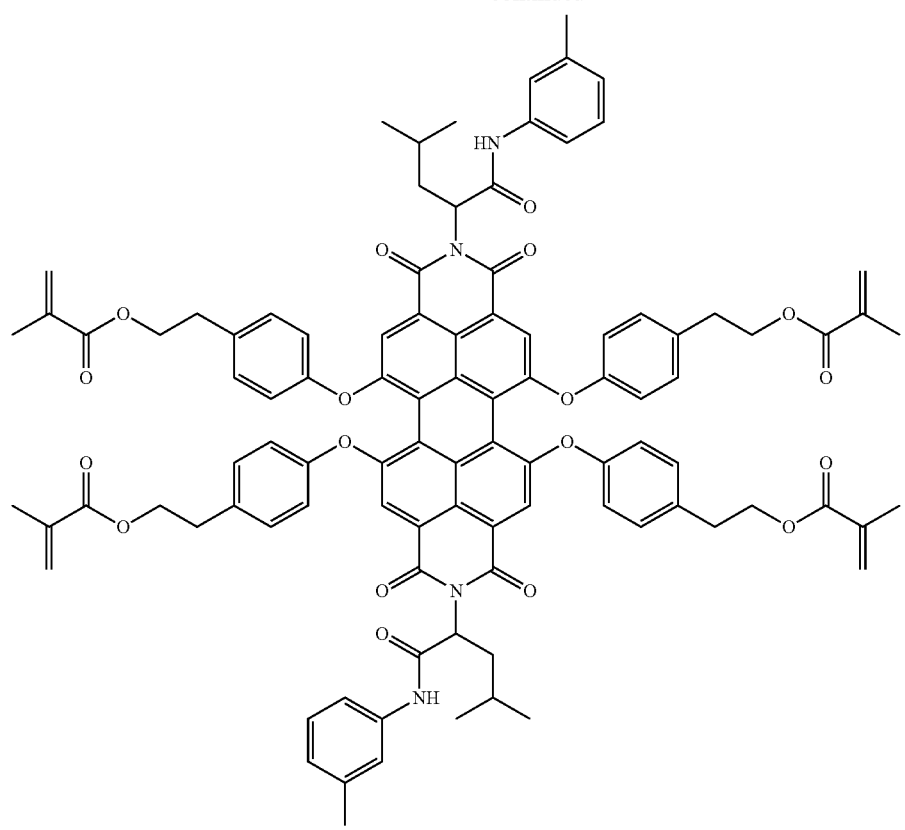
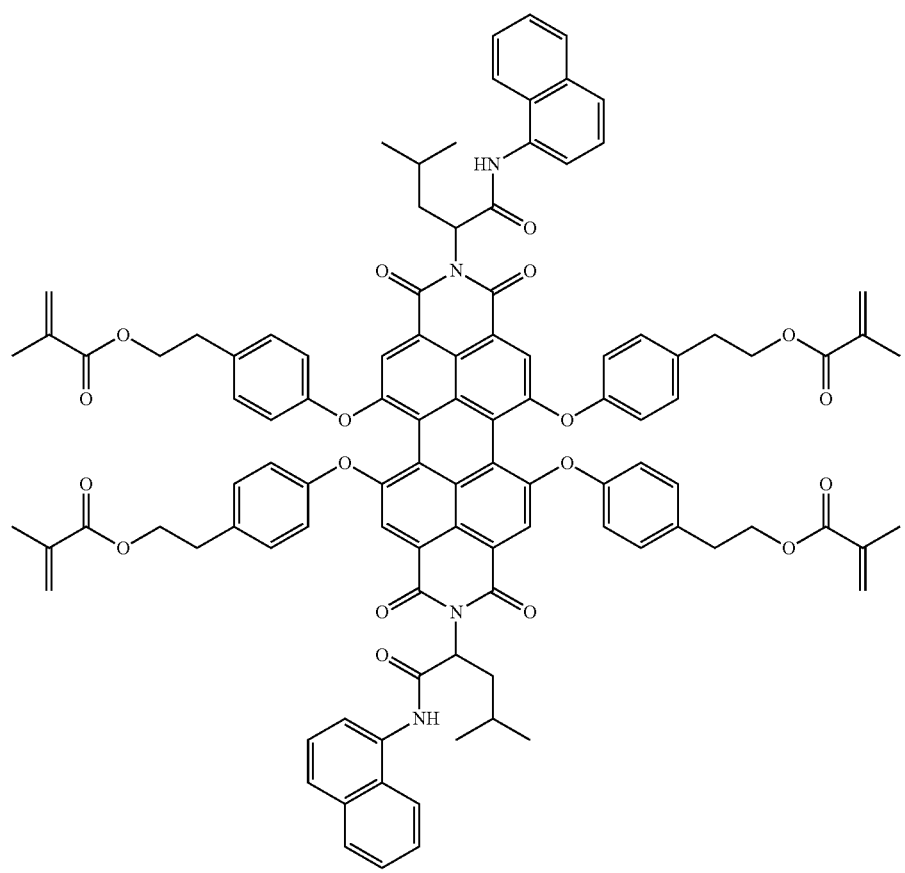

-continued
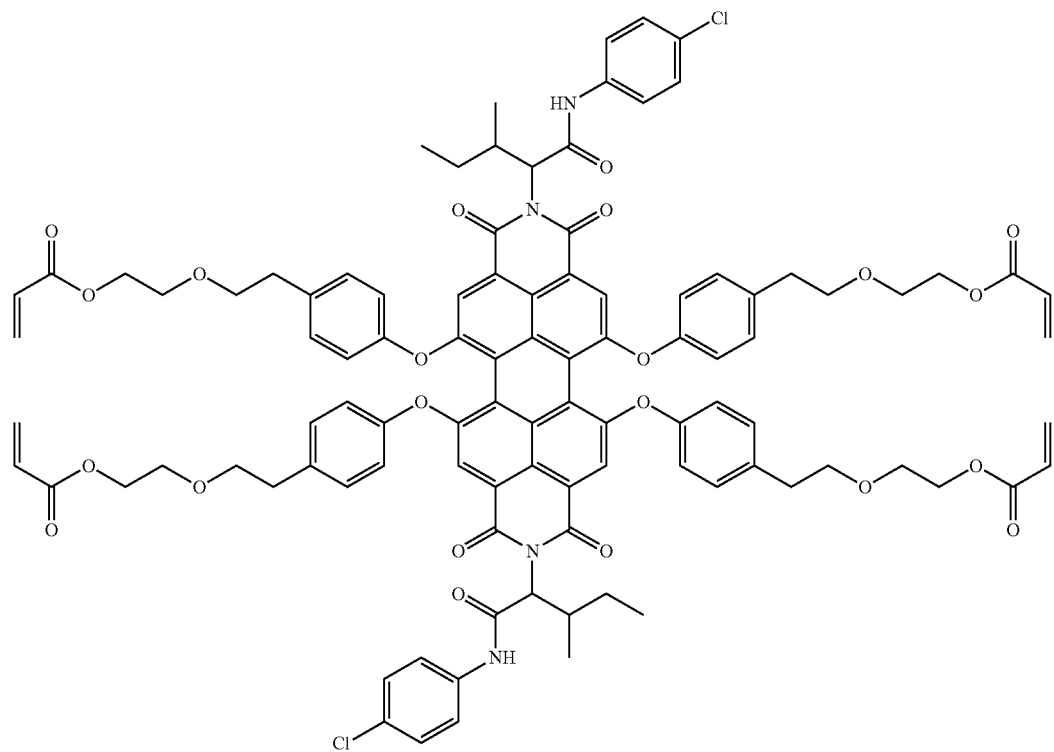
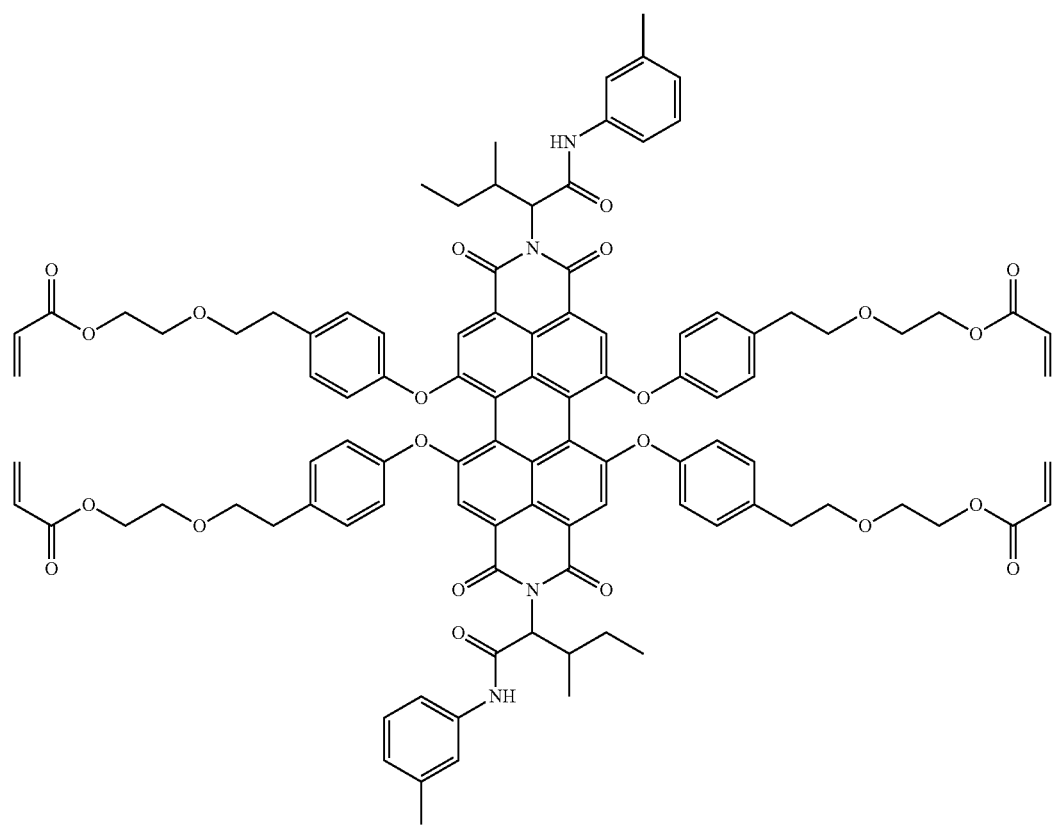

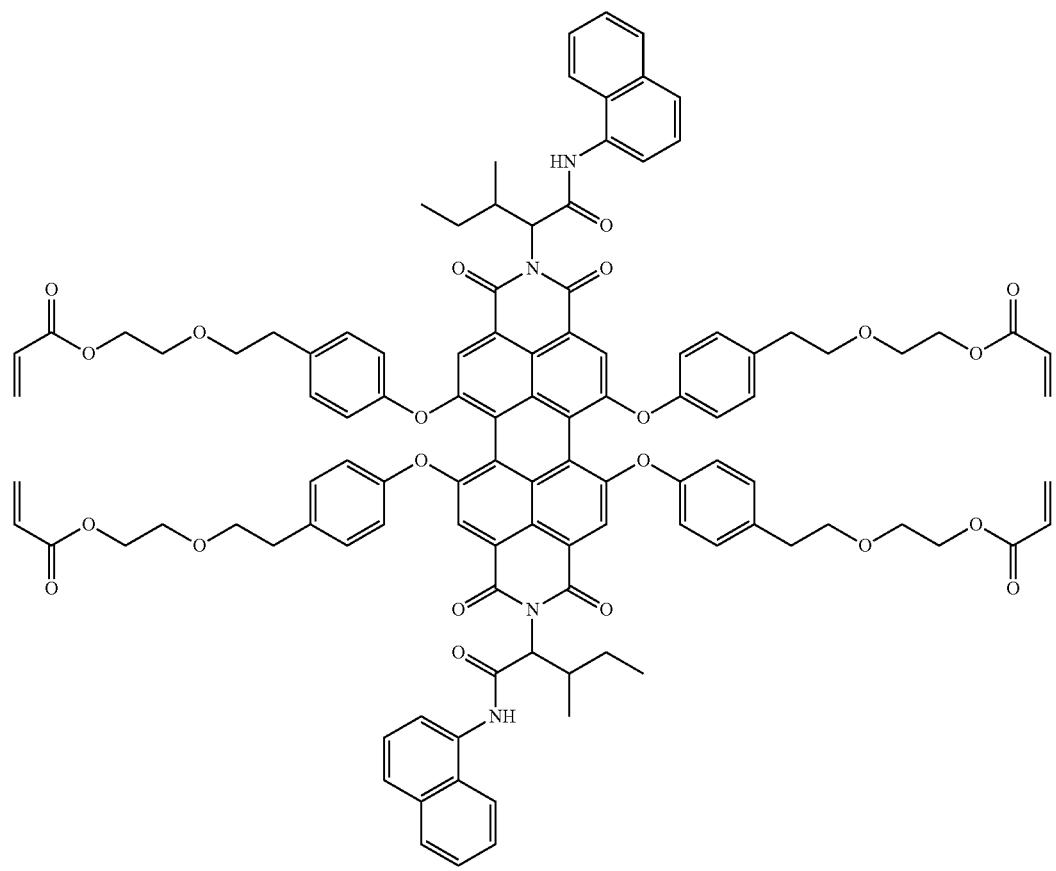
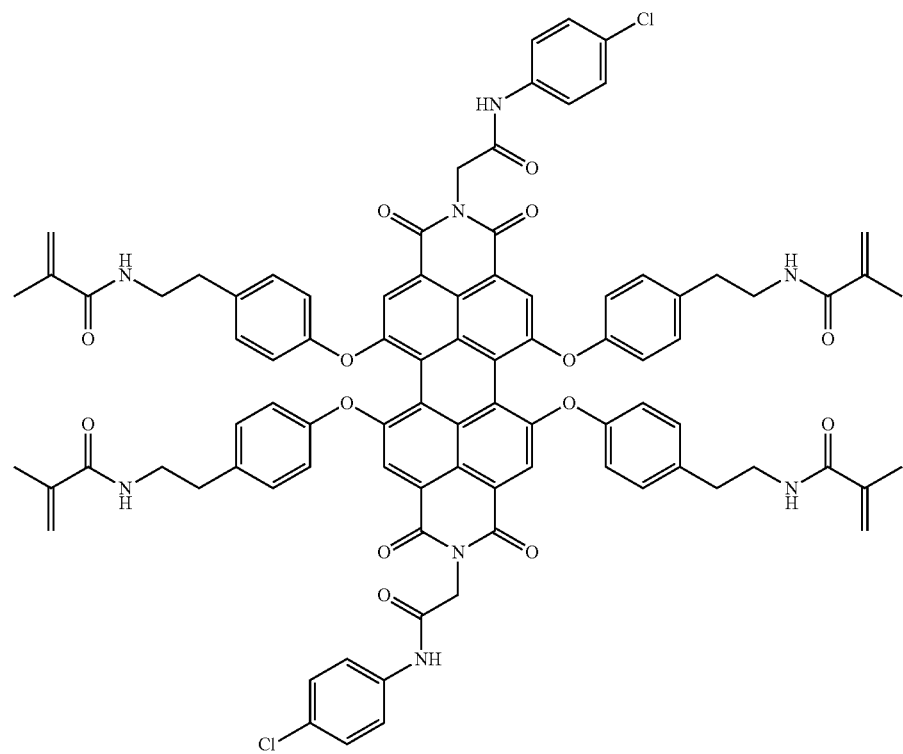

-continued
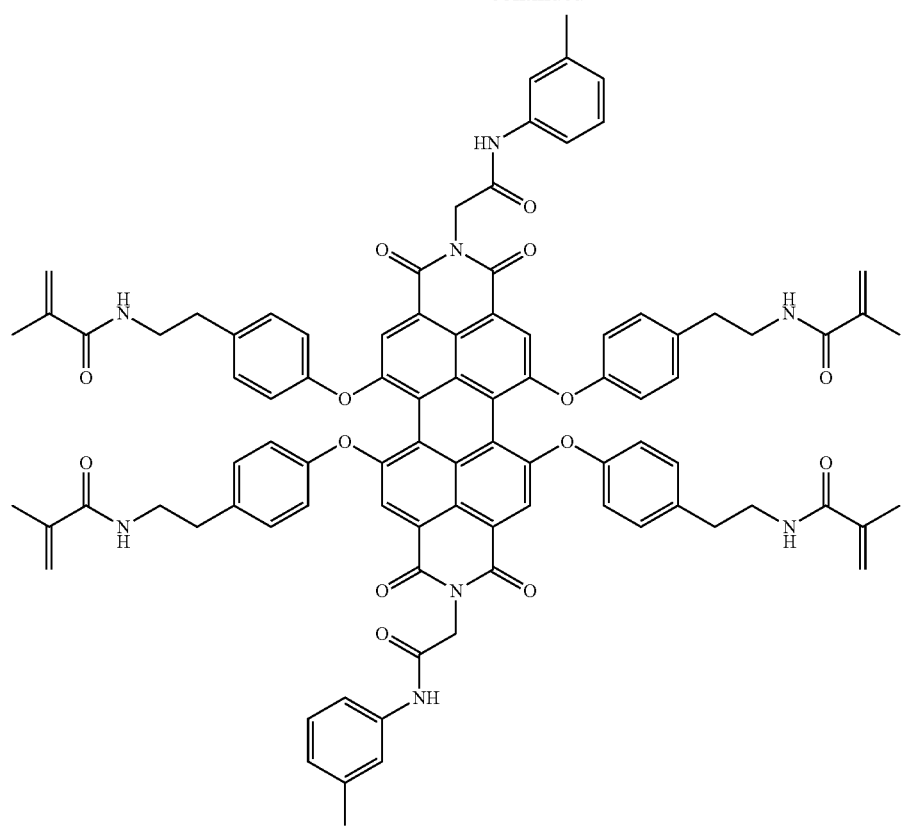
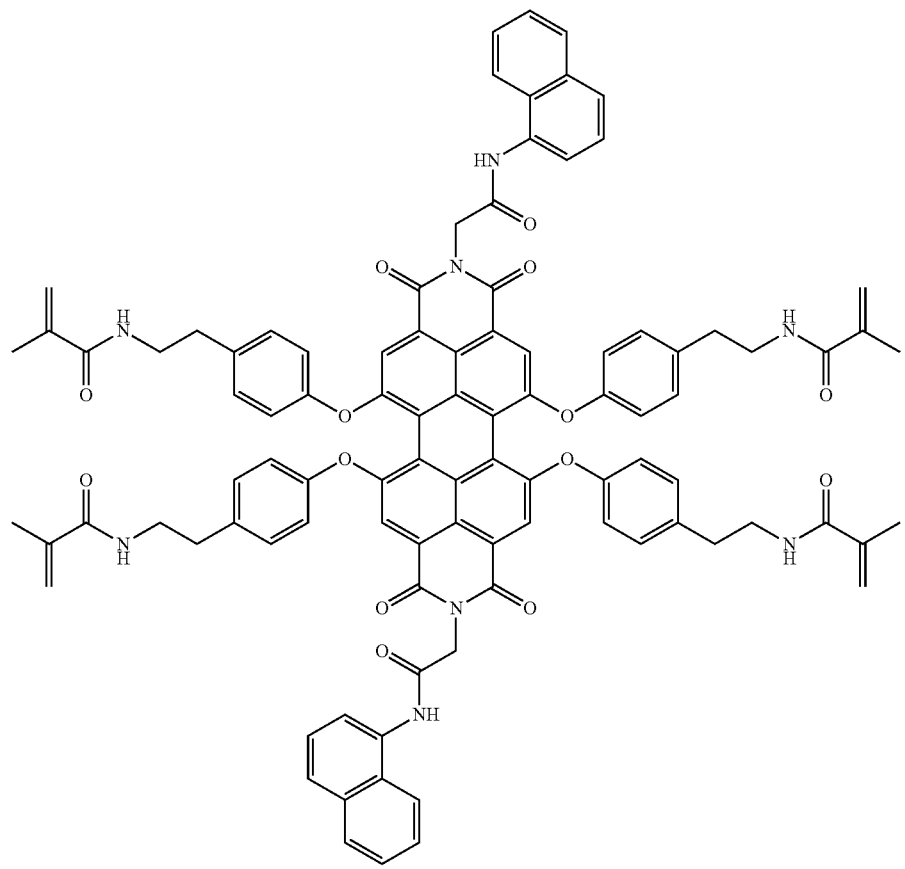

-continued
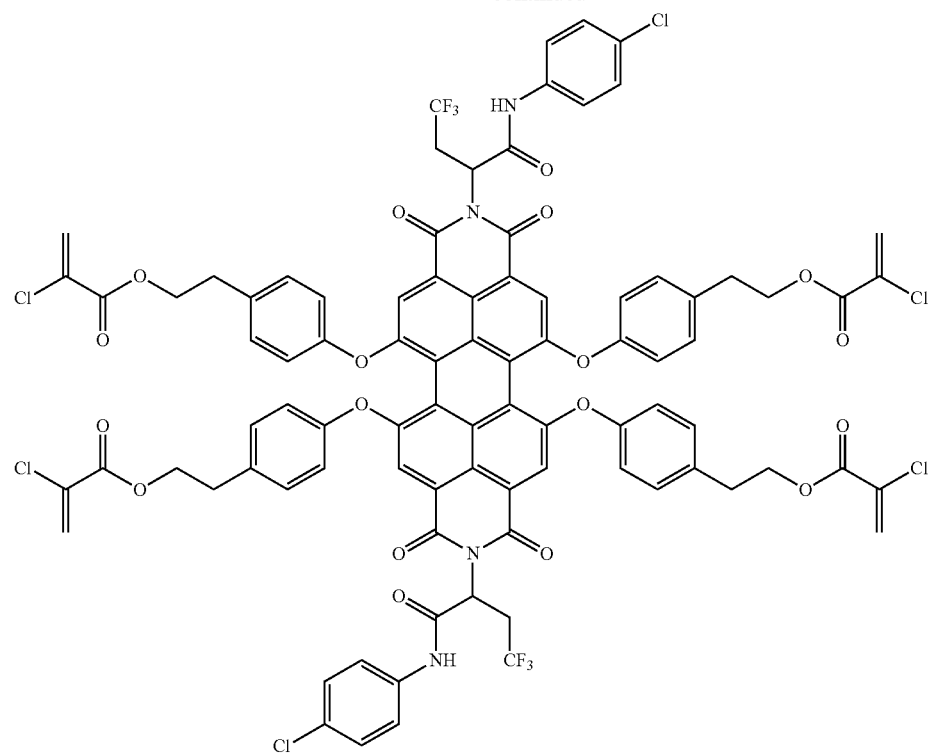
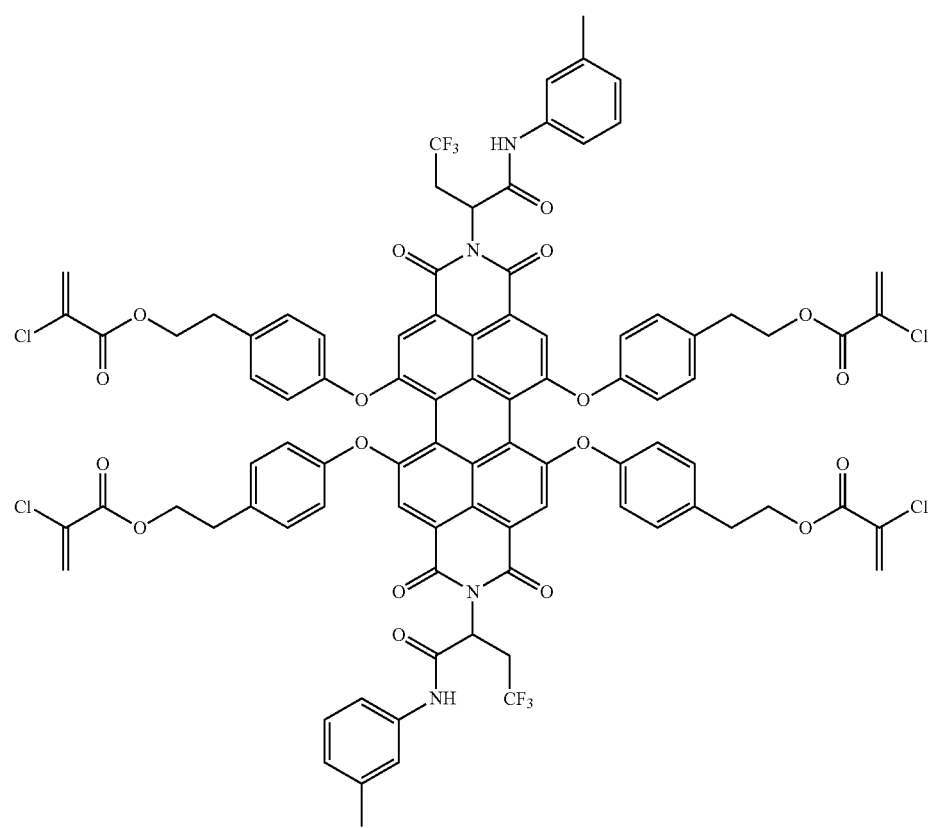

-continued
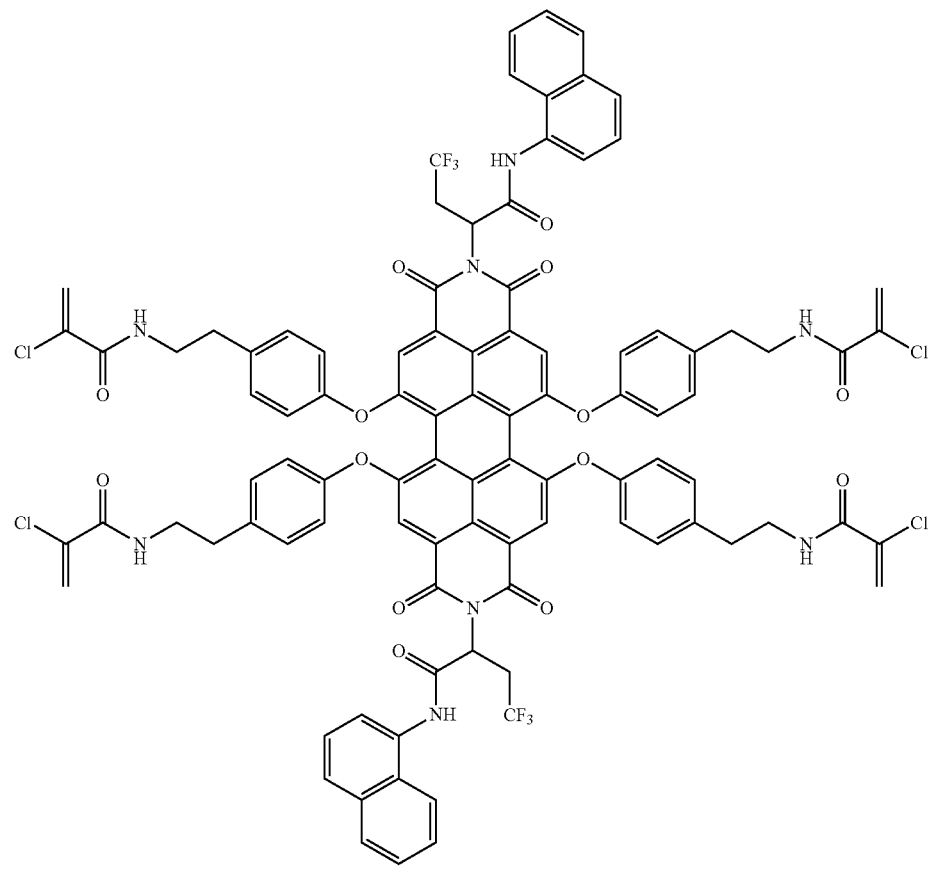
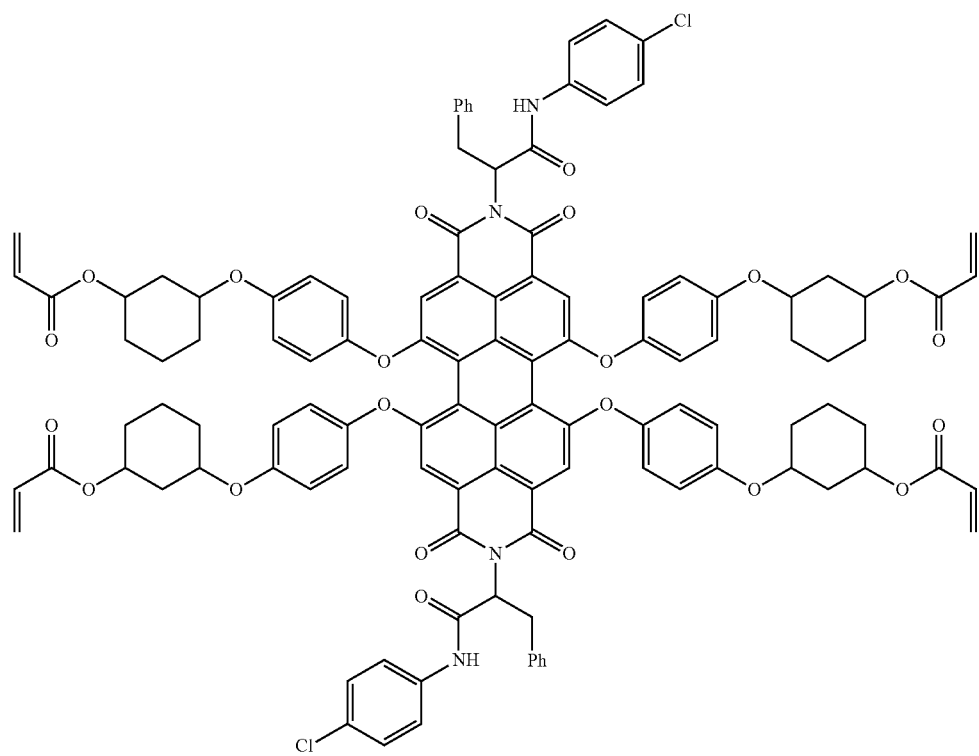

-continued
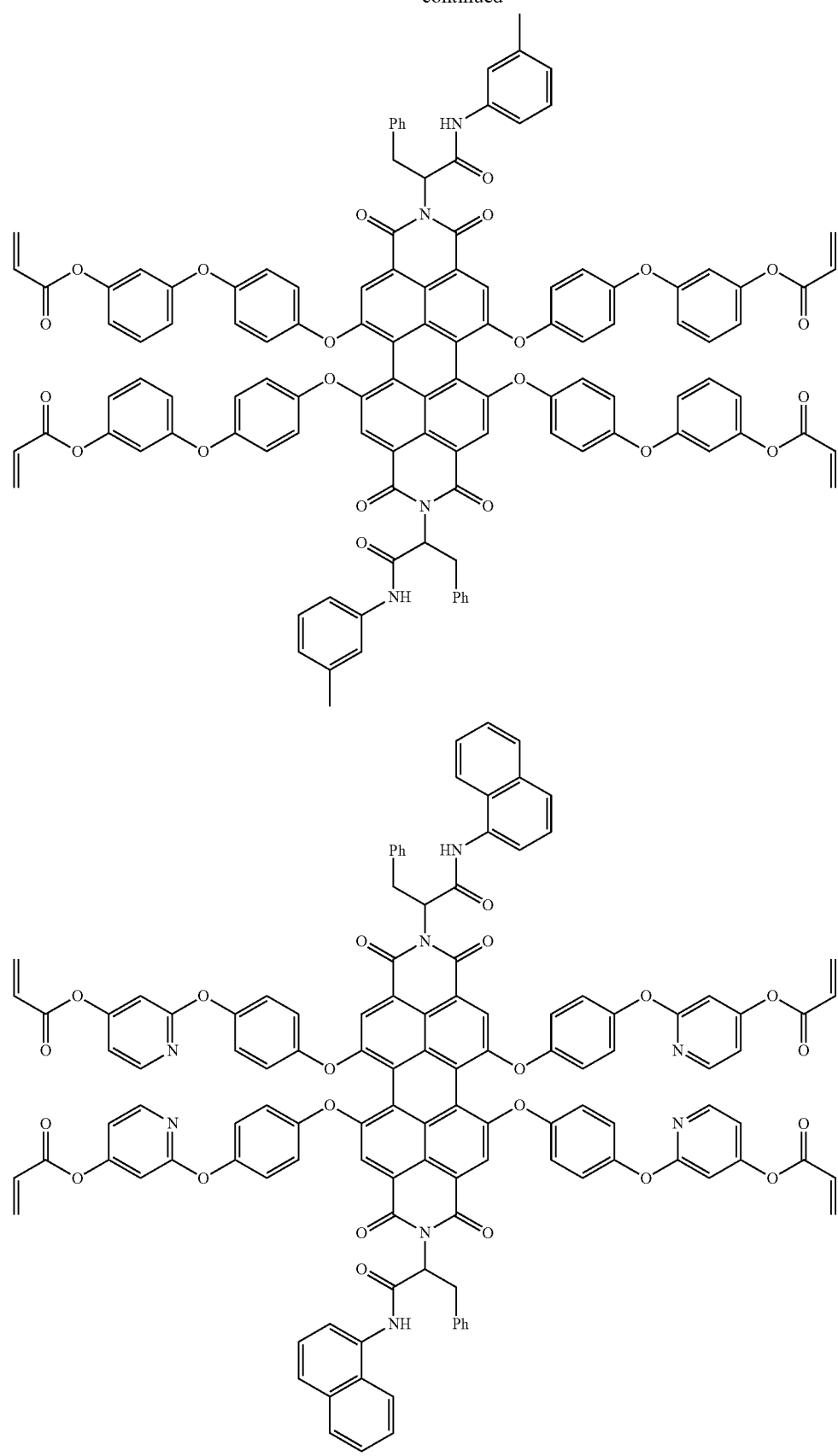

-continued
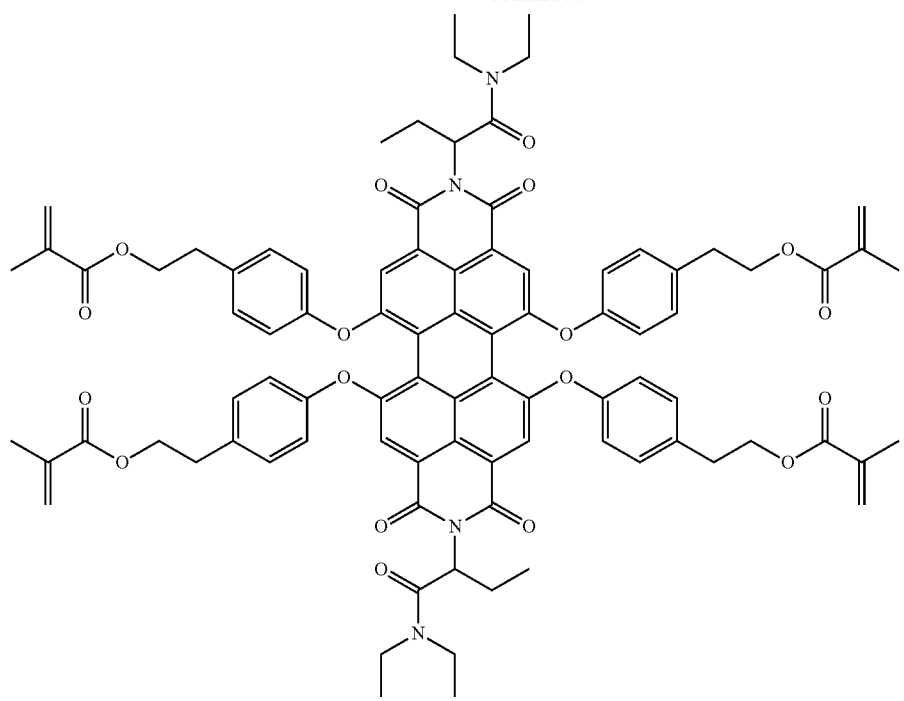
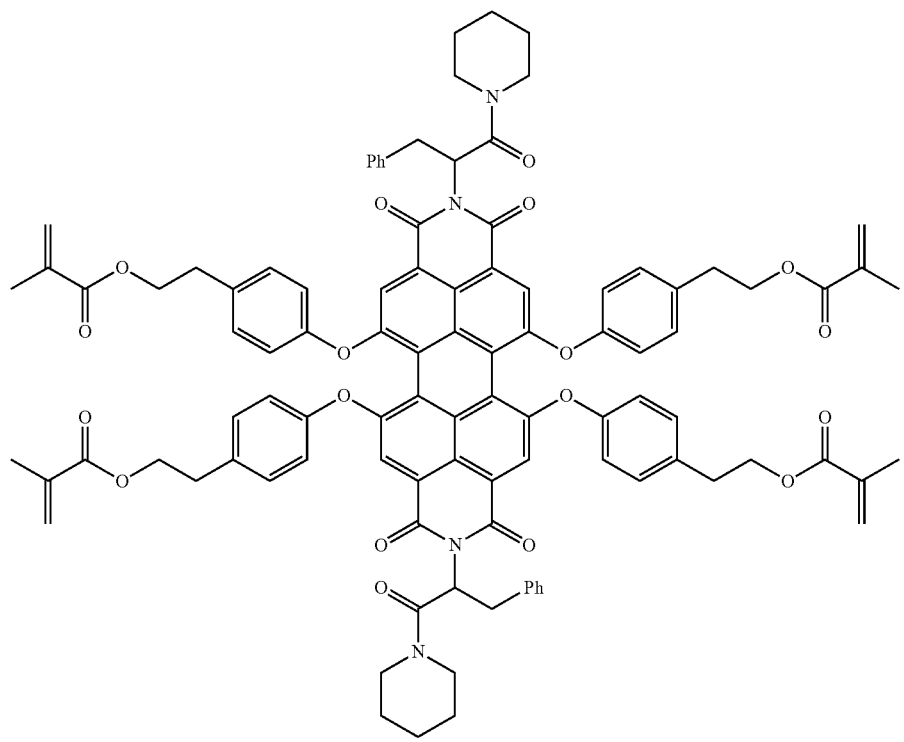

-continued
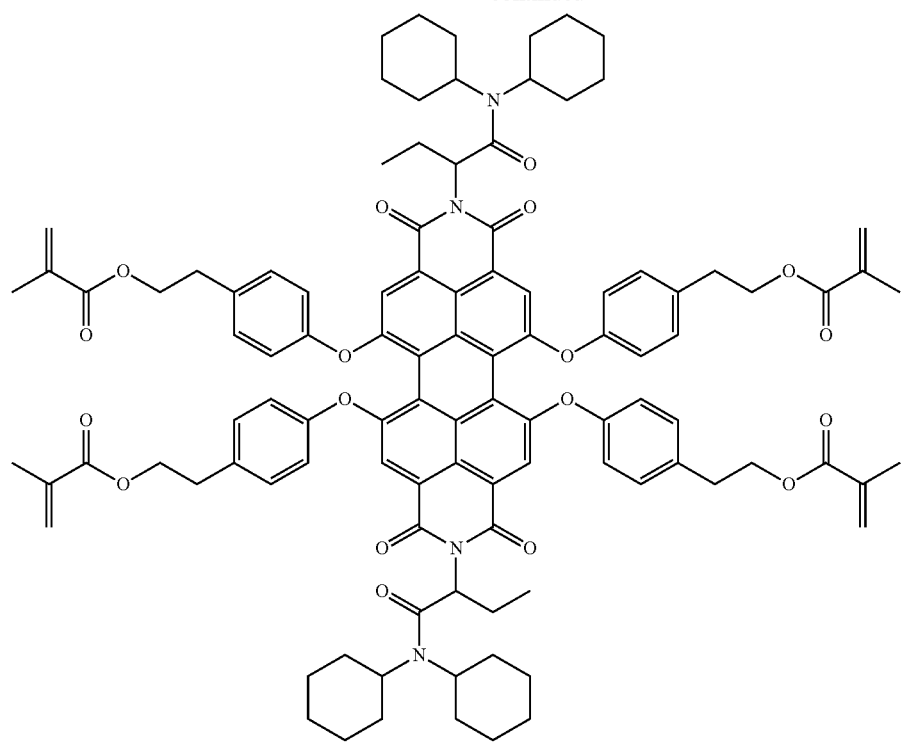
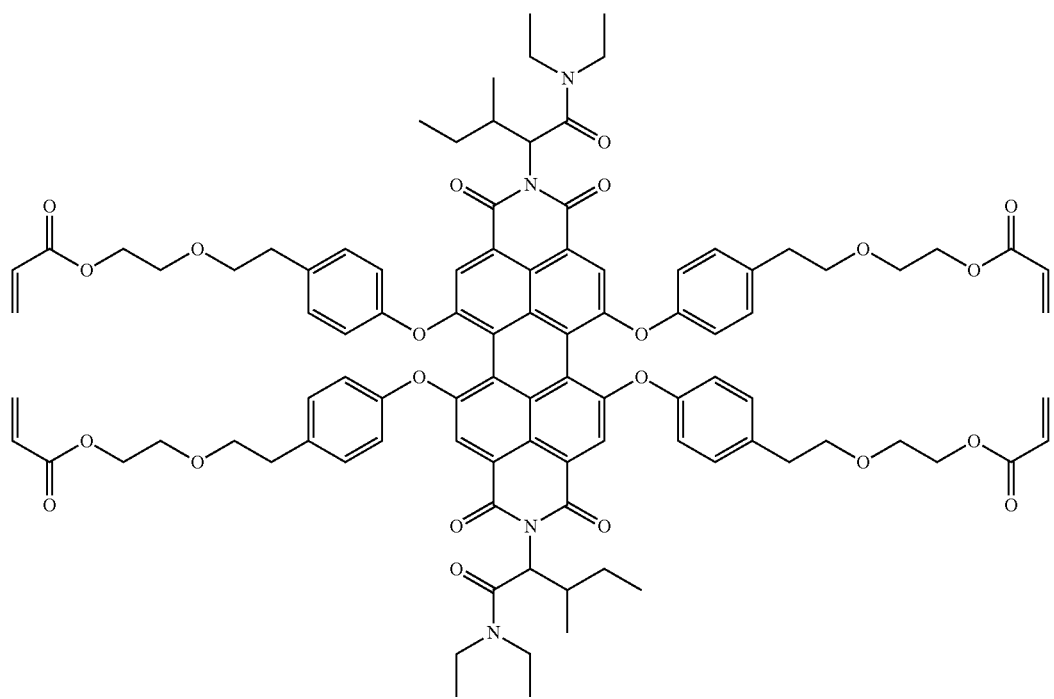

-continued
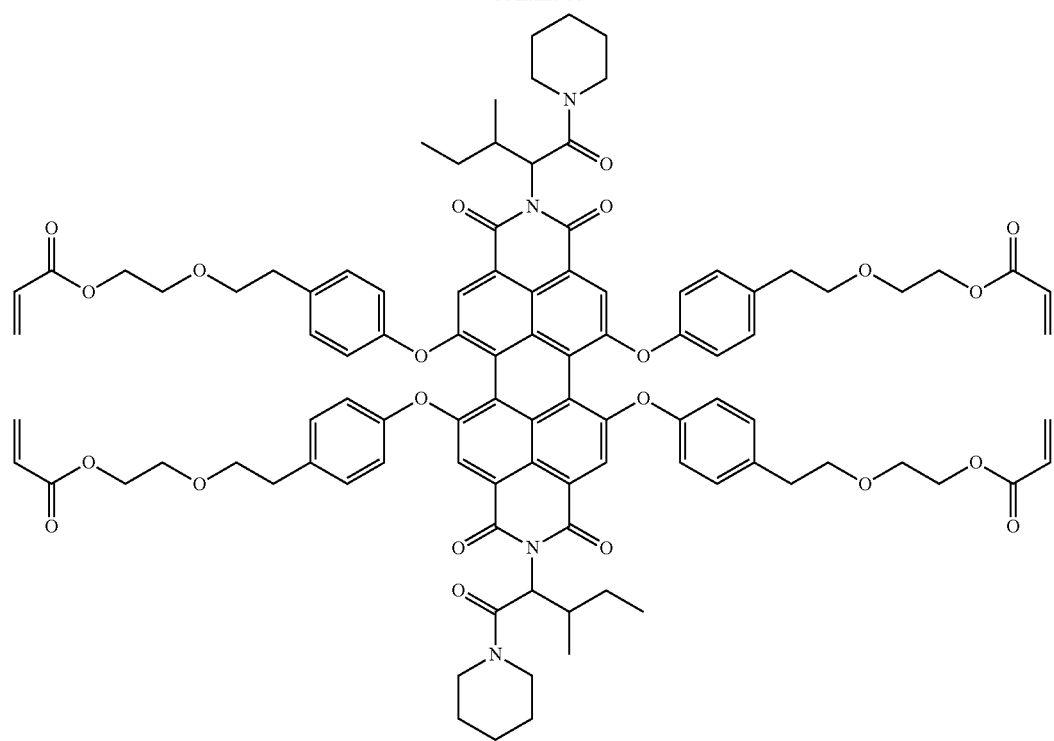
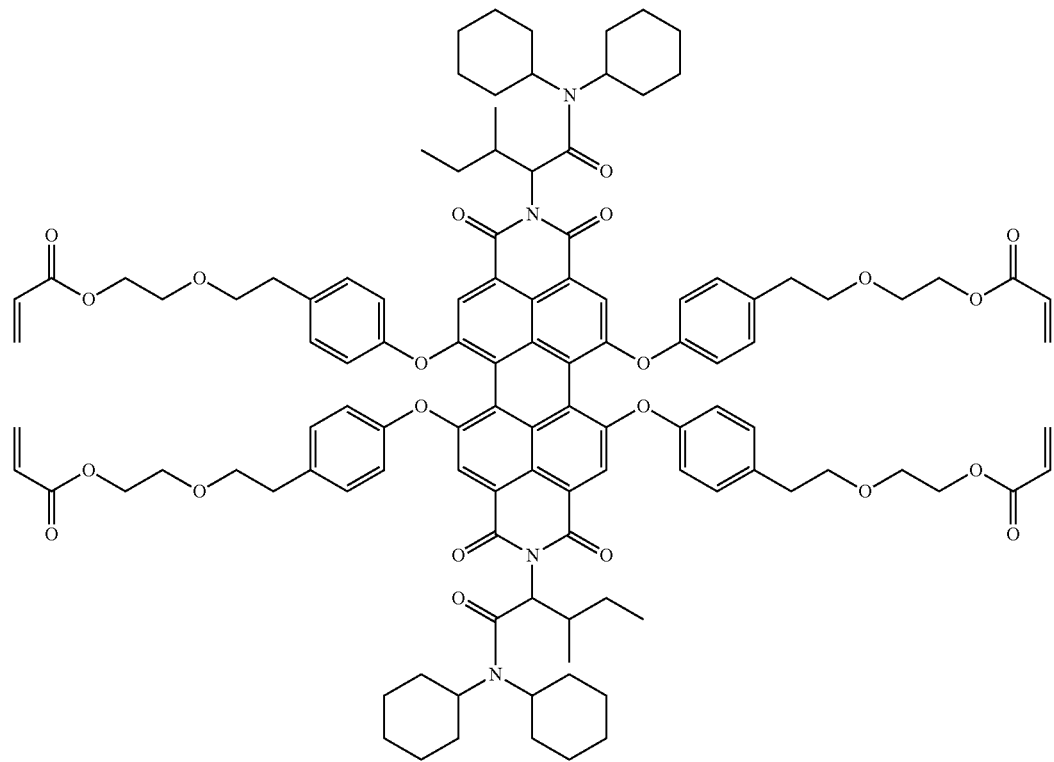

-continued
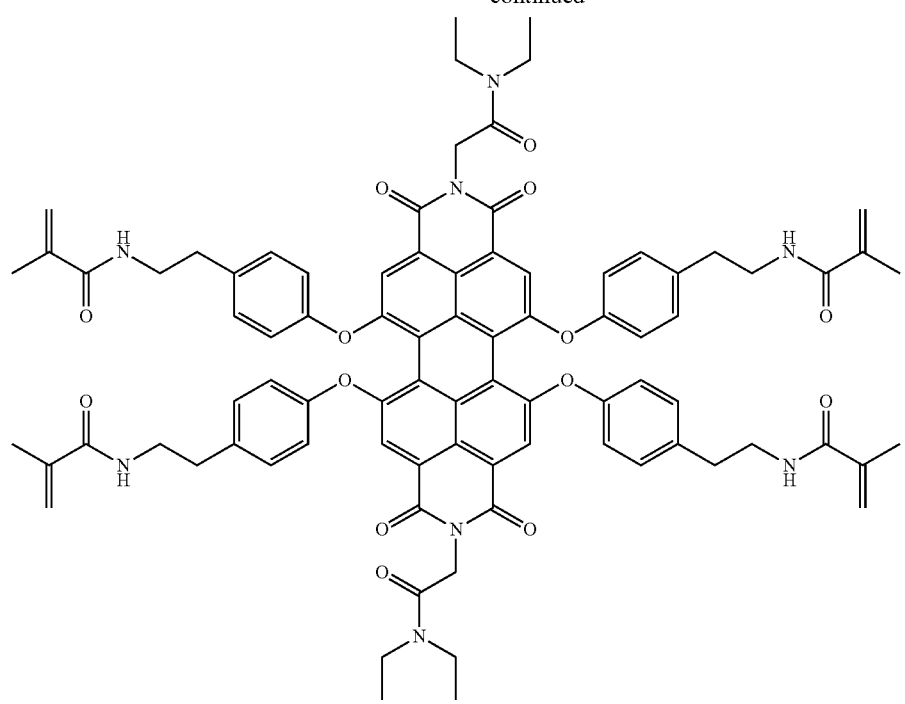
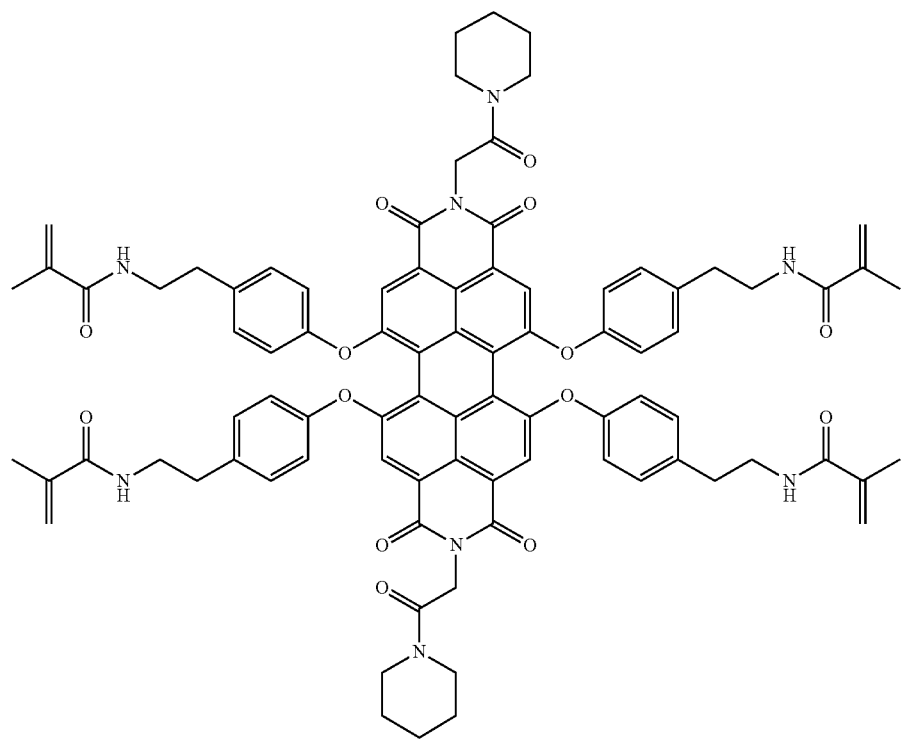

-continued
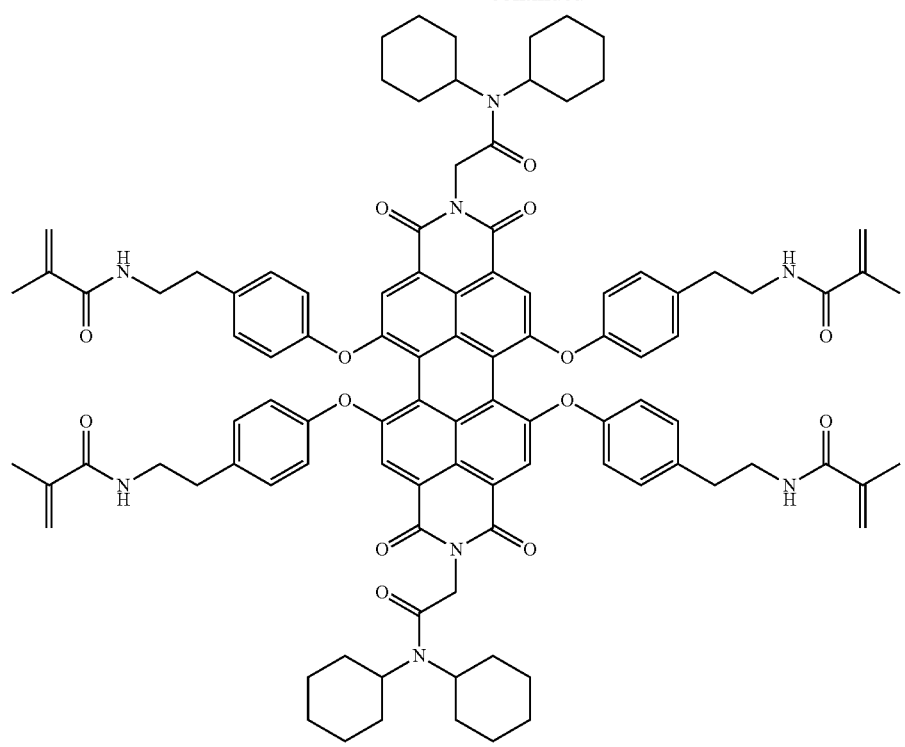
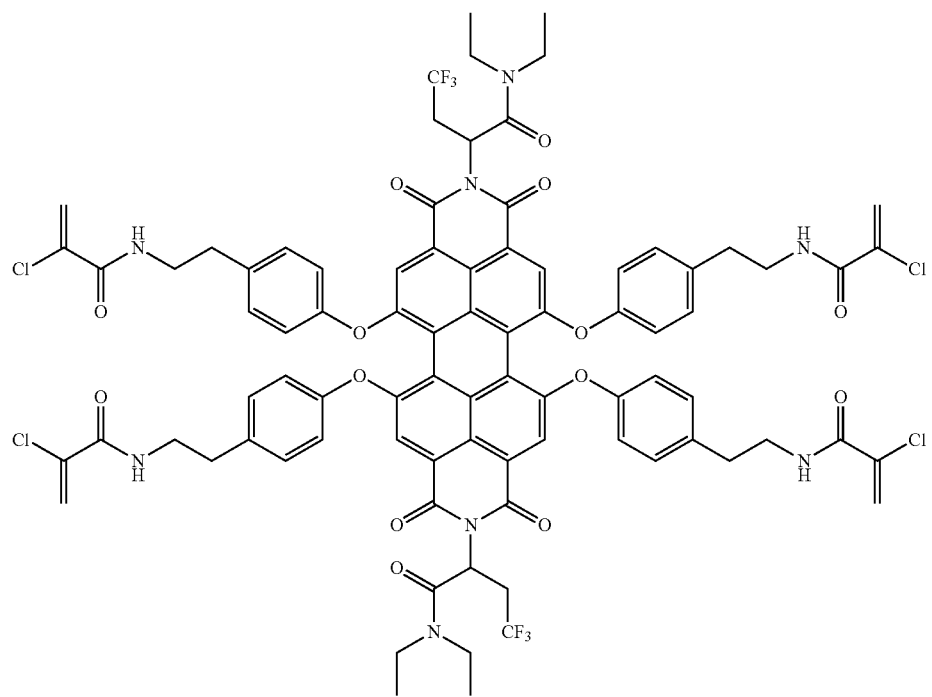

-continued
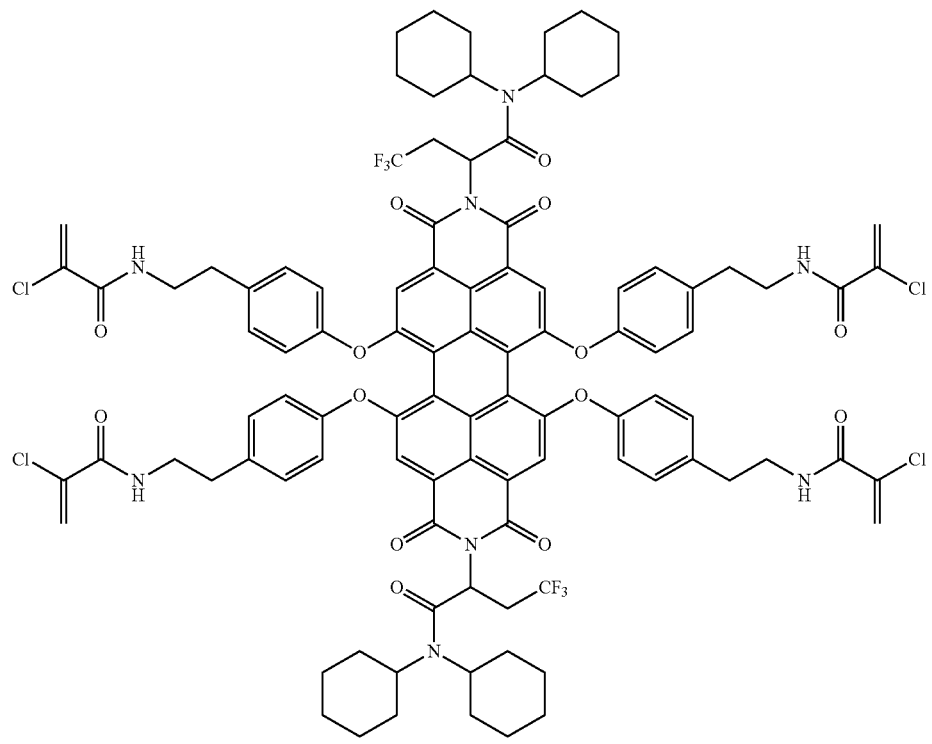

-continued
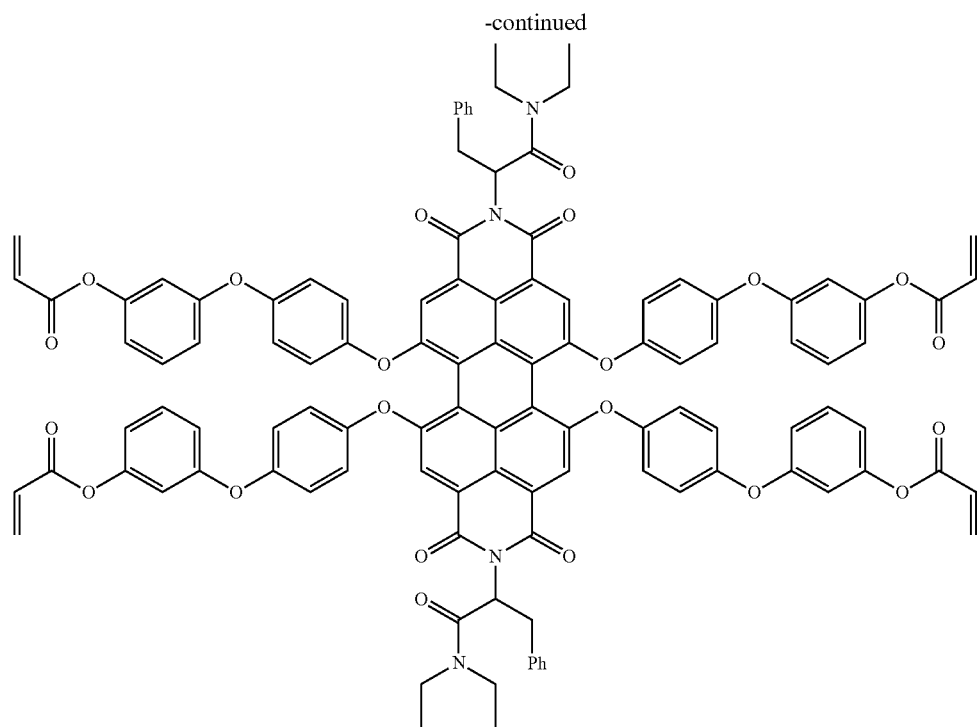
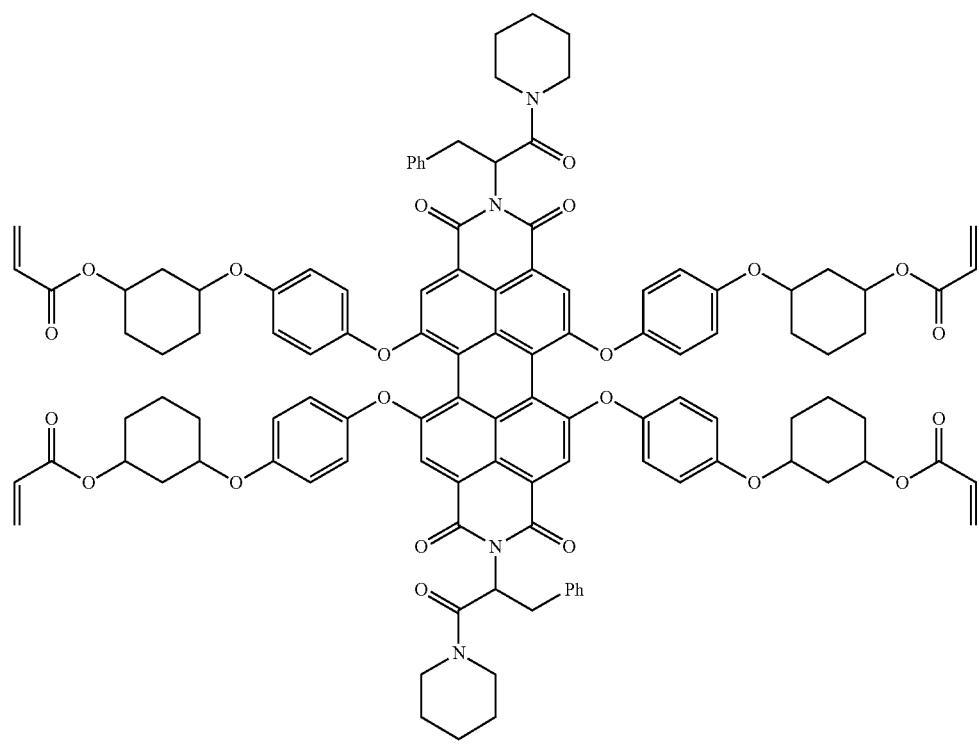

-continued
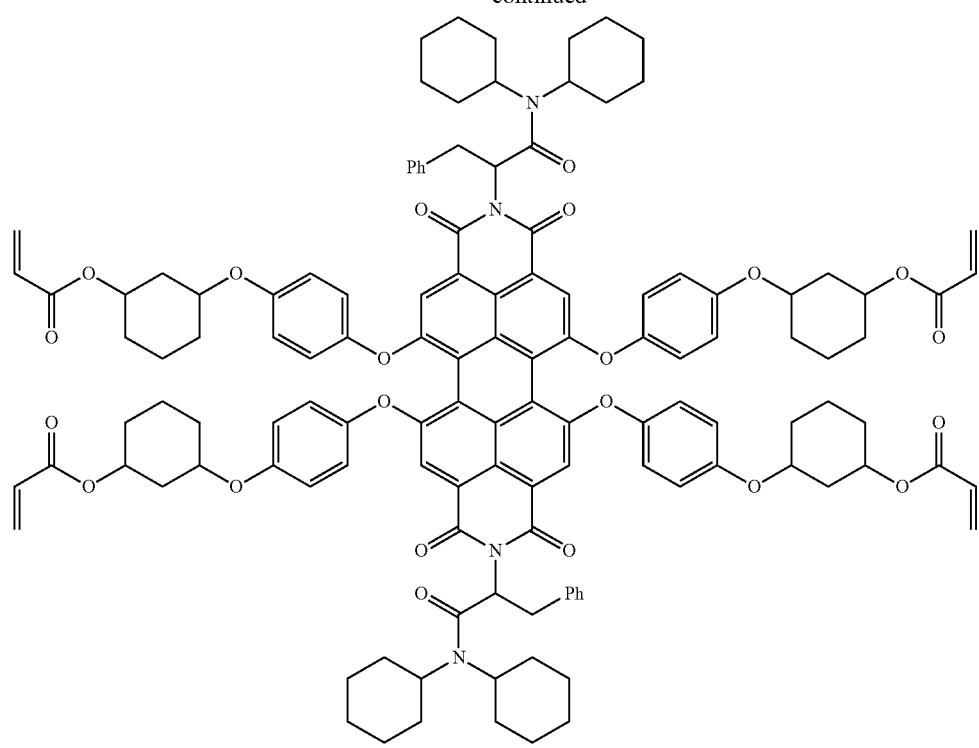
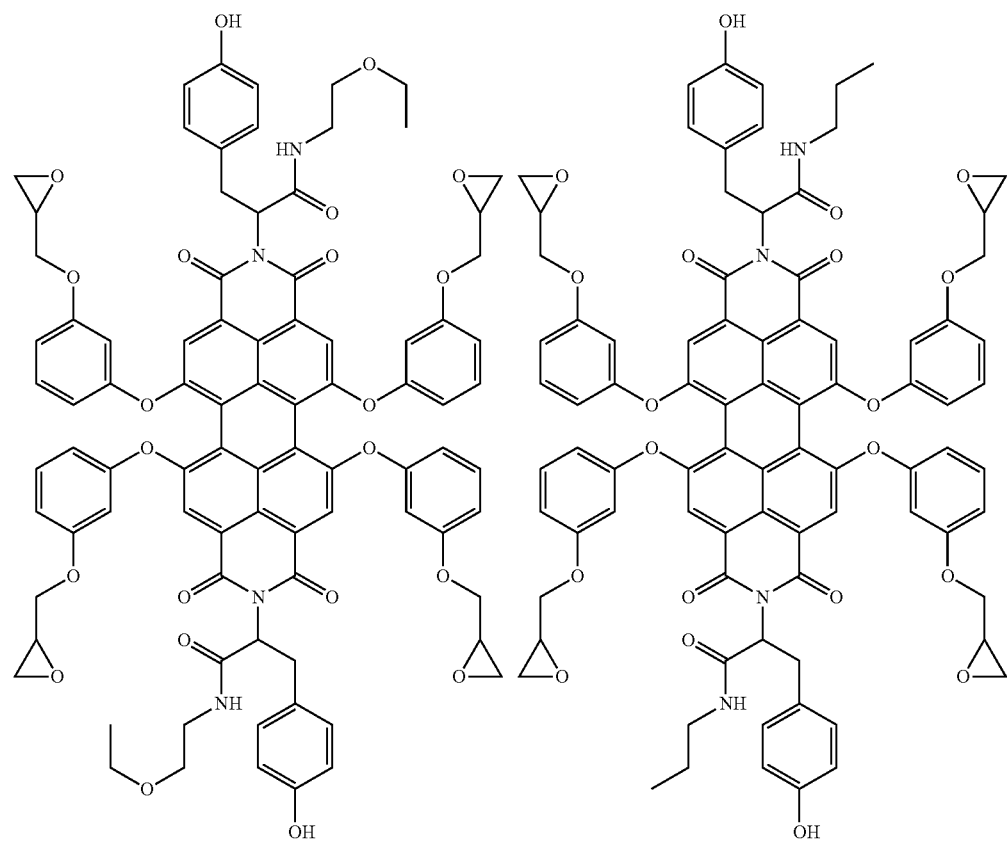

-continued
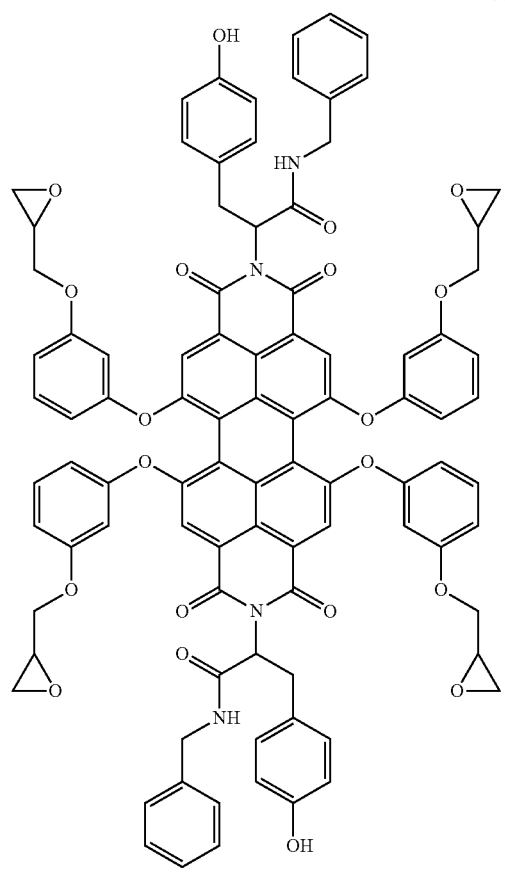
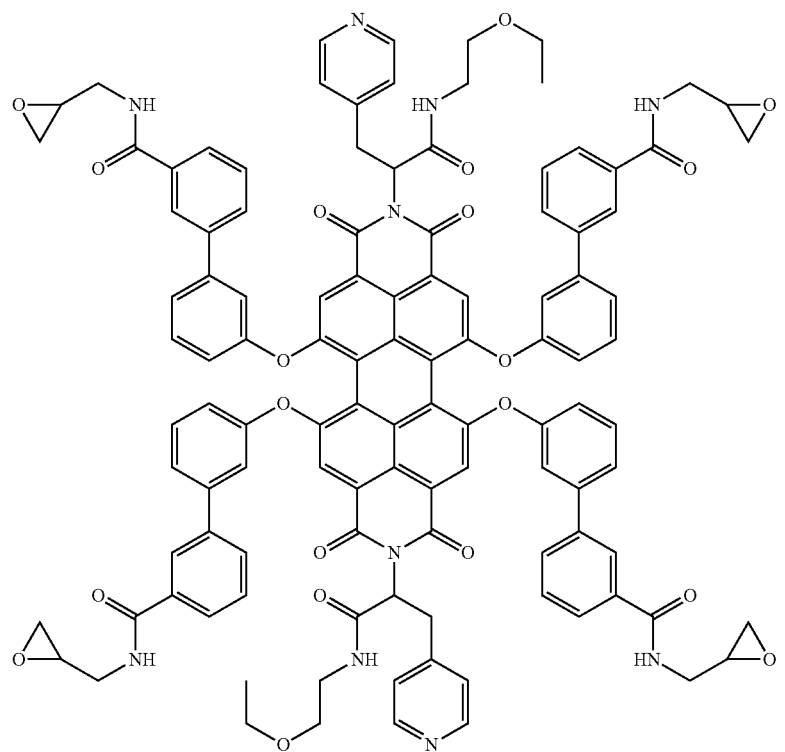

-continued
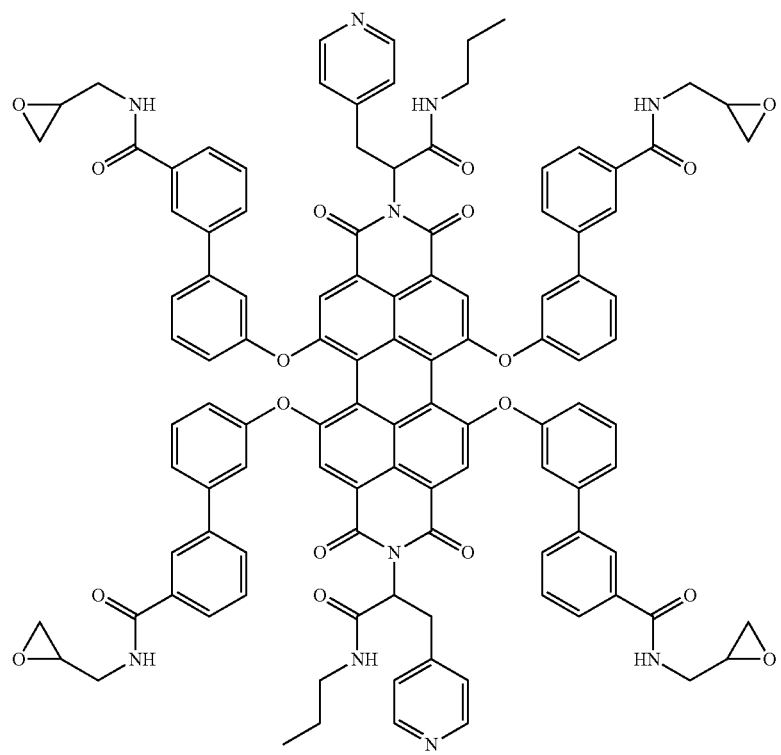
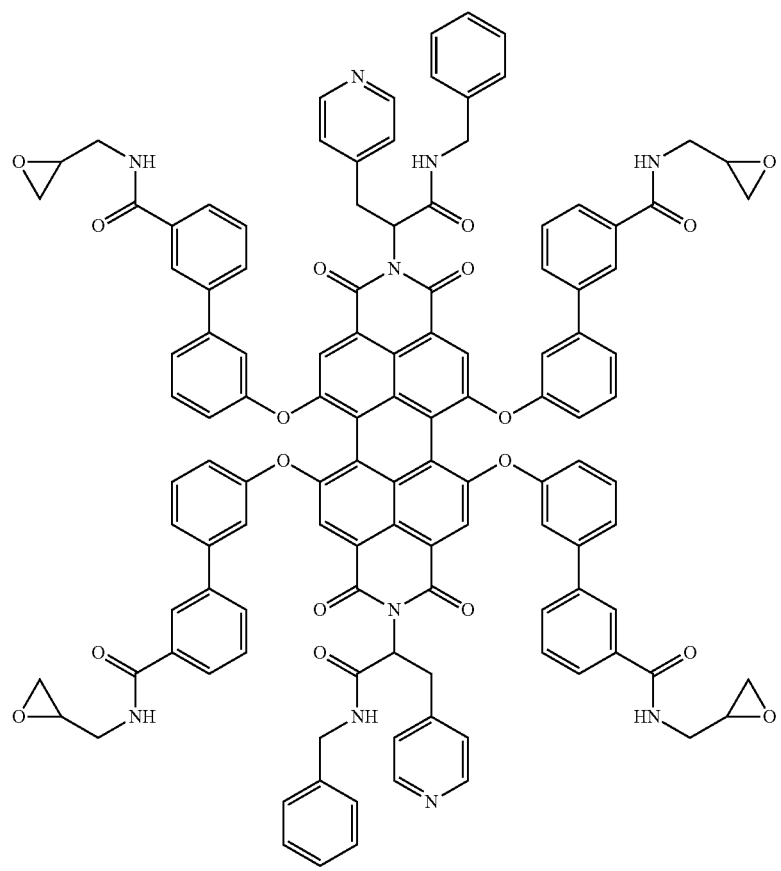

-continued
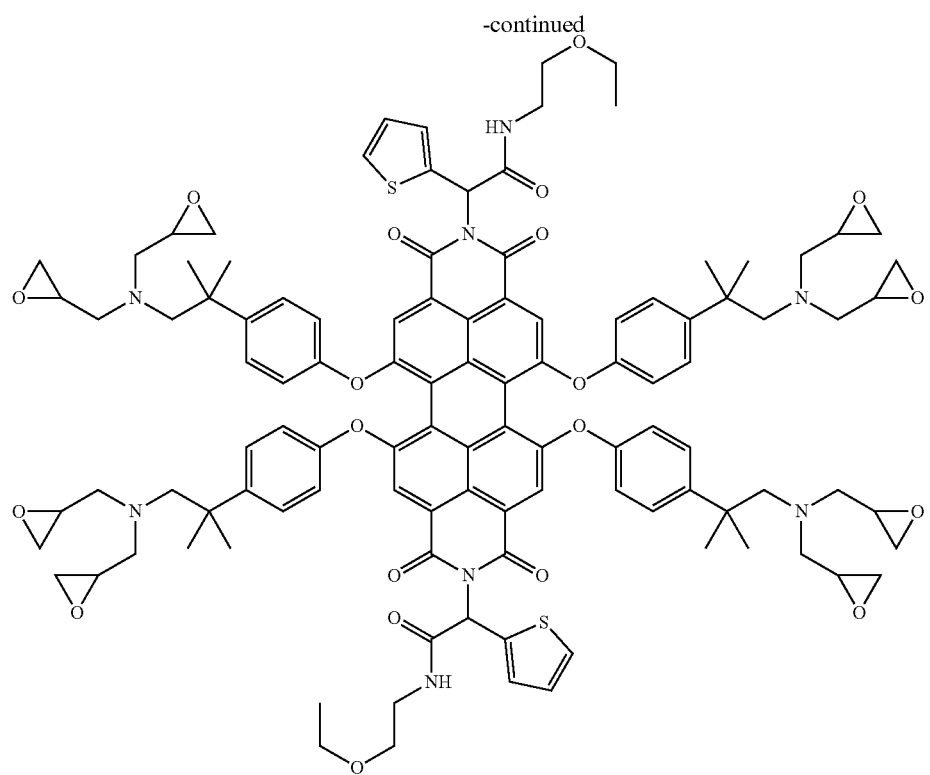
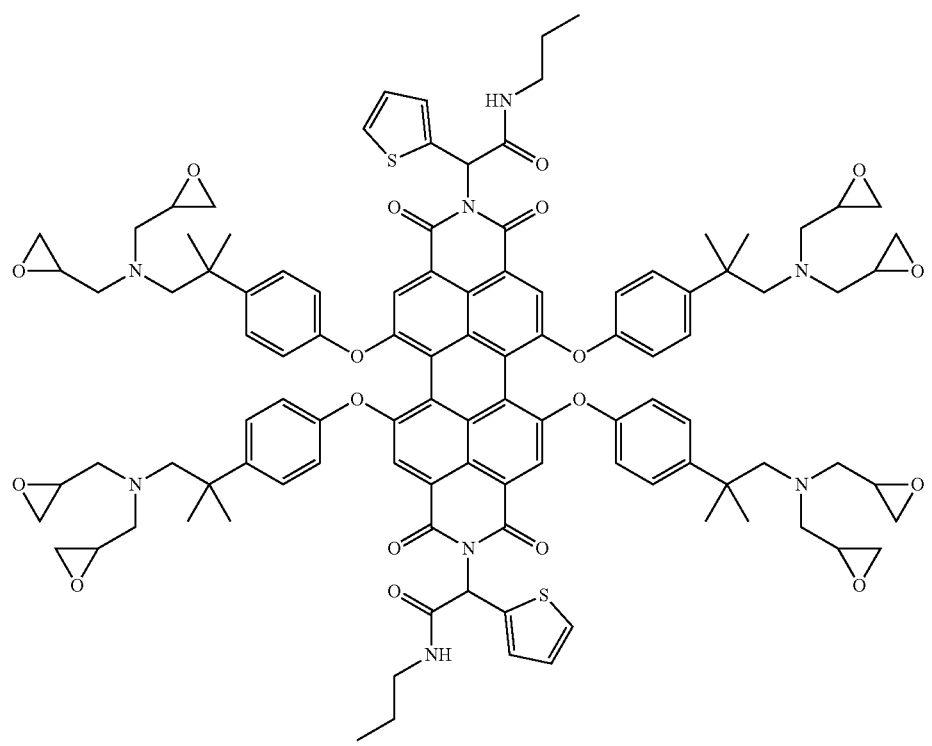

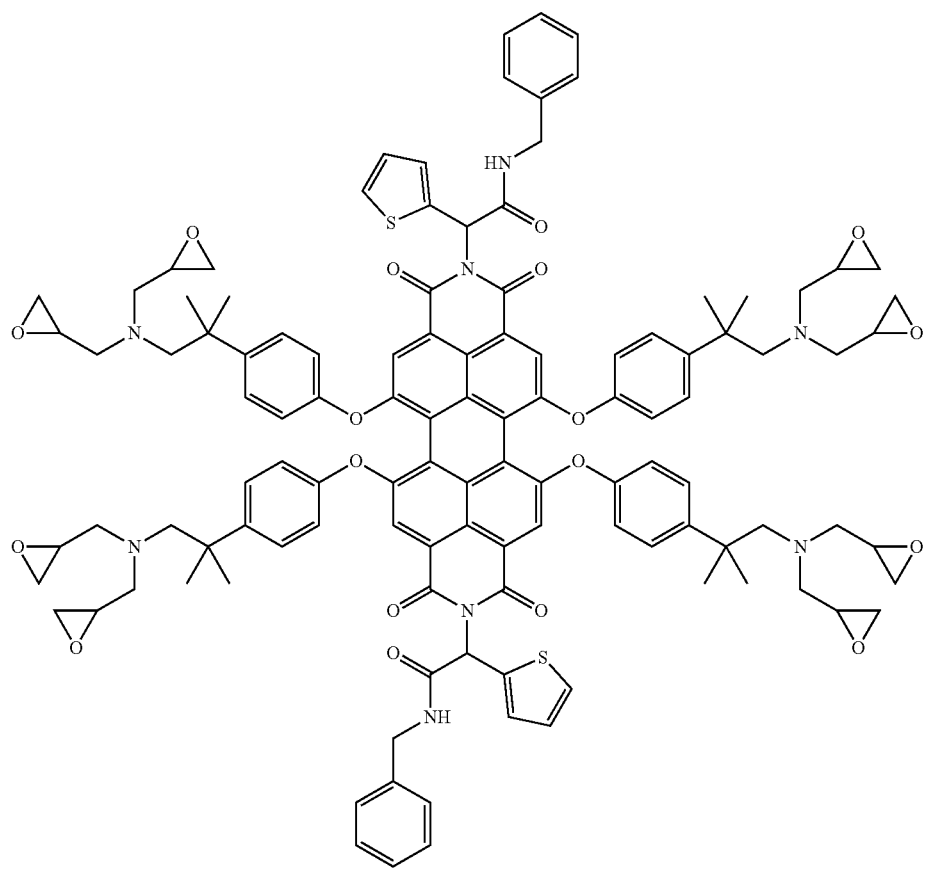
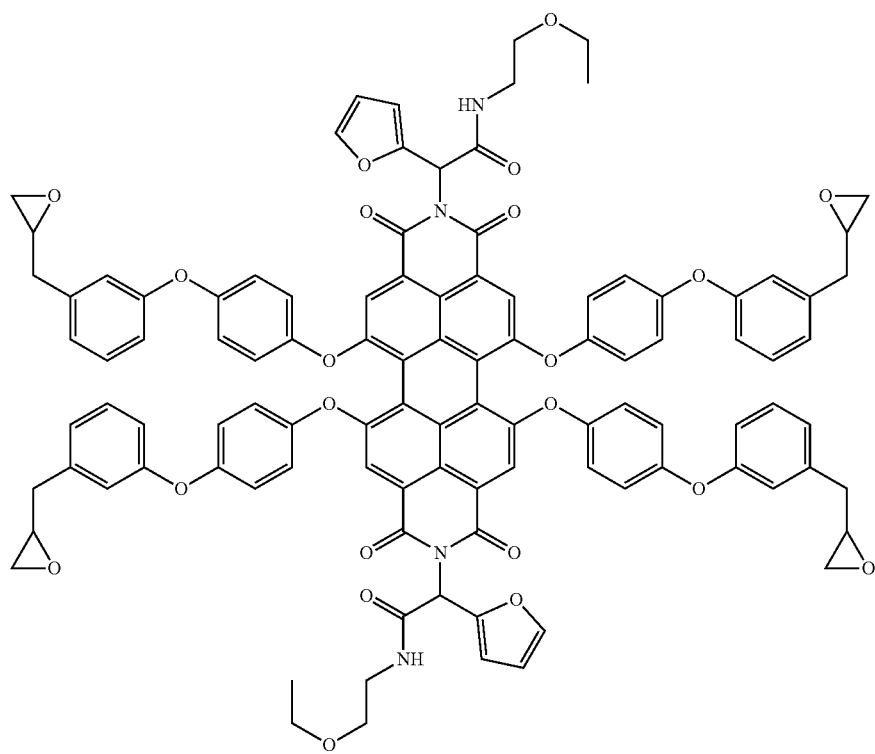

-continued
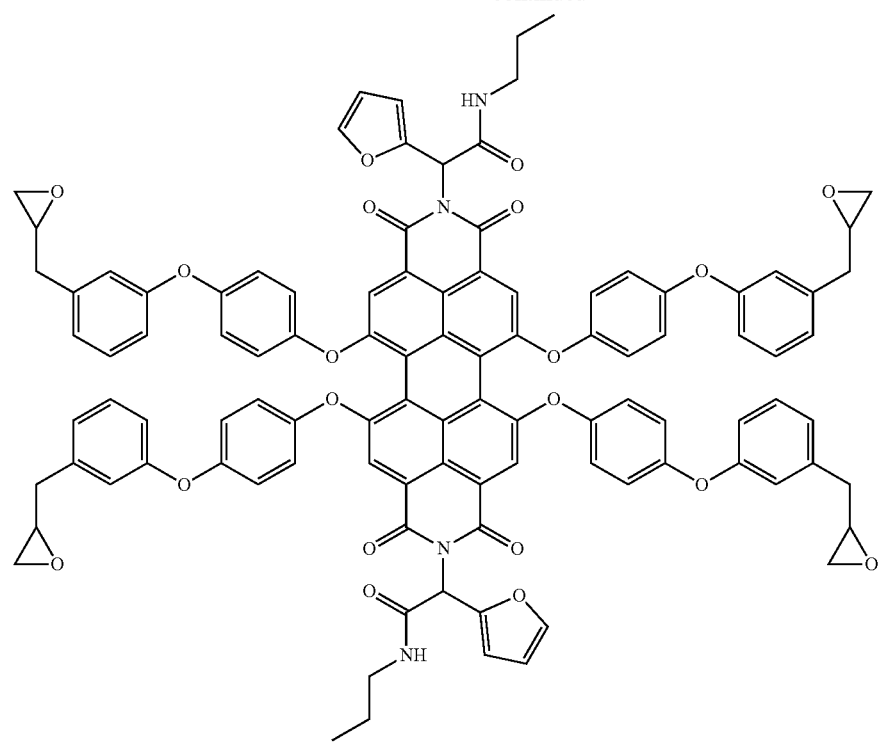
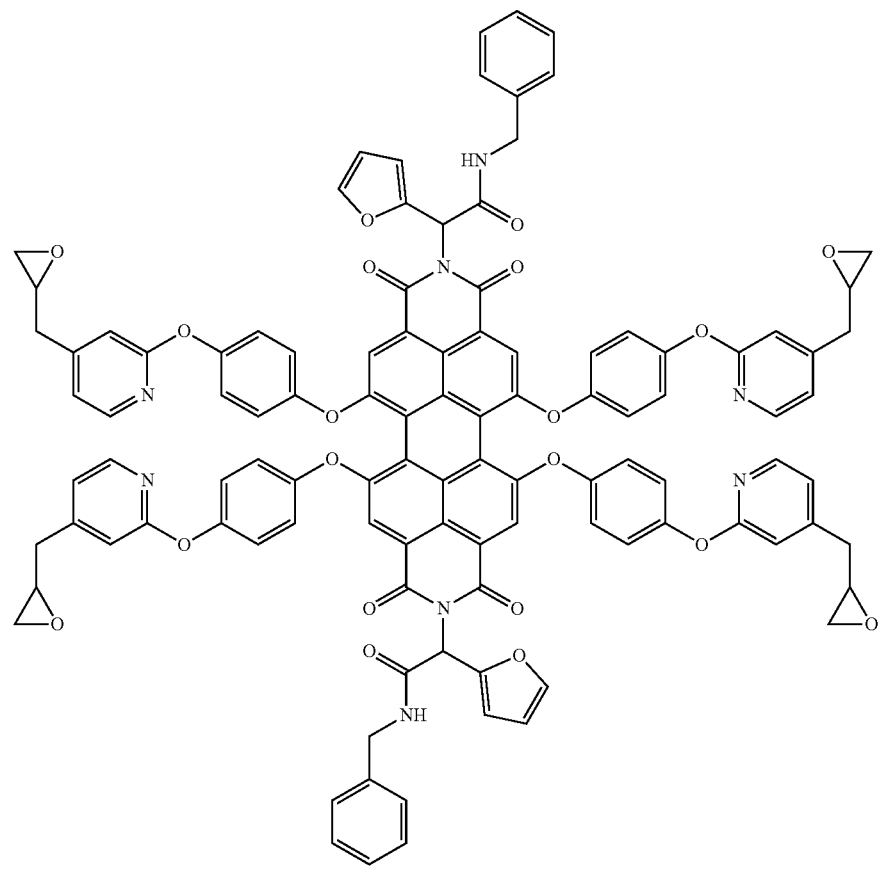

-continued
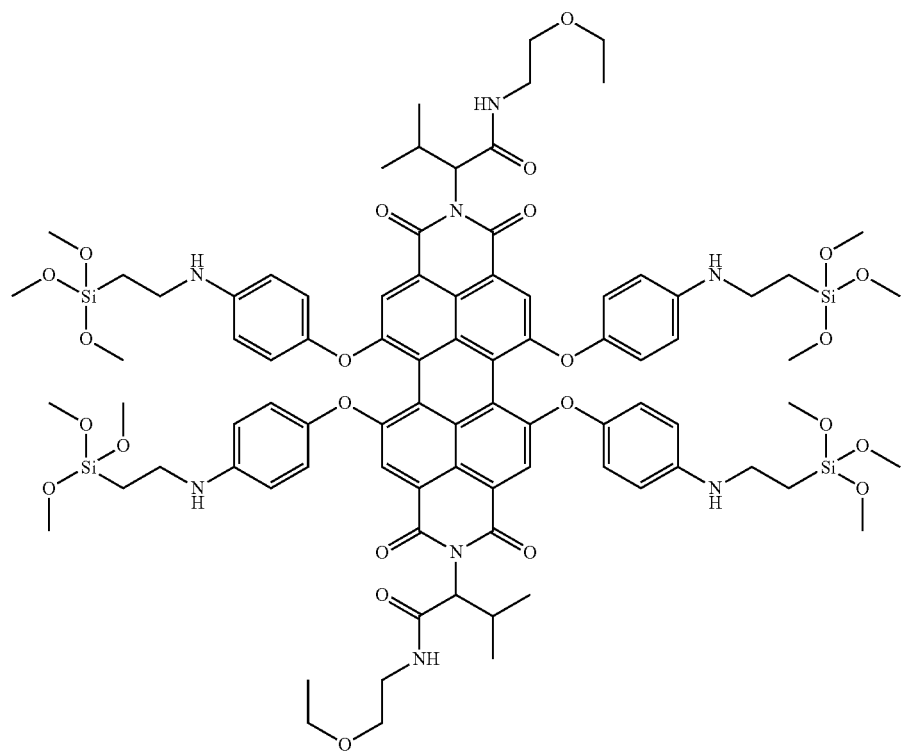
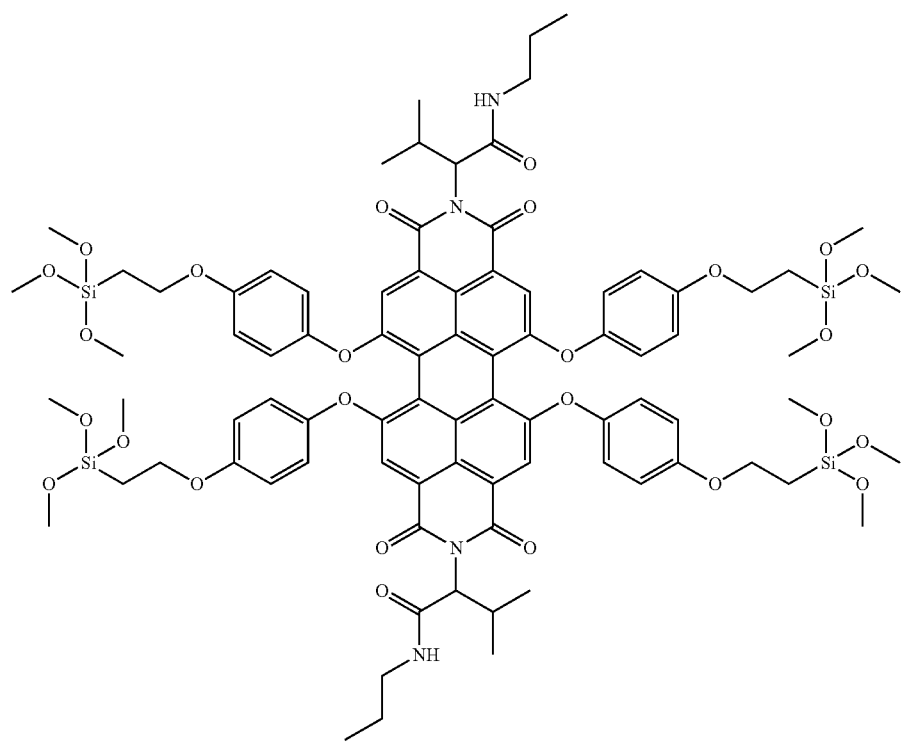

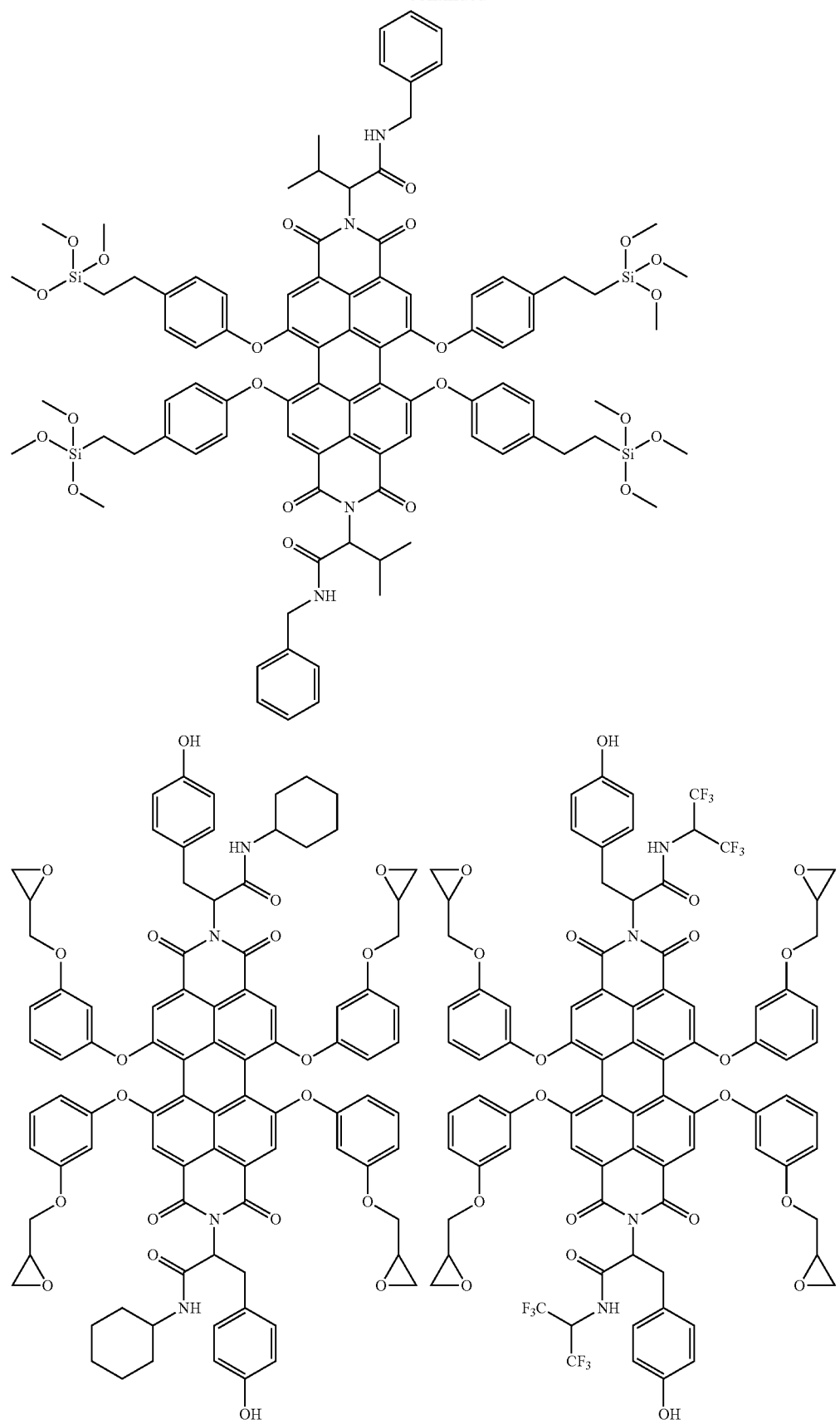

-continued
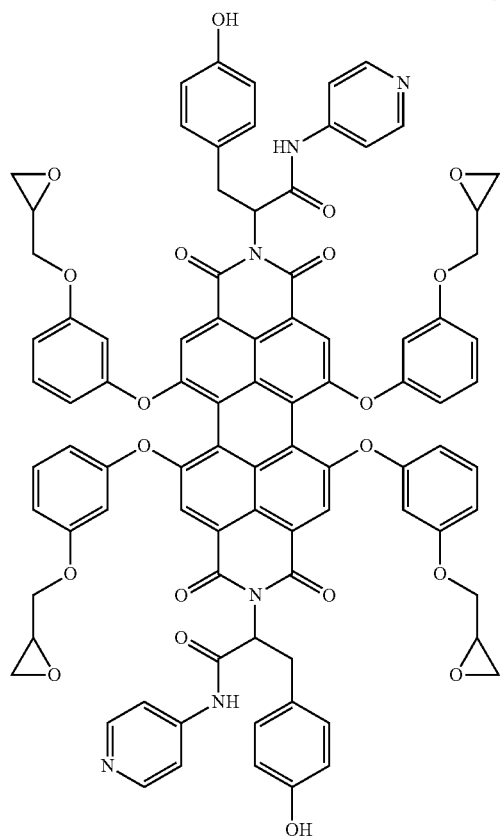
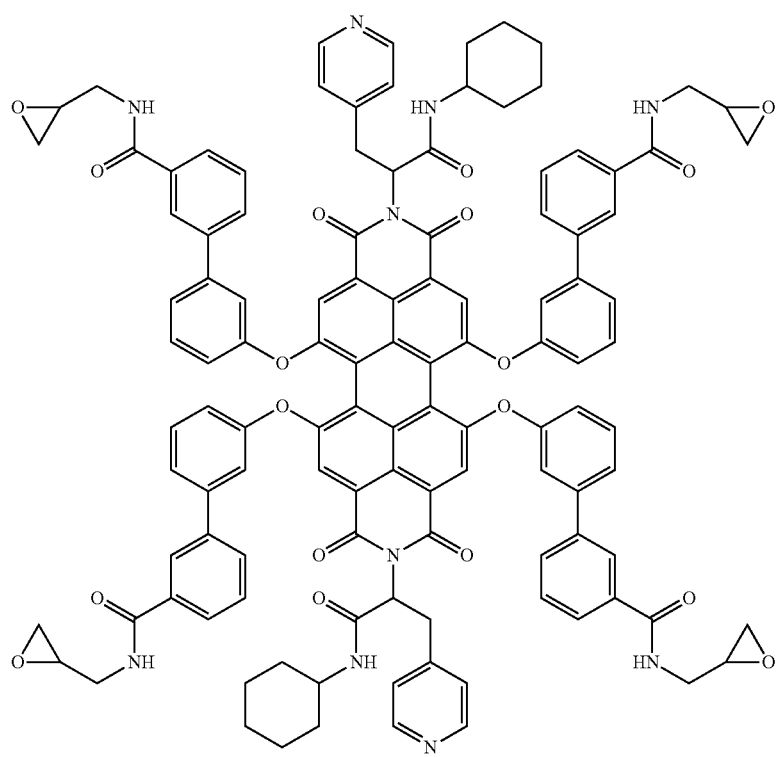

-continued
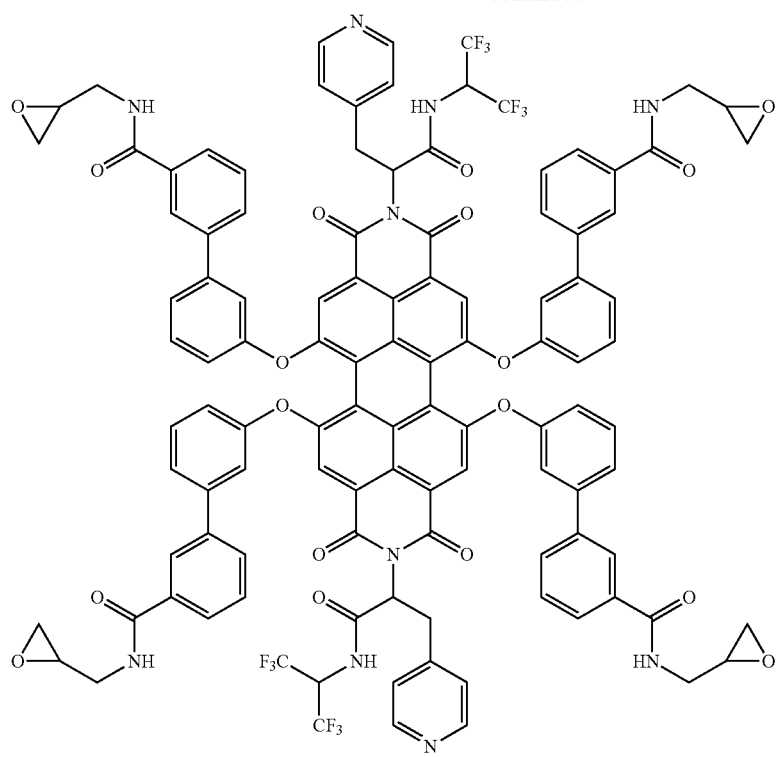
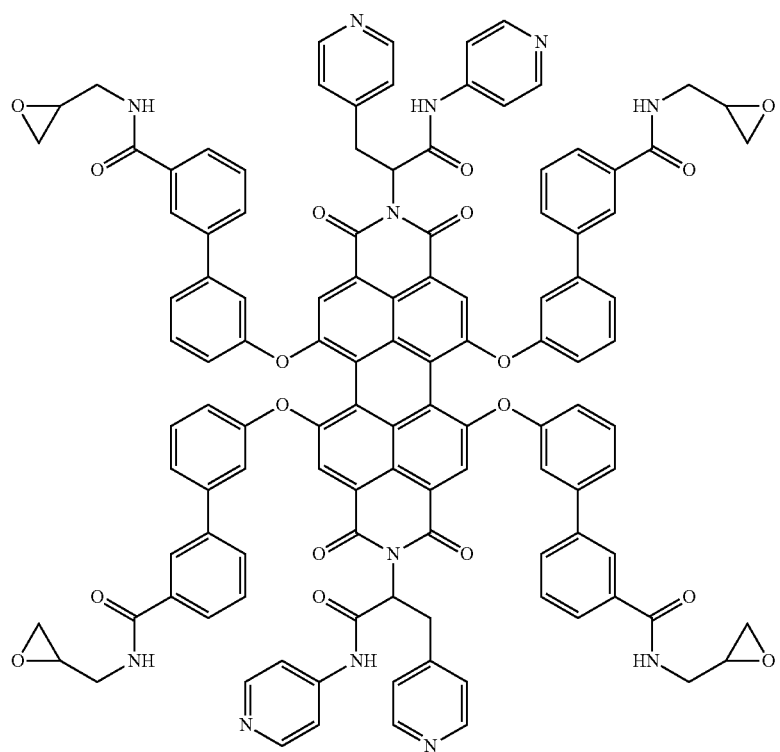

-continued
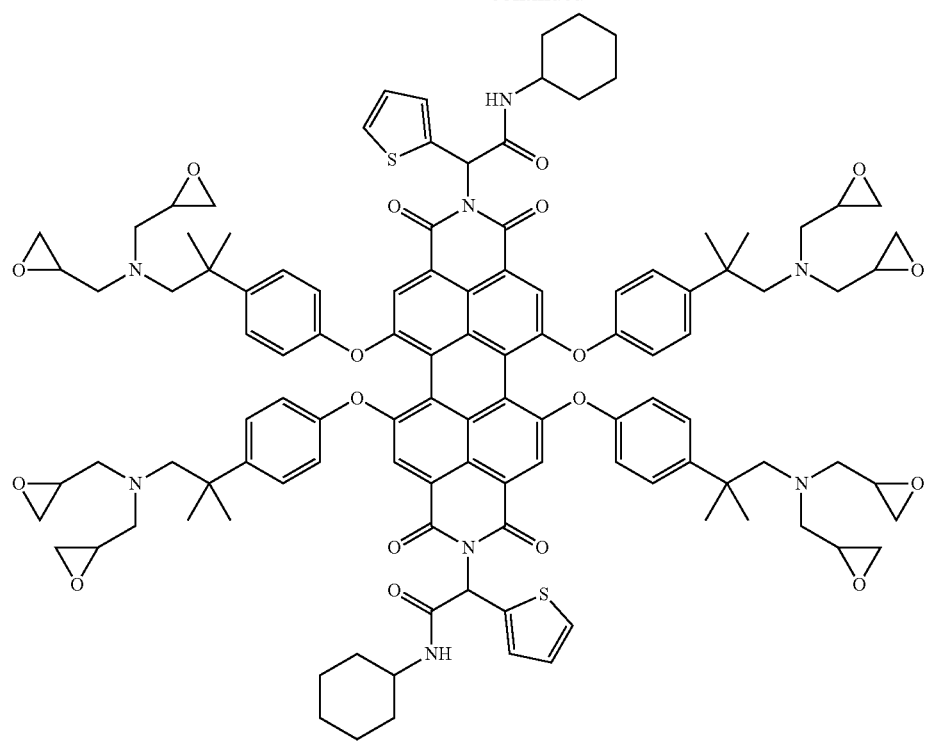
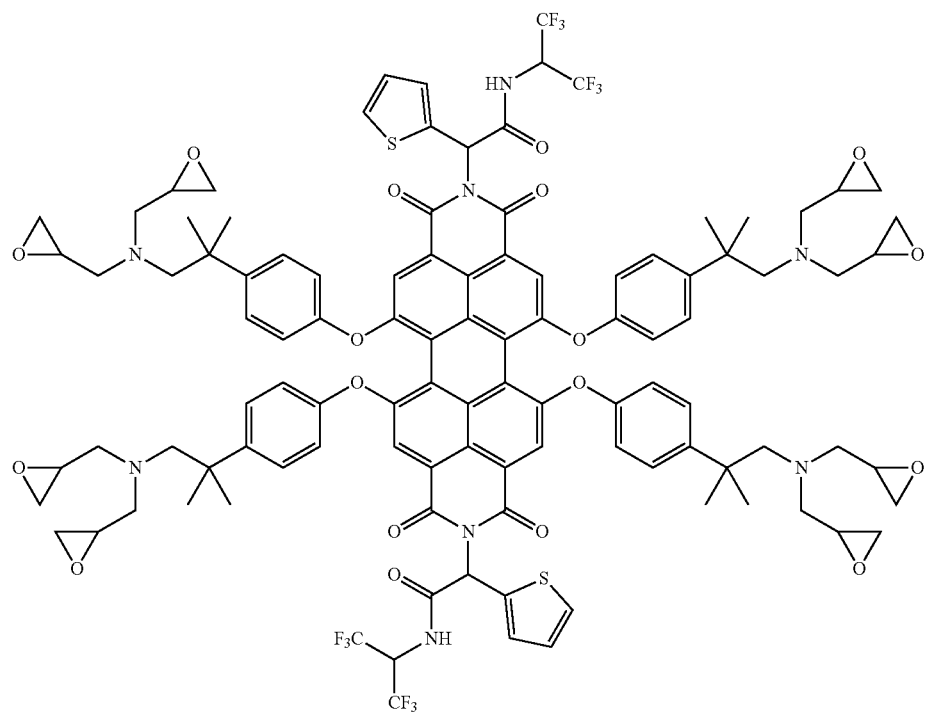

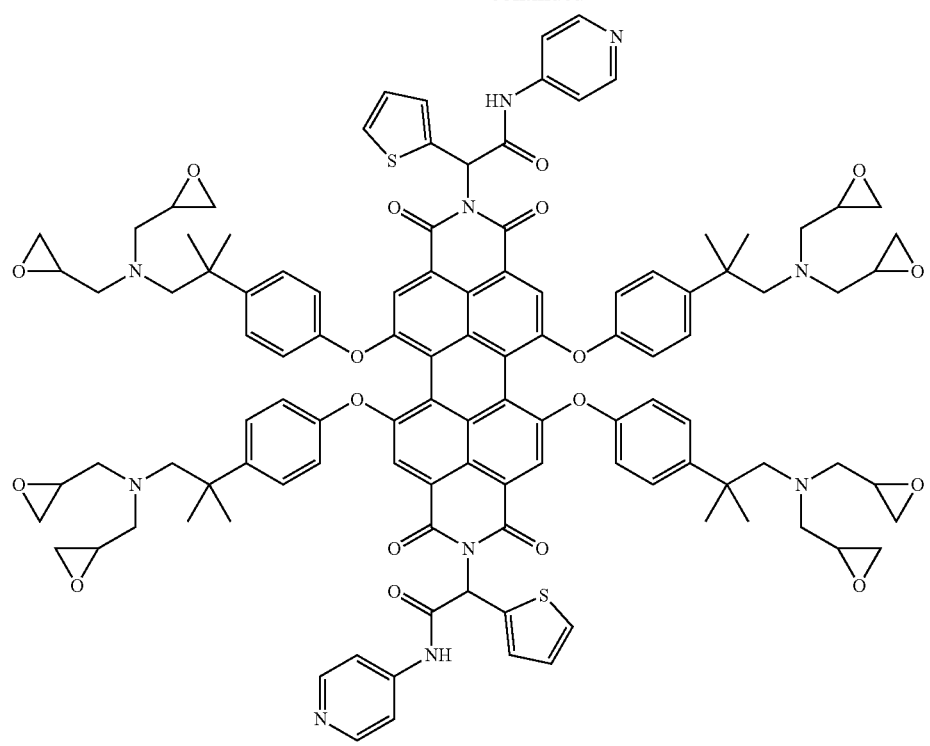
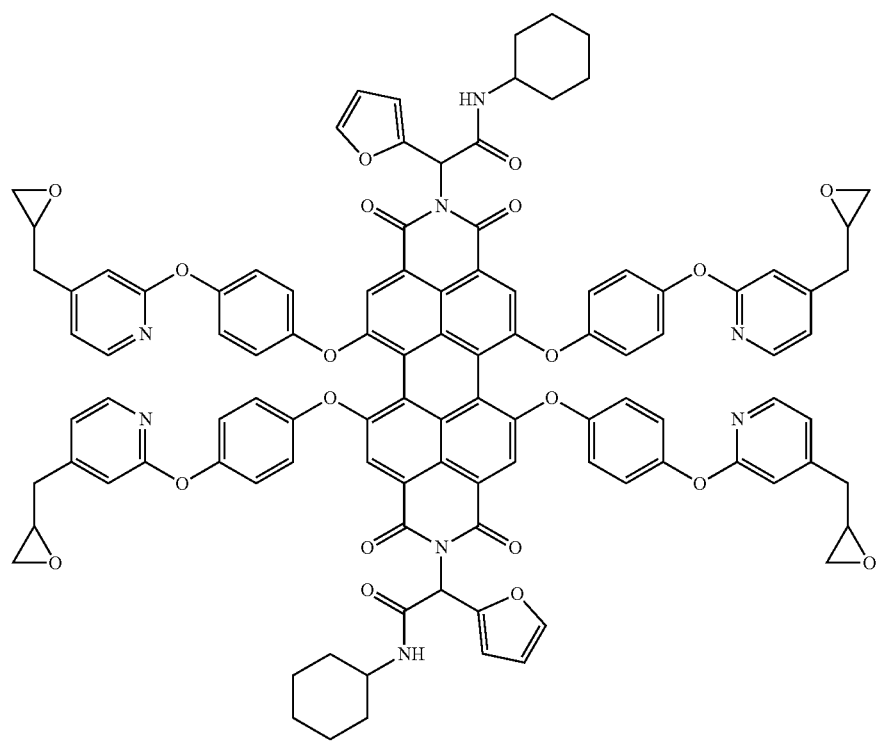

-continued
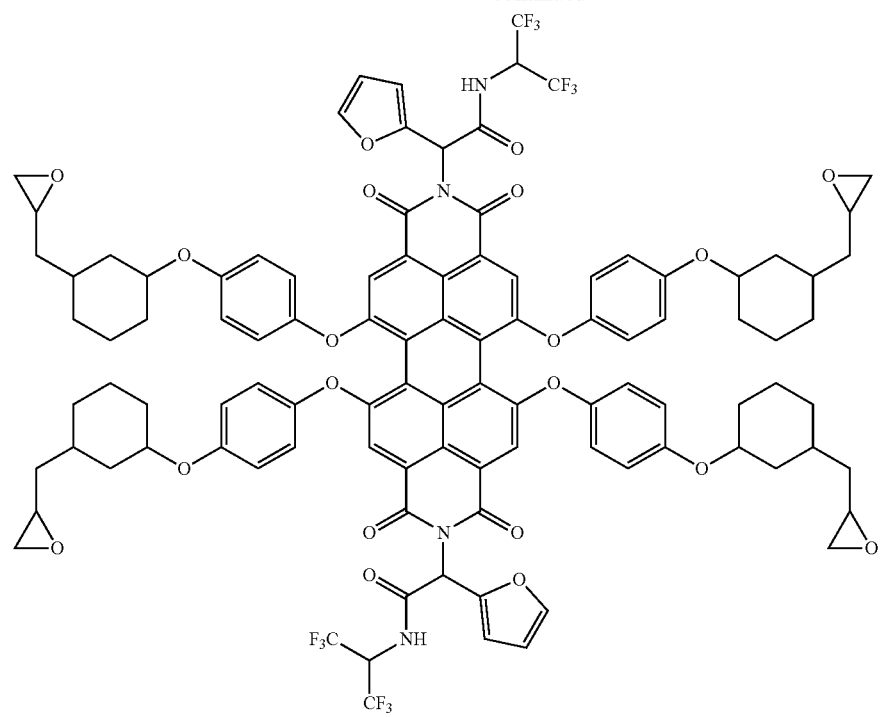
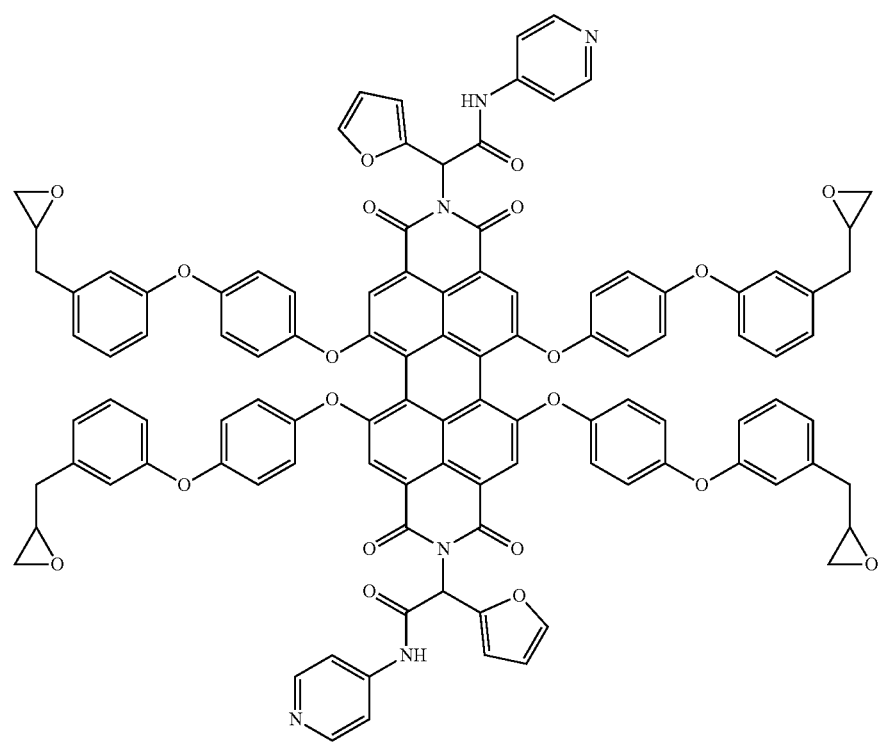

-continued
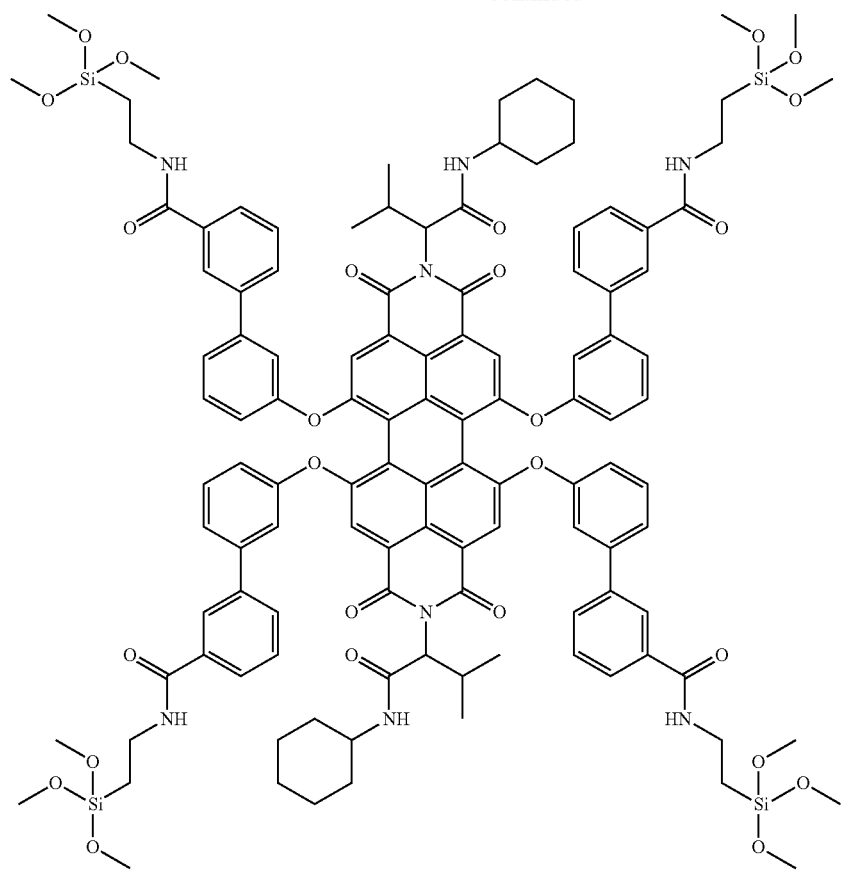
201
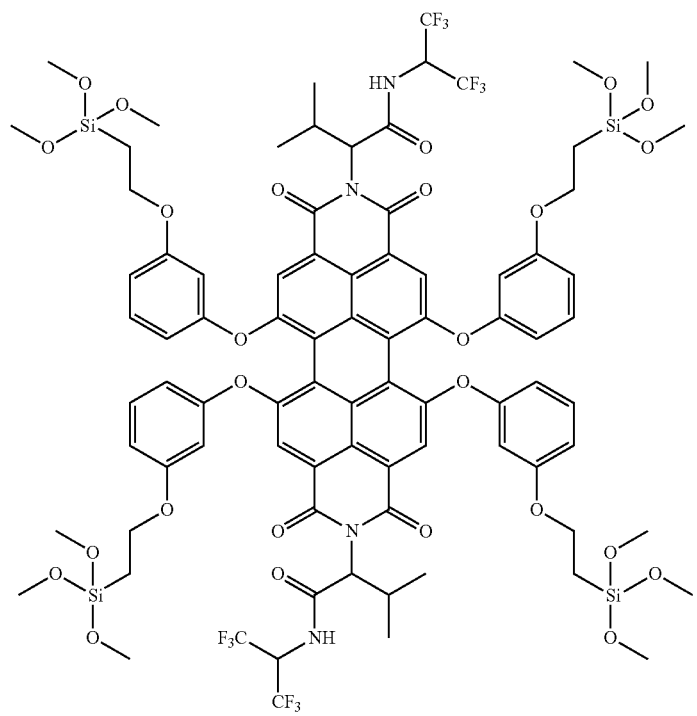
202

-continued
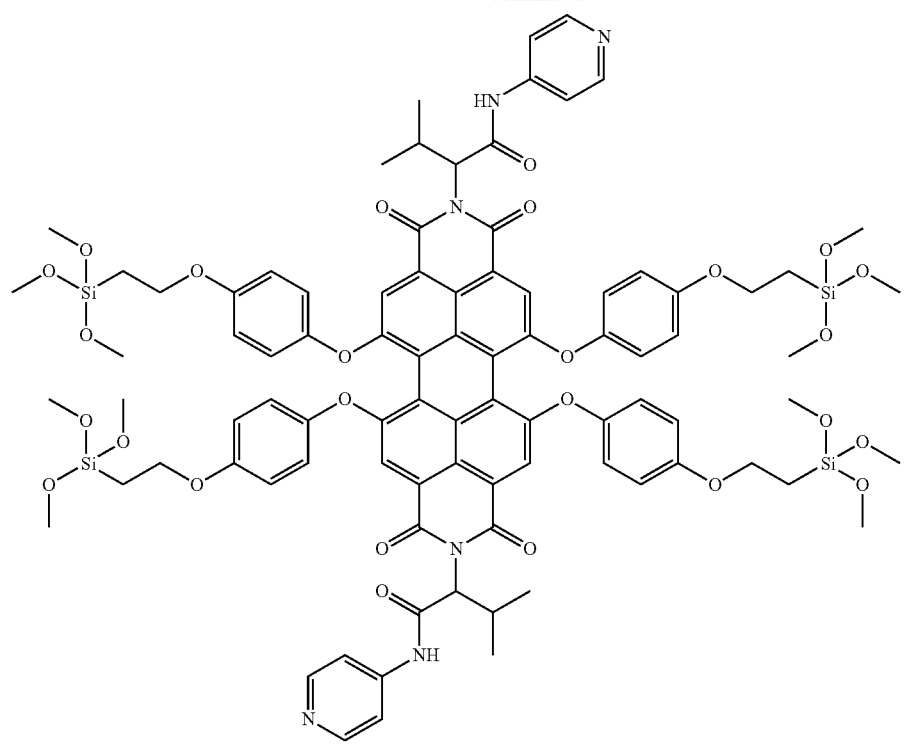
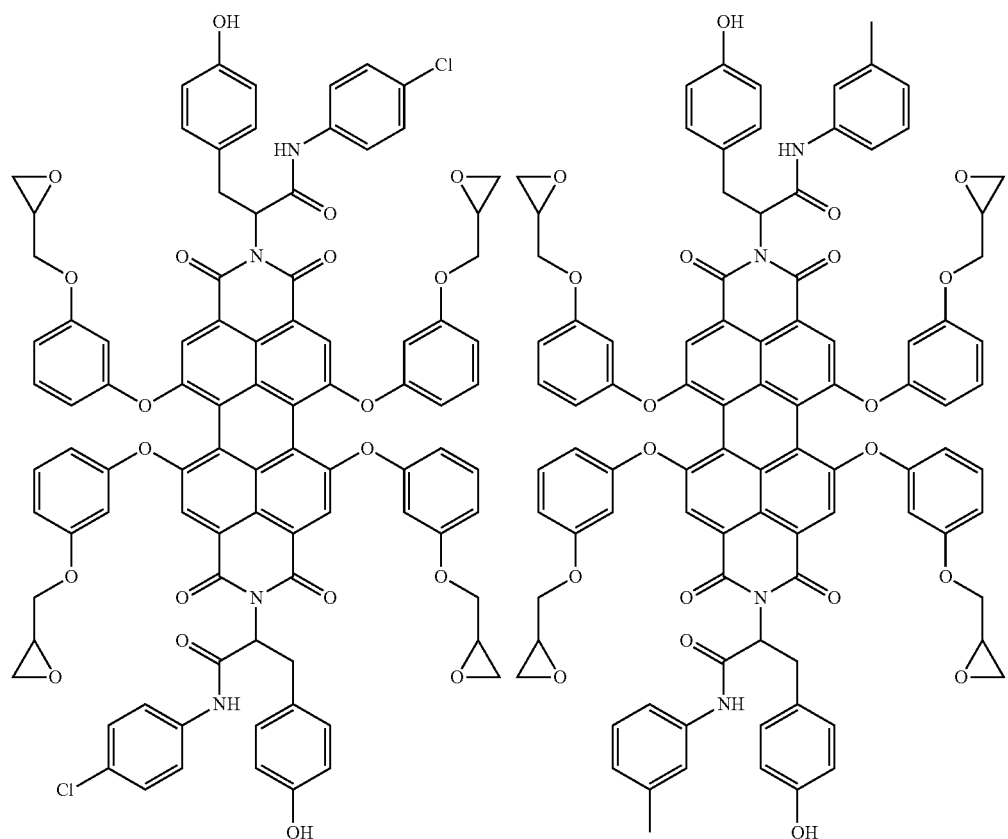

205
206
-continued
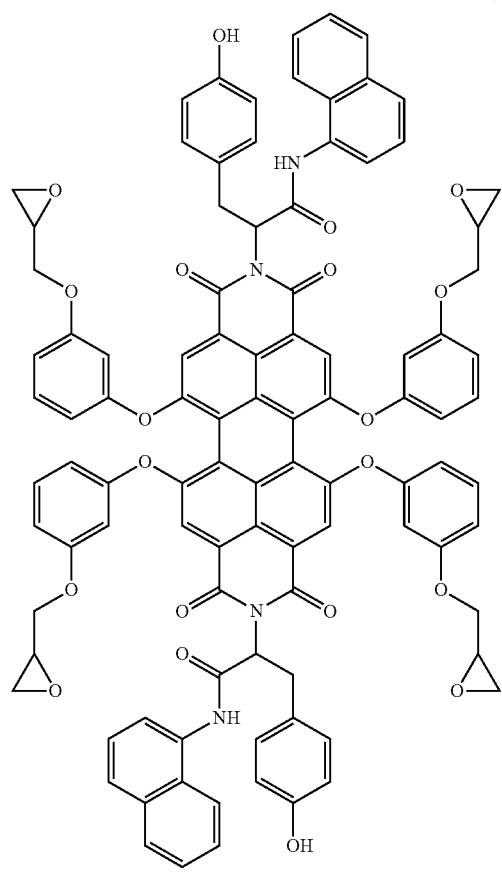
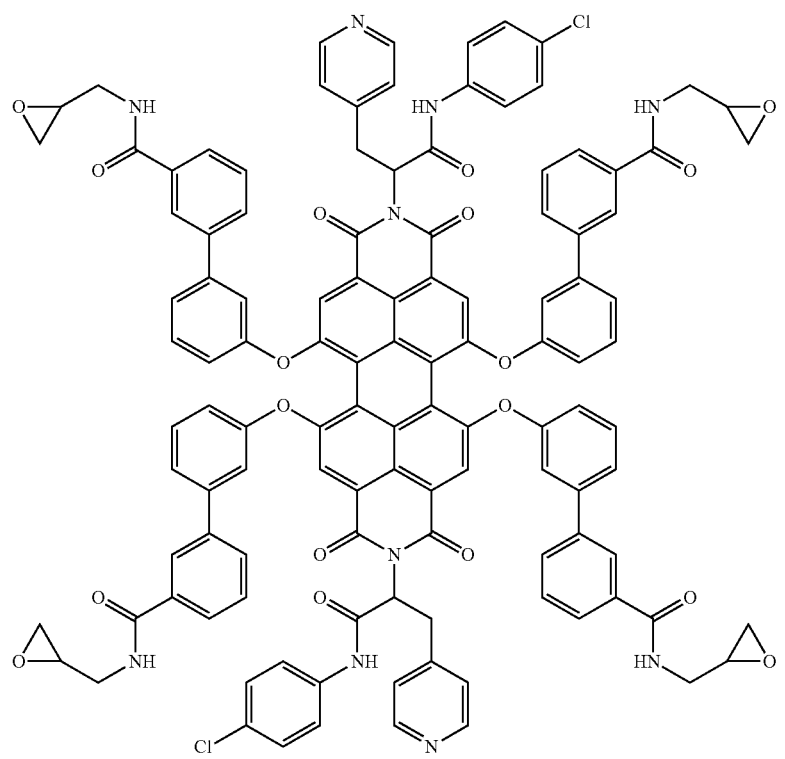

-continued
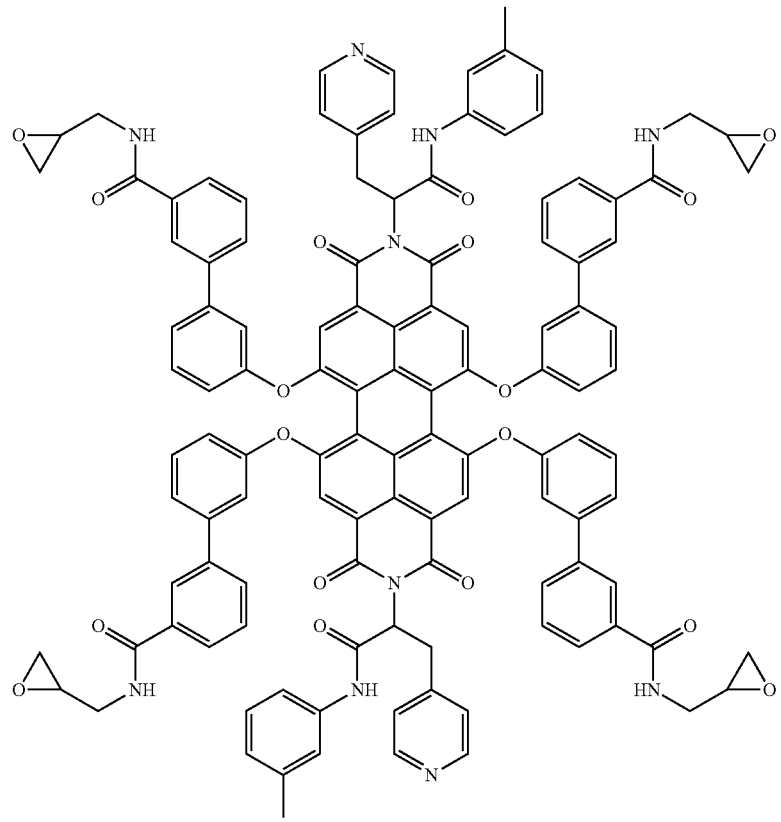
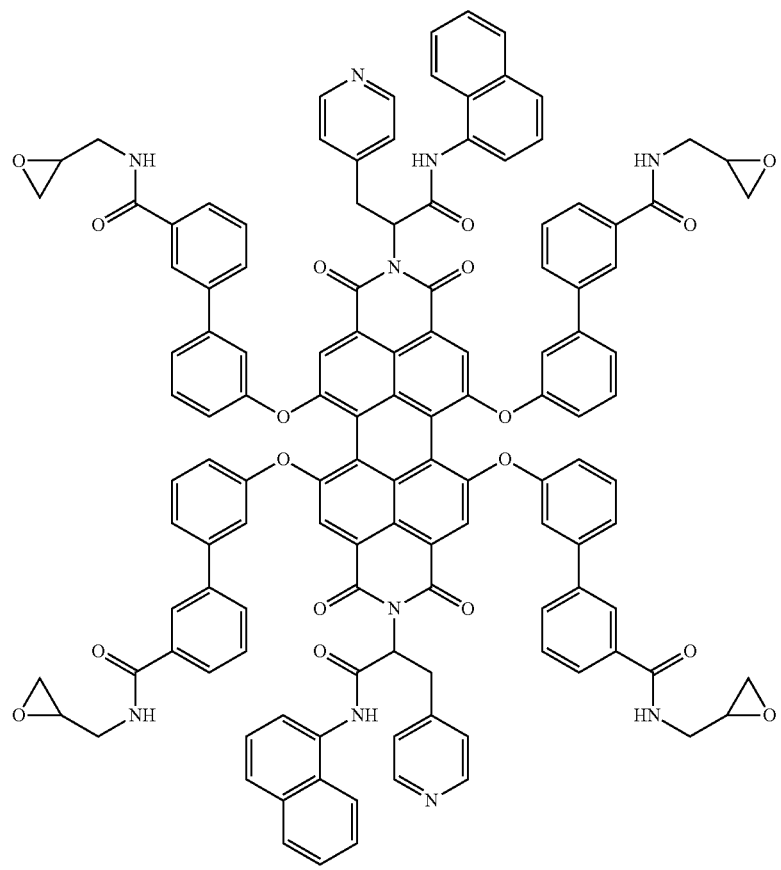

-continued
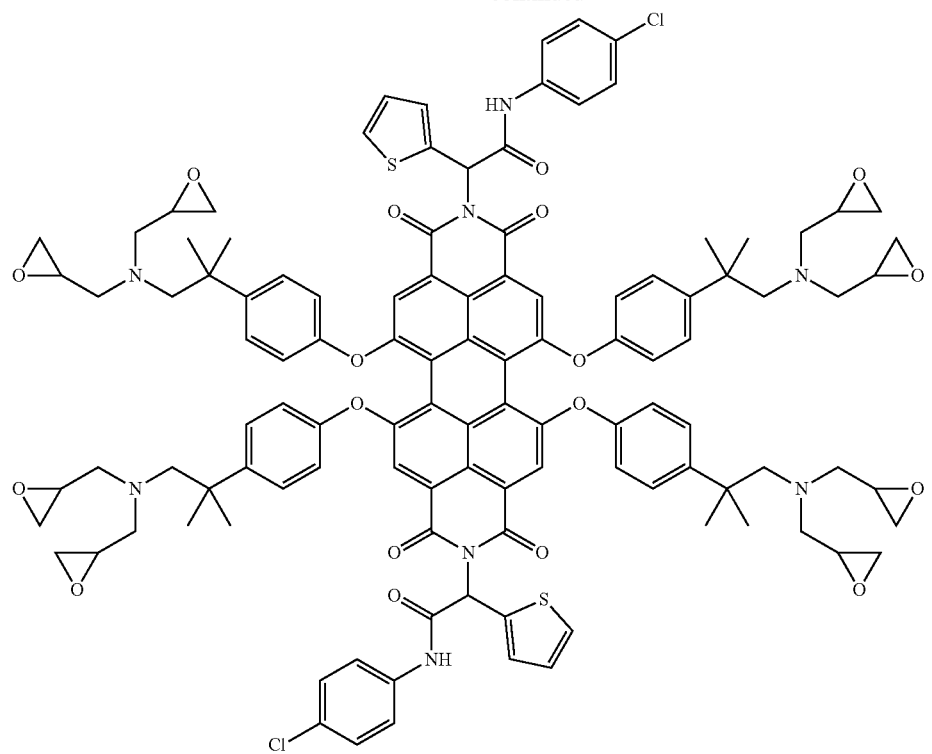
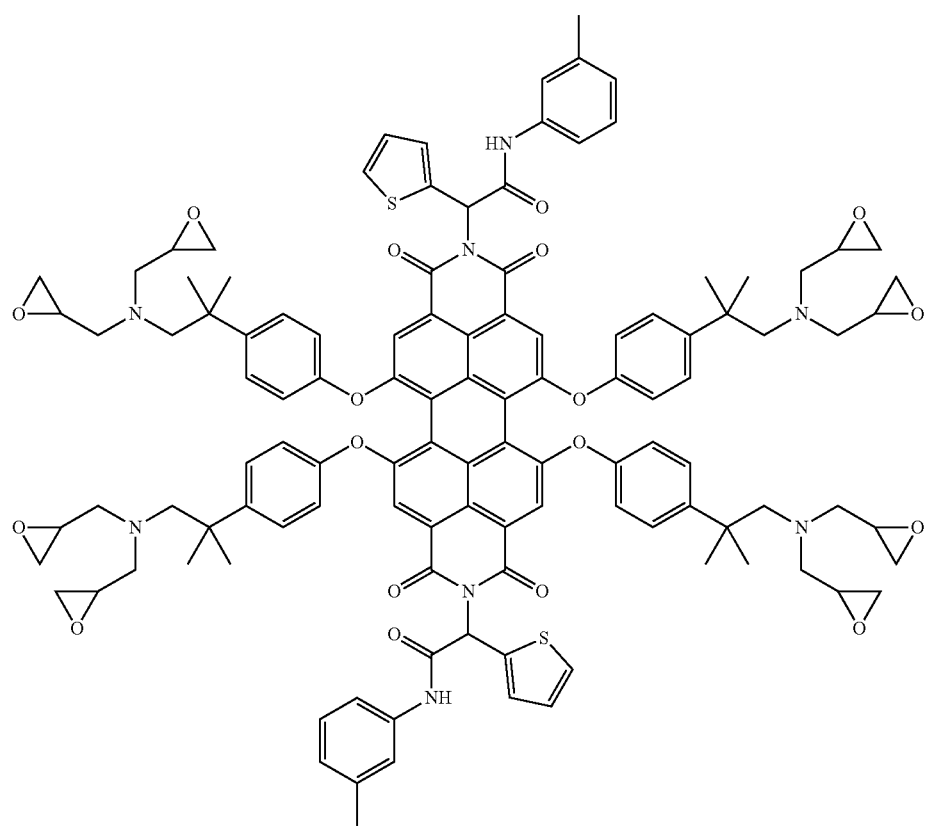

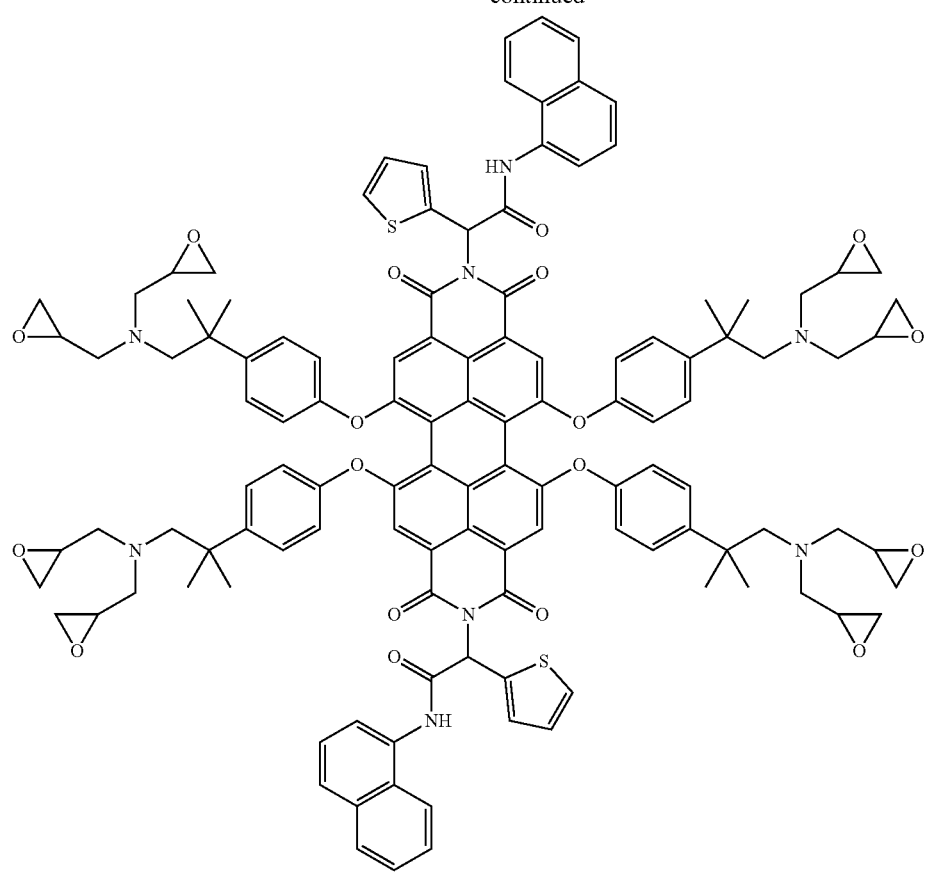
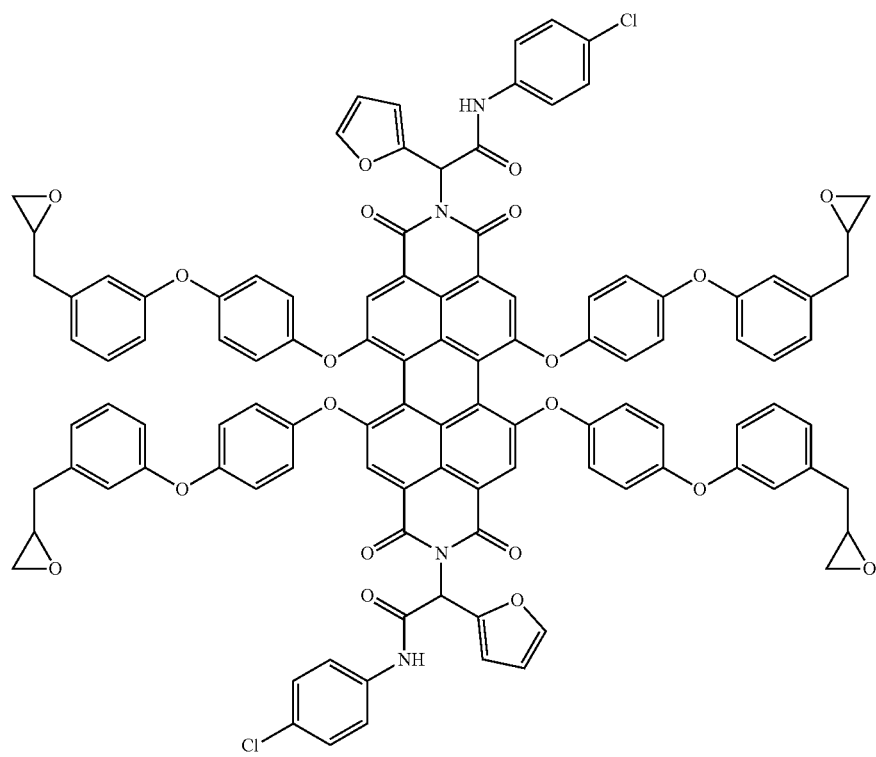

-continued
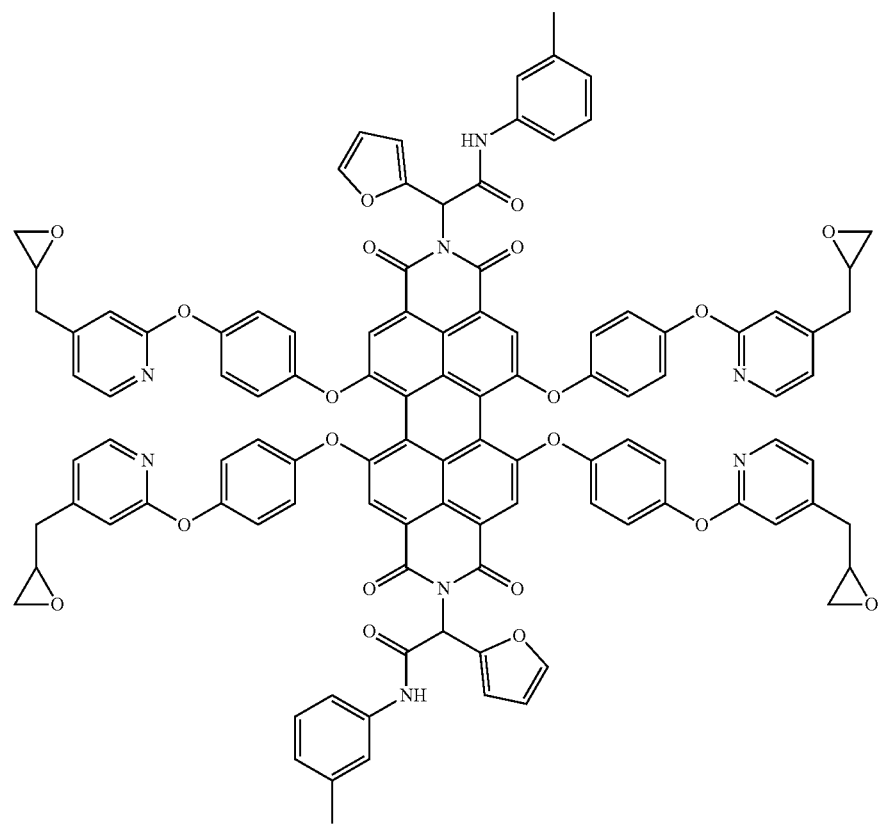
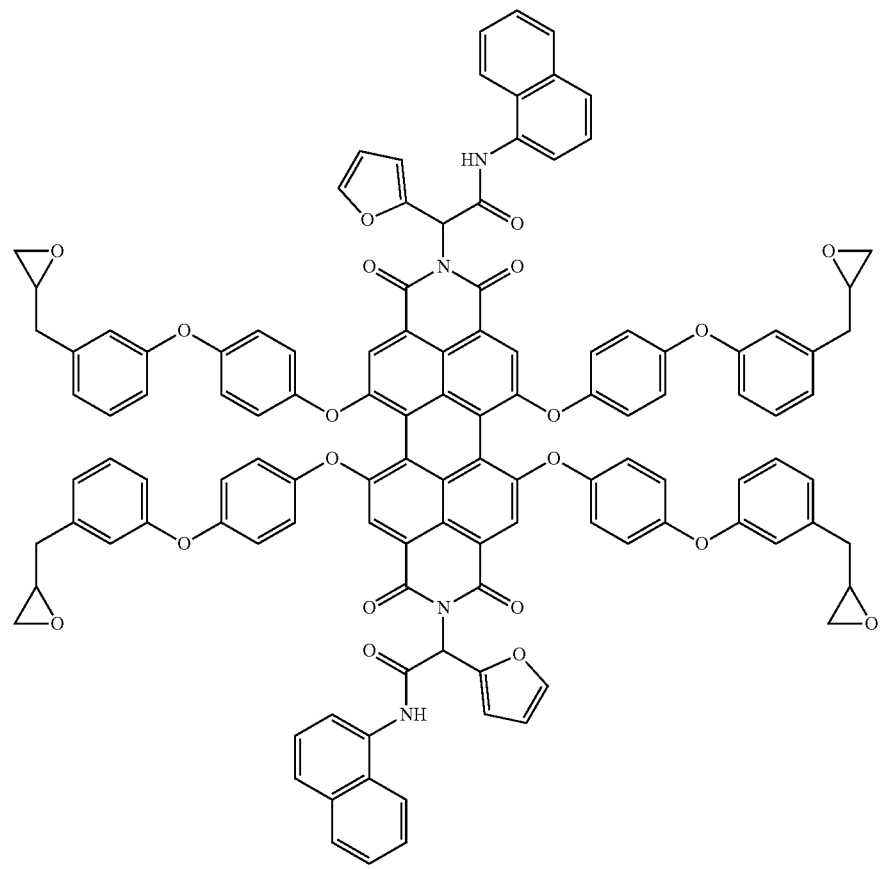

-continued
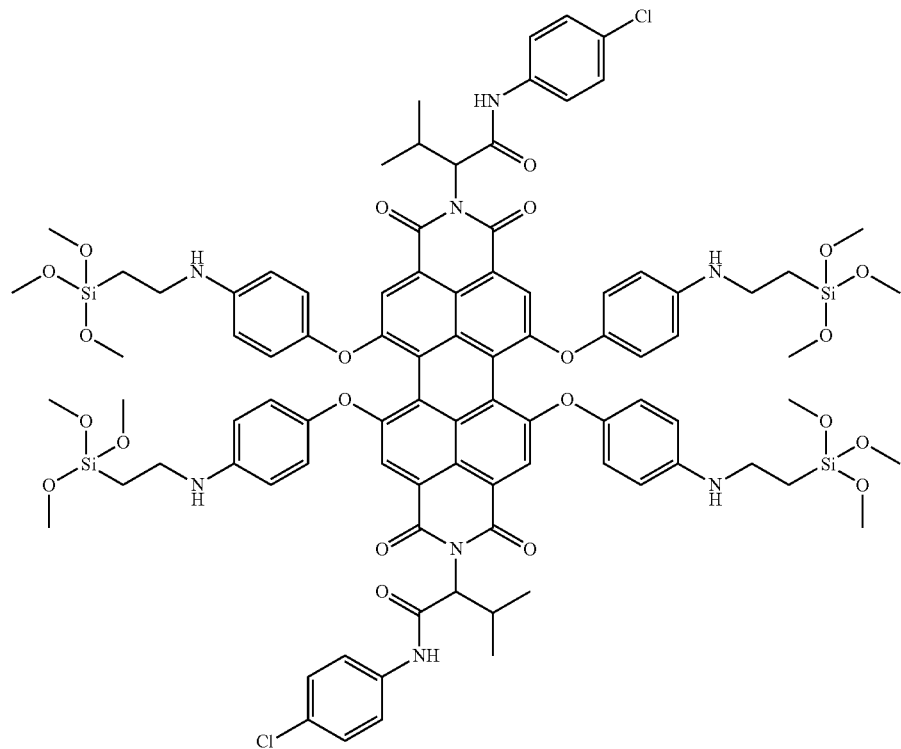
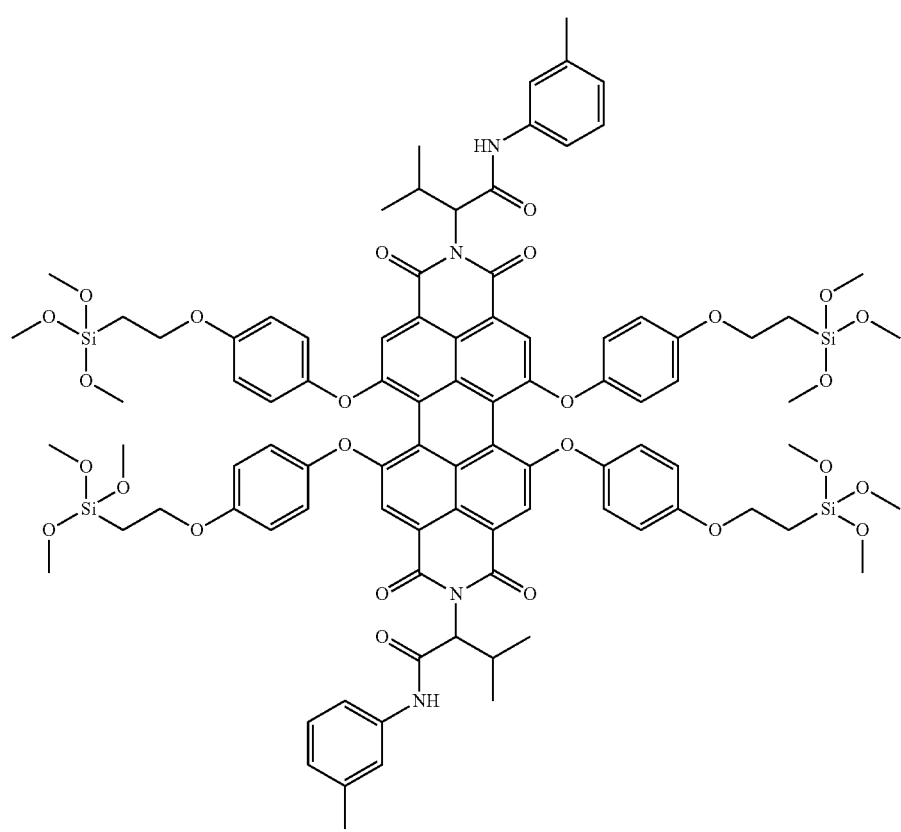

-continued
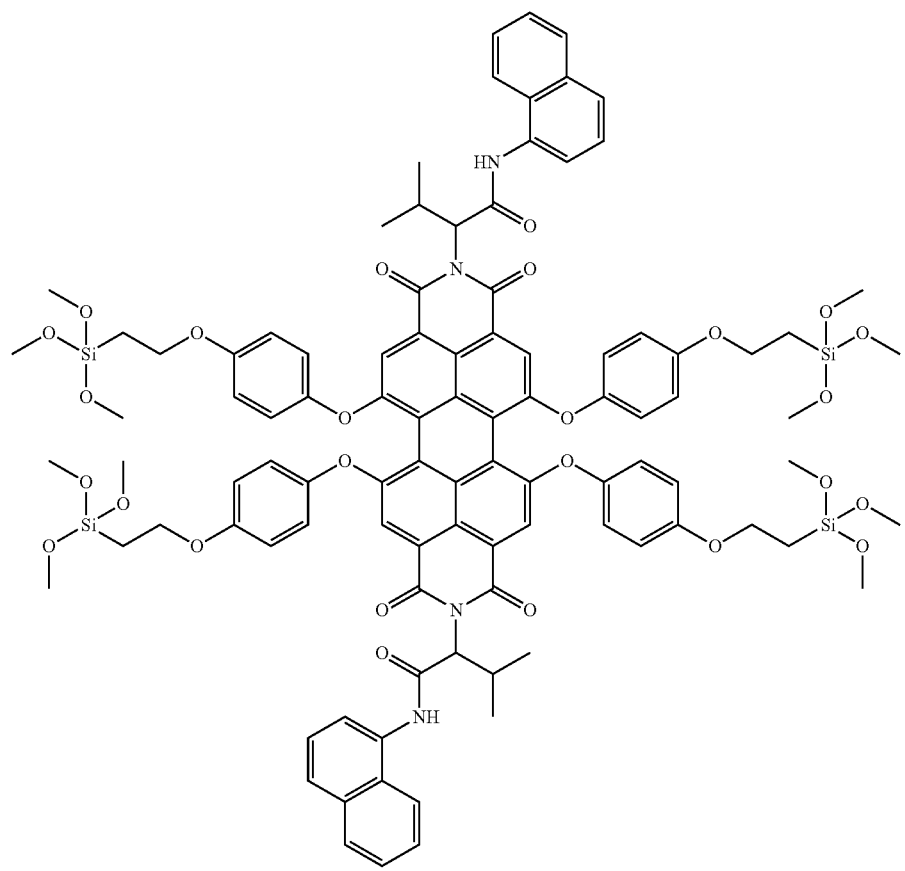
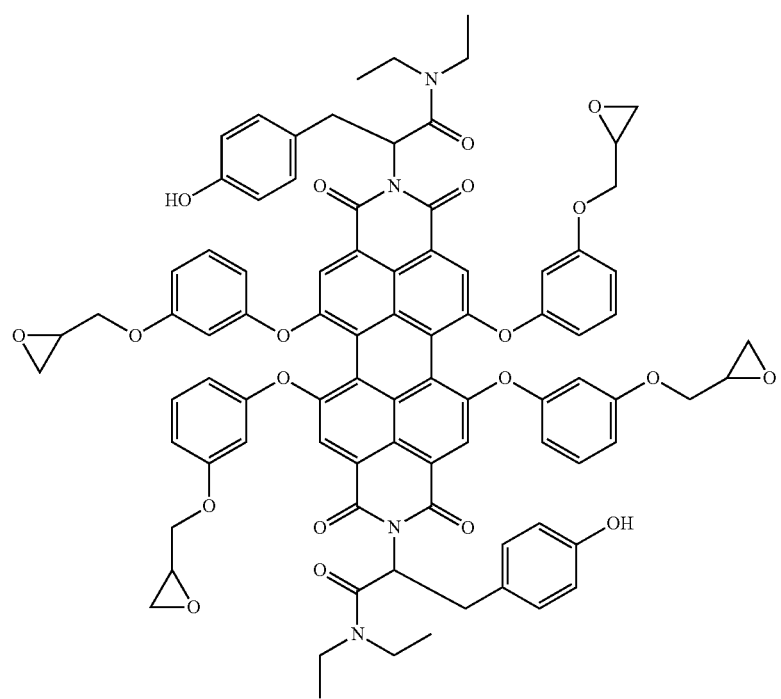

-continued
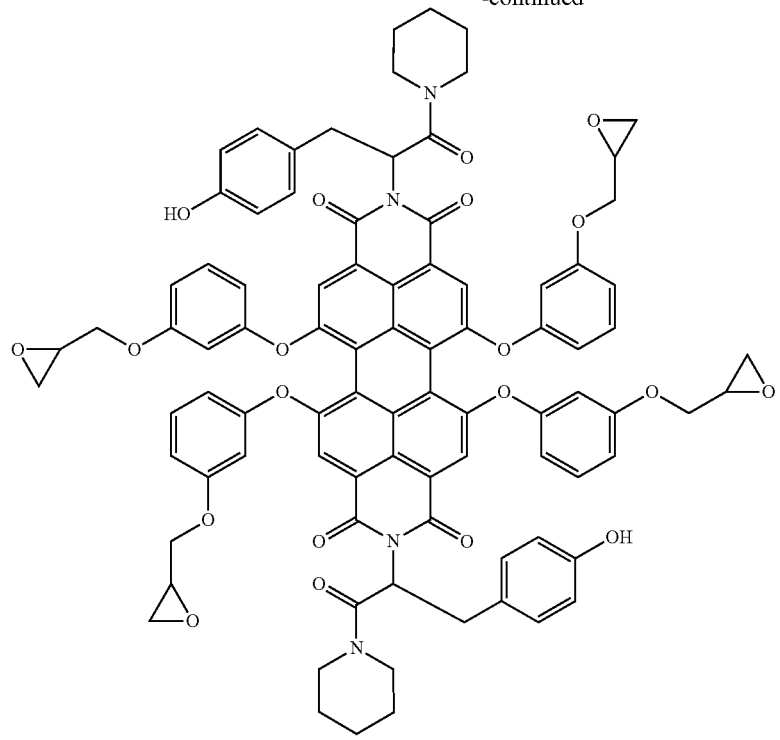
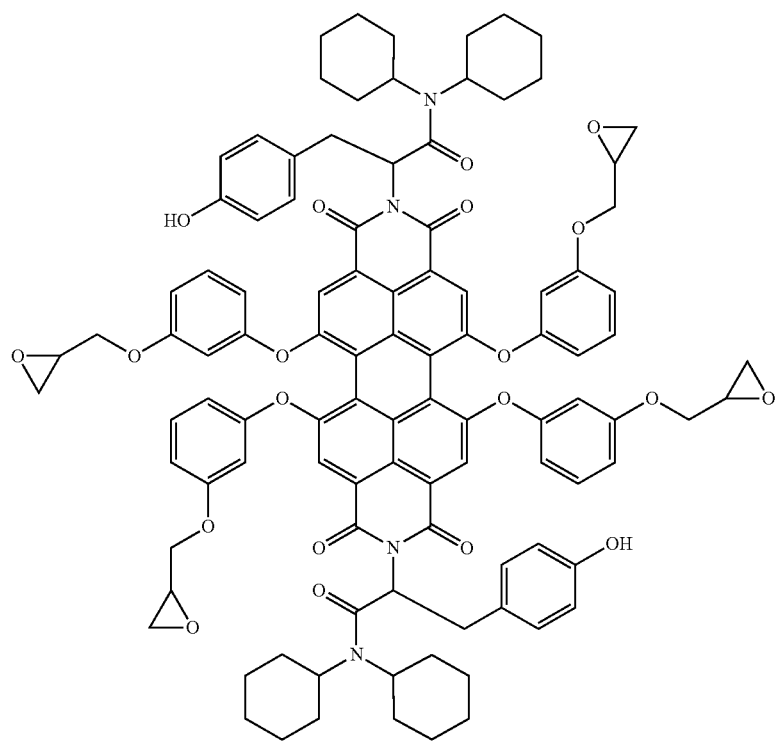

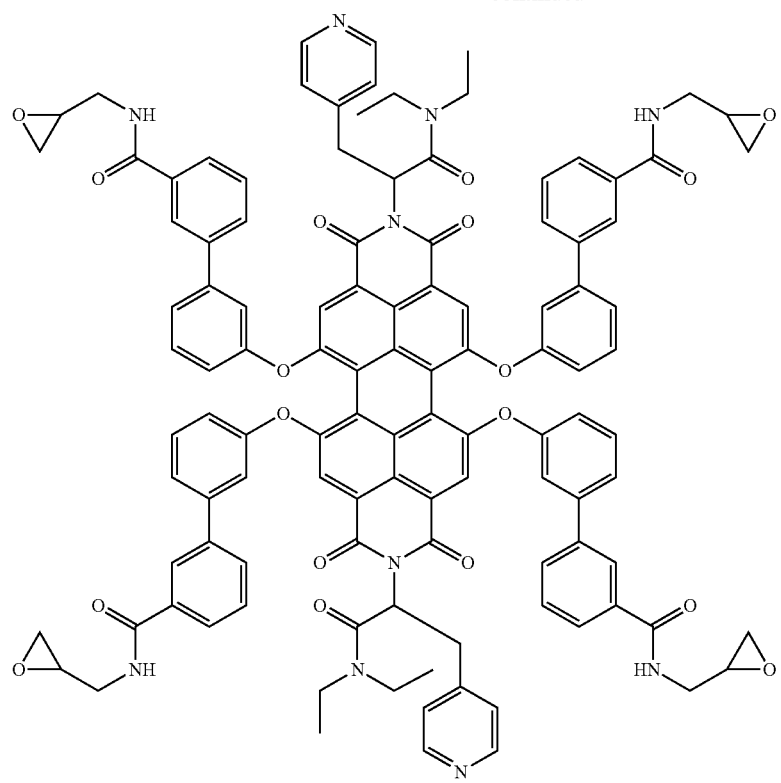
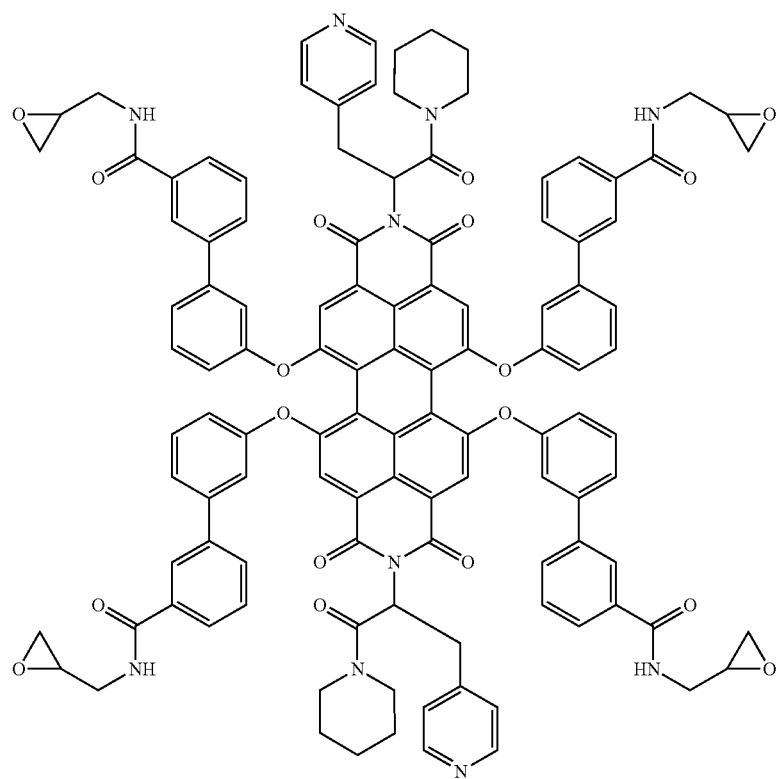

-continued
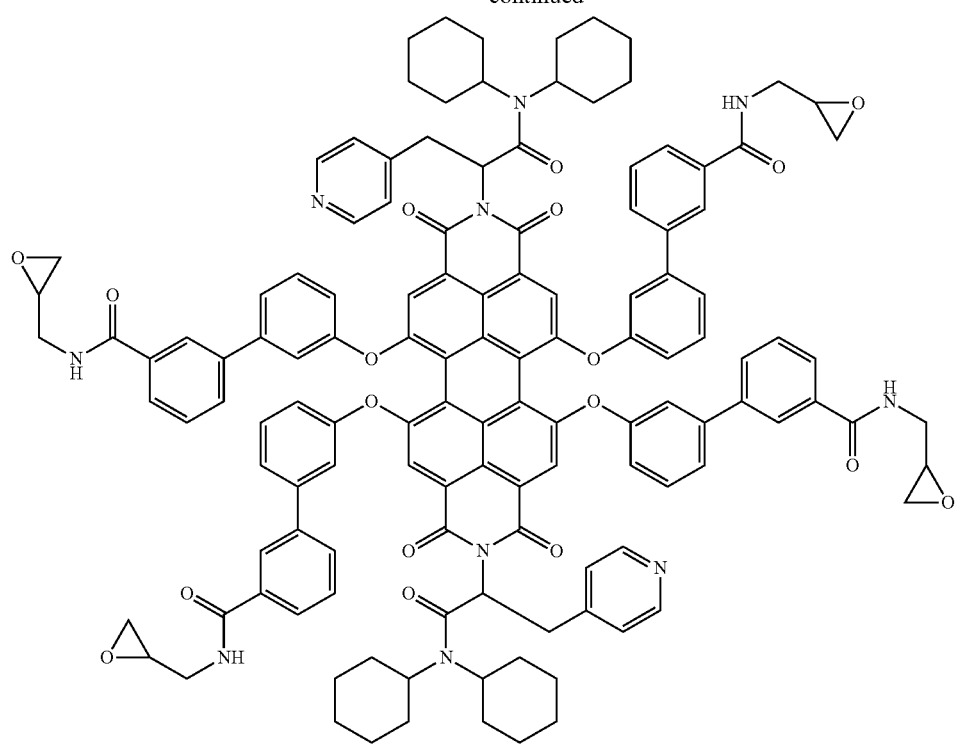
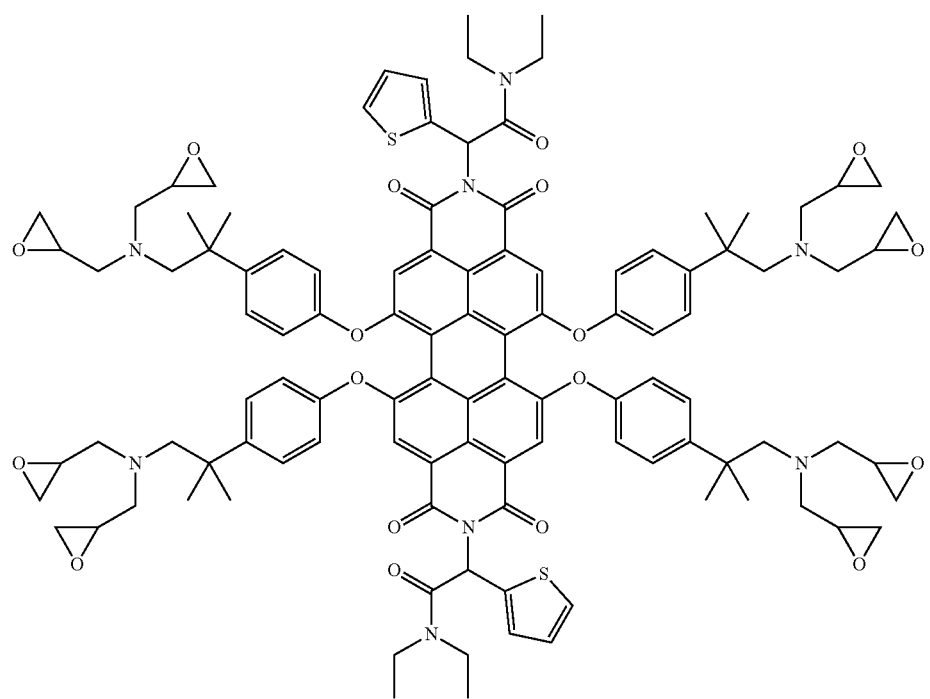

-continued
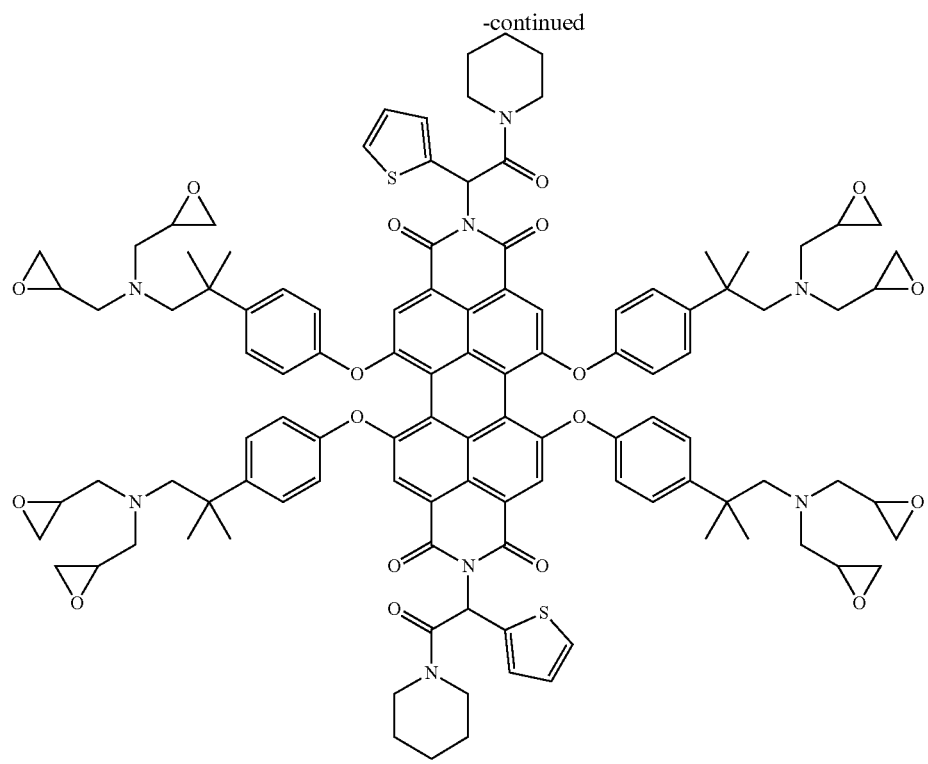
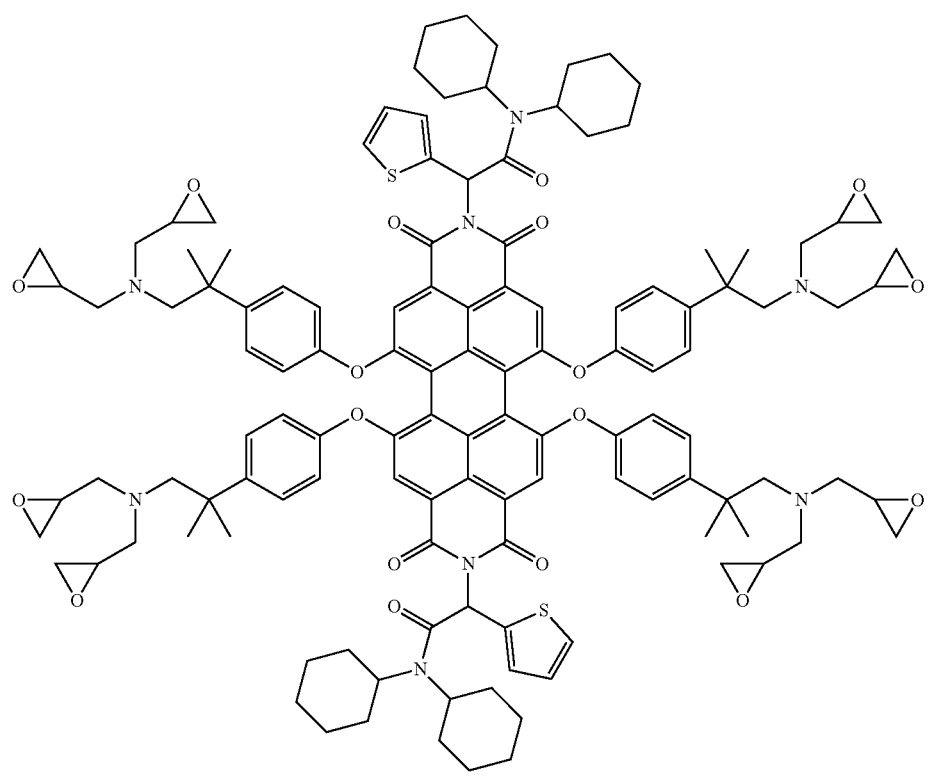

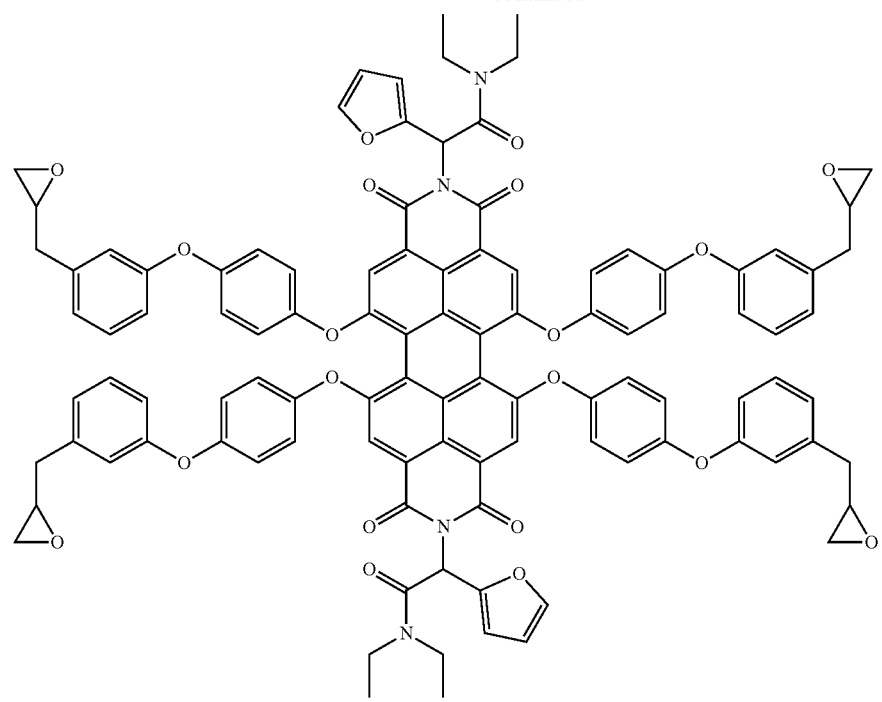
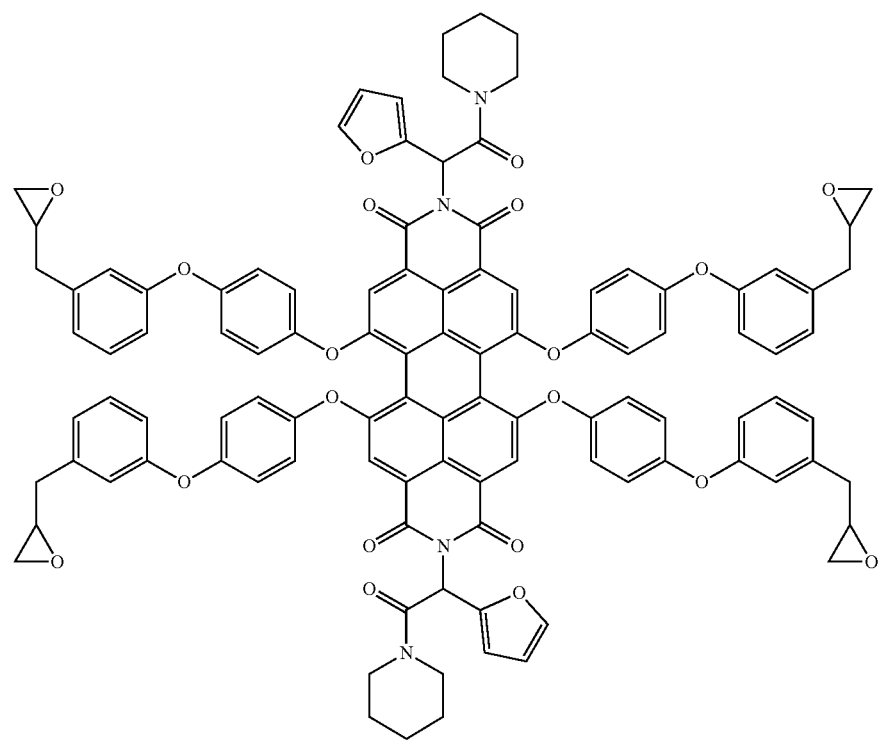

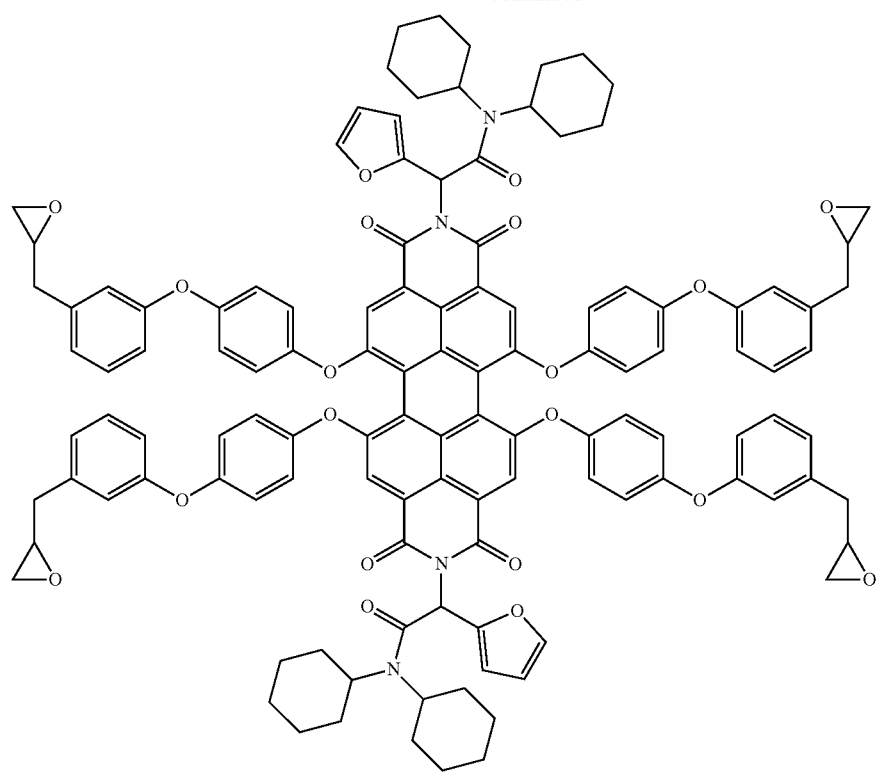
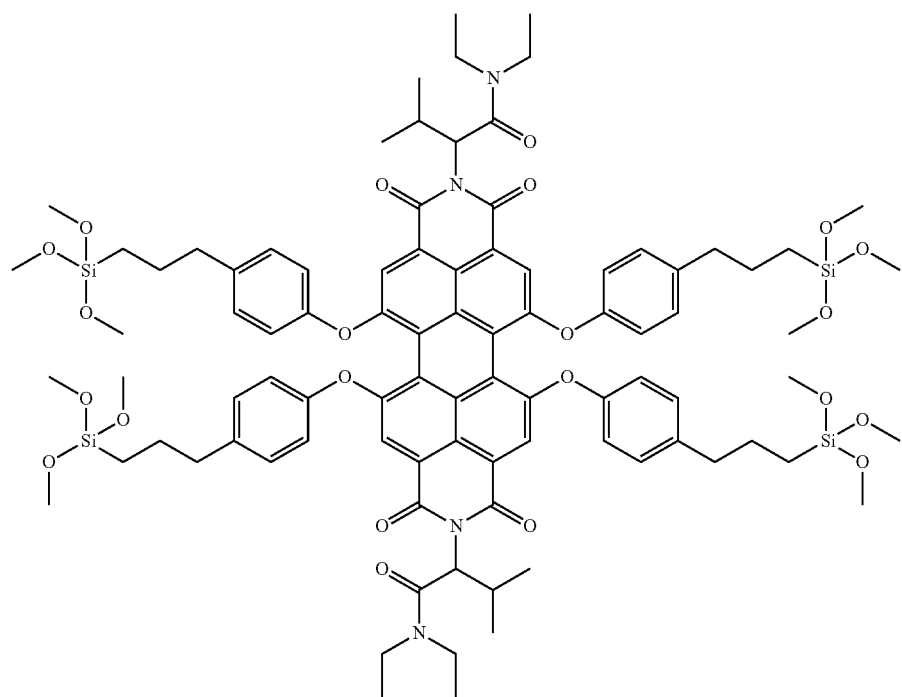

-continued
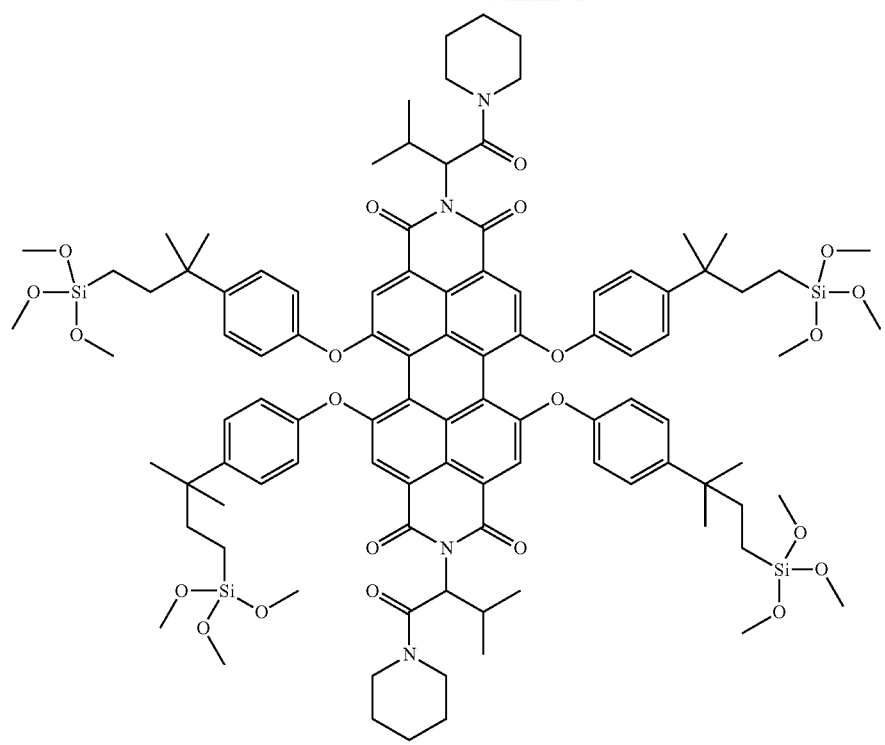
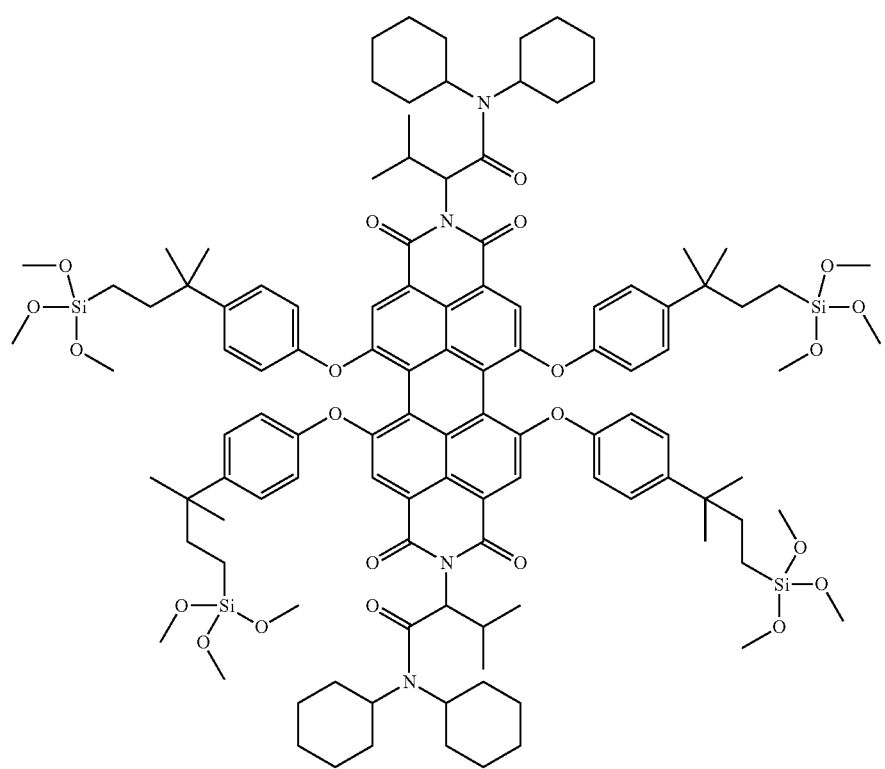

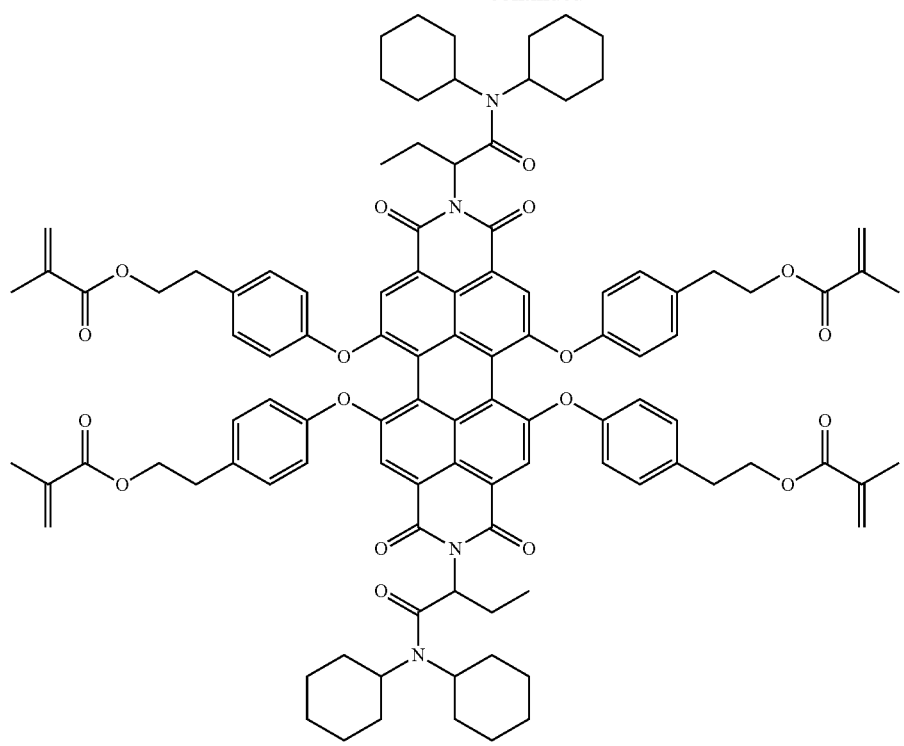
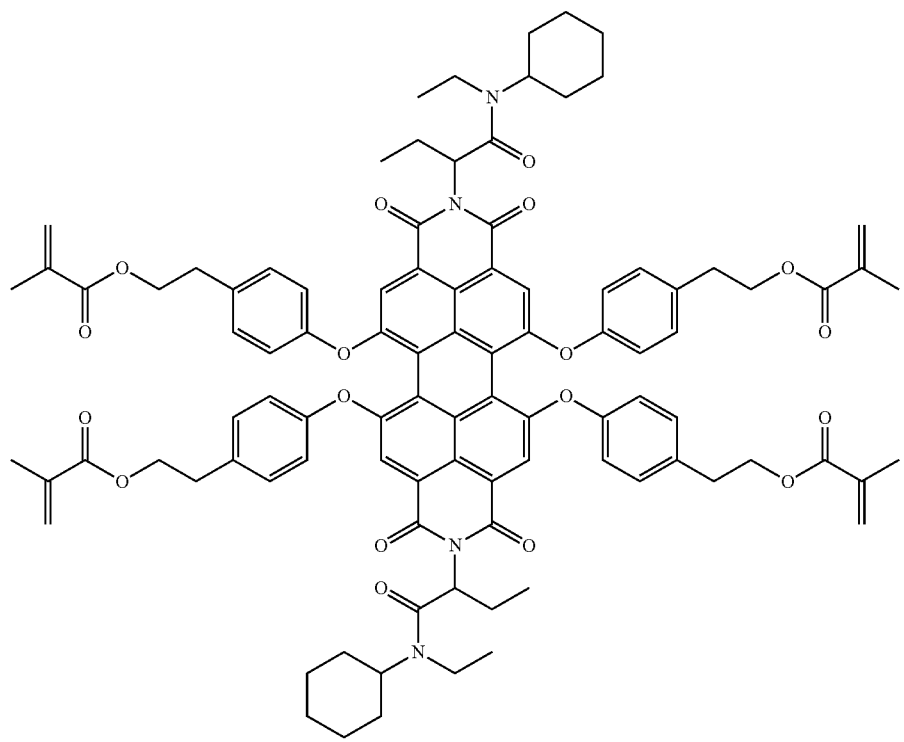

-continued
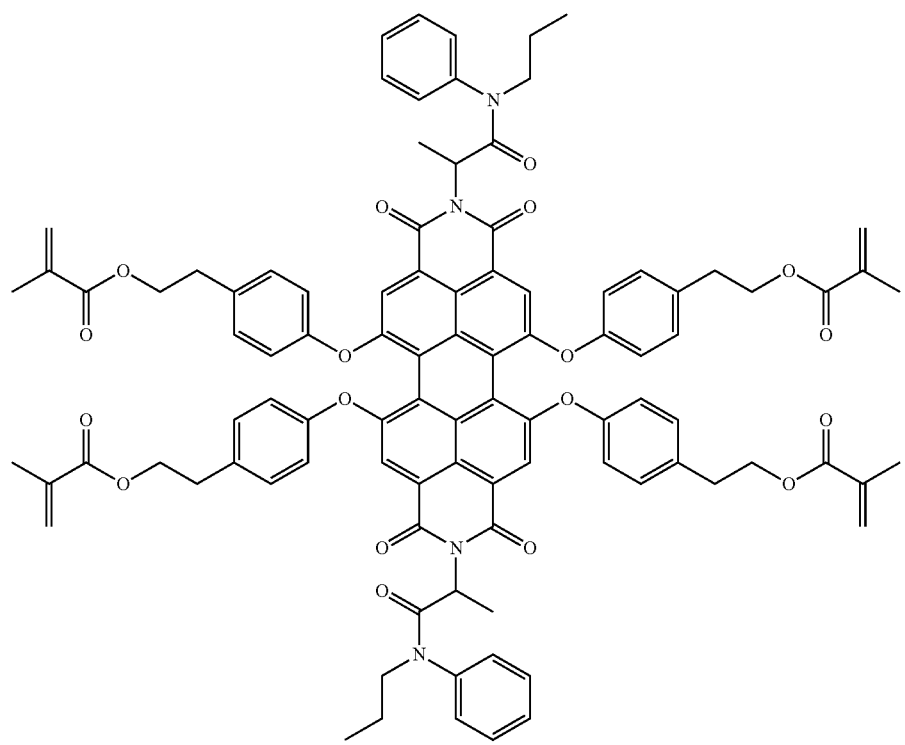
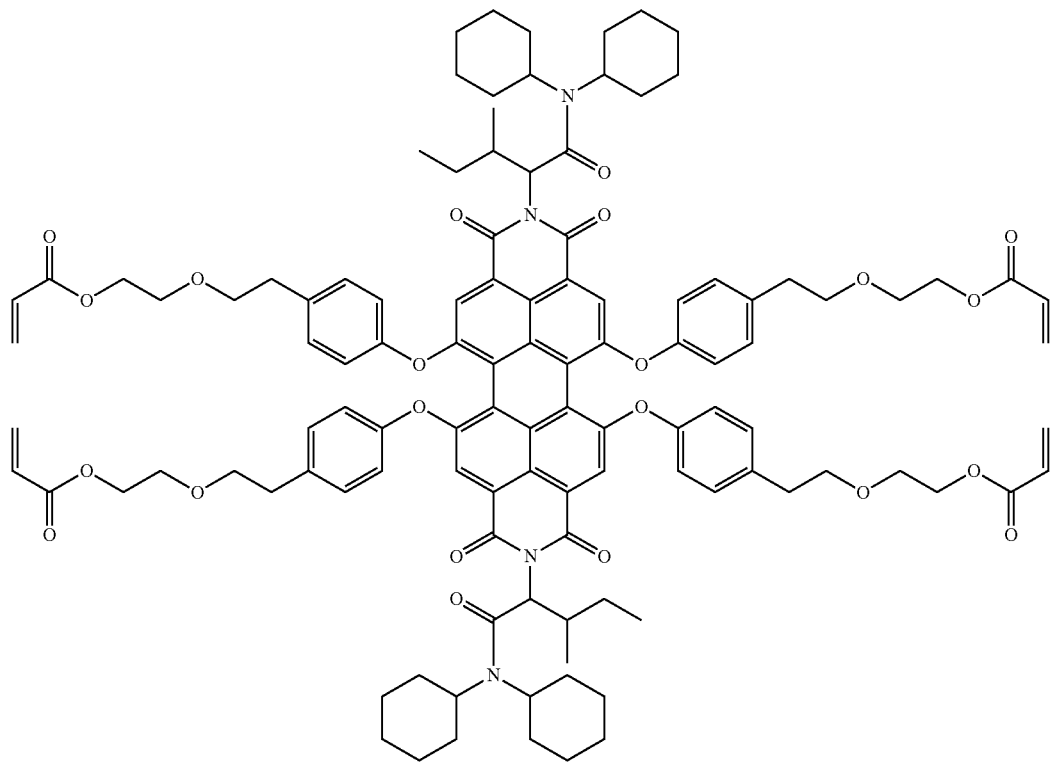

-continued
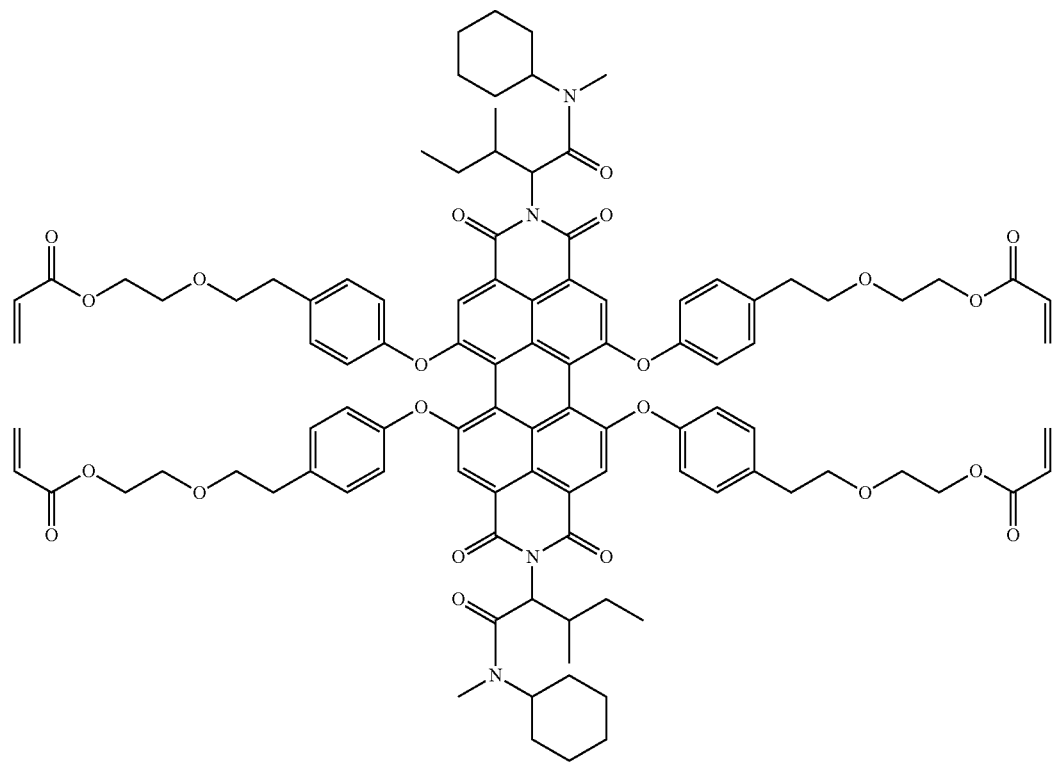
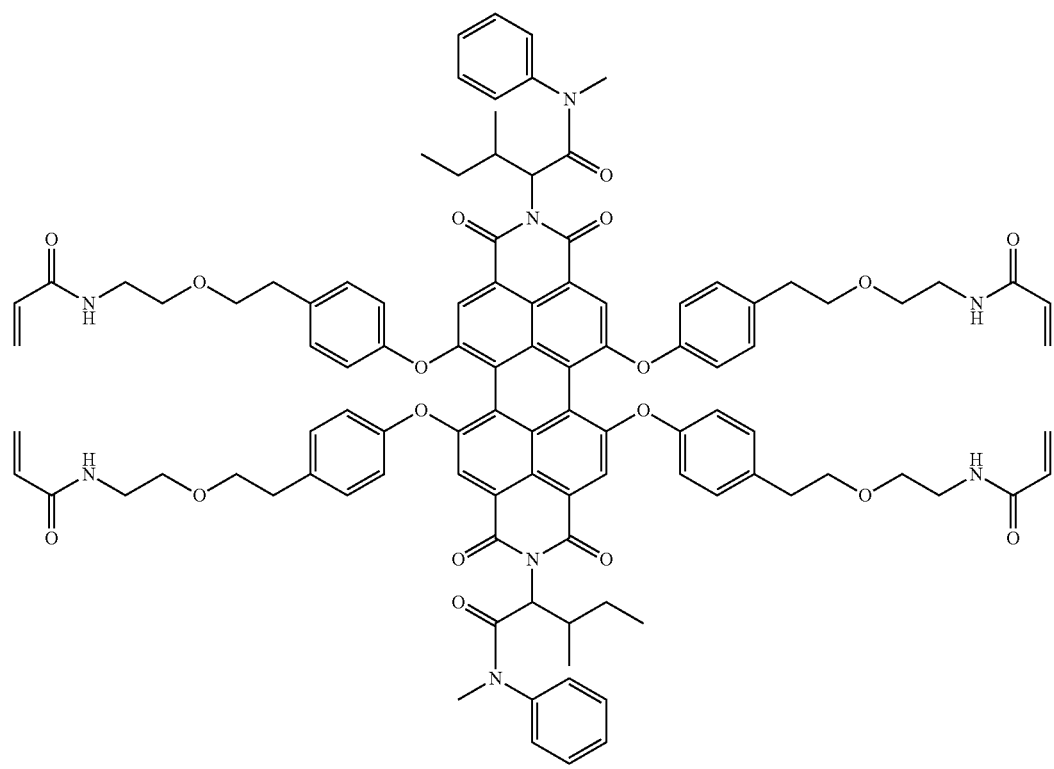

-continued
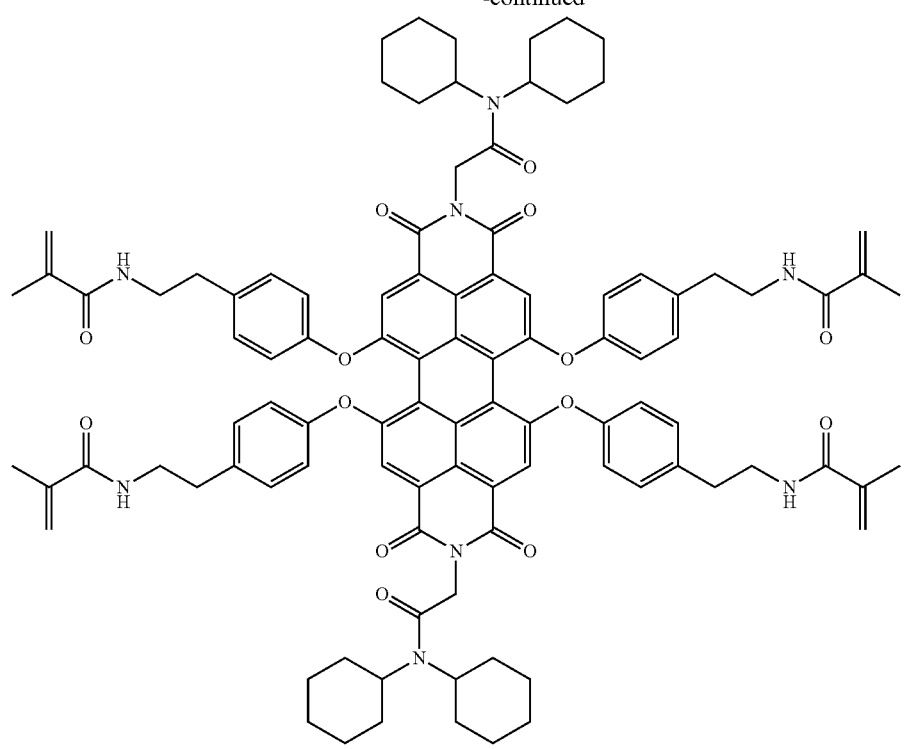
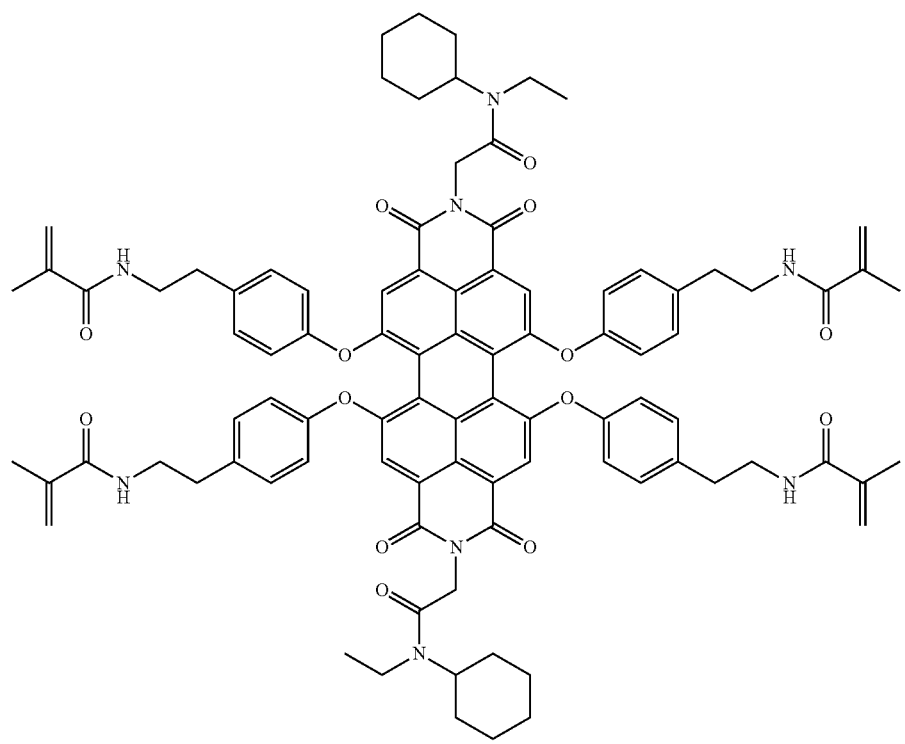

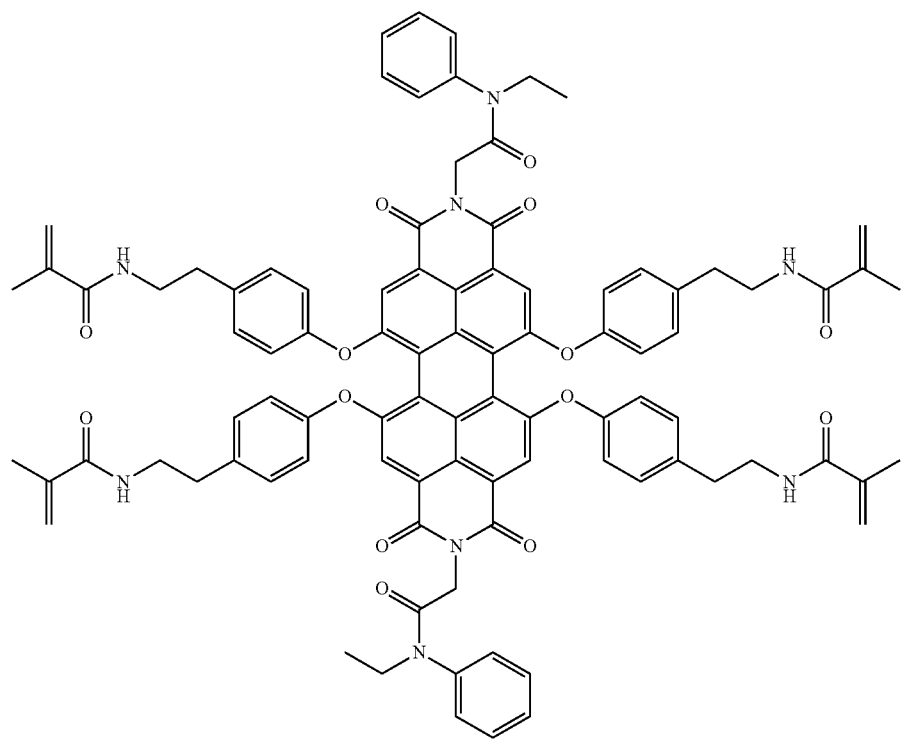
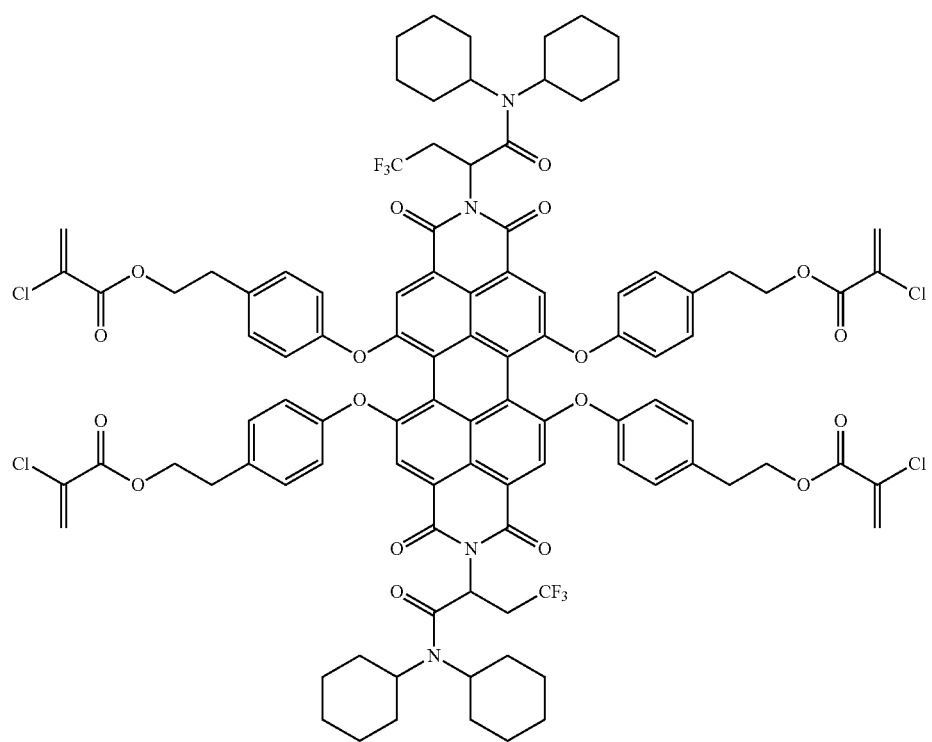

-continued
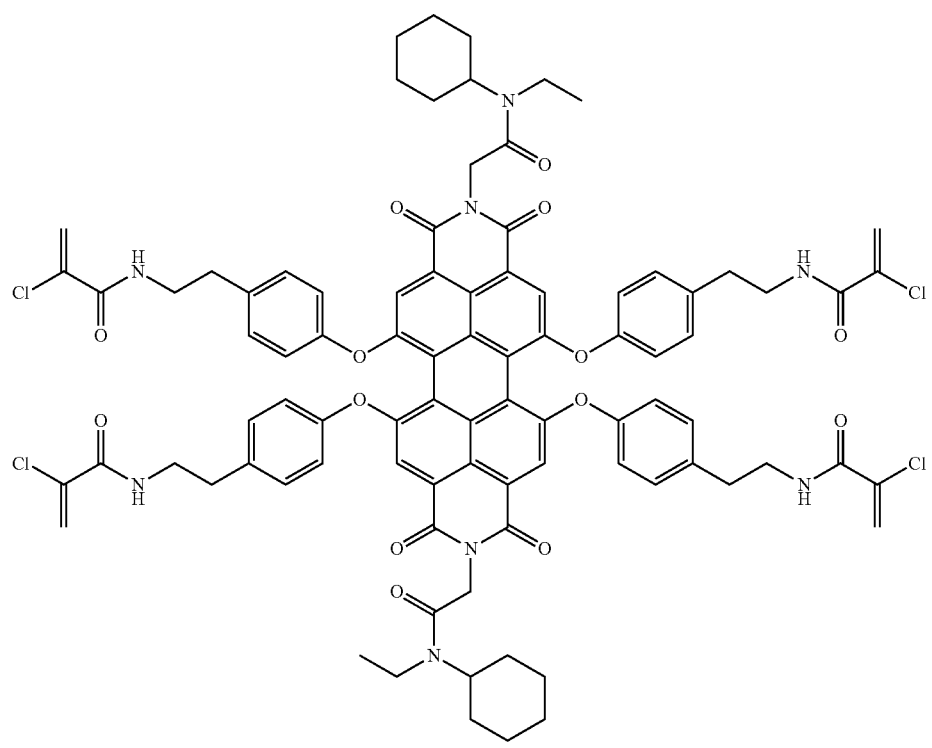
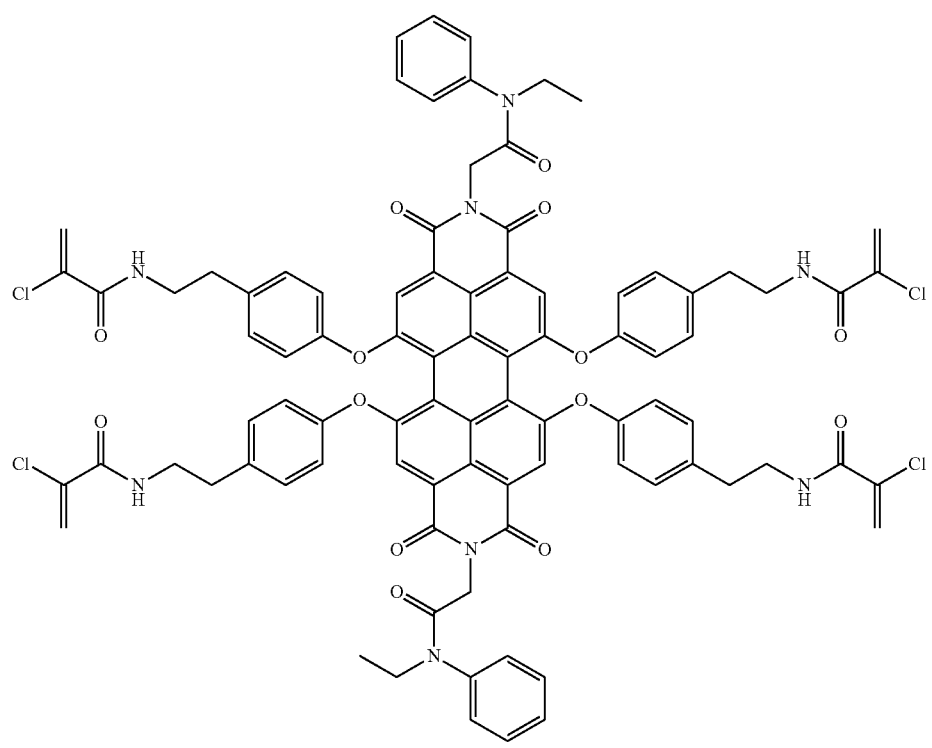

-continued
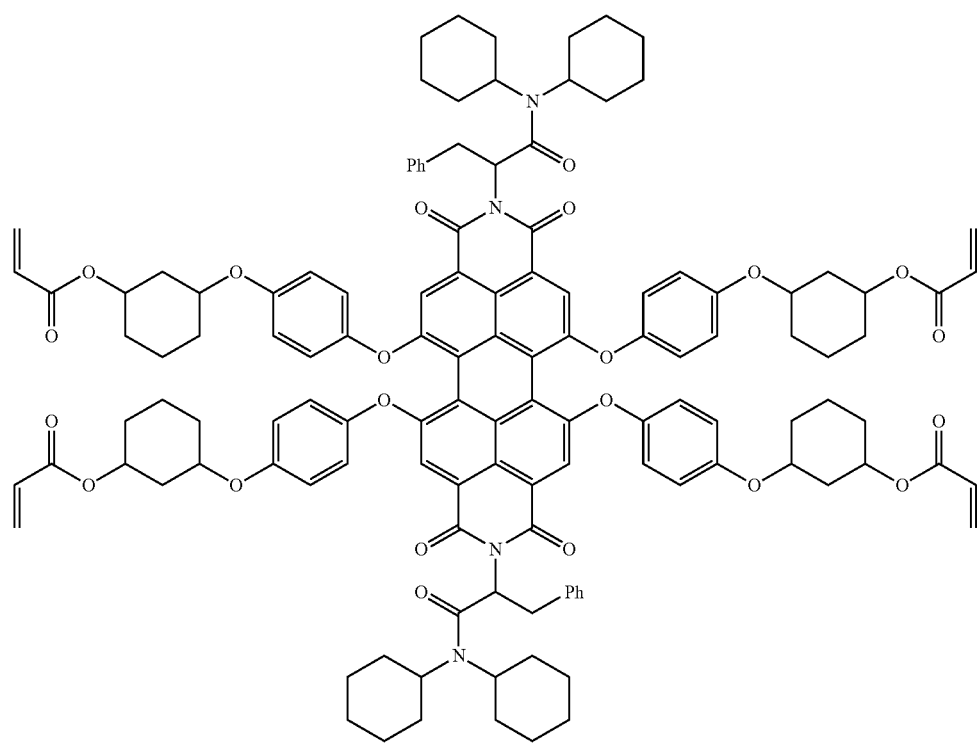
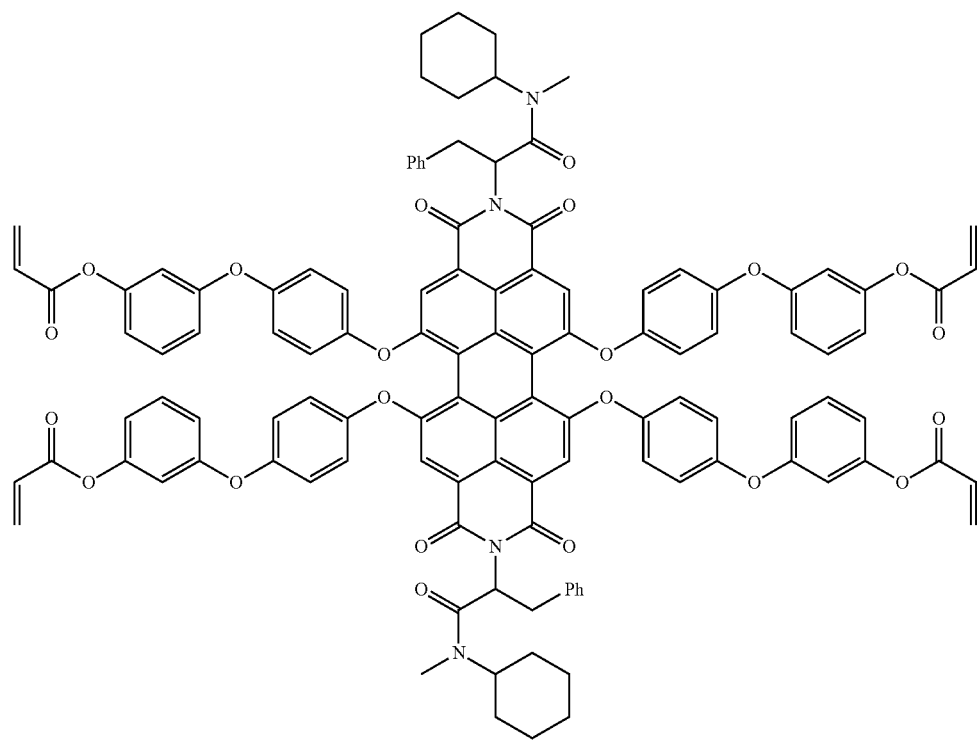

-continued
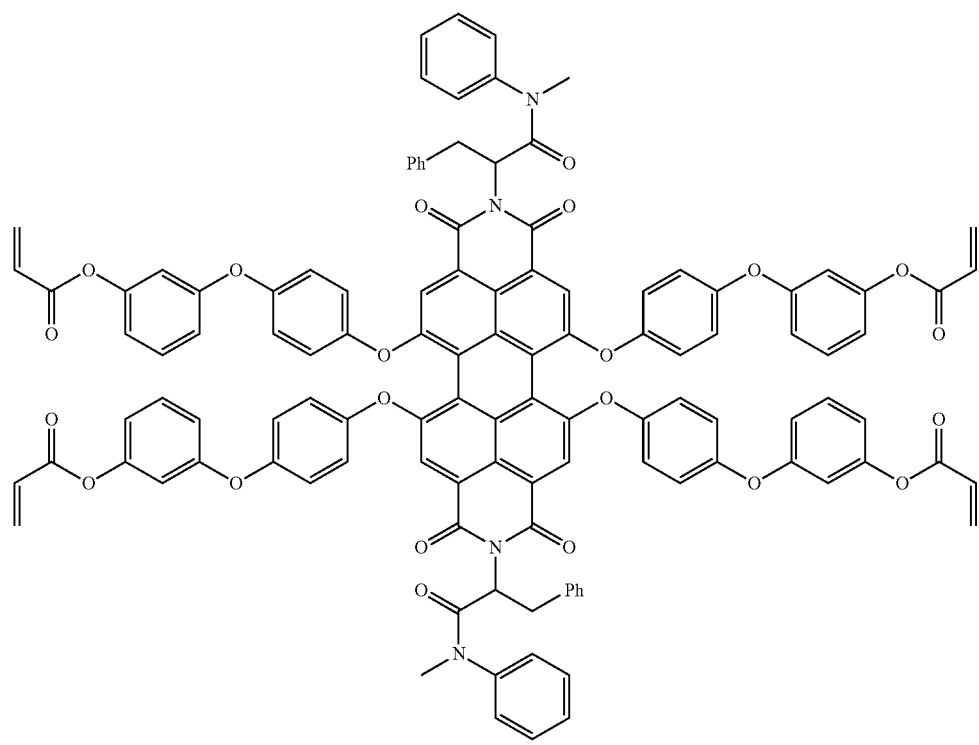 [SMILES: C=CC(=O)Oc1cccc(Oc2ccc(Oc3cc4c5c(cc(Oc6ccc(Oc7cccc(OC(=O)C=C)c7)cc6)c6c7c(Oc8ccc(Oc9cccc(OC(=O)C=C)c9)cc8)cc8c9c(cc(Oc%10ccc(Oc%11cccc(OC(=O)C=C)c%11)cc%10)c(c3c56)c97)C(=O)N(C(Cc3ccccc3)C(=O)N(C)c3ccccc3)C8=O)C(=O)N(C(Cc3ccccc3)C(=O)N(C)c3ccccc3)C4=O)cc2)c1]
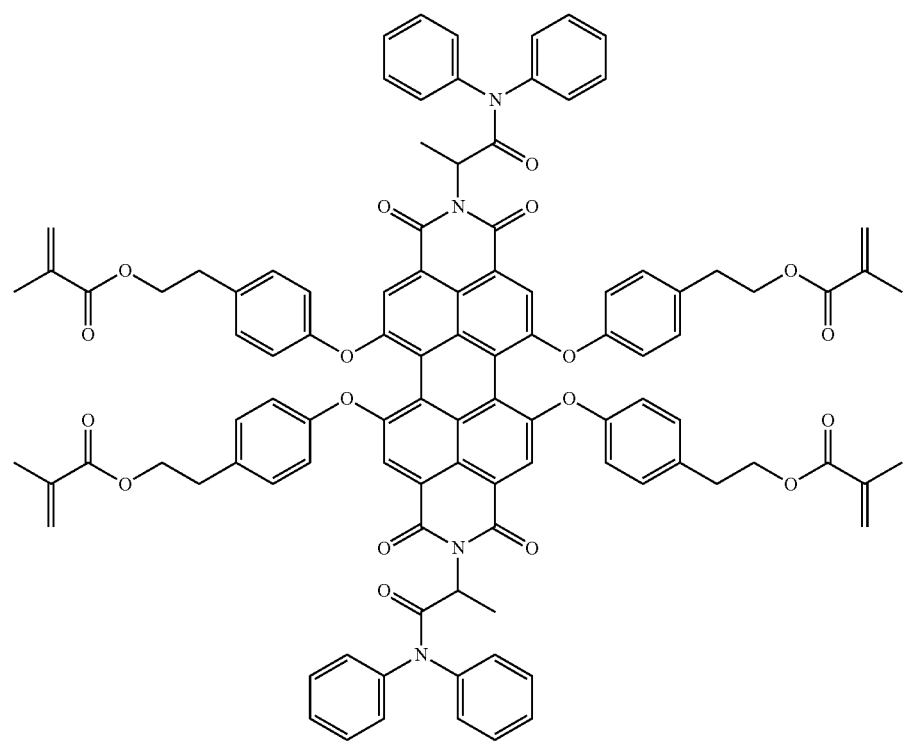

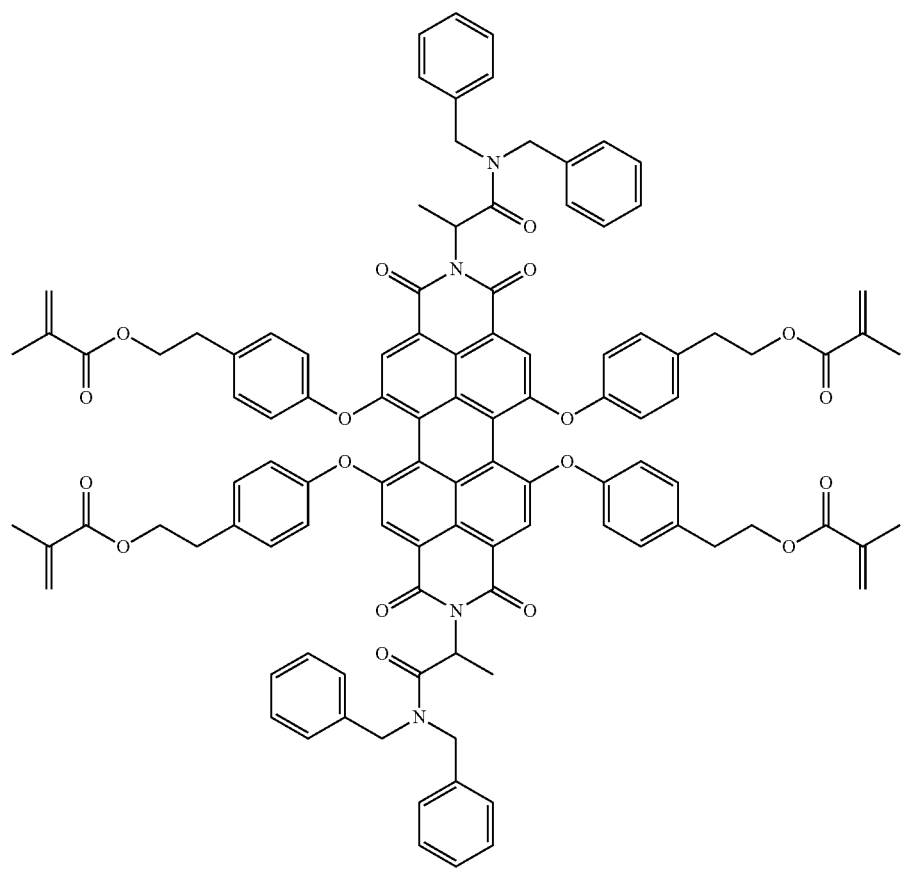
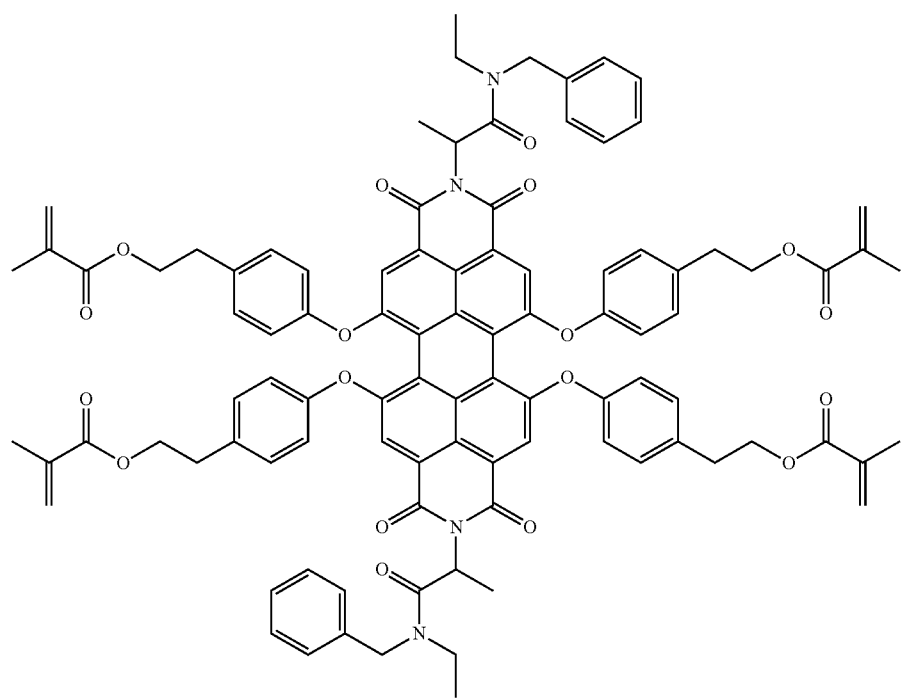

-continued
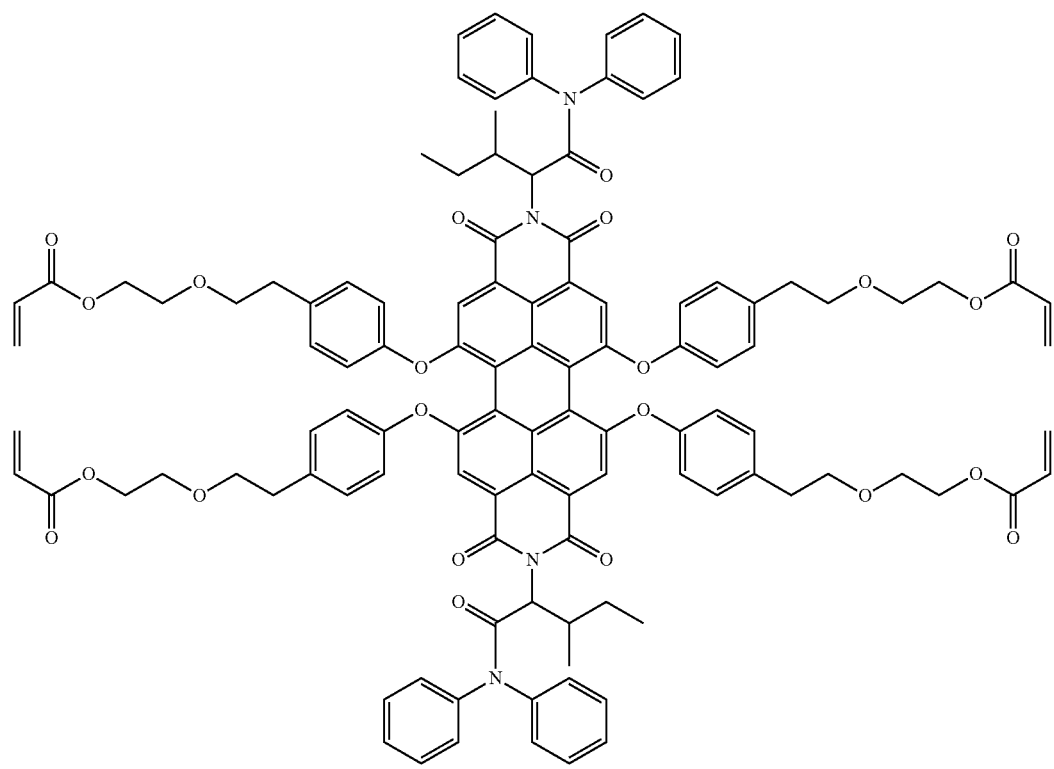
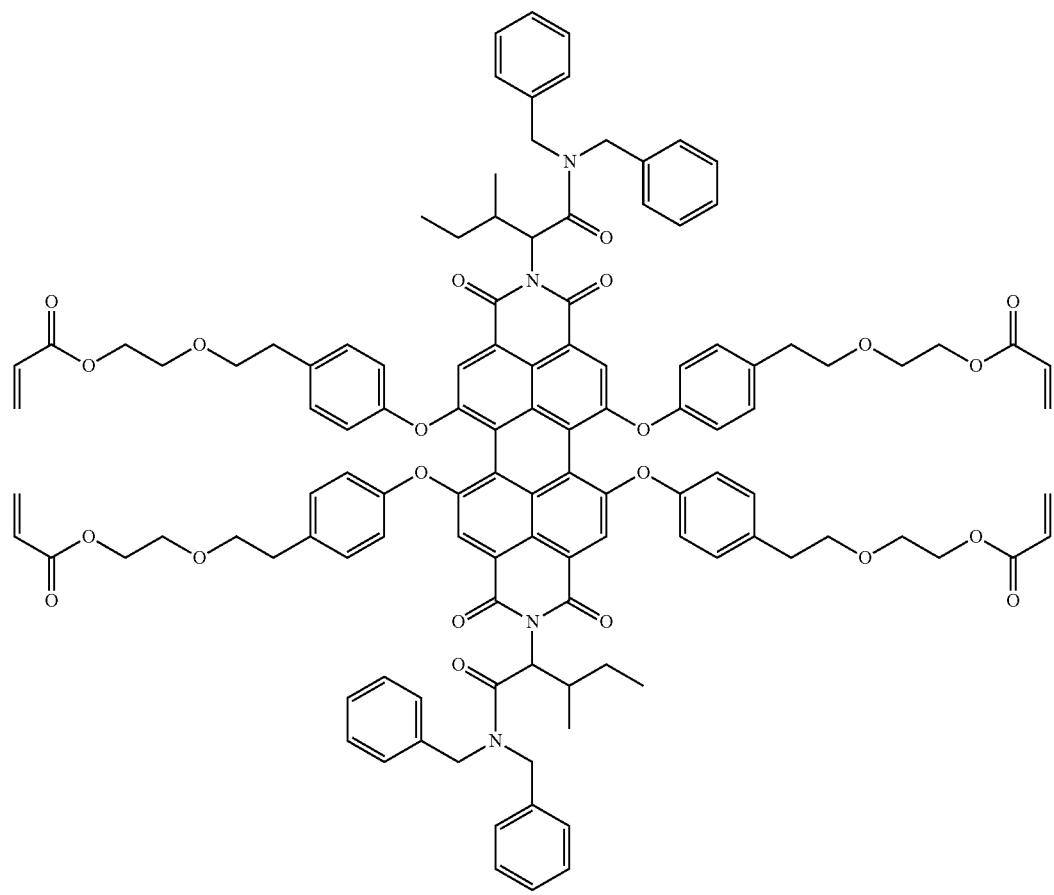

-continued
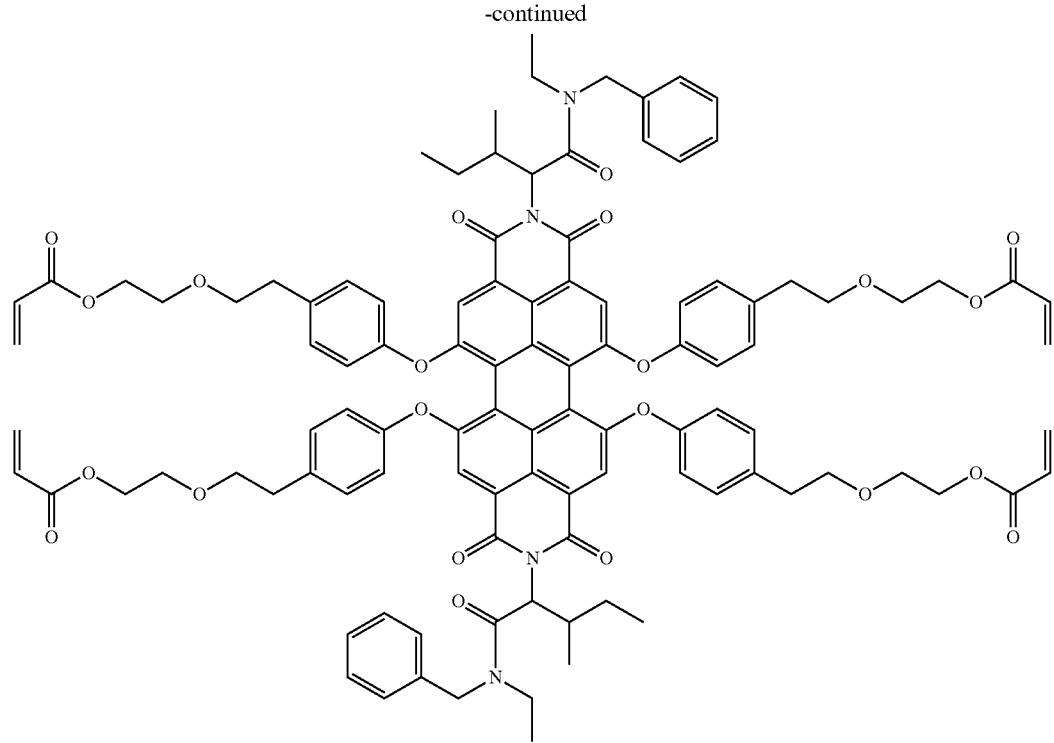
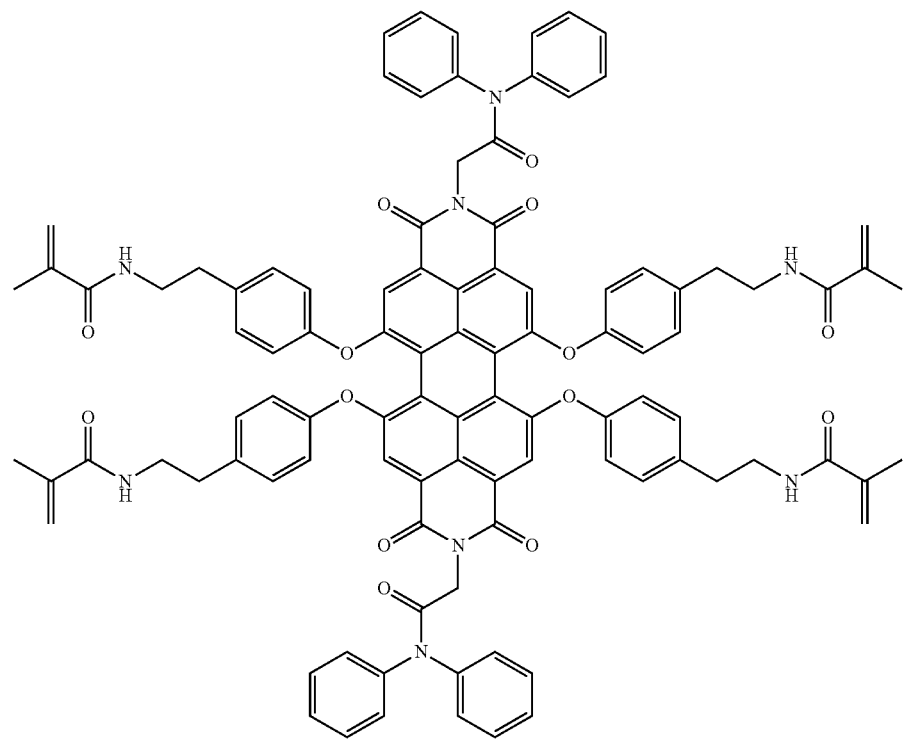

-continued
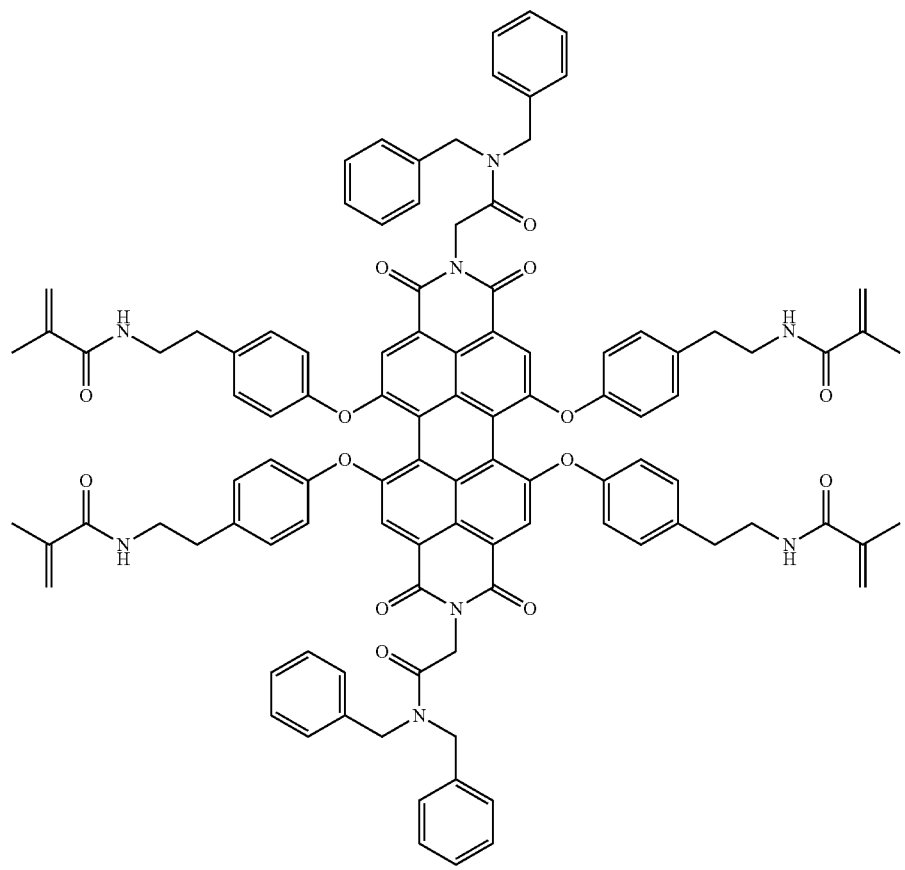
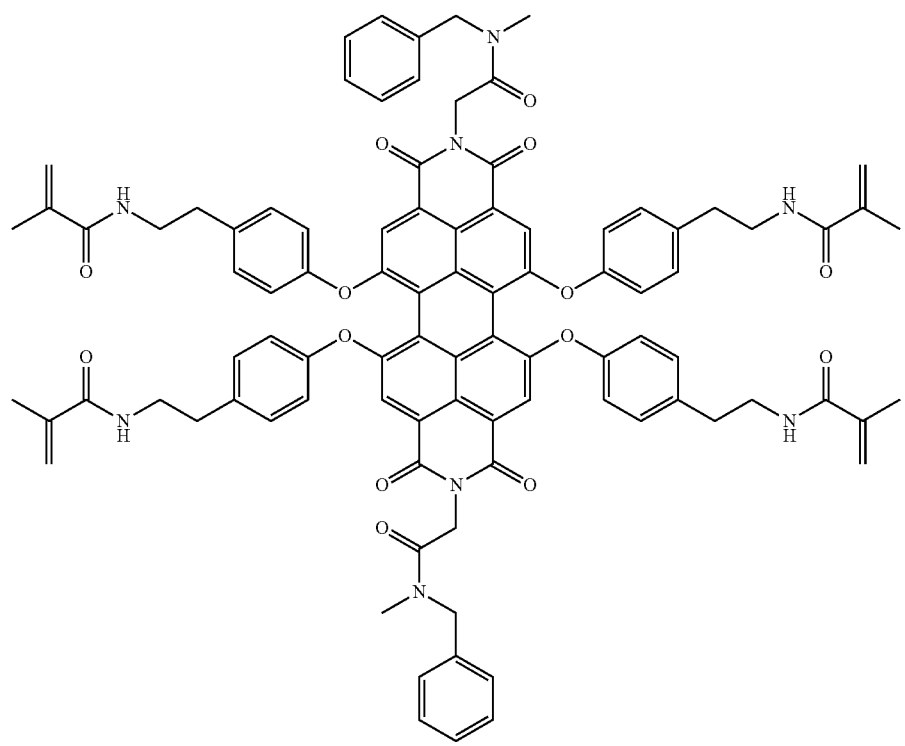

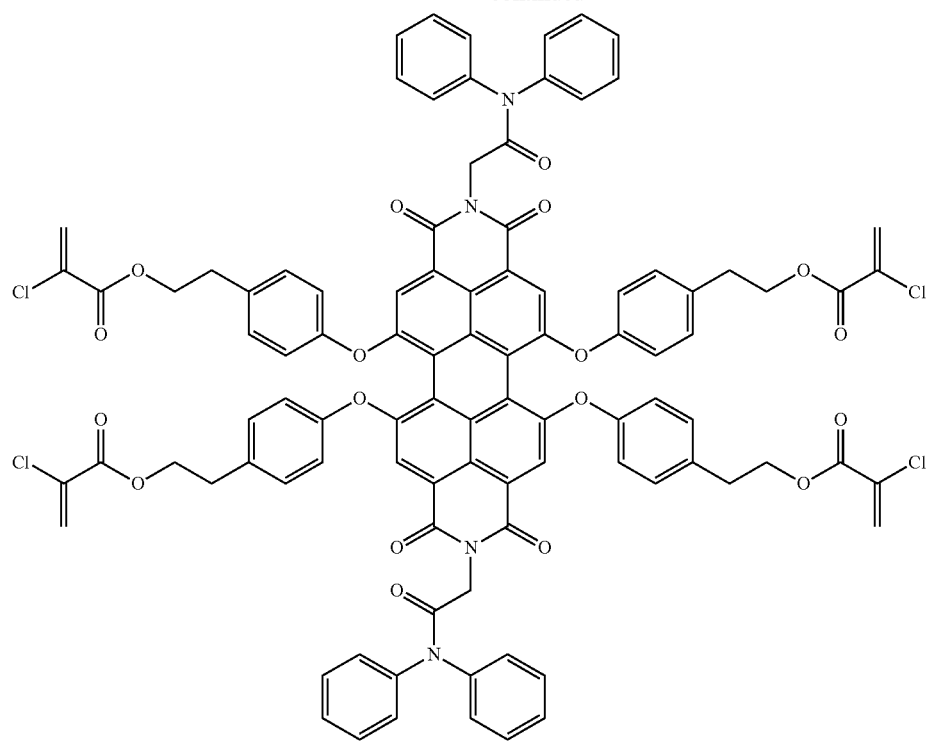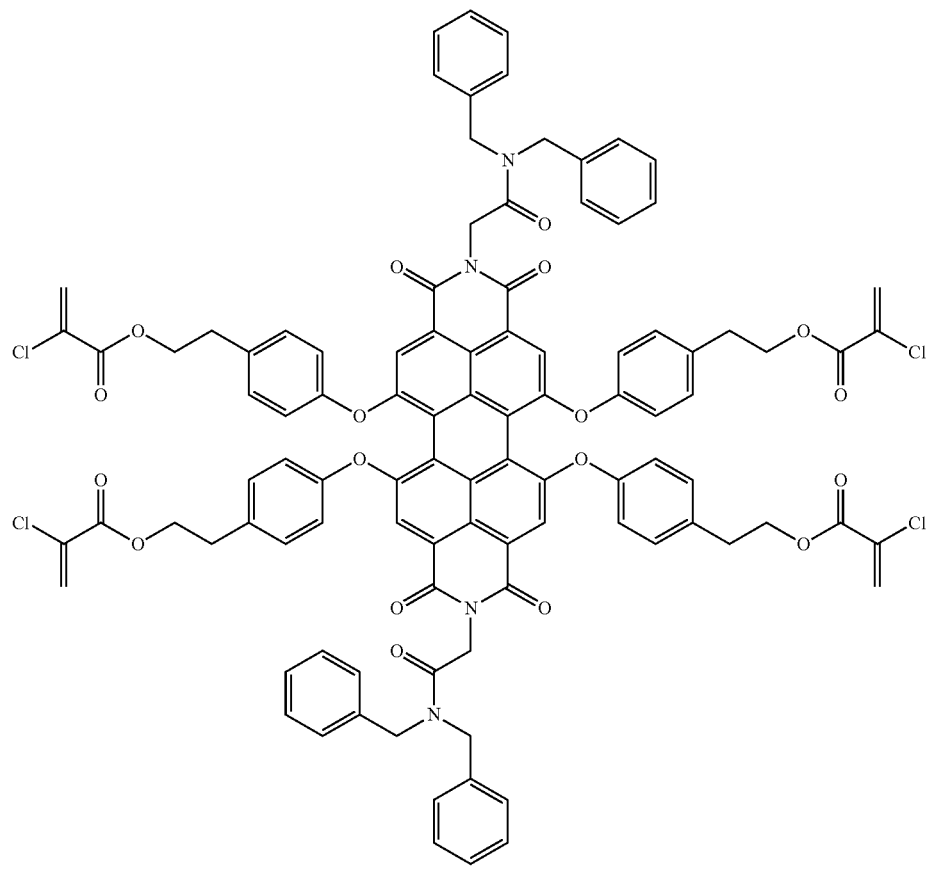

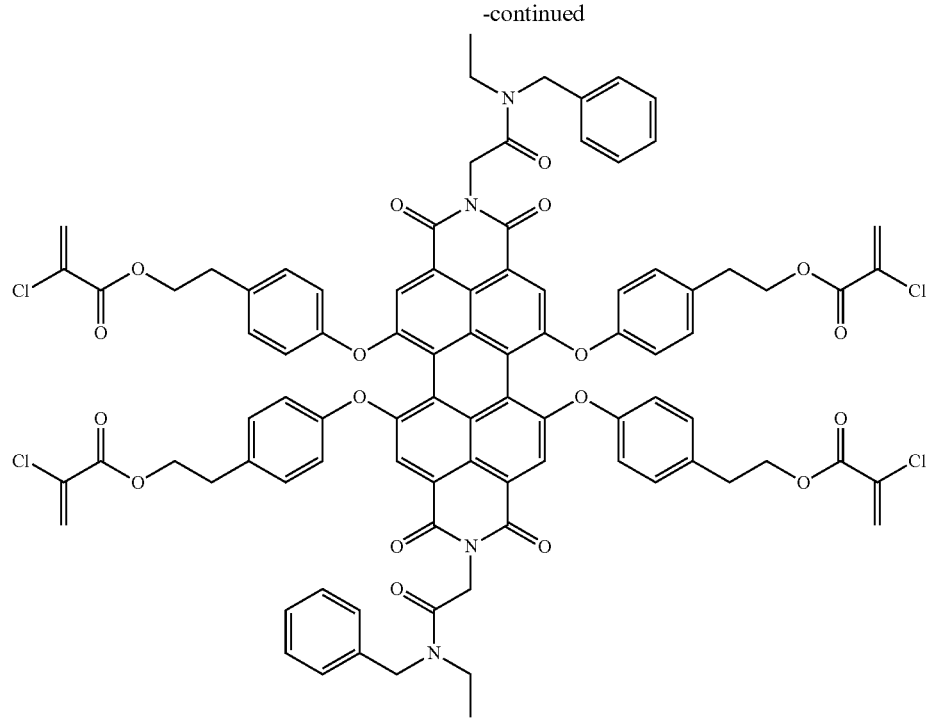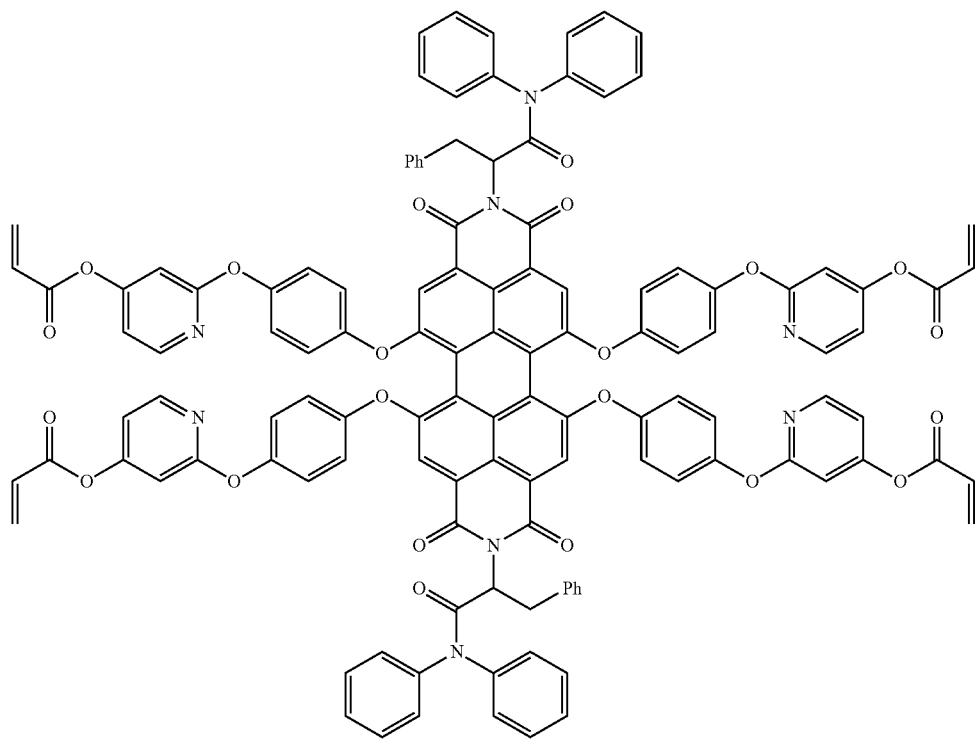

-continued
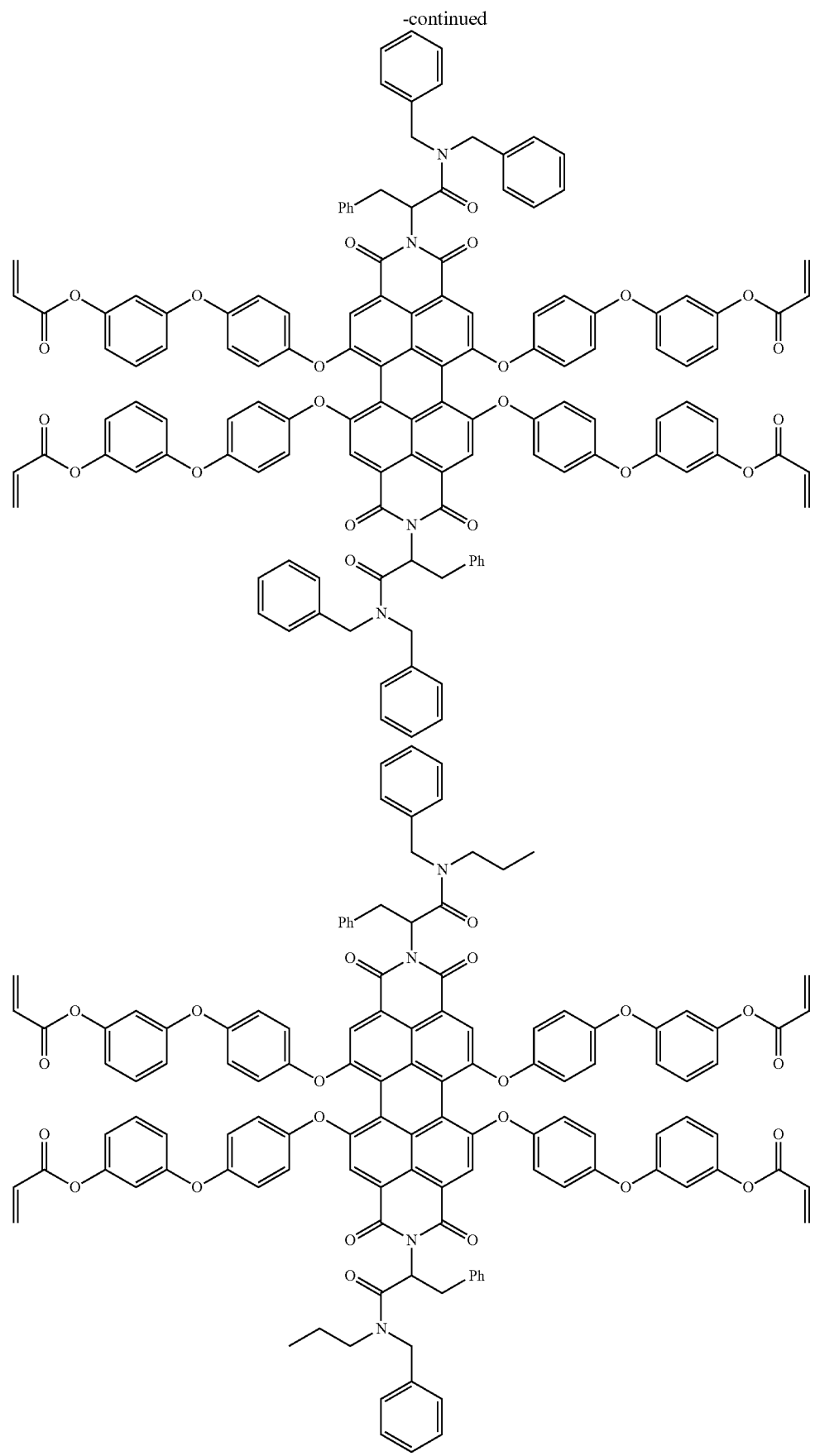

263
-continued
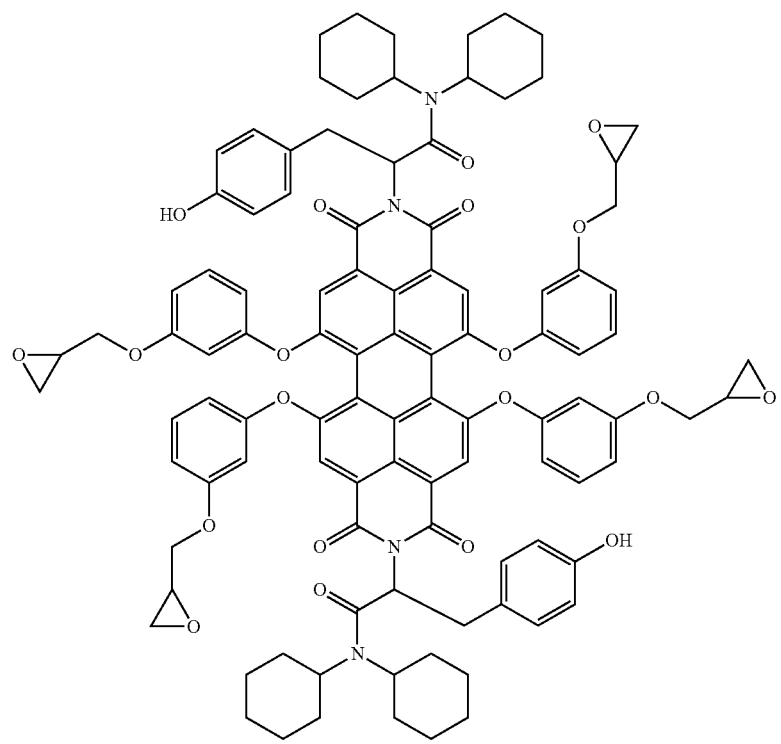
264
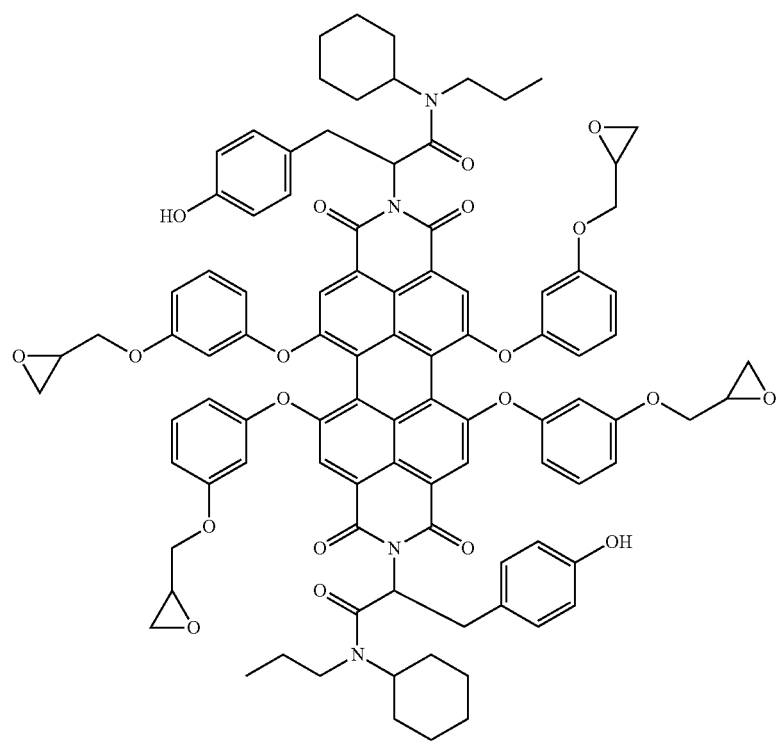

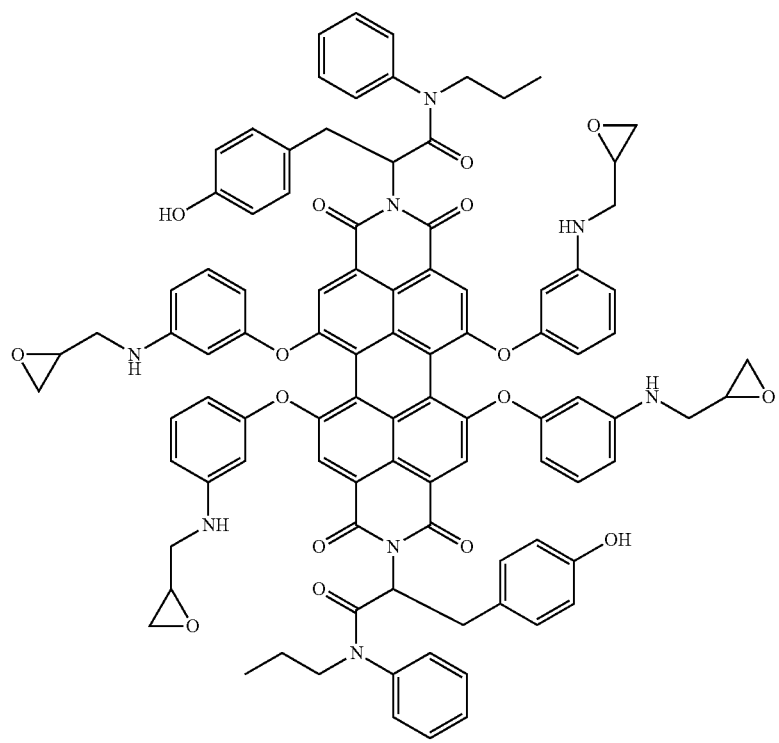
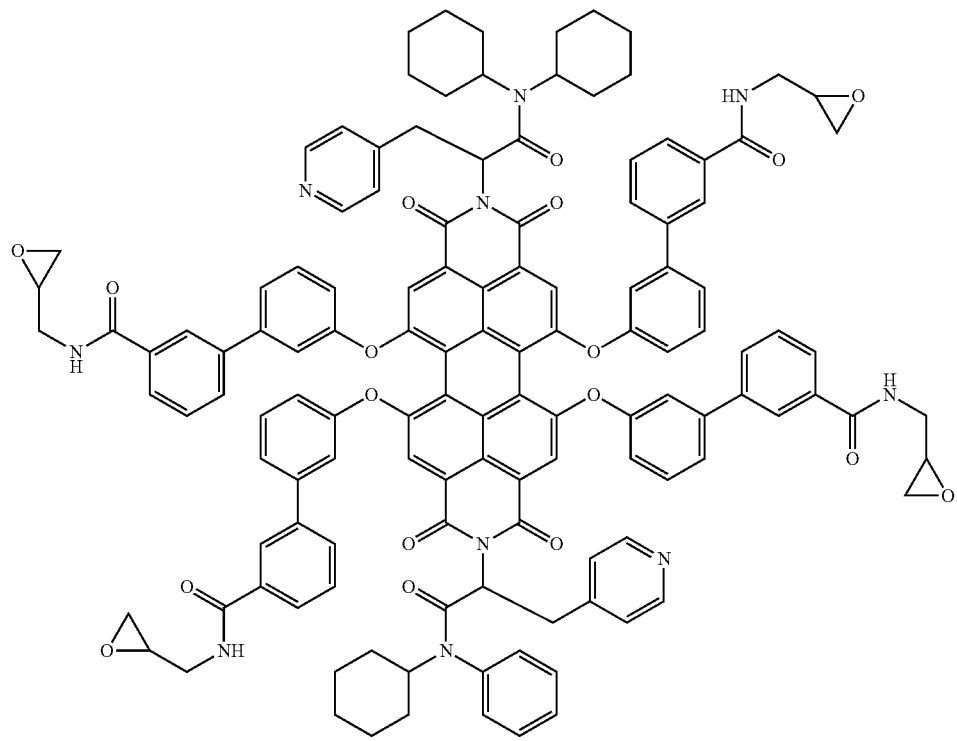

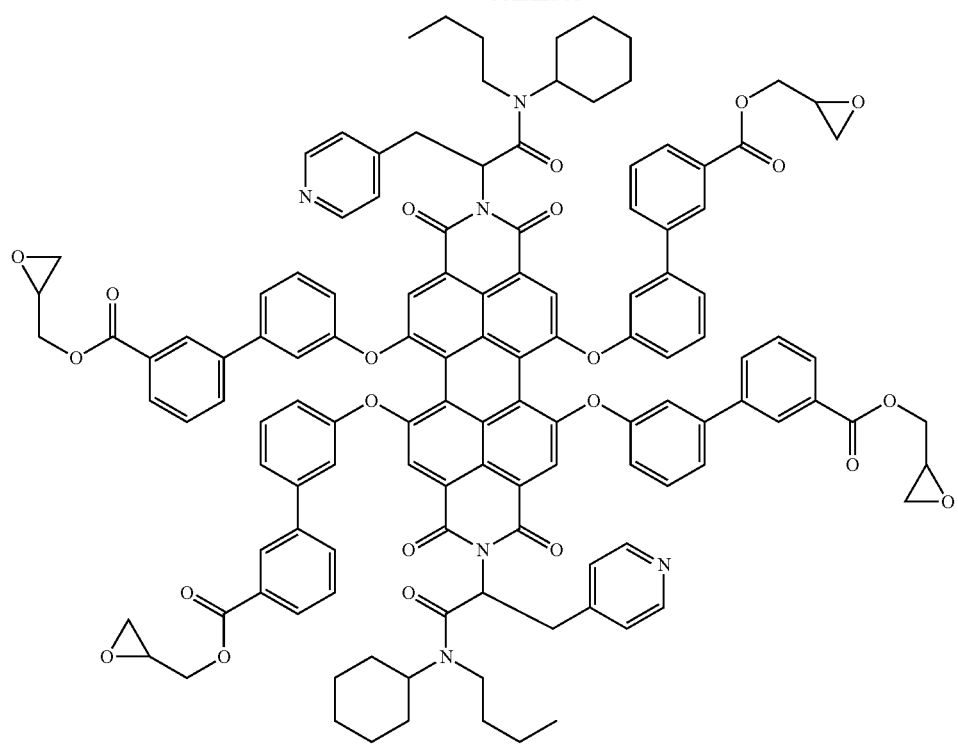
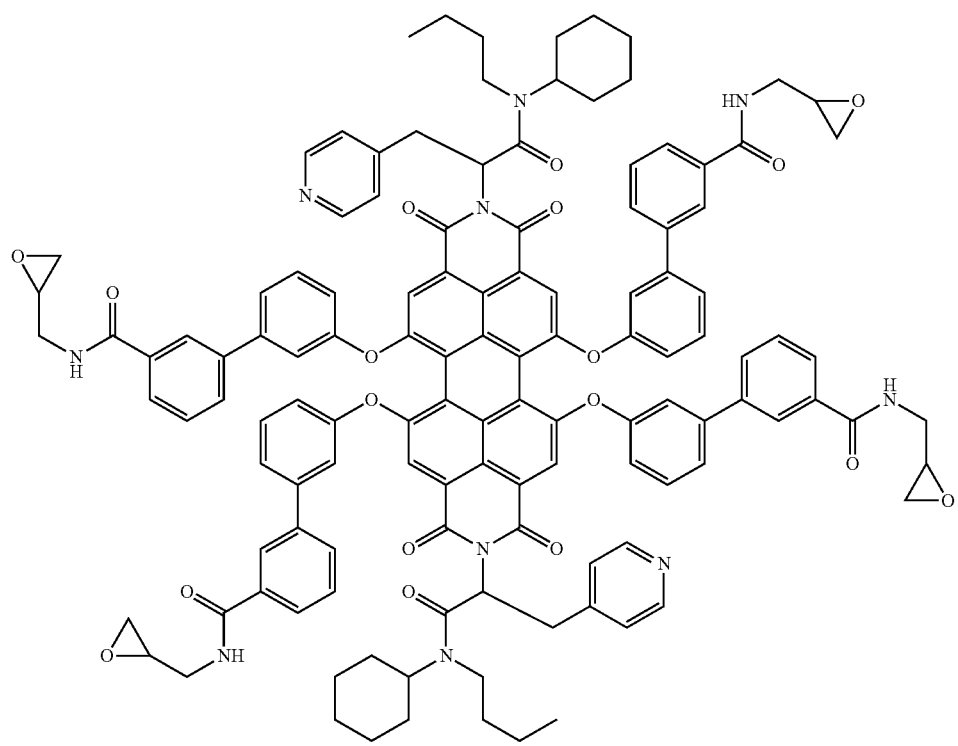

-continued
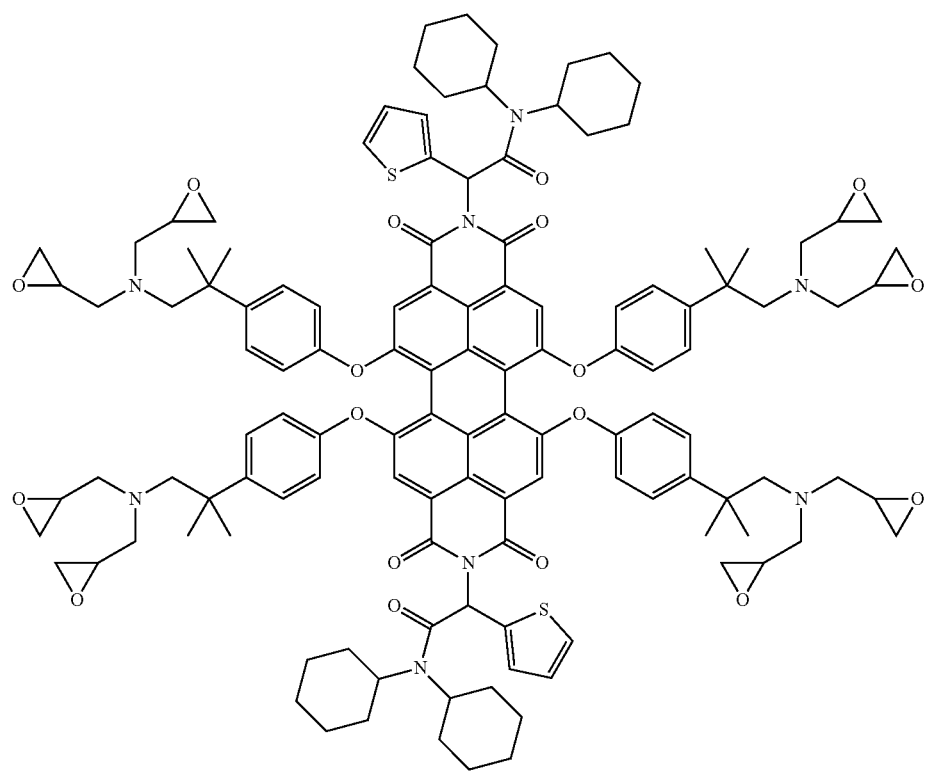
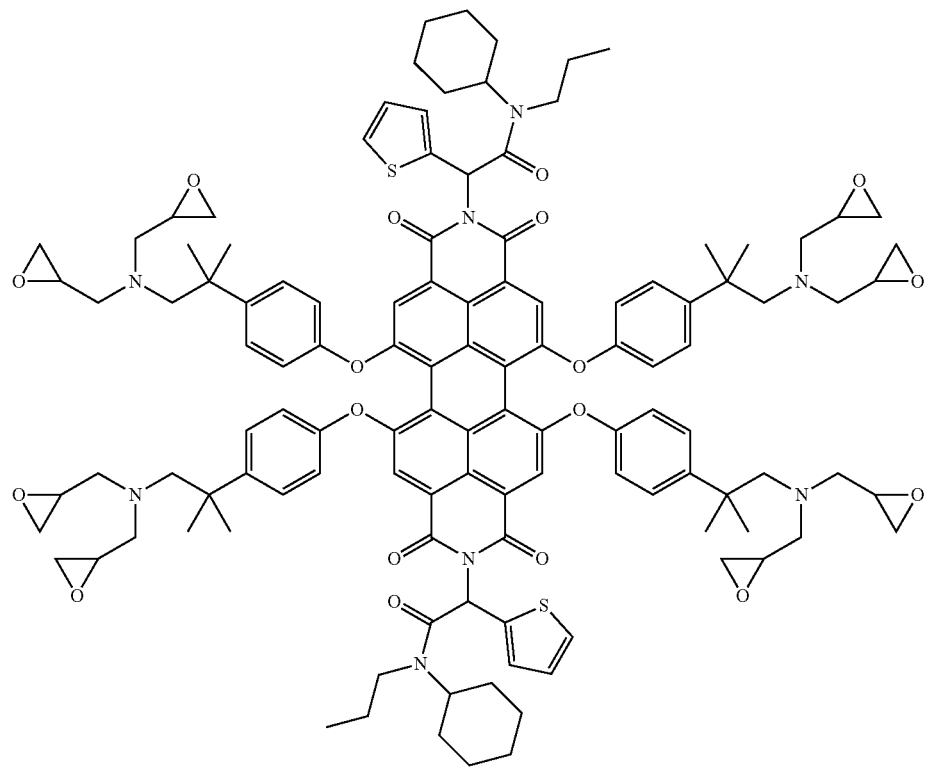

-continued
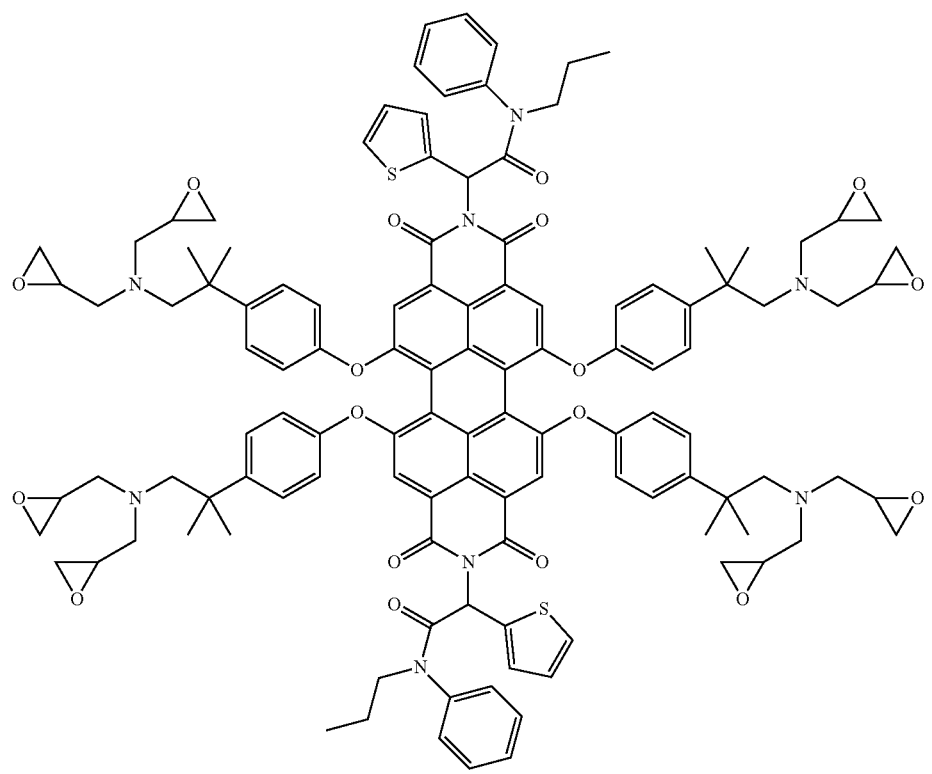
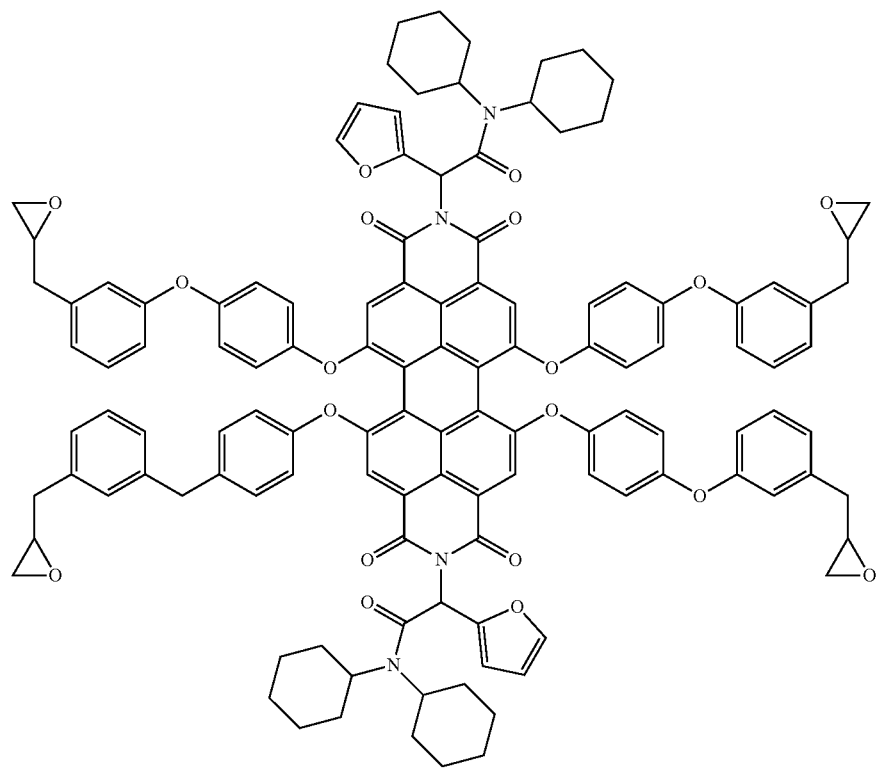

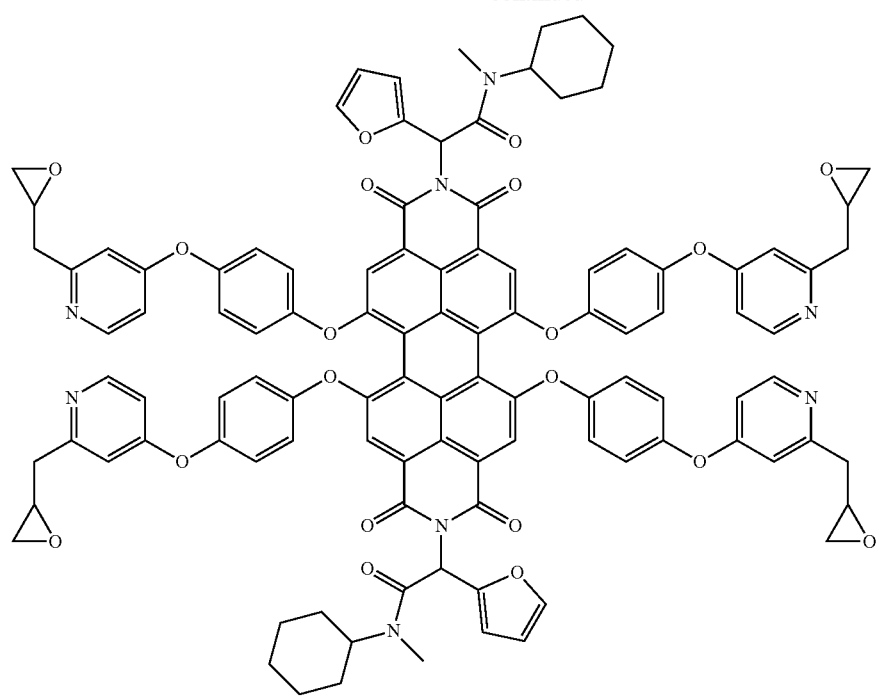
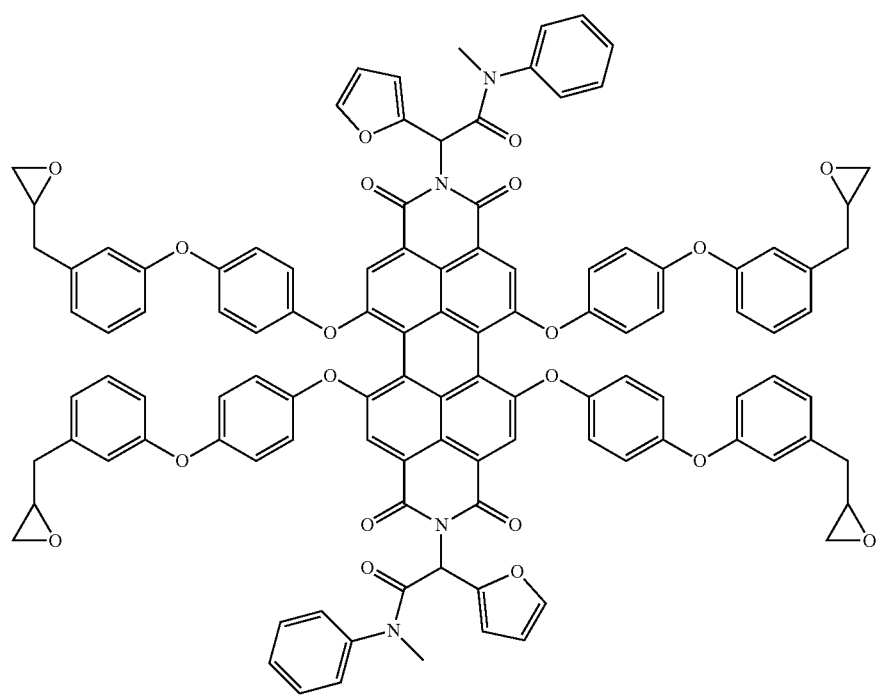

-continued
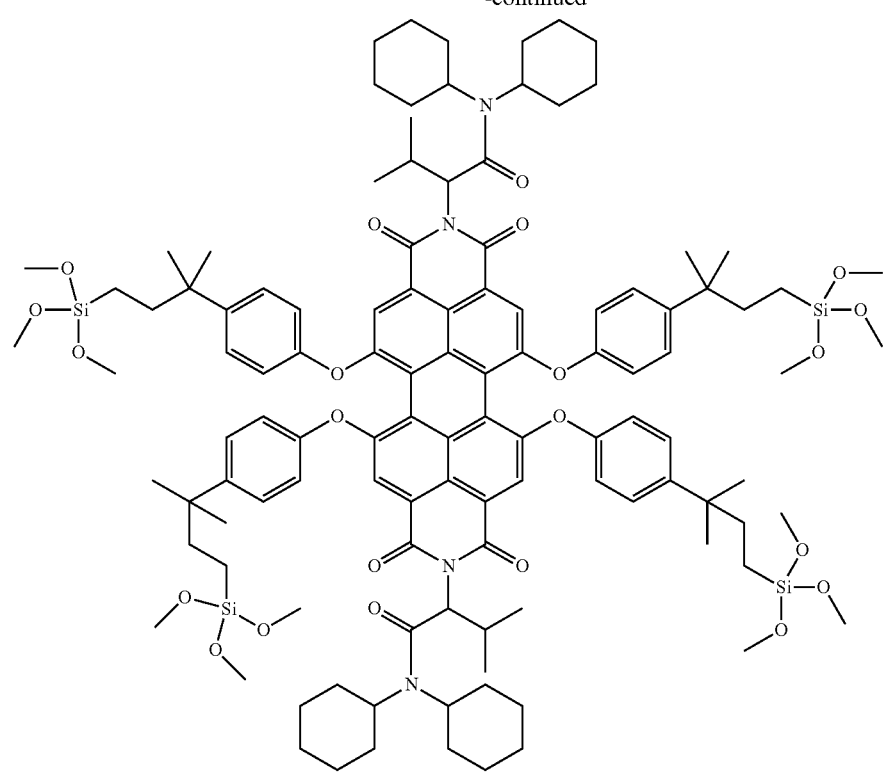
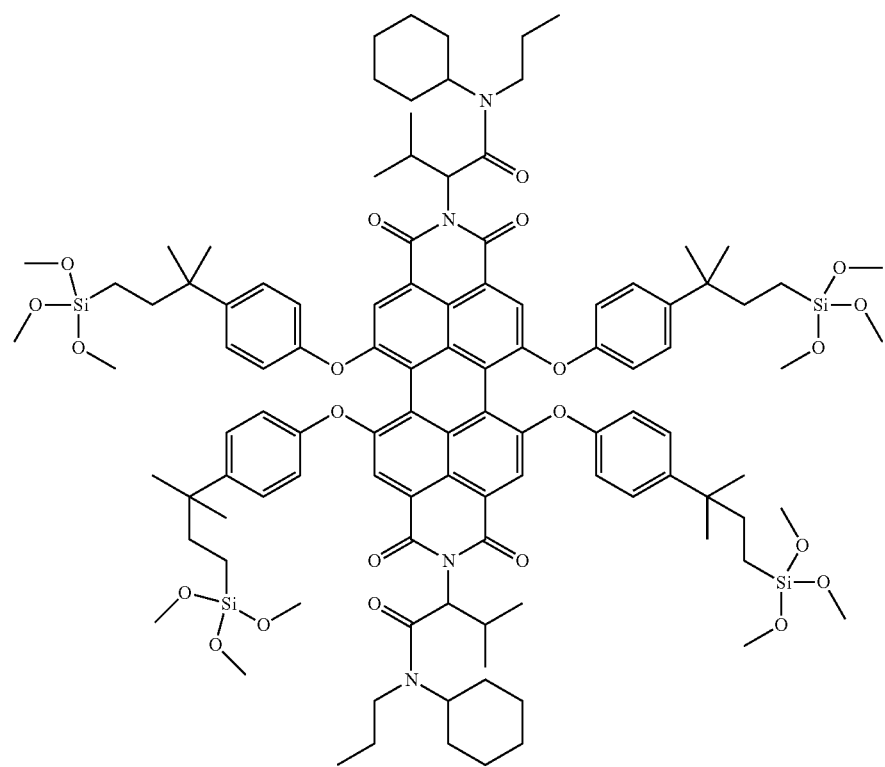

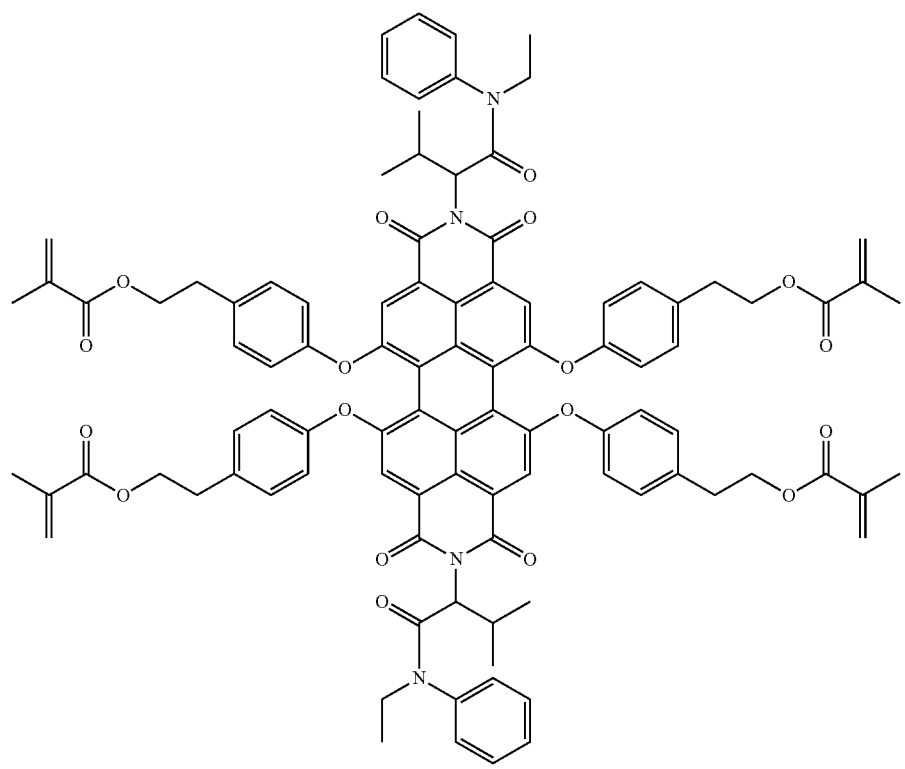 [SMILES: C=C(C)C(=O)OCCc1ccc(Oc2cc3c4c(cc(Oc5ccc(CCOC(=O)C(=C)C)cc5)c5c6c(Oc7ccc(CCOC(=O)C(=C)C)cc7)cc7c8c(cc(Oc9ccc(CCOC(=O)C(=C)C)cc9)c(c2c45)c86)C(=O)N(C(C(=O)N(CC)c2ccccc2)C(C)C)C7=O)C(=O)N(C(C(=O)N(CC)c2ccccc2)C(C)C)C3=O)cc1]
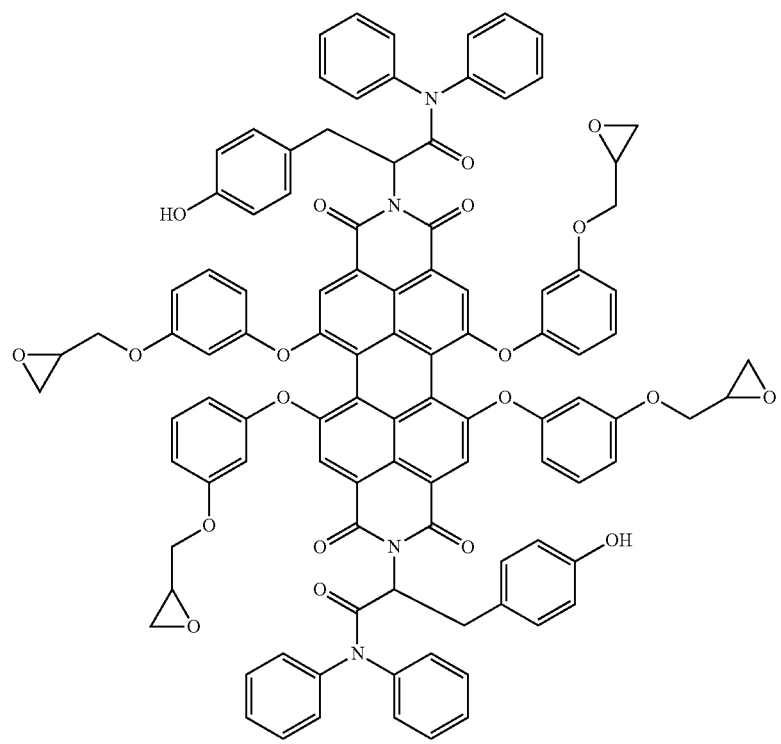

-continued
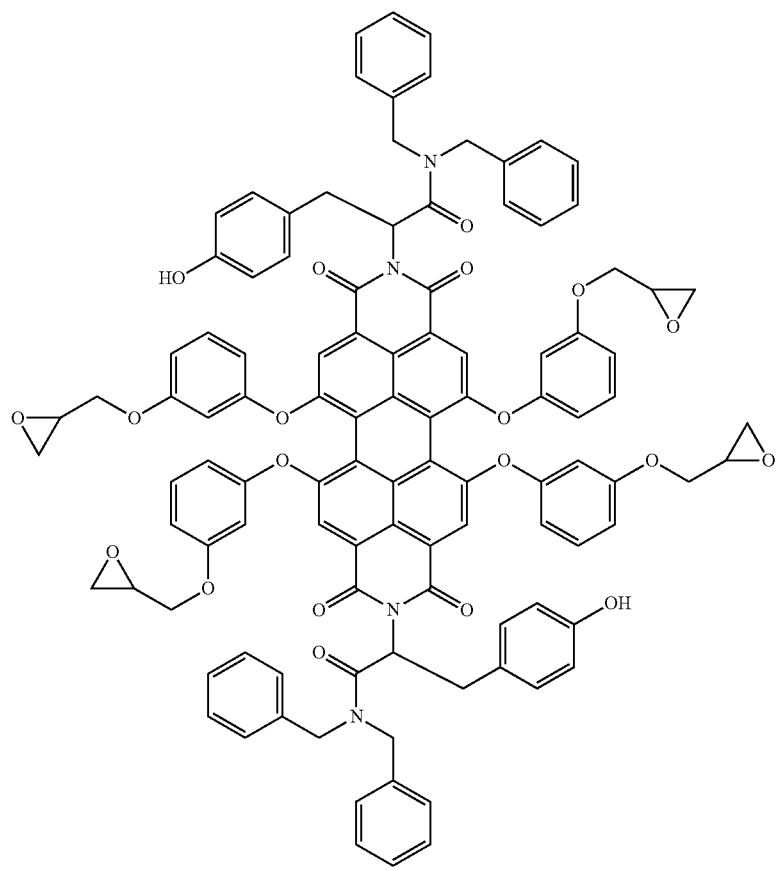
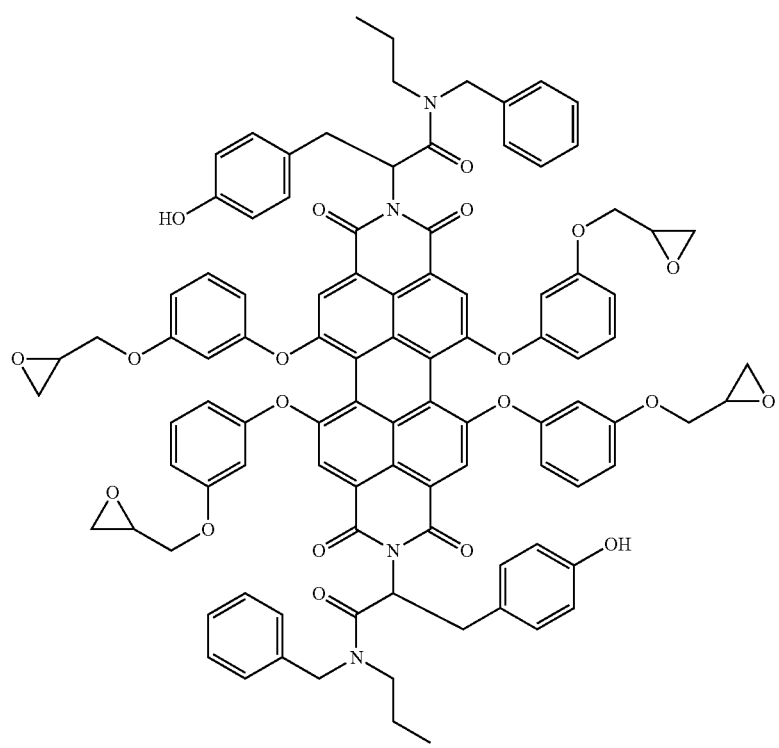

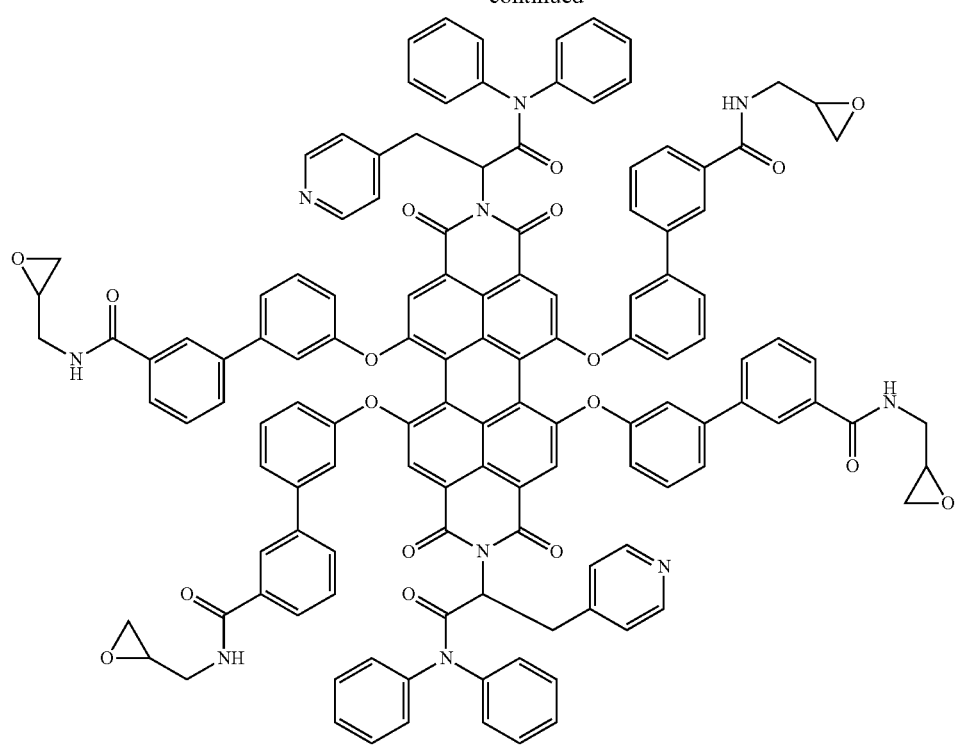
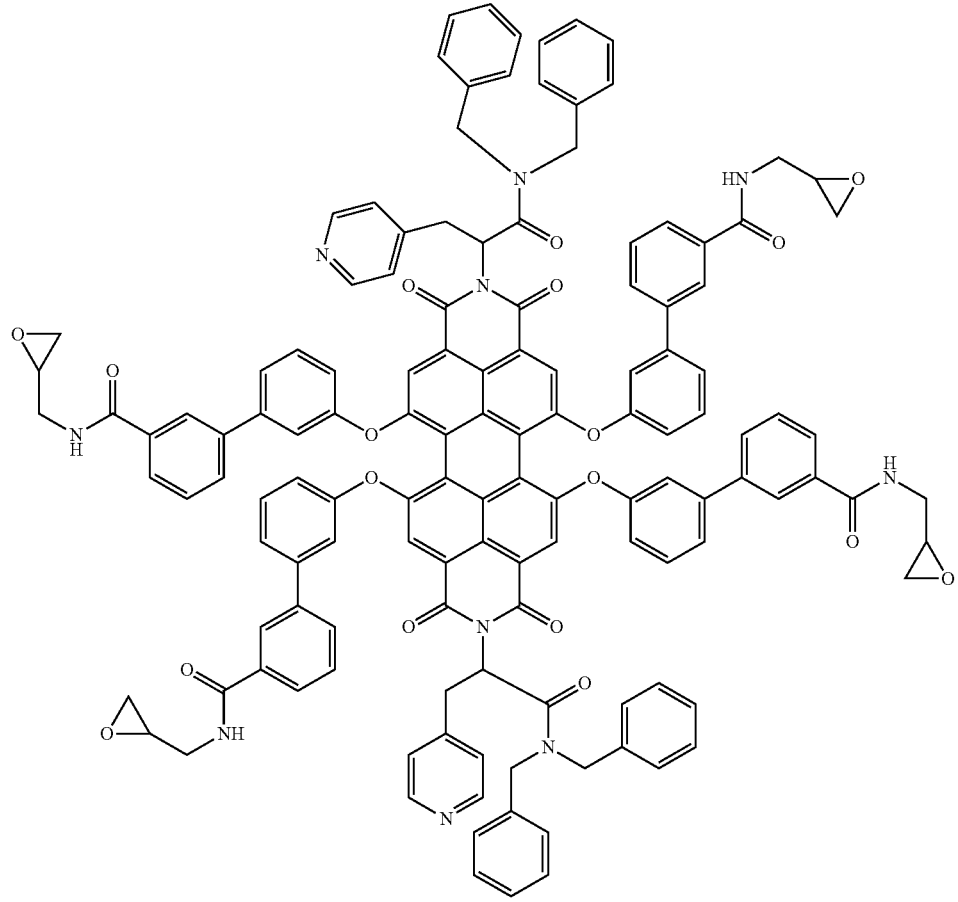

-continued
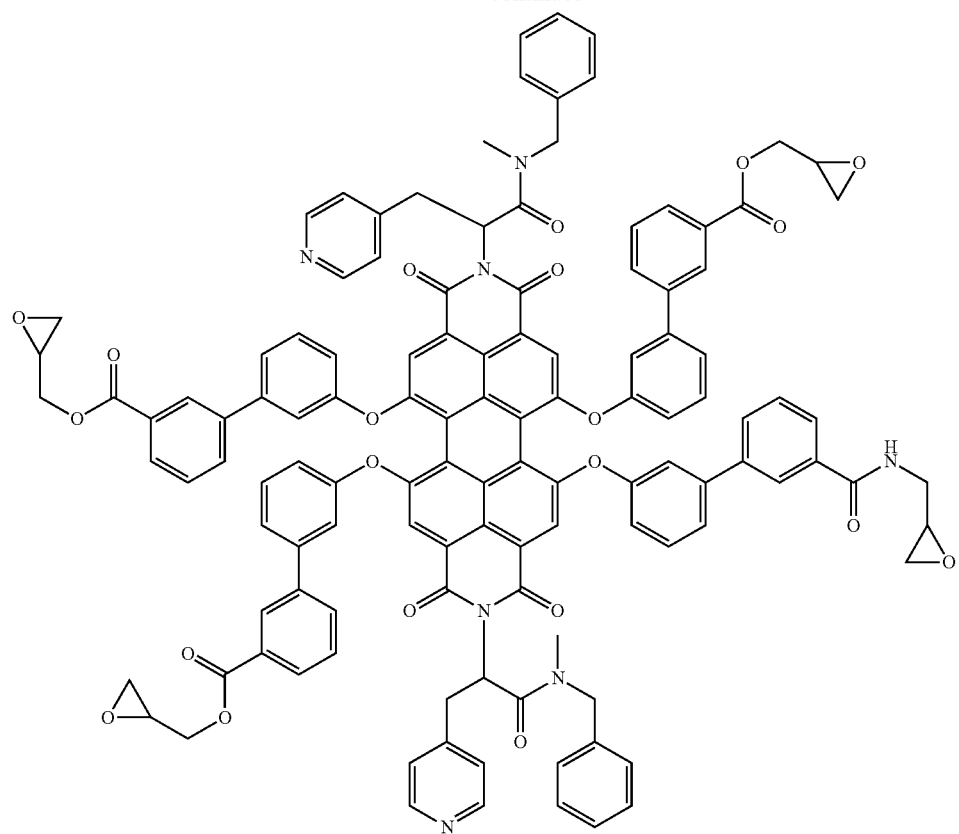
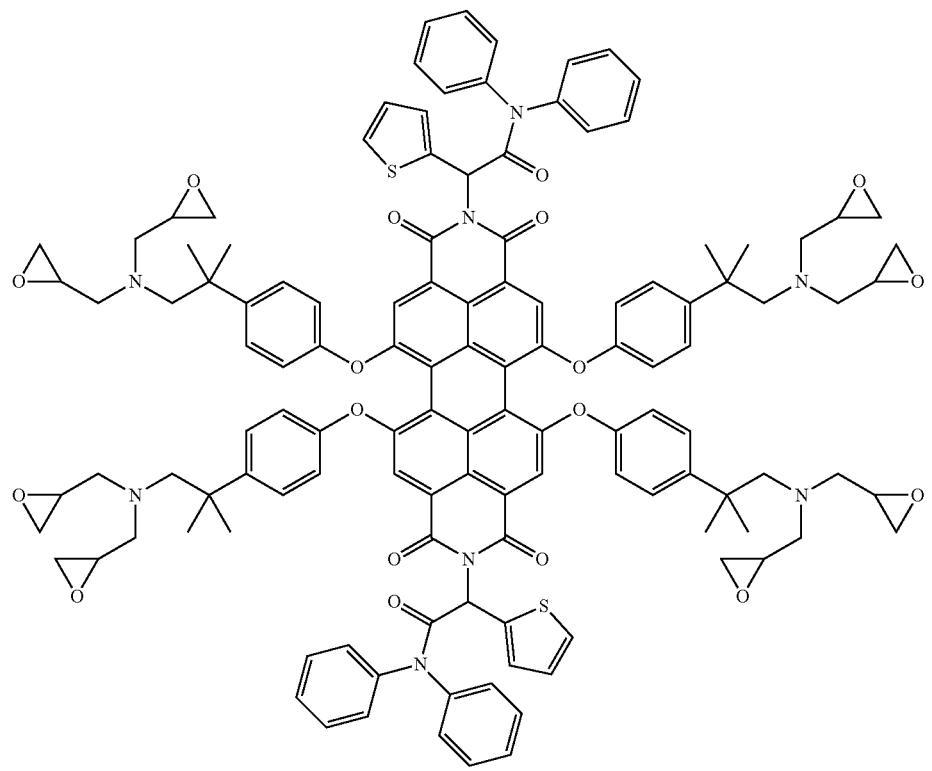

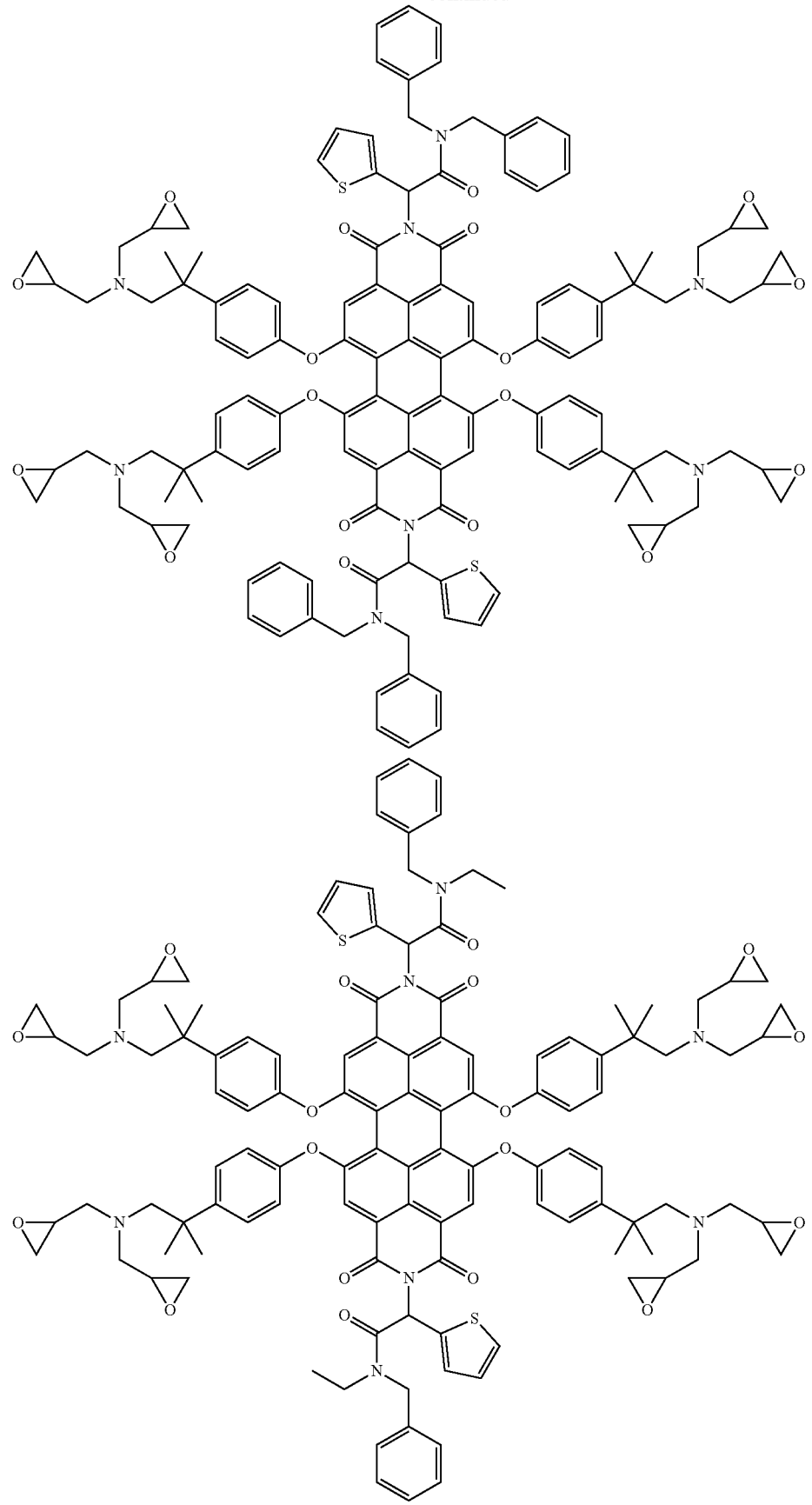

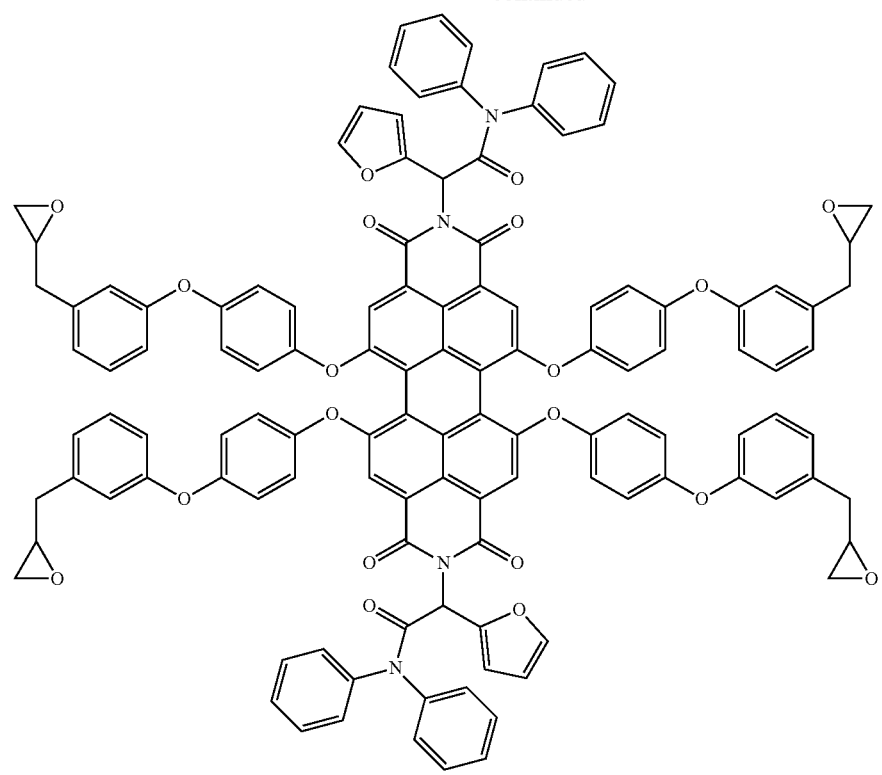
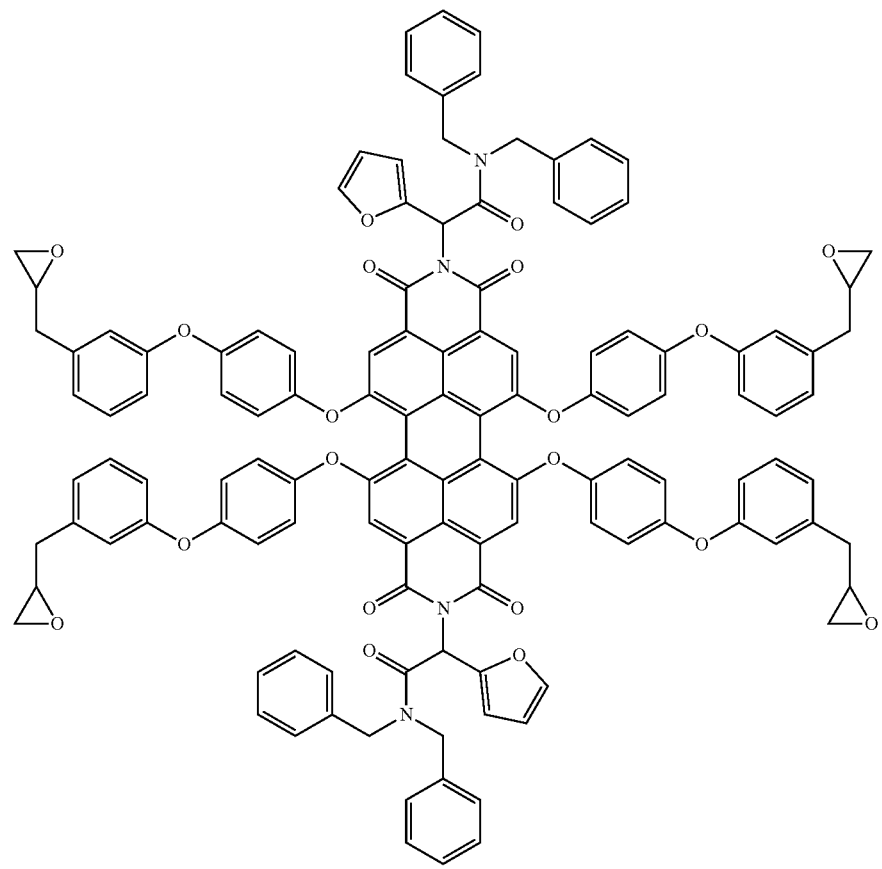

-continued
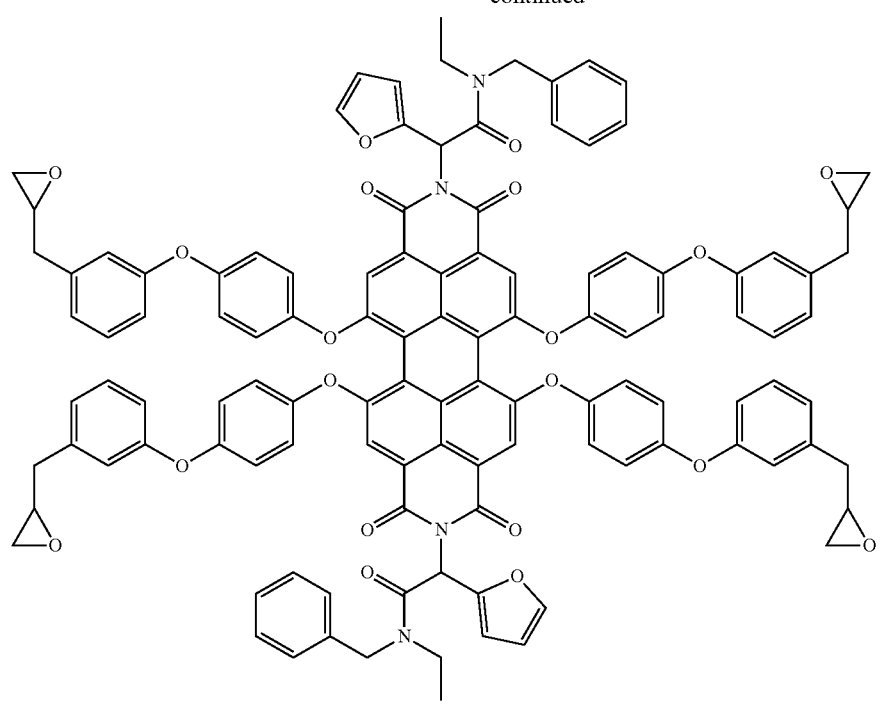
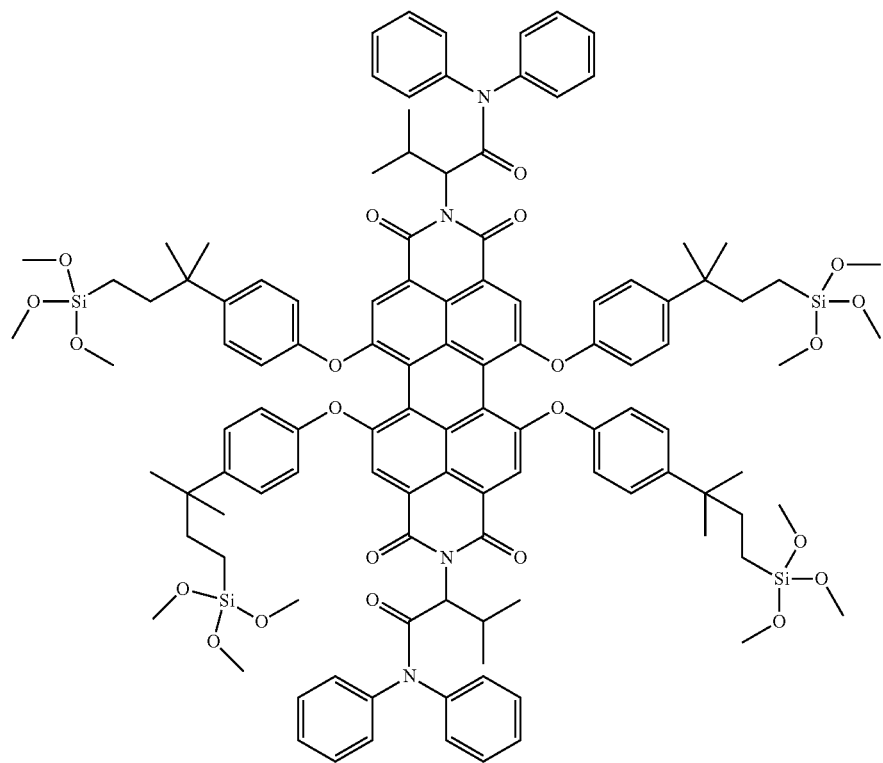

-continued
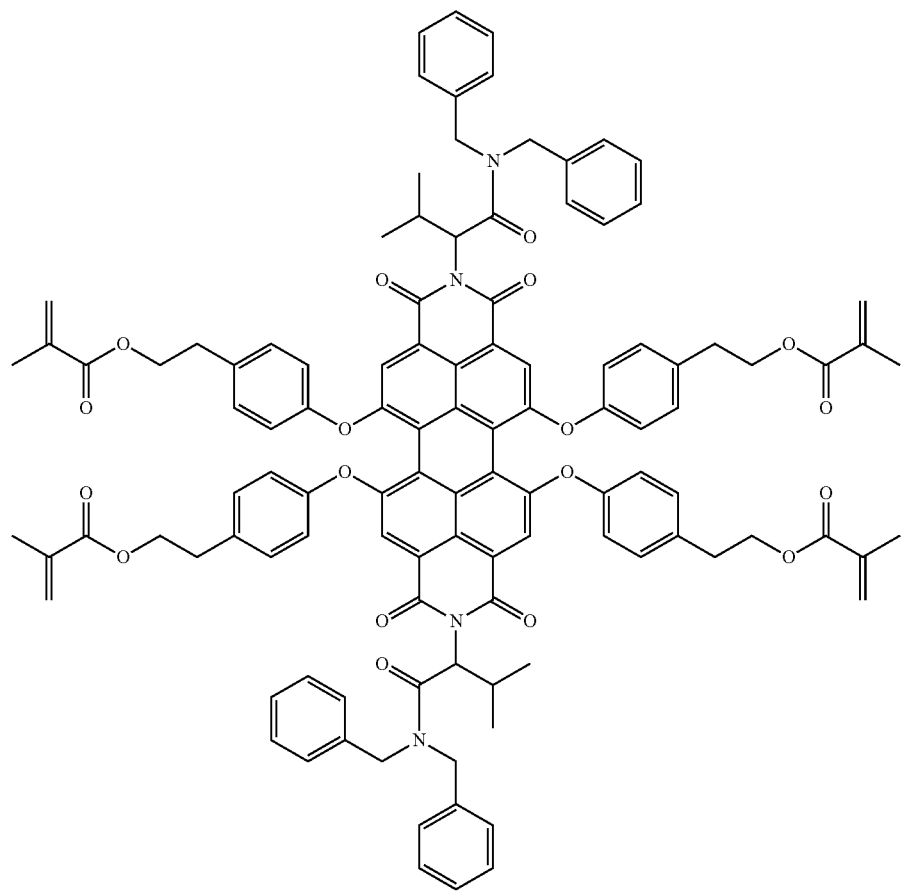

-continued
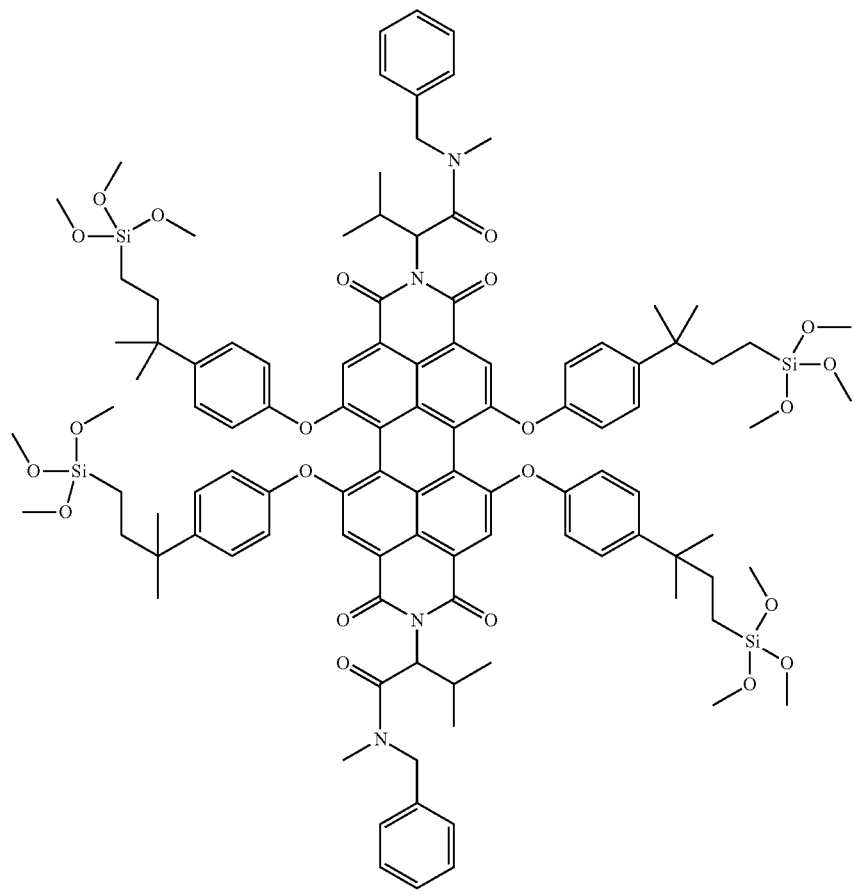

-continued
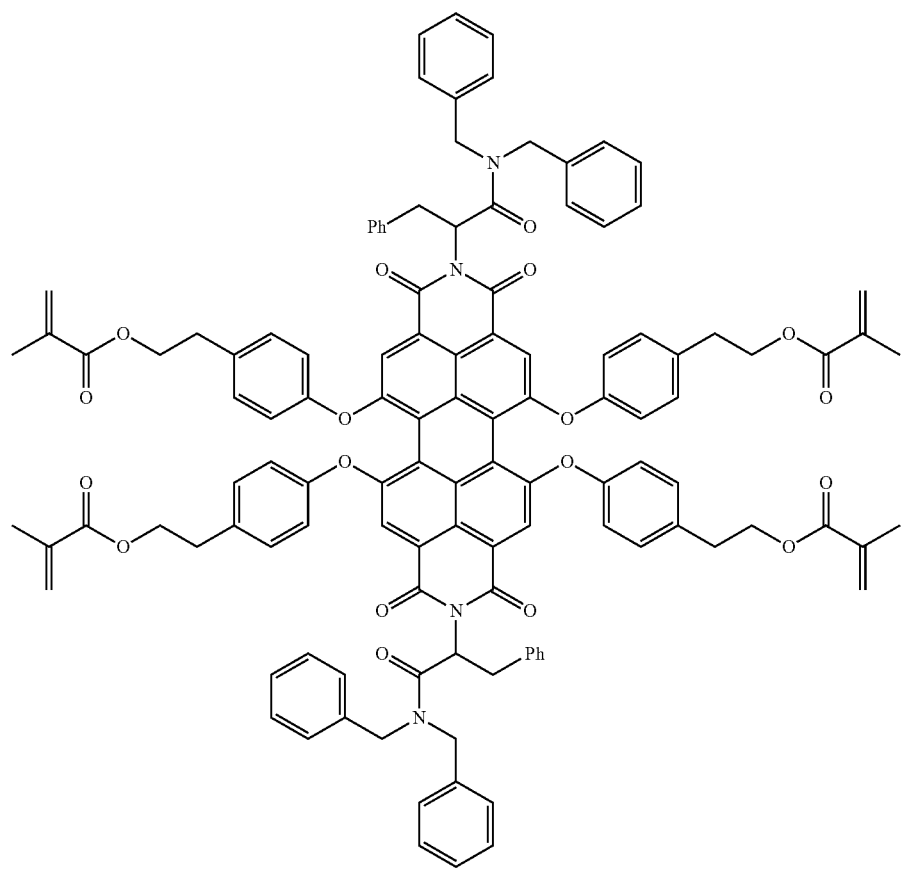
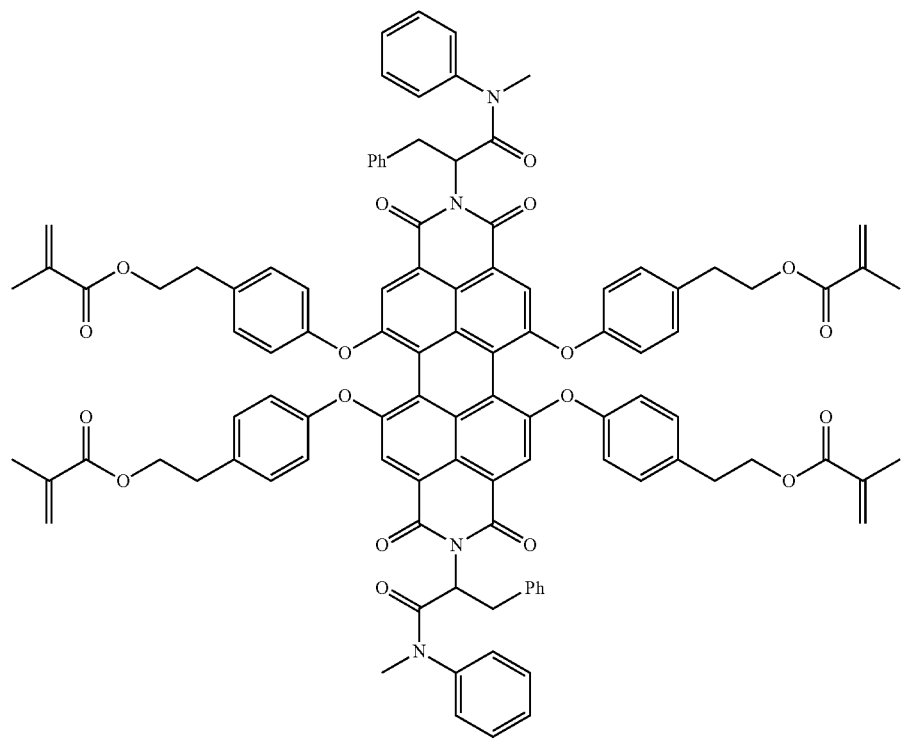

-continued
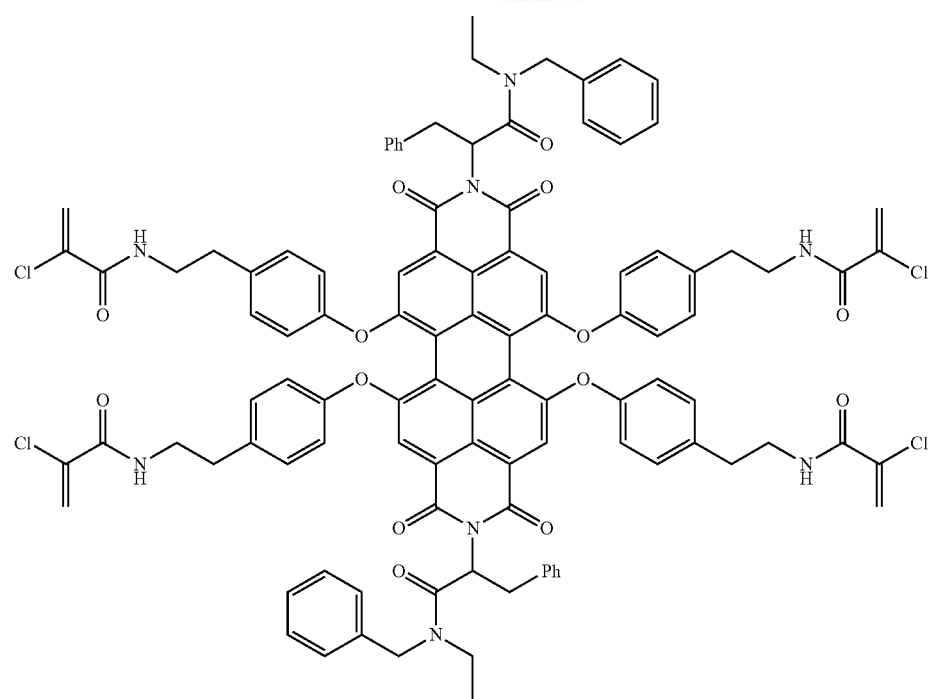
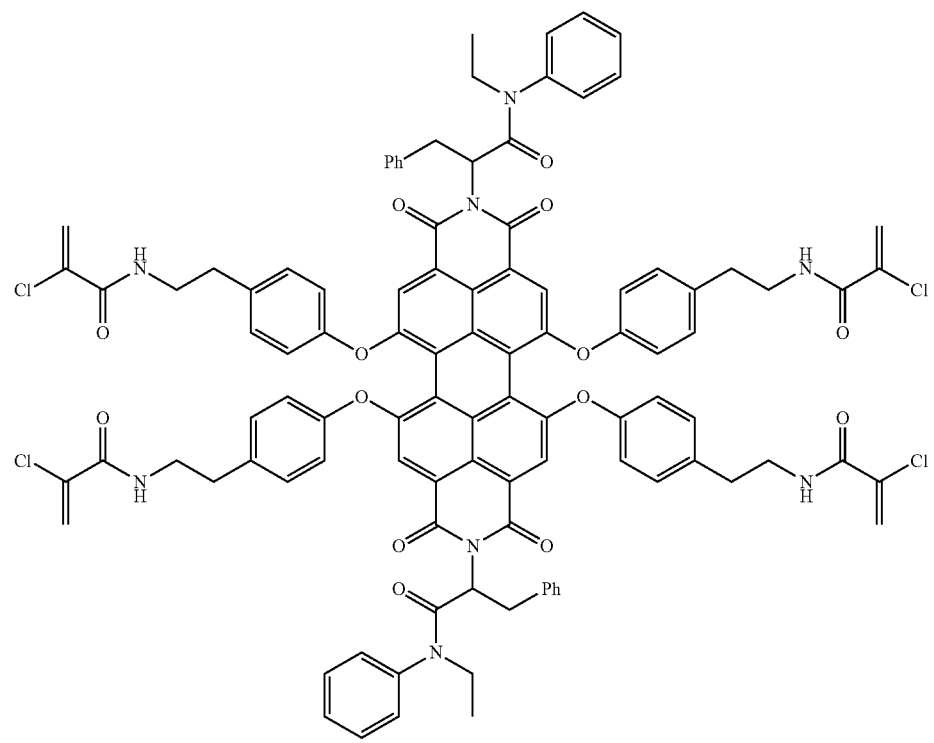

-continued
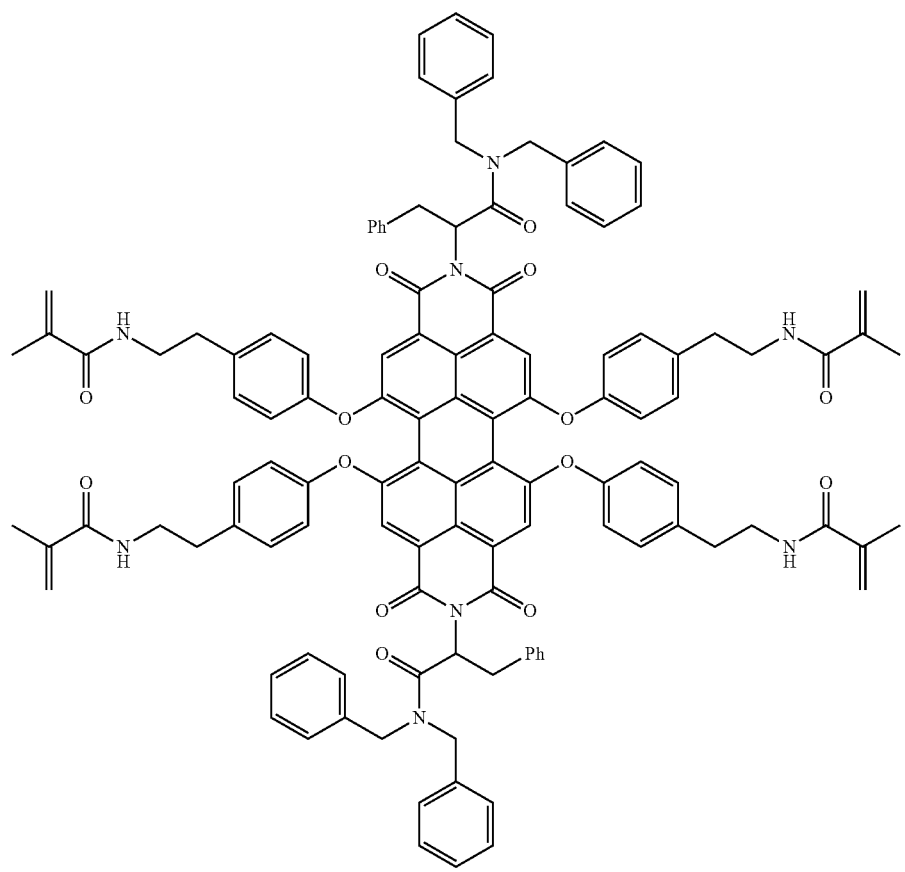
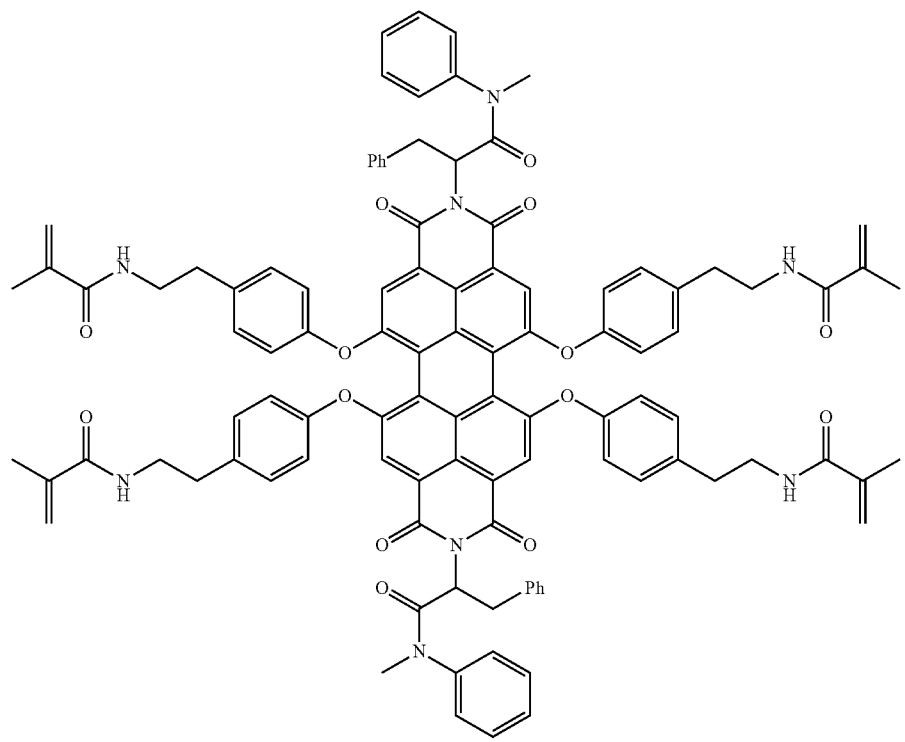

-continued
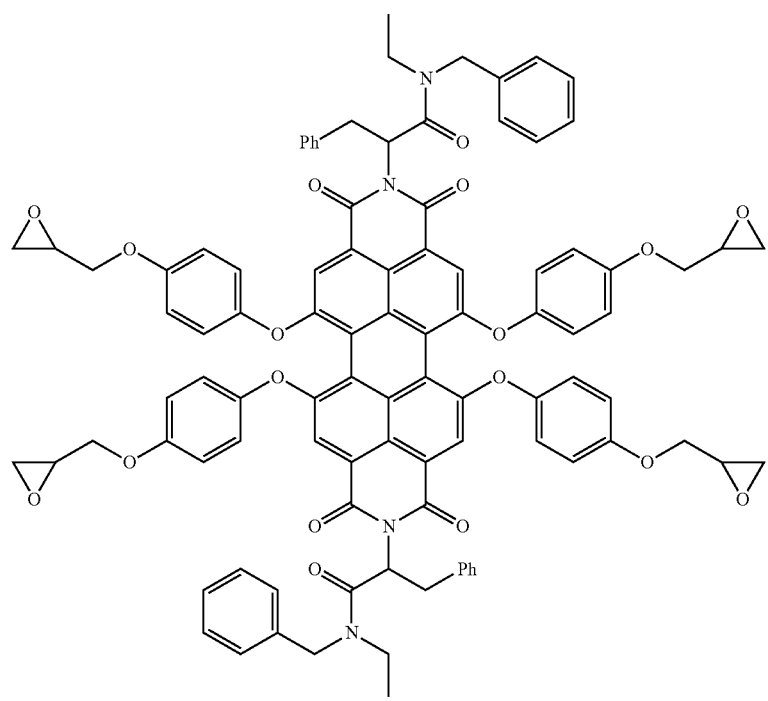
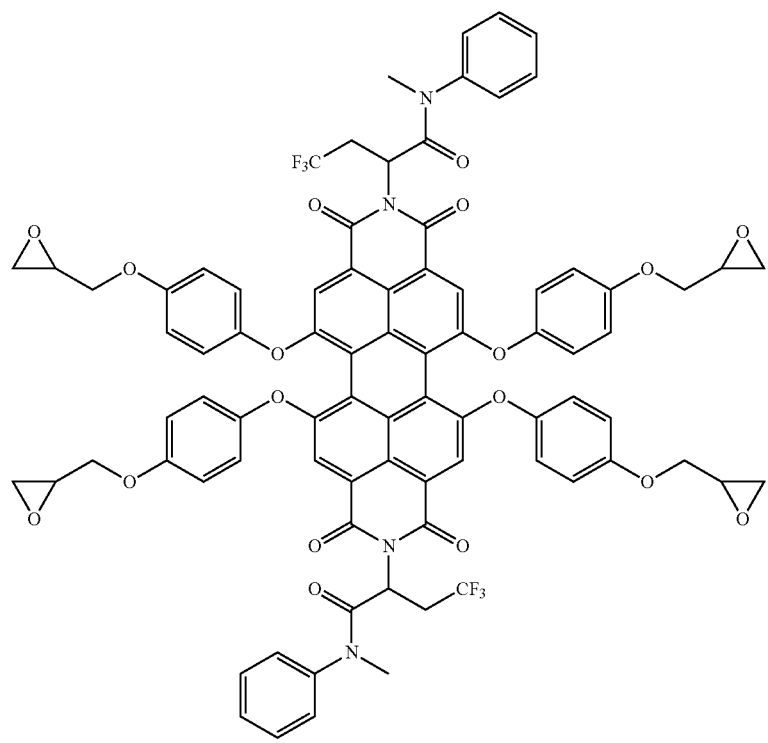

-continued
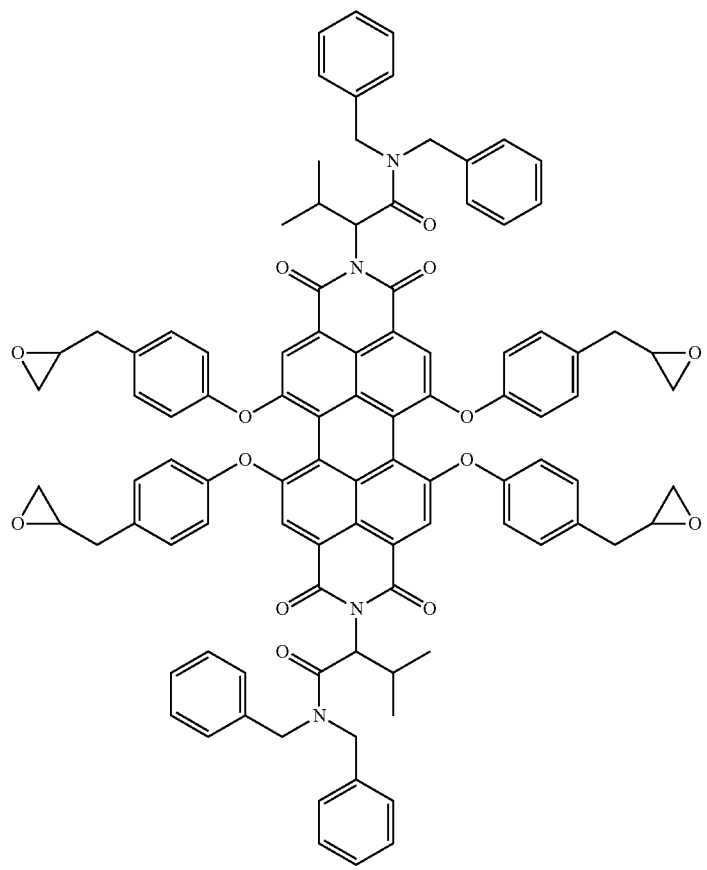
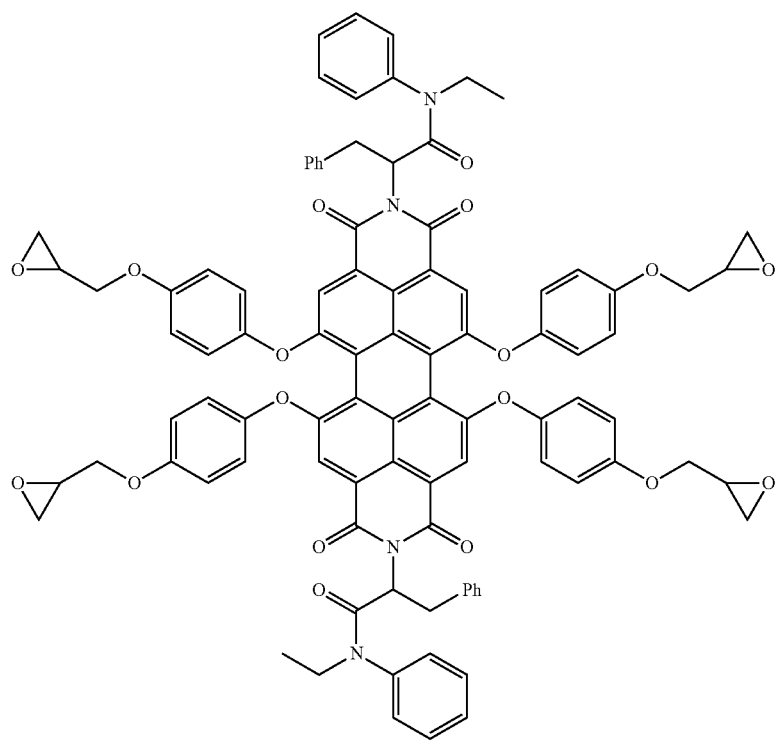

-continued
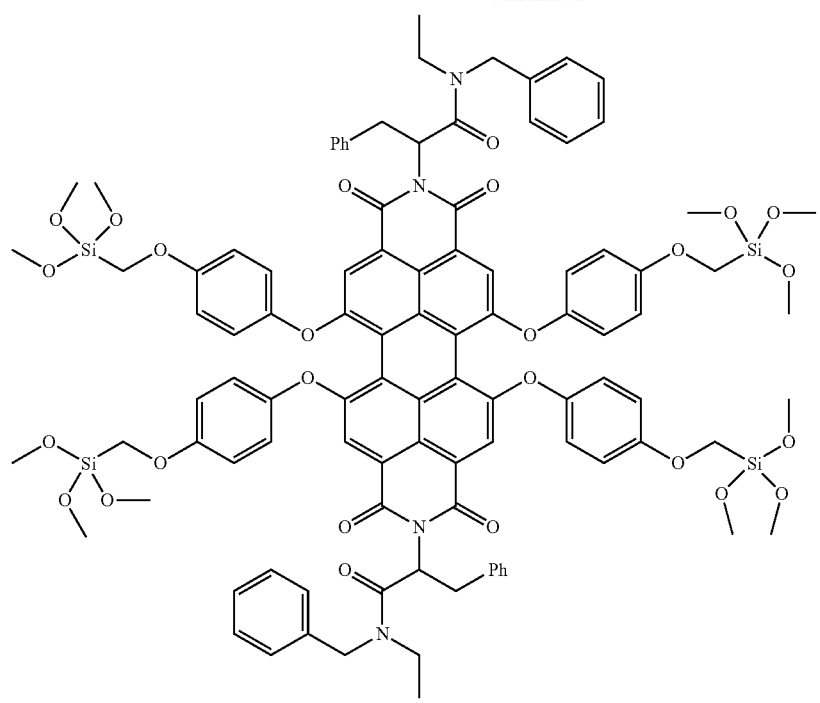
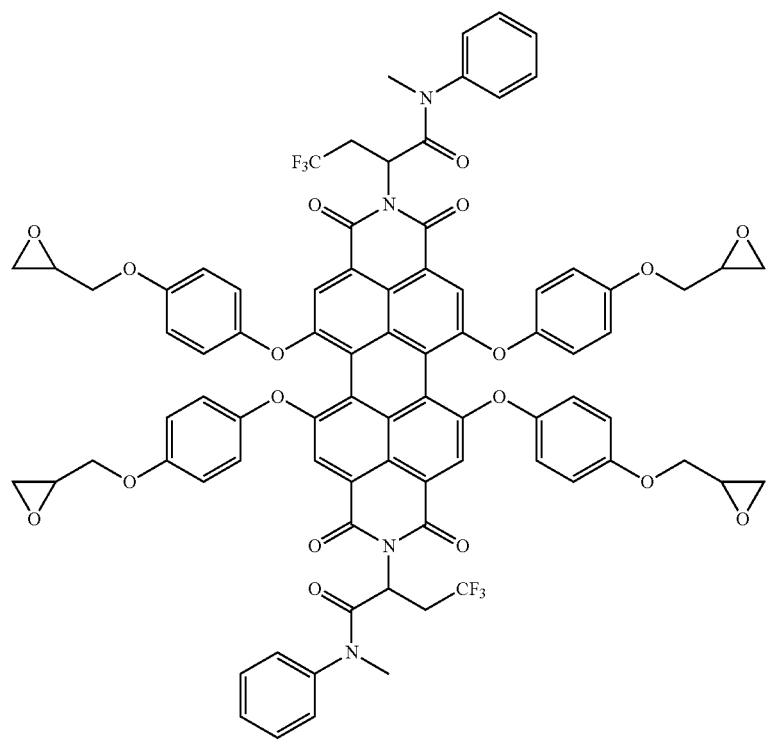

-continued
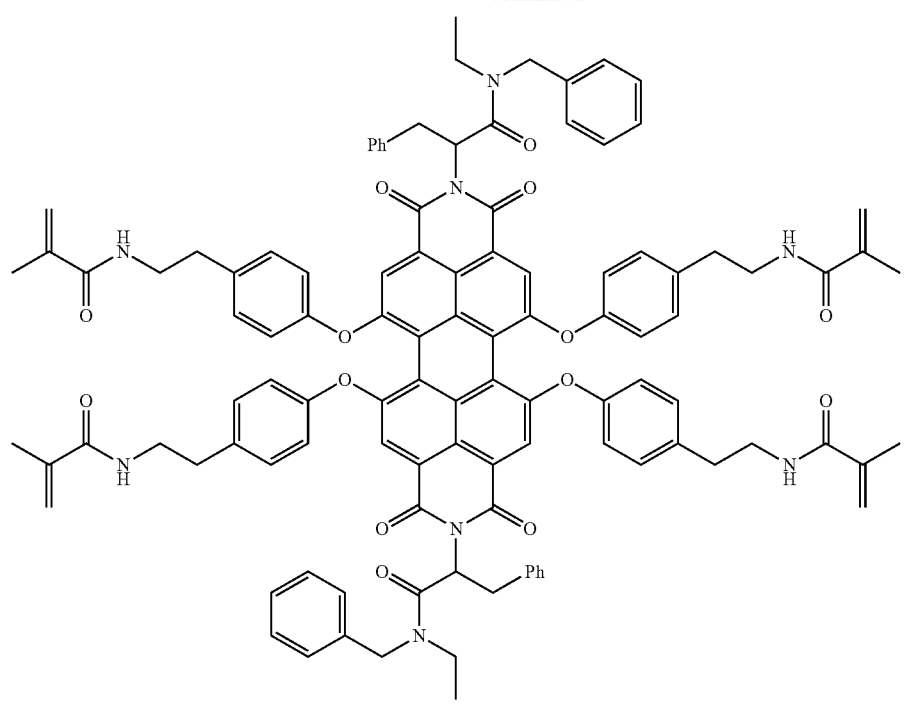
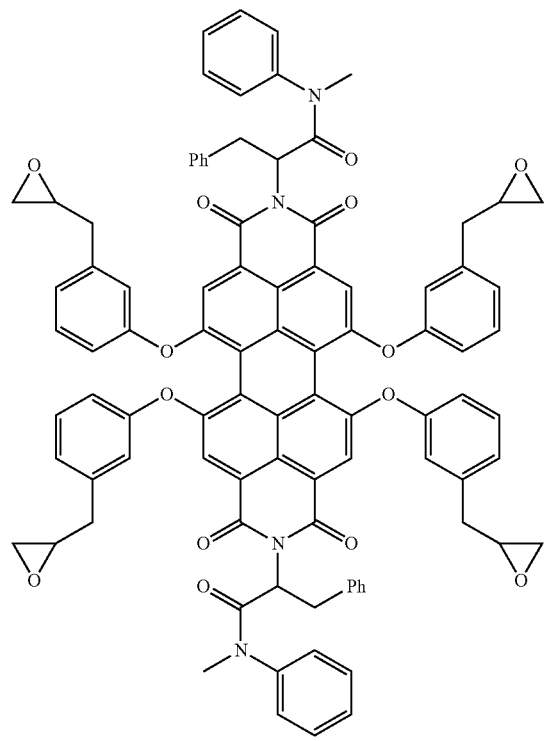

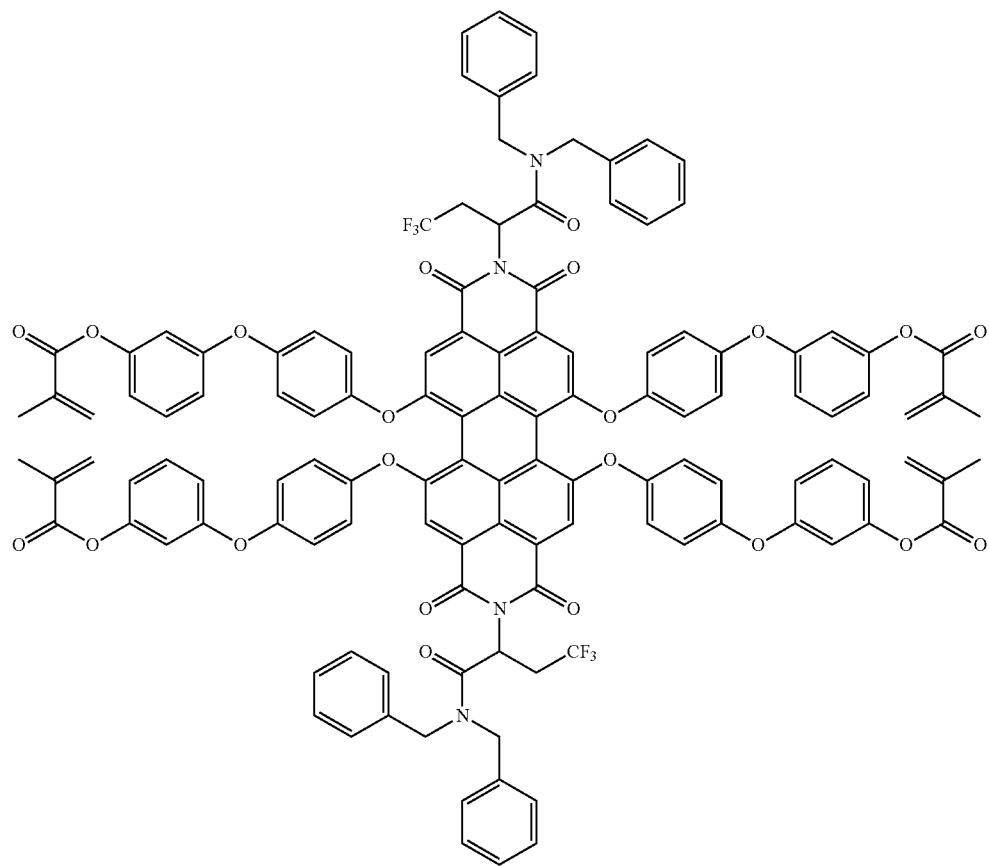
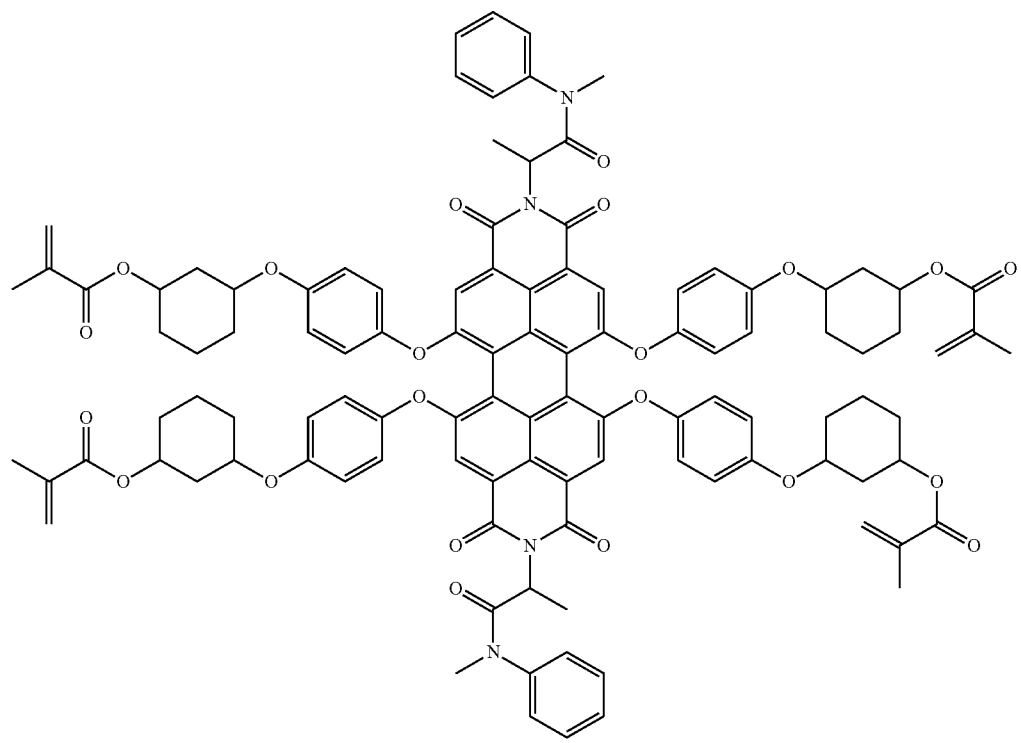

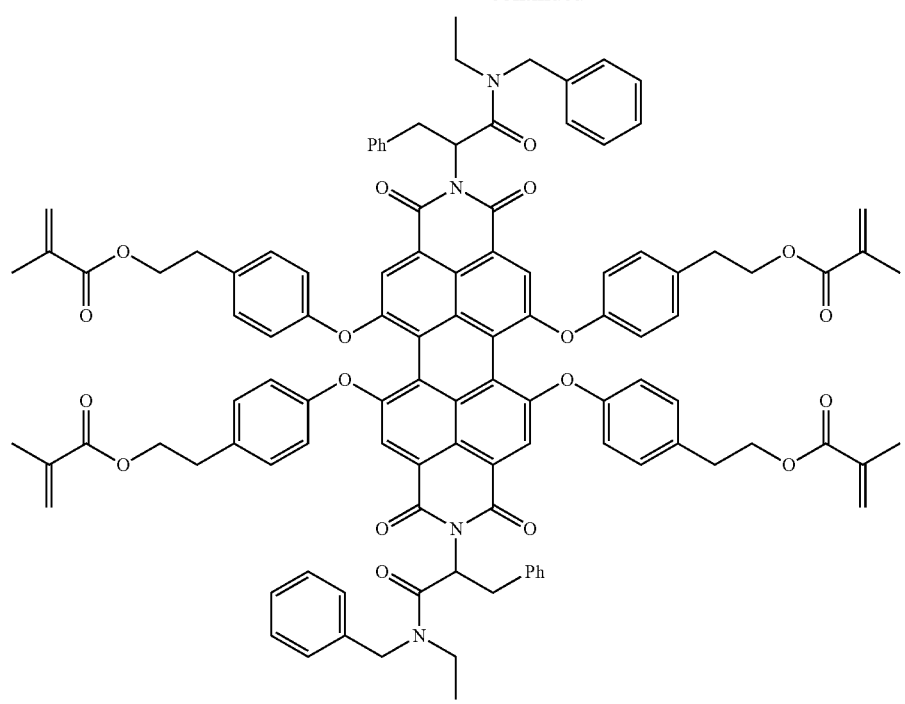
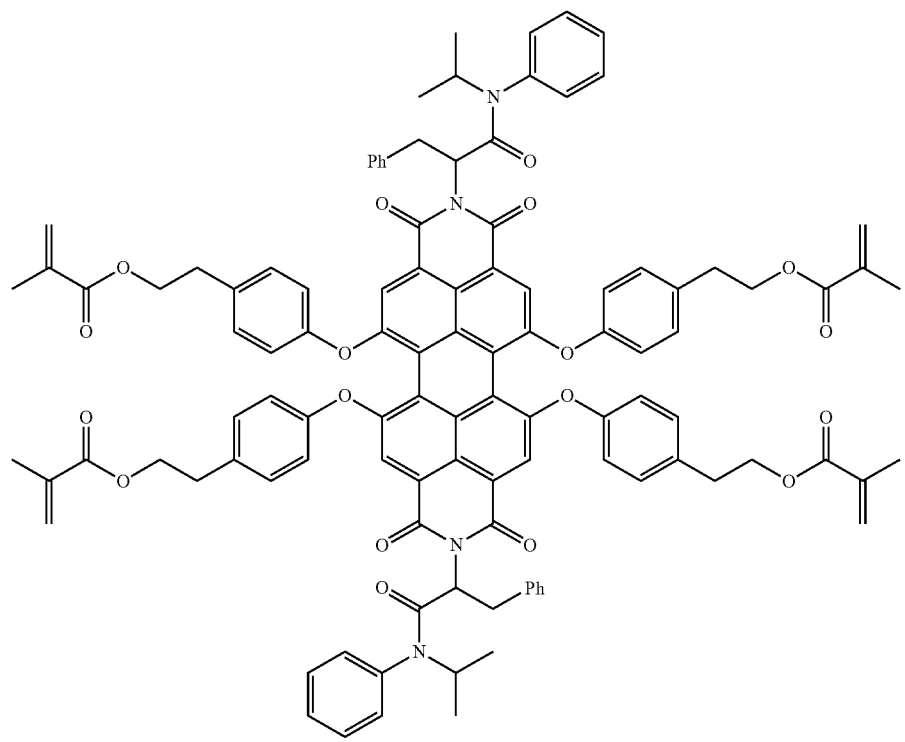

-continued
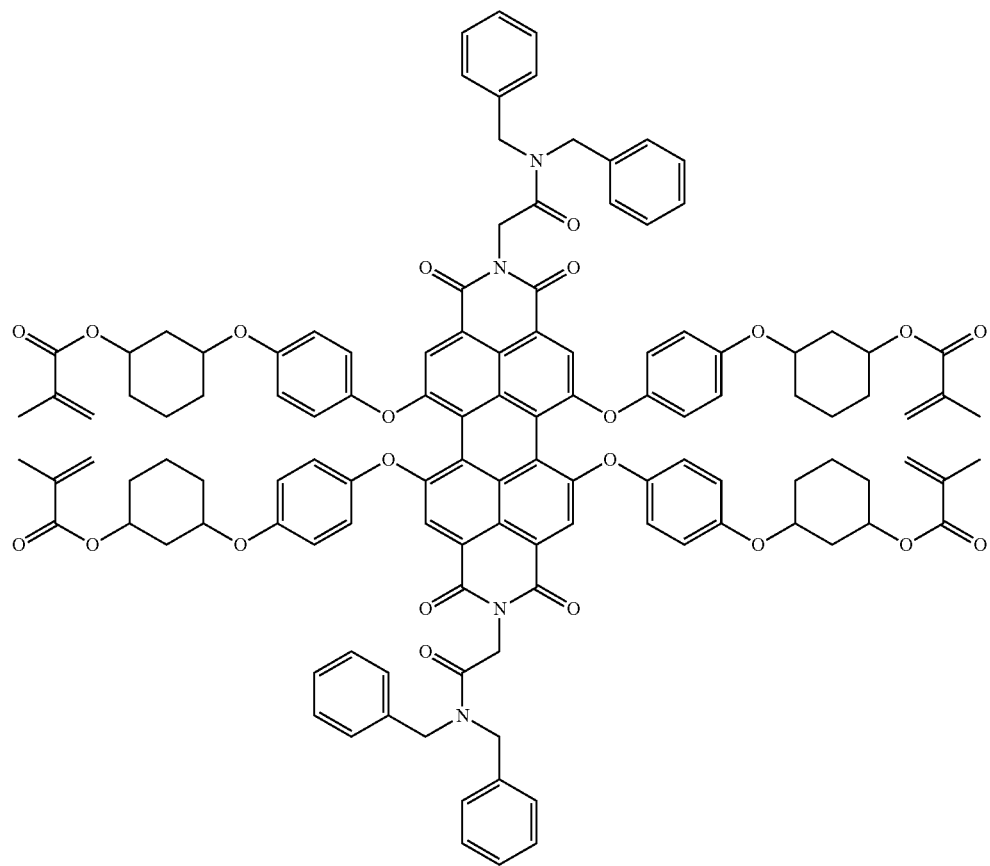
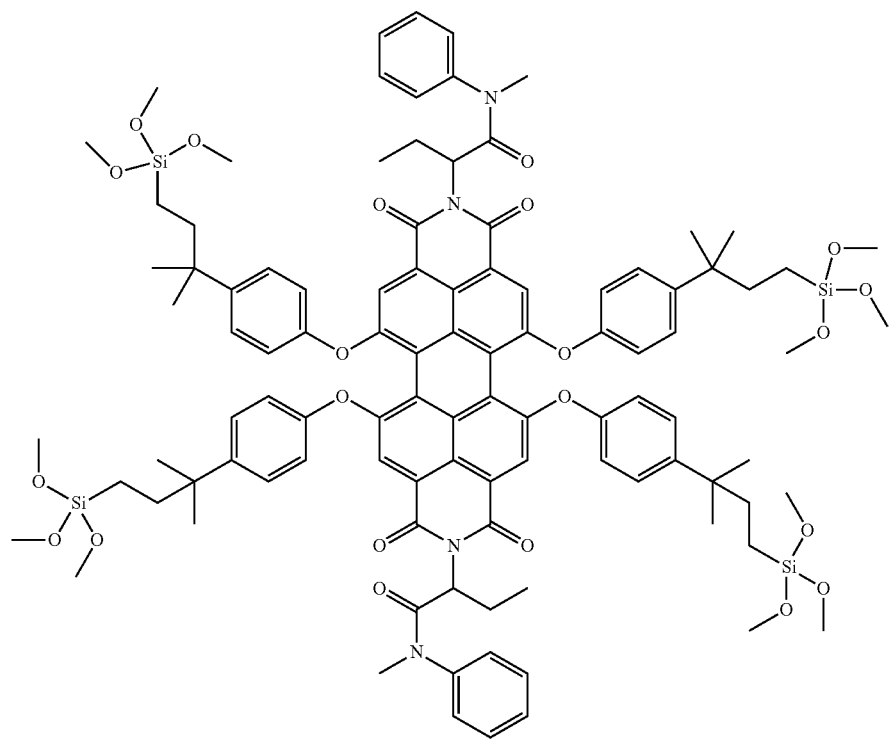

In the compounds, Ph is a phenyl group.

One embodiment of the present specification provides a photoresist fluorescent resin composition including a binder resin; a multifunctional monomer; and the compound described above.

A content of the compound may be from 0.005% by weight to 70% by weight based on a total solid weight of the photoresist fluorescent resin composition, but is not limited thereto.

A content of the compound may be from 0.001% by weight to 15% by weight based on a total weight of the photoresist fluorescent resin composition, but is not limited thereto.

The compound may have a maximum absorption wavelength ($\lambda_{max}$) of 570 nm to 590 nm.

As the binder resin, a copolymer resin of a monomer providing mechanical strength and a monomer providing alkali solubility may be used.

The monomer providing mechanical strength of the film may be any one or more of unsaturated carboxylic acid esters; aromatic vinyls; unsaturated ethers; unsaturated imides; and acid anhydrides.

Specific examples of the unsaturated carboxylic acid esters may be selected from the group consisting of benzyl (meth)acrylate, methyl (meth)acrylate, ethyl (meth)acrylate, butyl (meth)acrylate, dimethylaminoethyl (meth)acrylate, isobutyl (meth)acrylate, t-butyl (meth)acrylate, cyclohexyl (meth)acrylate, isobornyl (meth)acrylate, ethylhexyl (meth)acrylate, 2-phenoxyethyl (meth)acrylate, tetrahydrofurfuryl (meth)acrylate, hydroxyethyl (meth)acrylate, 2-hydroxypropyl (meth)acrylate, 2-hydroxy-3-chloropropyl (meth)acrylate, 4-hydroxybutyl (meth)acrylate, acyloctyloxy-2-hydroxypropyl (meth)acrylate, glycerol (meth)acrylate, 2-methoxyethyl (meth)acrylate, 3-methoxybutyl (meth)acrylate, ethoxy diethylene glycol (meth)acrylate, methoxy triethylene glycol (meth)acrylate, methoxy tripropylene glycol (meth)acrylate, poly(ethylene glycol)methyl ether (meth)acrylate, phenoxy diethylene glycol (meth)acrylate, p-nonylphenoxy polyethylene glycol (meth)acrylate, p-nonylphenoxy polypropylene glycol (meth)acrylate, glycidyl (meth)acrylate, tetrafluoropropyl (meth)acrylate, 1,1,1,3,3,3-hexafluoroisopropyl (meth)acrylate, octafluoropentyl (meth)acrylate, heptadecafluorodecyl (meth)acrylate, tribromophenyl (meth)acrylate, methyl α-hydroxynnethyl acrylate, ethyl α-hydroxynnethyl acrylate, propyl α-hydroxynnethyl acrylate and butyl α-hydroxynnethyl acrylate, but are not limited thereto.

Specific examples of the aromatic vinyls may be selected from the group consisting of styrene, α-nnethylstyrene, (o,m,p)-vinyl toluene, (o,m,p)-methoxystyrene and (o,m,p)-chlorostyrene, but are not limited thereto.

Specific examples of the unsaturated ethers may be selected from the group consisting of vinyl methyl ether, vinyl ethyl ether and allyl glycidyl ether, but are not limited thereto.

Specific examples of the unsaturated imides may be selected from the group consisting of N-phenylmaleimide, N-(4-chlorophenyl)maleimide, N-(4-hydroxyphenyl)maleimide and N-cyclohexylmaleimide, but are not limited thereto.

Specific examples of the acid anhydride may include maleic anhydride, methyl maleic anhydride, tetrahydrophthalic anhydride and the like, but are not limited thereto.

The monomer providing alkali solubility may be a monomer containing an acid group. The monomer containing an acid group may use one or more types selected from the group consisting of (meth)acrylic acid, crotonic acid, itaconic acid, maleic acid, fumaric acid, monomethyl maleic acid, isoprenesulfonic acid, styrenesulfonic acid, 5-norbornene-2-carboxylic acid and the like, but is not limited thereto.

A content of the binder resin may be greater than or equal to 1% by weight and less than or equal to 60% by weight based on a total solid weight of the photoresist fluorescent resin composition, but is not limited thereto.

A content of the binder resin may be greater than or equal to 1% by weight and less than or equal to 30% by weight based on a total weight of the photoresist fluorescent resin composition, but is not limited thereto.

The binder resin may have an acid value of greater than or equal to 50 KOH mg/g and less than or equal to 130 KOH mg/g, and a weight average molecular weight of greater than or equal to 1,000 g/mol and less than or equal to 40,000 g/mol, however, the acid value and the weight average molecular weight are not limited thereto.

The multifunctional monomer means a compound having two or more polymerizable functional groups, and acts as a crosslinking agent in the photoresist fluorescent resin composition. Herein, the polymerizable functional group is not particularly limited as long as it is capable of polymerization, and examples thereof may include an ethylenically unsaturated group, a siloxane group, a hydroxyl group, an epoxy group and the like. Specifically, the multifunctional monomer may include an ethylenically unsaturated bond.

The multifunctional monomer may be one or more types selected from among ethylene glycol di(meth)acrylate, polyethylene glycol di(meth)acrylate having 2 to 14 ethylene groups, trimethylolpropane di(meth)acrylate, trimethylolpropane tri(meth)acrylate, pentaerythritol tri(meth)acrylate, pentaerythritol tetra(meth)acrylate, propylene glycol di(meth)acrylate having 2 to 14 propylene groups, dipentaerythritol penta(meth)acrylate and dipentaerythritol hexa(meth)acrylate, but is not limited thereto.

A content of the multifunctional monomer may be from 1% by weight to 60% by weight based on a total solid weight of the photoresist fluorescent resin composition, but is not limited thereto.

A content of the multifunctional monomer may be from 1% by weight to 30% by weight based on a total weight of the photoresist fluorescent resin composition, but is not limited thereto.

The photoresist fluorescent resin composition may further include a photoinitiator.

In the photoresist fluorescent resin composition according to the present disclosure, the photoinitiator may be any one or more selected from among acetophenone-based compounds; biimidazole-based compounds; triazine-based compounds; and oxime-based compounds.

Examples of the acetophenone-based compound may include 2-hydroxy-2-methyl-1-phenyl propa n-1-one, 1-(4-isopropylphenyl)-2-hydroxy-2-methylpropa n-1-one, 4-(2- hydroxyethoxy)-phenyl-(2-hydroxy-2-propyl)ketone, 1-hydroxycyclohexylphenyl ketone, benzoin methyl ether, benzoin ethyl ether, benzoin isobutyl ether, benzoin butyl ether, 2,2-dimethoxy-2-phenylacetophenone, 2-methyl-(4-methylthio)phenyl-2-morpholino-1-propan-1-one, 2-benzyl-2-dimethylamino-1-(4-morpholinophenyl)-butan-1-one, 2-methyl-1-[4-(methylthio)phenyl]-2-morpholinopropan-1-one or the like, but are not limited thereto.

Examples of the biimidazole-based compound may include 2,2'-bis(2-chlorophenyl)-4,4',5,5'-tetraphenyl biimidazole, 2,2'-bis(o-chlorophenyl)-4,4',5,5'-tetrakis(3,4,5-trimethoxyphenyl)-1,2'-biimidazole, 2,2'-bis(2,3-dichlorophenyl)-4,4',5,5'-tetra phenyl biimidazole, 2,2'-bis(o-chlorophenyl)-4,4',5,5'-tetraphenyl-1,2'-biimidazole or the like, but are not limited thereto.

Examples of the triazine-based compound may include 3-{4-[2,4-bis(trichloromethyl)-s-triazin-6-yl]phenylthio}propionic acid, 1,1,1,3,3,3-hexafluoroisopropyl-3-{4-[2,4-bis(trichloromethyl)-s-triazin-6-yl]phenylthio}propionate, ethyl-2-{4-[2,4-bis(trichloromethyl)-s-triazin-6-yl]phenylthio}acetate, 2-epoxyethyl-2-{4-[2,4-bis(trichloromethyl)-s-triazin-6-yl]phenylthio}acetate, cyclohexyl-2-{4-[2,4-bis(trichloromethyl)-s-triazin-6-yl]phenylthio}acetate, benzyl-2-{4-[2,4-bis(trichloromethyl)-s-triazin-6-yl]phenylthio}acetate, 3-{chloro-4-[2,4-bis(trichloromethyl)-s-triazin-6-yl]phenylthio}propionic acid, 3-{4-[2,4-bis(trichloromethyl)-s-triazin-6-yl]phenylthio}propionamide, 2,4-bis(trichloromethyl)-6-p-methoxystyryl-s-triazine, 2,4-bis(trichloromethyl)-6-(1-p-dimethylaminophenyl)-1,3-butadienyl-s-triazine, 2-trichloromethyl-4-amino-6-p-methoxystyryl-s-triazine or the like, but are not limited thereto.

Examples of the oxime-based compound may include CGI-242, CGI-124 of Ciba Specialty Chemicals, and the like, but are not limited thereto.

A content of the photoinitiator may be from 0.1% by weight to 20% by weight based on a total solid content of the photoresist fluorescent resin composition, but is not limited thereto.

A content of the photoinitiator may be from 0.1% by weight to 15% by weight based on a total weight of the photoresist fluorescent resin composition, but is not limited thereto.

The photoresist fluorescent resin composition according to one embodiment of the present disclosure may further include a solvent.

The solvent may be one or more types selected from the group consisting of acetone, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methylethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxypropanol, 2-methoxypropanol, 3-methoxybutanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, propylene glycol monomethyl ether and dipropylene glycol monomethyl ether, but is not limited thereto.

A content of the total solid may be from 10% by weight to 50% by weight, and a content of the solvent may be from 50% by weight to 90% by weight based on a total weight of the photoresist fluorescent resin composition, however, the content is not limited thereto.

The photoresist composition according to one embodiment of the present disclosure may further include one or more types of additives selected from the group consisting of a dispersant, a curing accelerator, a thermal polymerization inhibitor, a surfactant, a photosensitizer, a plasticizer, an adhesion promoter, a filler and an adhesion aid.

As the photosensitizer, the plasticizer, the adhesion promoter, the filler and the like, all compounds that may be included in existing photoresist fluorescent resin compositions may be used.

The additives may be each independently included in 0.01% by weight to 5% by weight based on a total weight of the photoresist fluorescent resin composition, however, each content is not limited thereto.

The additives may be each independently included in 0.01% by weight to 5% by weight based on a total solid weight of the photoresist fluorescent resin composition, however, each content is not limited thereto.

One embodiment of the present specification provides a color conversion film including the compound described above bonding to a binder resin.

More specifically, a thin-film type photoresist material is formed by coating the photoresist fluorescent resin composition of the present disclosure on a substrate using a proper method.

The coating method is not particularly limited, and a spray method, a roll coating method, a spin coating method and the like may be used, and a spin coating method is generally widely used. In addition, after forming the coated film, some of the residual solvent may be removed under vacuum in some cases.

Examples of a light source for curing the photoresist fluorescent resin composition according to the present disclosure include mercury vapor arc, carbon arc, Xe arc, which emit light with a wavelength of 250 nm to 450 nm, and the like, but are not limited thereto.

When curing the photoresist fluorescent resin composition, the compound represented by Chemical Formula 1 has a polymerizable group capable of binding with a binder resin. In this case, an advantage of having no dyeing in the process is obtained.

The color conversion film of the present specification has a maximum emission peak in a 610 nm to 640 nm region, and specifically, has a maximum emission peak in a 615 nm to 640 nm region and preferably in a 619 nm to 640 nm region. In this case, an advantage of high color reproduction is obtained.

In the color conversion film of the present specification, the maximum emission peak may have a full width at half maximum of 41 nm or less, and specifically greater than or equal to 35 nm and less than or equal to 41 nm. The full width at half maximum means, when converting light absorbed from an external light source to light having another wavelength and emitting the light, a width of the emission peak at half the maximum height in the maximum emission peak of the emitted light, and color gamut is excellent as the full width at half maximum is smaller.

The color conversion film may further include additional fluorescent materials in addition to the compound represented by Chemical Formula 1. When using a light source emitting blue light, the color conversion film preferably includes both a green light emitting fluorescent material and a red light emitting fluorescent material. In addition, when using a light source emitting blue light and green light, the color conversion film may only include a red light emitting fluorescent material. However, the color conversion film is not limited thereto, and even when using a light source emitting blue light, the color conversion film may only include a red light emitting compound when a separate film including a green light emitting fluorescent material is laminated. On the other hand, even when using a light source emitting blue light, the color conversion film may only include a green light emitting compound when a separate film including a red light emitting fluorescent material is laminated.

The color conversion film may further include an additional layer including a resin matrix; and a compound dispersed into the resin matrix and emitting light in a wavelength different from the wavelength of the compound represented by Chemical Formula 1. The compound emitting light in a wavelength different from the wavelength of the compound represented by Chemical Formula 1 may also be the compound represented by Chemical Formula 1, or may be other known fluorescent materials.

The resin matrix material is preferably a thermoplastic polymer or a thermocurable polymer. Specifically, a poly(meth)acryl-based such as polymethyl methacrylate (PMMA), a polycarbonate (PC)-based, a polystyrene (PS)-based, a polyarylene (PAR)-based, a polyurethane (PU)-based, a styrene-acrylonitrile (SAN)-based, a polyvinylidene fluoride (PVDF)-based, a modified polyvinylidene fluoride (modified-PVDF)-based and the like may be used as the resin matrix material.

According to one embodiment of the present specification, the color conversion film according to the embodiments described above additionally includes light diffusing particles. By dispersing light diffusing particles into the color conversion film instead of a light diffusing film used in the art for enhancing luminance, higher luminance may be exhibited compared to using a separate light diffusing film, and an adhering process may be skipped as well.

As the light diffusing particles, particles having a high refractive index with the resin matrix may be used, and examples thereof may include $TiO_2$, silica, borosilicate, alumina, sapphire, air or other gas-filled hollow beads or particles (for example, air/gas-filled glass or polymers); polystyrene, polycarbonate, polymethyl methacrylate, acryl, methyl methacrylate, styrene, a melamine resin, a formaldehyde resin, or polymer particles including melamine and formaldehyde resins; or any suitable combination thereof.

The light diffusing particles may have particle diameters in a range of 0.1 μm to 5 μm, for example, in a range of 0.3 μm to 1 μm. The content of the light diffusing particles may be determined as necessary.

The color conversion film according to the embodiments described above may have a thickness of 2 μm to 200 μm. Particularly, the color conversion film may exhibit high luminance even with a small thickness of 2 μm to 20 μm. This is due to the fact that the content of the fluorescent material molecules included in the unit volume is higher compared to quantum dots.

The color conversion film according to the embodiments described above may have a substrate provided on one surface. This substrate may function as a support when preparing the color conversion film. Types of the substrate are not particularly limited, and the material or thickness is not limited as long as it is transparent and is capable of functioning as the support. Herein, being transparent means having visible light transmittance of 70% or higher. For example, a PET film may be used as the substrate.

One embodiment of the present specification provides a backlight unit including the color conversion film. The backlight unit may have backlight unit constitutions known in the art except for including the color conversion film. FIG. 1 illustrates a mimetic diagram of a backlight unit structure according to one embodiment. According to FIG. 1, the color conversion film including the compound represented by Chemical Formula 1 is provided on a surface opposite to a surface facing a reflecting plate of a light guide plate. FIG. 1 illustrates a constitution including a light source and a reflecting plate surrounding the light source, however, the constitution is not limited to such a structure, and may vary depending on the backlight unit structure known in the art. In addition, as the light source, a direct type as well as a side chain type may be used, and the reflecting plate or the reflective layer may not be included or may be replaced with other constituents as necessary, and as necessary, additional films such as a light diffusing film, a light concentrating film and a luminance enhancing film may be further provided. Preferably, a prism sheet, a multilayer reflective polarizer film, a light concentrating film or a luminance enhancing film is further provided on the color conversion film.

In the constitution of the backlight unit as in FIG. 1, a scattering pattern may be provided as necessary on an upper surface or a lower surface of the light guide plate. Light introduced into the light guide plate has non-uniform light distribution due to repetition of optical processes such as reflection, total reflection, refraction or transmission, and the scattering pattern may be used to induce the non-uniform light distribution to uniform brightness.

One embodiment of the present specification provides a display apparatus including the backlight unit. The display apparatus is not particularly limited as long as it includes the backlight unit. For example, the display apparatus includes a display module and a backlight unit. FIG. 2 illustrates a structure of the display apparatus. However, the structure is not limited thereto, and between the display module and the backlight unit, additional films such as a light diffusing film, a light concentrating film and a luminance enhancing film may be further provided as necessary.

Hereinafter, the present specification will be described in more detail with reference to examples. However, the following examples are for illustrative purposes only, and are not to limit the present specification.

EXAMPLE

[Preparation Example 1] Synthesis of Compound A

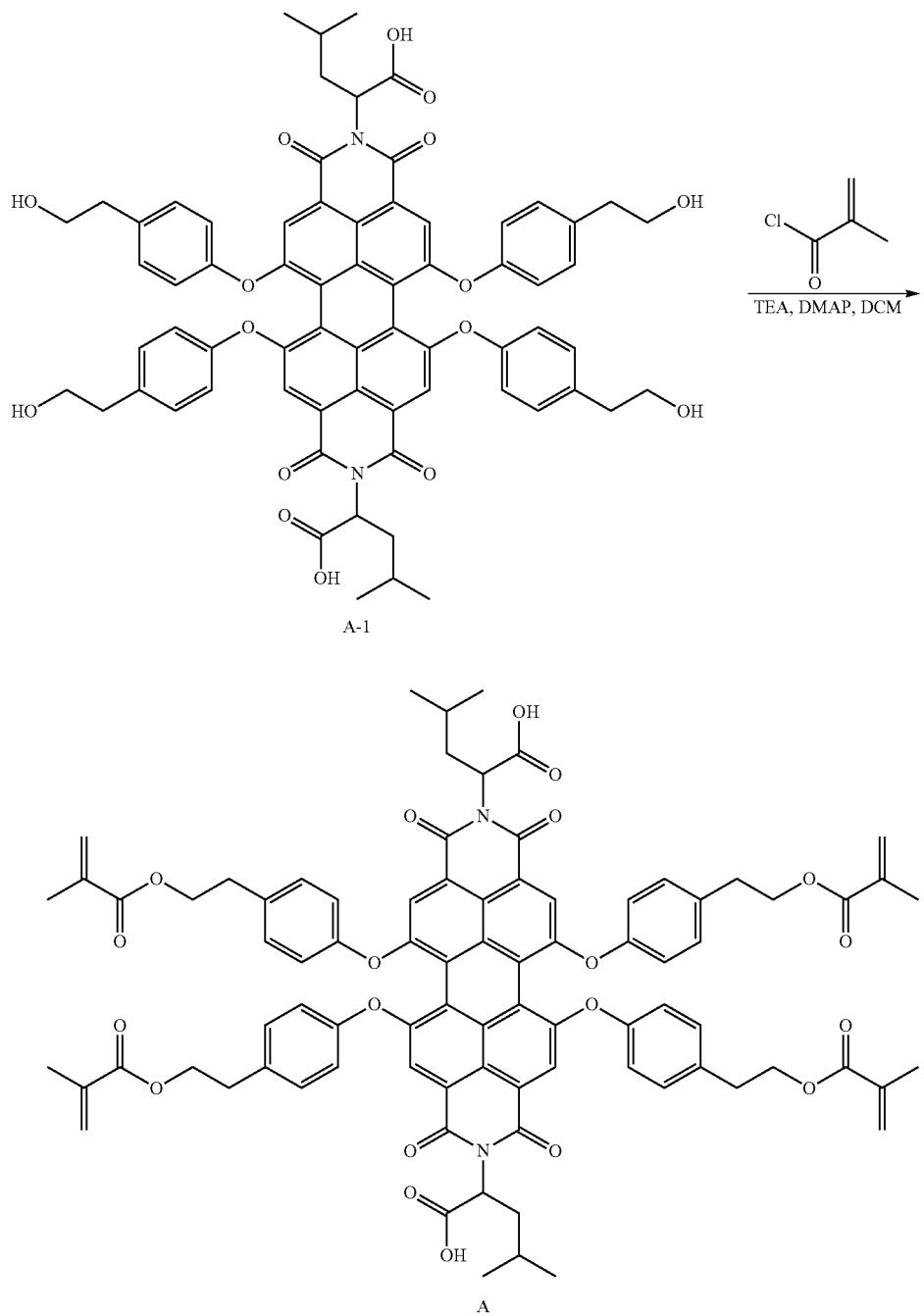

After dissolving 1 equivalent of Compound A-1 and 6 equivalents of triethylamine (TEA) in a dichloromethane (DCM) solvent in a reaction container, the result was stirred in an ice bath. To this reaction container, 6 equivalents of methacryloyl chloride dissolved in dichloromethane was slowly introduced, then 4-dimethylaminopyridine (DMAP) was introduced thereto, and the result was stirred at room temperature under nitrogen. After the reaction was completed, the result was extracted using dichloromethane and water, and water was removed from the separated organic layer using anhydrous magnesium sulfate ($MgSO_4$). The water-removed organic layer was concentrated through vacuum distillation, and then recrystallized with methyl tertiary-butyl ether and hexane to obtain Compound A by suction filtration. Compound A was dried under a vacuum condition at 80° C.

HR LC/MS/MS m/z calculated for $C_{84}H_{78}N_2O_{20}$ (M+): 1434.5148; found: 1434.5149.

[Preparation Example 2] Synthesis of Compound B
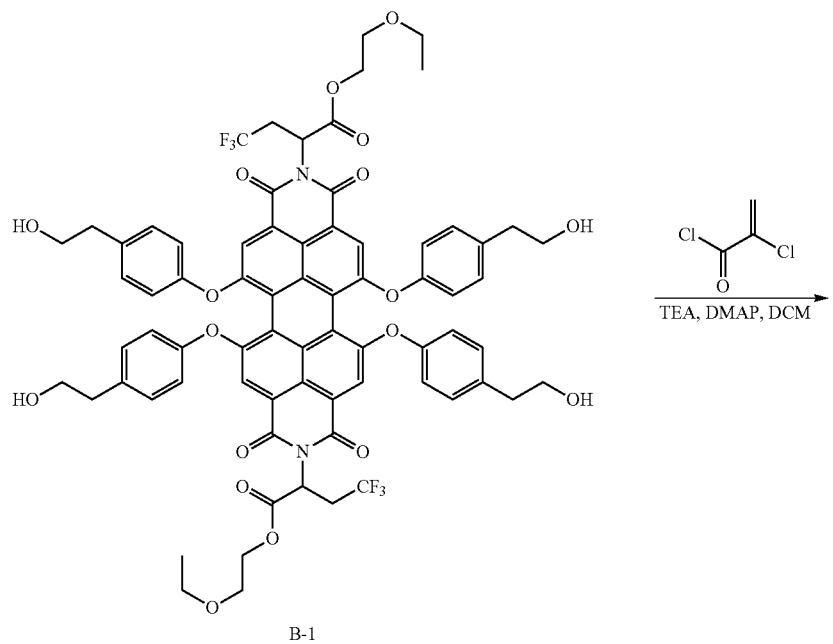
B-1
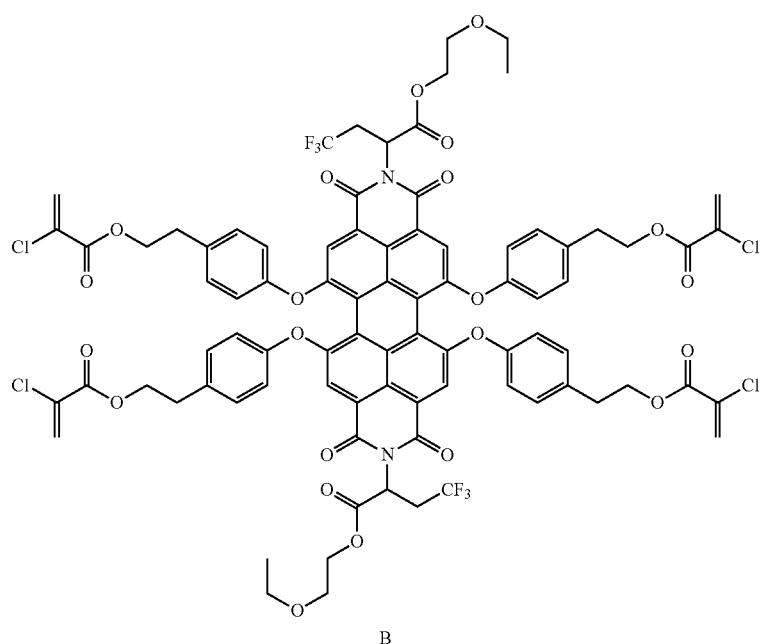
B
Synthesis was conducted in the same manner as in Preparation Example 1 except that, in Synthesis of Compound A, Compound B-1 and 2-chloroacryloyl chloride were used instead of Compound A-1 and methacryloyl chloride, and Compound B was synthesized therethrough.
HR LC/MS/MS m/z calculated for $C_{84}H_{68}Cl_4F_6N_2O_{22}$ (M+): 1710.2922; found: 1710.2925.

[Preparation Example 3] Synthesis of Compound C
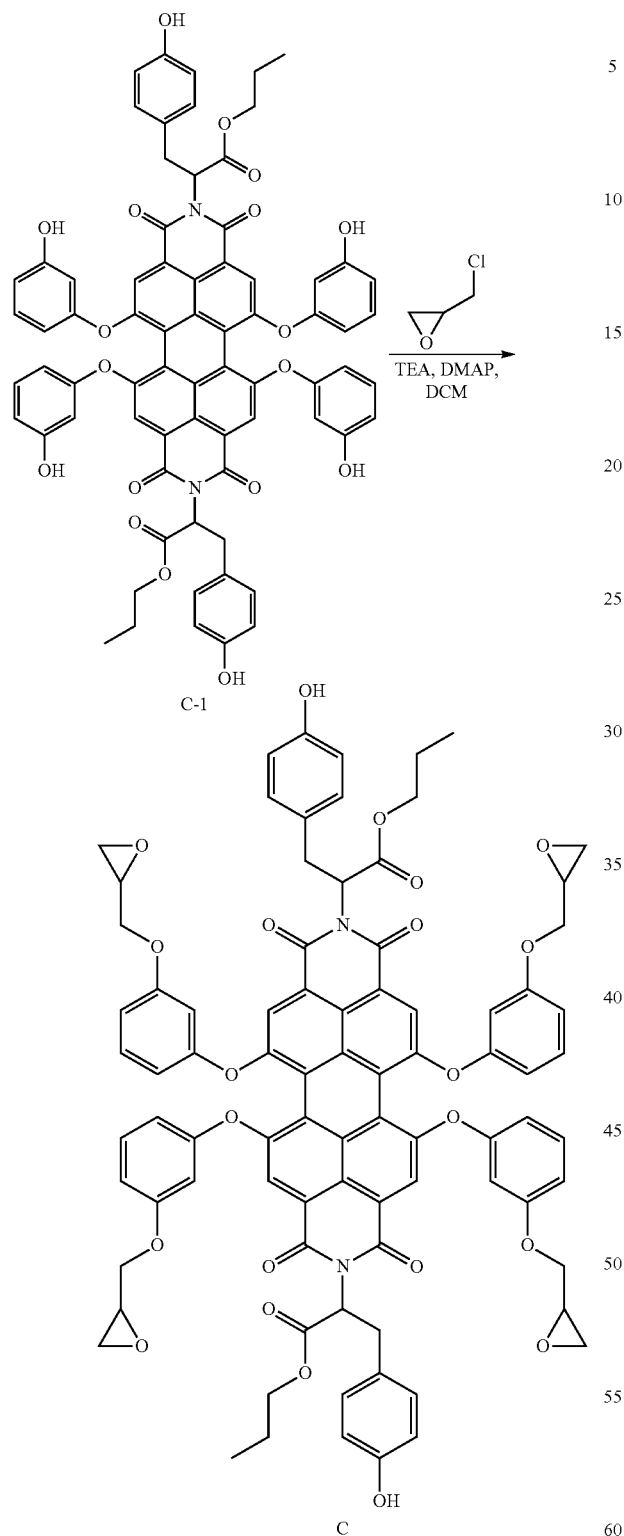
Synthesis was conducted in the same manner as in Preparation Example 1 except that, in Synthesis of Compound A, Compound C-1 and epichlorohydrin were used instead of Compound A-1 and methacryloyl chloride, and Compound C was synthesized therethrough.
HR LC/MS/MS m/z calculated for C84H70N2O22 (M+): 1458.4420; found: 1458.4420.

[Preparation Example 4] Synthesis of Compound D
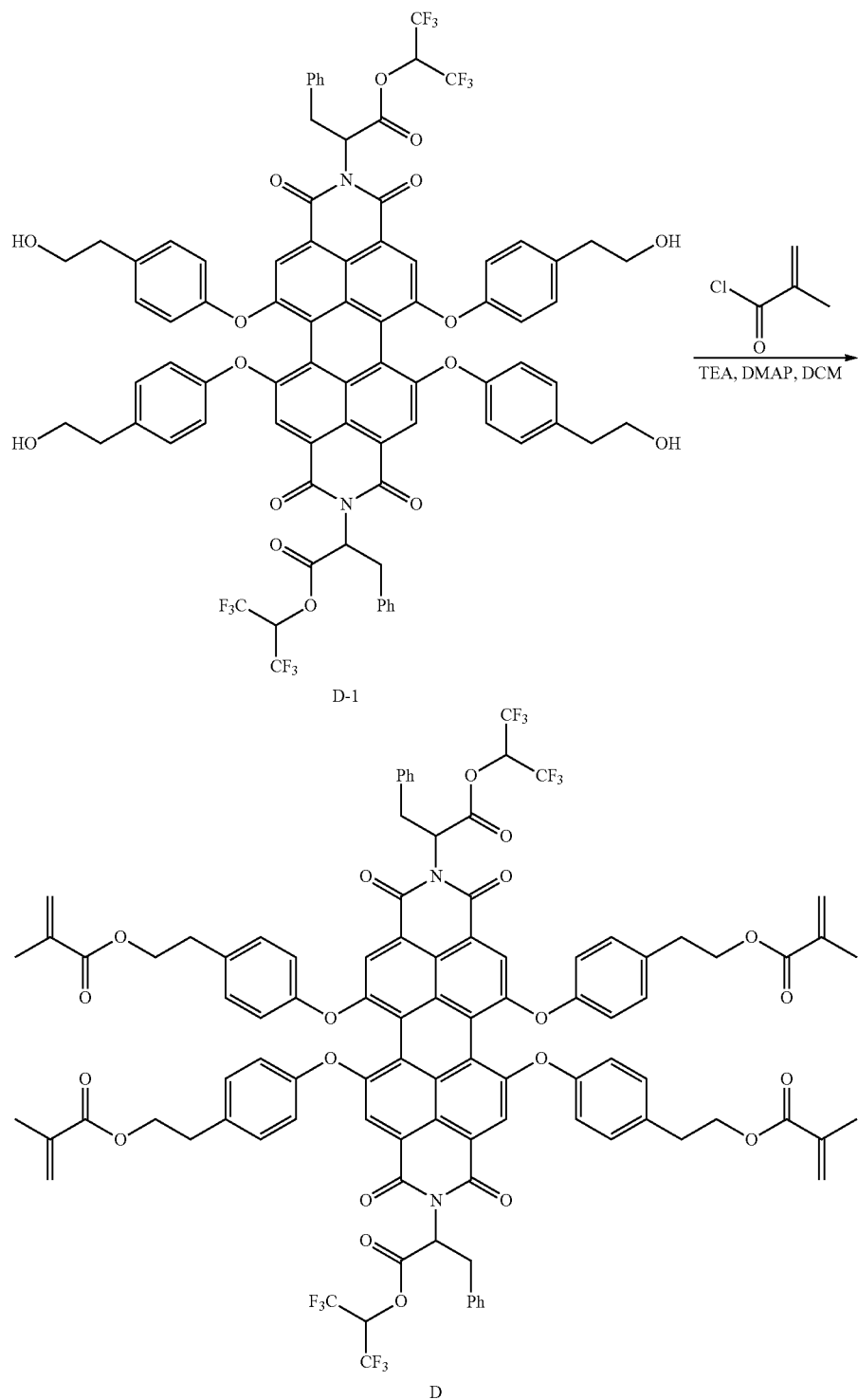
Synthesis was conducted in the same manner as in Preparation Example 1 except that, in Synthesis of Compound A, Compound D-1 was used instead of Compound A-1, and Compound D was synthesized therethrough.
HR LC/MS/MS m/z calculated for C96H74F12N2O20 (M+): 1802.4643; found: 1802.4645.

[Preparation Example 5] Synthesis of Compound E
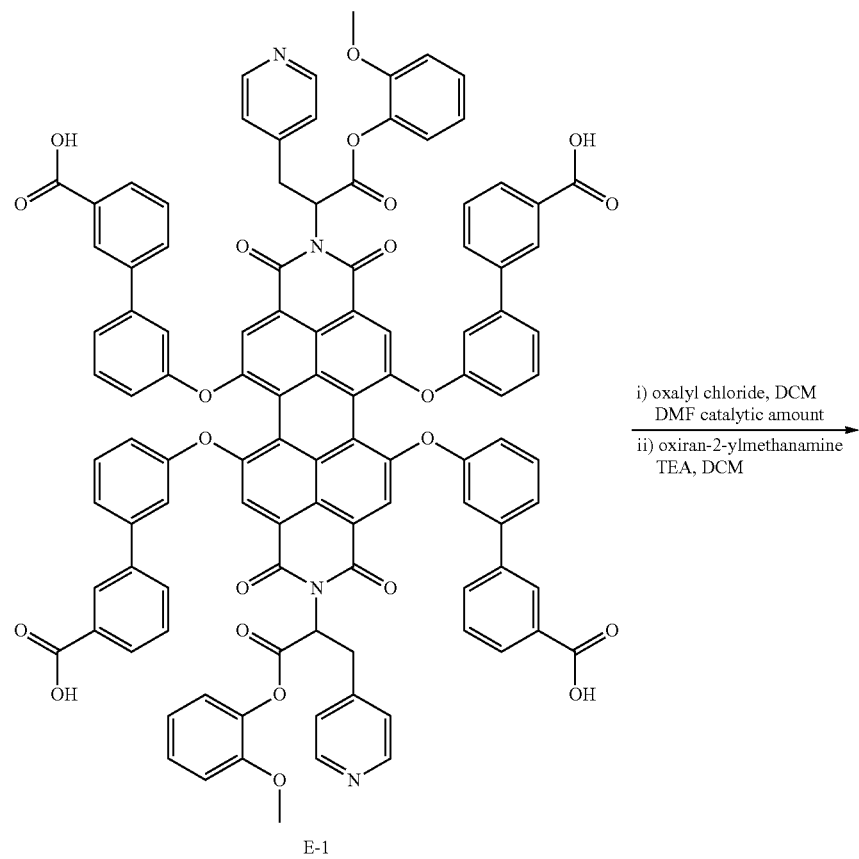
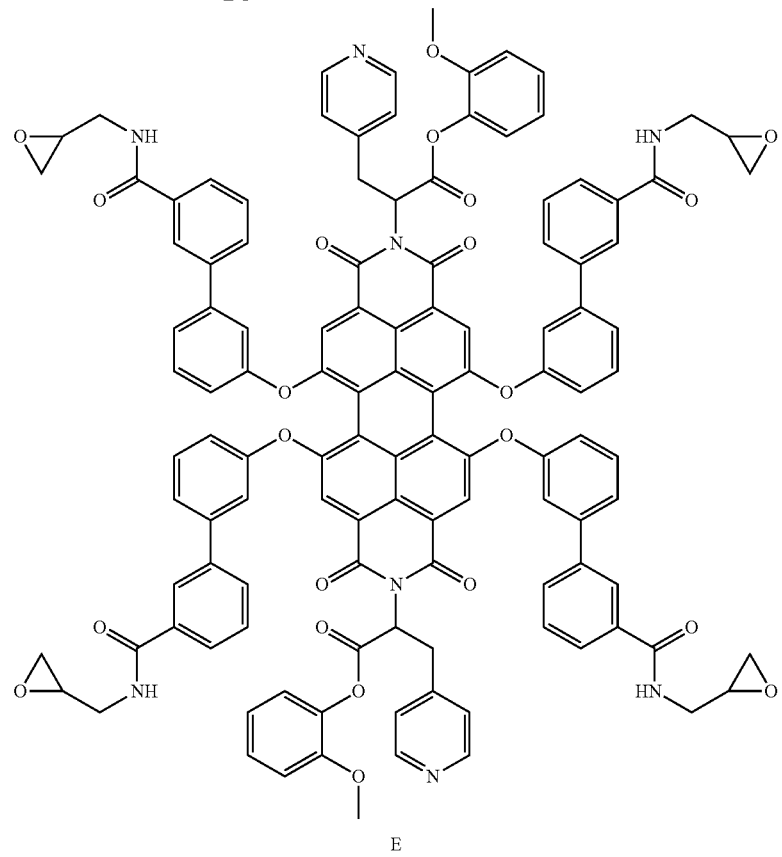

After dissolving 1 equivalent of Compound E-1 and a catalytic amount of dimethylformamide (DMF) in a dichloromethane (DCM) solvent in a reaction container, 8 equivalents of oxalyl chloride was slowly introduced thereto in an ice bath. The result was stirred at room temperature under nitrogen, and dichloromethane was evaporated using a rotary evaporator. An acyl chloride in which a hydroxyl group is replaced with a chlorine group in the carboxyl group of Compound E-1 was synthesized.

After dissolving 8 equivalents of oxiran-2-ylmethanamine and 20 equivalents of triethylamine (TEA) in a dichloromethane solvent in another reaction container, the synthesized acyl chloride dissolved in dichloromethane was slowly introduced thereto in an ice bath. The mixture was stirred at room temperature under nitrogen. After the reaction was completed, the result was extracted using dichloromethane and water, and water was removed from the separated organic layer using anhydrous magnesium sulfate ($MgSO_4$). The water-removed organic layer was concentrated through vacuum distillation, and then recrystallized with dichloromethane and hexane to obtain Compound E by suction filtration. Compound E was dried under a vacuum condition at 80° C.

HR LC/MS/MS m/z calculated for C118H88N8O22 (M+): 1968.6013; found: 1968.6014.

[Preparation Example 6] Synthesis of Compound F

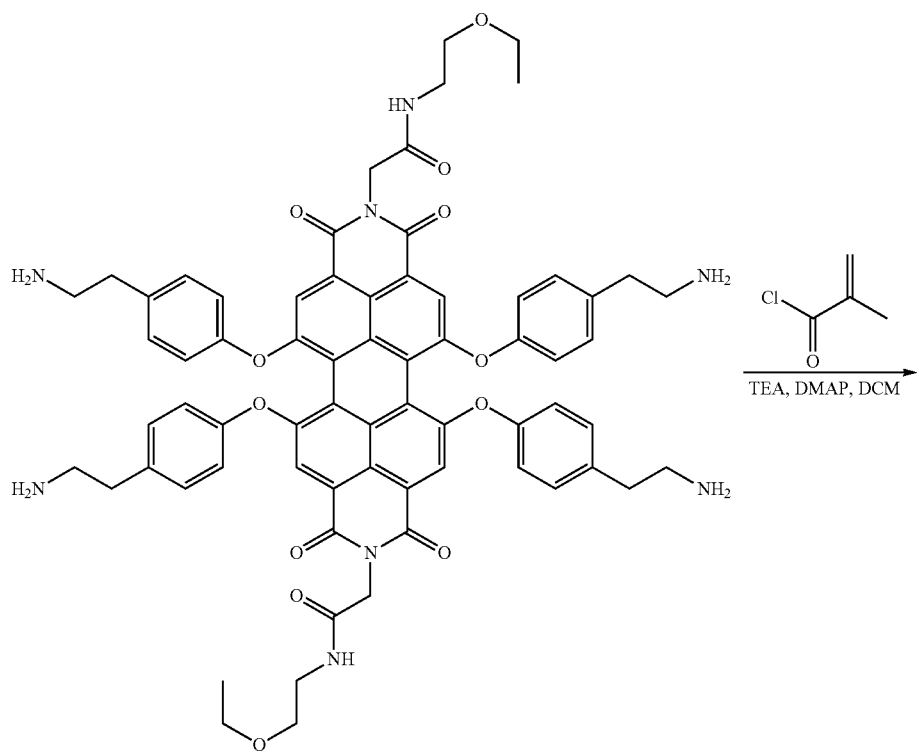

F-1

-continued
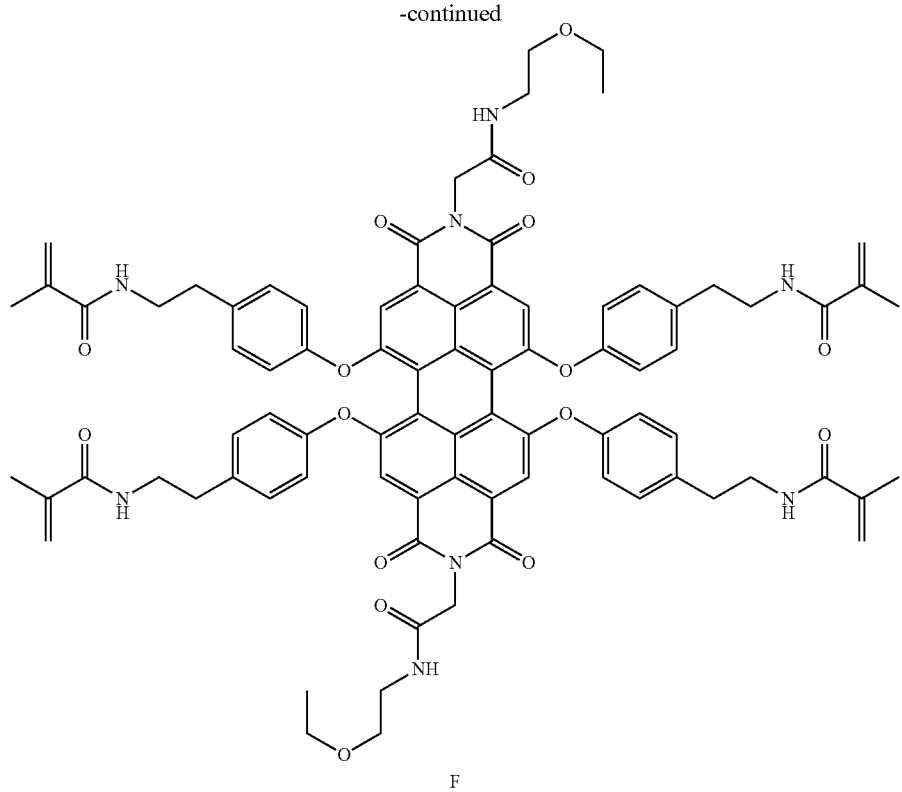
F
Synthesis was conducted in the same manner as in Preparation Example 1 except that, in Synthesis of Compound A, Compound F-1 was used instead of Compound A-1, and Compound F was synthesized therethrough.
HR LC/MS/MS m/z calculated for C84H84N8O16 (M+): 1460.6005; found: 1460.6009.
[Preparation Example 7] Synthesis of Compound G
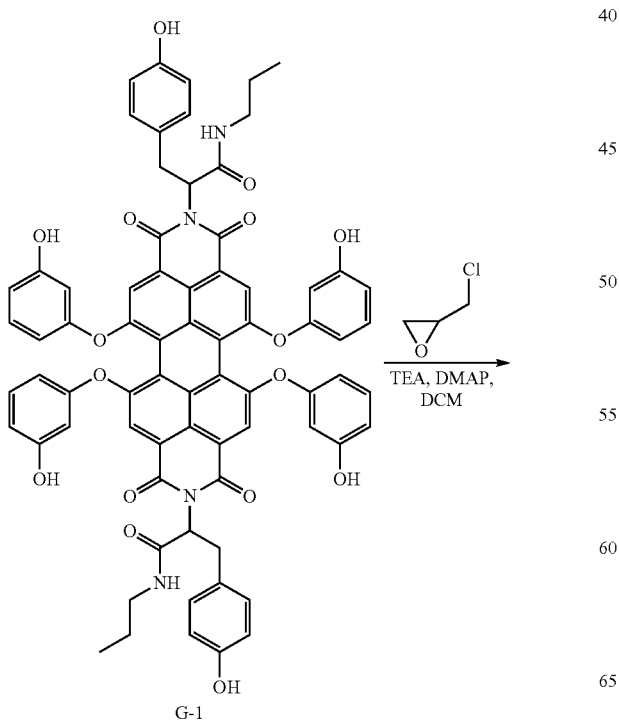
G-1

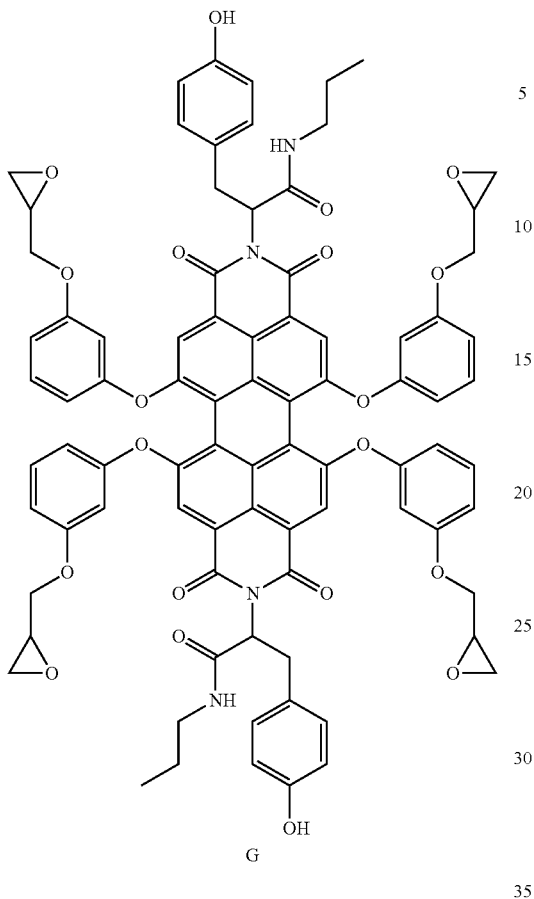
G
Synthesis was conducted in the same manner as in Preparation Example 1 except that, in Synthesis of Compound A, Compound G-1 and epichlorohydrin were used instead of Compound A-1 and methacryloyl chloride, and Compound G was synthesized therethrough.
HR LC/MS/MS m/z calculated for C84H72N4O20 (M+): 1456.4740; found: 1456.4743.

[Preparation Example 8] Synthesis of Compound H
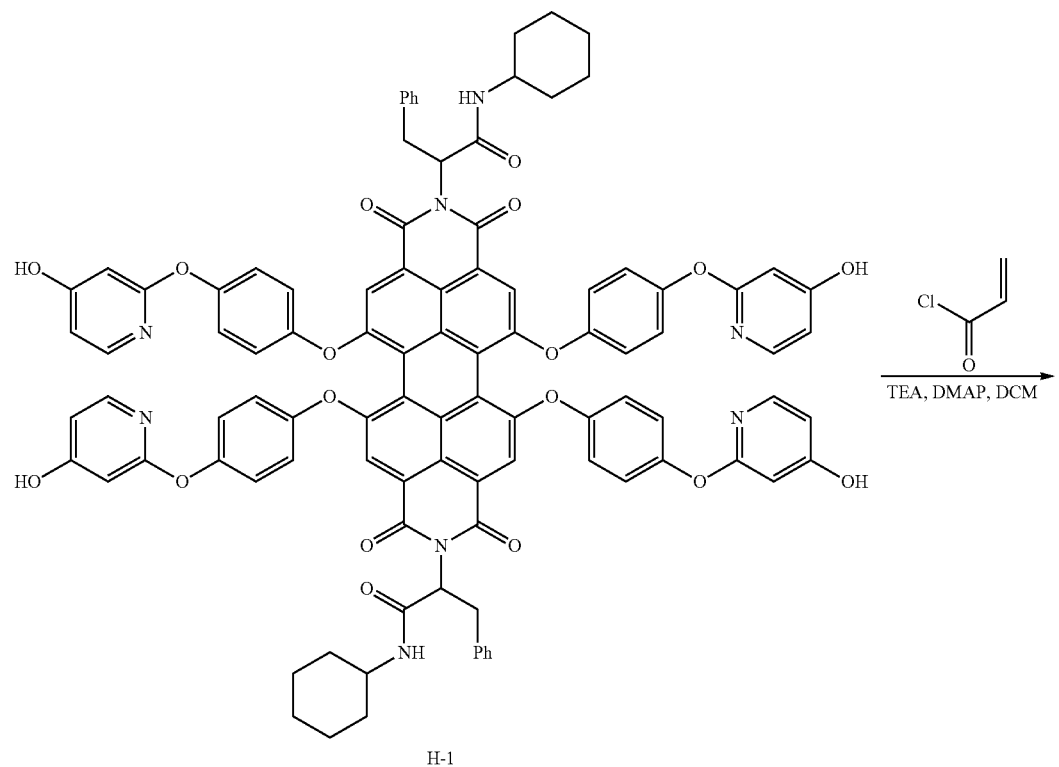
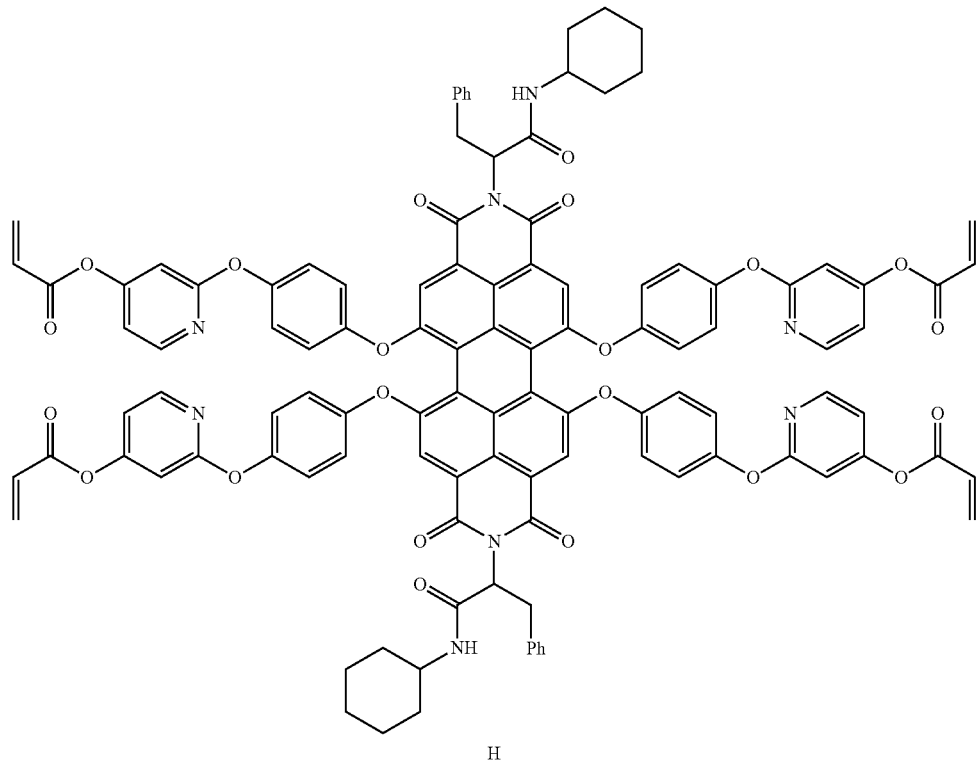

Synthesis was conducted in the same manner as in Preparation Example 1 except that, in Synthesis of Compound A, Compound H-1 and acrylyl chloride were used instead of Compound A-1 and methacryloyl chloride, and Compound H was synthesized therethrough.
HR LC/MS/MS m/z calculated for C110H84N8O22 (M+):1868.5700; found: 1868.5702.
[Preparation Example 9] Synthesis of Compound I
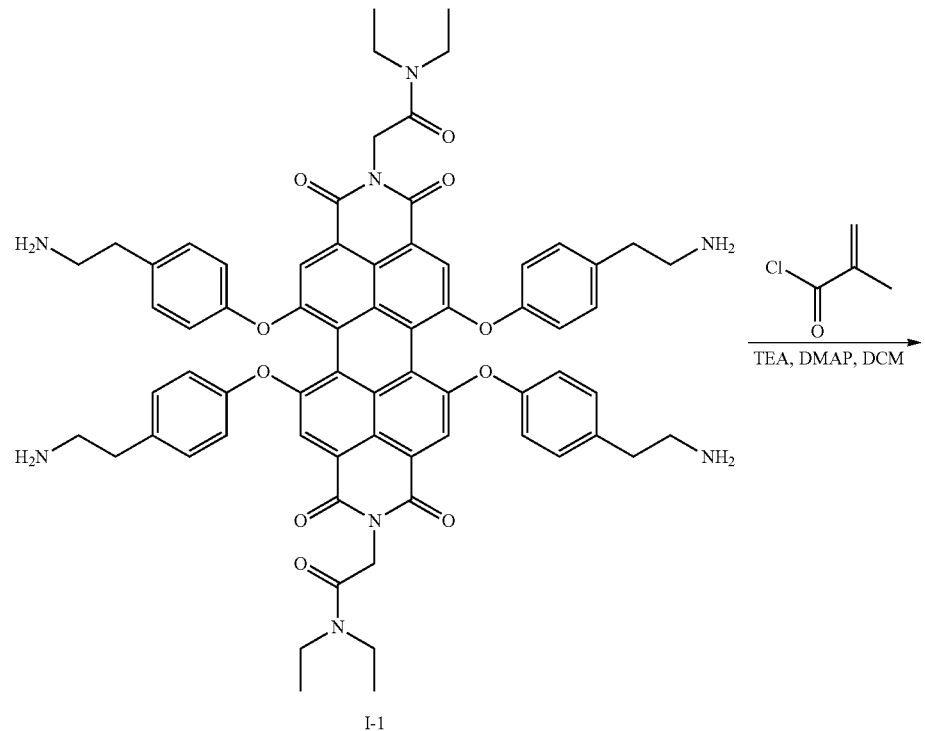
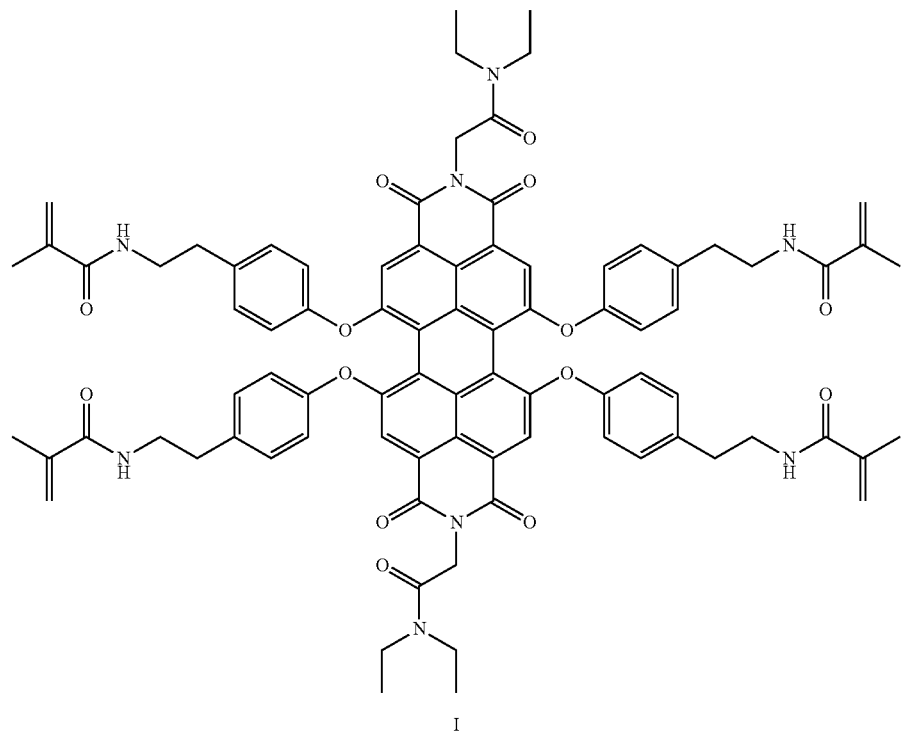

Synthesis was conducted in the same manner as in Preparation Example 1 except that, in Synthesis of Compound A, Compound 1-1 was used instead of Compound A-1, and Compound I was synthesized therethrough.
HR LC/MS/MS m/z calculated for C84H84N8O14 (M+): 1428.6107; found: 1428.6107.
[Preparation Example 10] Synthesis of Compound J
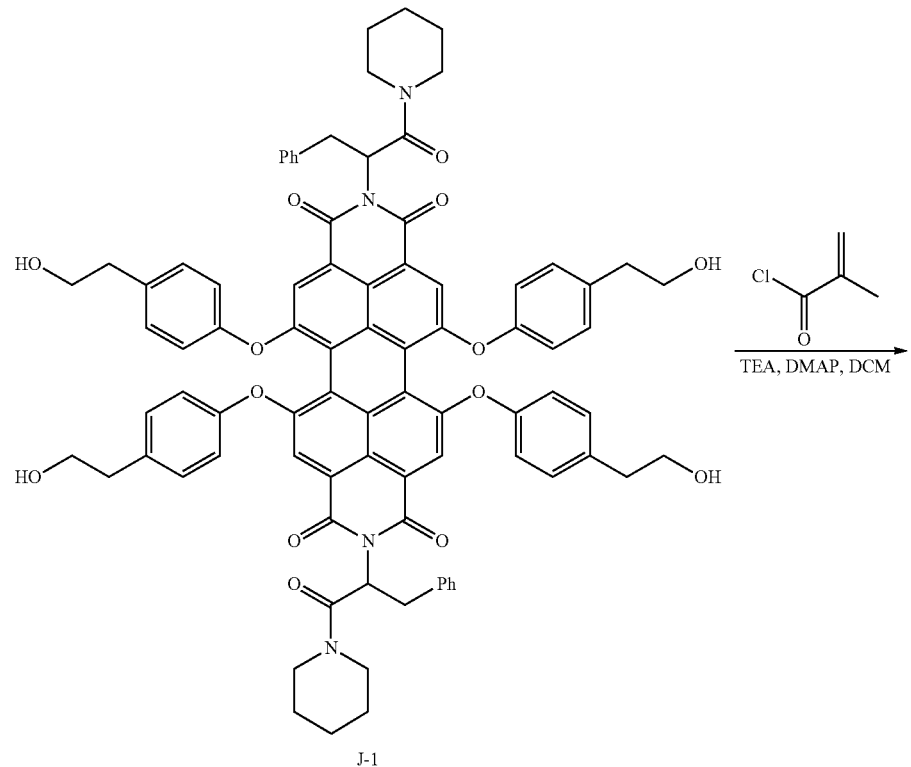
J-1
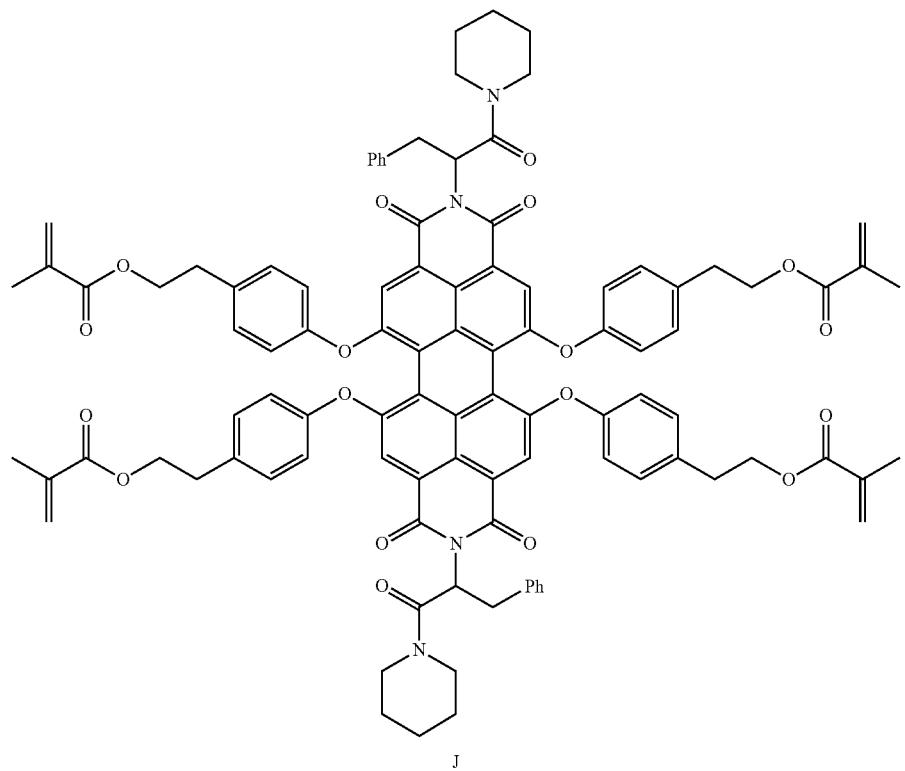
J Synthesis was conducted in the same manner as in Preparation Example 1 except that, in Synthesis of Compound A, Compound 1-1 was used instead of Compound A-1, and Compound 1 was synthesized therethrough.
HR LC/MS/MS m/z calculated for C100H92N4O18 (M+):1636.6407; found: 1636.6407.
[Preparation Example 11] Synthesis of Compound K
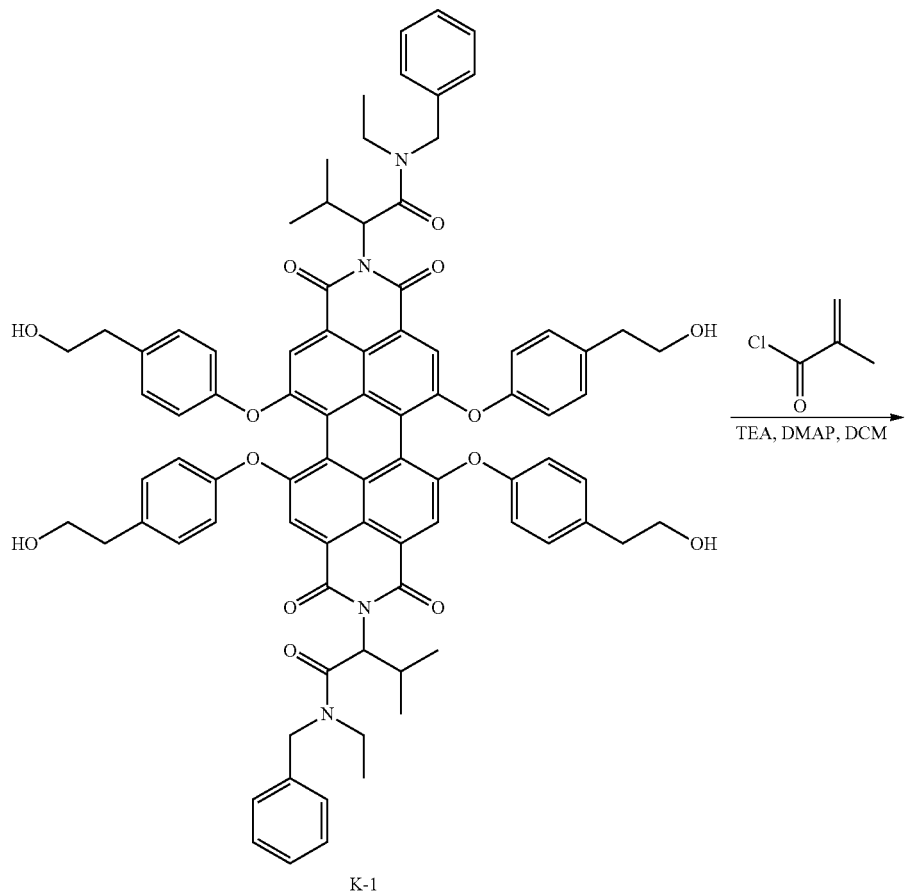
K-1

-continued
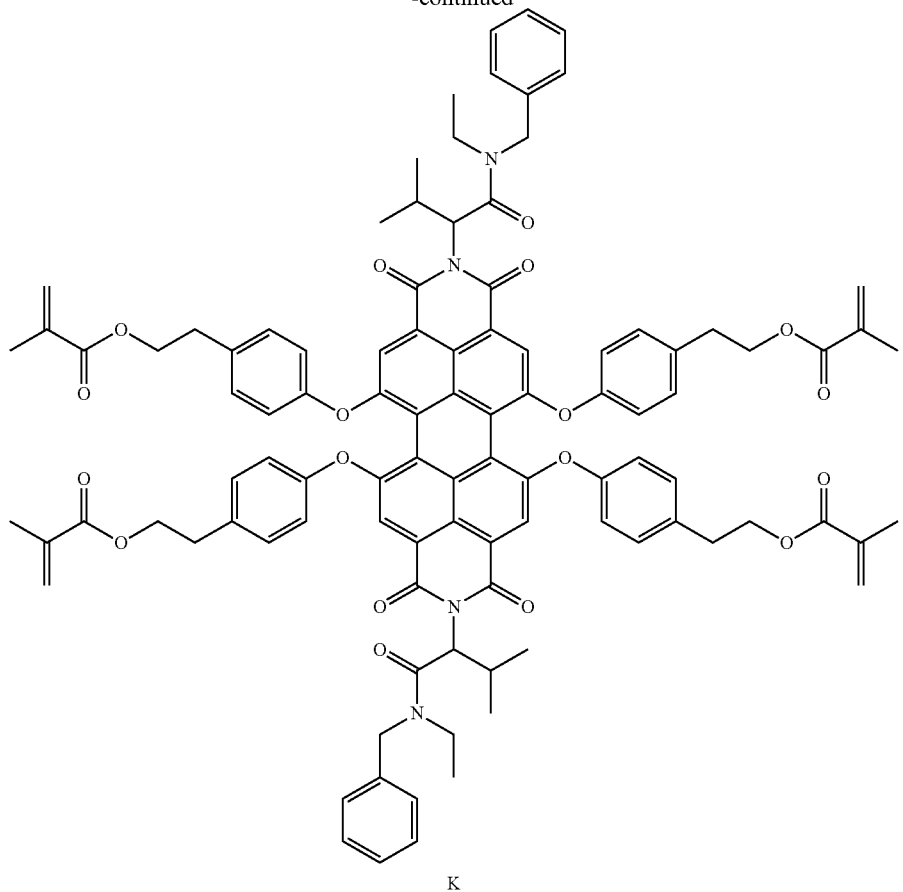
K
Synthesis was conducted in the same manner as in Preparation Example 1 except that, in Synthesis of Compound A, Compound K-1 was used instead of Compound A-1, and Compound K was synthesized therethrough.
HR LC/MS/MS m/z calculated for C100H96N4O18 (M+):1640.6720; found: 1640.6722.

[Preparation Example 12] Synthesis of Compound L
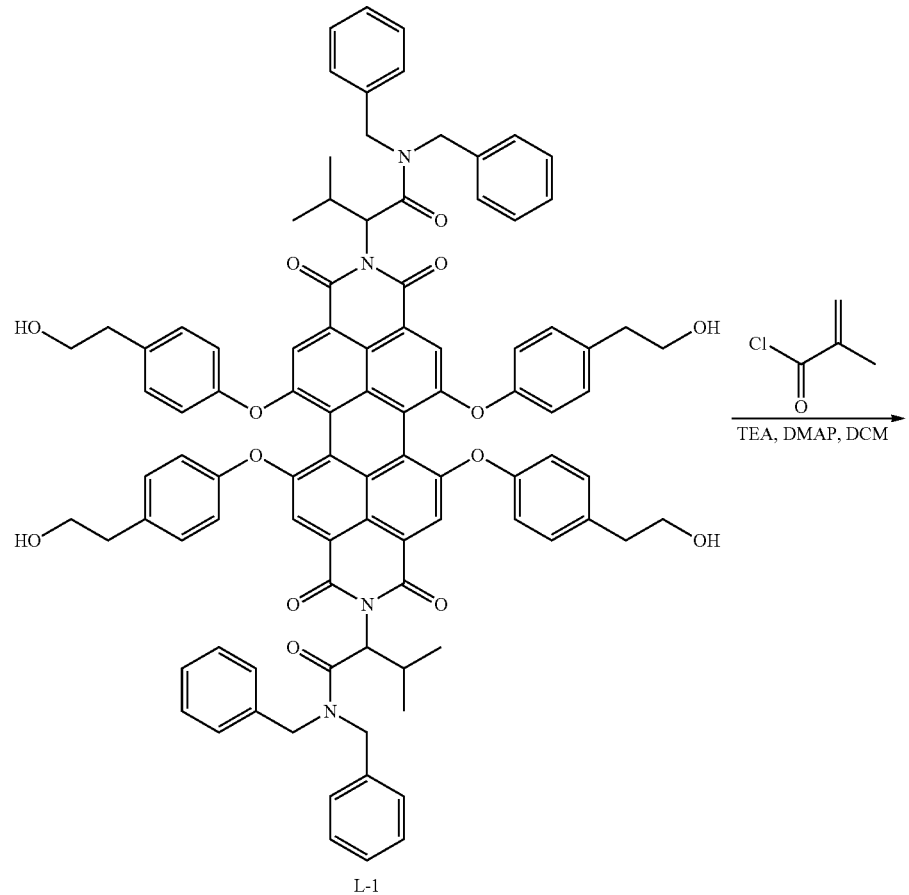
L-1

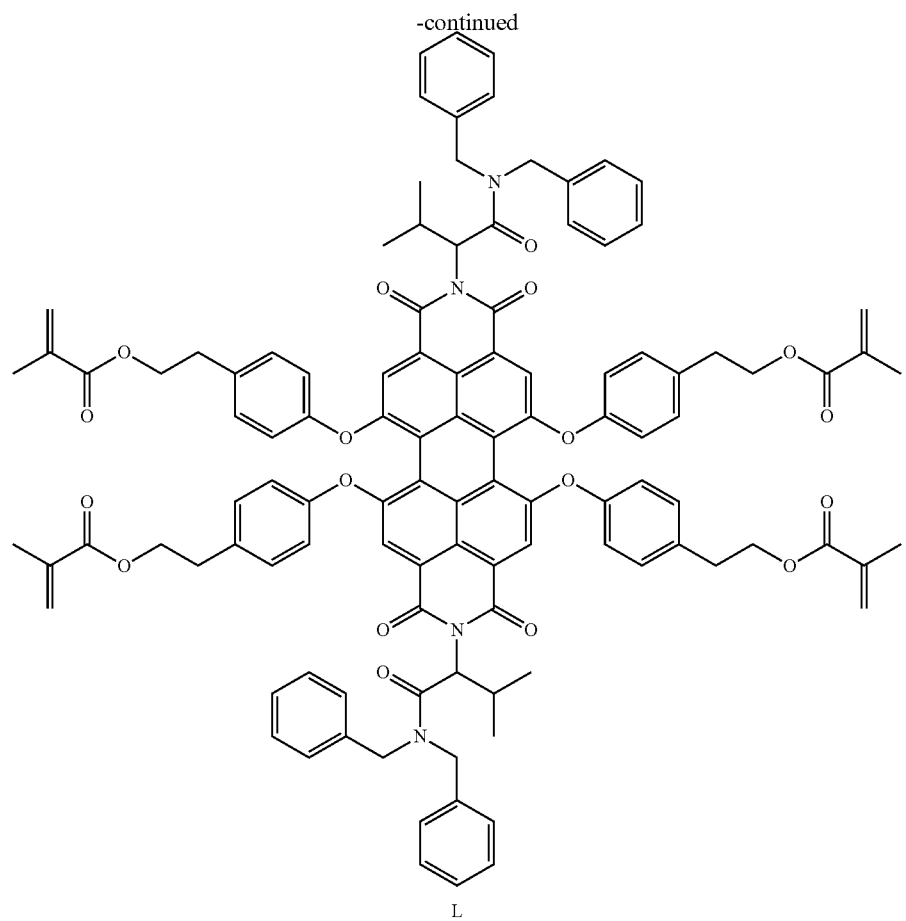
L
Synthesis was conducted in the same manner as in Preparation Example 1 except that, in Synthesis of Compound A, Compound L-1 was used instead of Compound A-1, and Compound L was synthesized therethrough.
HR LC/MS/MS m/z calculated for $C_{110}H_{100}N_4O_{18}$ (M+): 1764.7033; found: 1764.7033.

[Preparation Example 13] Synthesis of Compound M
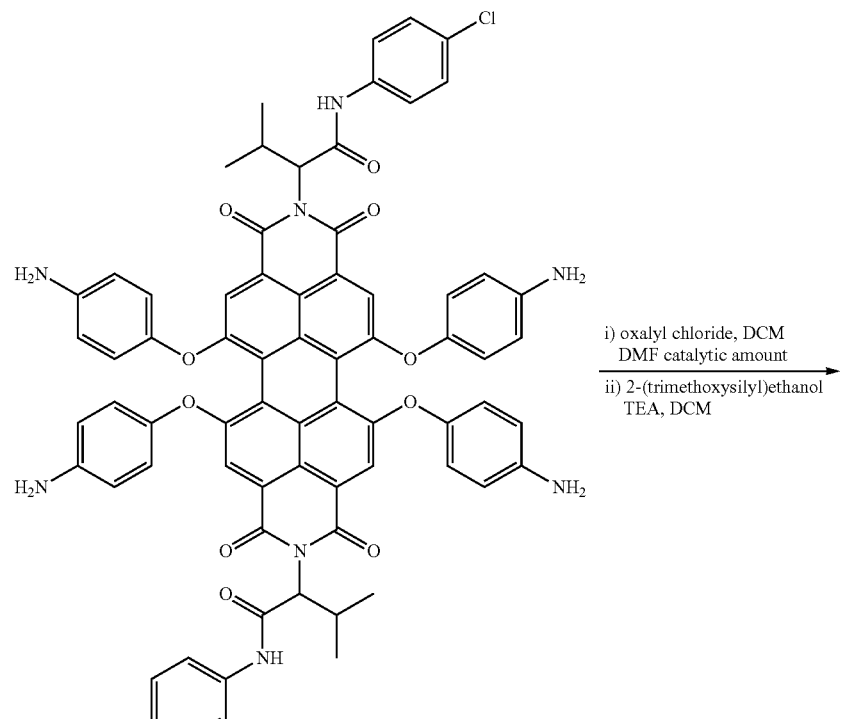
M-1
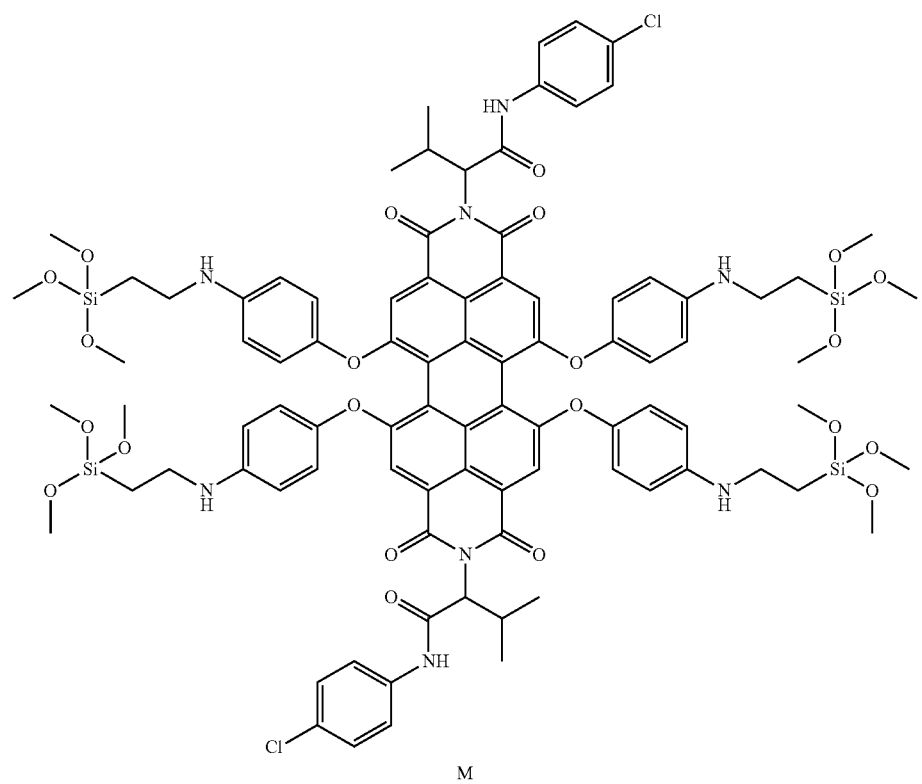
M

Synthesis was conducted in the same manner as in Preparation Example 5 except that, in Synthesis of Compound E, Compound M-1 and 2-(trimethoxysilyl)ethanol were used instead of Compound E-1 and oxiran-2-ylmethanamine, and Compound M was synthesized therethrough.
HR LC/MS/MS m/z calculated for C90H102Cl2N8O22Si4 (M+):1828.5563; found: 1828.5565.
[Preparation Example 14] Synthesis of Compound N
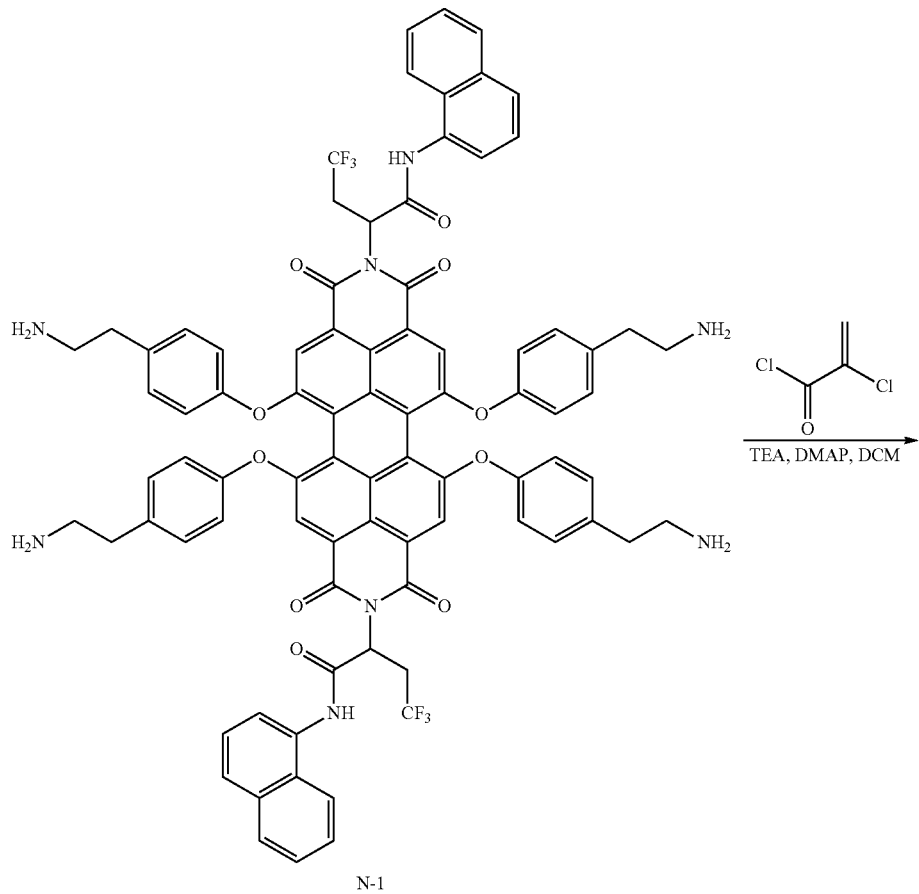
N-1

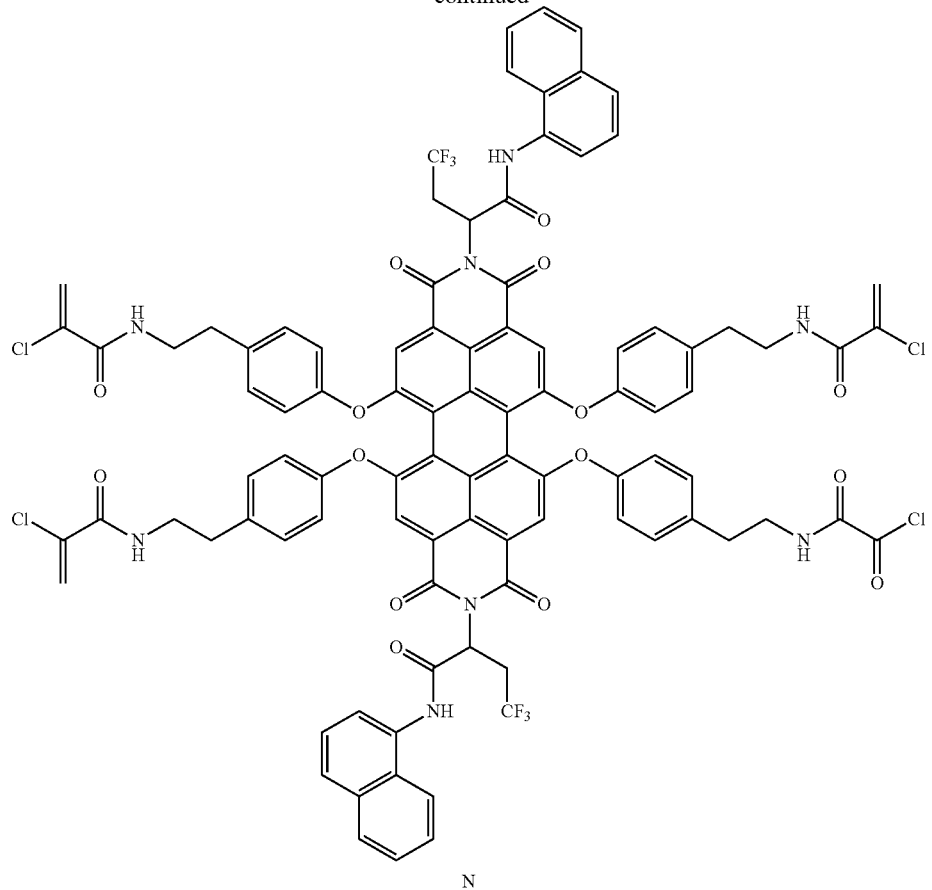
N
Synthesis was conducted in the same manner as in Preparation Example 1 except that, in Synthesis of Compound A, Compound N-1 and 2-chloroacryloyl chloride were used instead of Compound A-1 and methacryloyl chloride, and Compound N was synthesized therethrough.
HR LC/MS/MS m/z calculated for C96H70Cl4F6N8O14 (M+): 1812.3670; found: 1812.3671.

[Comparative Preparation Example 1] Synthesis of Compound O

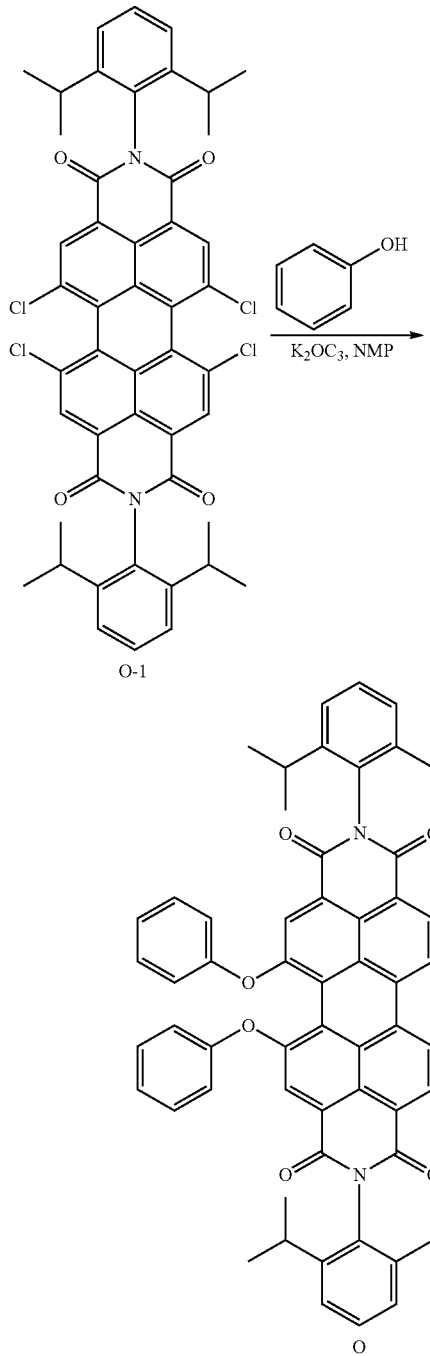

After dissolving 1 equivalent of Compound O-1, 8 equivalents of phenol and 6 equivalents of potassium carbonate in a methylpyrrolidone (NMP) solvent in a reaction container, the result was stirred at 110° C. After the reaction was completed, a compound was obtained using water and then suction filtration. The obtained compound was extracted using dichloromethane and water, and then water was removed from the separated organic layer using anhydrous magnesium sulfate. The water-removed organic layer was concentrated through vacuum distillation, and then recrystallized using dichloromethane and ethanol to obtain Compound O by suction filtration. Compound O was dried under a vacuum condition at 80° C.

HR LC/MS/MS m/z calculated for C72H58N2O8 (M+): 1078.4193; found: 1078.4195.

[Comparative Preparation Example 2] Synthesis of Compound P

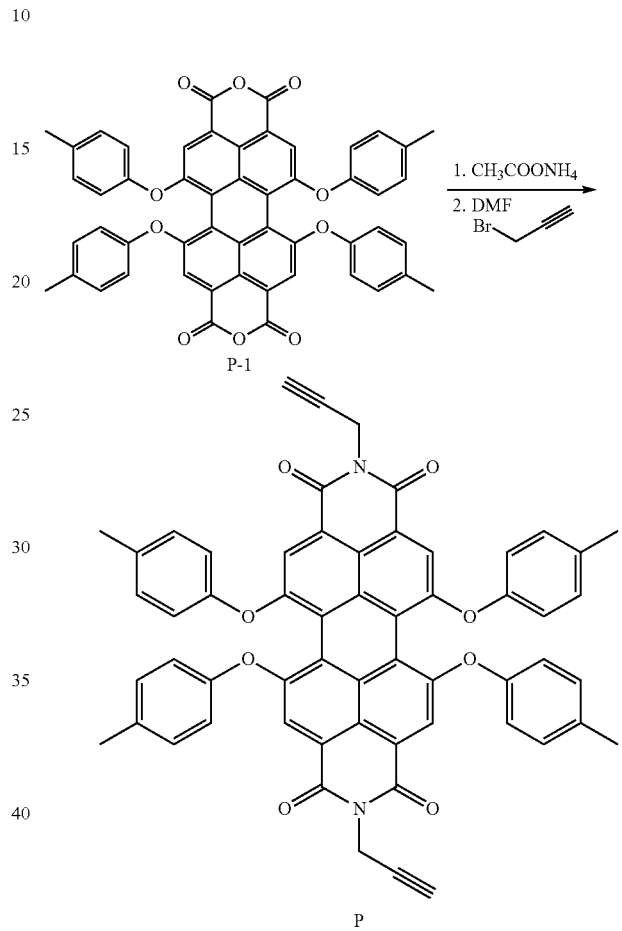

After dissolving 1 equivalent of Compound P-1 and 10 equivalents of ammonium acetate in a propionic acid solvent in a reaction container, the result was refluxed for 24 hours. After the reaction was completed, precipitates were collected using water. The precipitates were obtained by suction filtration, and used in a next reaction without separate purification. After dissolving 1 equivalent of the precipitates in a dimethylformamide (DMF) solvent, 1 equivalent of sodium methoxide was introduced thereto, and the result was stirred for 4 hours. After that, 6 equivalents of 3-bromo-1-propyne was introduced thereto, and the result was stirred for 24 hours. After the reaction was completed, the result was extracted using water, and water was removed from the separated organic layer using anhydrous magnesium sulfate. The water-removed organic layer was concentrated through vacuum distillation, and then recrystallized using dichloromethane and ethanol to obtain Compound P by suction filtration. Compound P was dried under a vacuum condition at 80° C.

HR LC/MS/MS m/z calculated for C58H38N2O8 (M+): 890.2628; found: 890.2628.

[Comparative Preparation Example 3] Synthesis of Compound Q

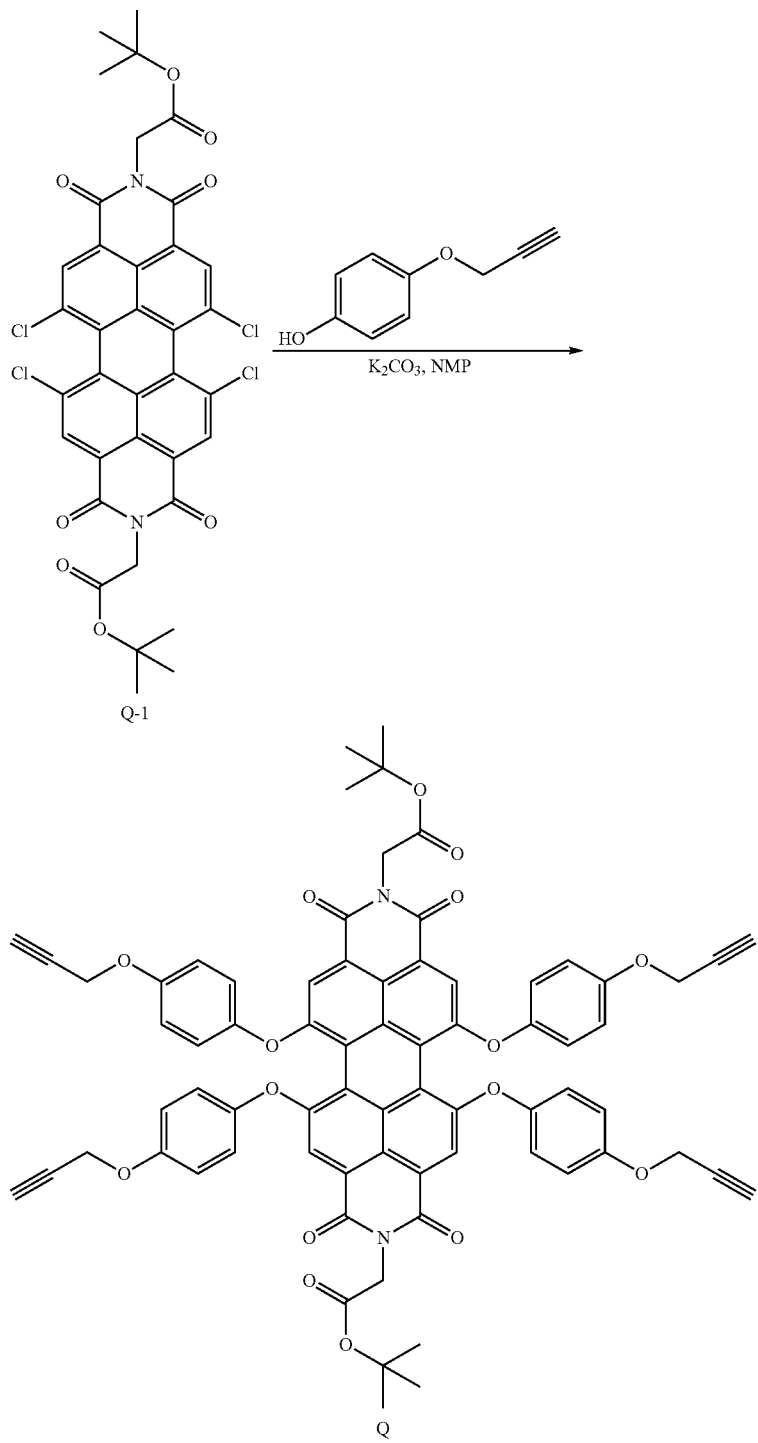

Synthesis was conducted in the same manner as in Comparative Preparation Example 1 except that, in Synthesis of Compound O, Compound Q-1 and 4-propargyloxyphenol were used instead of Compound O-1 and phenol, and Compound Q was synthesized therethrough.

HR LC/MS/MS m/z calculated for C72H54N2O16 (M+): 1202.3473; found: 1202.3473.

Example 1

A solution was prepared by dissolving 1.5 parts by weight of Compound A (maximum absorption wavelength 579 nm and maximum emission wavelength 608 nm in toluene solution) prepared in Preparation Example 1, 33.9 parts by weight of an acryl-based binder (VS12A80, LG Chem.), 59.3 parts by weight of a multifunctional monomer (pentaerythritol triacrylate, Nippon Kayaku), 2.3 parts by weight of an adhesive aid and surfactant (KBM 503, Shinetsu) and 3.0 parts by weight of a photoinitiator (Tinuvin® 477, BASF) in a propylene glycol monomethyl ether acetate (PGMEA) solvent so that the solid content became 21% by weight. The mixed solution was sufficiently stirred, and coated as a thin film on a glass substrate, and then dried to prepare a color conversion film.

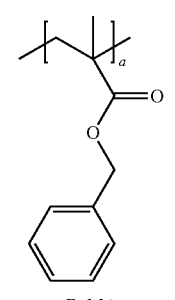

BzMA

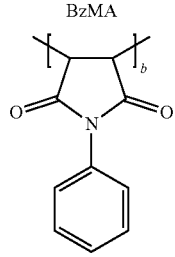

N-PMI

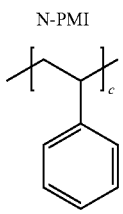

Styrene

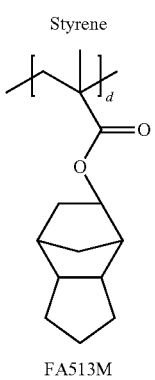

FA513M

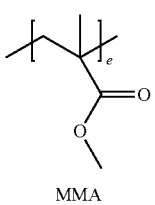

MMA

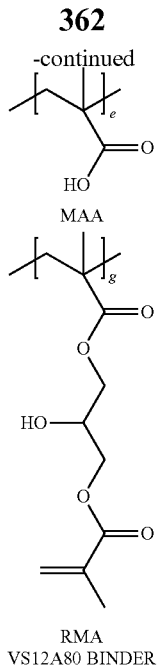

RMA
VS12A80 BINDER

Herein, a to g are each independently the number of repeating units in the parentheses, and for example, a tog are each independently an integer of 2 to 10,000.

Example 2

Preparation was made in the same manner as in Example 1 except that Compound B (maximum absorption wavelength 583 nm and maximum emission wavelength 612 nm in toluene solution) was used instead of Compound A.

Example 3

Preparation was made in the same manner as in Example 1 except that Compound C (maximum absorption wavelength 580 nm and maximum emission wavelength 609 nm in toluene solution) was used instead of Compound A.

Example 4

Preparation was made in the same manner as in Example 1 except that Compound D (maximum absorption wavelength 585 nm and maximum emission wavelength 614 nm in toluene solution) was used instead of Compound A.

Example 5

Preparation was made in the same manner as in Example 1 except that Compound I (maximum absorption wavelength 582 nm and maximum emission wavelength 612 nm in toluene solution) was used instead of Compound A.

Example 6

Preparation was made in the same manner as in Example 1 except that Compound I (maximum absorption wavelength 579 nm and maximum emission wavelength 610 nm in toluene solution) was used instead of Compound A.

Example 7

Preparation was made in the same manner as in Example 1 except that Compound K (maximum absorption wavelength 584 nm and maximum emission wavelength 614 nm in toluene solution) was used instead of Compound A.

Example 8

Preparation was made in the same manner as in Example 1 except that Compound L (maximum absorption wavelength 586 nm and maximum emission wavelength 615 nm in toluene solution) was used instead of Compound A.

Comparative Example 1

Preparation was made in the same manner as in Example 1 except that Compound O (maximum absorption wavelength 572 nm and maximum emission wavelength 601 nm in toluene solution) was used instead of Compound A.

Comparative Example 2

Preparation was made in the same manner as in Example 1 except that Compound P (maximum absorption wavelength 570 nm and maximum emission wavelength 599 nm in toluene solution) was used instead of Compound A.

Comparative Example 3

Preparation was made in the same manner as in Example 1 except that Compound Q (maximum absorption wavelength 575 nm and maximum emission wavelength 604 nm in toluene solution) was used instead of Compound A.

Experimental Example 1

1) Measurement of Absorption and Emission Spectra in Film State

A luminance spectrum of each of the color conversion films prepared in Examples 1 to 8 and Comparative Examples 1 to 3 was measured using a spectroradiometer (SR series of TOPCON Corporation). Specifically, the prepared color conversion film was laminated on one surface of a light guide plate of a backlight unit including an LED blue backlight (maximum emission wavelength 450 nm) and the light guide plate, and after laminating a prism sheet and a double brightness enhance film (DBEF) on the color conversion film, an initial value was set so that the brightness of the blue LED light was 600 nit based on the film.

2) Measurement of Absorption and Emission Spectra in Solution State

In order to measure absorption and emission wavelengths, the sample was dissolved to a concentration of $10^{-5}$ M using toluene as a solvent, and absorption and emission spectra thereof were measured.

3) Checking of Degree of Dyeing

A photoresist fluorescent resin composition was prepared by dissolving, based on 100 wt % of the photoresist fluorescent resin composition, 0.63 wt % (3.0 wt % in solid content) of a dye subject to measurement (compound of Table 1), 7.37 wt % of a binder (VS12A80, LG Chem.) and 13 wt % of a polyfunctional monomer (dipentaerythritol hexaacrylate) in 79 wt % of propylene glycol monomethyl ether acetate (PGMEA).

The prepared photoresist fluorescent resin composition was spin coated on 5 cm×5 cm glass (Corning Incorporated), and pre-baked for 70 seconds at 110° C. to form a coating film. Then, the distance between the coating film and a photo mask was set to 200 μm, and an exposure dose of 40 mJ/cm² was irradiated using an exposure device (Hoya-Schott). The exposed coating film was developed for 60 seconds using a developing solution (KOH, 0.04%) to form a pattern layer having a pattern width and a space width of 90 μm and 180 μm, respectively.

After forming the pattern layer, first post-bake (PB) was conducted for 20 minutes at 30° C. in an oven. After that, a solution obtained by dissolving 33 wt % of a photocurable epoxy acrylic resin in a solvent mixture of PGMEA, methyl-3-methoxy propionate (MMP) and methyl ethyl di glycol (MEDG), was overcoated on the pattern layer using a negative type coating method, and second post-bake (PB) was conducted for 30 minutes at 30° C. in an oven to complete the color conversion film. A colorimetric value of a pattern portion of the pattern layer without the overcoating layer and a colorimetric value of a pattern portion of the pattern layer after forming the overcoating layer were measured, and a degree of dyeing was checked through a difference between the two measured values (ΔEab).

Properties of the compounds used in Examples 1 to 8 and Comparative Examples 1 to 3 in the solution, and absorption and emission wavelengths in the thin film when used in the color conversion film, and a ΔEab value are as shown in Table 1.

TABLE 1

| Example | Compound | Solution | | Film | | |
| --- | --- | --- | --- | --- | --- | --- |
| | | $\lambda_{max}$(UV) | $\lambda_{max}$(PL) | $\lambda_{max}$(UV) | $\lambda_{max}$(PL) | ΔEab |
| 1 | A | 579 | 608 | 583 | 619 | 2.23 |
| 2 | B | 583 | 612 | 585 | 625 | 2.12 |
| 3 | C | 580 | 609 | 585 | 621 | 1.99 |
| 4 | D | 585 | 614 | 589 | 627 | 2.01 |
| 5 | I | 582 | 612 | 586 | 623 | 1.93 |
| 6 | J | 579 | 610 | 585 | 622 | 2.04 |
| 7 | K | 584 | 614 | 590 | 626 | 2.14 |
| 8 | L | 586 | 615 | 589 | 628 | 1.91 |
| Comparative Example 1 | O | 572 | 601 | 575 | 612 | 4.81 |
| Comparative Example 2 | P | 570 | 599 | 572 | 610 | 3.99 |
| Comparative Examples | Q | 575 | 604 | 576 | 615 | 3.54 |

Through Table 1, it was identified that the compound according to the disclosure of the present application had longer absorption and emission wavelengths in the solution and in the thin film compared to the comparative examples, and the ΔEab value was 3 or less, and as a result, it was seen that there was less dyeing compared to the comparative examples.

The invention claimed is:

1. A compound represented by the following Chemical Formula 1:

[Chemical Formula 1]

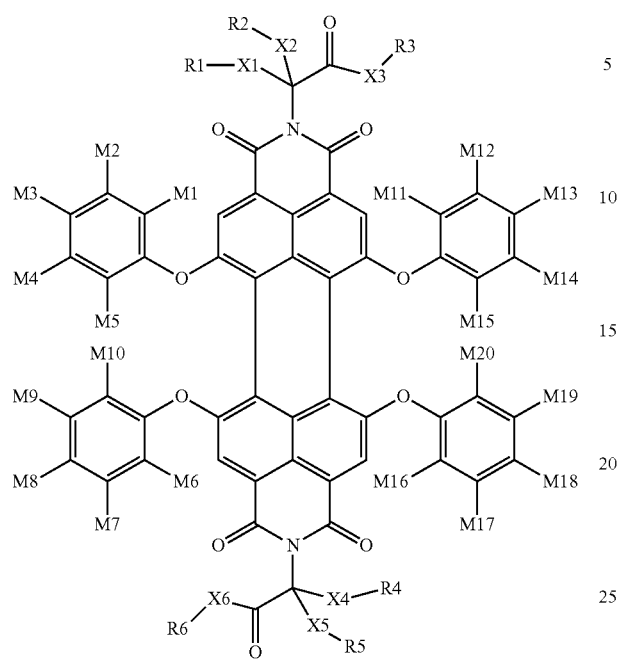

wherein, in the Chemical Formula 1,
X1, X2, X4 and X5 are the same as or different from each other, and each independently a direct bond, or a substituted or unsubstituted alkylene group;
X3 and X6 are the same as or different from each other, and each independently O or NR';
R' and R1 to R6 are the same as or different from each other, and each independently hydrogen, a halogen group, a substituted or unsubstituted alkyl group, a substituted or unsubstituted cycloalkyl group, a substituted or unsubstituted aryl group, or a substituted or unsubstituted heterocyclic group, or bond to adjacent groups to form a ring; and
at least one of M1 to M5, at least one of M6 to M10, at least one of M11 to M15 and at least one of M16 to M20 are each independently a substituent represented by the following Chemical Formula 2, and the rest are hydrogen,

[Chemical Formula 2]

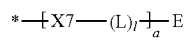

in the Chemical Formula 2,
X7 is a direct bond, O, C(=O) NH, or NH;
L is a substituted or unsubstituted alkylene group, a substituted or unsubstituted cycloalkylene group, a substituted or unsubstituted arylene group, or a substituted or unsubstituted divalent heterocyclic group;
a and l are each 1 or 2;
when a and l are each 2, structures in the parentheses are the same as or different from each other;
E is a polymerizable group; and
* represents a bonding position,
wherein the polymerizable group is a group having at least one selected from the group consisting of a substituted or unsubstituted ethylenically unsaturated group, a substituted or unsubstituted siloxane group, and a substituted or unsubstituted epoxy group.

2. The compound of claim 1, wherein the polymerizable group is any one of the following groups:

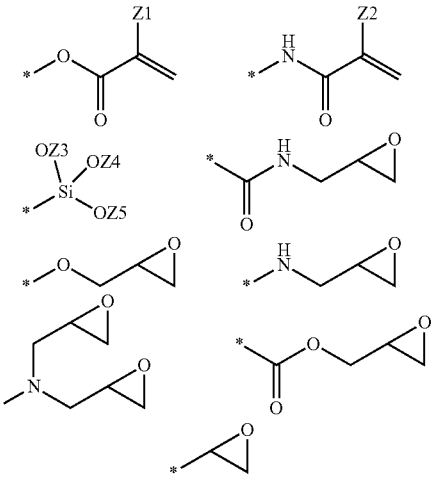

wherein,
Z1 and Z2 are each independently hydrogen, a halogen group, or a substituted or unsubstituted alkyl group;
Z3 to Z5 are each independently a substituted or unsubstituted alkyl group; and
* represents a bonding position.

3. The compound of claim 1, wherein the Chemical Formula 1 is represented by the following Chemical Formula 3:

[Chemical Formula 3]

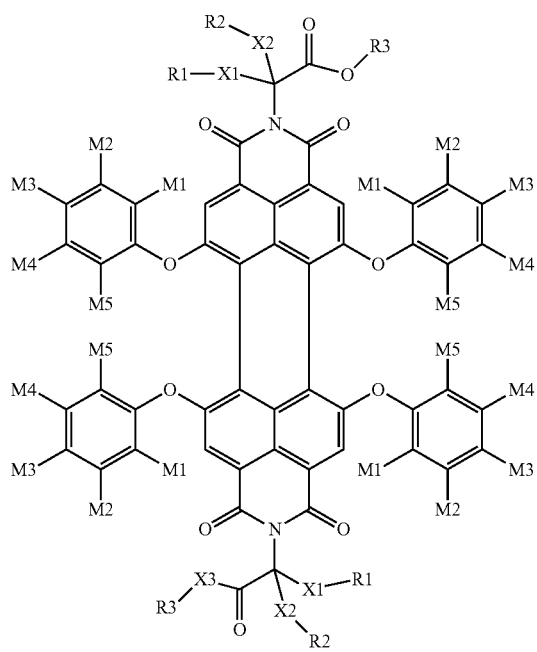

in the Chemical Formula 3,
X1 to X3, R1 to R3 and M1 to M5 have the same definitions as in the Chemical Formula 1.

4. The compound of claim 1, wherein any one of M1 to M5, any one of M6 to M10, any one of M11 to M15 and any one of M16 to M20 are each independently the substituent represented by the Chemical Formula 2, and the rest are hydrogen.

5. The compound of claim 1, wherein the Chemical Formula 1 is represented by the following Chemical Formula 4 or 5:

[Chemical Formula 4]

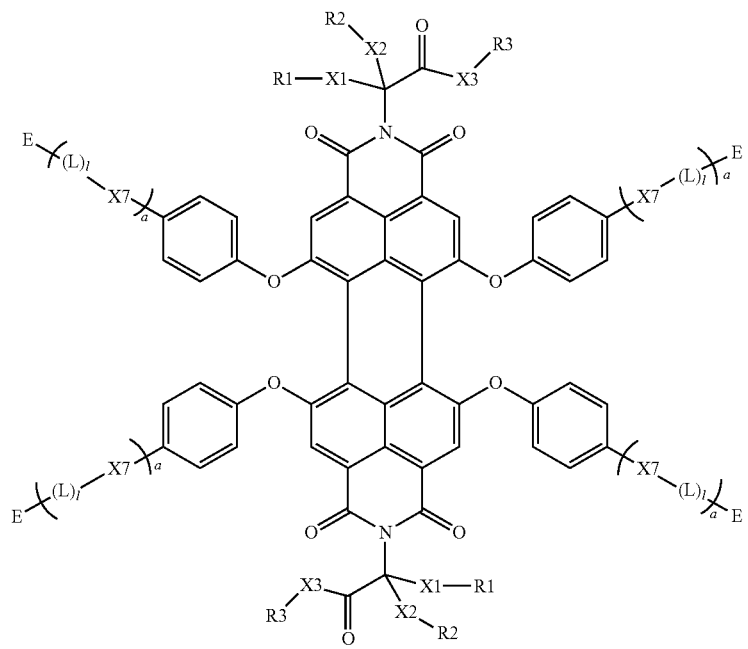

[Chemical Formula 5]

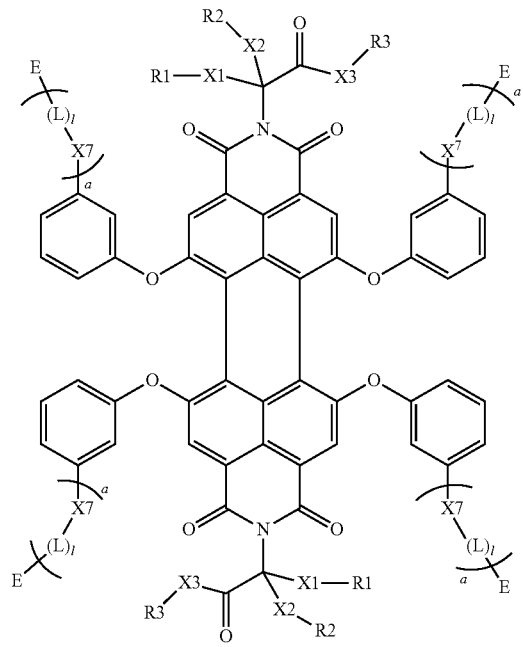

in the Chemical Formulae 4 and 5,

X1 to X3 and R1 to R3 have the same definitions as in the Chemical Formula 1; and X7, L, E, l and a have the same definitions as in the Chemical Formula 2.

6. The compound of claim 1, wherein the Chemical Formula 1 is represented by the following Chemical Formula 6:

[Chemical Formula 6]

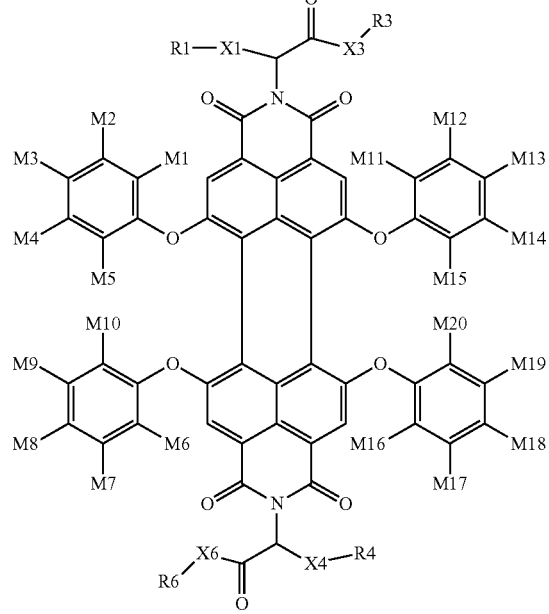

in Chemical Formula 6,

X1, X3, X4, X6, R1, R3, R4, R6 and M1 to M20 have the same definitions as in the Chemical Formula 1.

7. The compound of claim 1, wherein the Chemical Formula 1 is represented by any one of the following Chemical Formulae 6-1 to 6-3:

[Chemical Formula 6-1]

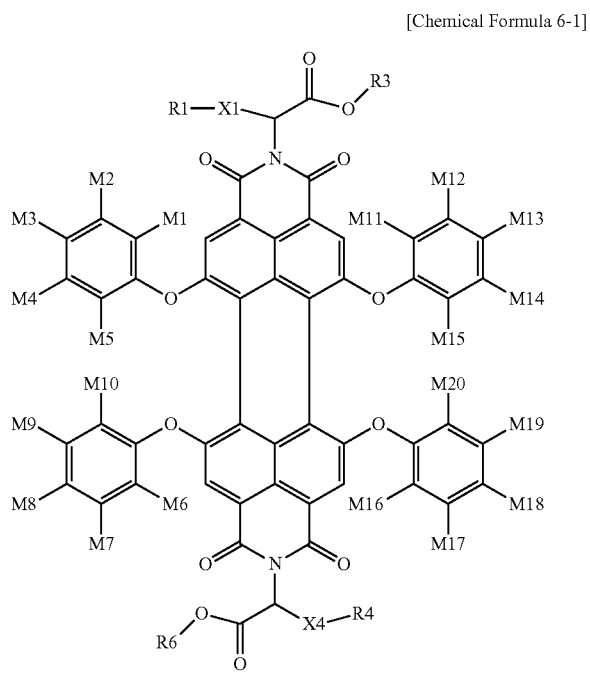

[Chemical Formula 6-2]

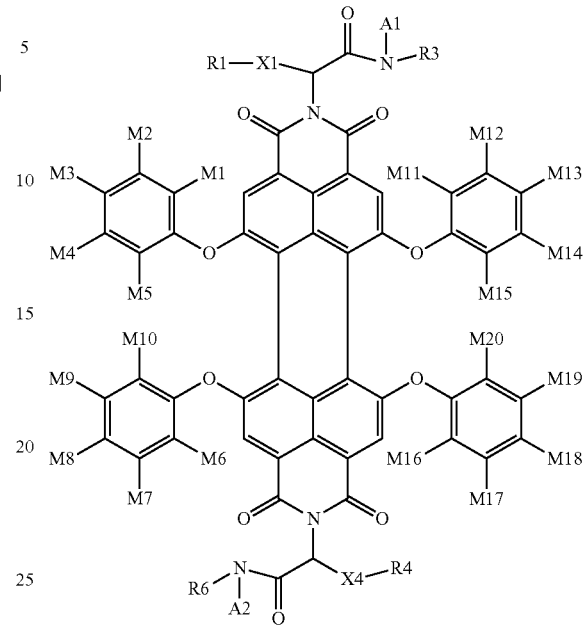

[Chemical Formula 6-3]

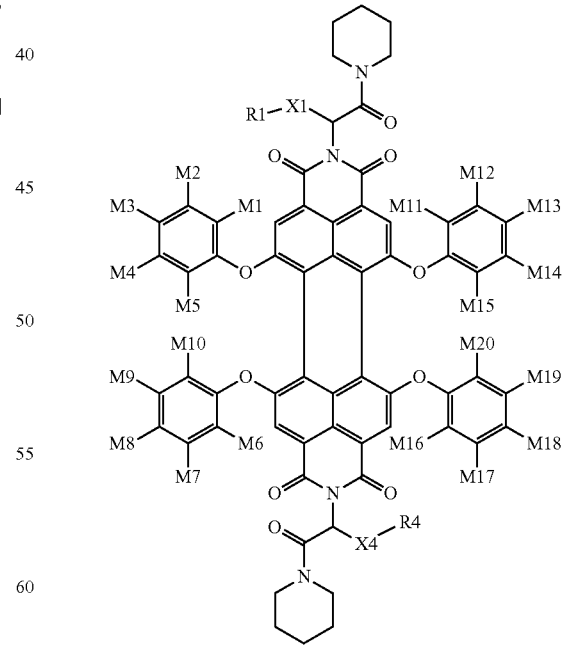

in the Chemical Formulae 6-1 to 6-3,

X1, X4, R1, R3, R4, R6 and M1 to M20 have the same definitions as in the Chemical Formula 1; and A1 and A2 are the same as or different from each other, and each independently hydrogen, a halogen group, a substituted or unsubstituted alkyl group, a substituted or unsubstituted cycloalkyl group, a substituted or unsubstituted aryl group, or a substituted or unsubstituted heterocyclic group.

8. The compound of claim 1, wherein the Chemical Formula 1 is represented by any one of the following Chemical Formulae 3-1 to 3-3:

[Chemical Formula 3-1]

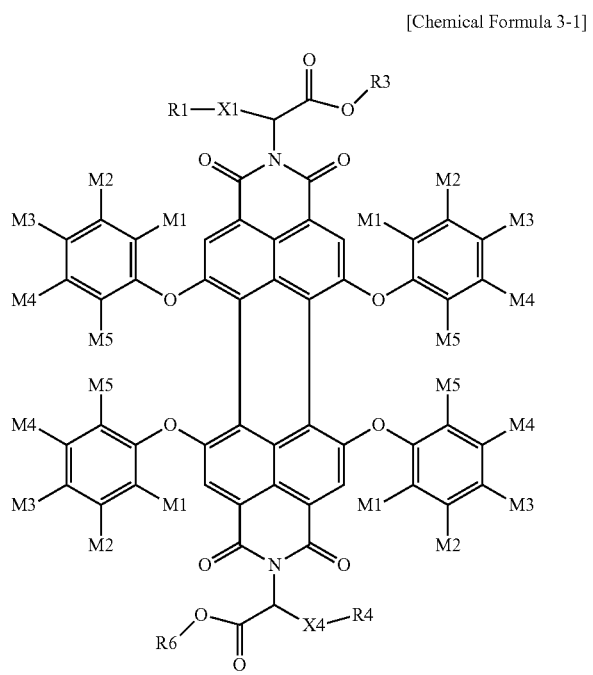

[Chemical Formula 3-2]

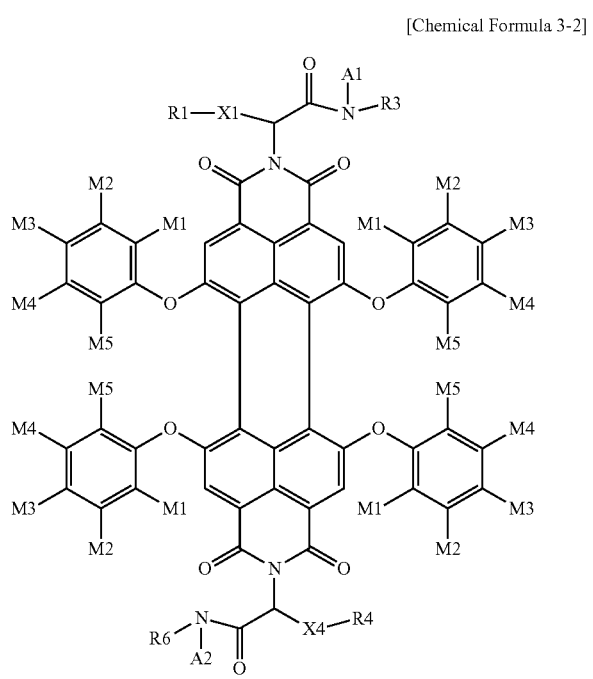

[Chemical Formula 3-3]

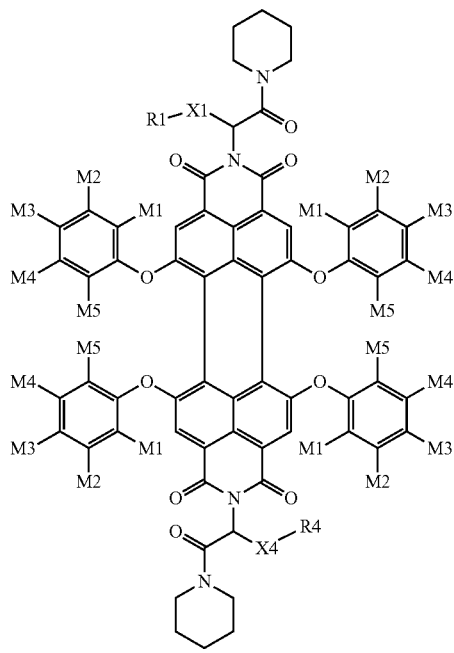

in the Chemical Formulae 3-1 to 3-3,

X1, X4, R1, R3, R4 and R6 have the same definitions as in the Chemical Formula 1;

any one of M1 to M5 is the substituent represented by the Chemical Formula 2, and the rest are hydrogen; and A1 and A2 are the same as or different from each other, and each independently hydrogen, a halogen group, a substituted or unsubstituted alkyl group, a substituted or unsubstituted cycloalkyl group, a substituted or unsubstituted aryl group, or a substituted or unsubstituted heterocyclic group.

9. A photoresist fluorescent resin composition comprising:
a binder resin;
a multifunctional monomer; and
the compound of claim 1.

10. A color conversion film comprising the compound in which the polymerizable group of the compound according to claim 1 is bound to a binder resin.

11. A backlight unit comprising the color conversion film of claim 10.

12. A display apparatus comprising the backlight unit of claim 11.

13. The compound of claim 1, wherein the compound represented by the Chemical Formula 1 is represented by any one of the following compounds:

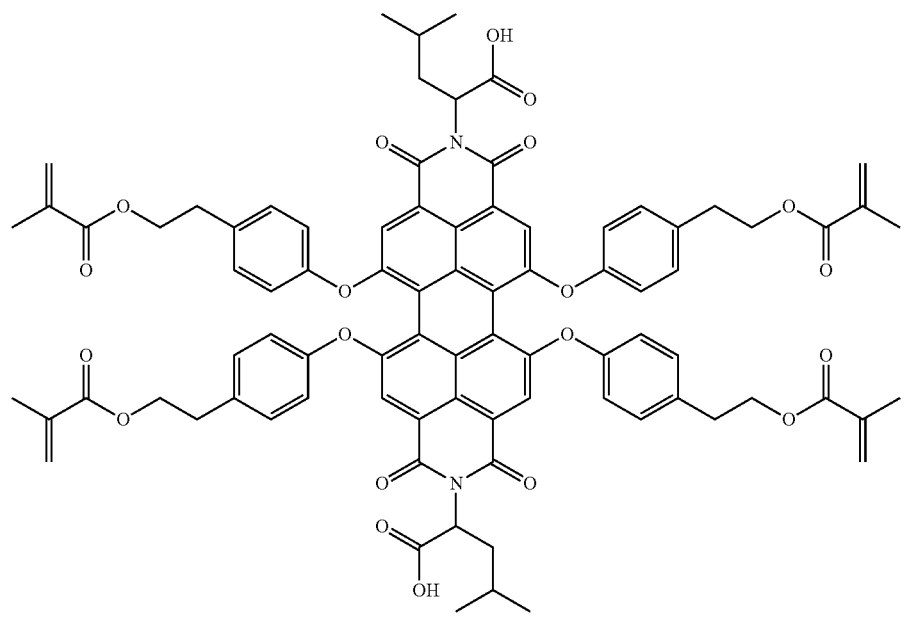
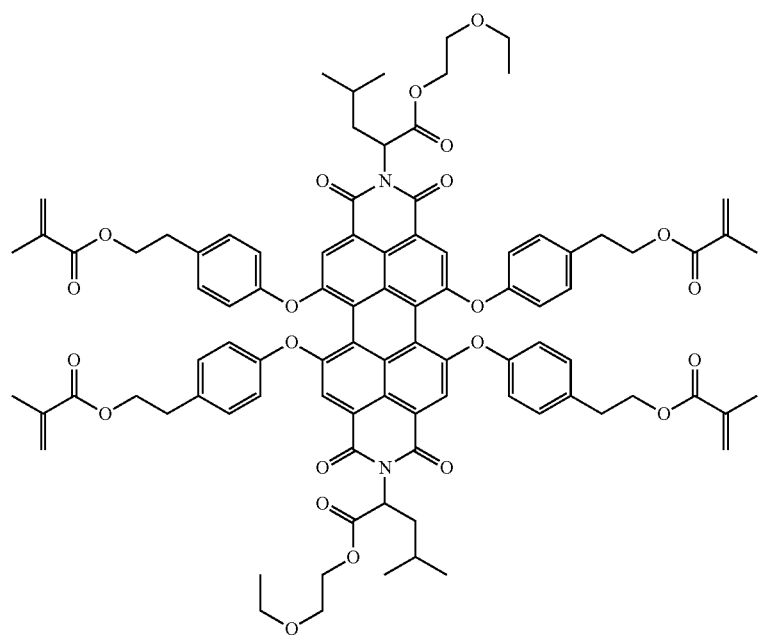

-continued
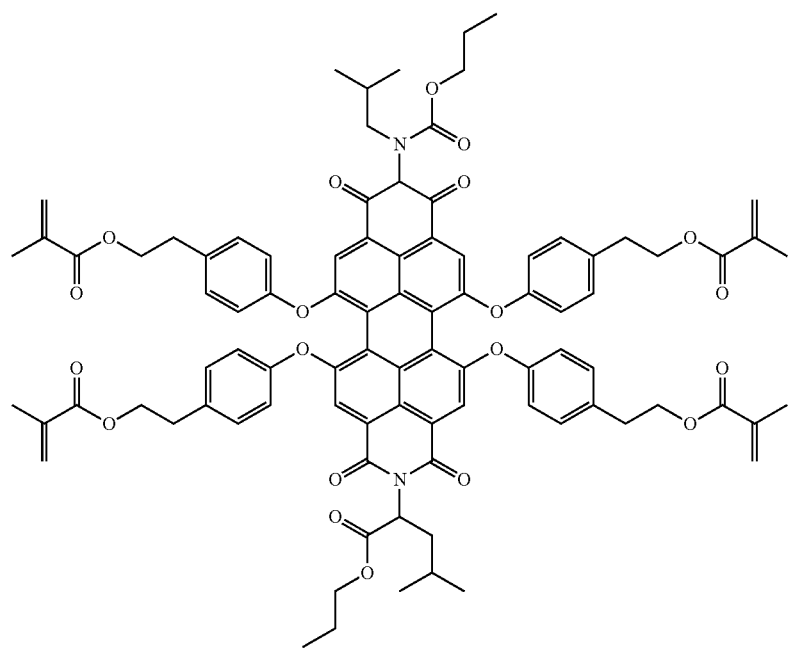
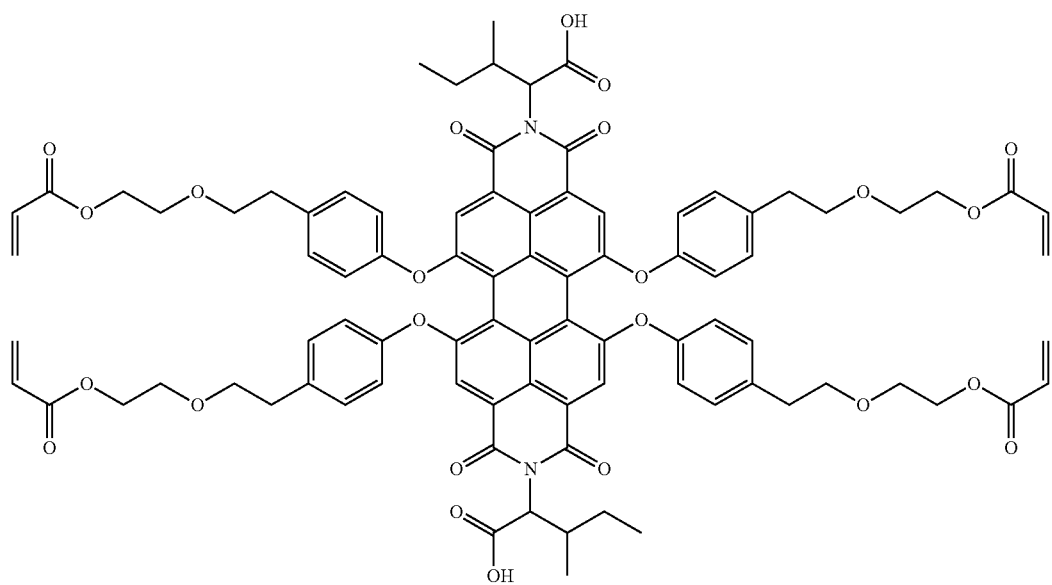

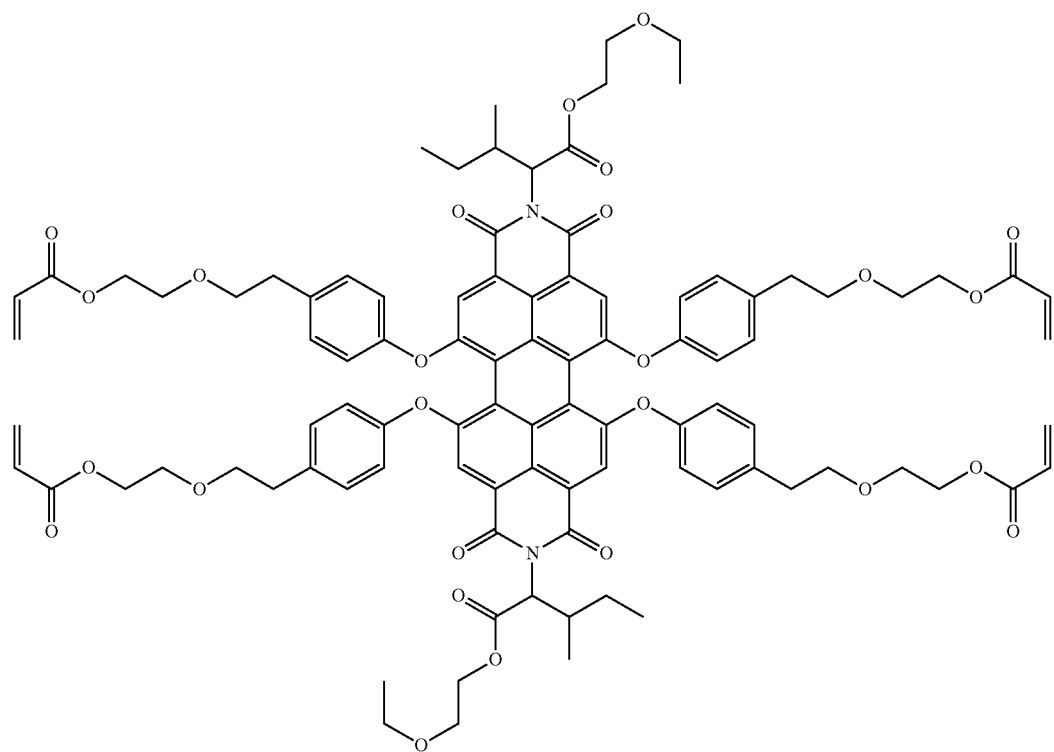
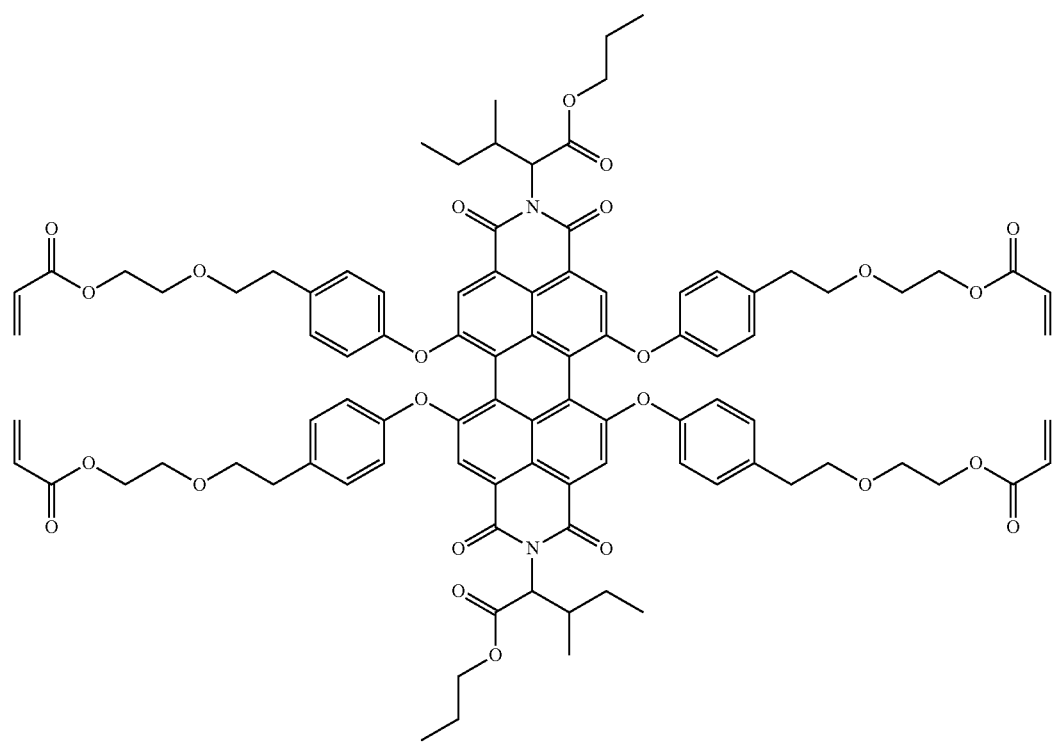

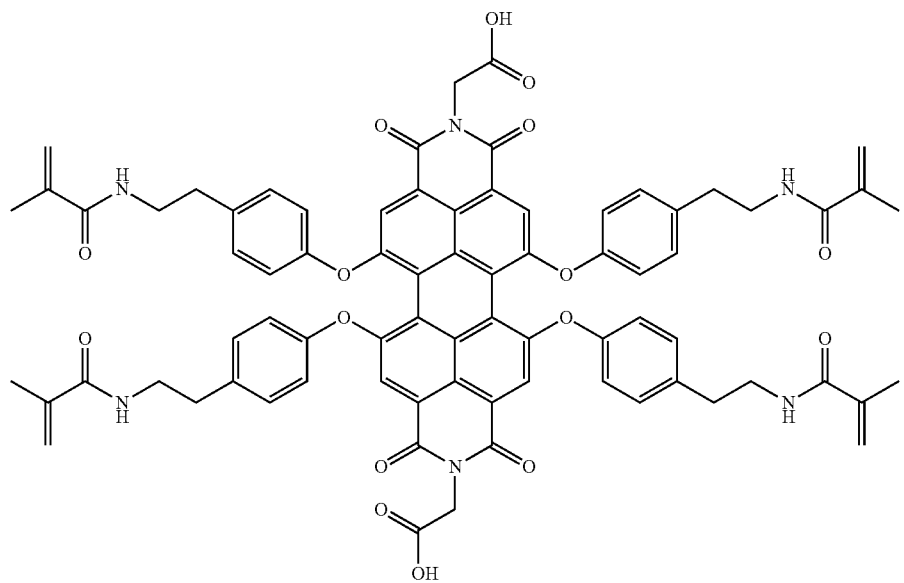
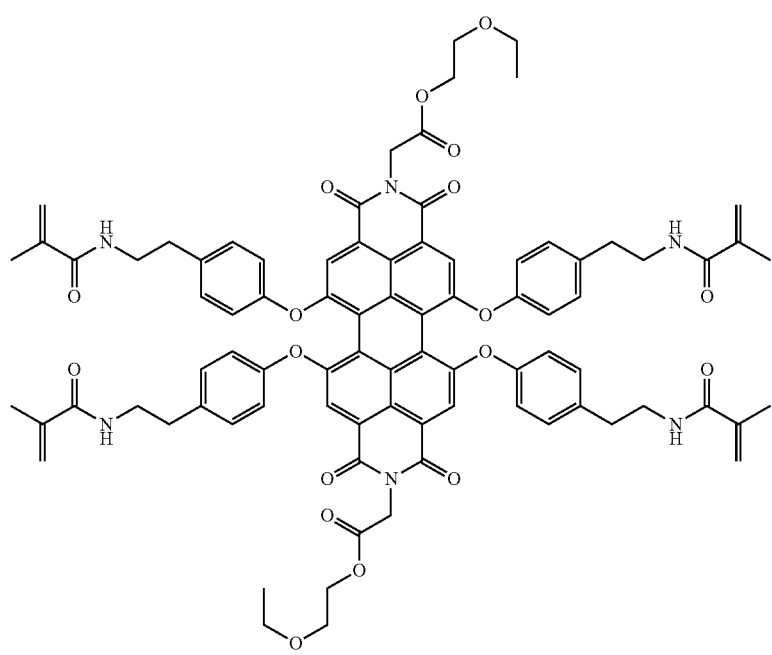

-continued
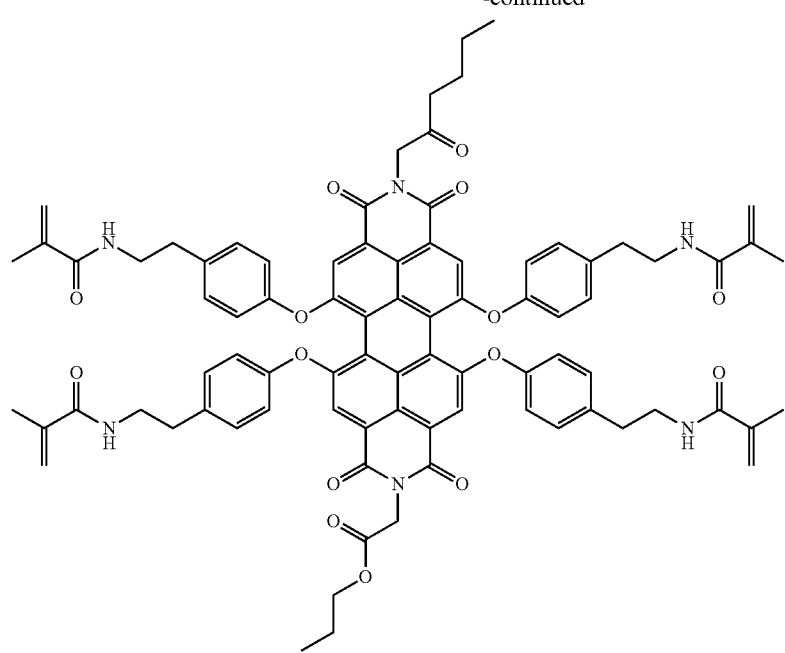
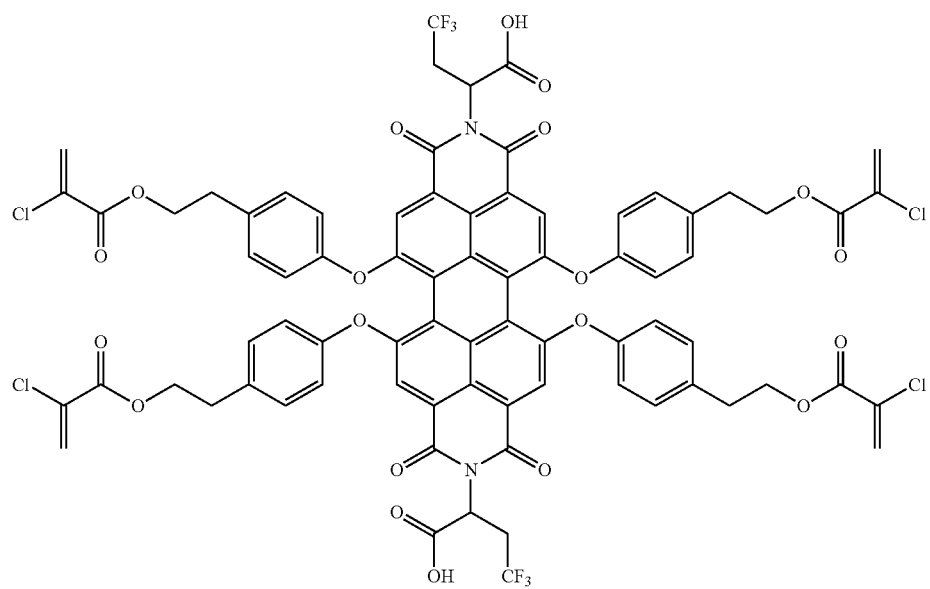

-continued
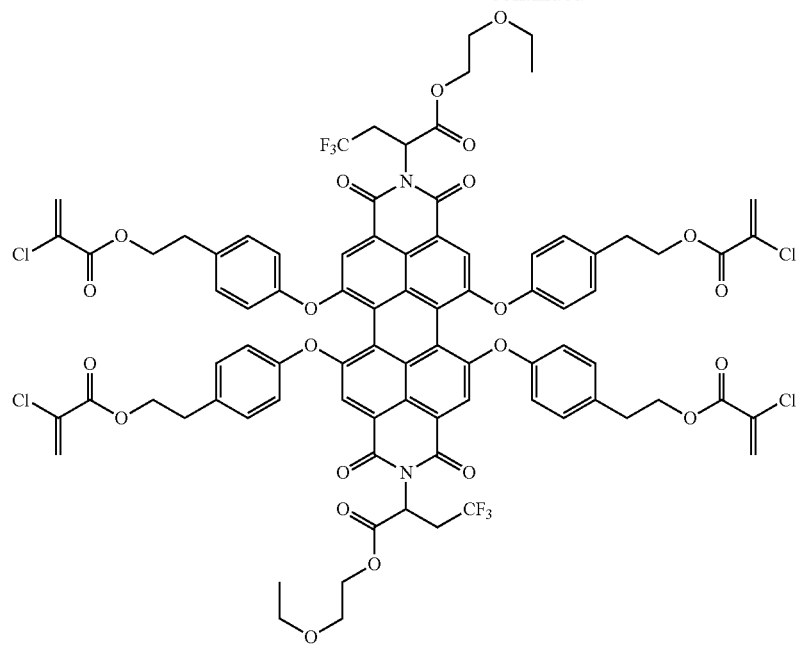
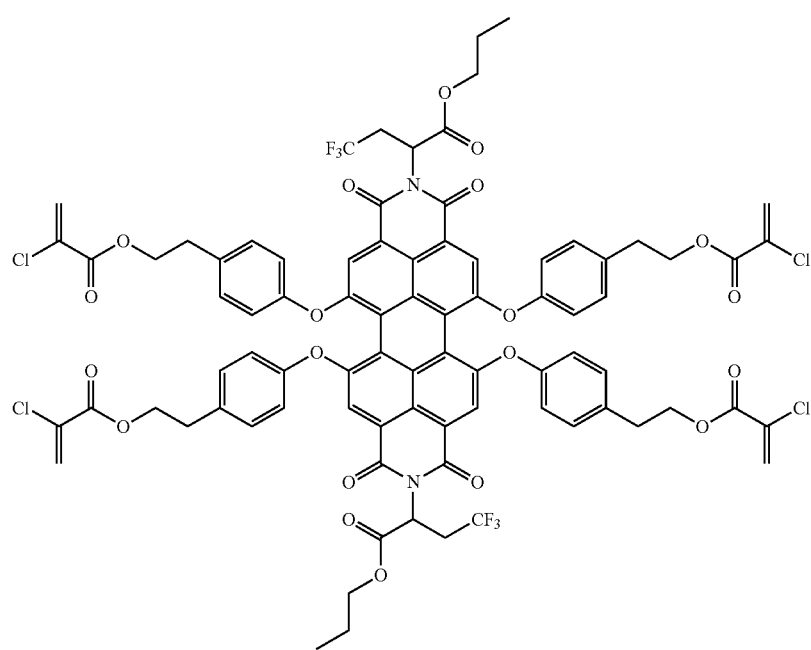

-continued
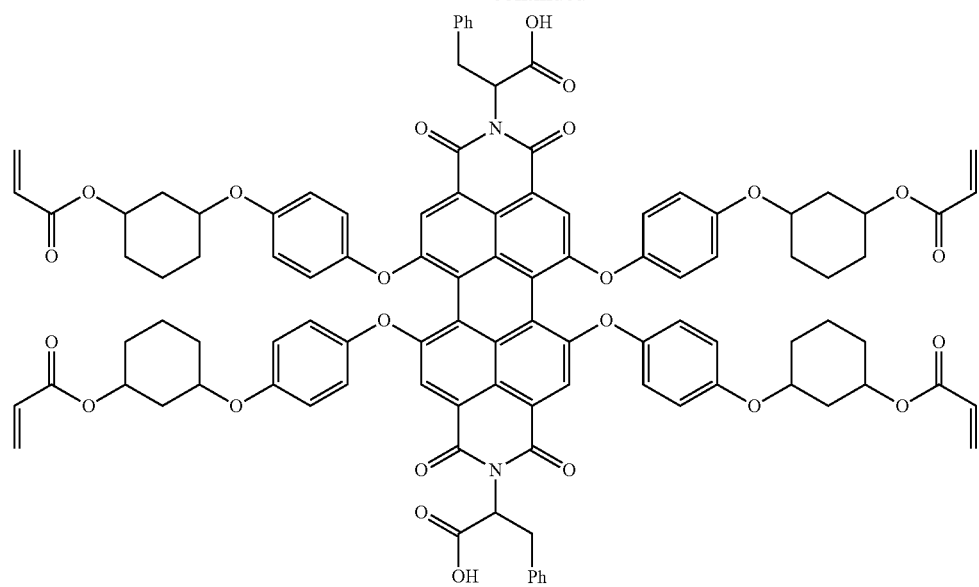
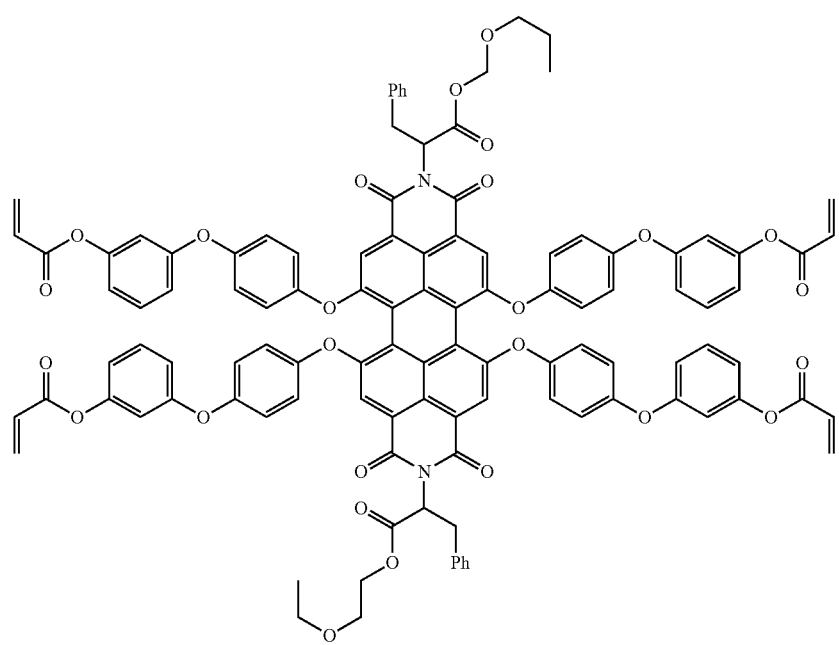

-continued
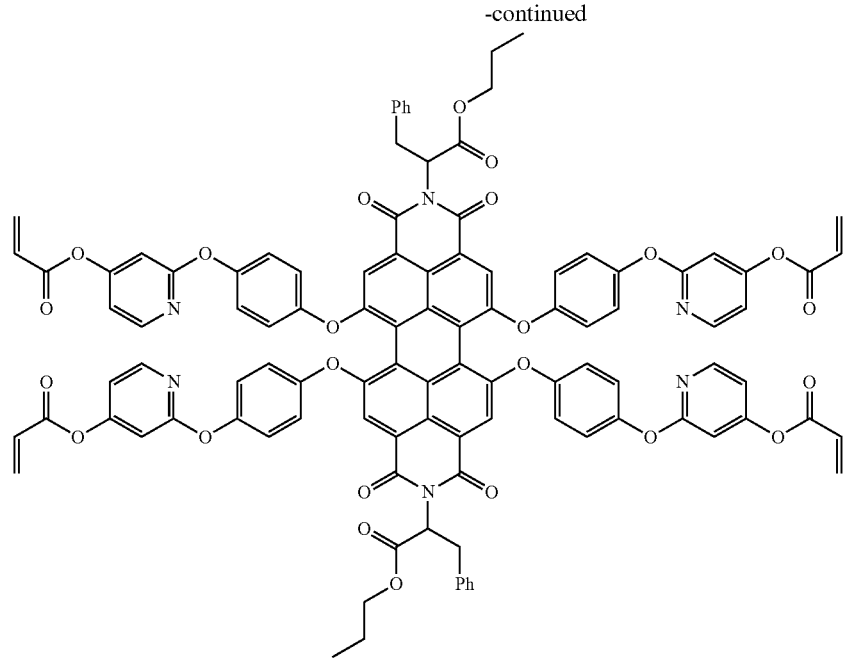
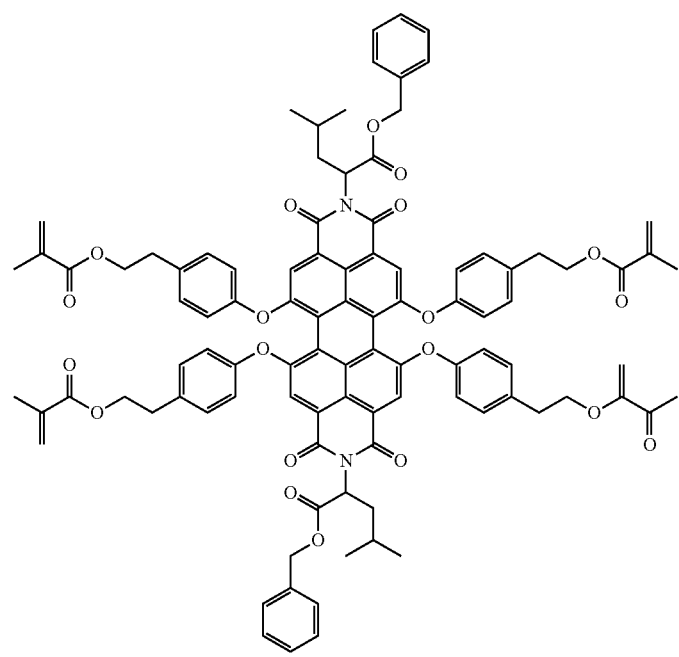

-continued
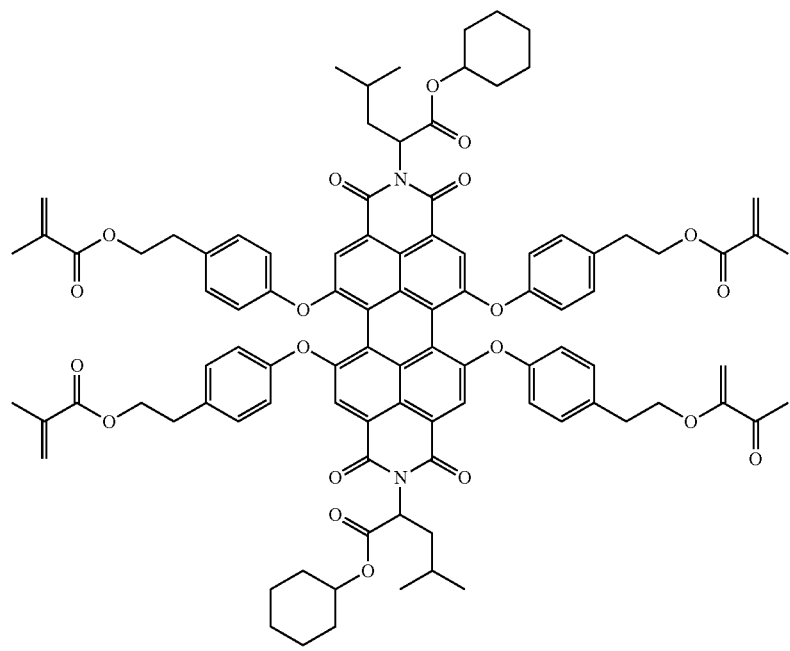
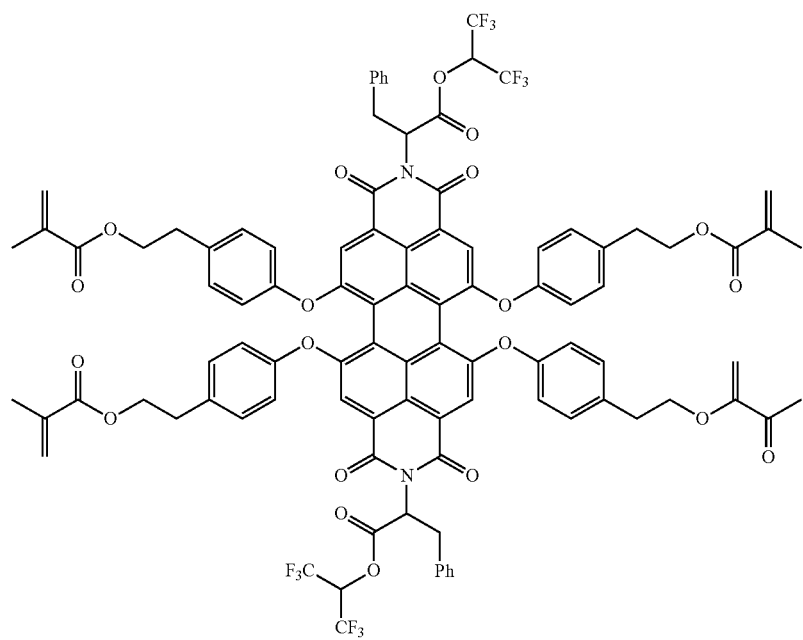

-continued
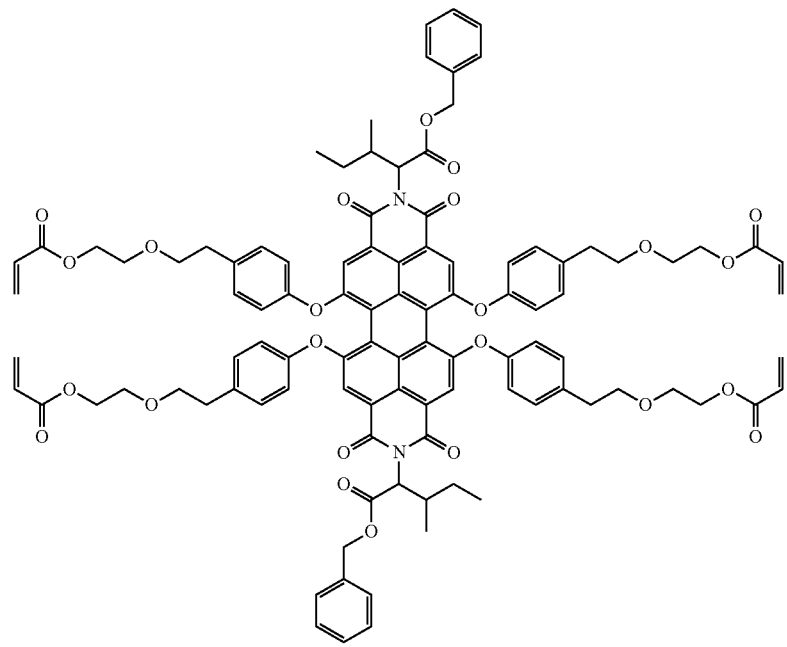
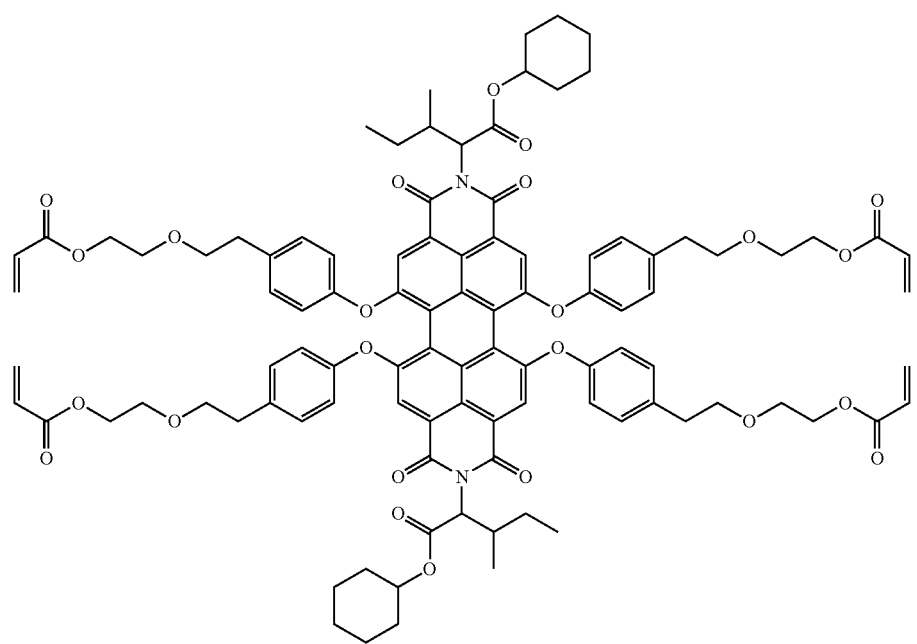

-continued
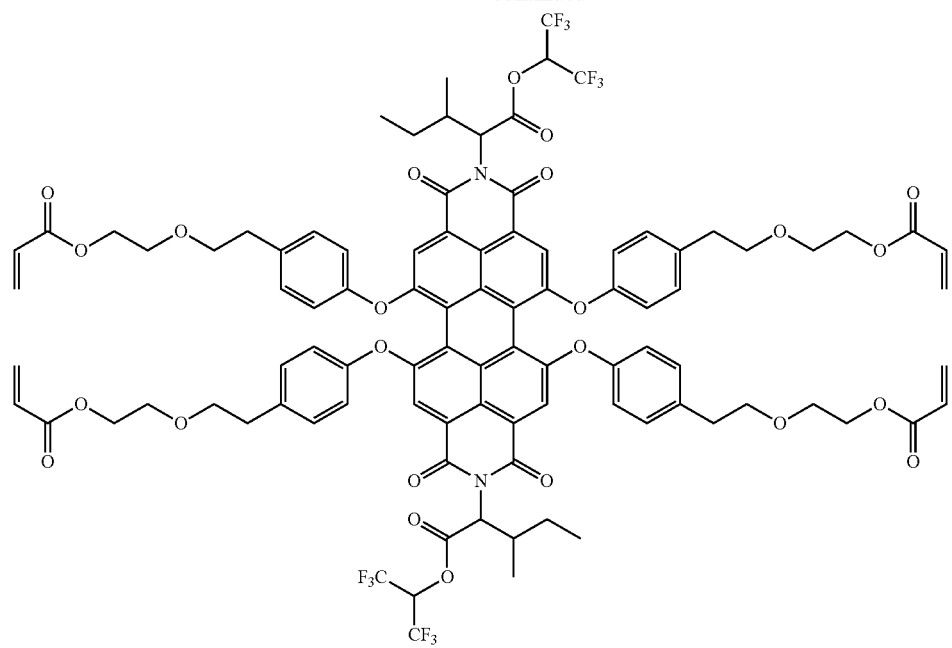
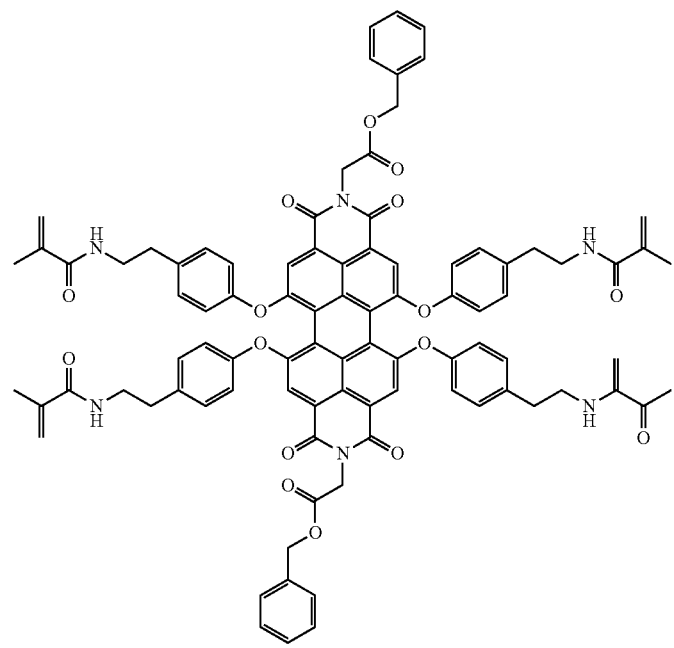

-continued
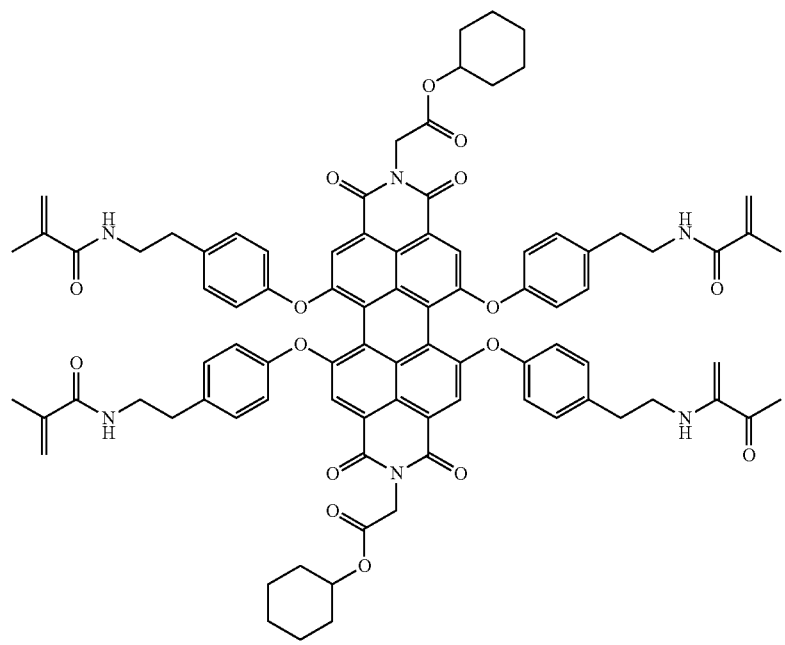
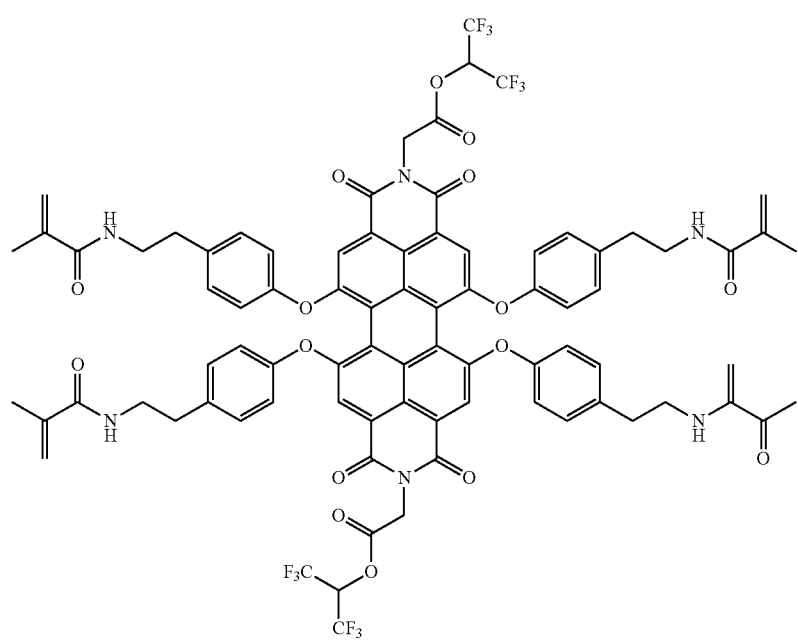

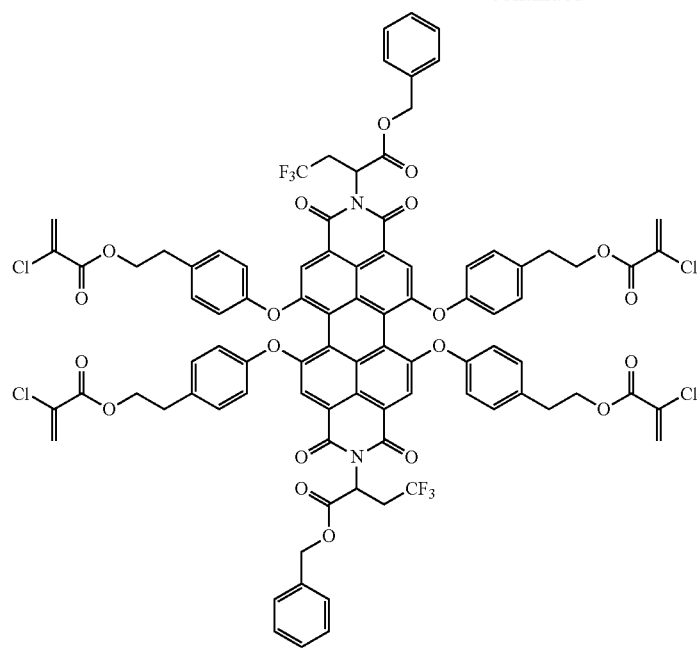
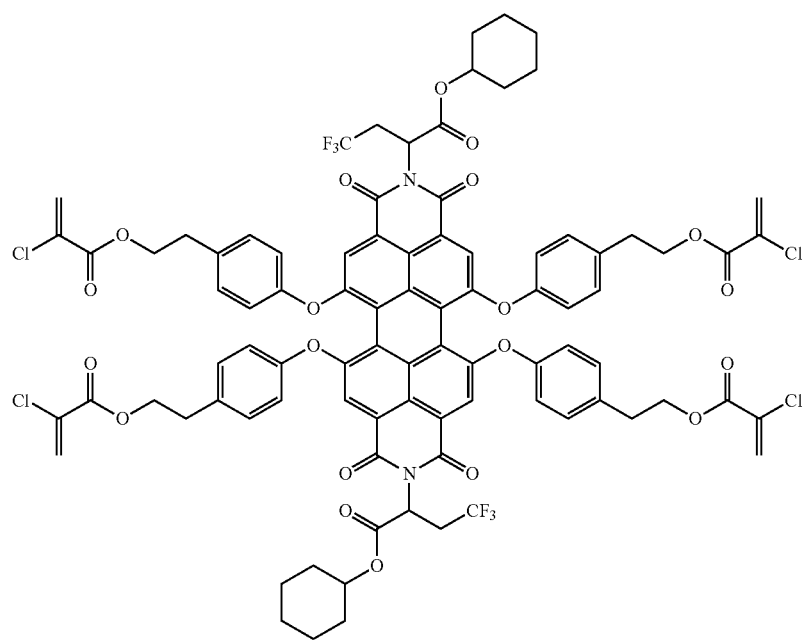

-continued
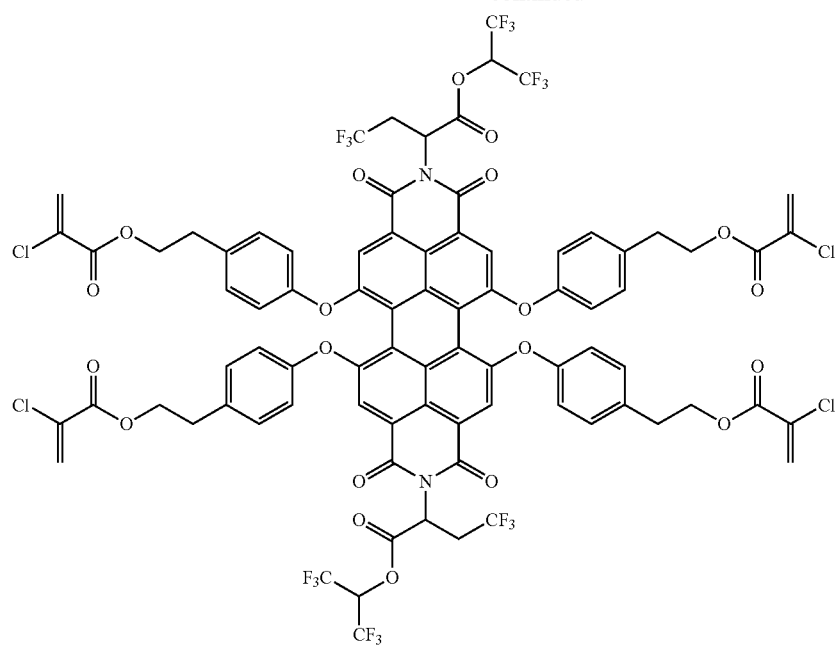
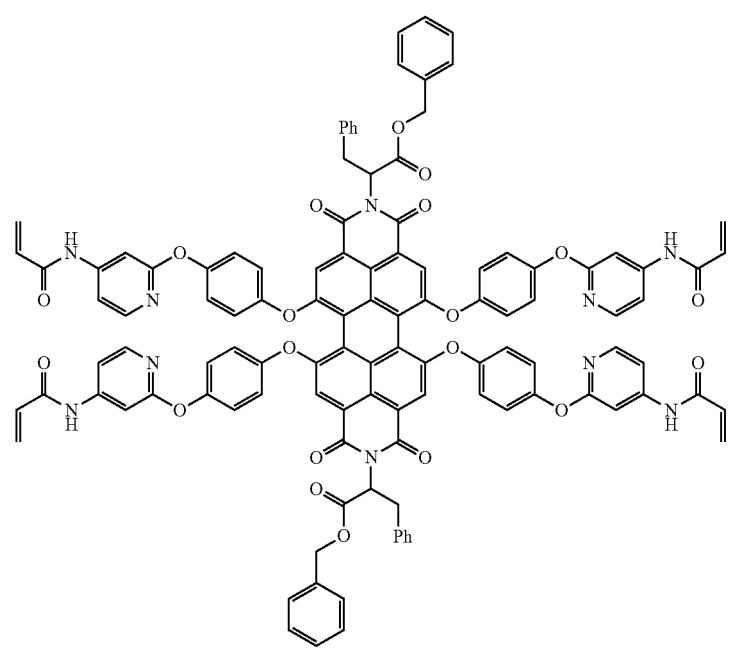

-continued
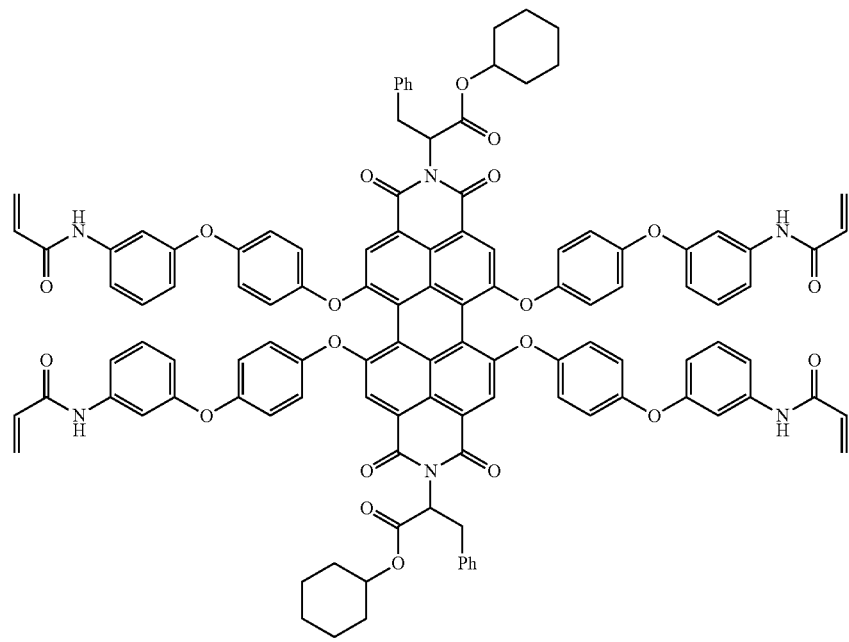
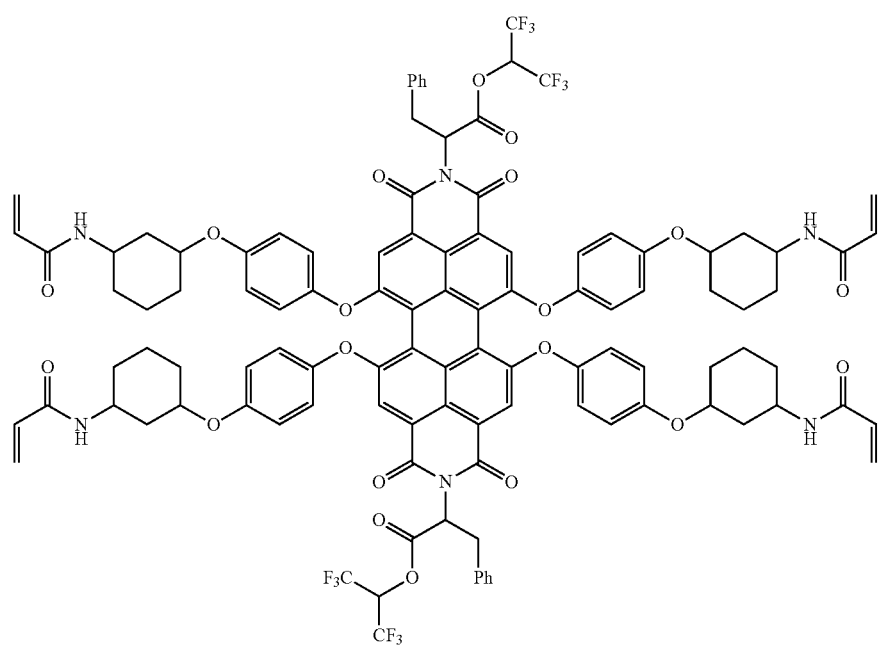

-continued
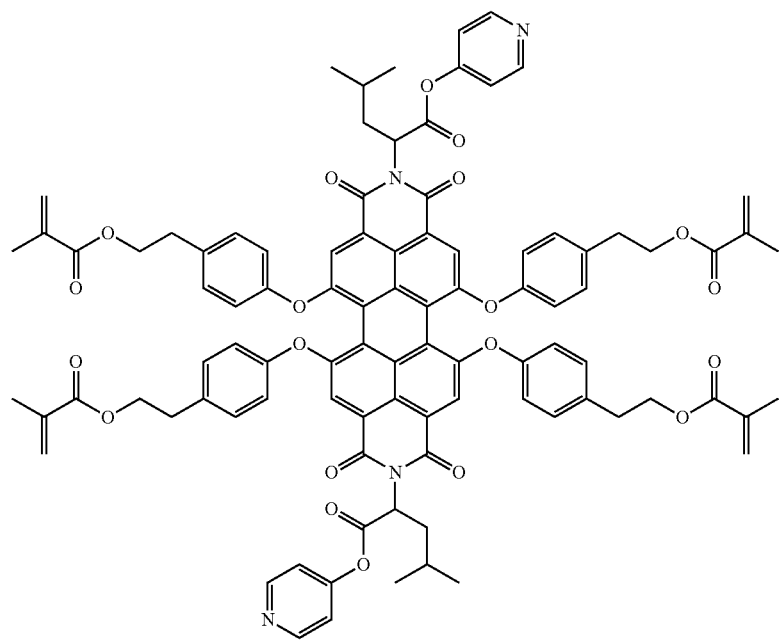
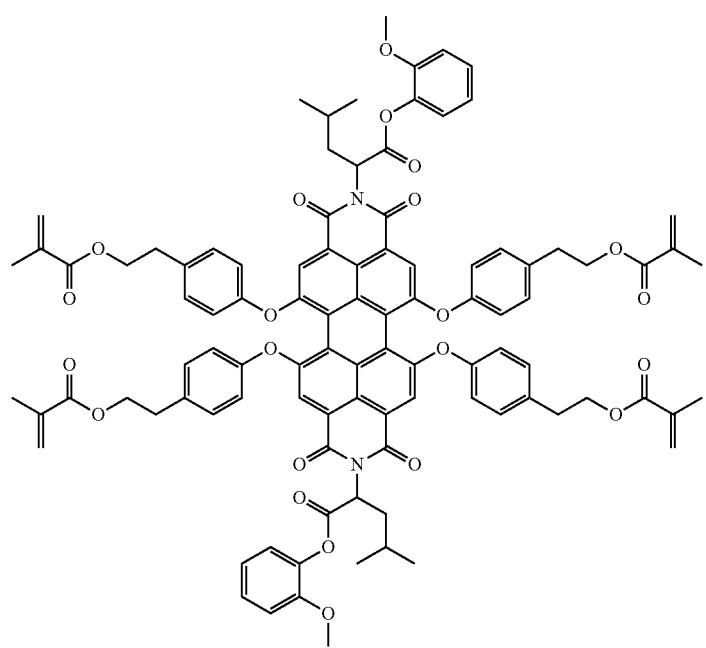

405
-continued
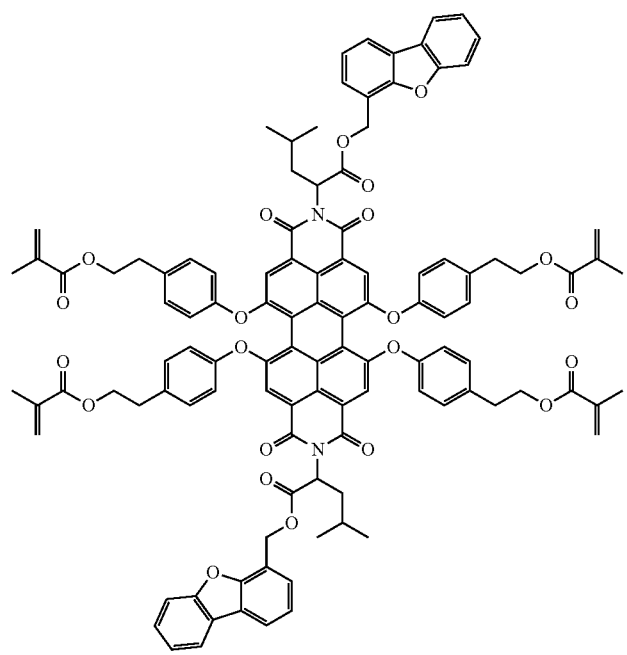
406
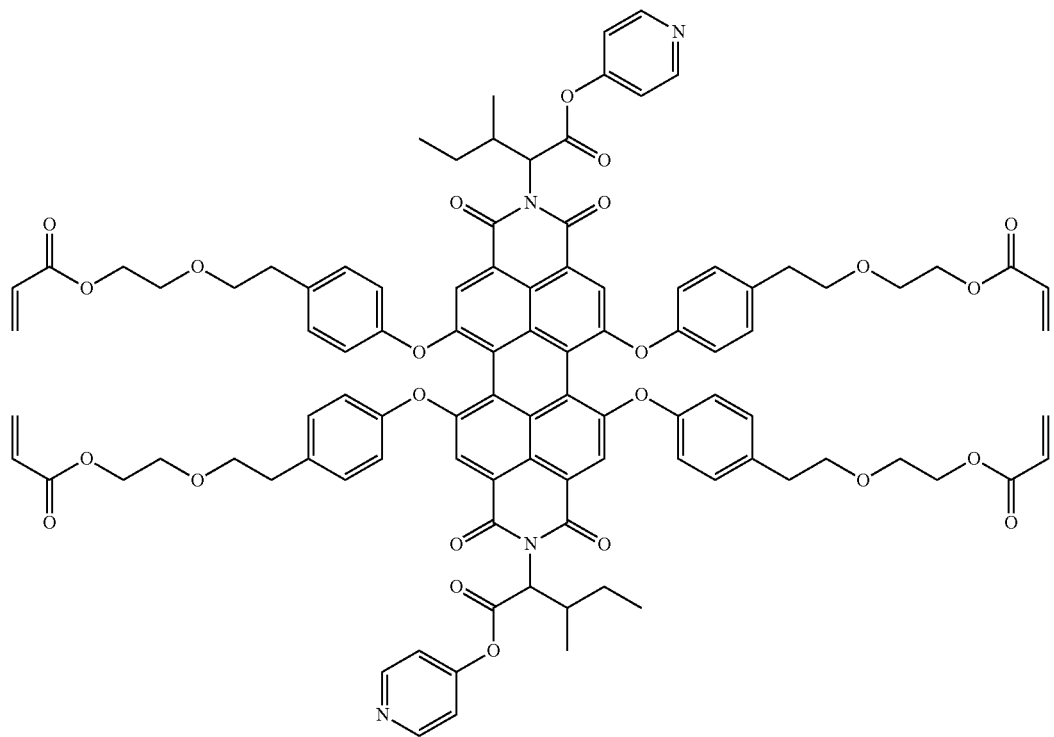

-continued
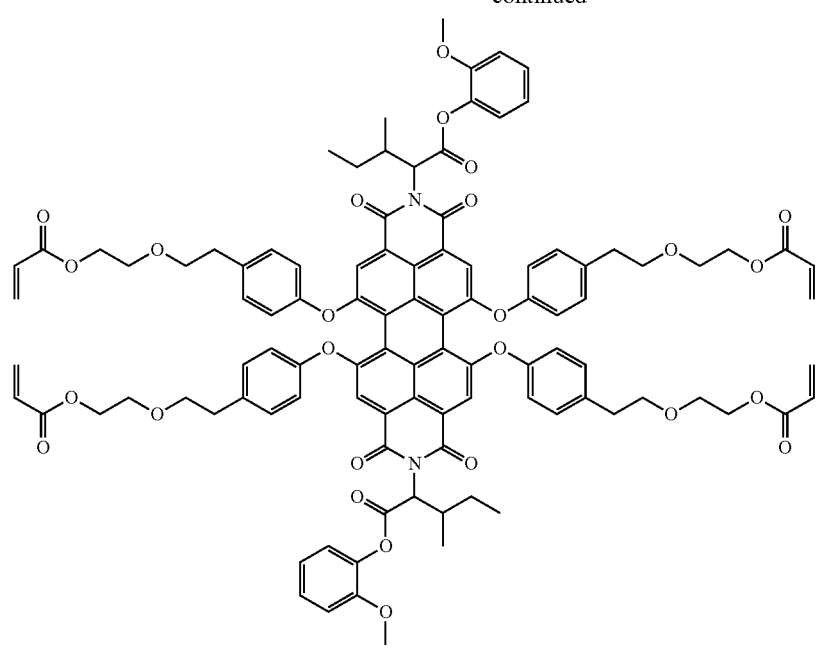
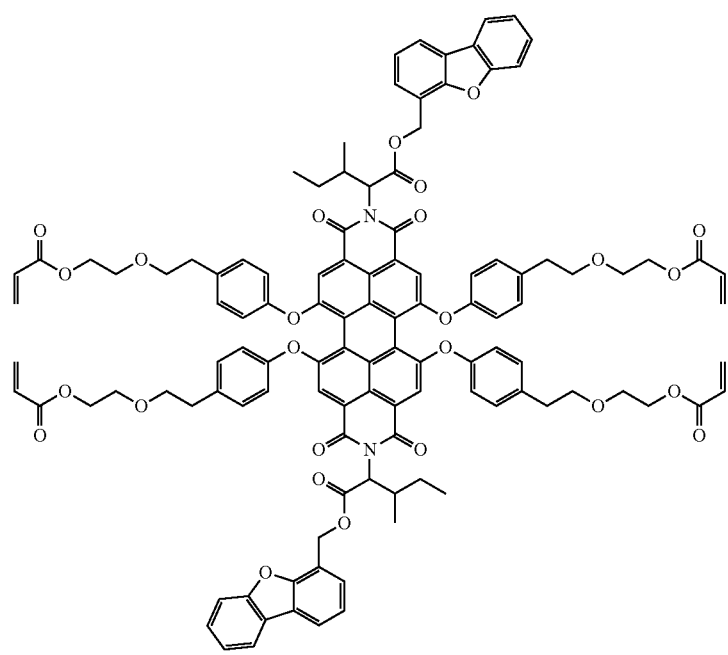

-continued
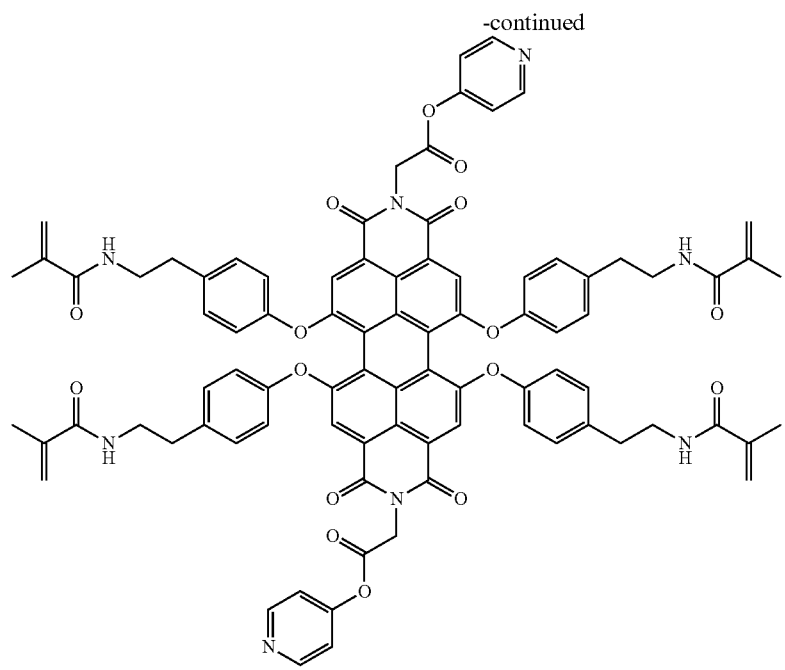
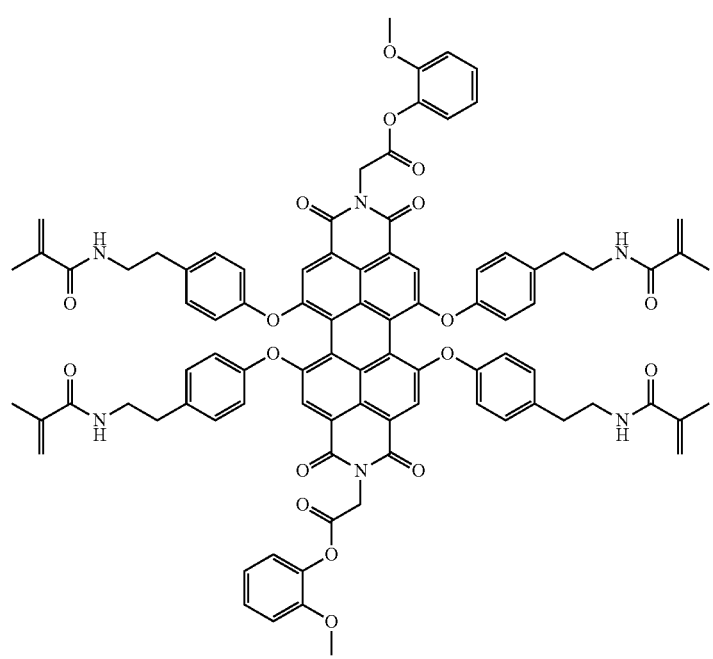

411
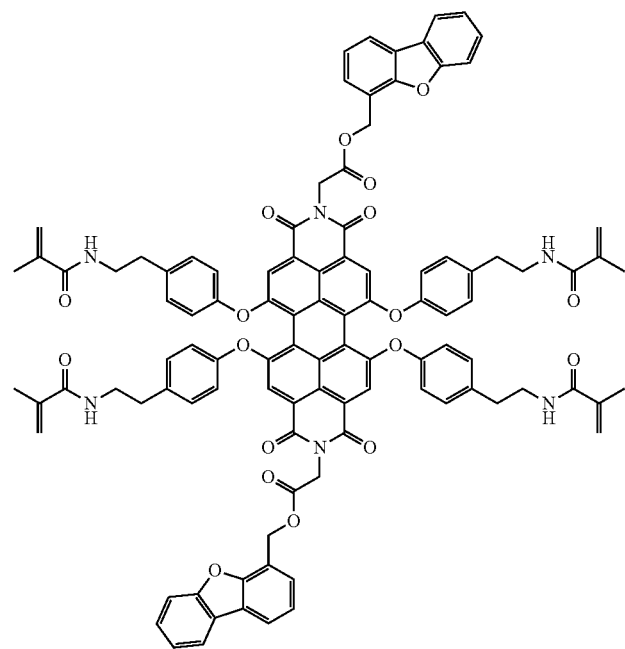
412
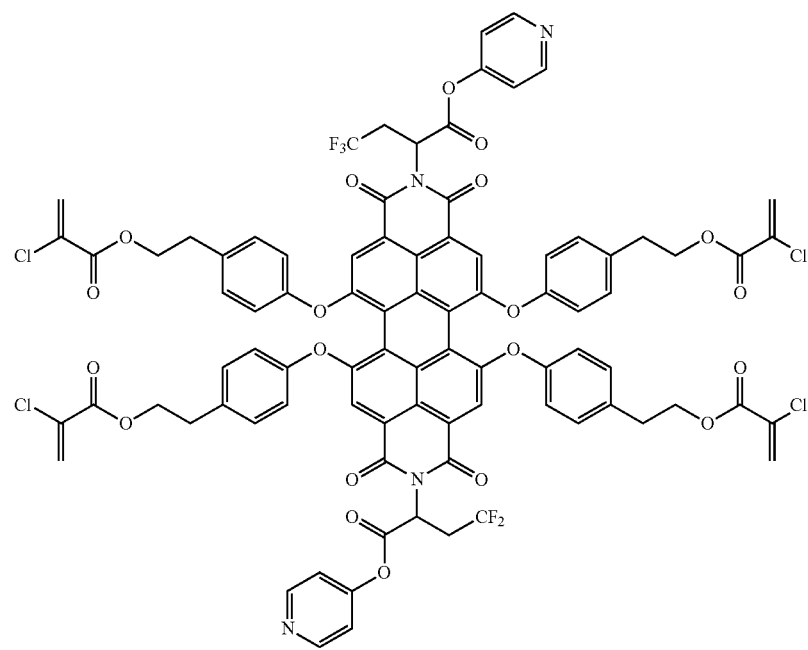

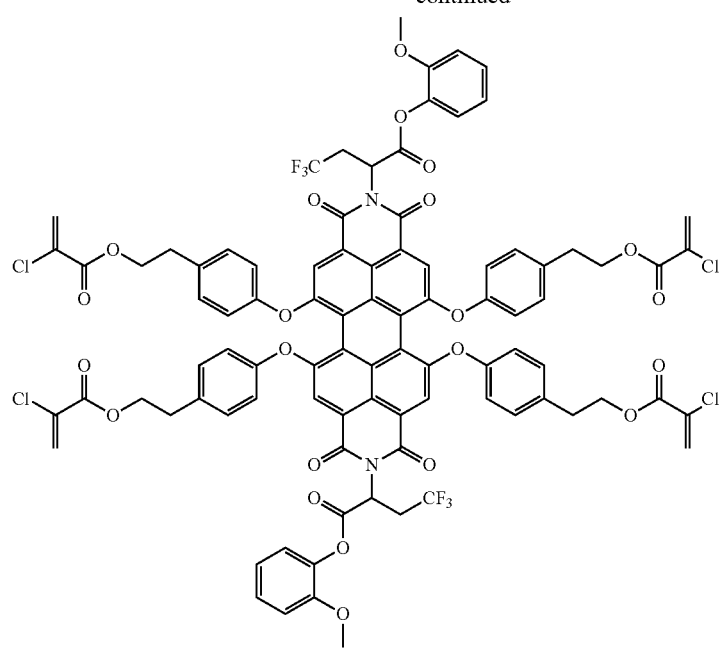
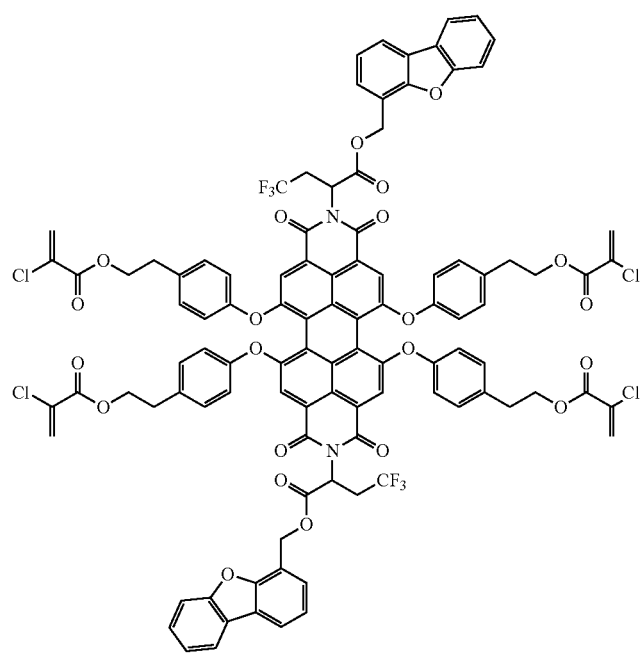

-continued
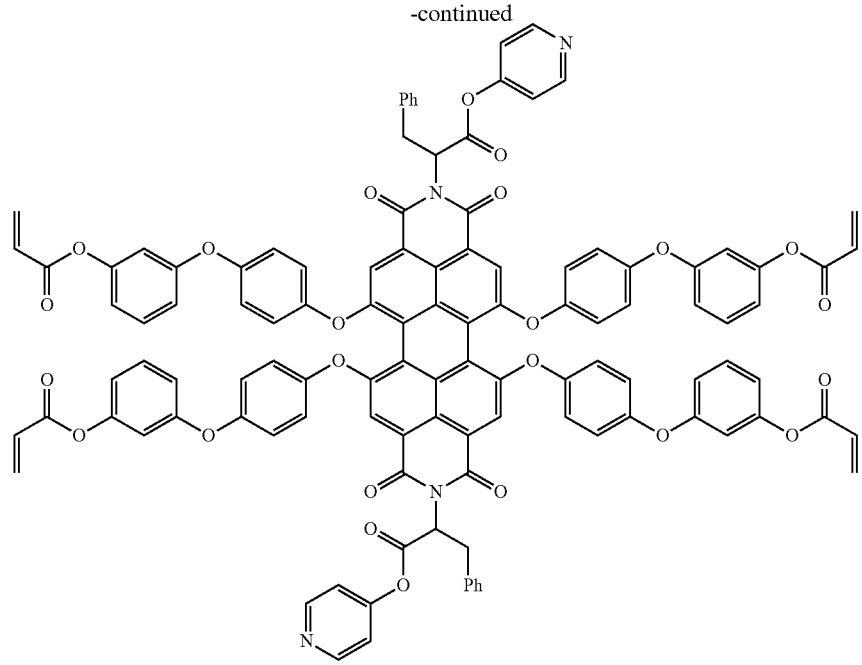
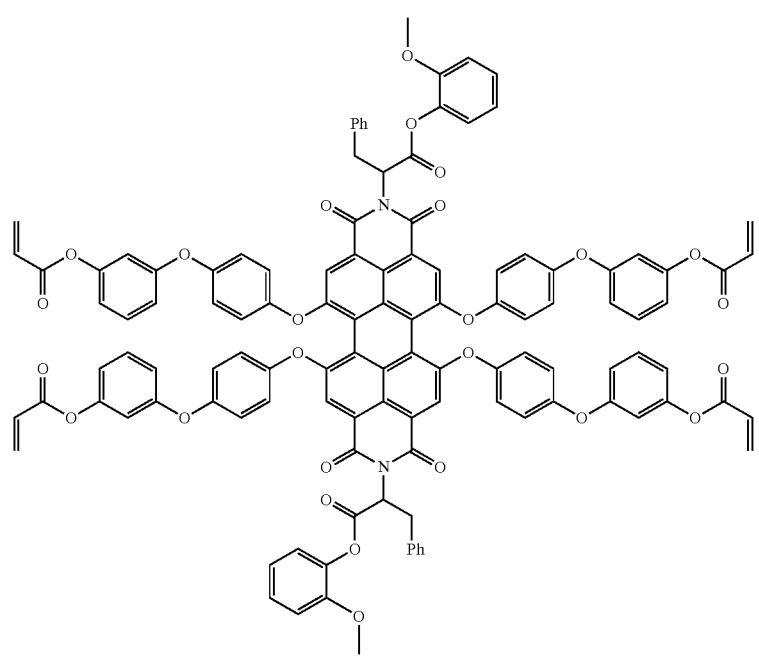

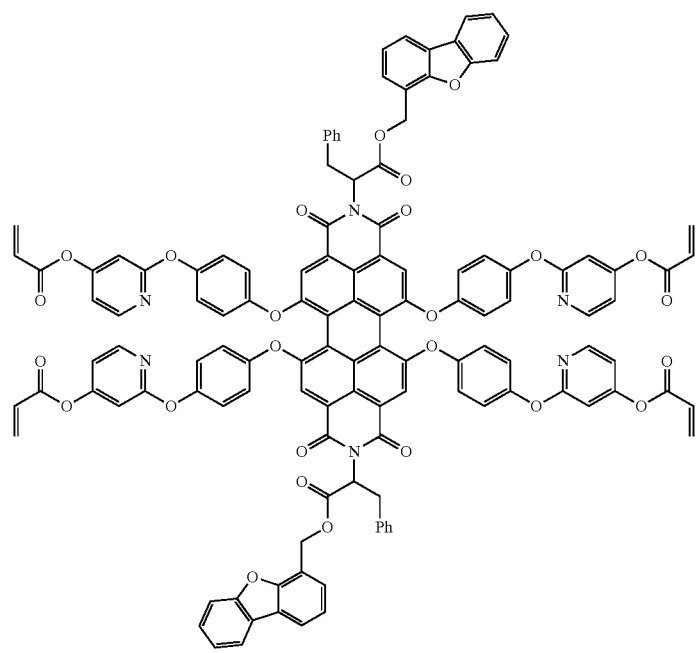
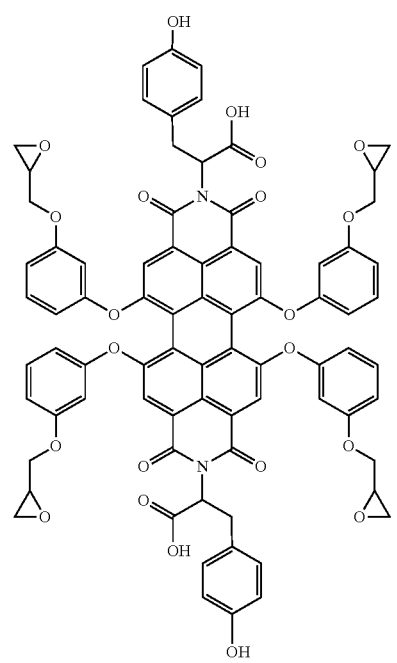

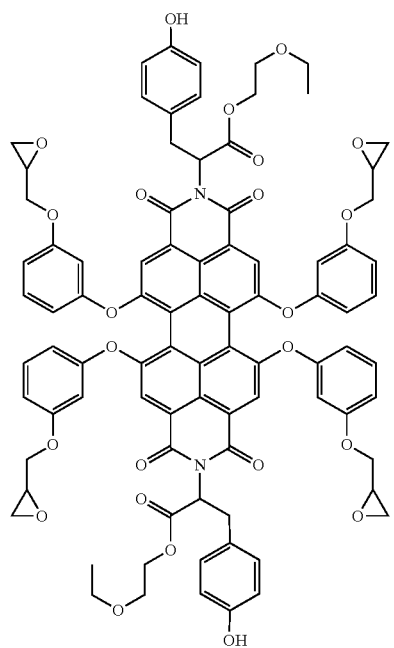
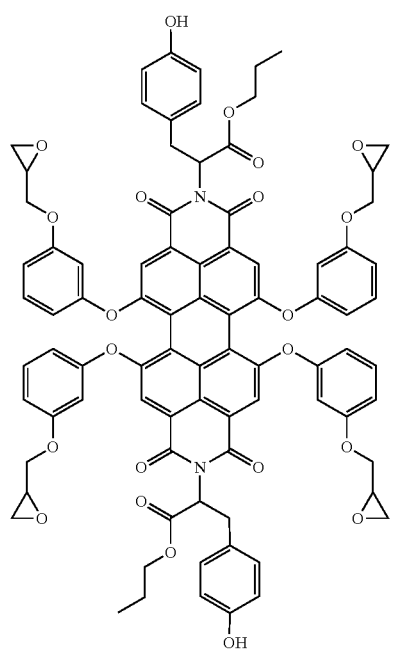

421
-continued
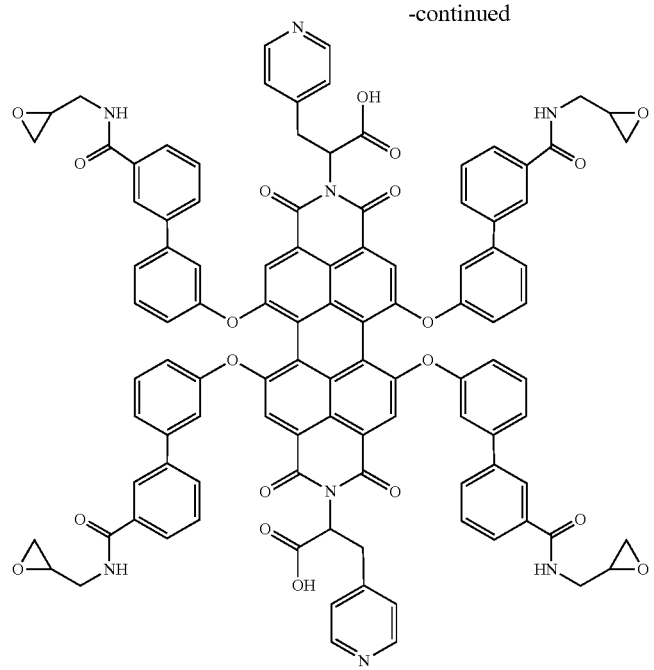
422
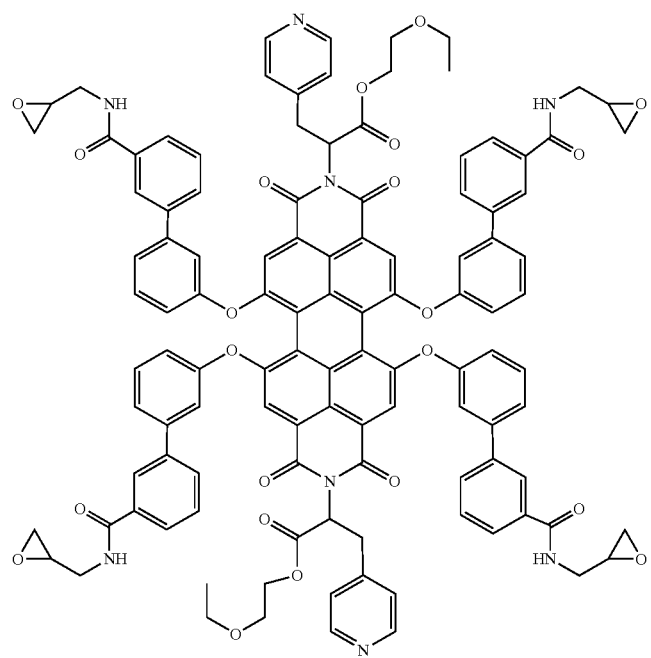

-continued
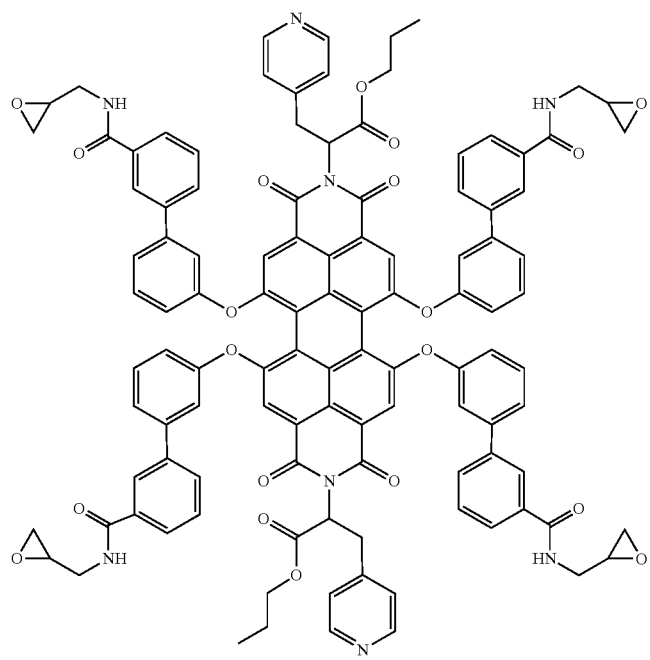
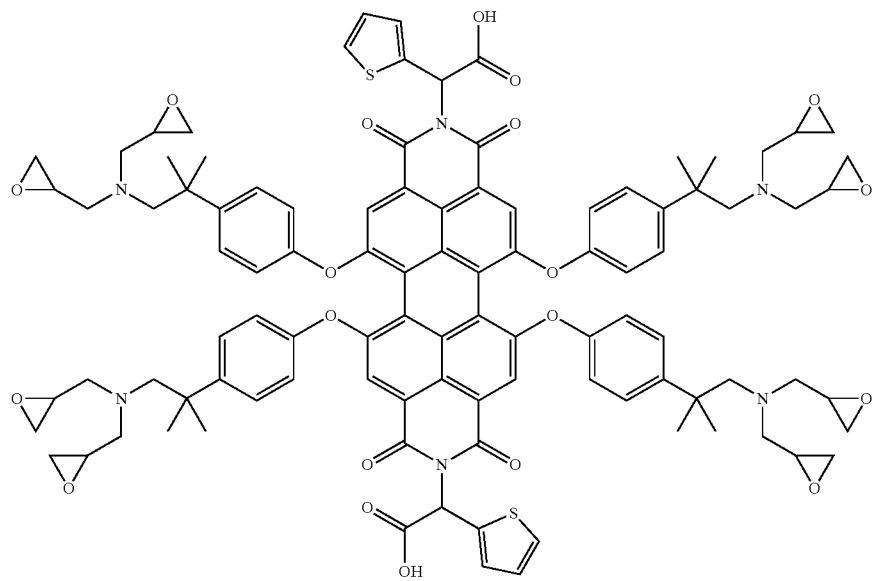

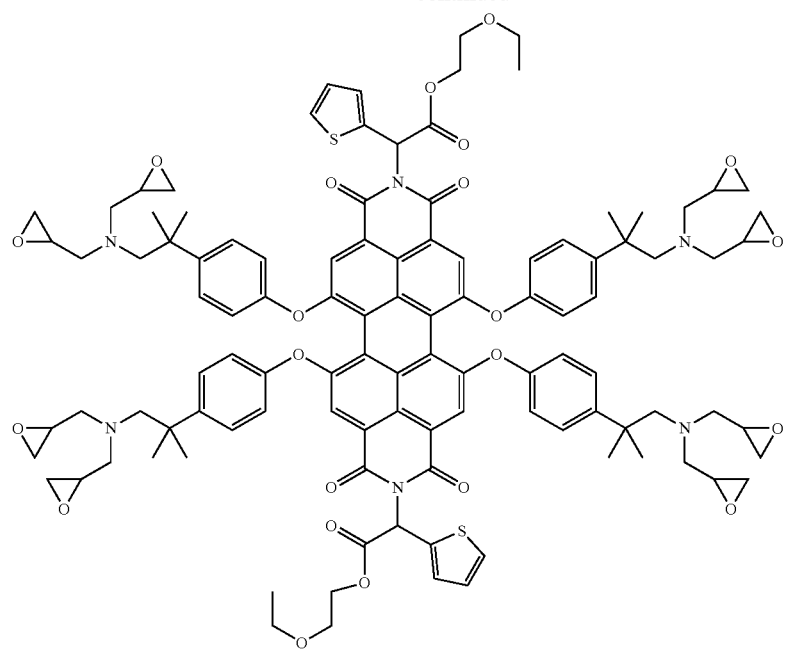
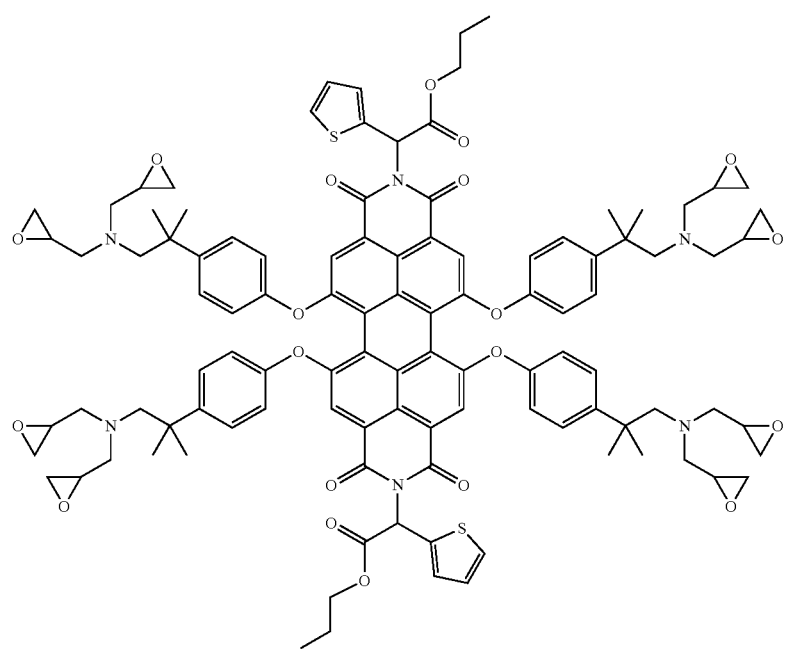

-continued
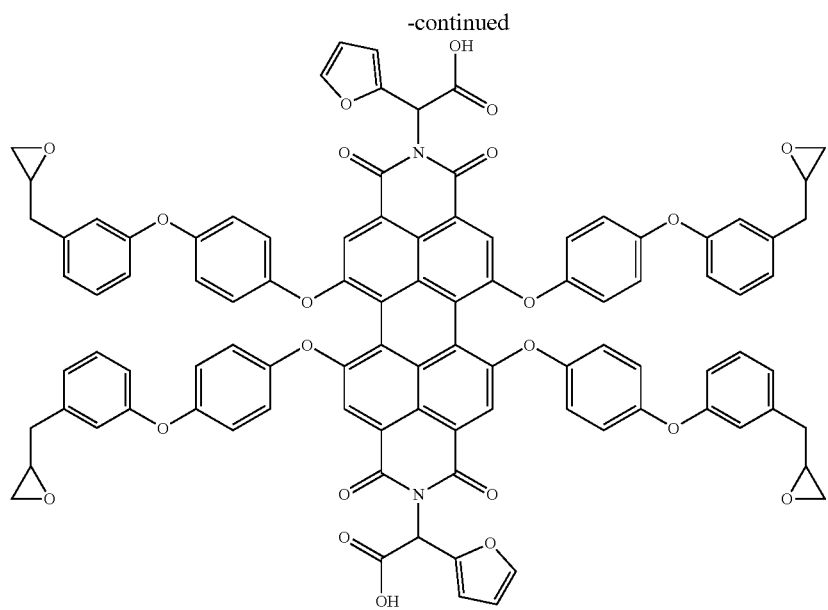
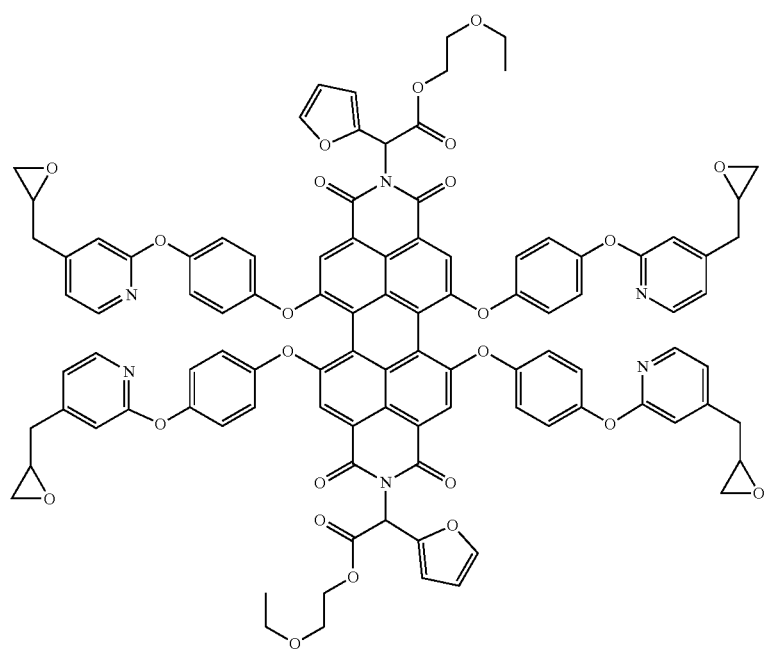

-continued
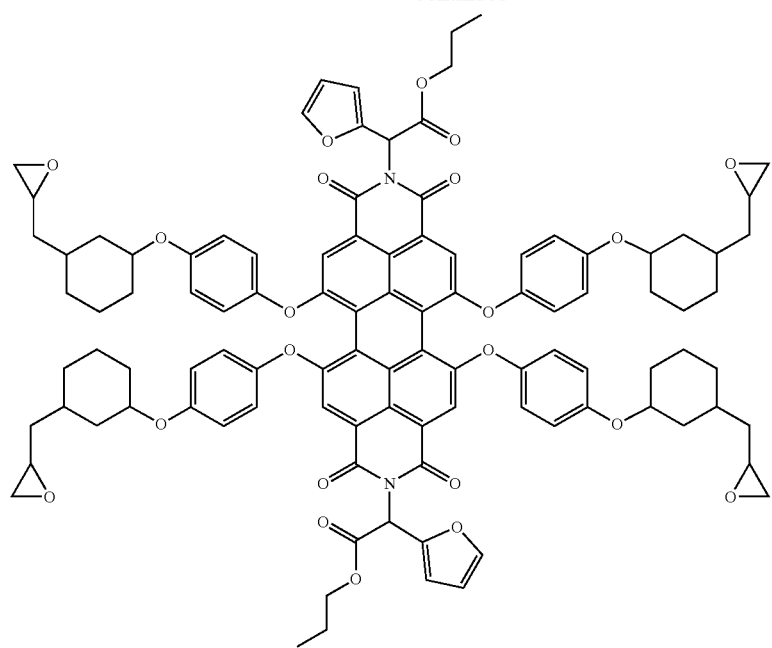
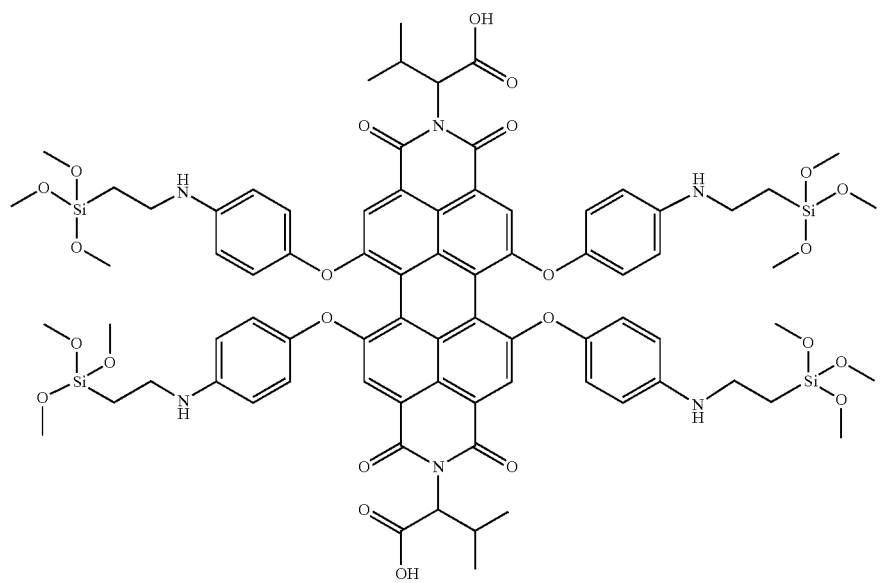

-continued
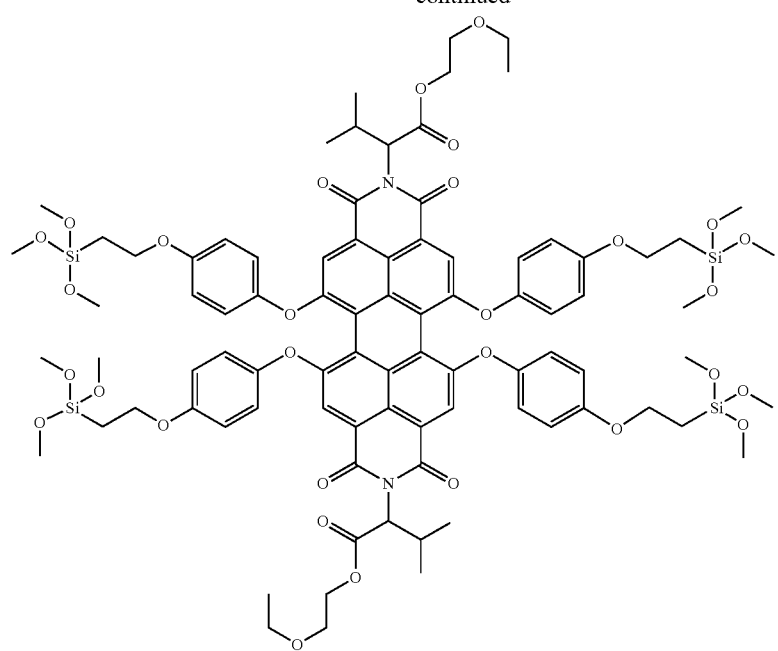
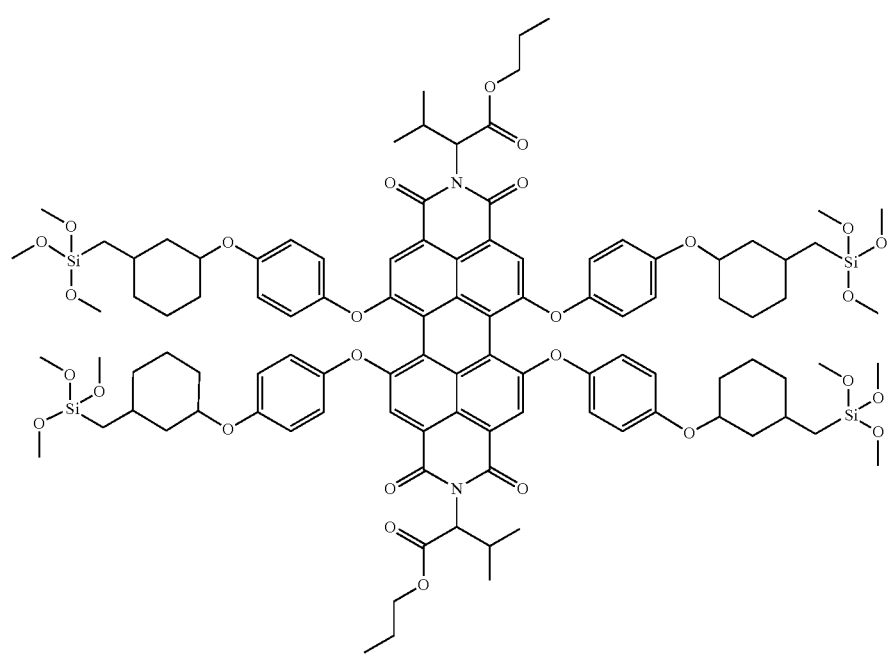

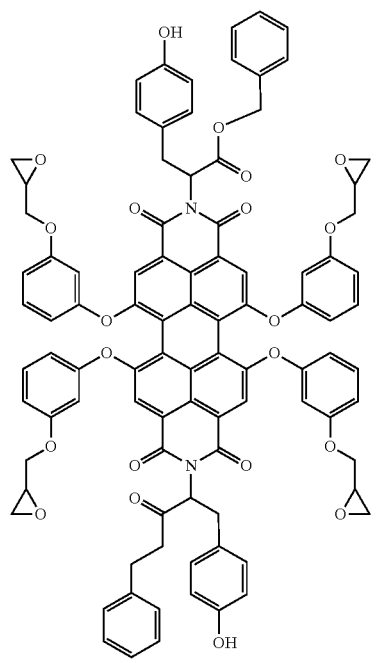
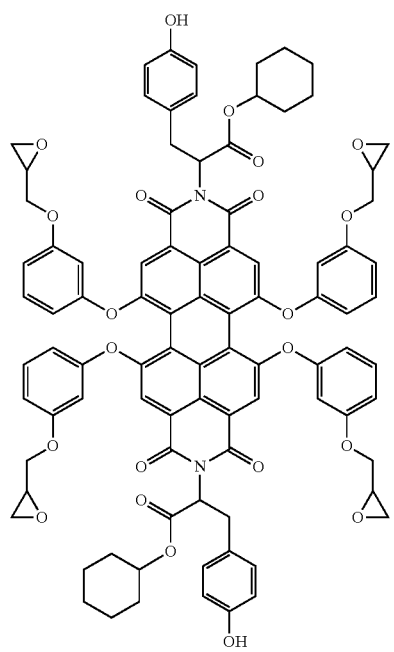

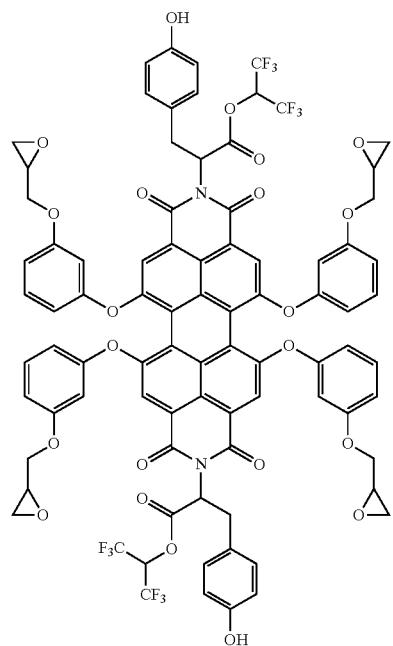
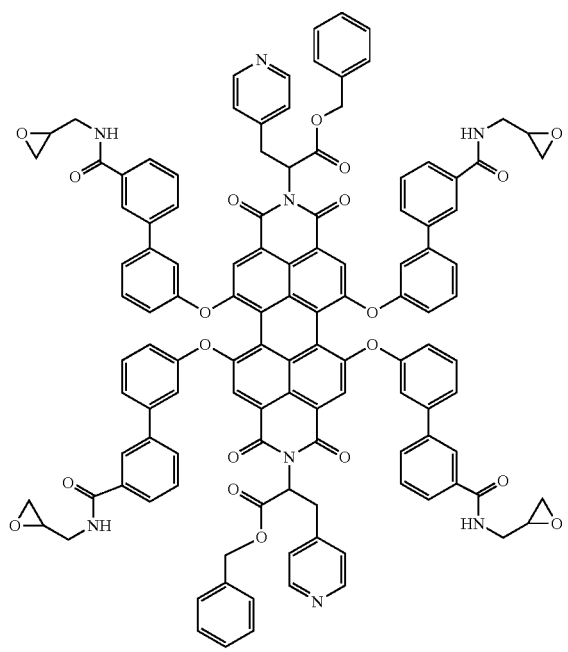

437
-continued
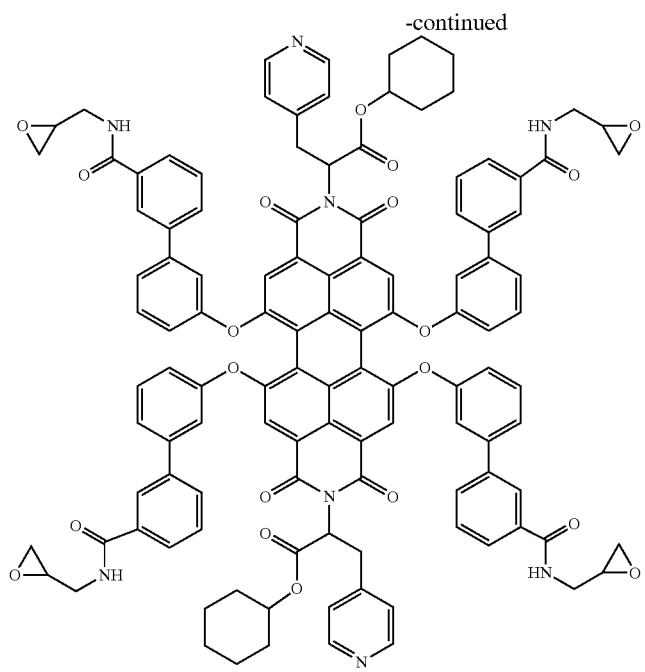
438
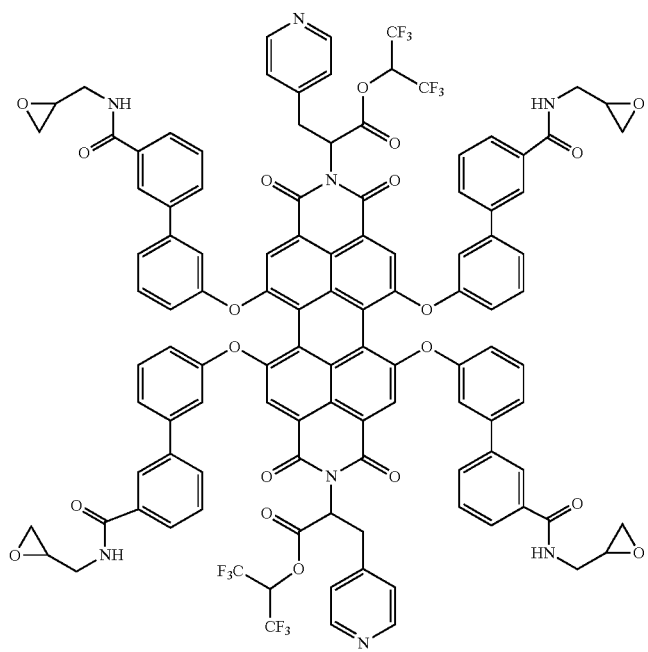

-continued
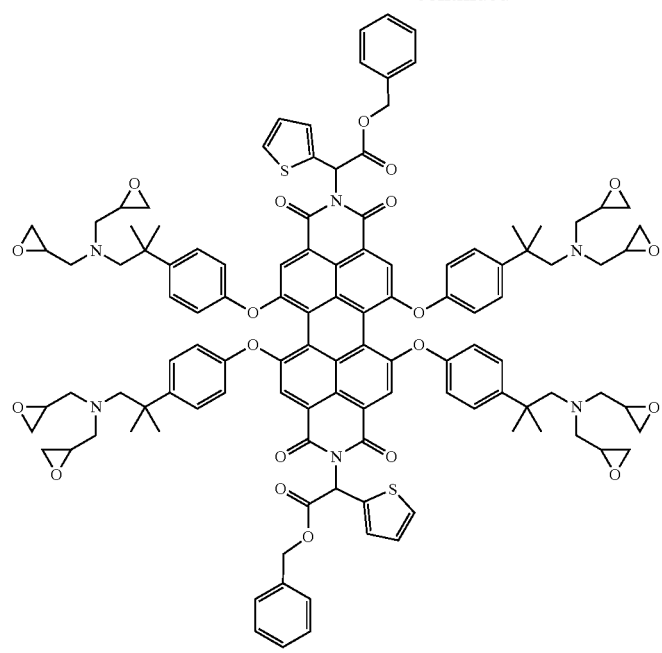
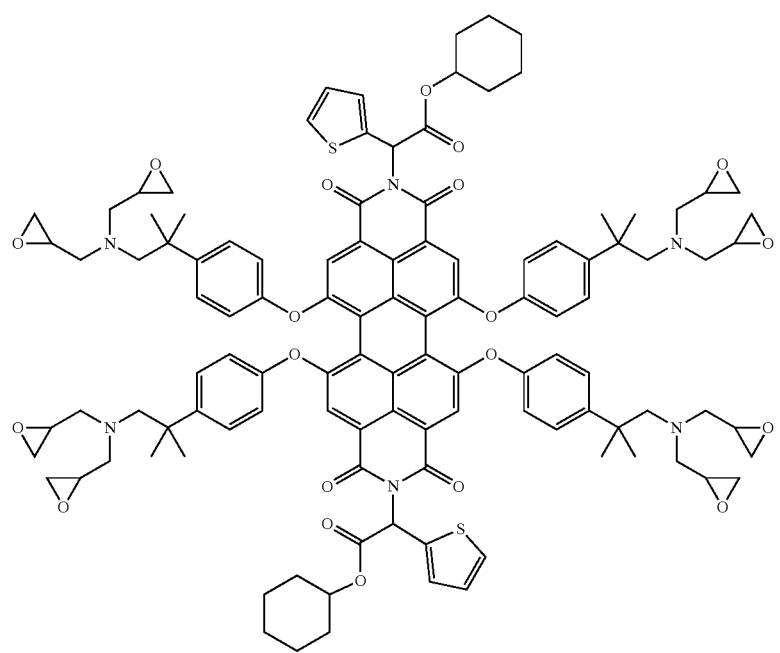

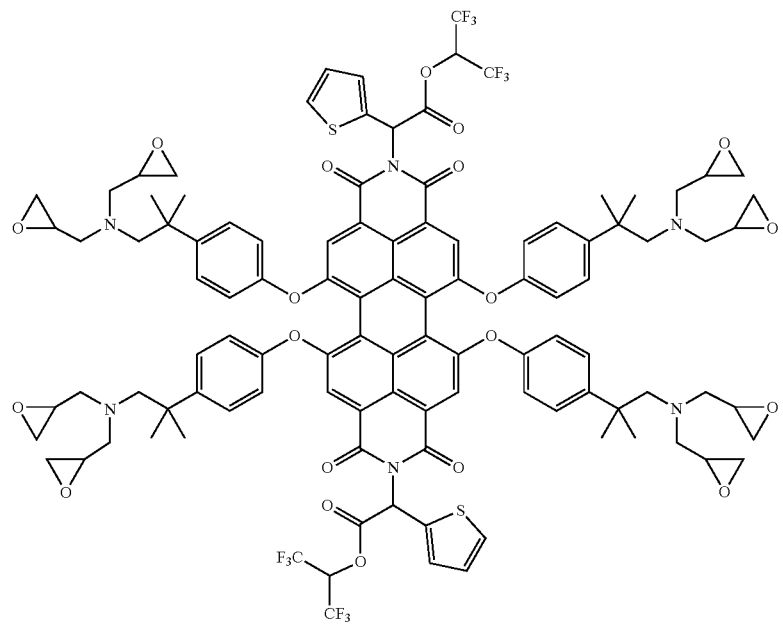
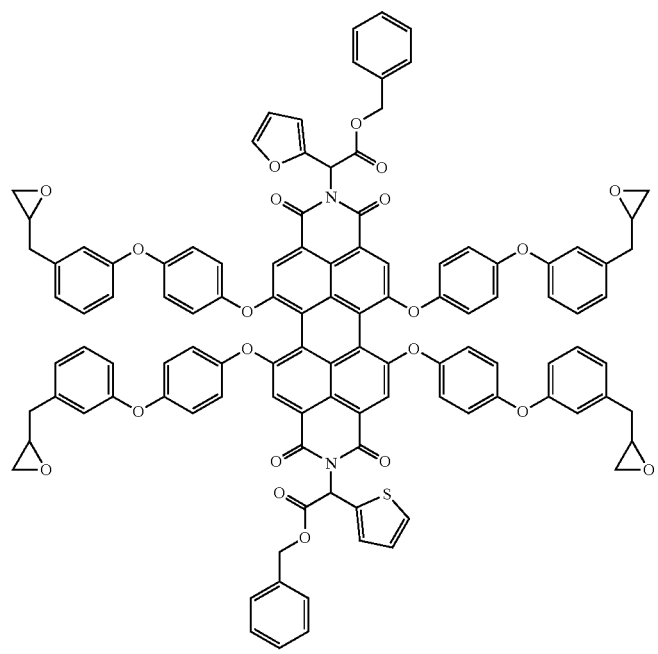

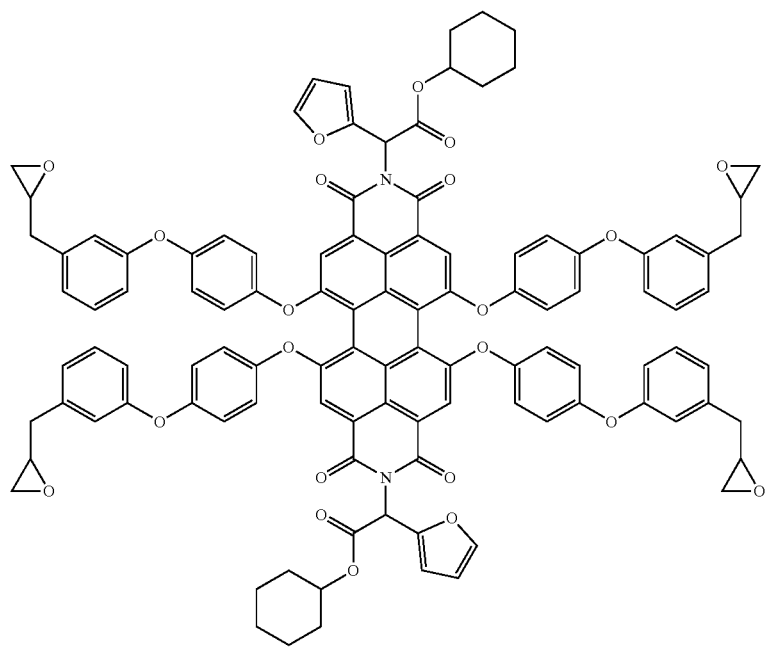
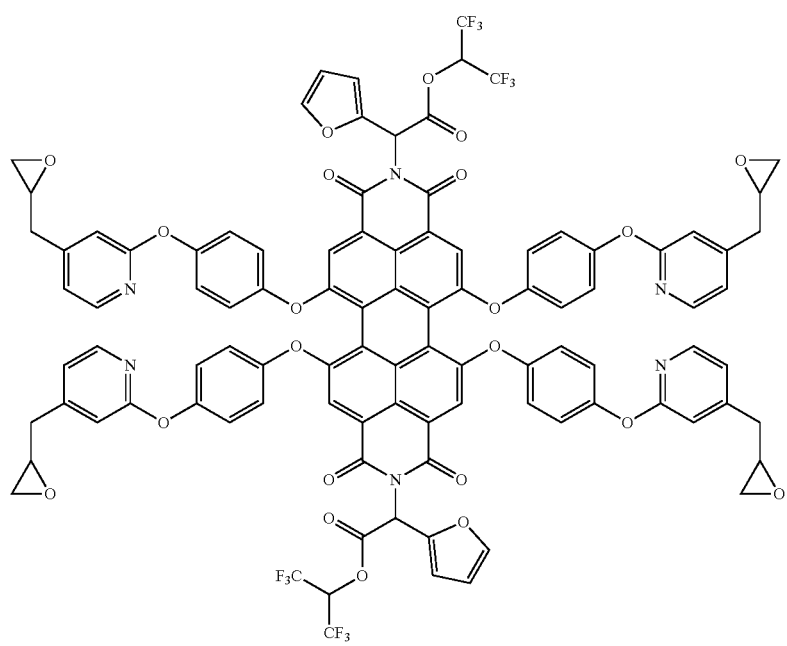

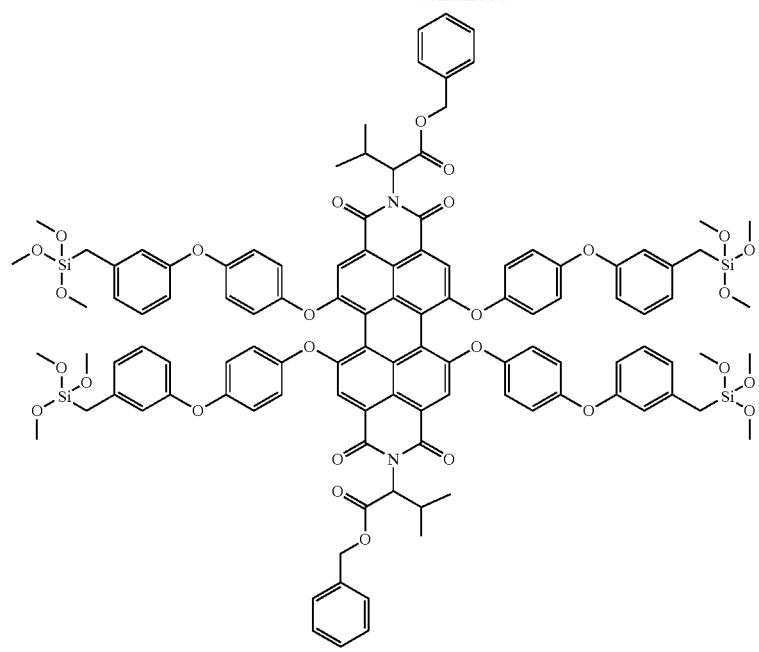
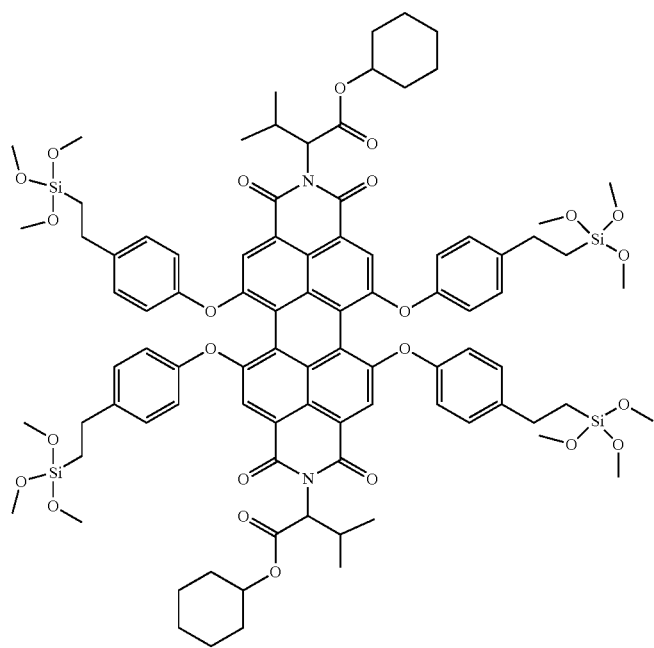

447
-continued
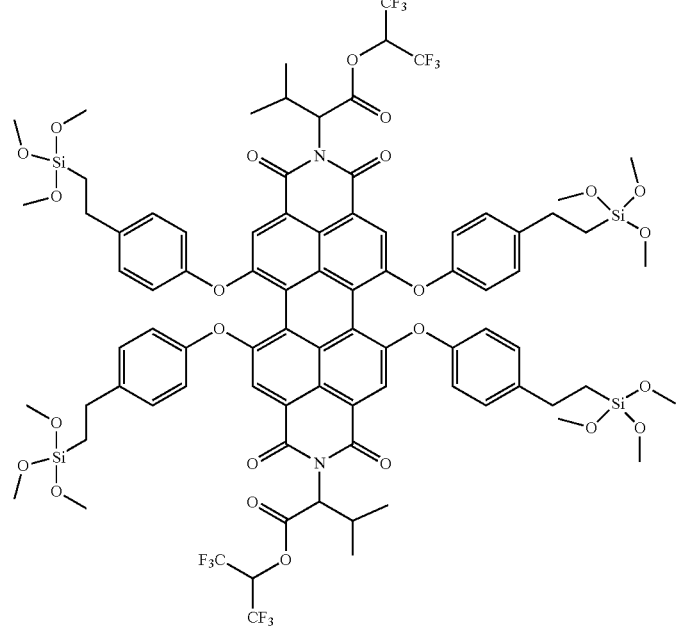
448
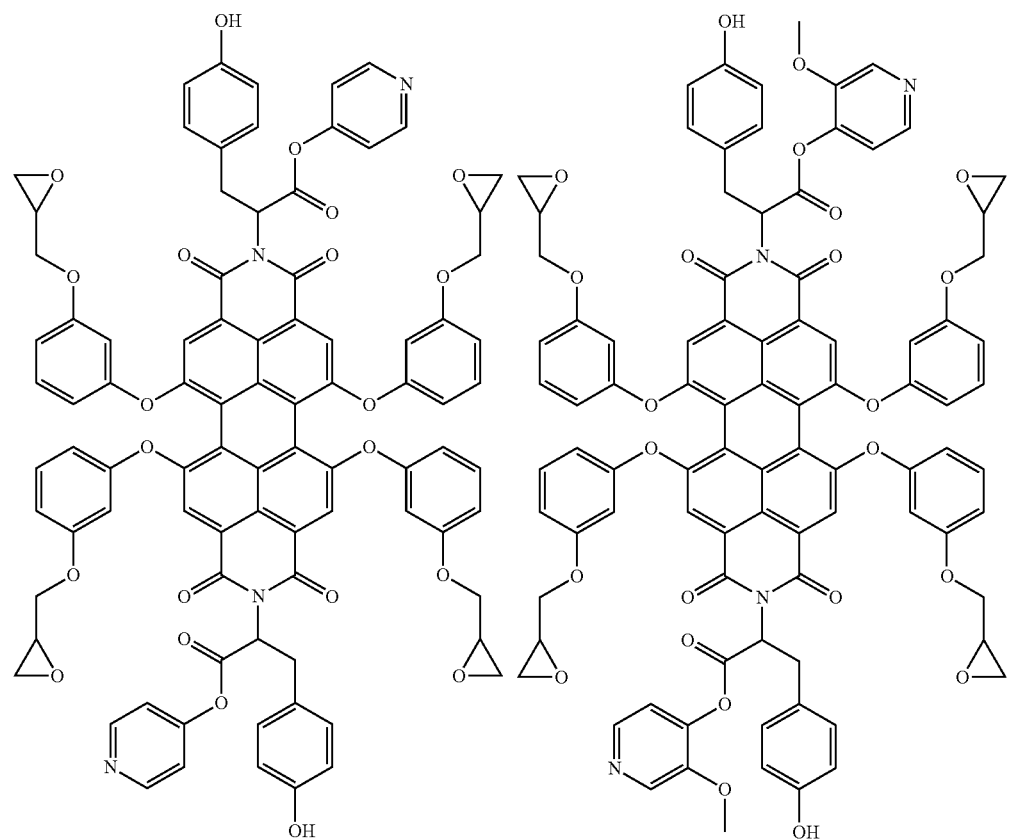

-continued
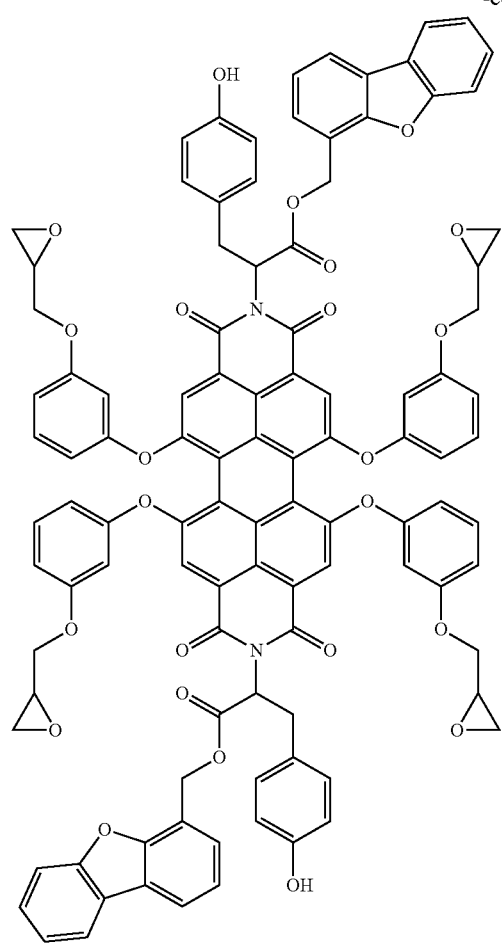
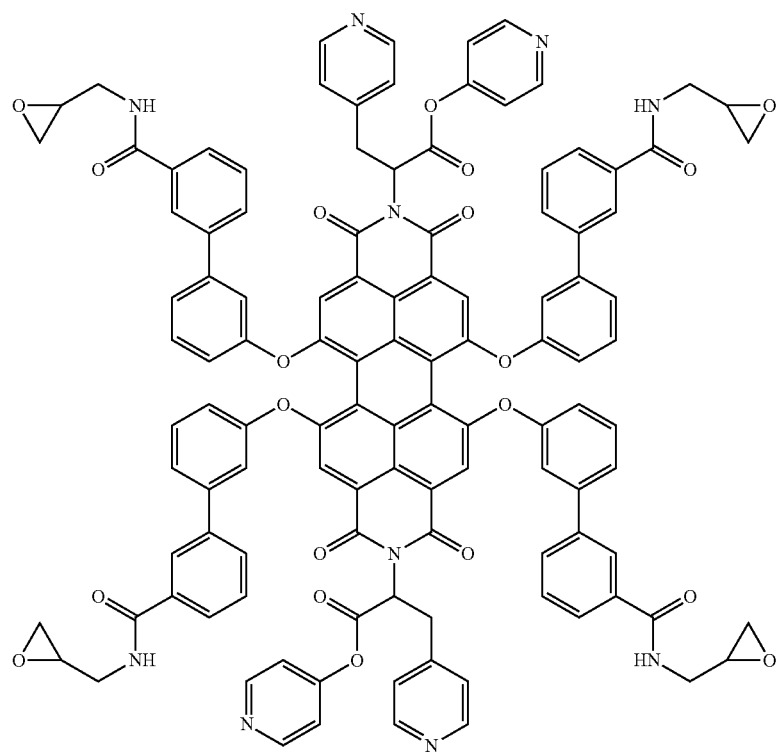

-continued
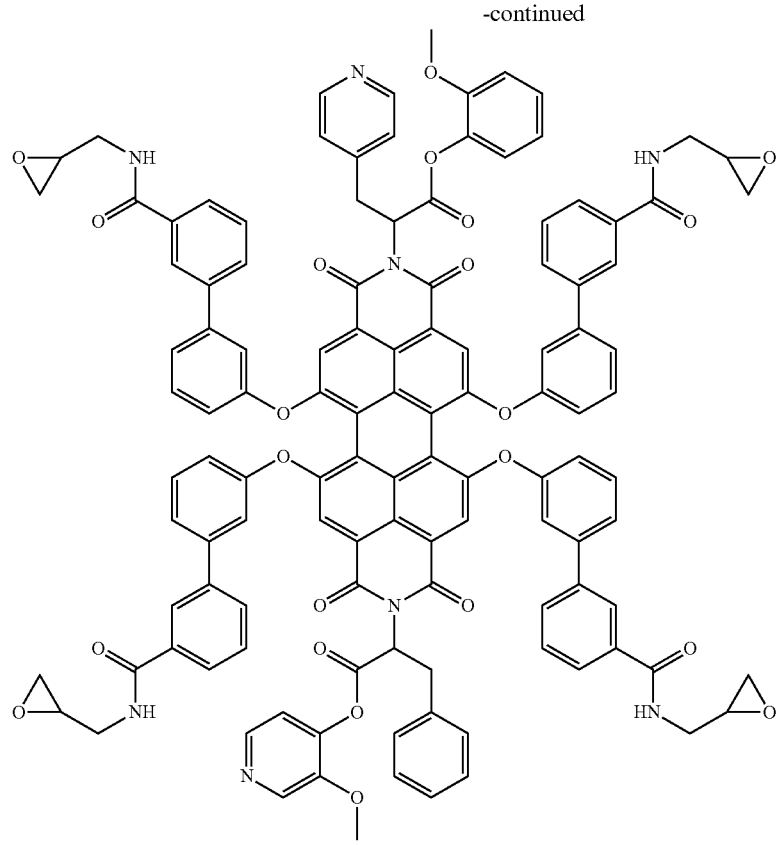

-continued
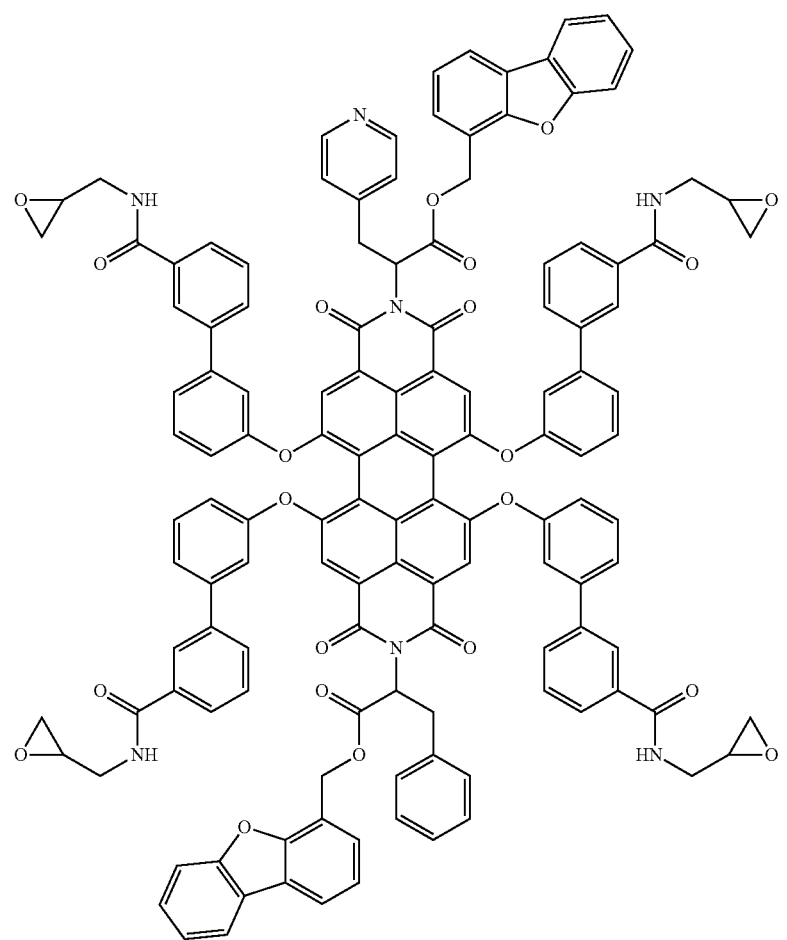
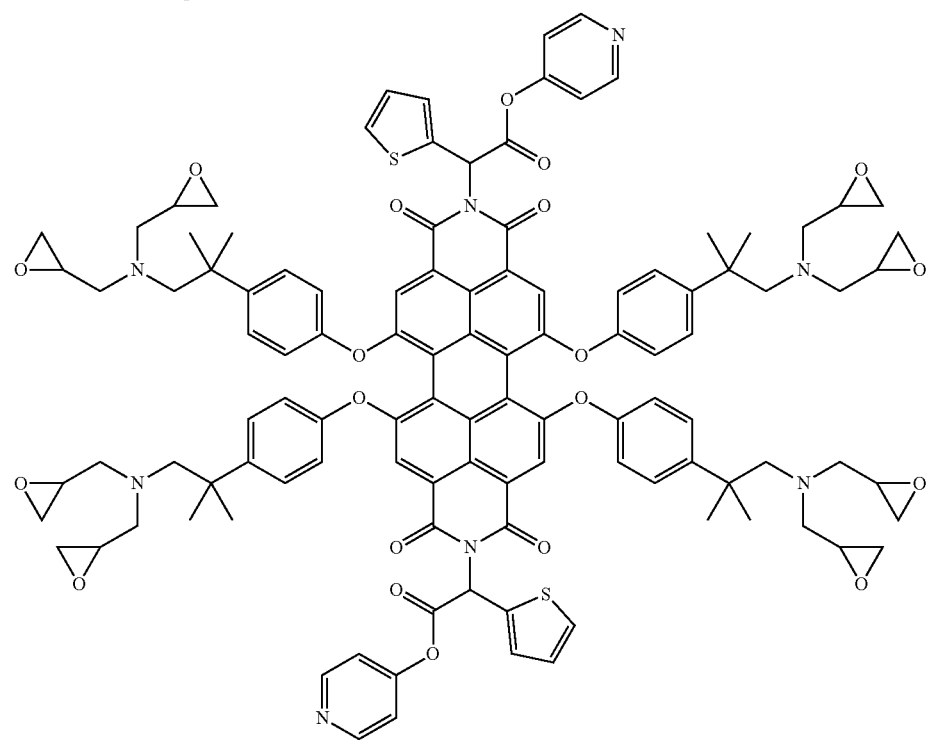

-continued
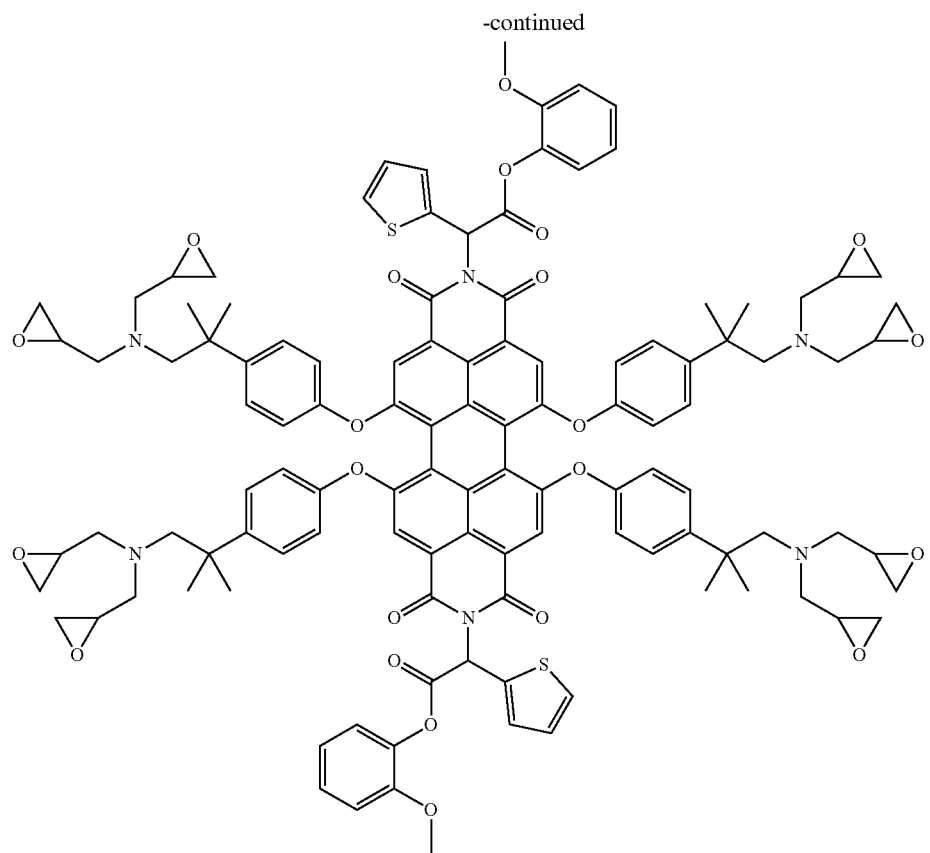

-continued
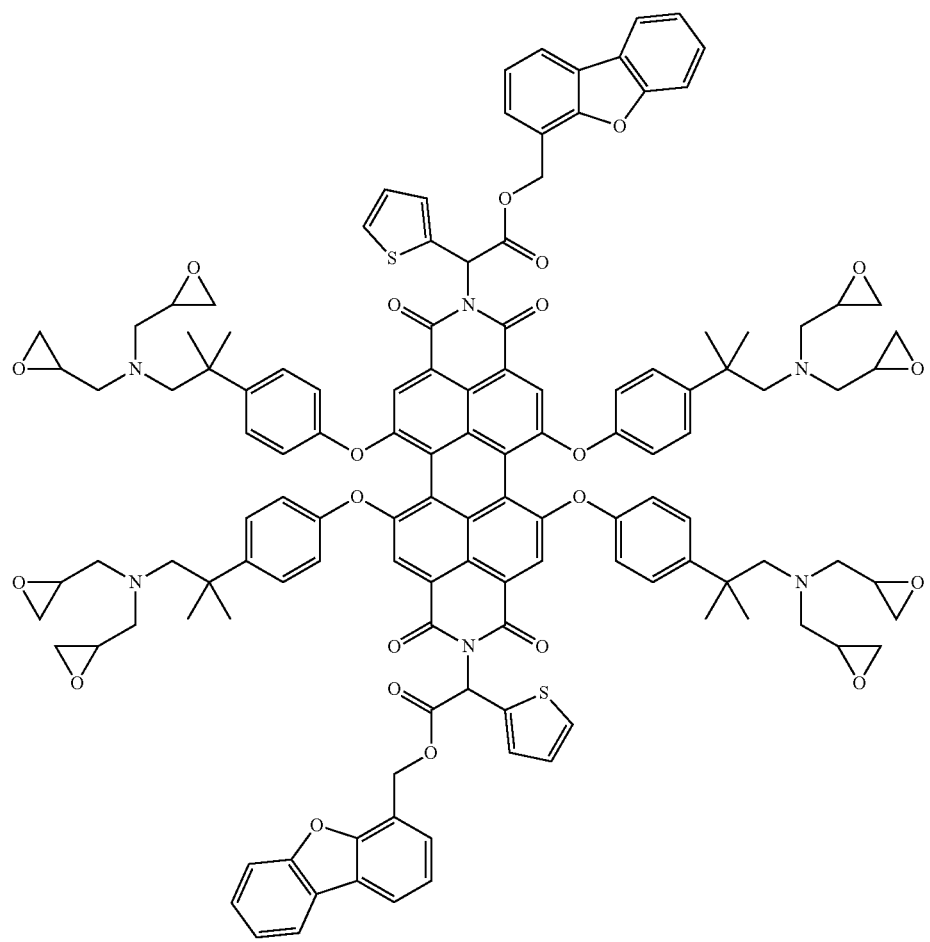
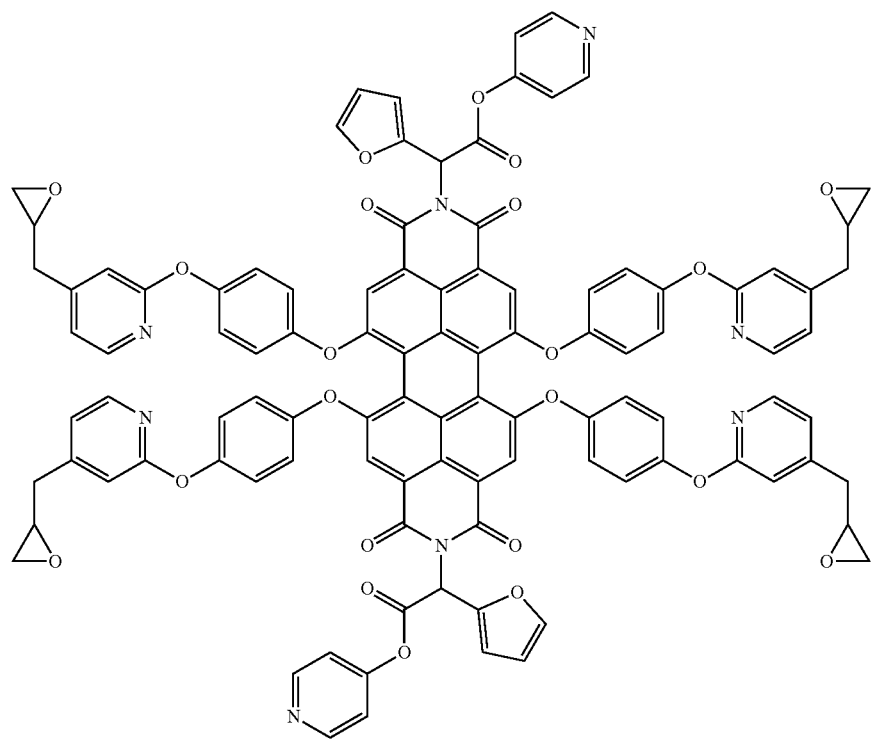

-continued
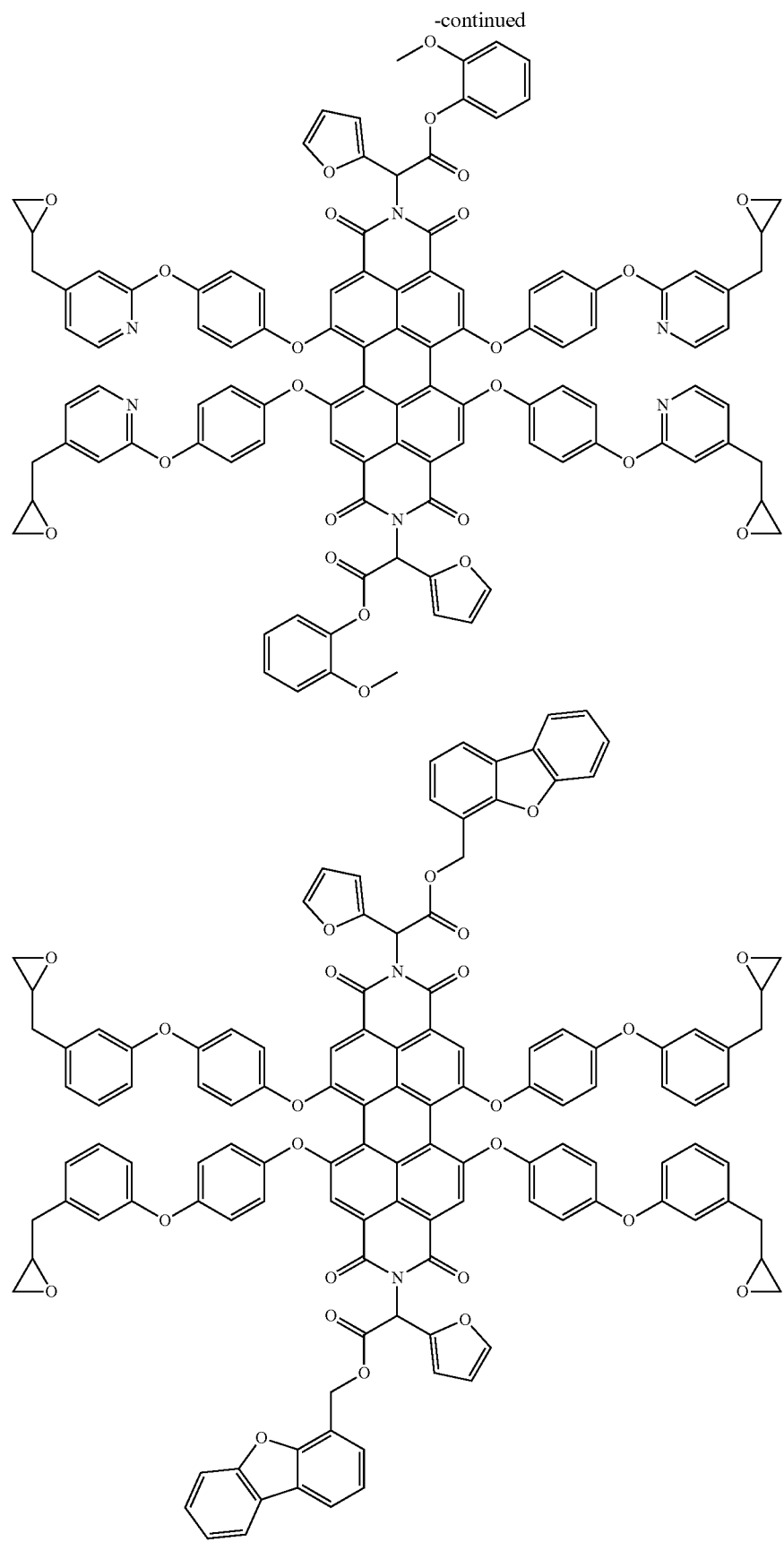

-continued
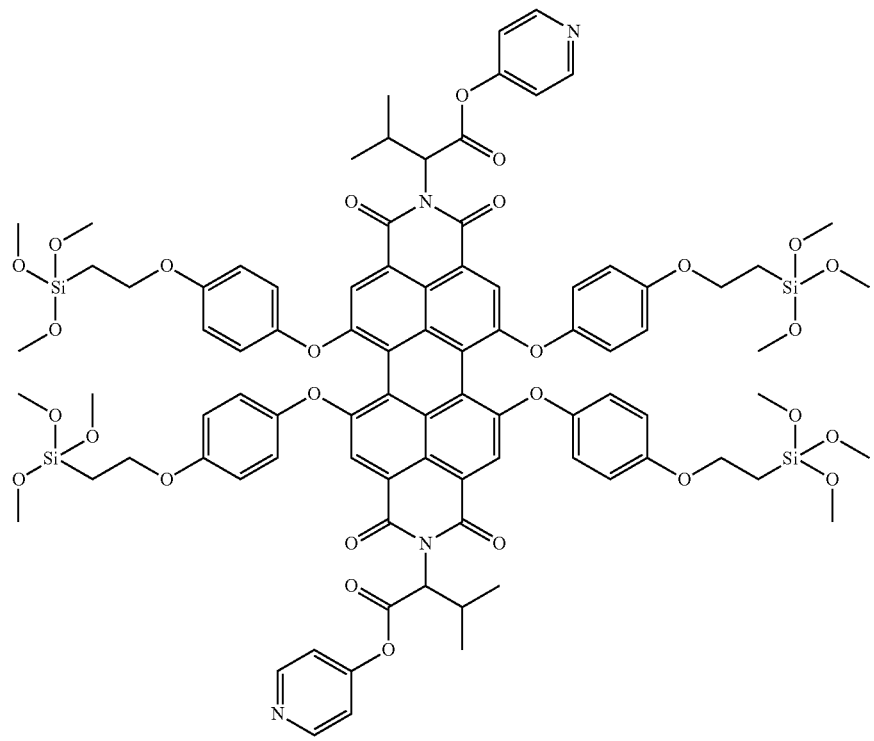
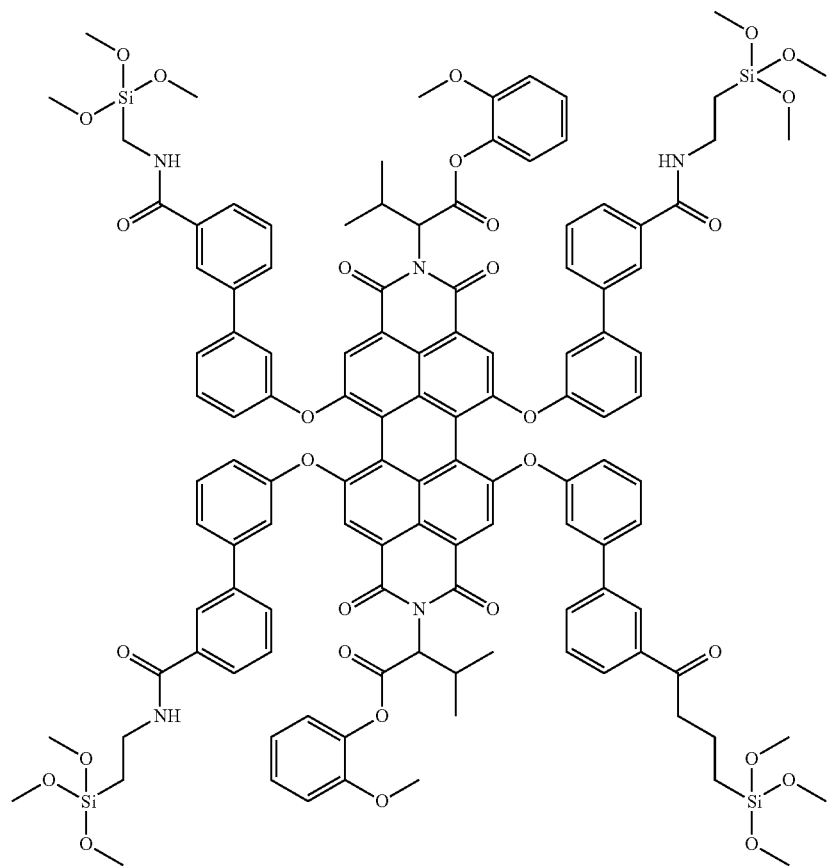

-continued
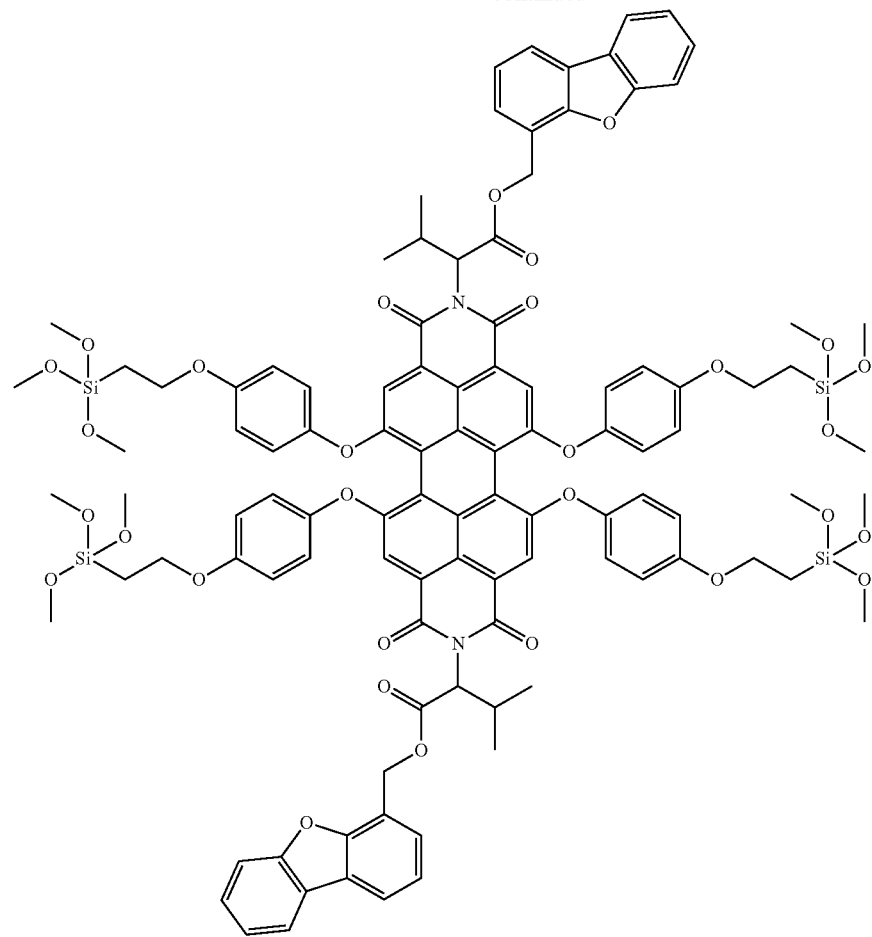

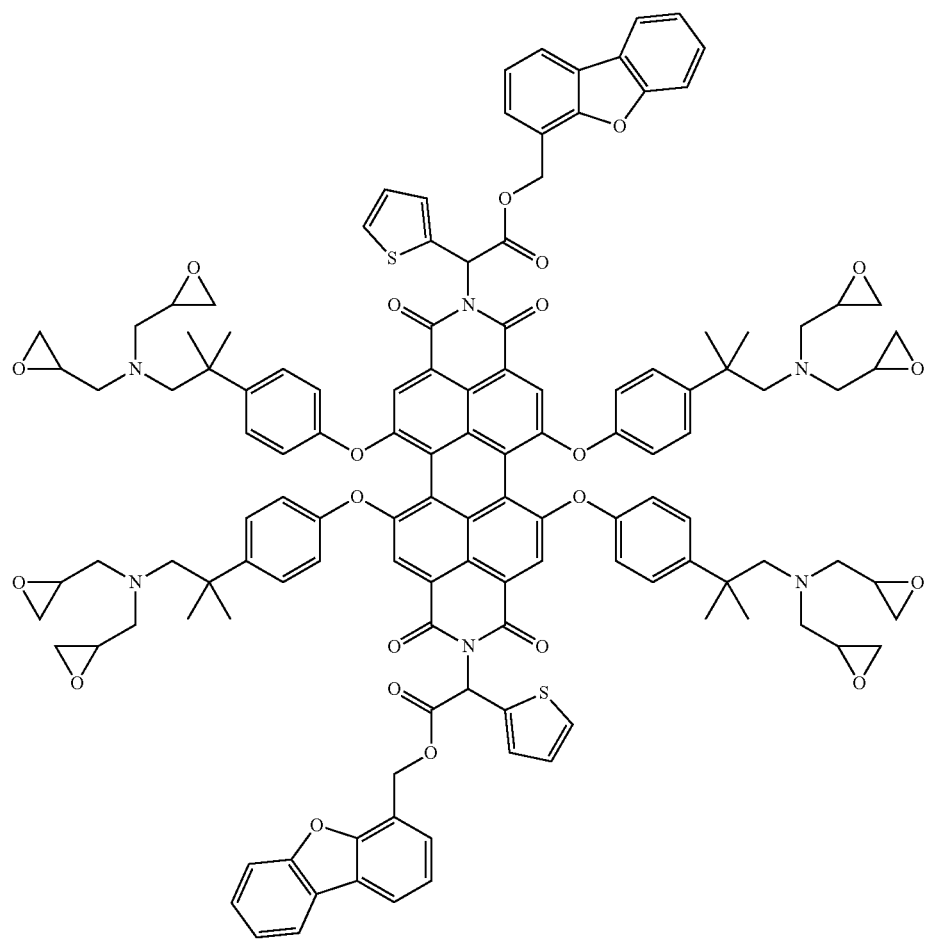
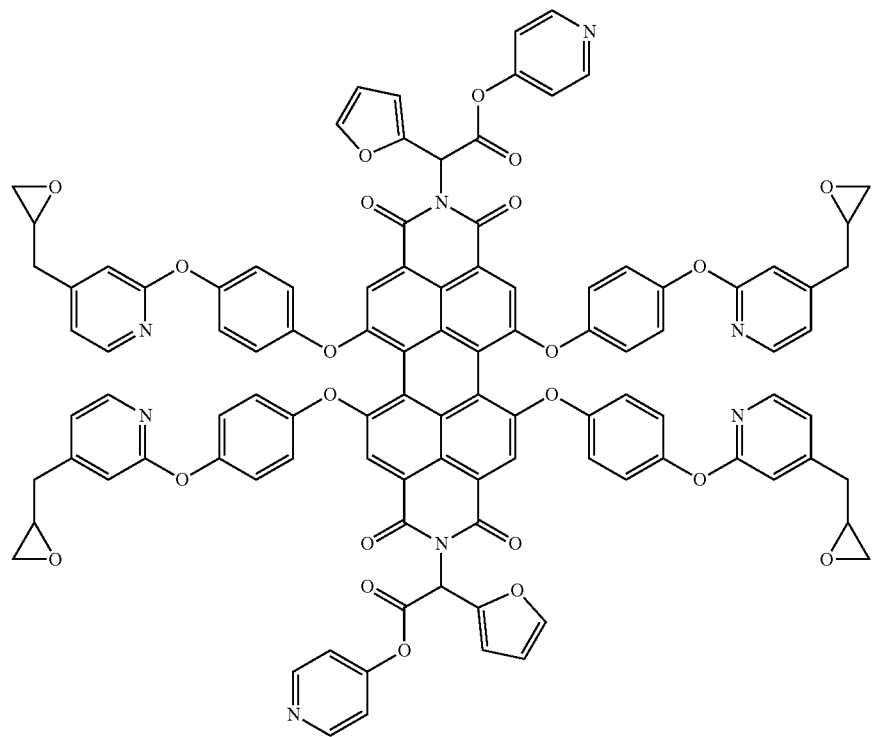

-continued
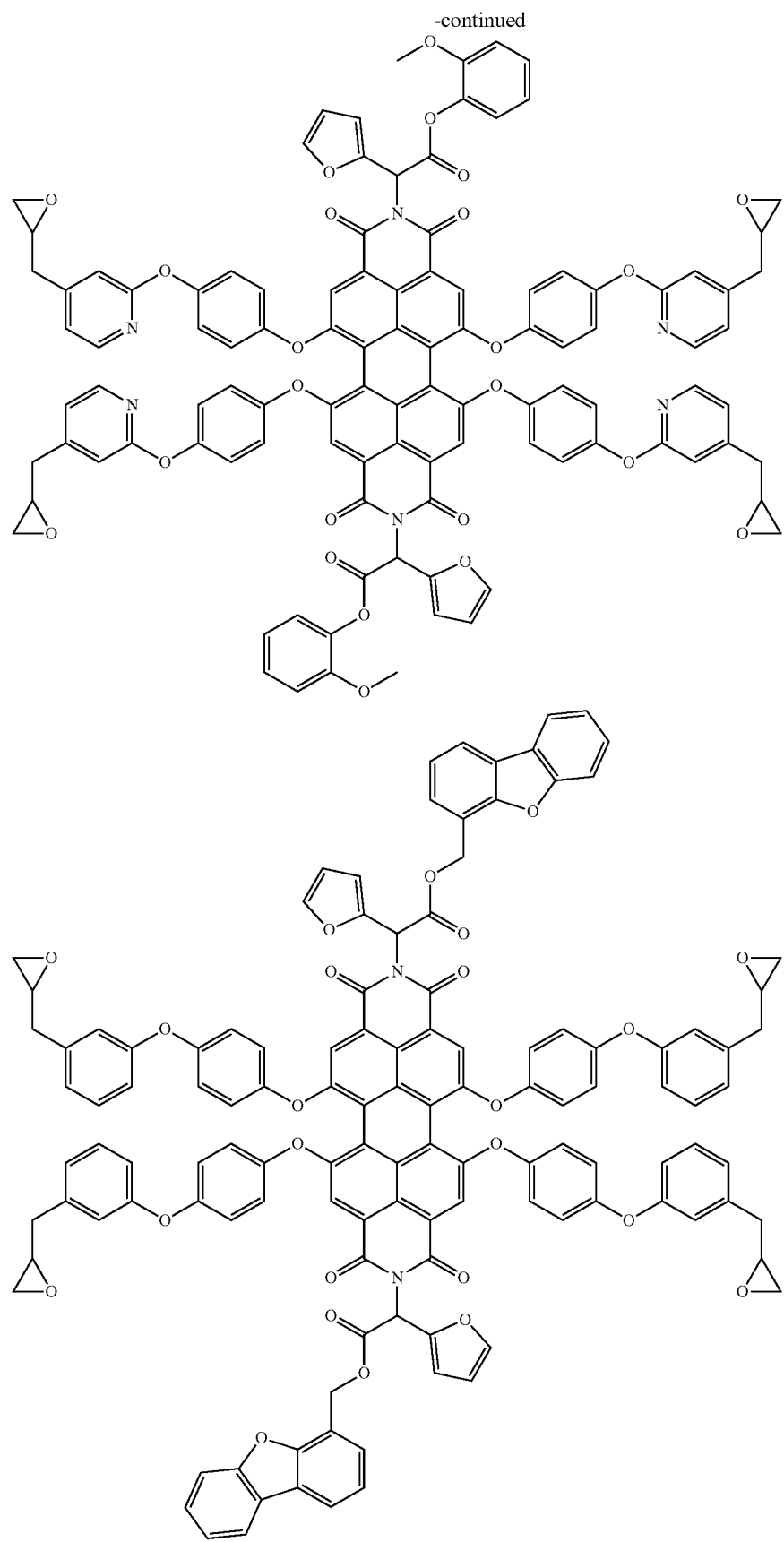

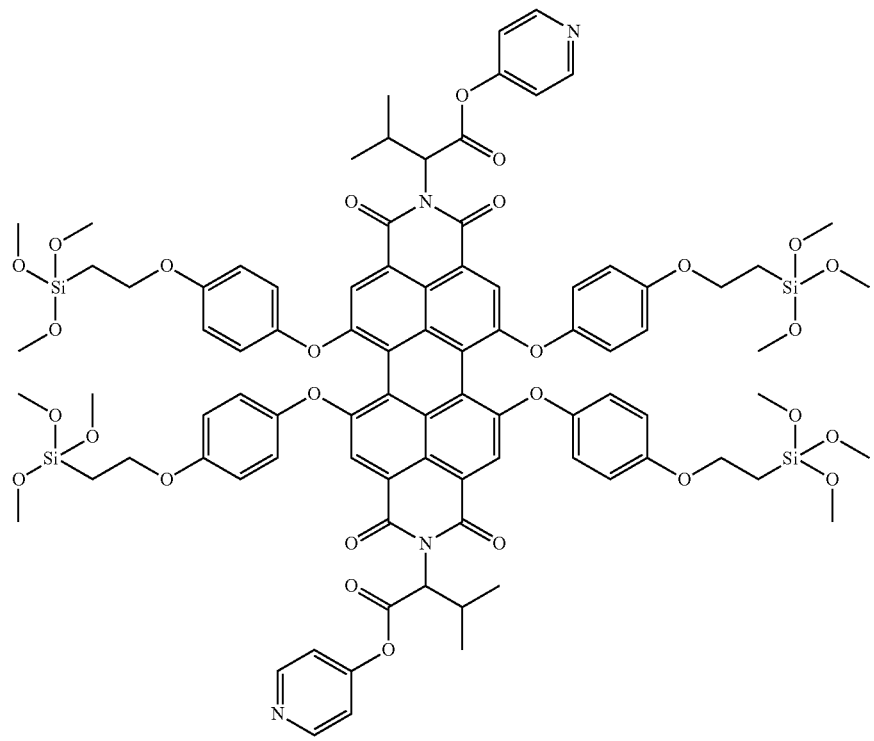
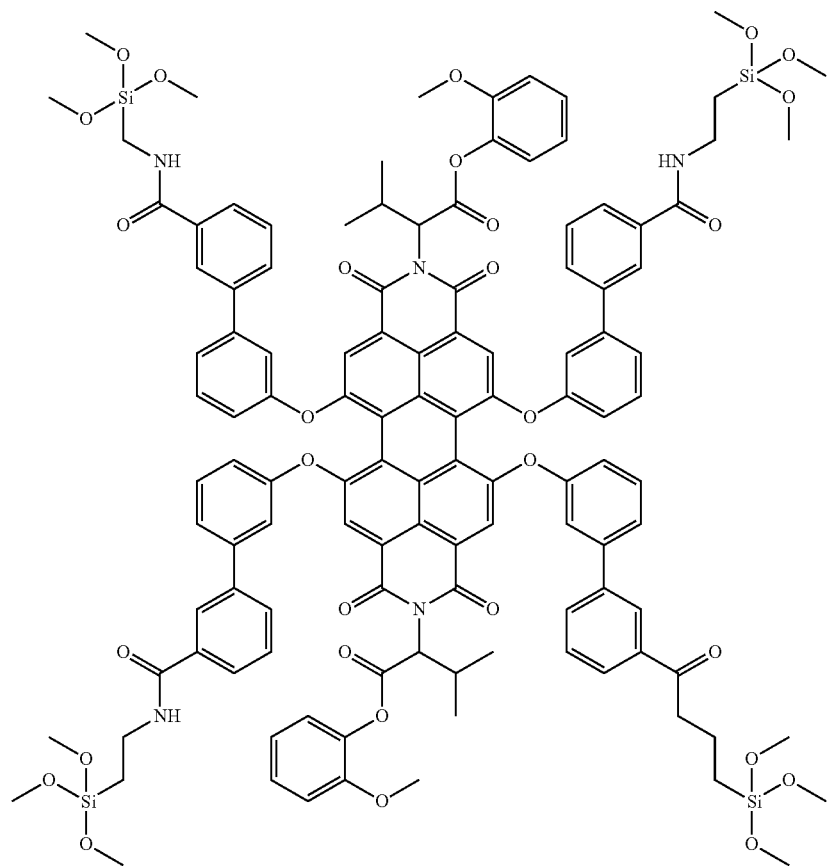

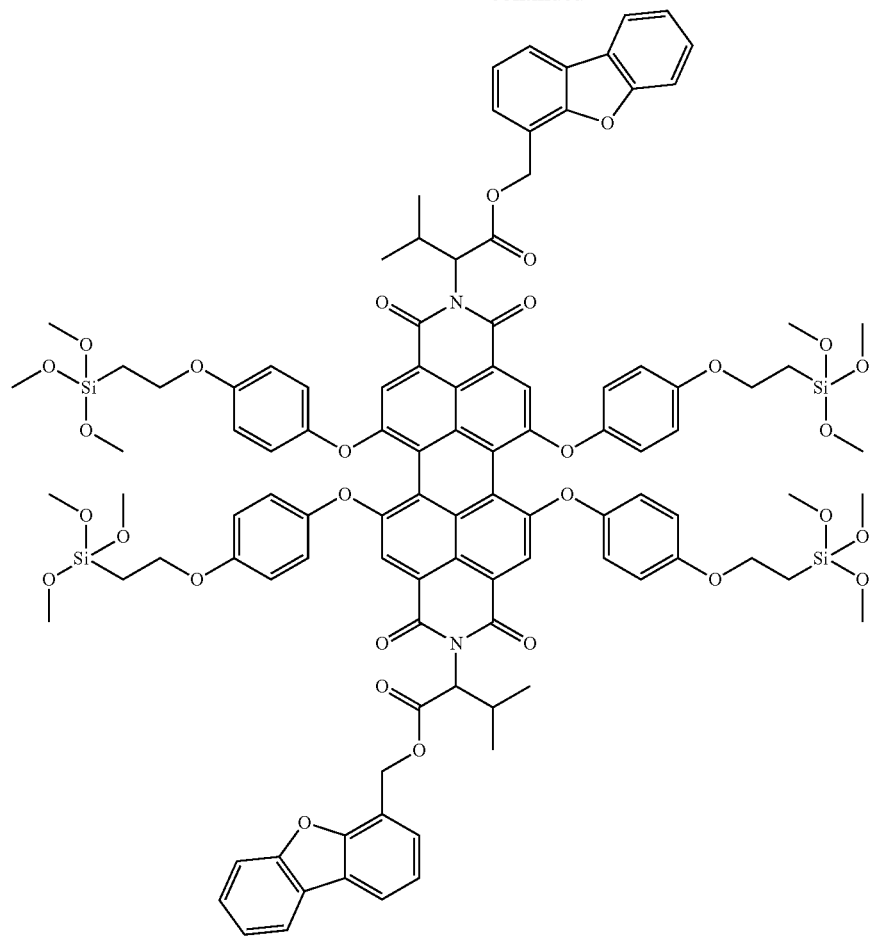

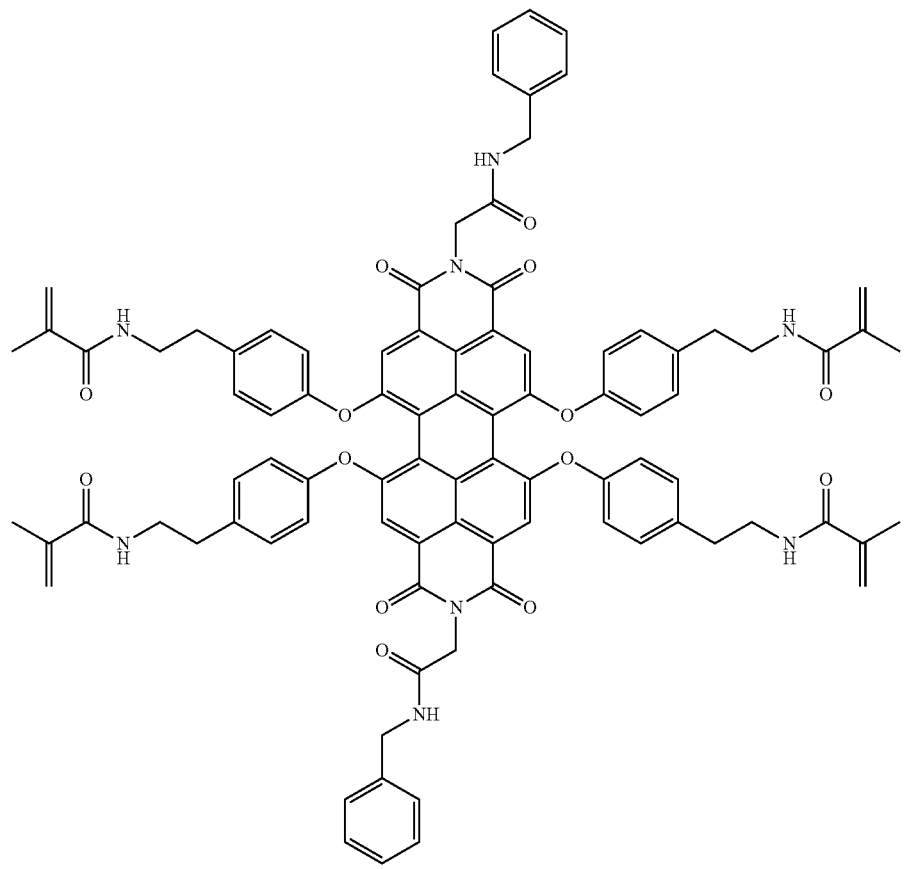
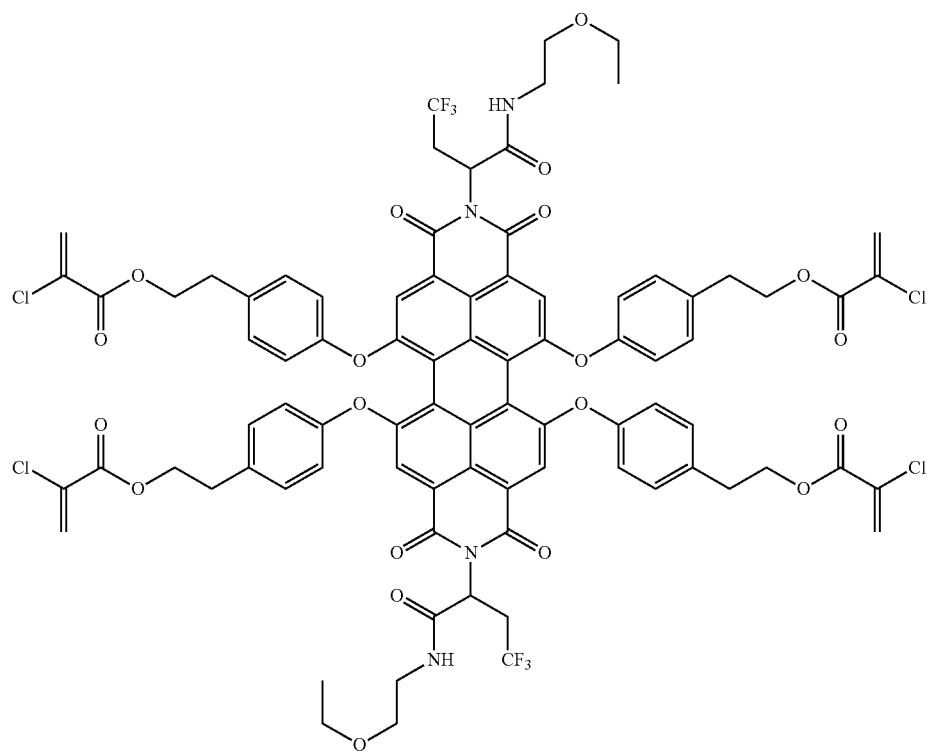

-continued
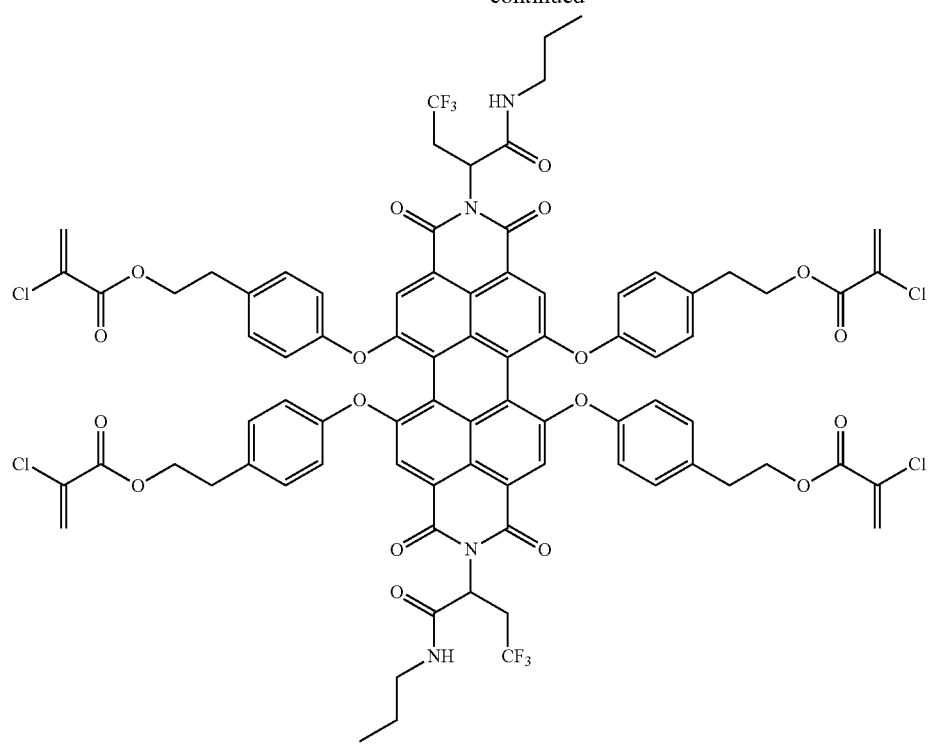
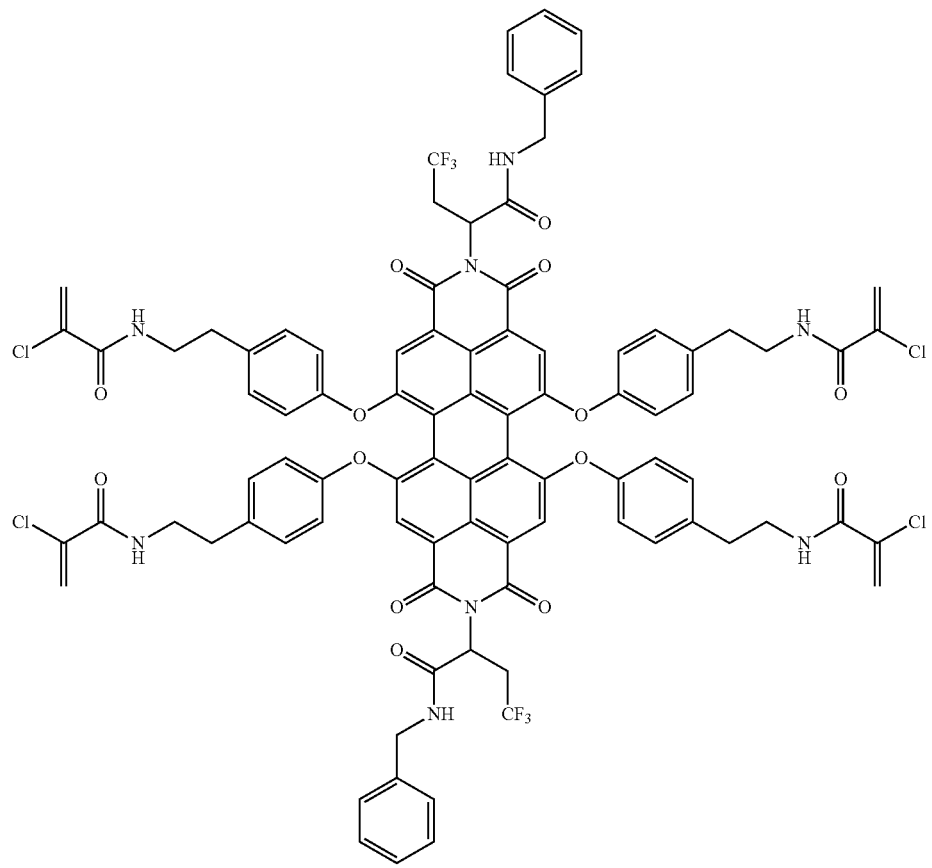

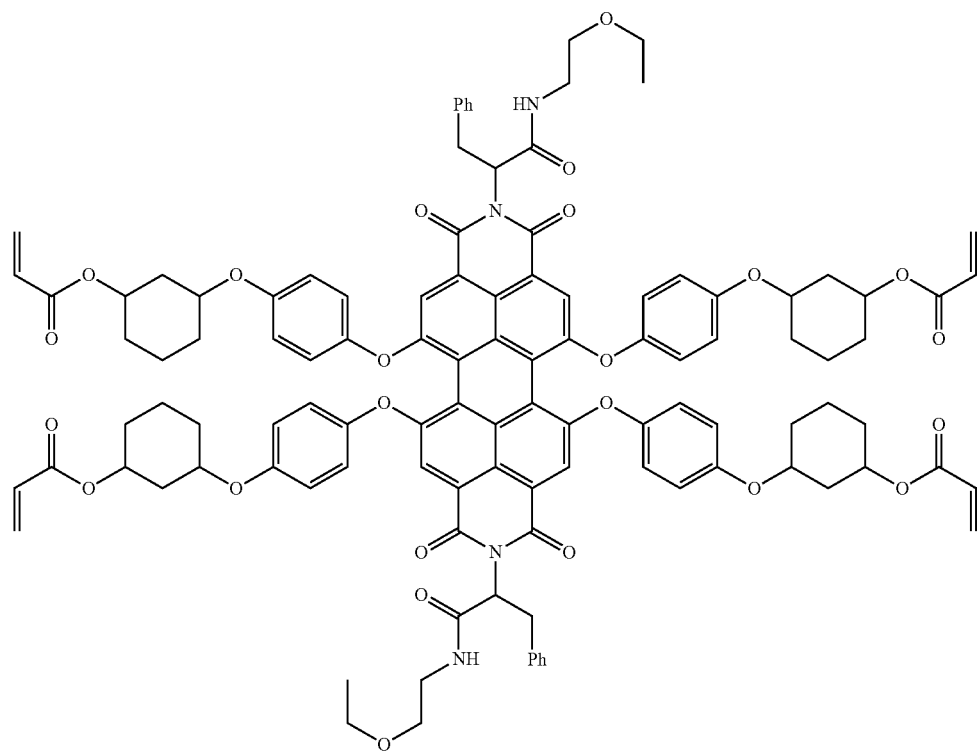
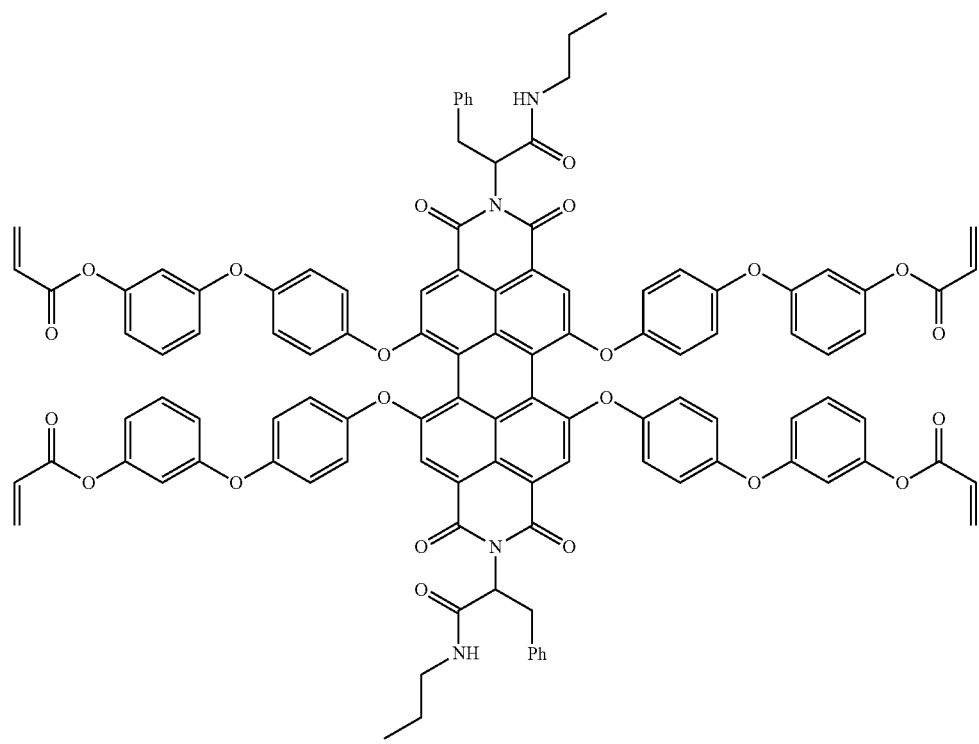 [SMILES: C=CC(=O)Oc1ccnc(Oc2ccc(Oc3cc4c5c(cc(Oc6ccc(Oc7cc(OC(=O)C=C)ccn7)cc6)c6c7c(Oc8ccc(Oc9cc(OC(=O)C=C)ccn9)cc8)cc8c9c(cc(Oc%10ccc(Oc%11cc(OC(=O)C=C)ccn%11)cc%10)c(c3c56)c97)C(=O)N(C(Cc3ccccc3)C(=O)OCCC)C8=O)C(=O)N(C(Cc3ccccc3)C(=O)OCCC)C4=O)cc2)c1]

-continued
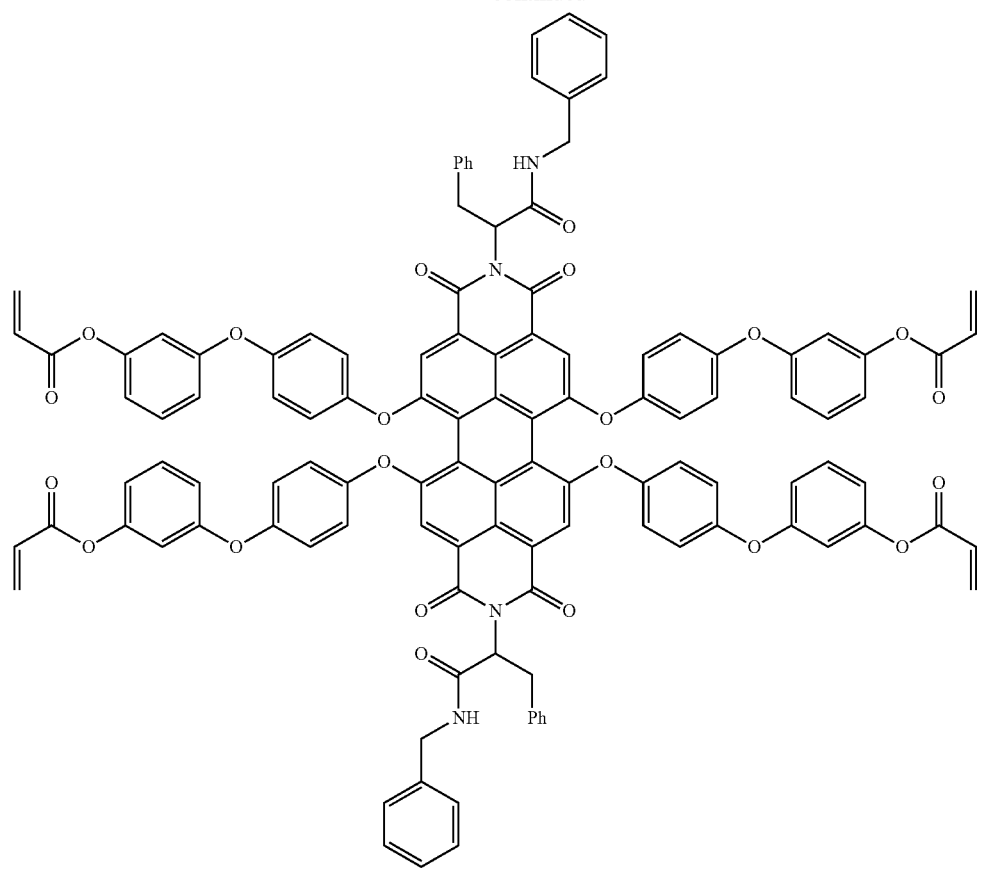
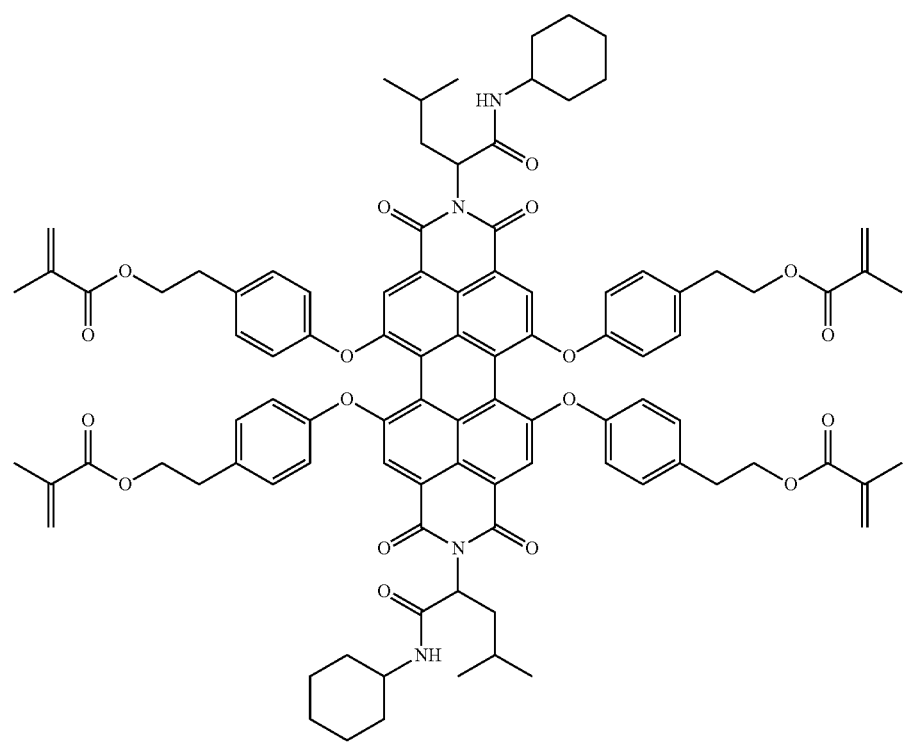

-continued
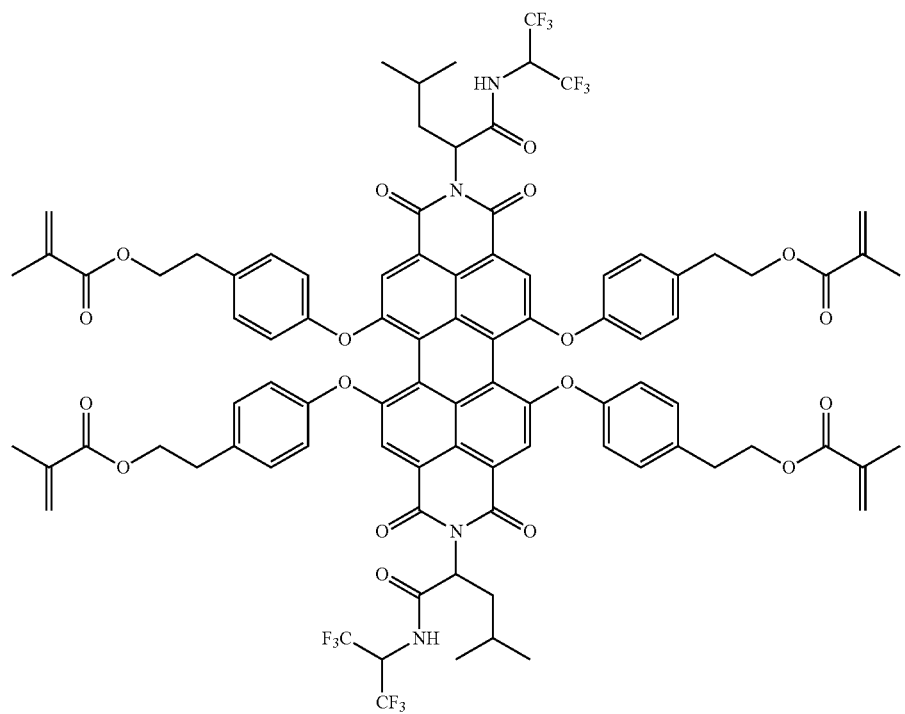
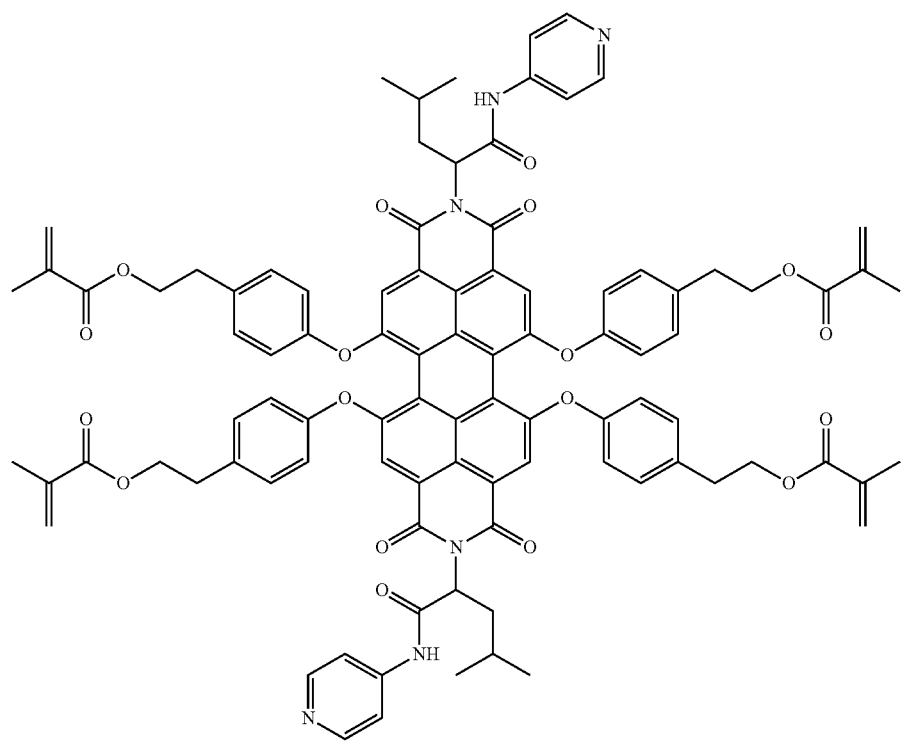

483
-continued
484
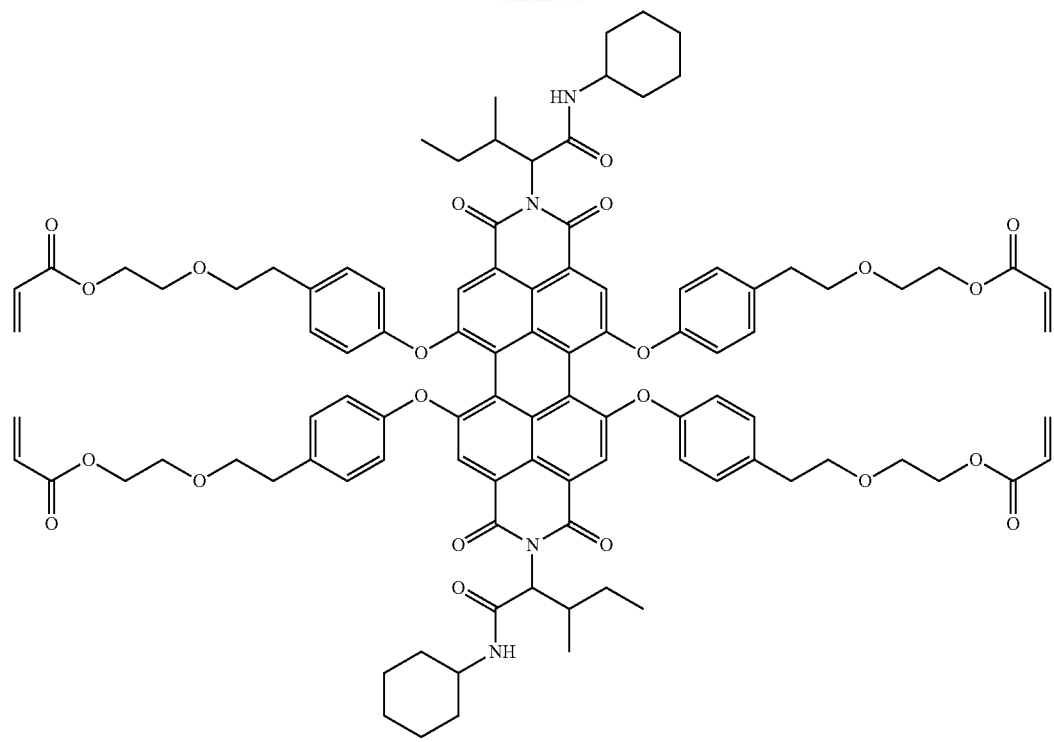
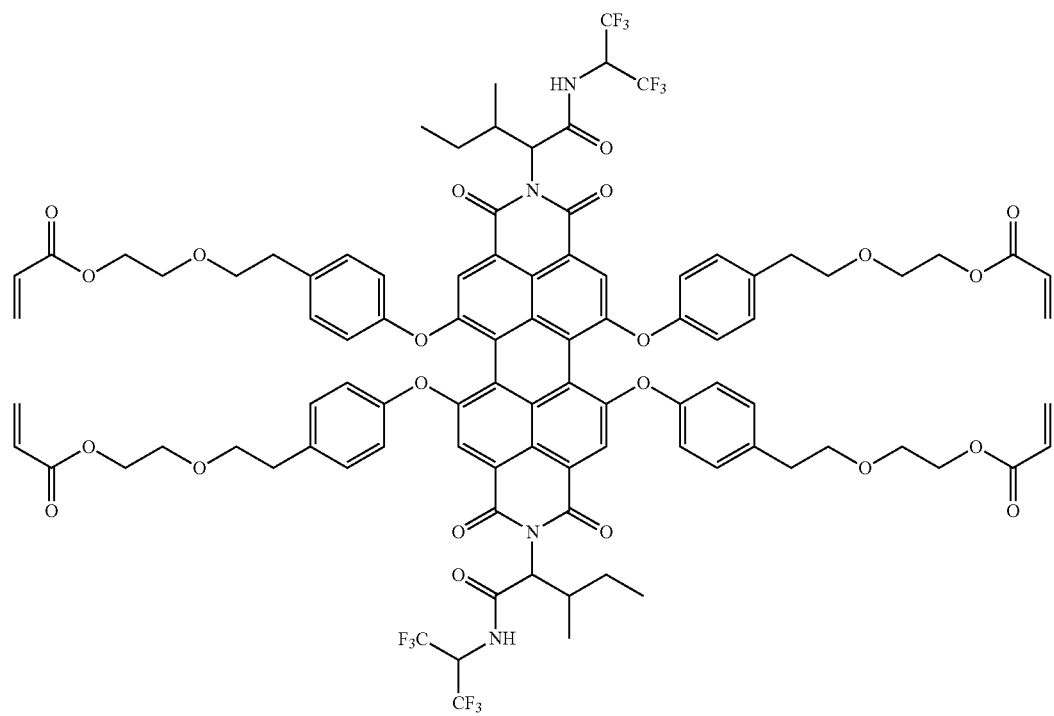

485
-continued
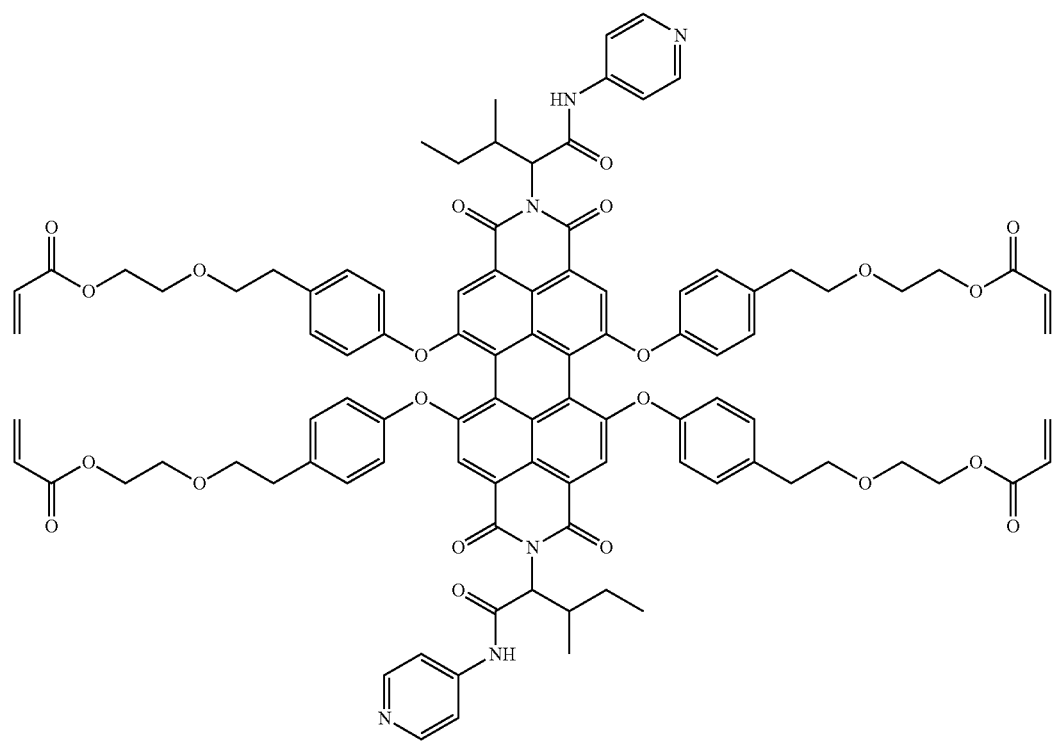
486
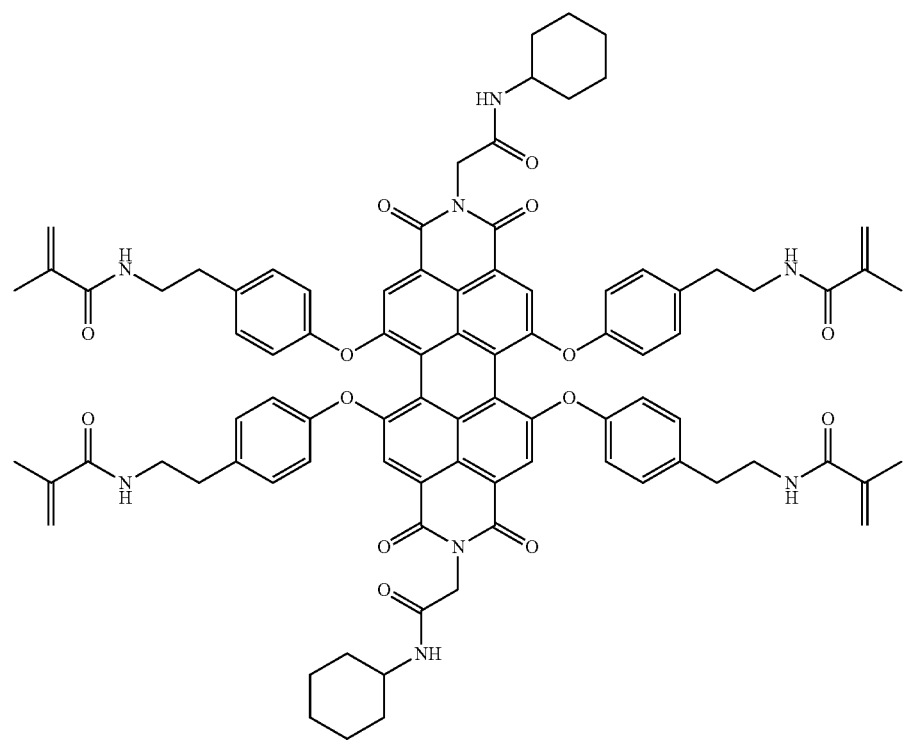

-continued
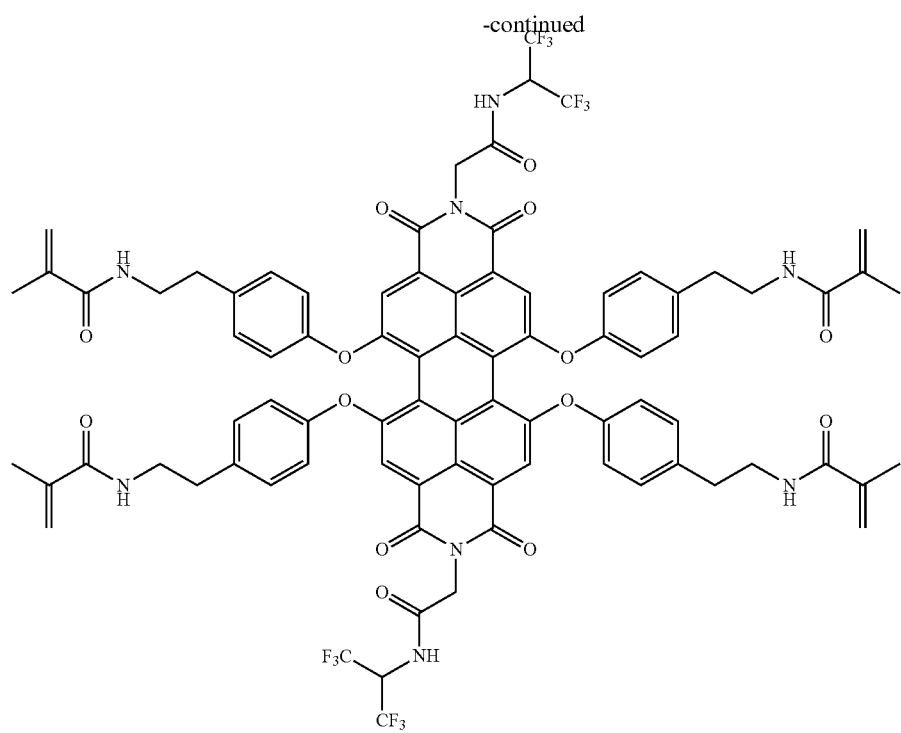
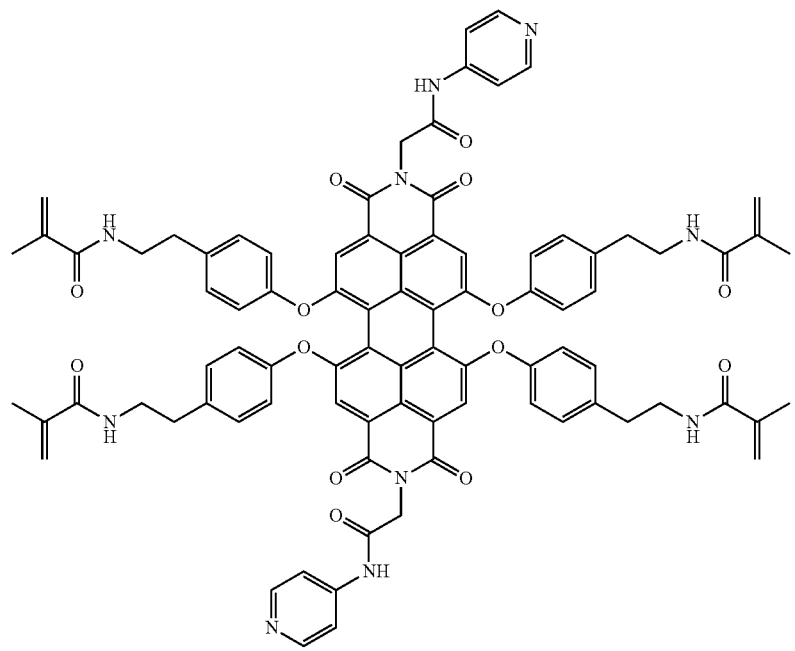

-continued
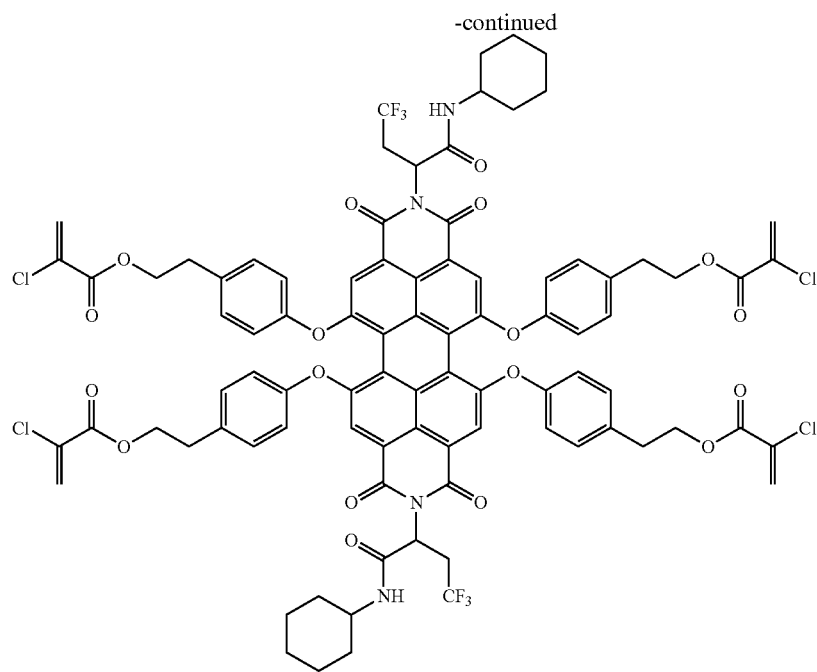
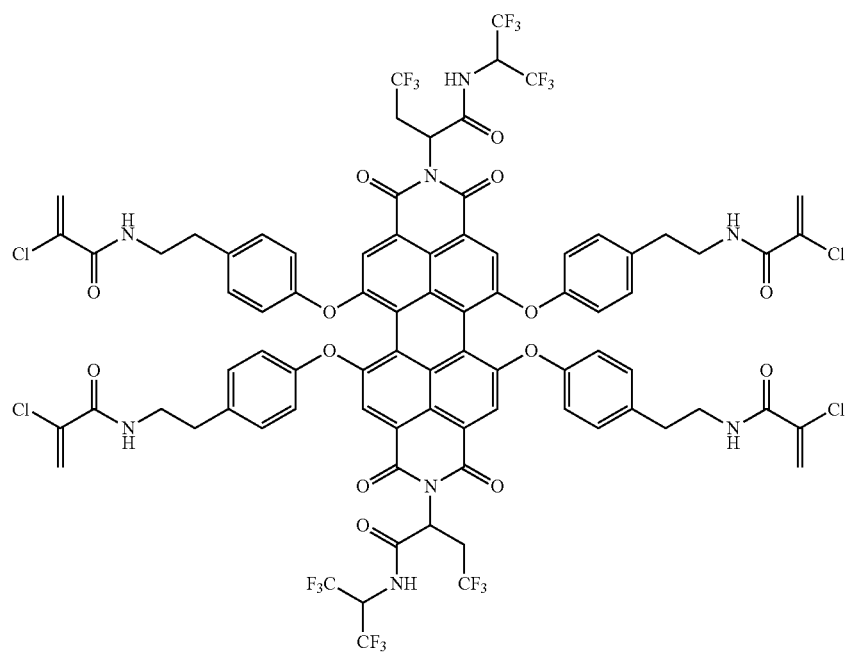

-continued
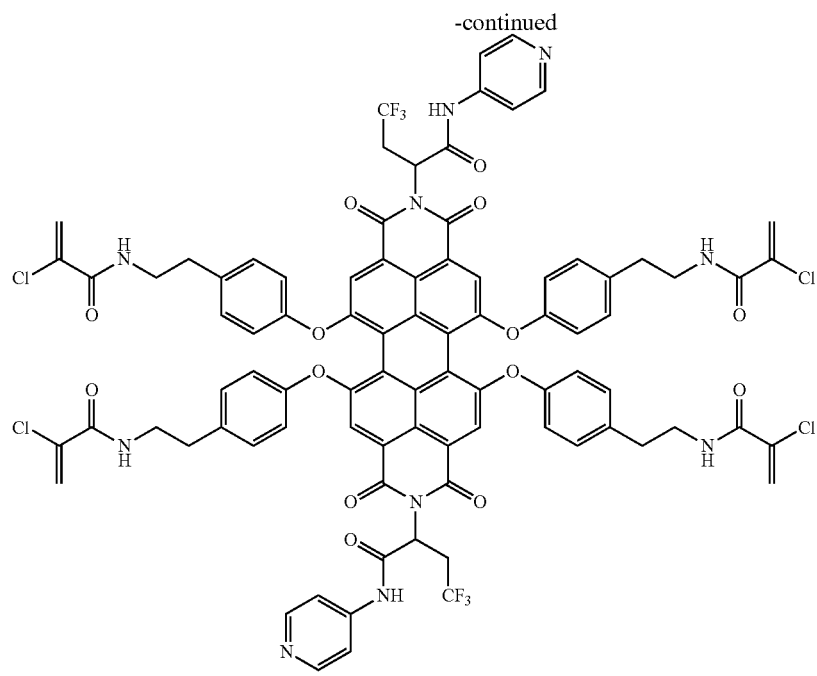
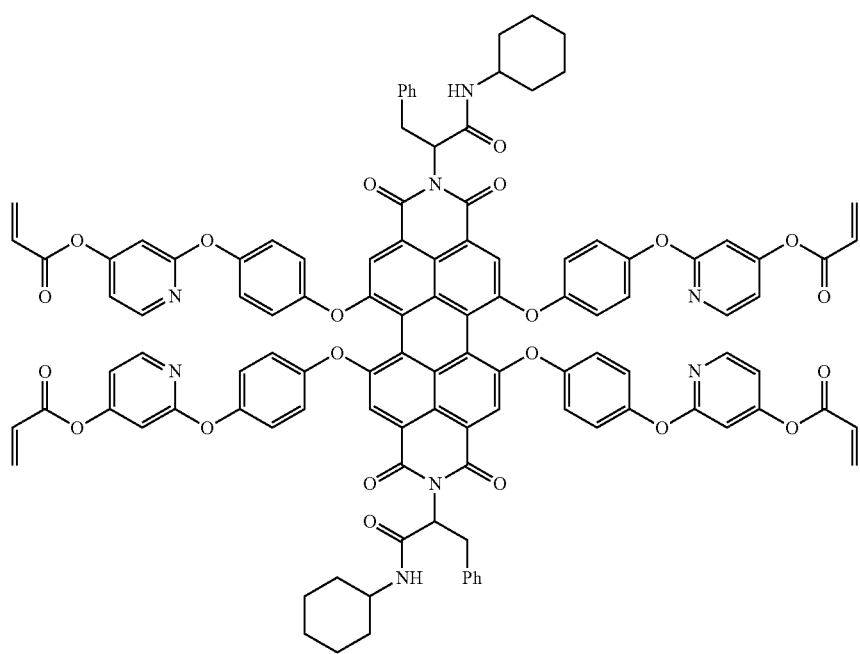

-continued
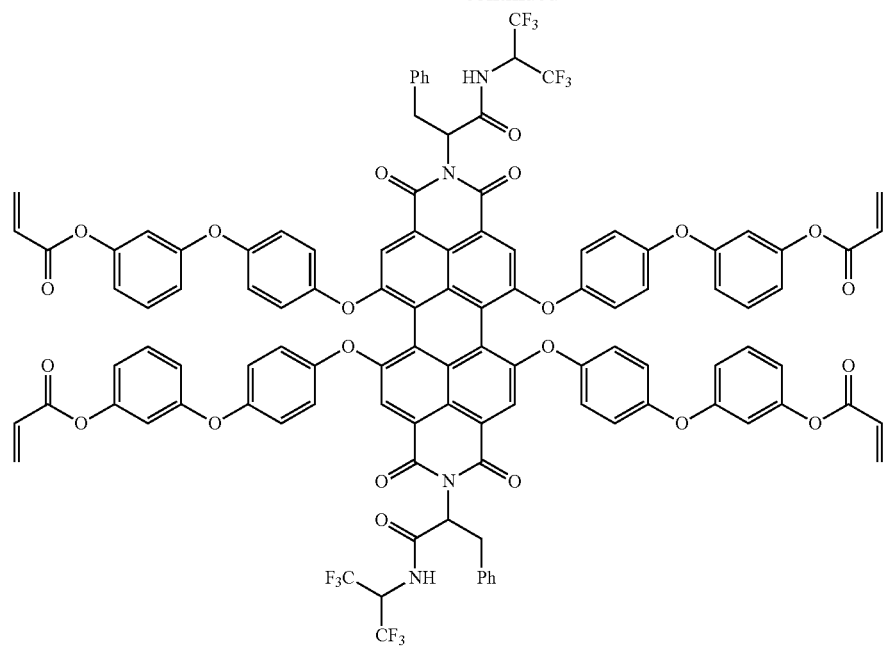
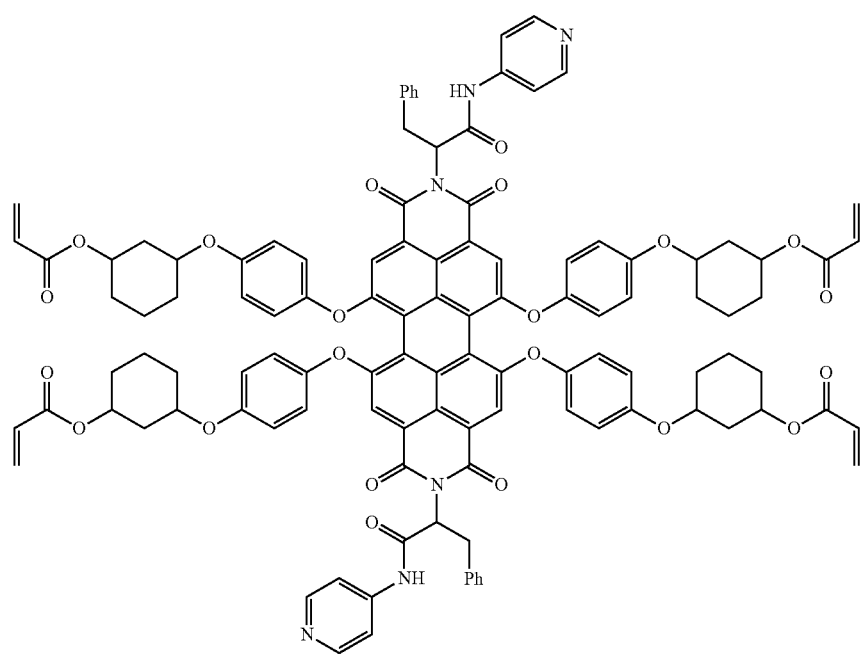 [SMILES: C=CC(=O)OC1CCCC(Oc2ccc(Oc3cc4c5c(cc(Oc6ccc(OC7CCCC(OC(=O)C=C)C7)cc6)c6c7c(Oc8ccc(OC9CCCC(OC(=O)C=C)C9)cc8)cc8c9c(cc(Oc%10ccc(OC%11CCCC(OC(=O)C=C)C%11)cc%10)c(c3c56)c97)C(=O)N(C(Cc3ccccc3)C(=O)Nc3ccncc3)C8=O)C(=O)N(C(Cc3ccccc3)C(=O)Nc3ccncc3)C4=O)cc2)C1]

-continued
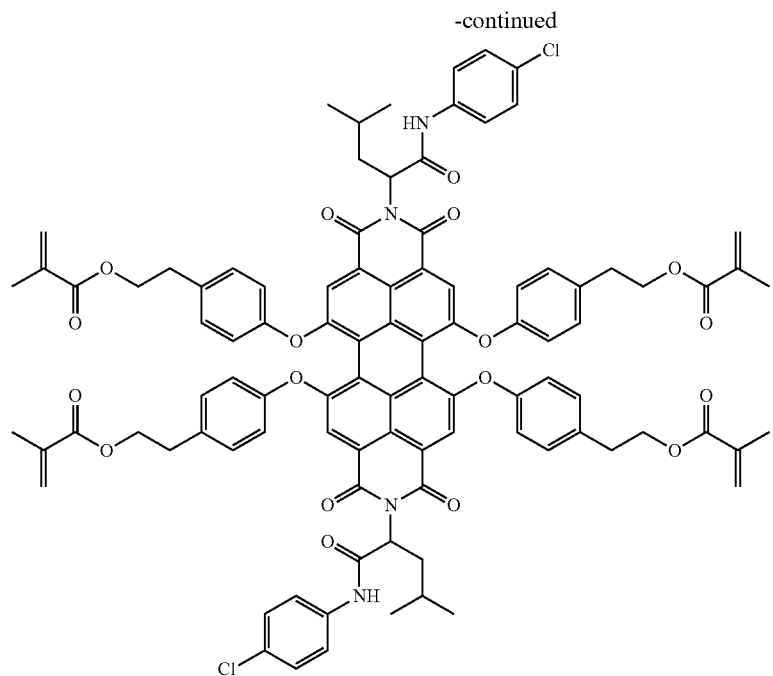
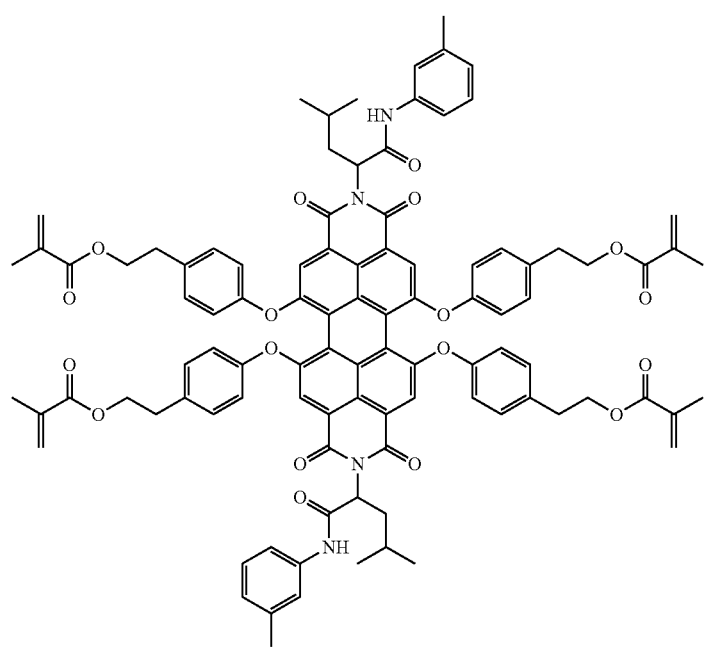

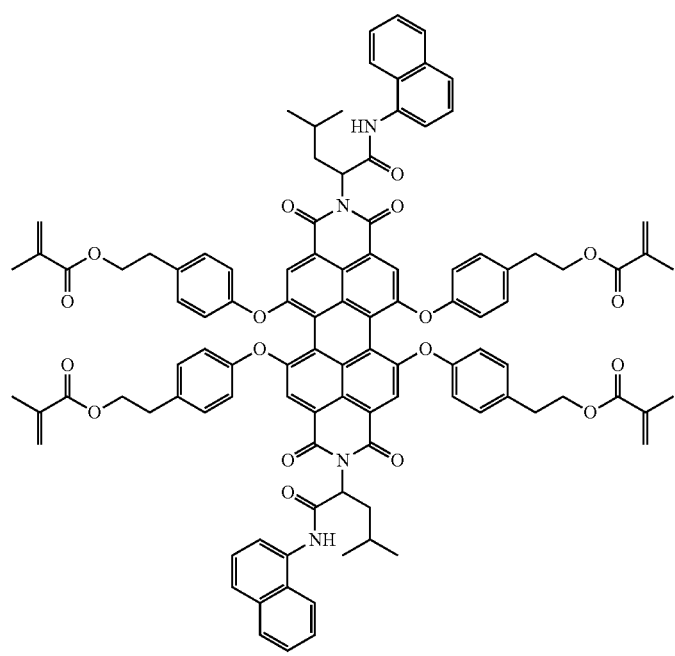
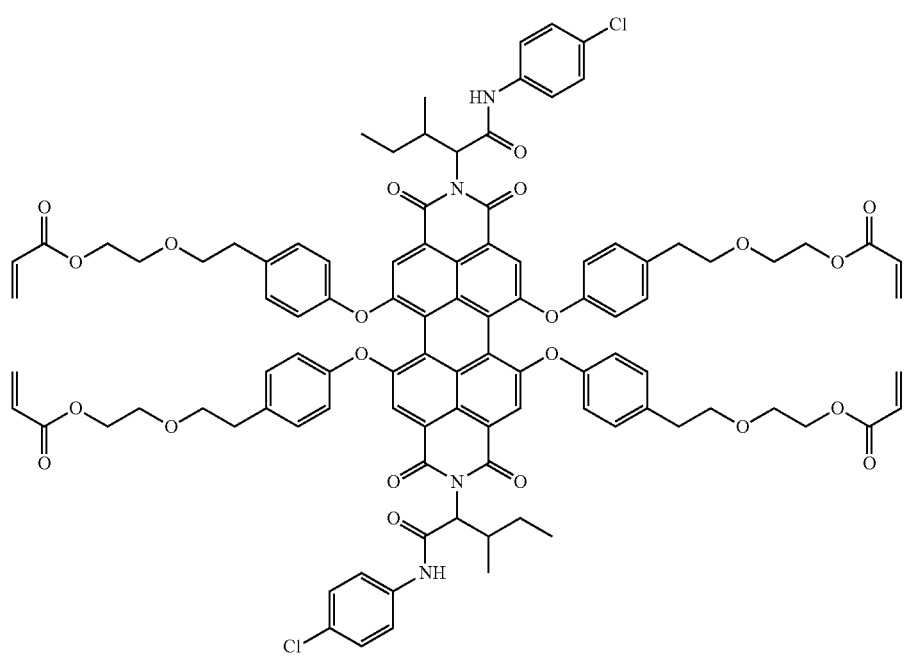

-continued
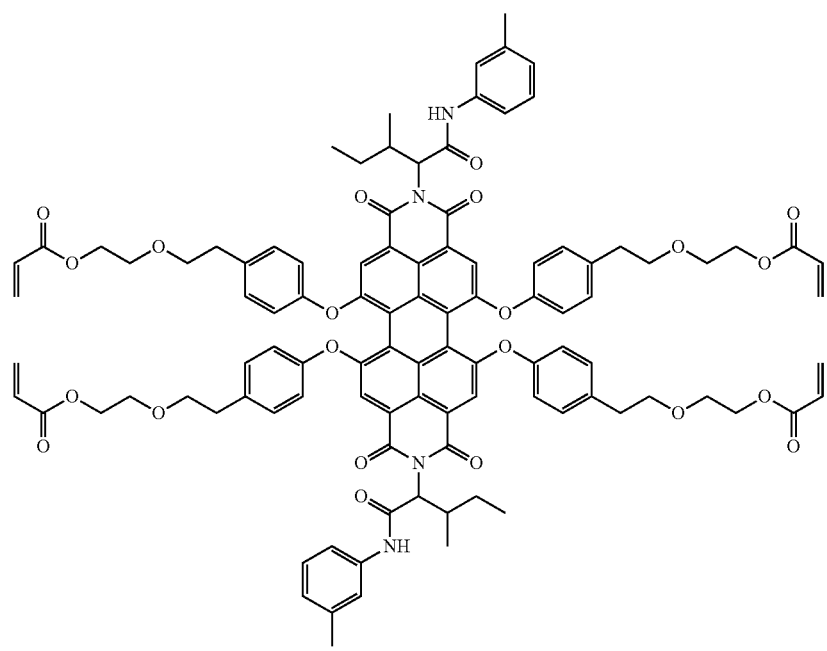
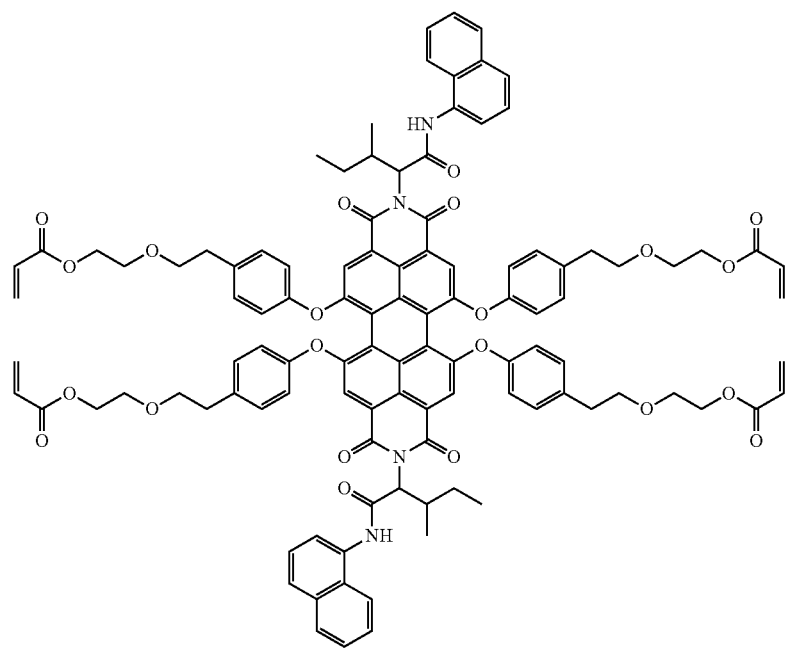

-continued
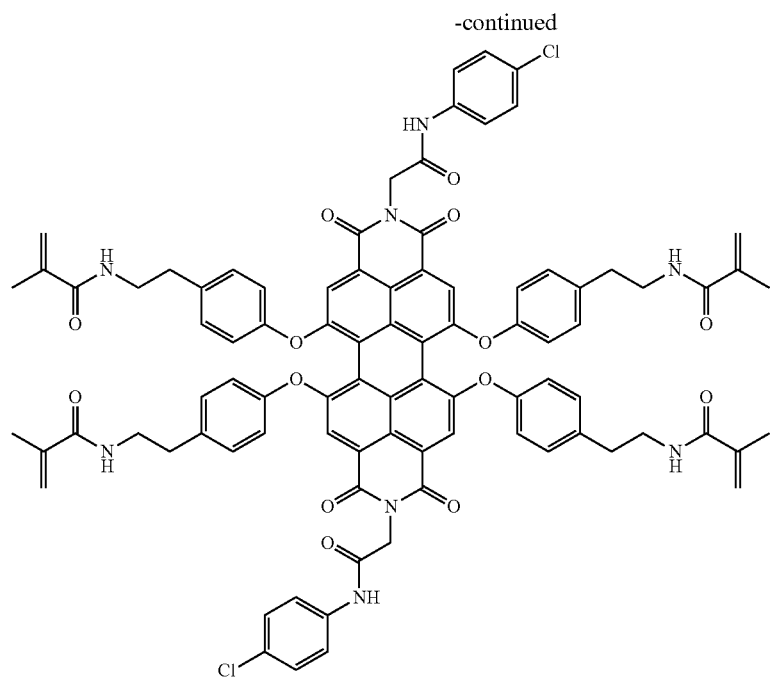
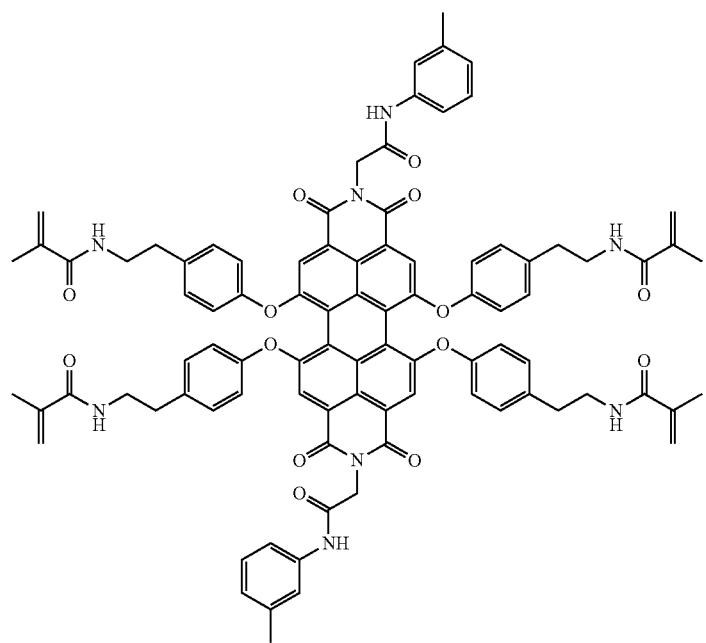

503 504
-continued
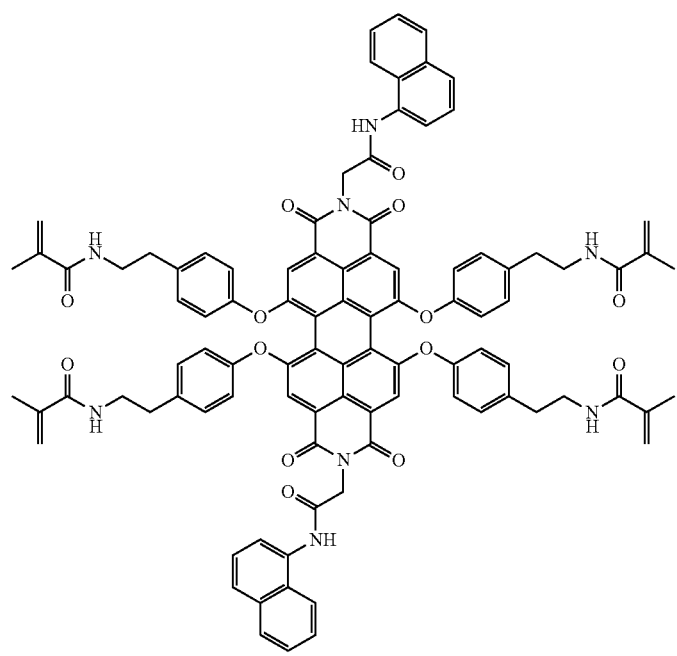
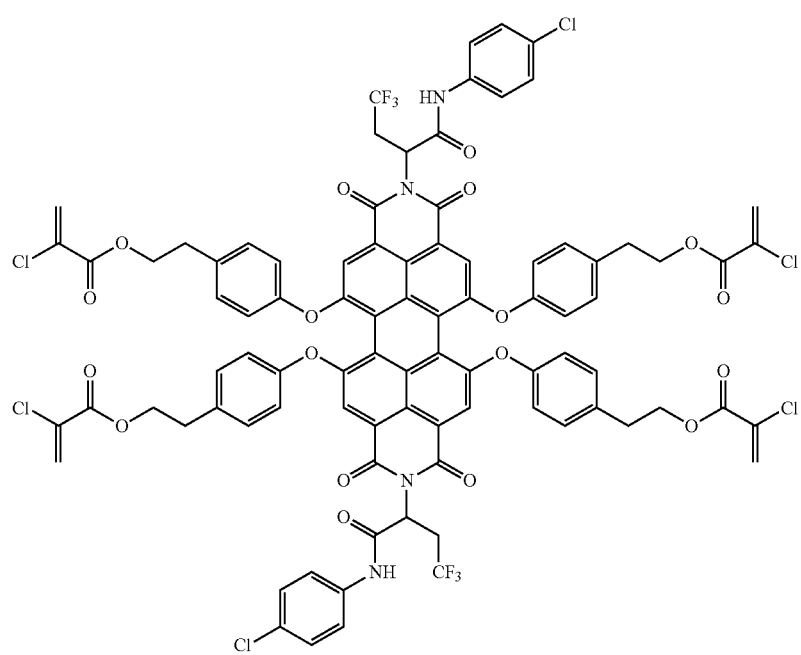

-continued
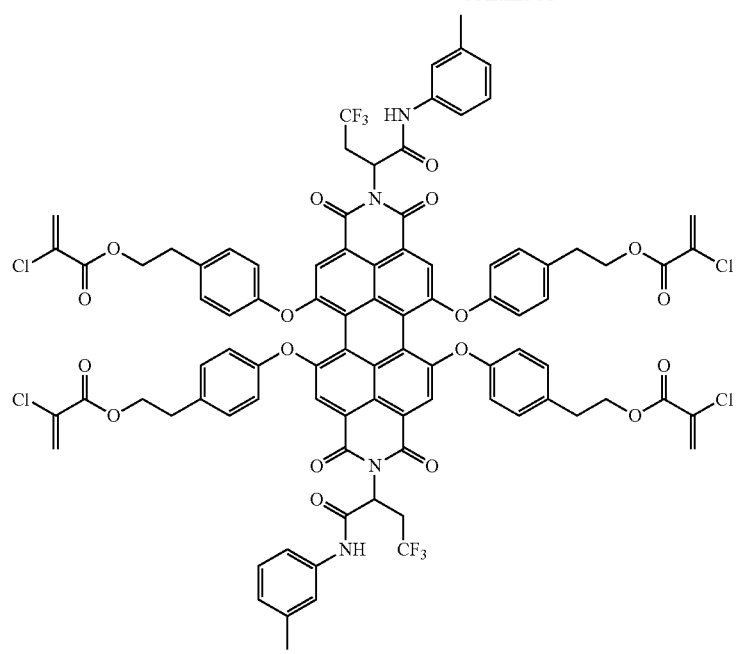
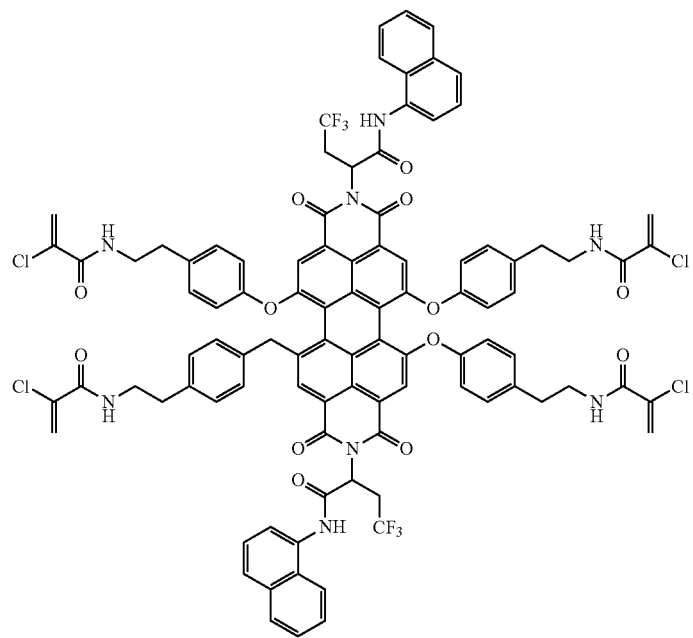

-continued
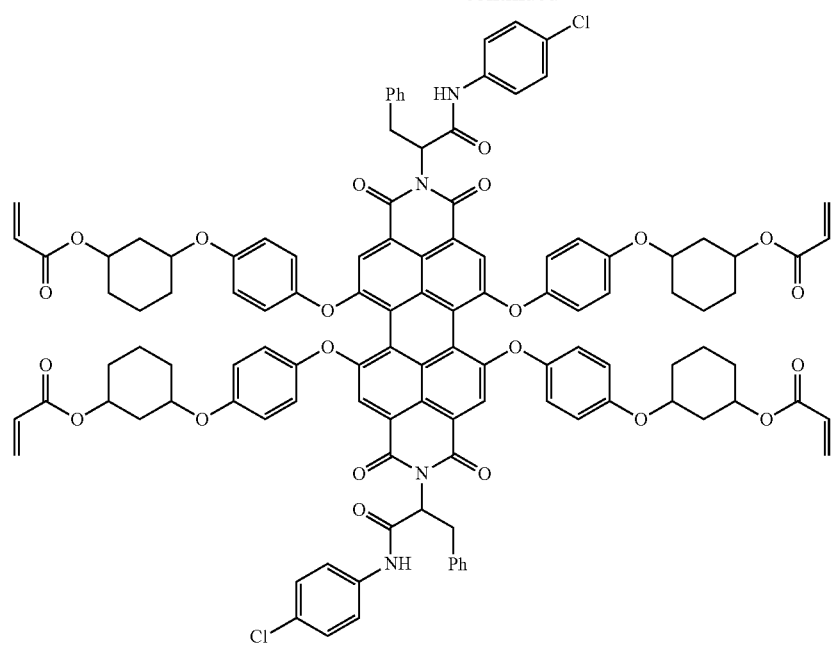
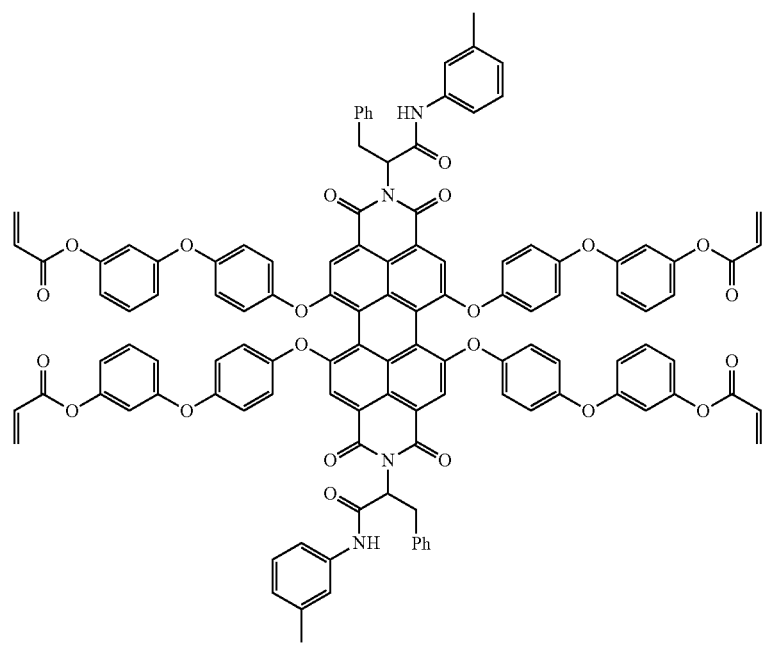

-continued
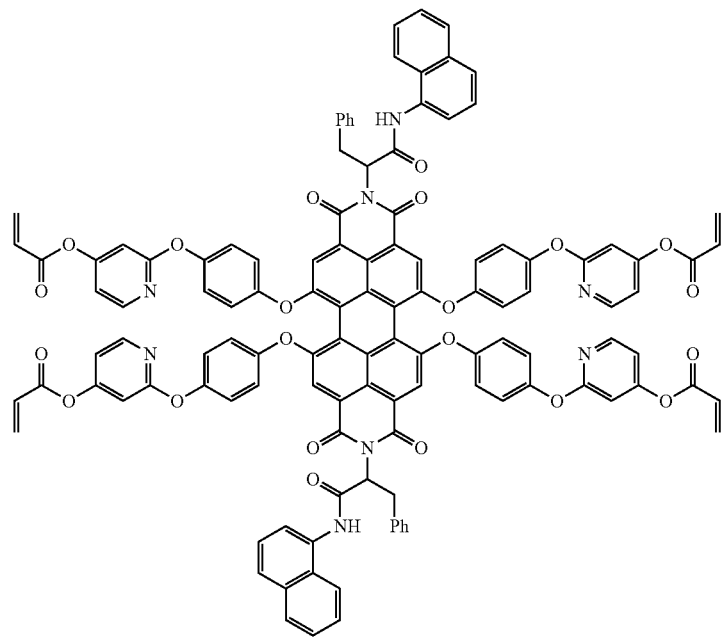 [SMILES: C=CC(=O)Oc1ccnc(Oc2ccc(Oc3cc4c5c(cc(Oc6ccc(Oc7cc(OC(=O)C=C)ccn7)cc6)c6c7c(Oc8ccc(Oc9cc(OC(=O)C=C)ccn9)cc8)cc8c9c(cc(Oc%10ccc(Oc%11cc(OC(=O)C=C)ccn%11)cc%10)c(c3c56)c97)C(=O)N(C(Cc3ccccc3)C(=O)Nc3cccc5ccccc35)C8=O)C(=O)N(C(Cc3ccccc3)C(=O)Nc3cccc5ccccc35)C4=O)cc2)c1]
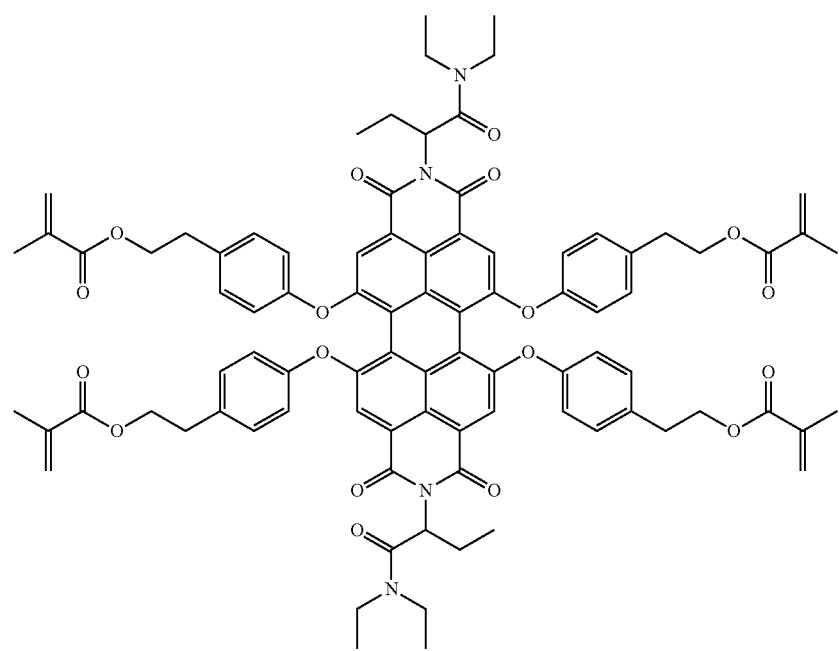

-continued
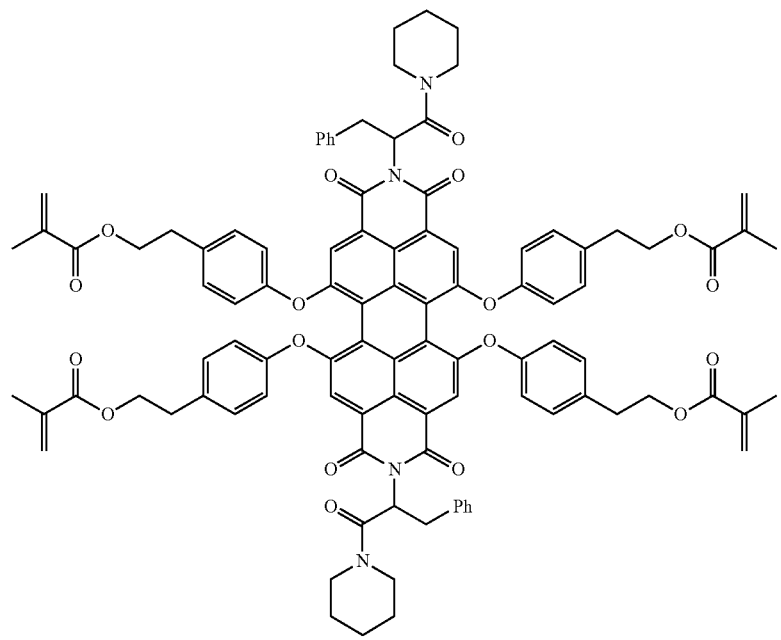
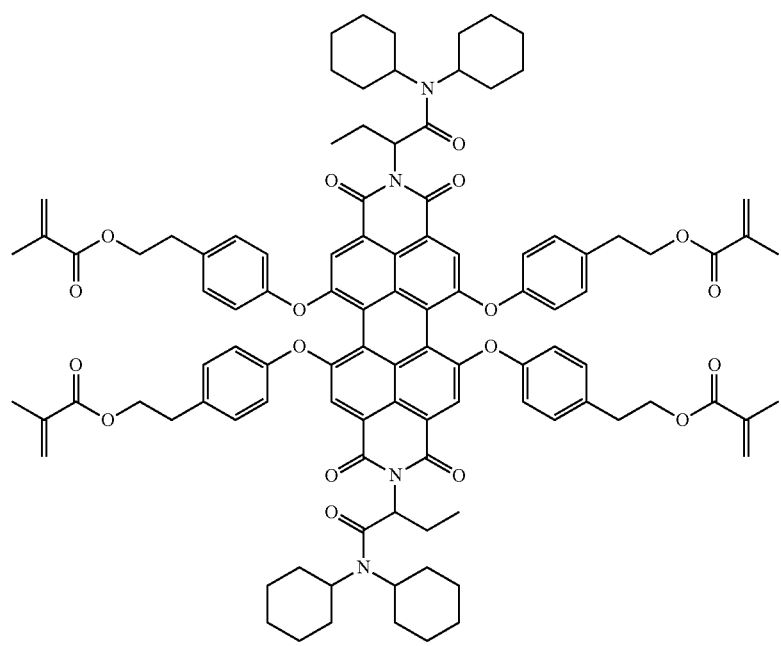

-continued
513
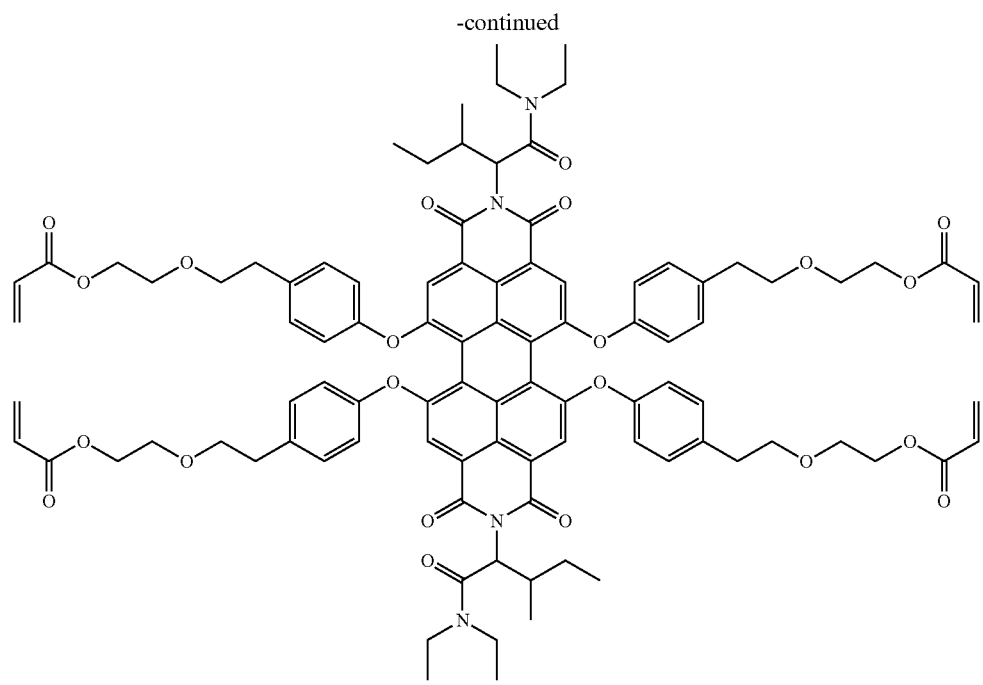
514
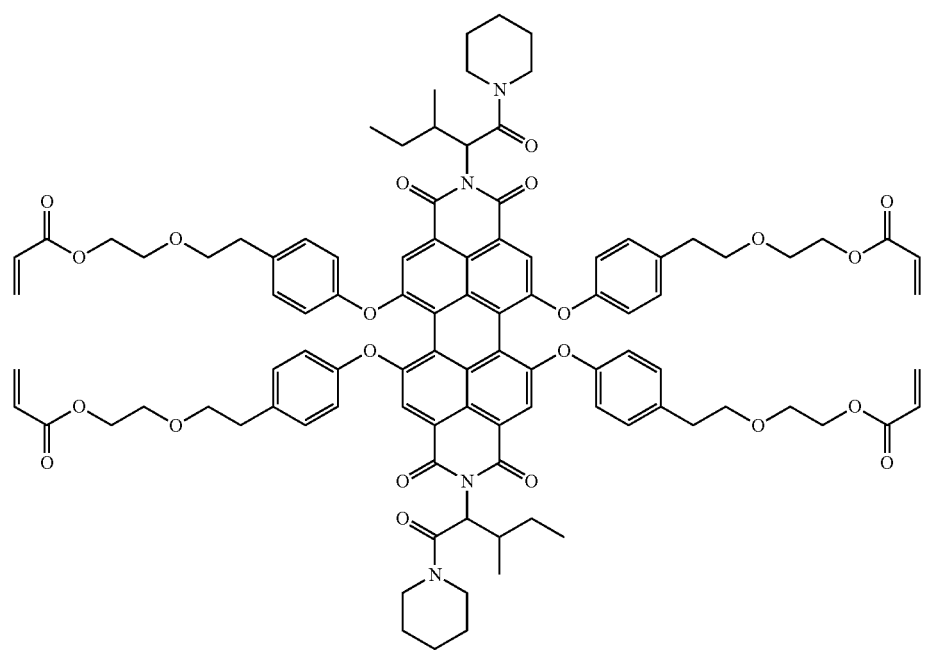

-continued
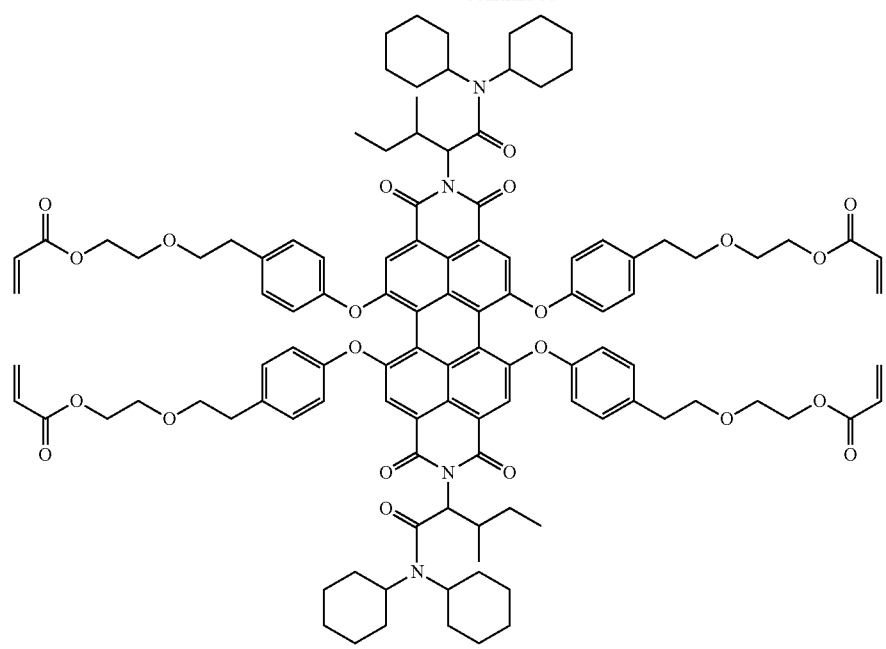
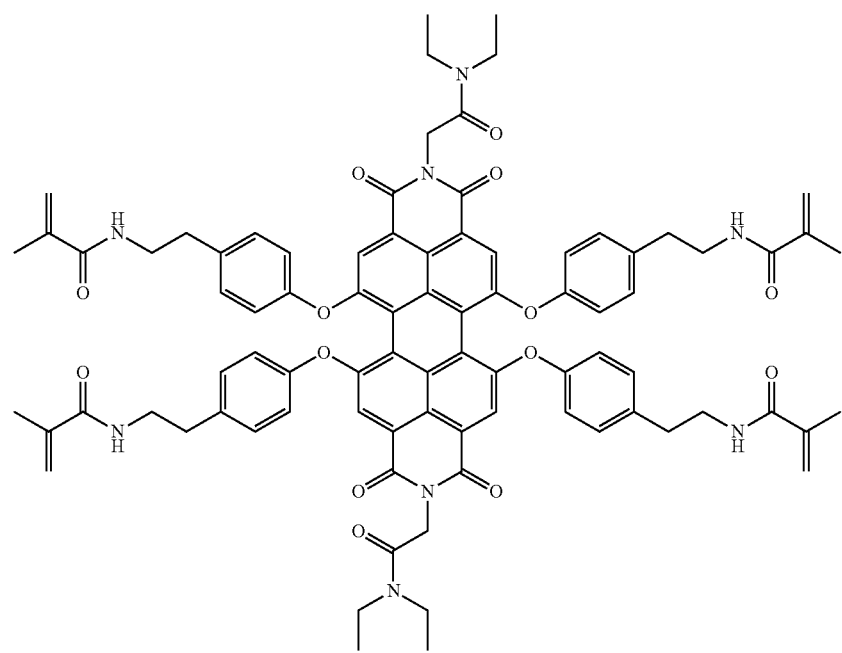

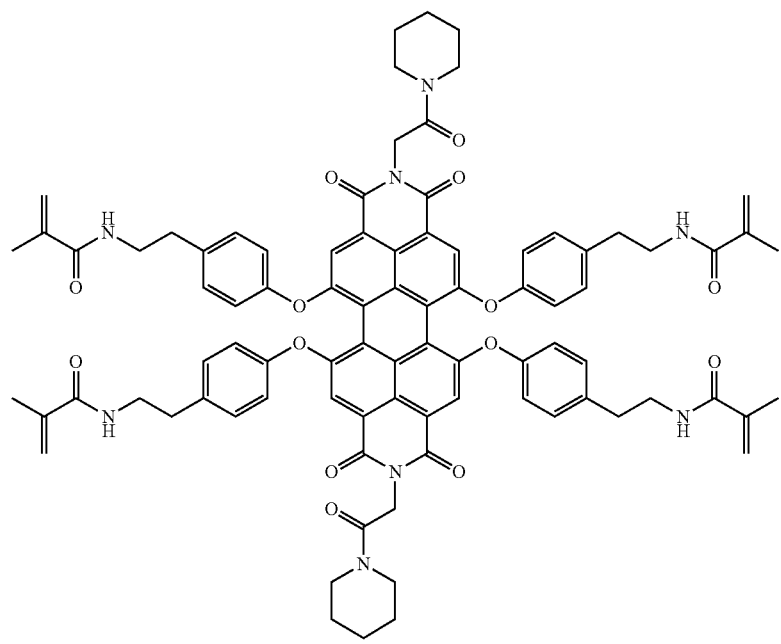
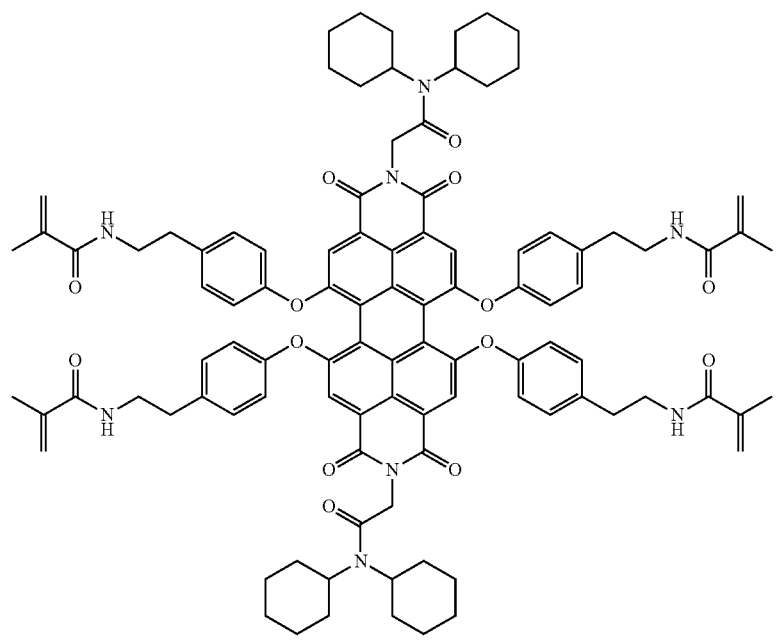

-continued
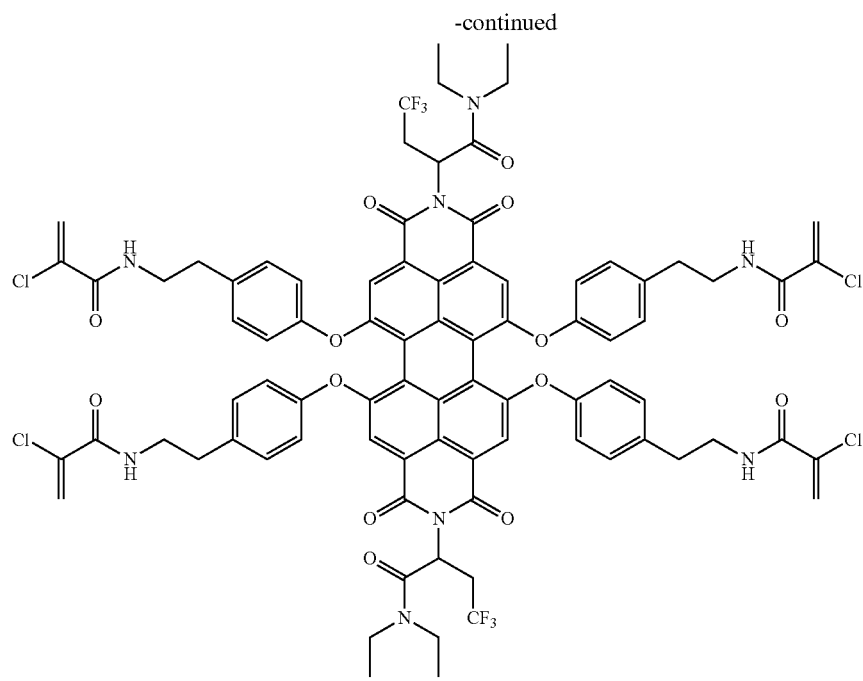
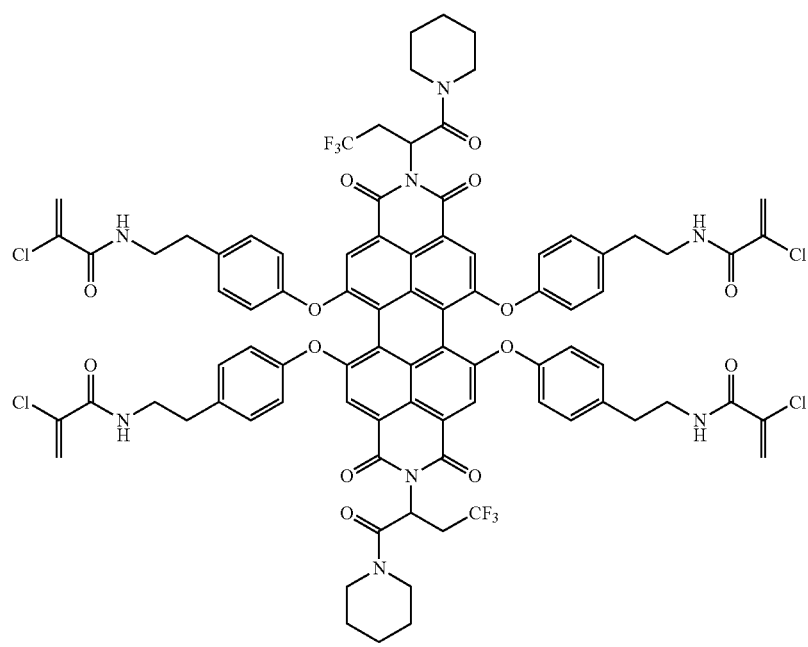

-continued
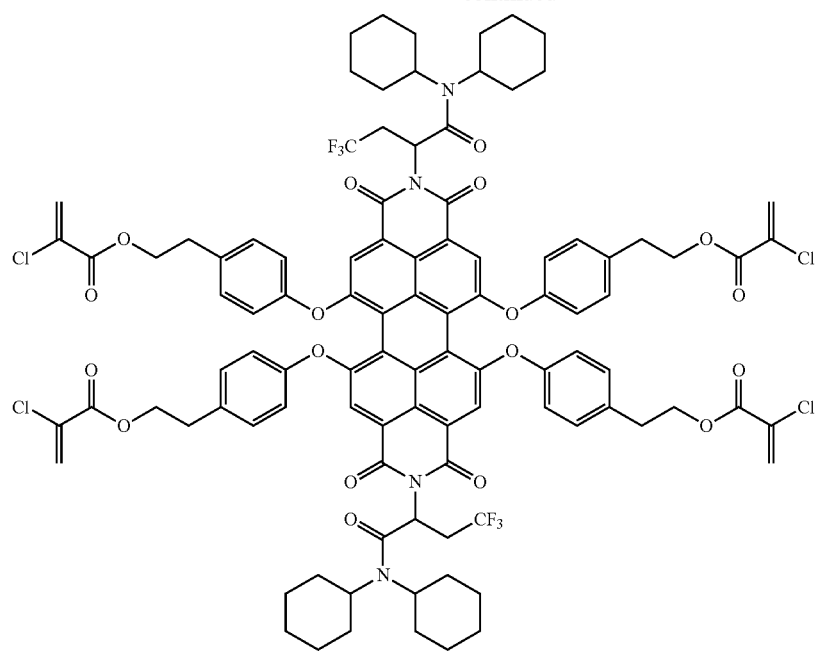
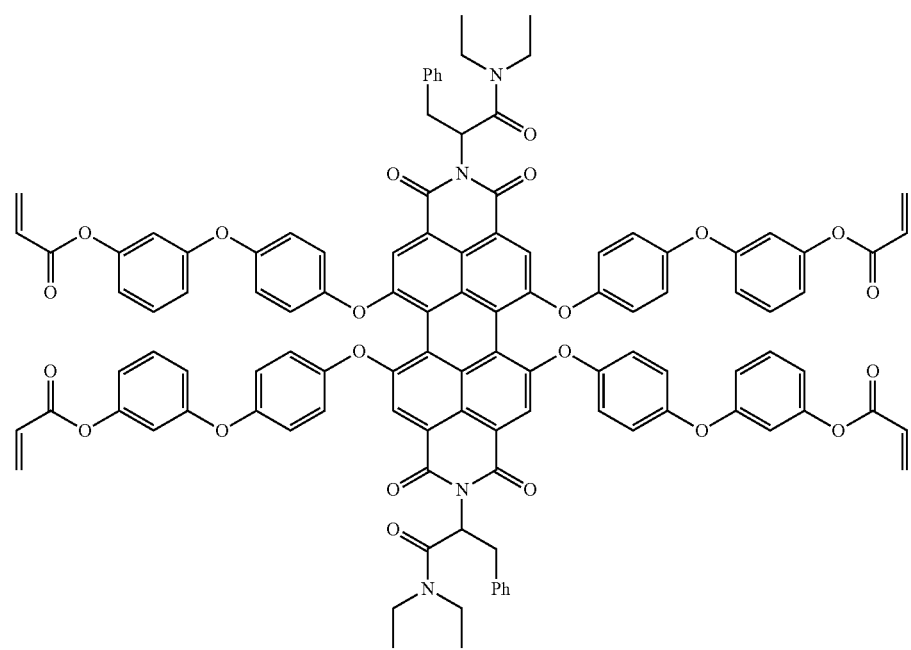

-continued
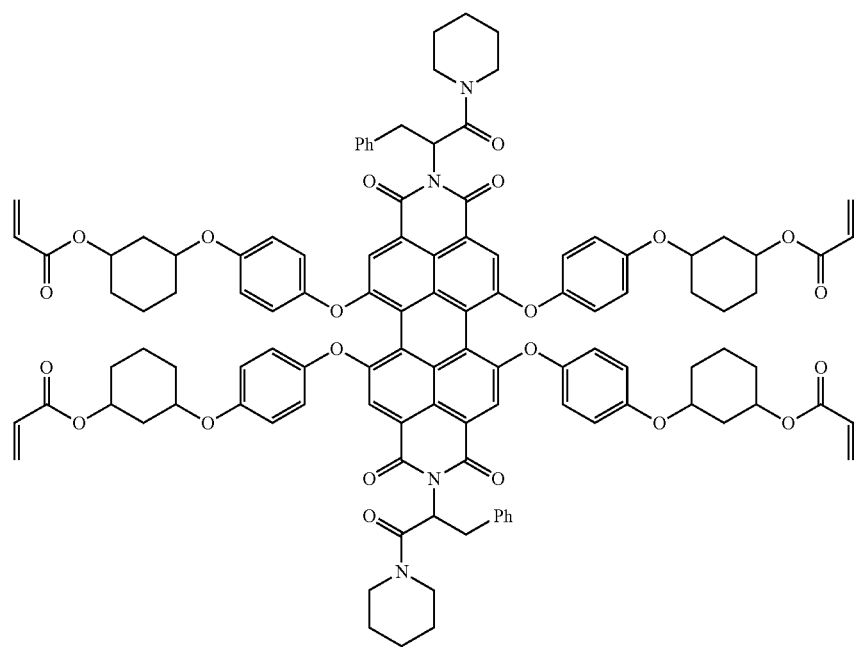
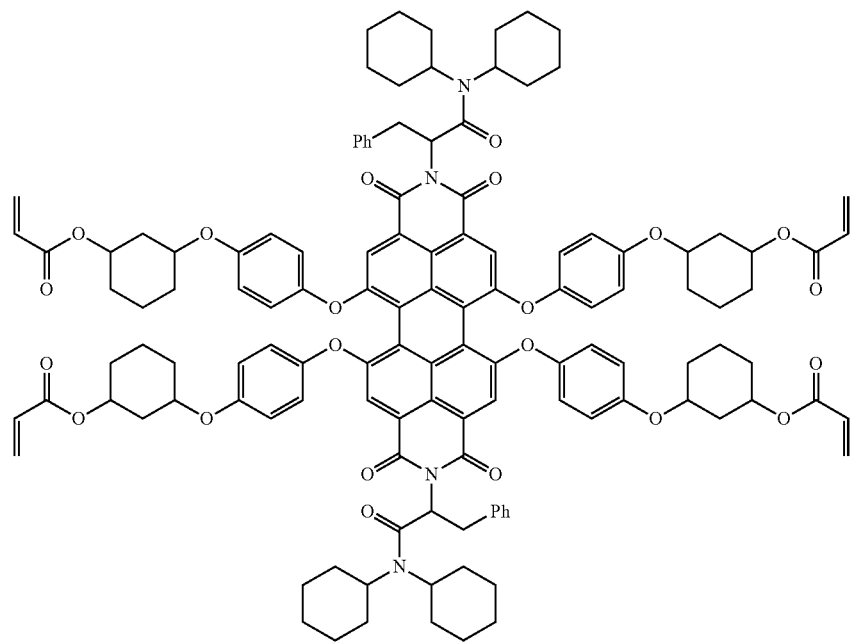

525         526
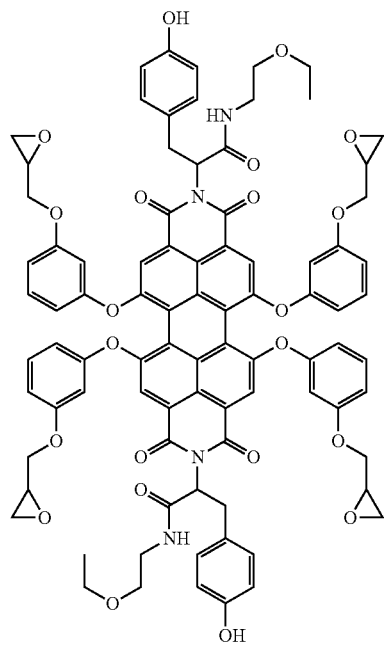
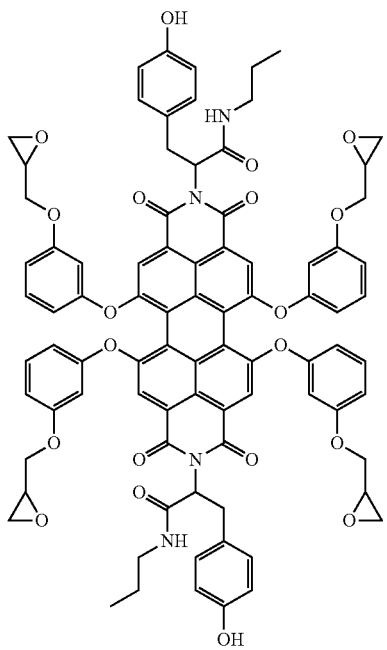
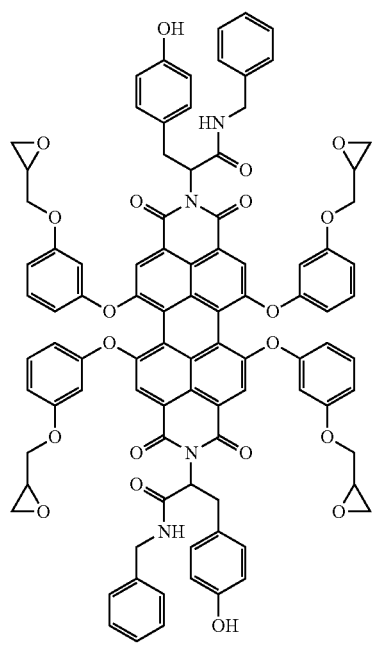
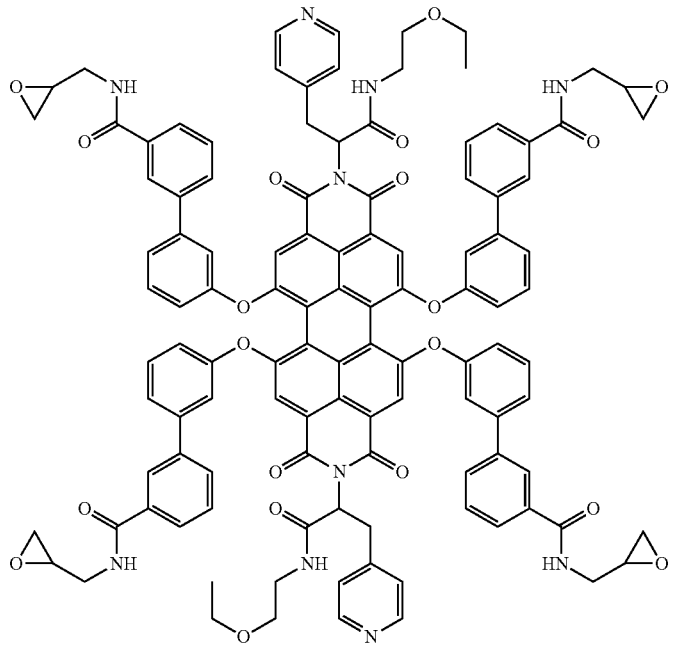

527
528
-continued
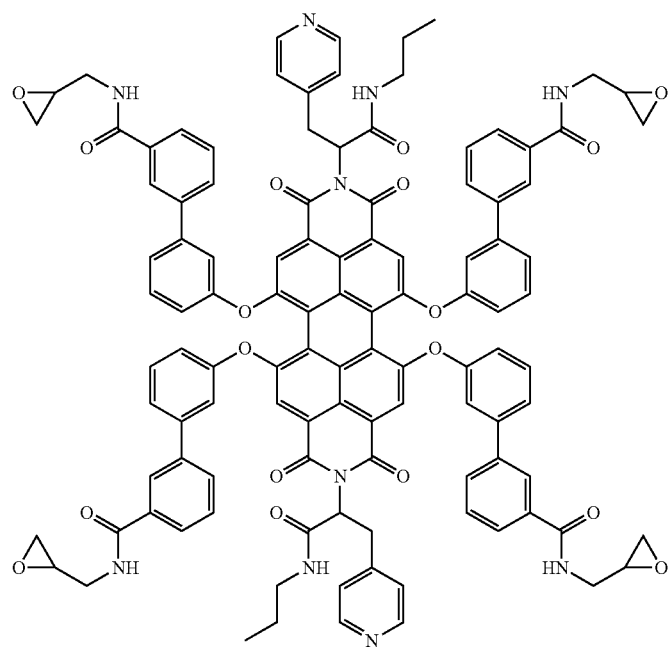
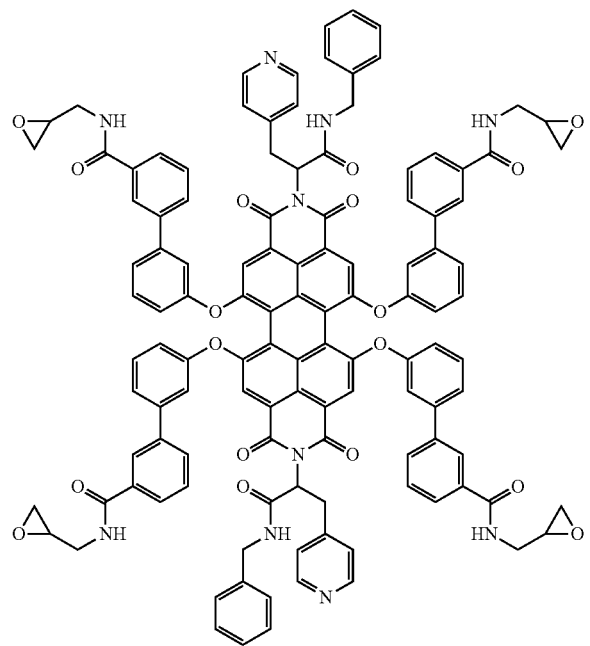

-continued
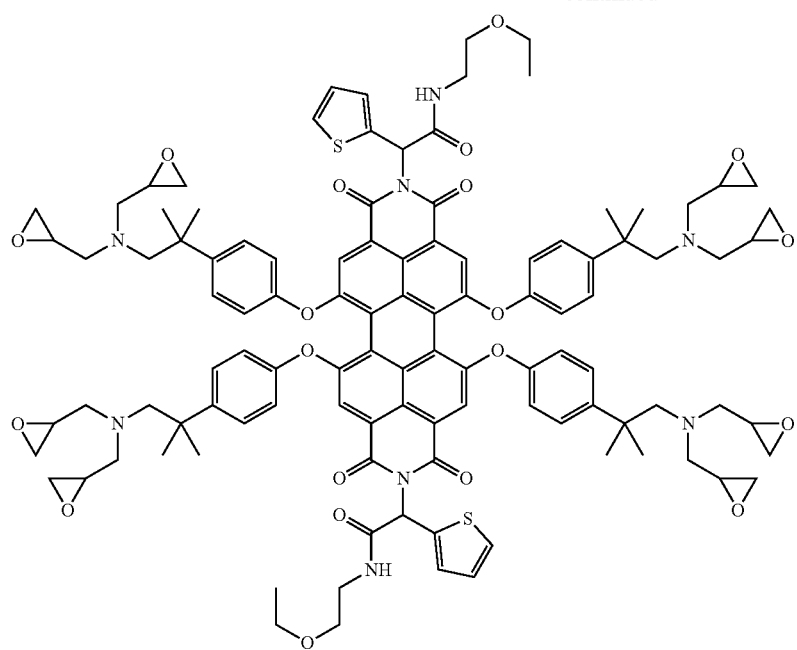
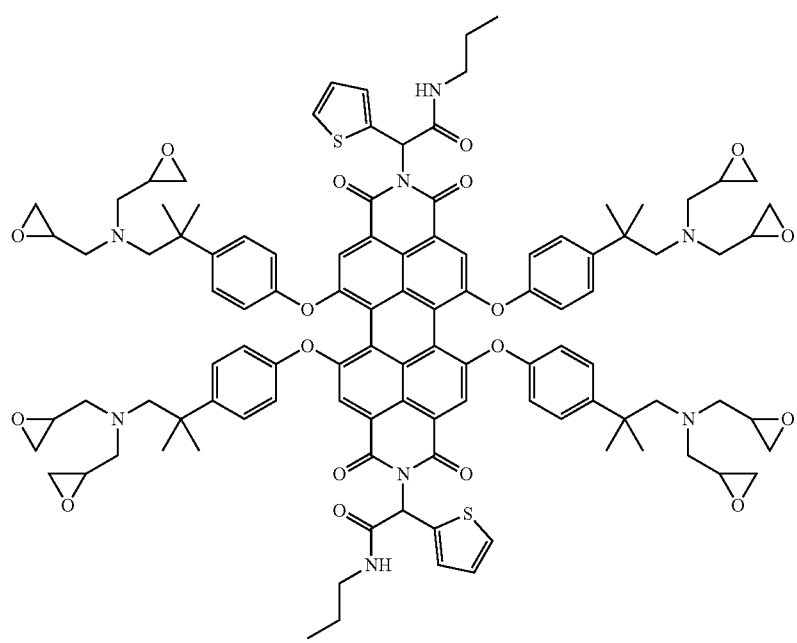

-continued
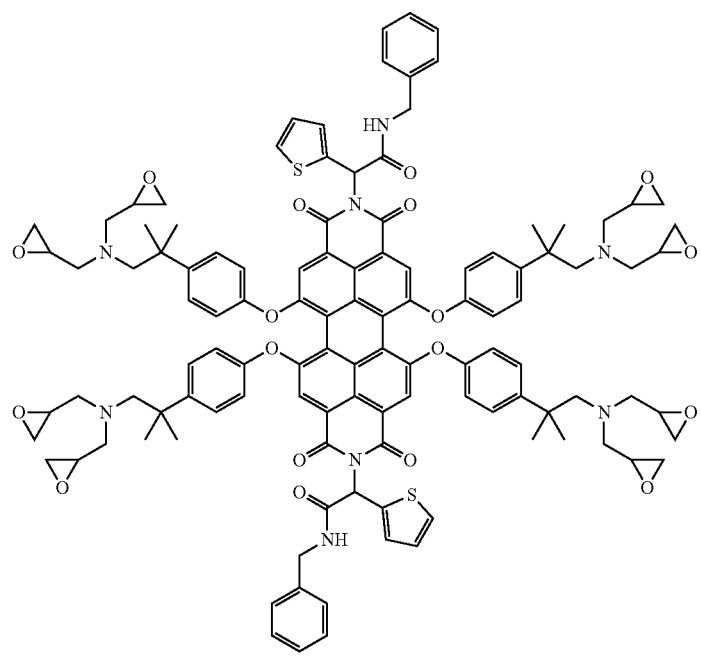
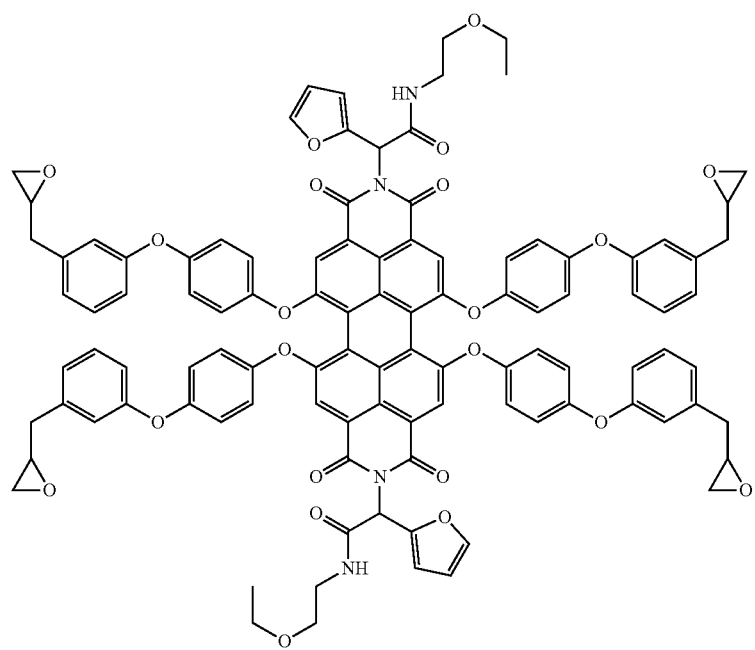

533
-continued
534
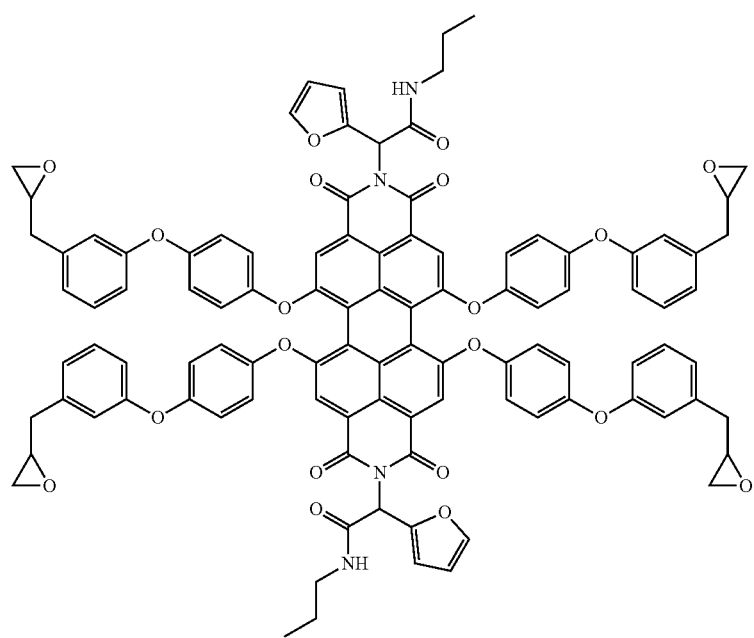
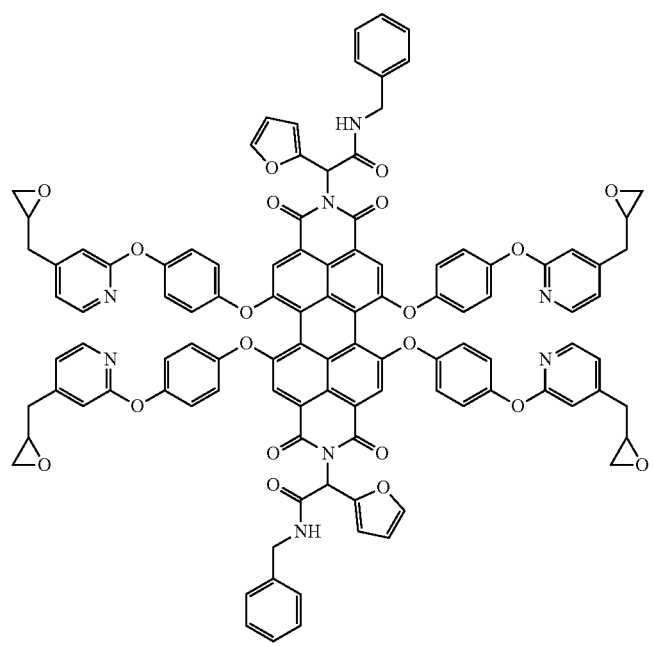

-continued
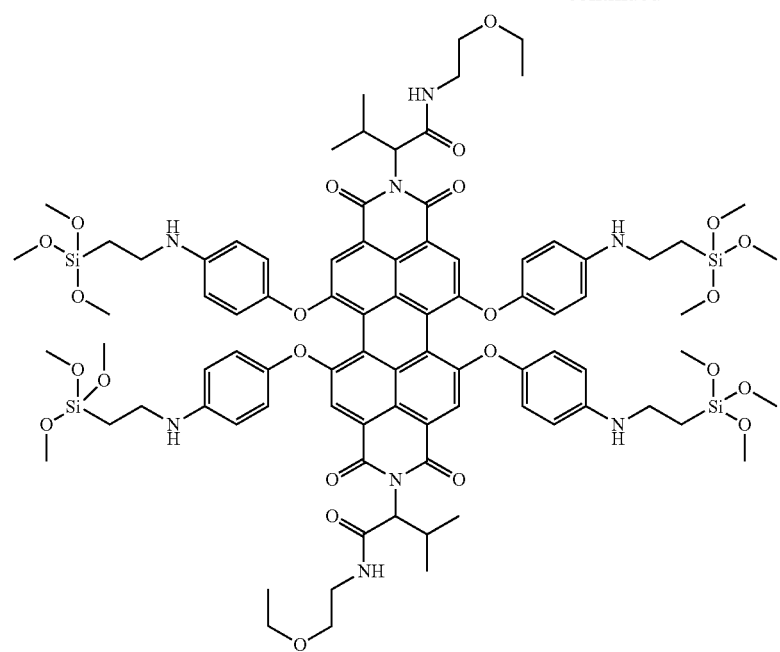
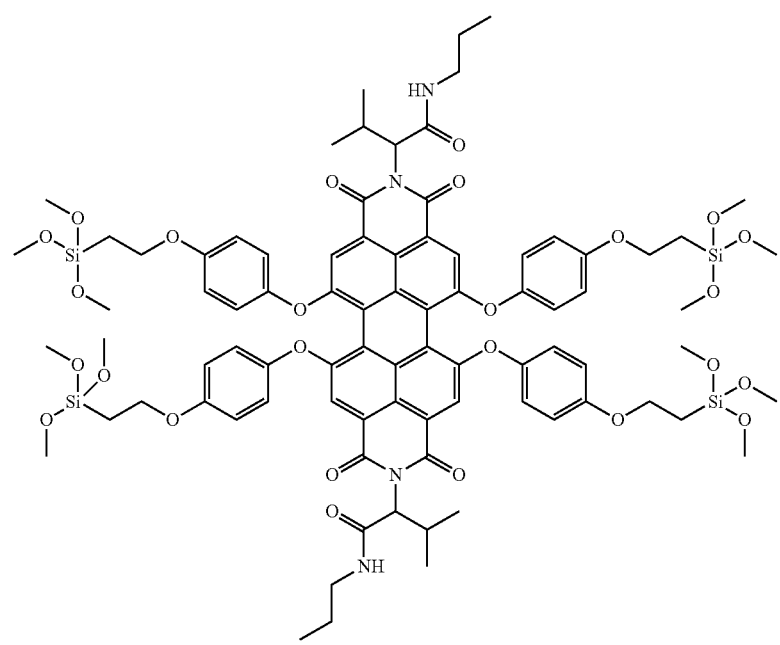

-continued
537
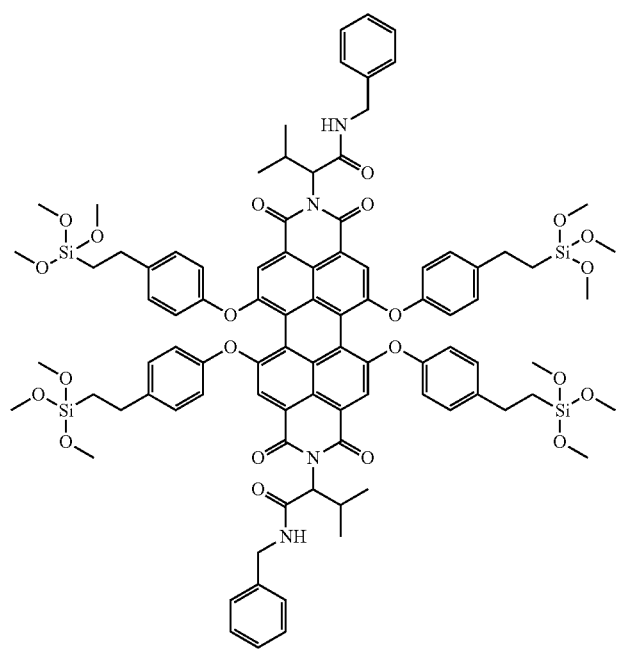
538
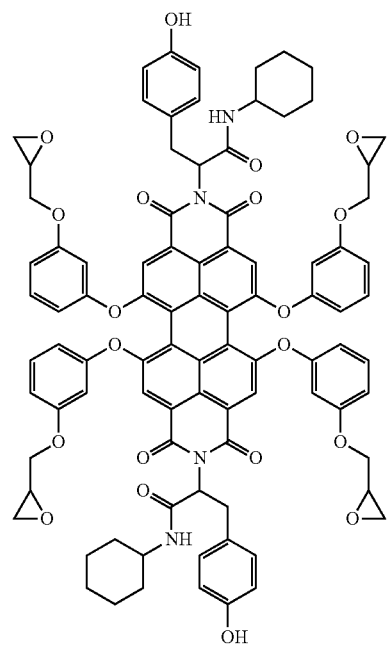
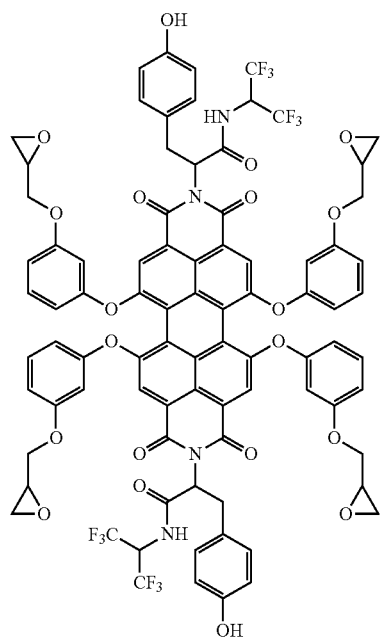
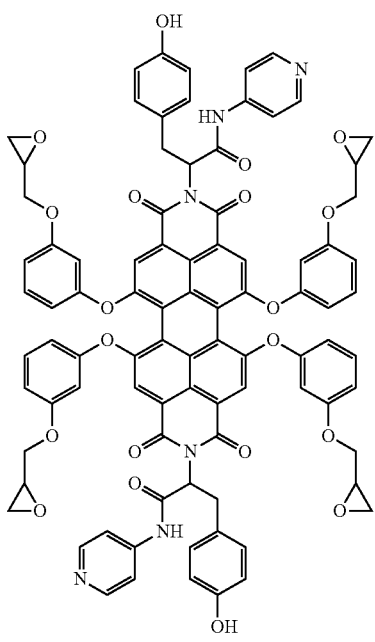

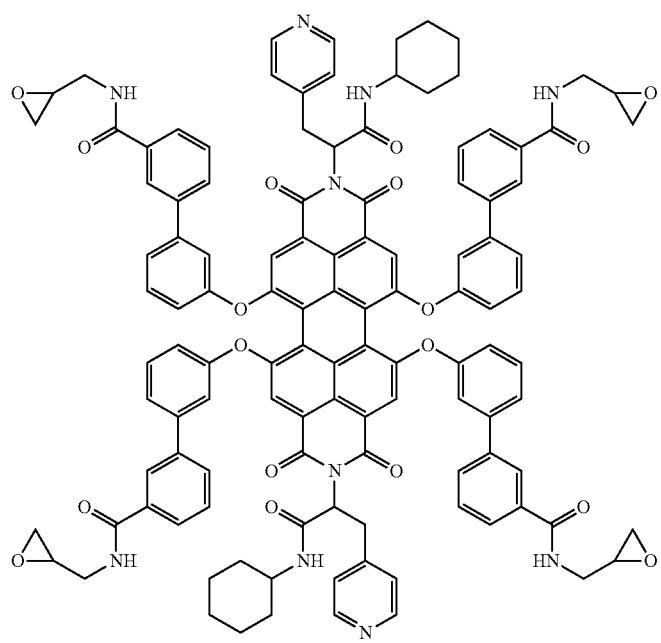
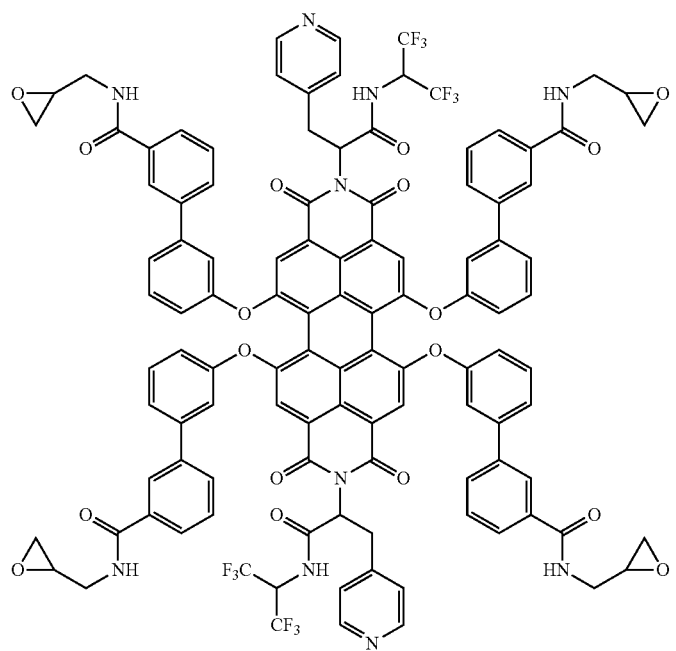

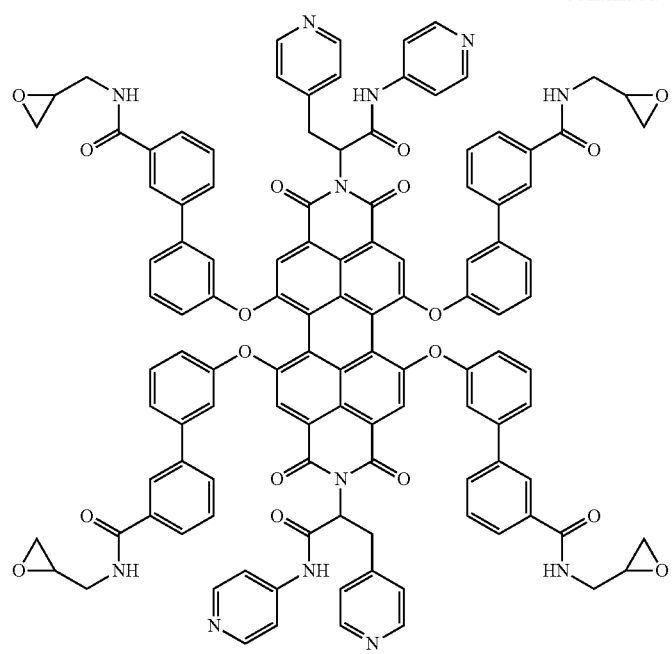
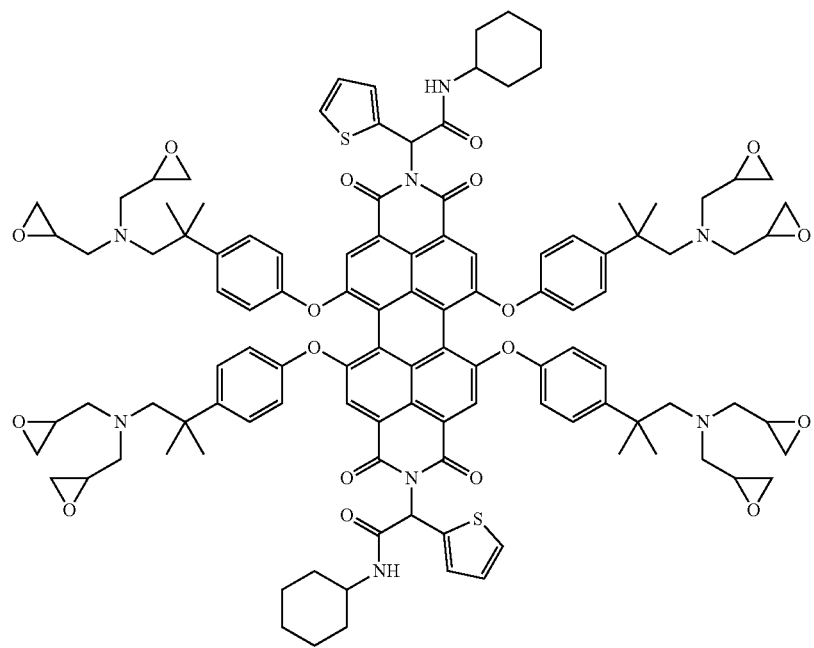

-continued
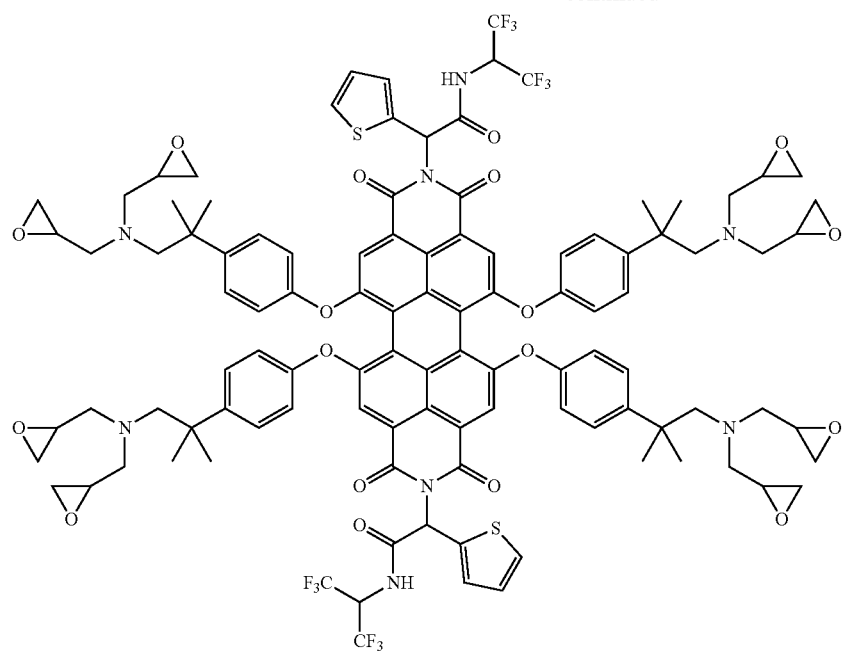
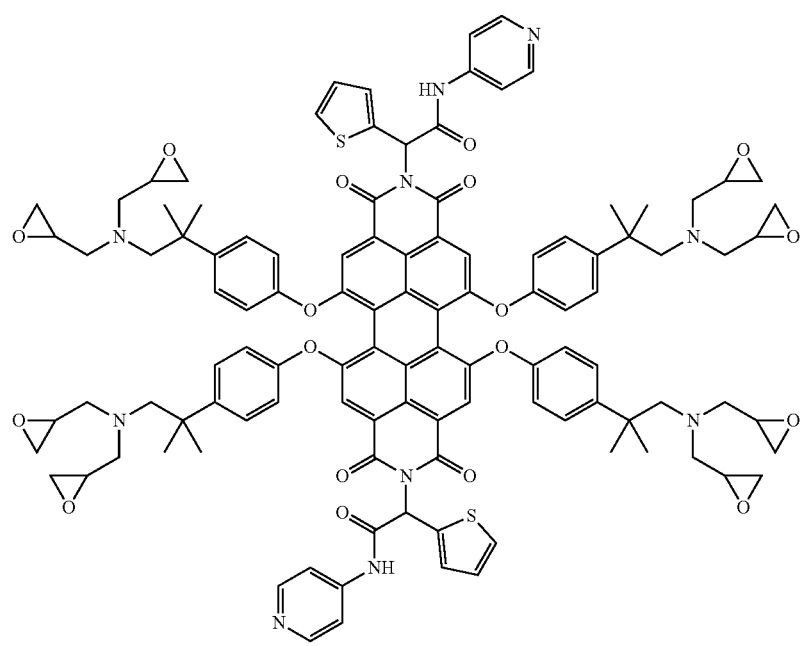

-continued
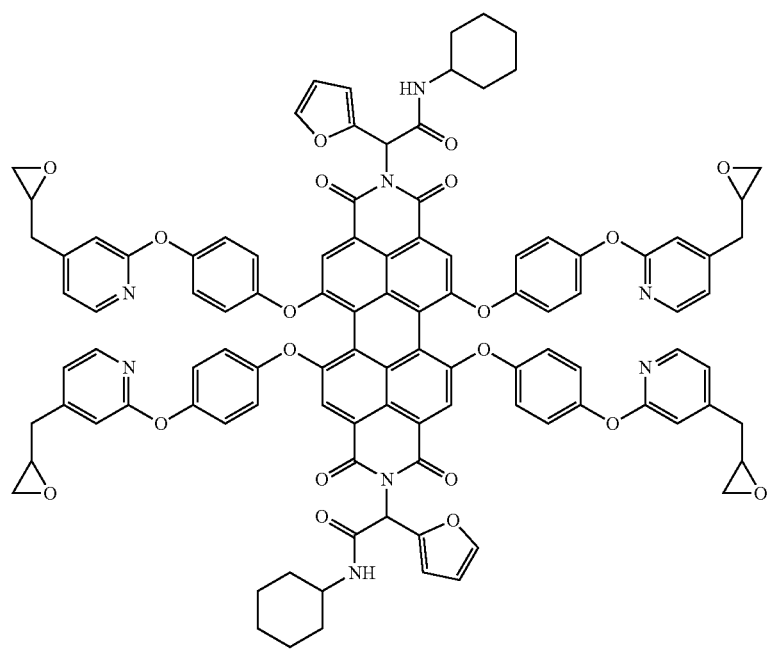
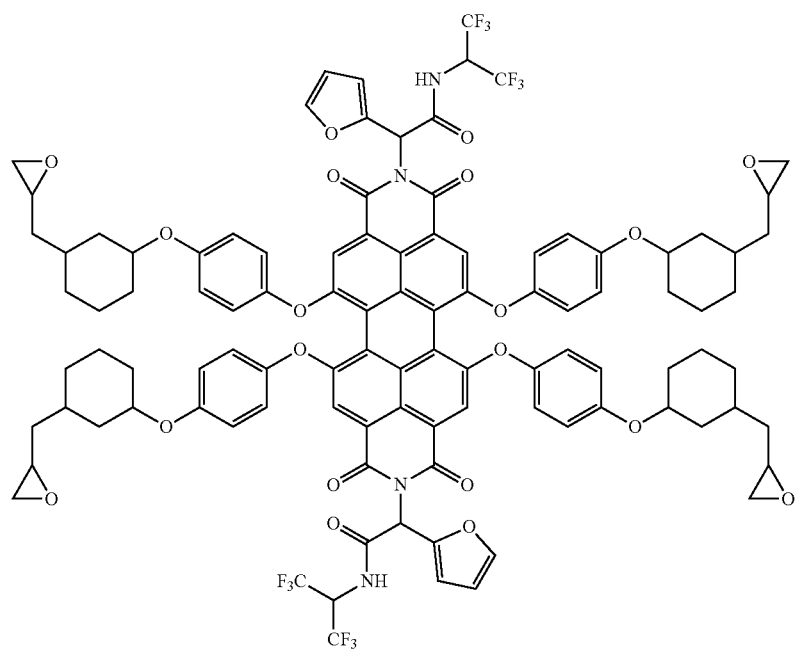

-continued
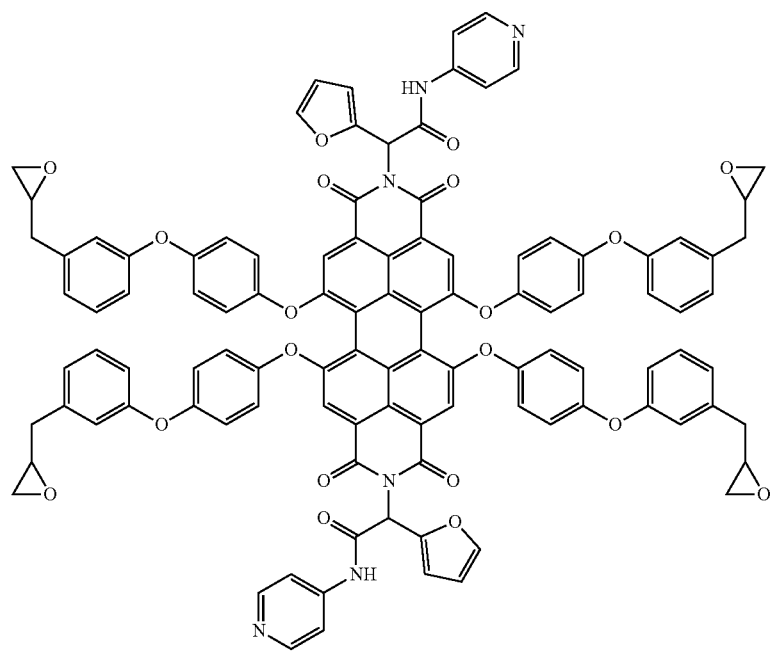
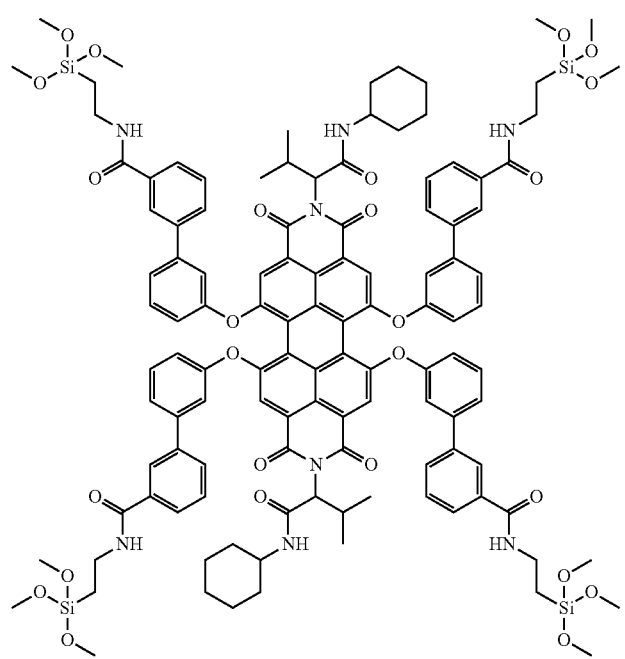

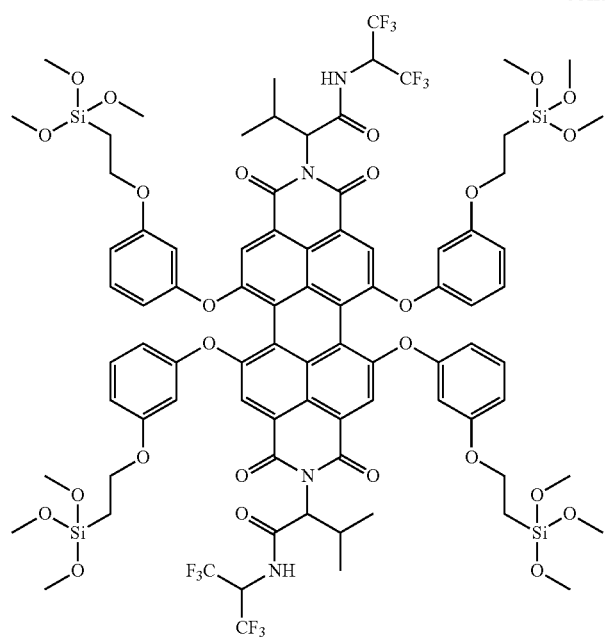
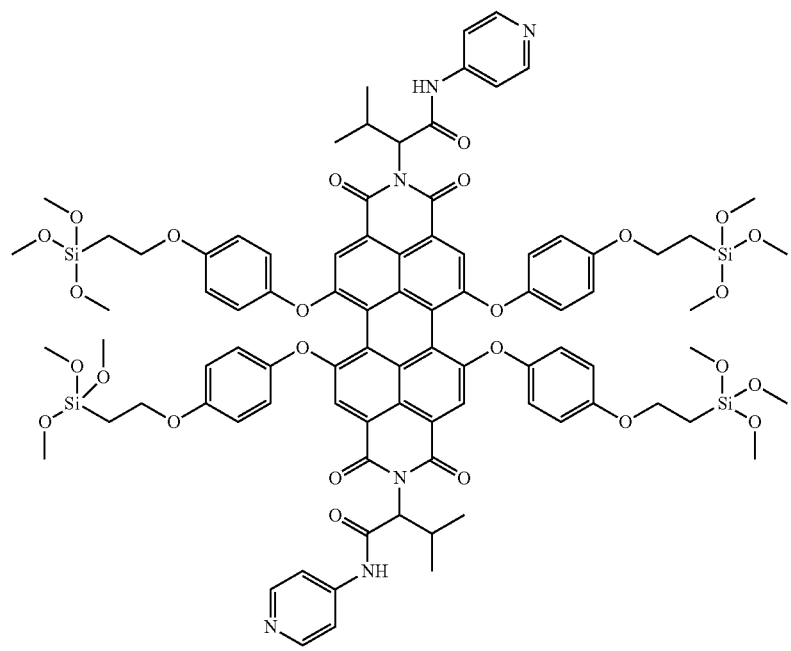

-continued
551
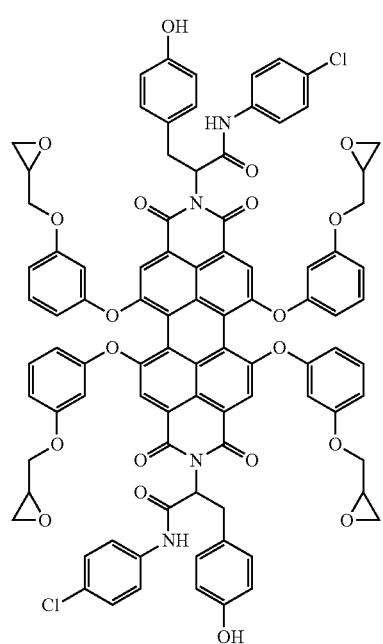
552
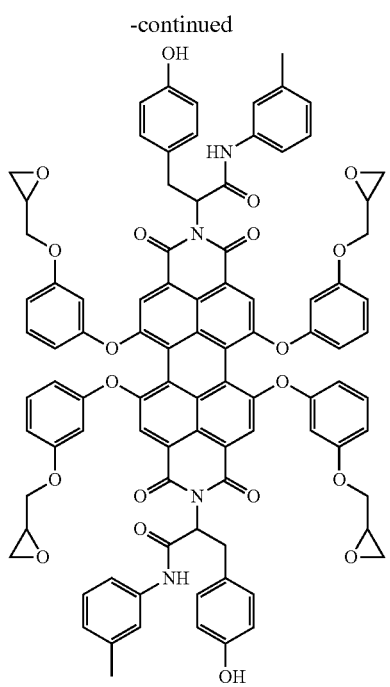
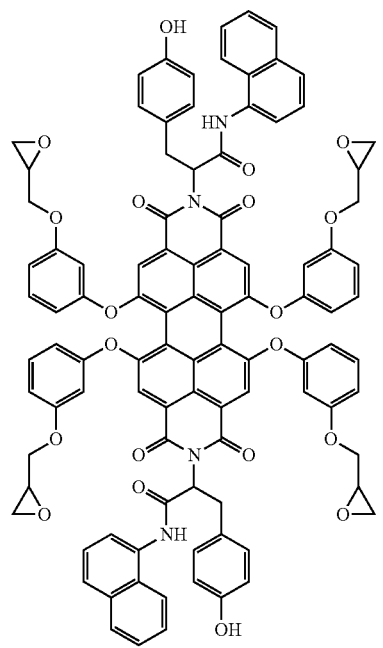
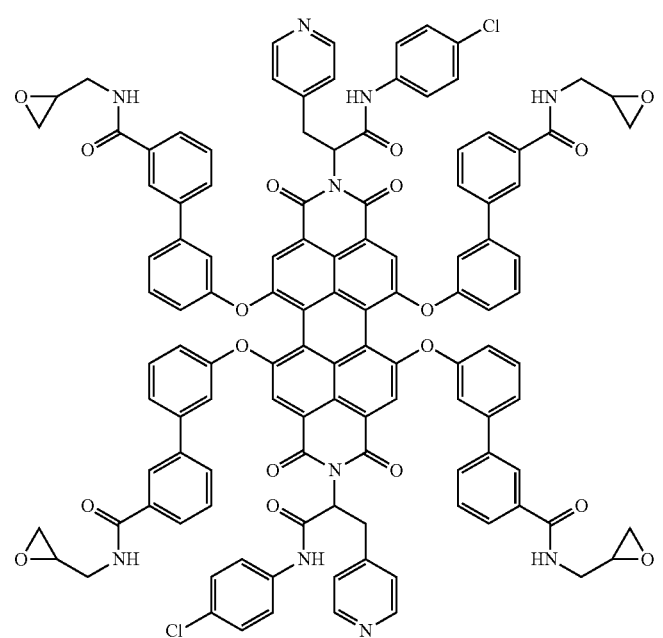

553 554
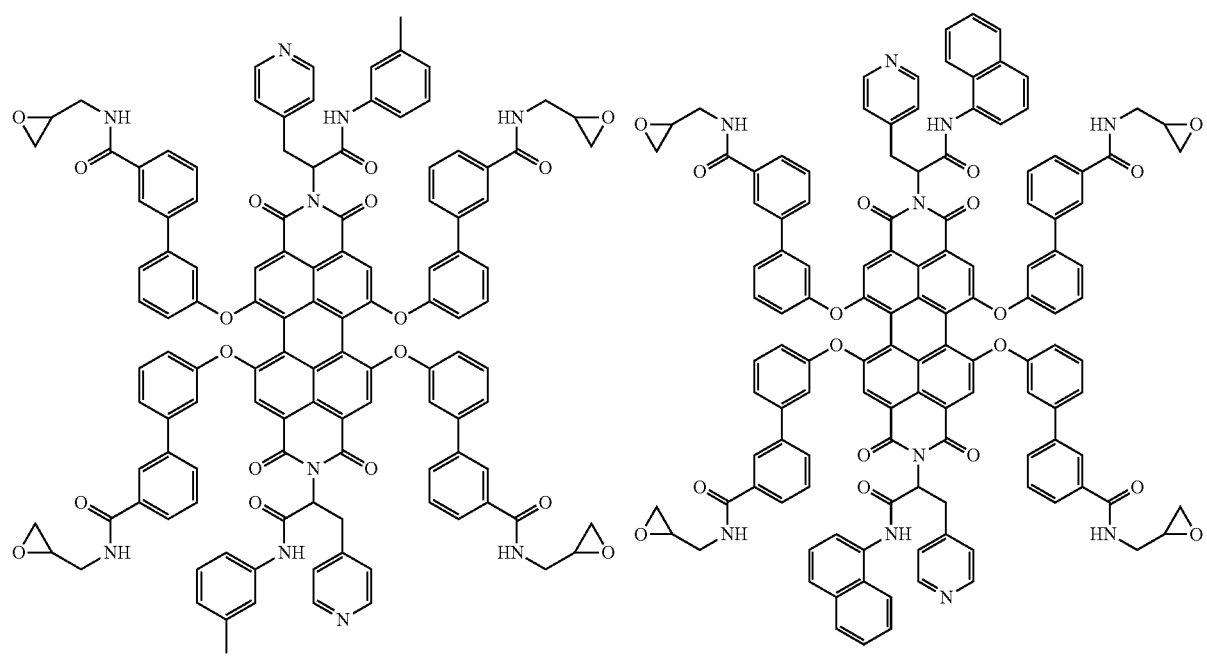
-continued
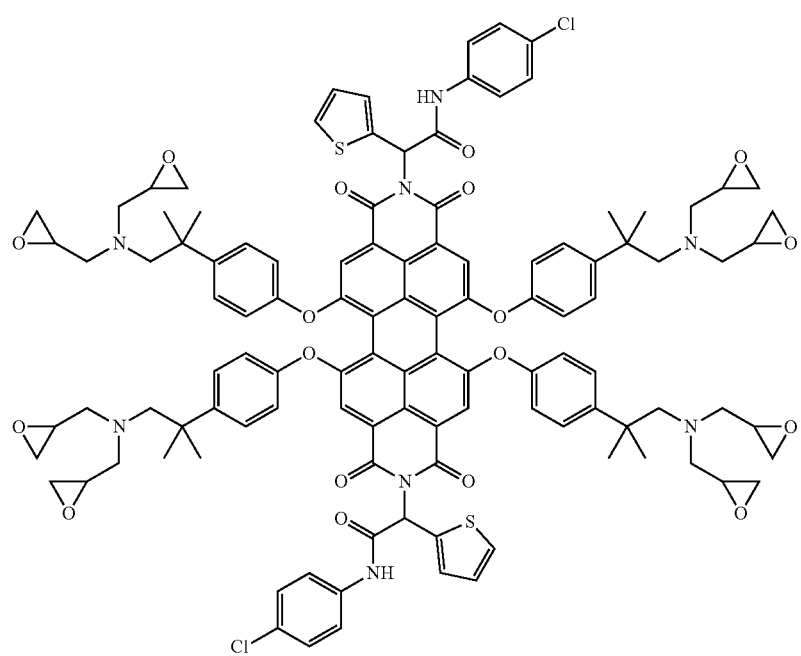

555 556
-continued
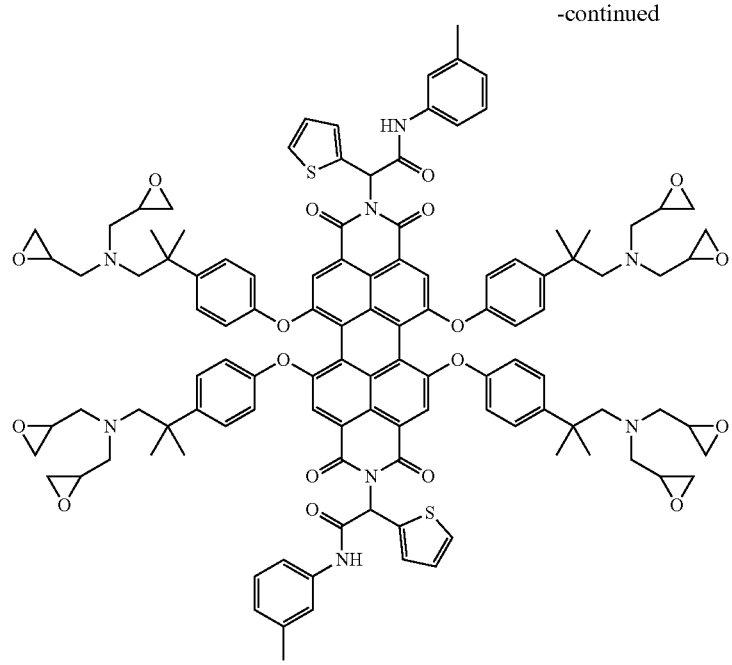
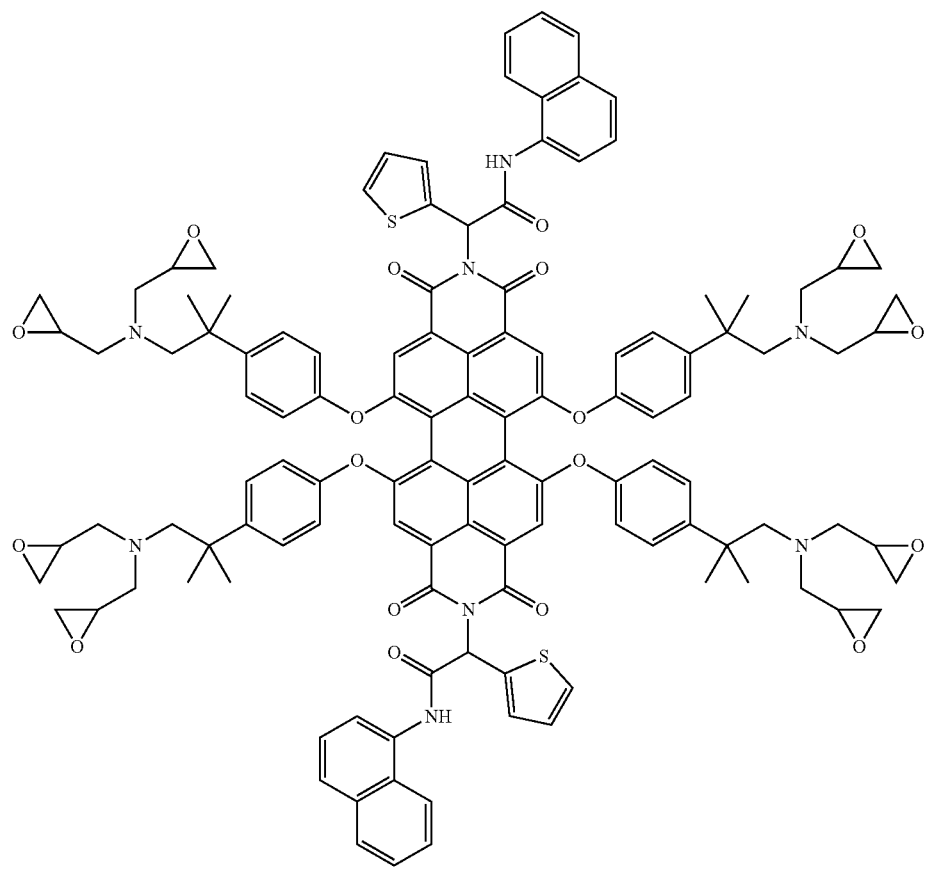

-continued
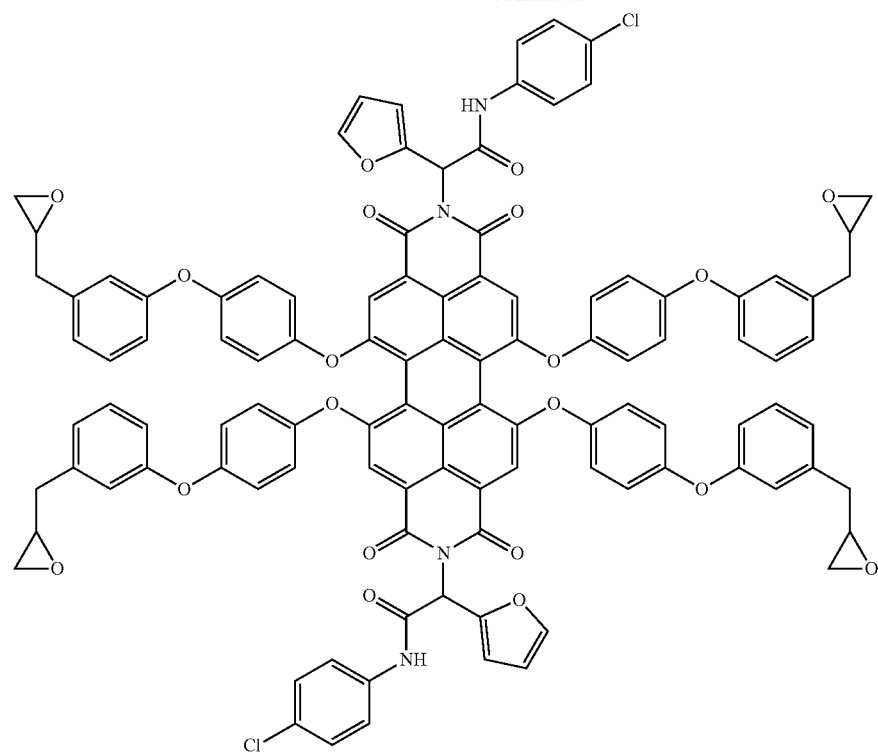
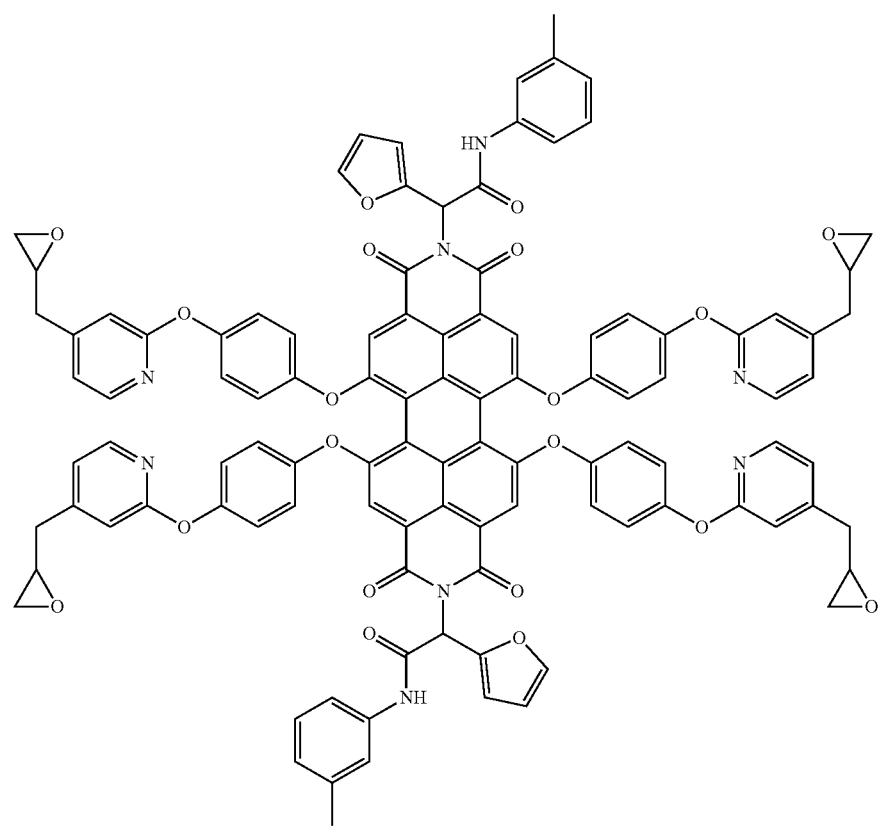

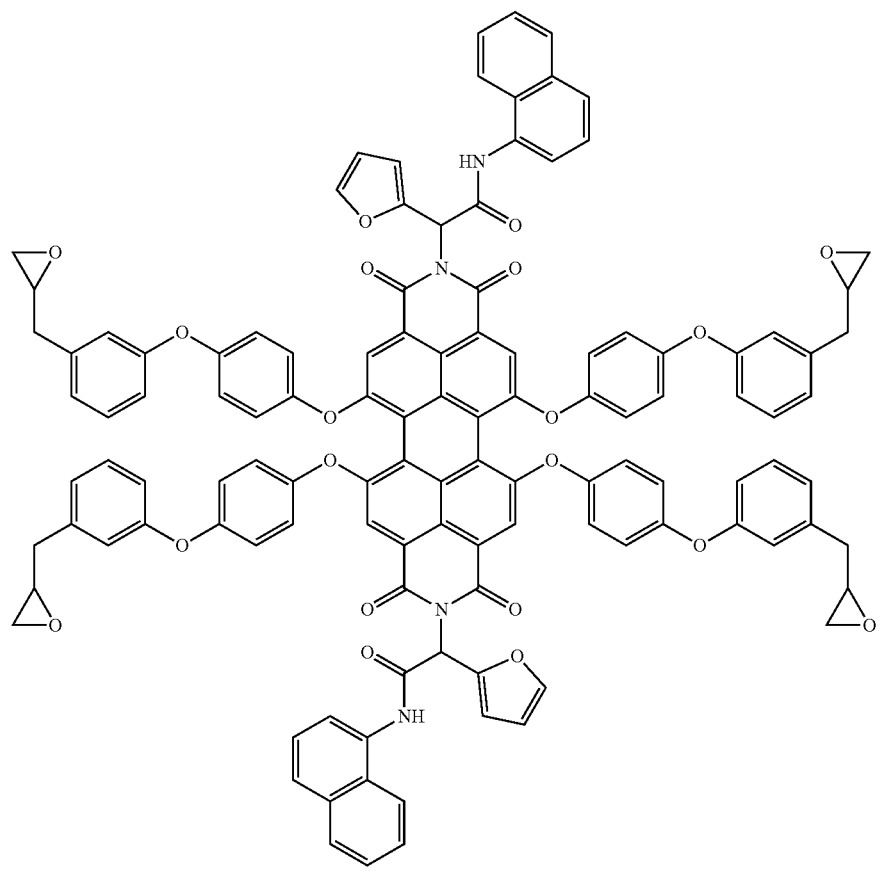
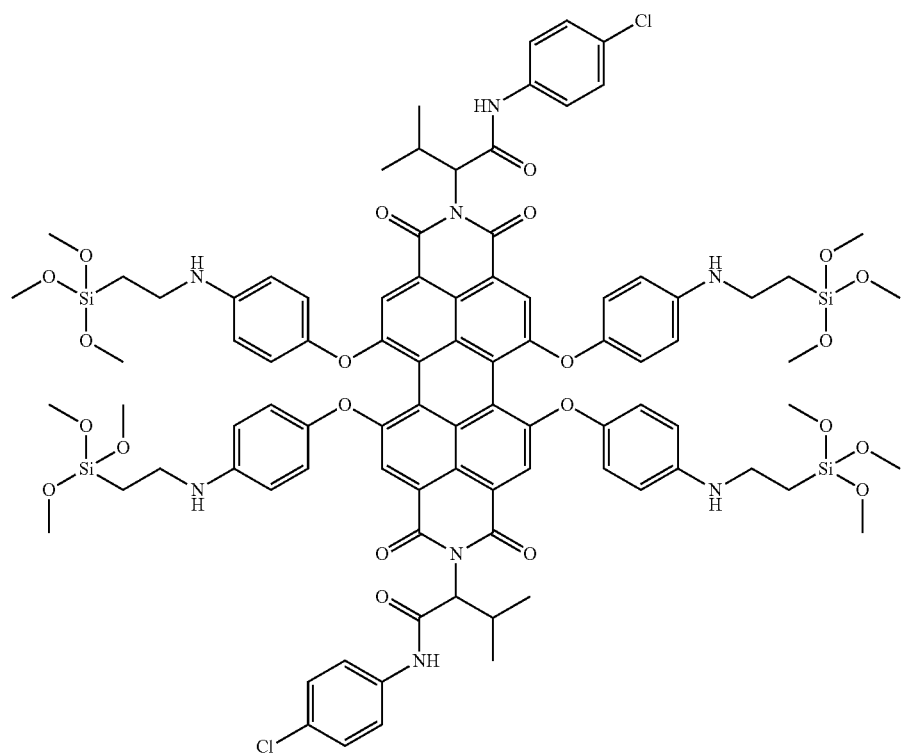

-continued
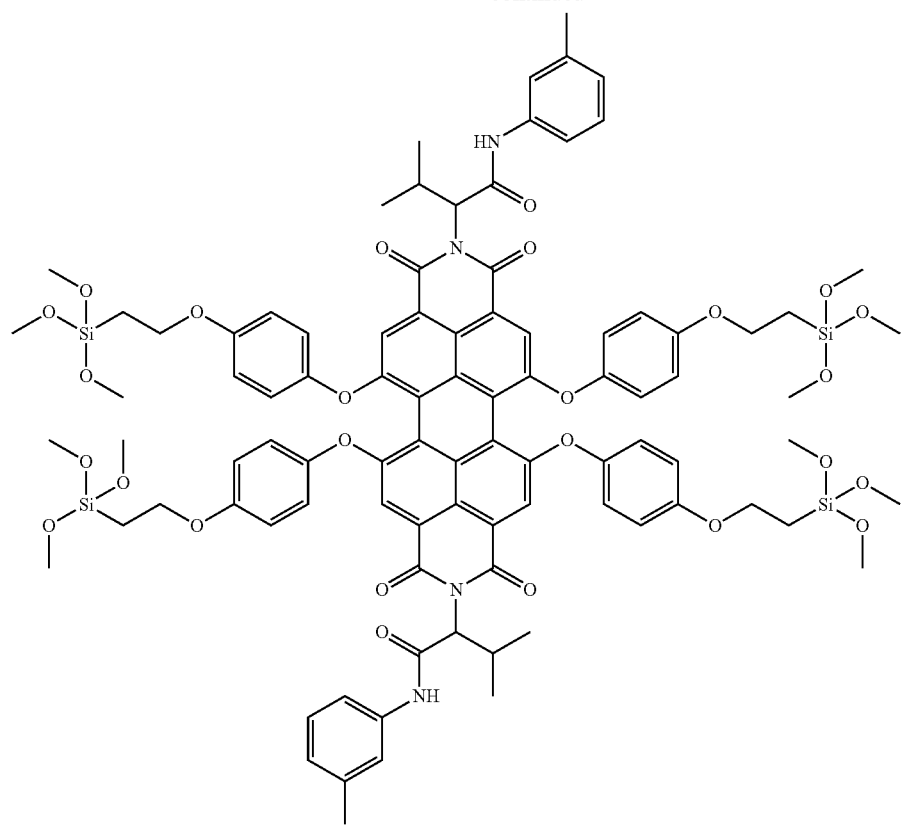
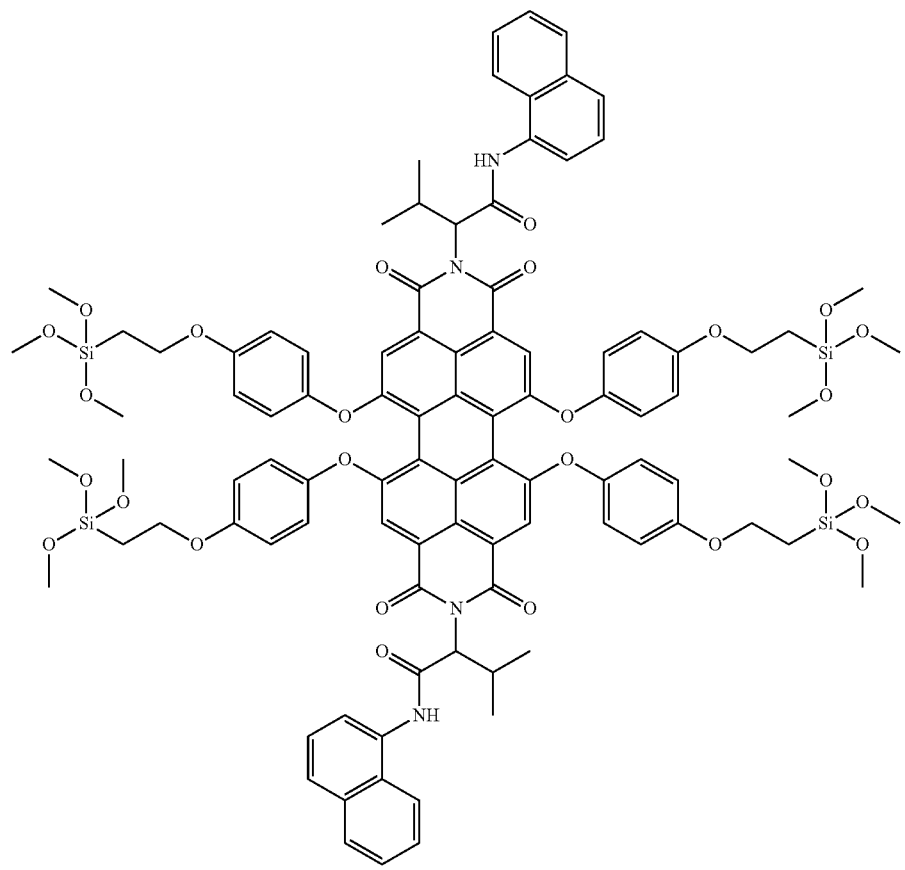

-continued
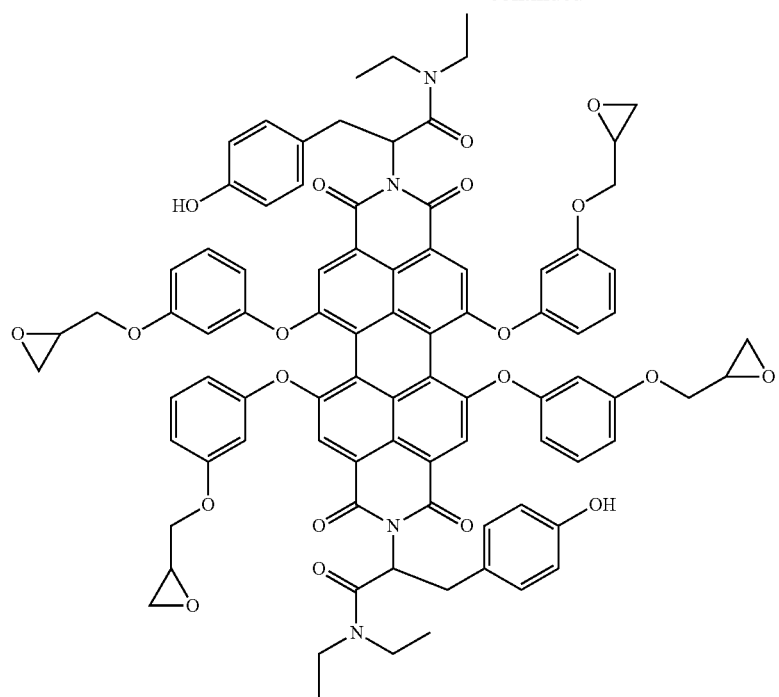
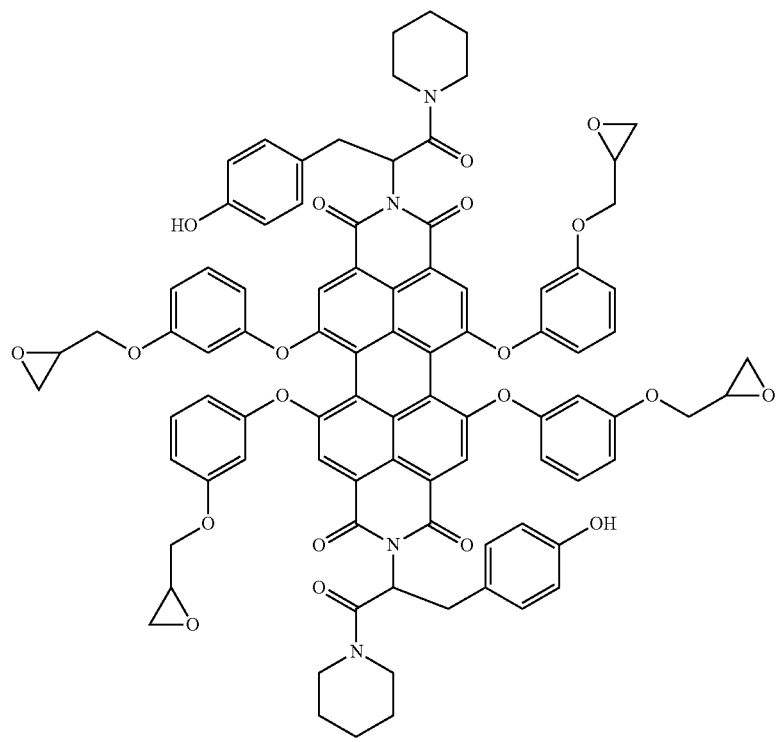

-continued
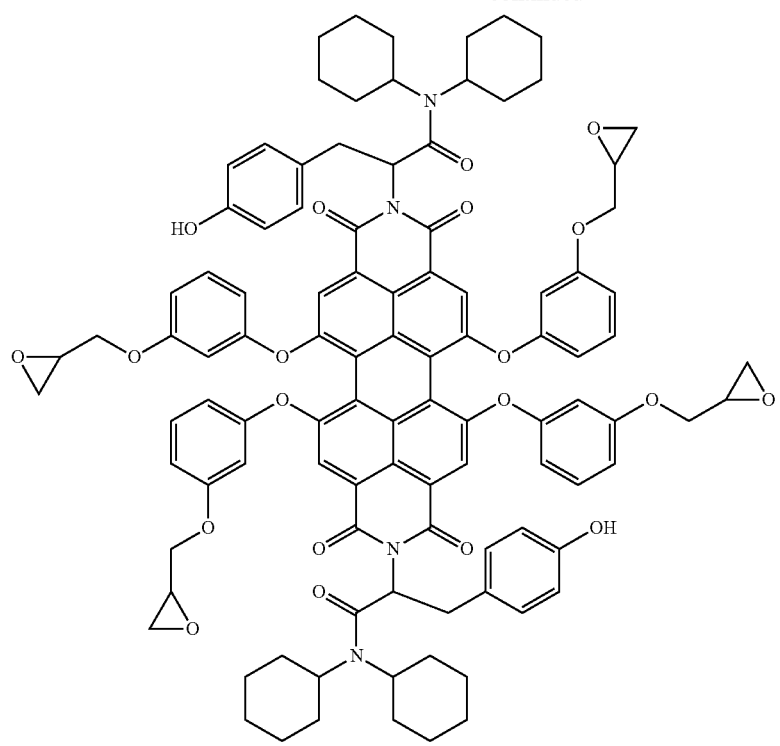
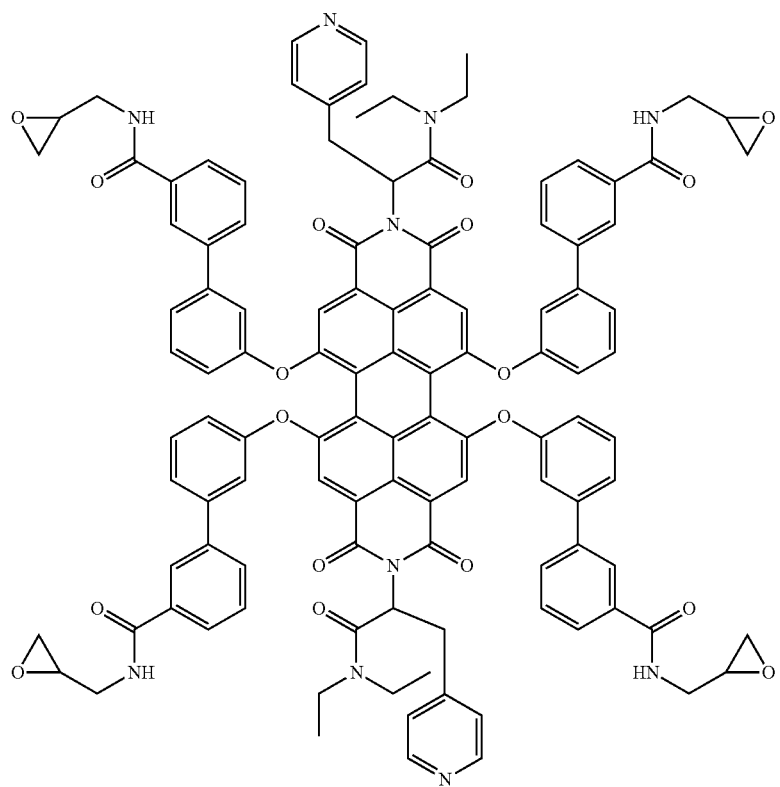

567
-continued
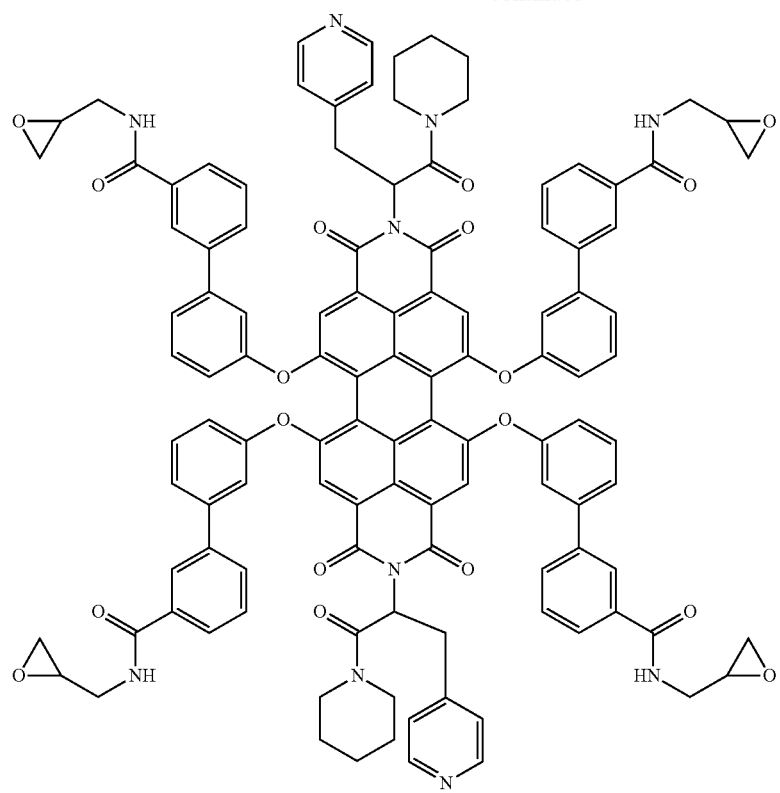
568
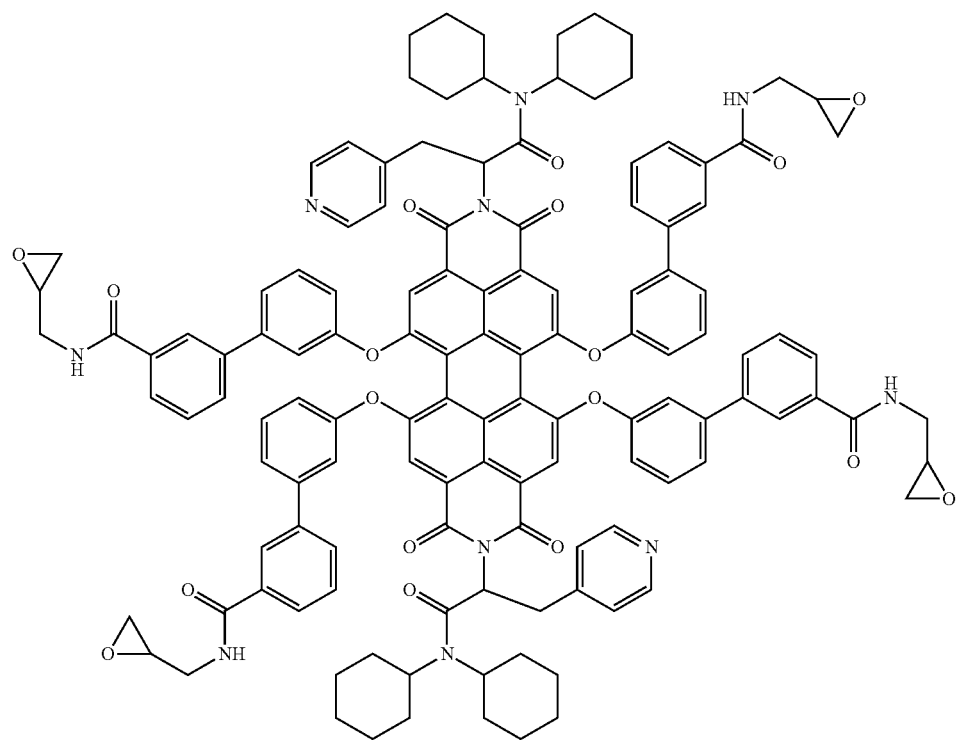

-continued
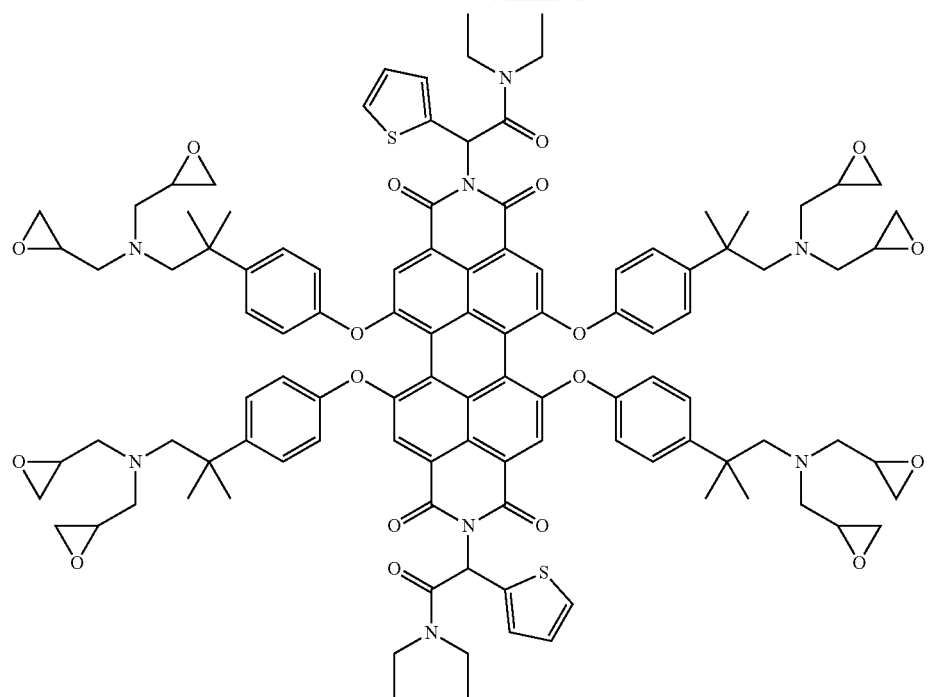
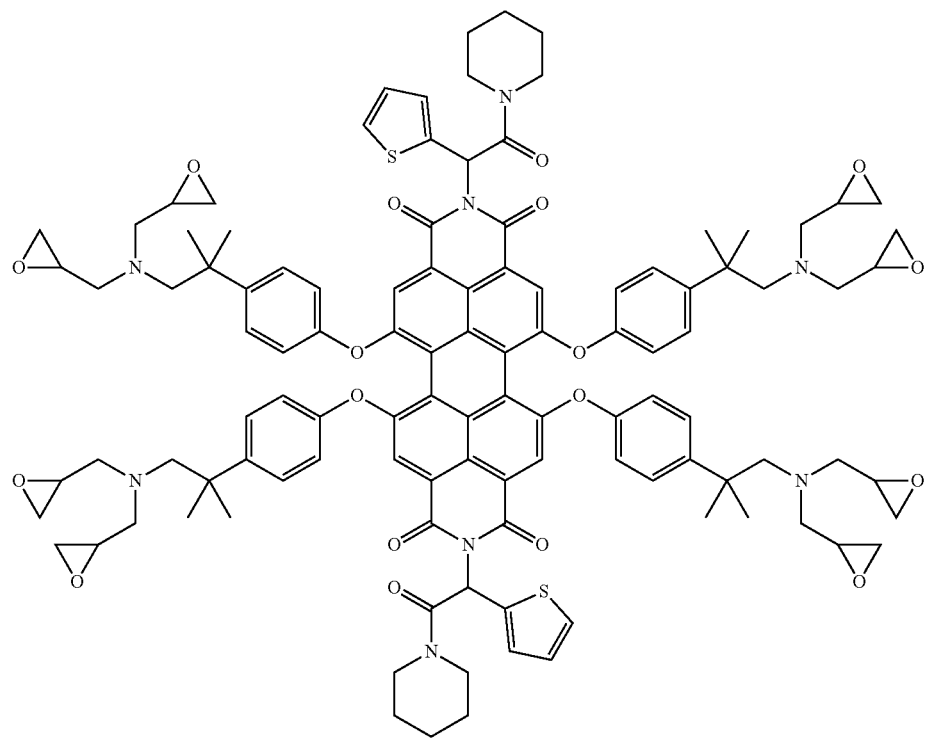

-continued
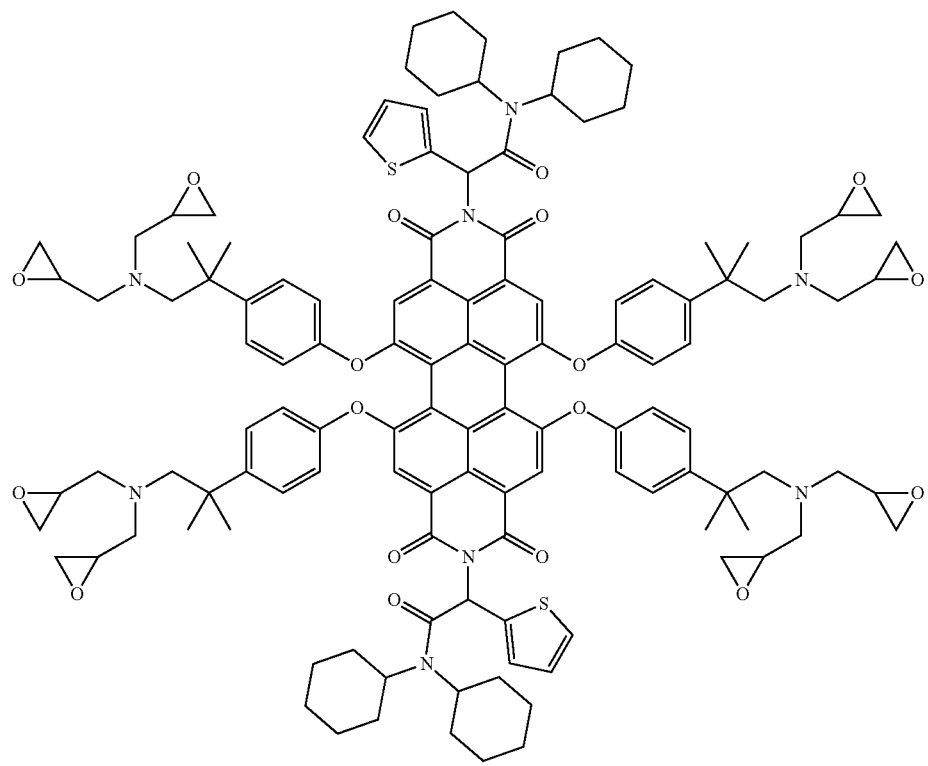
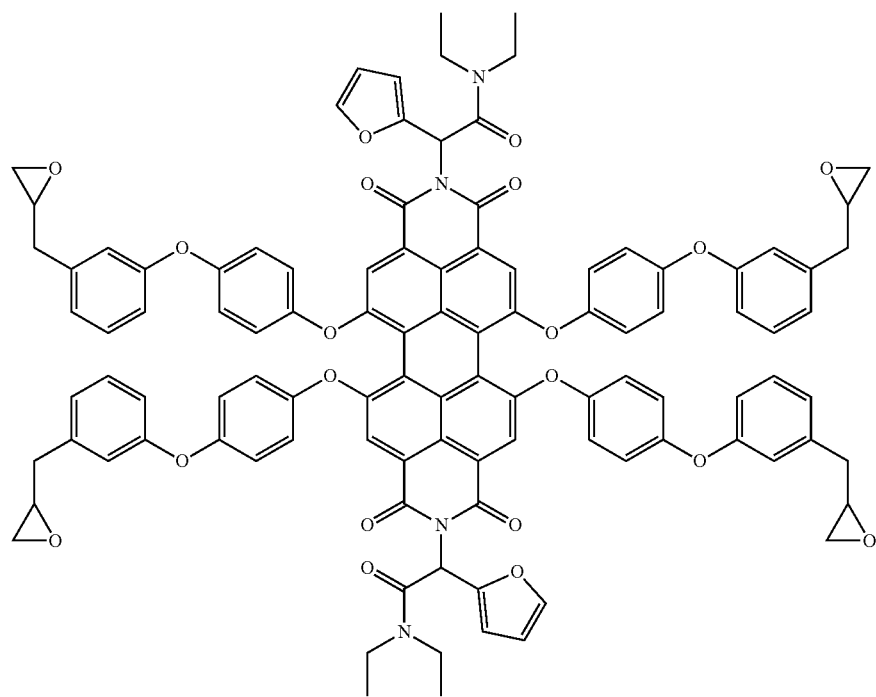

-continued
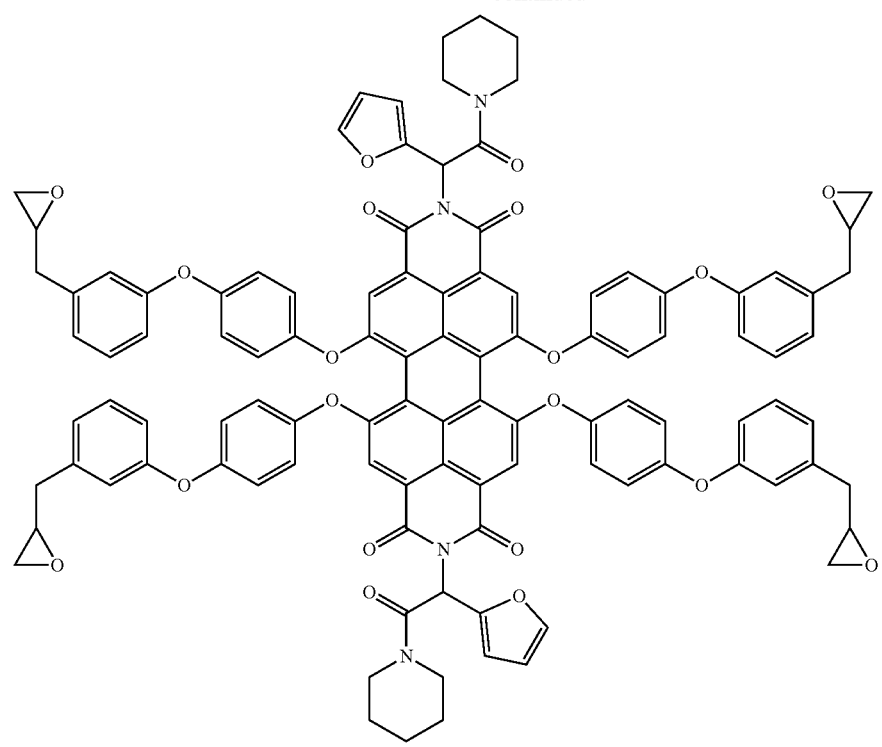
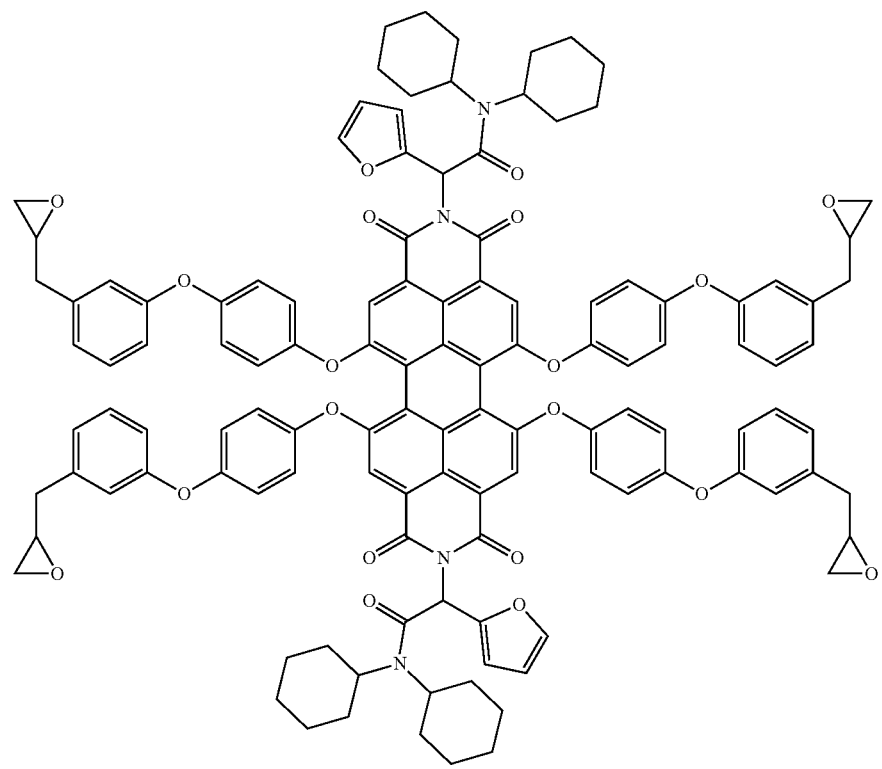

-continued
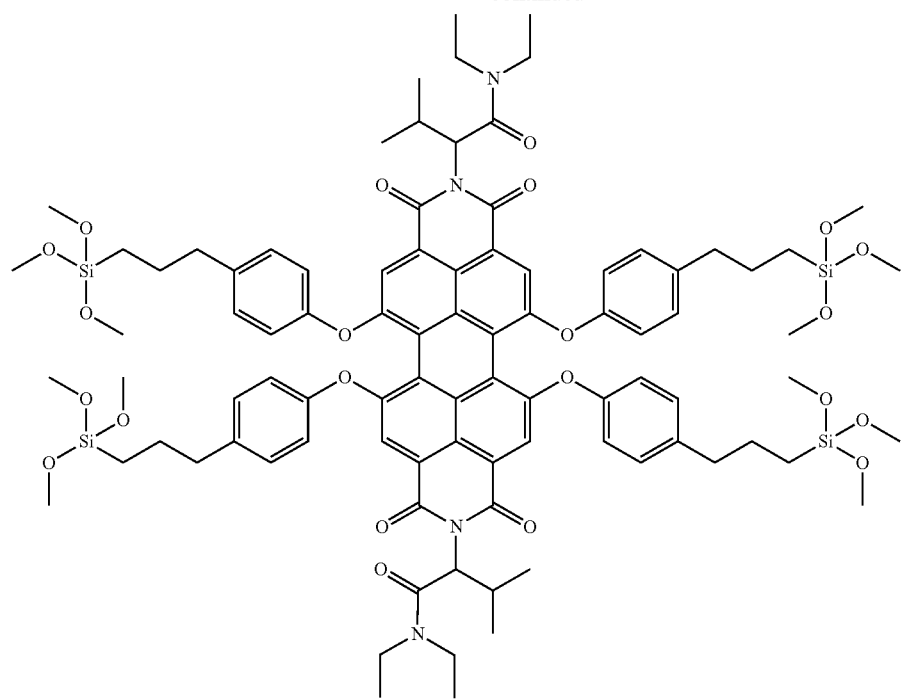
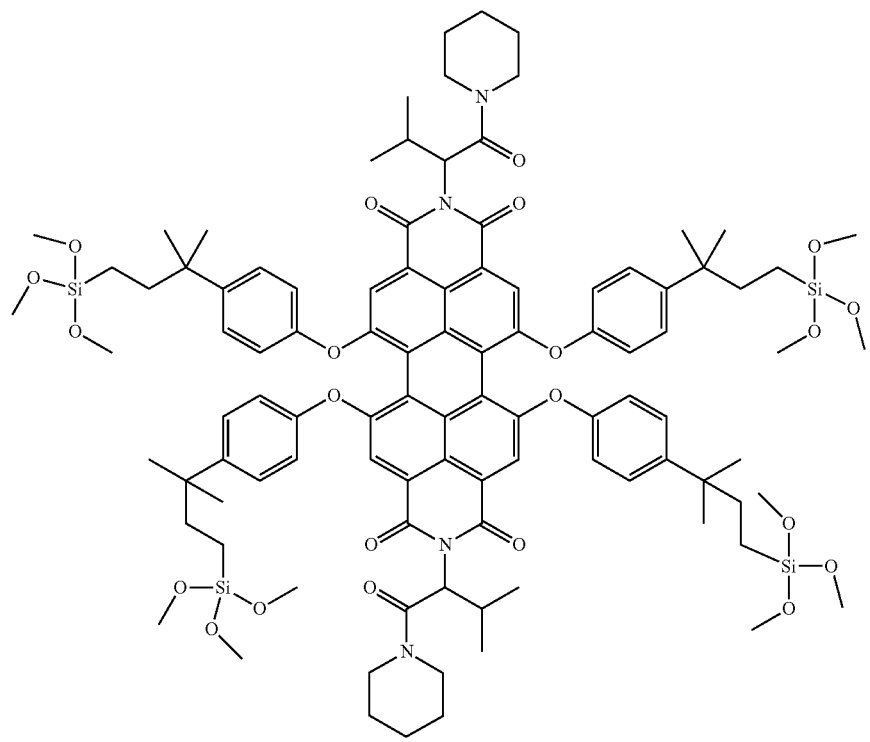

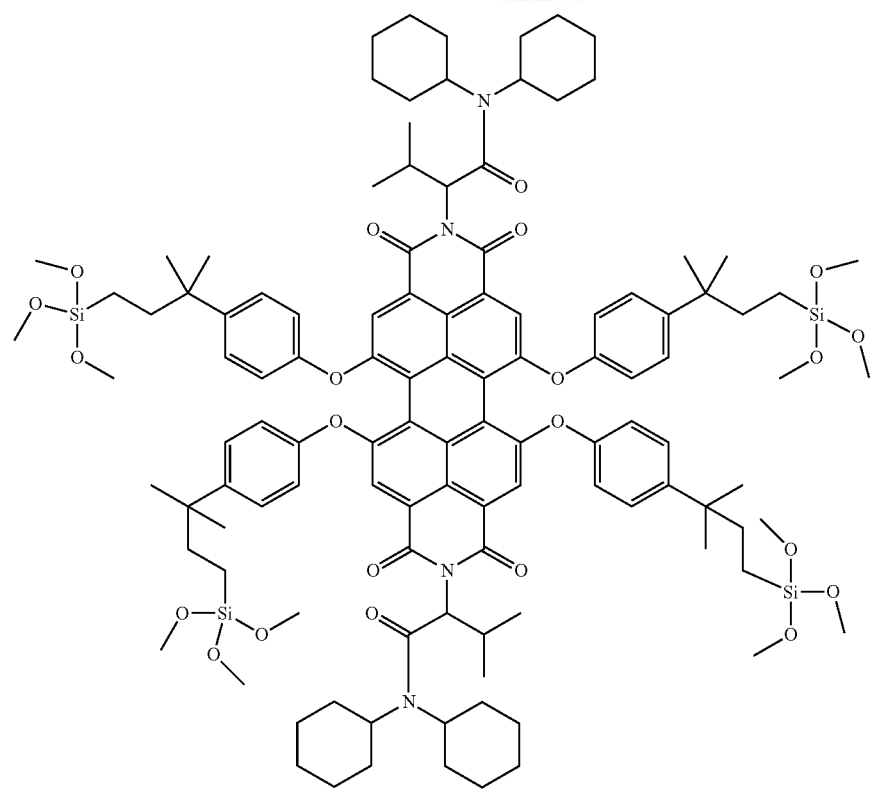
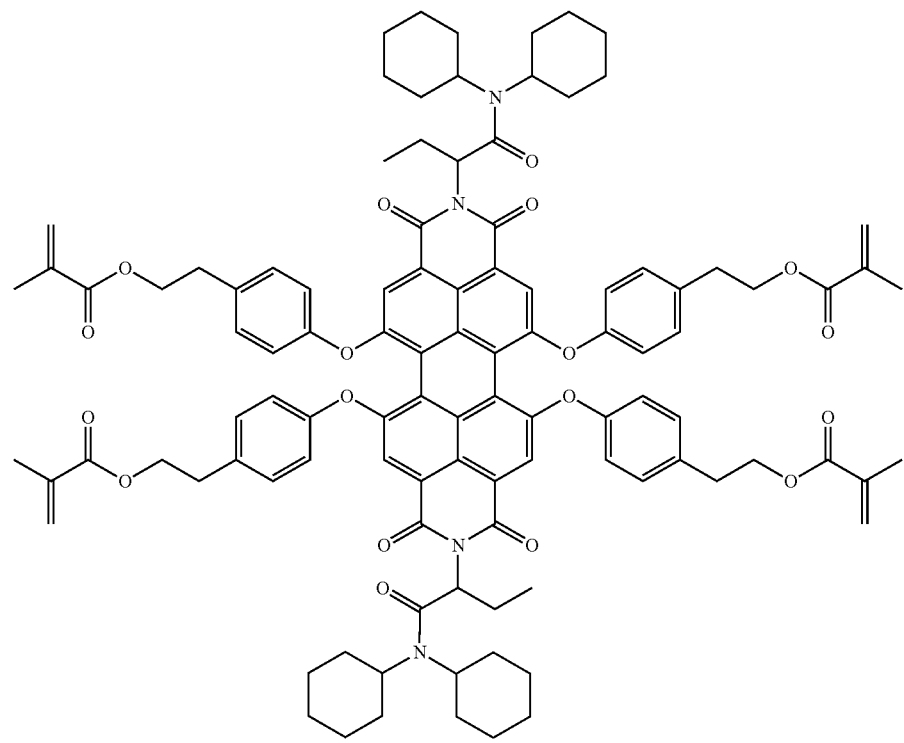

-continued
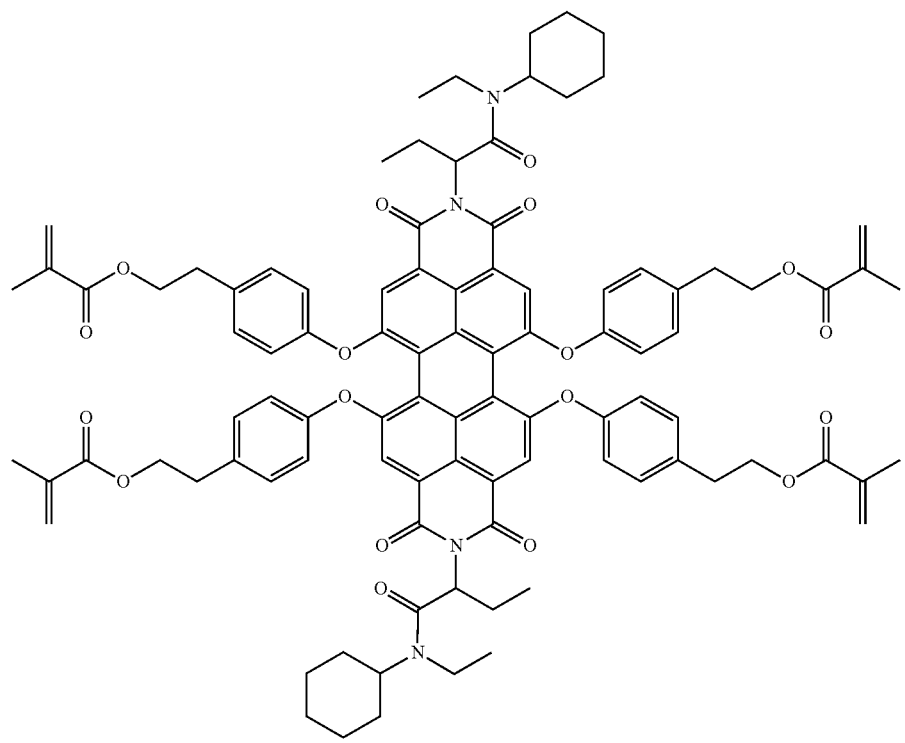
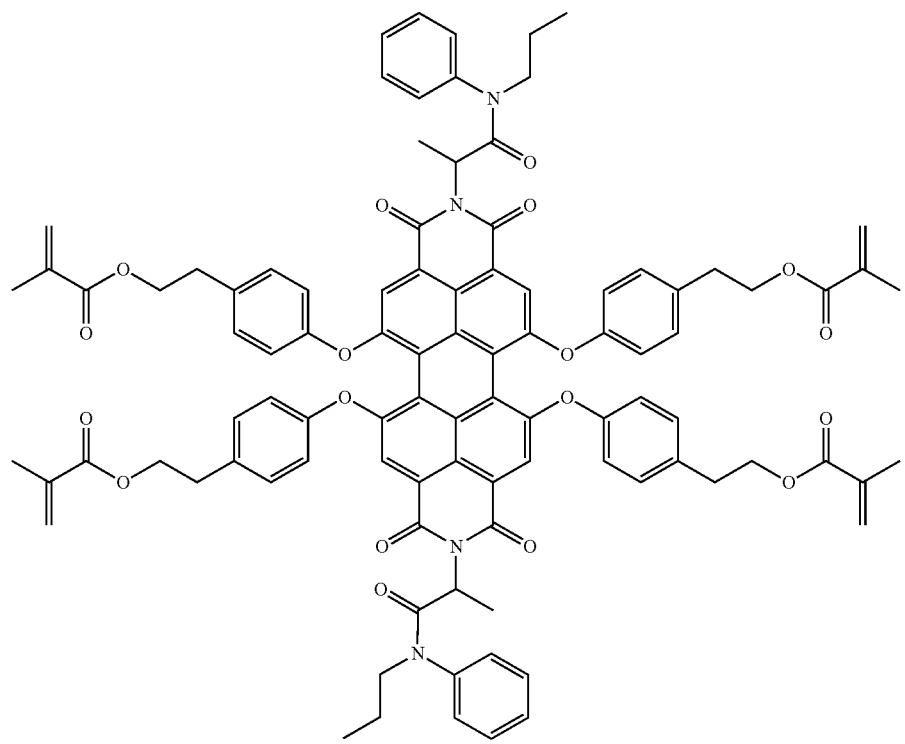

-continued
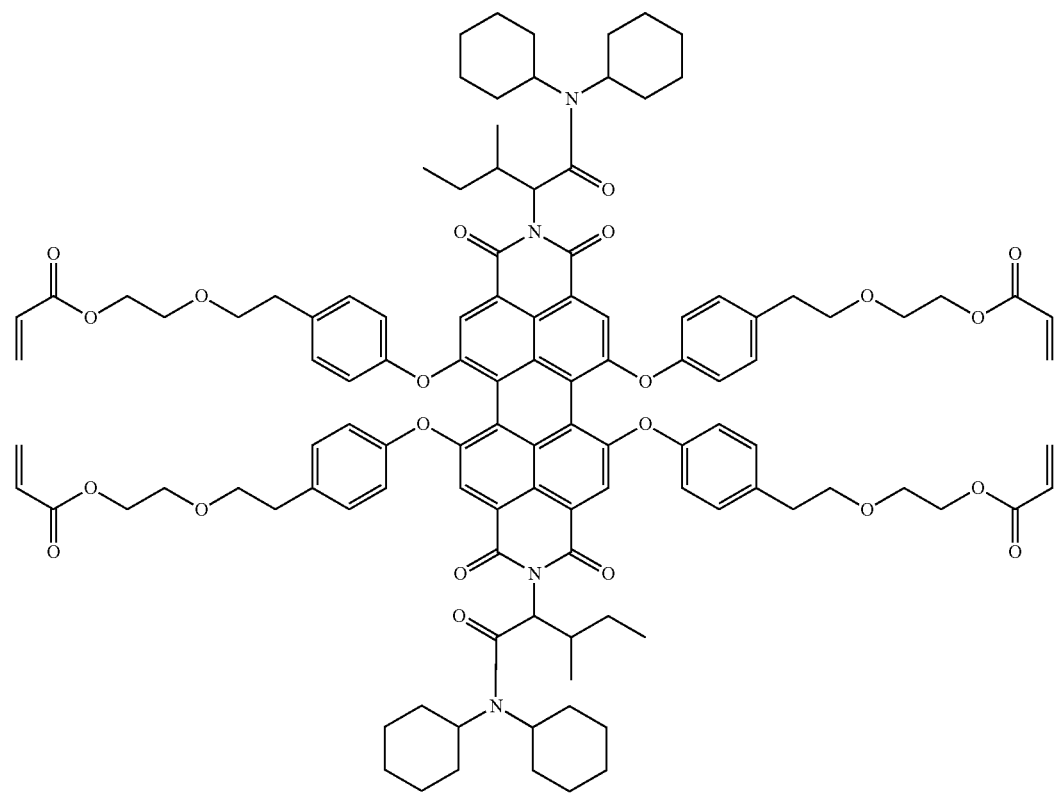
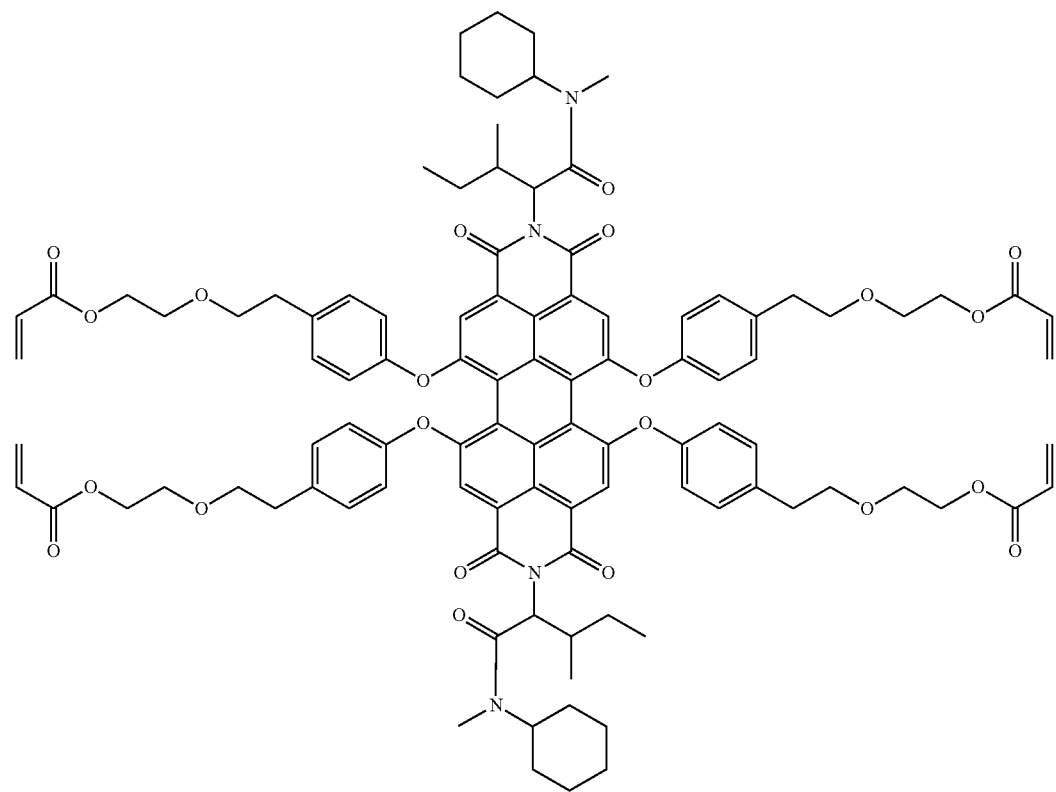

-continued
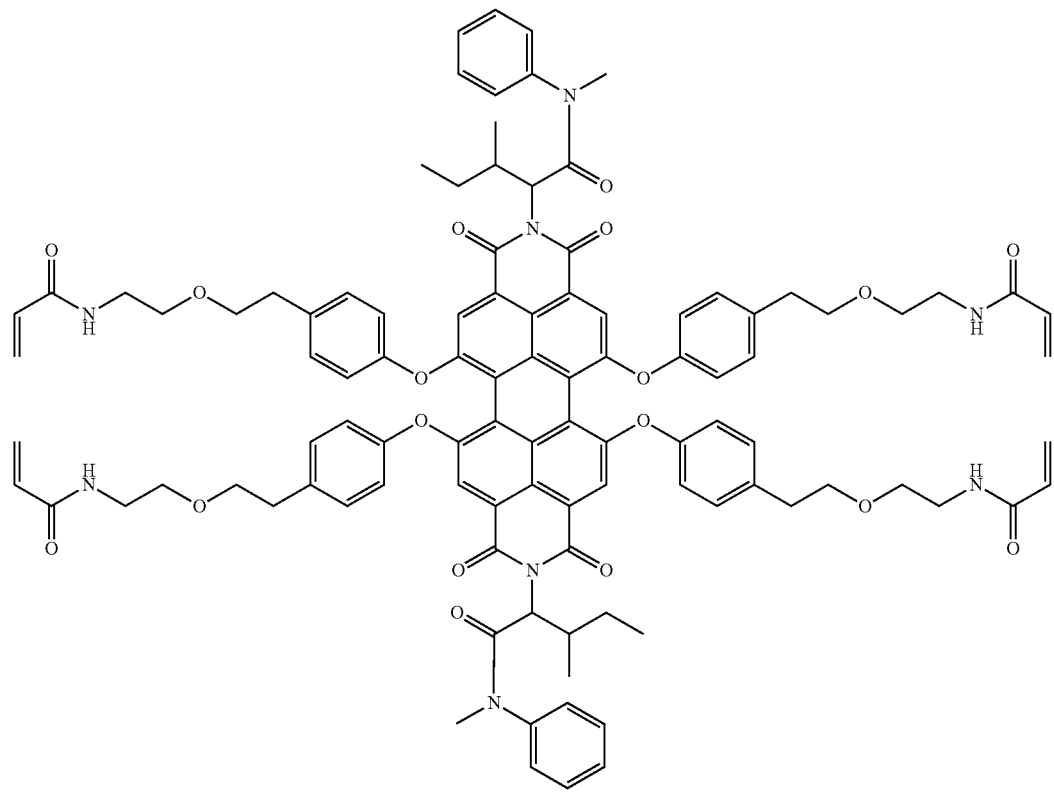
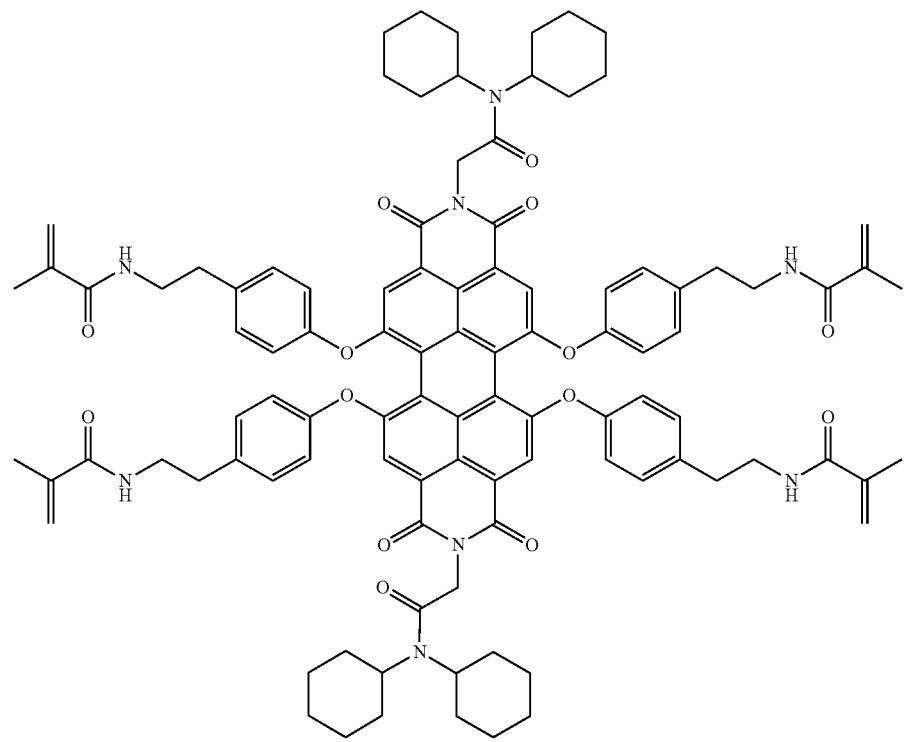

-continued
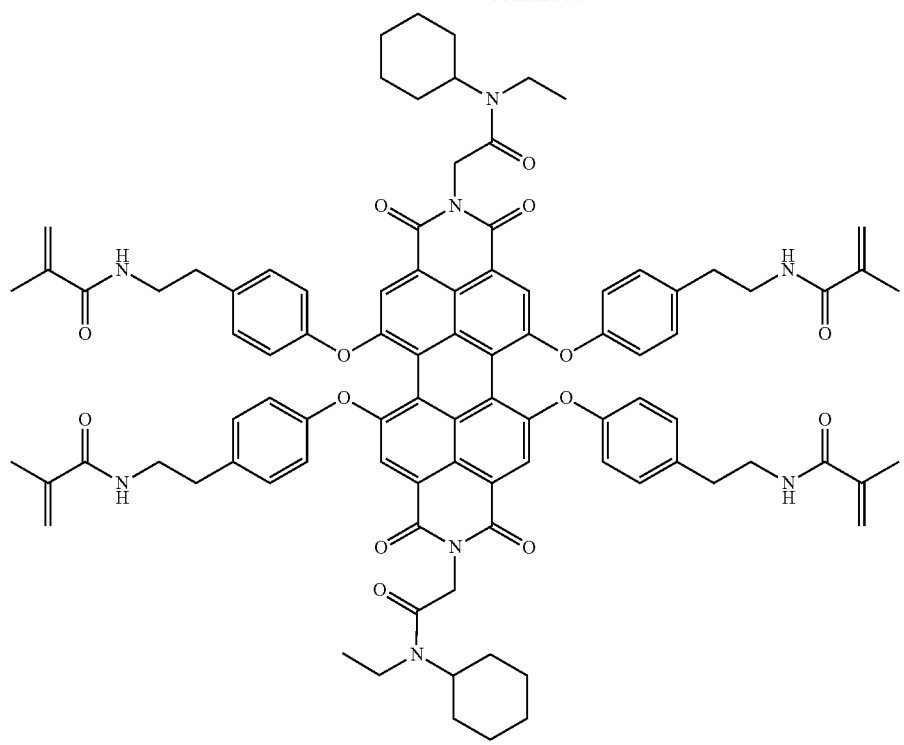
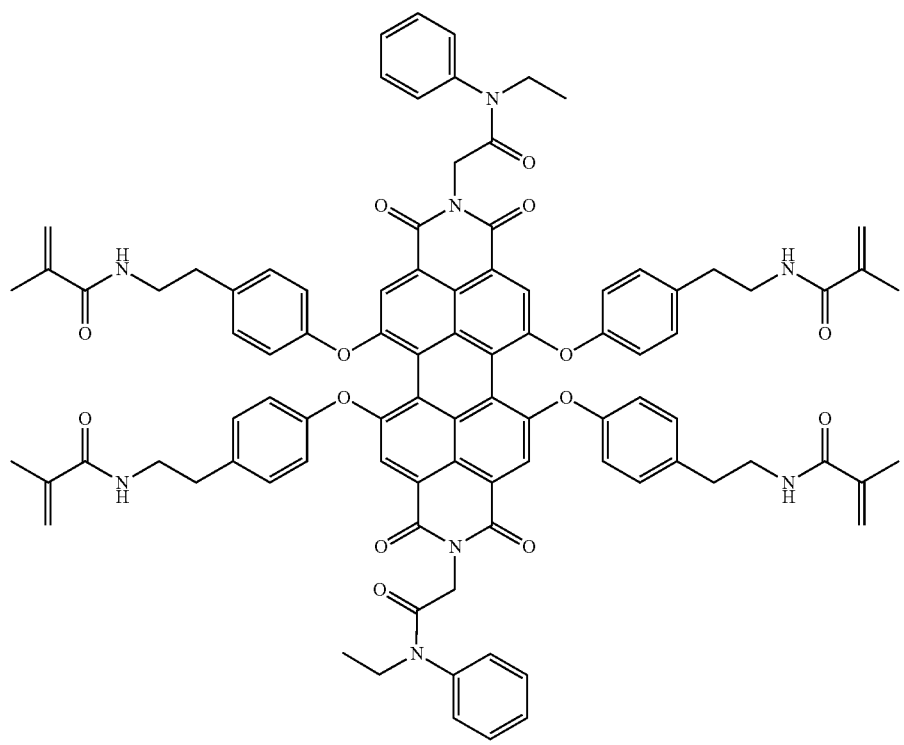

-continued
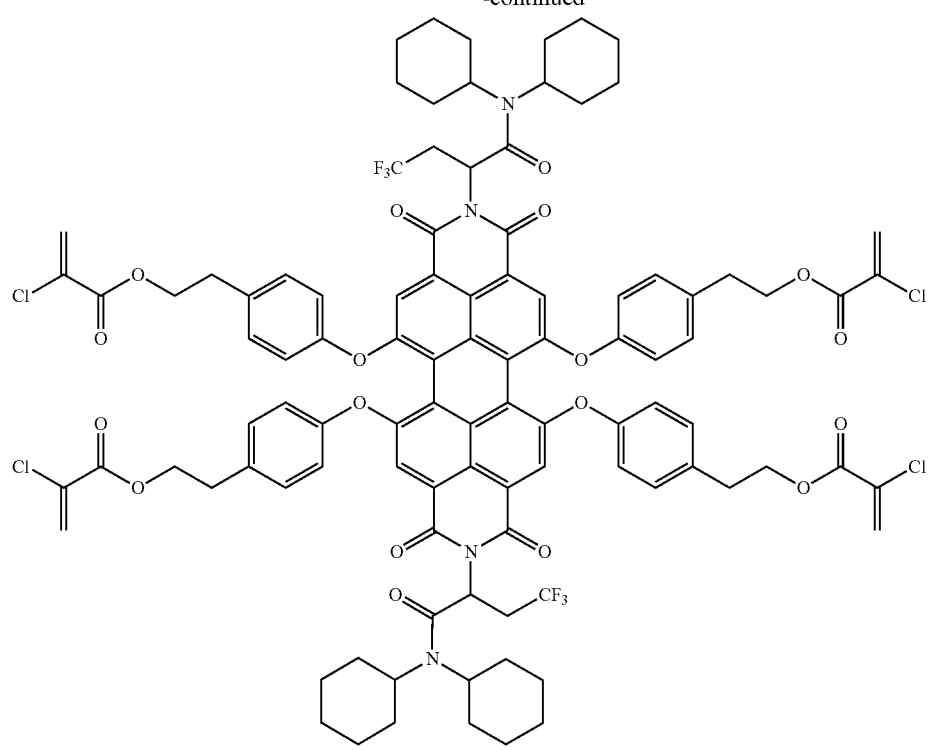
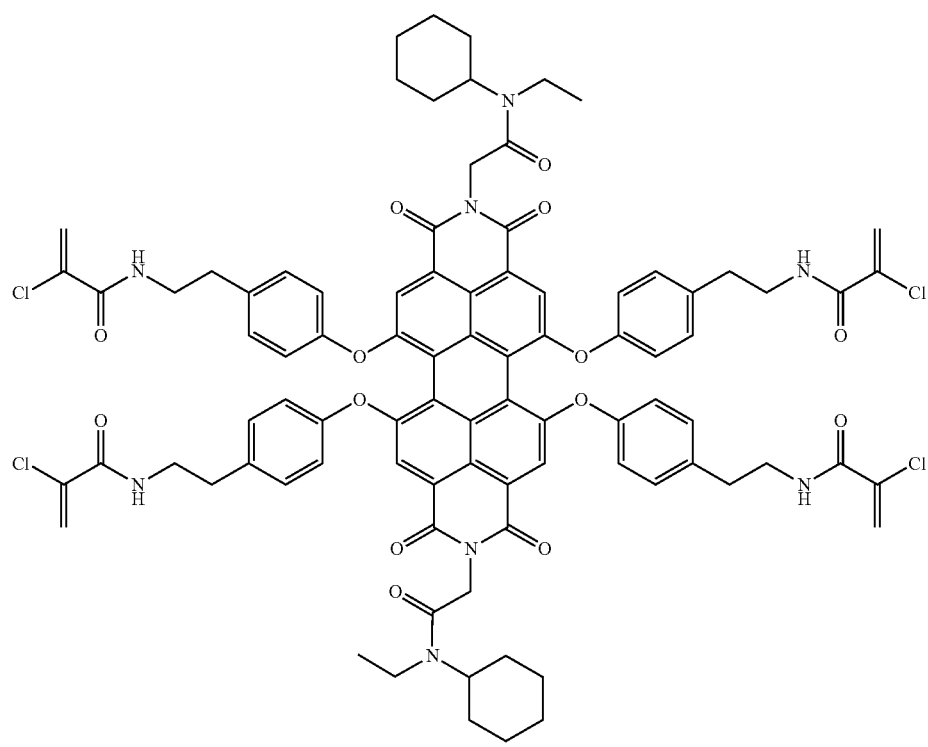

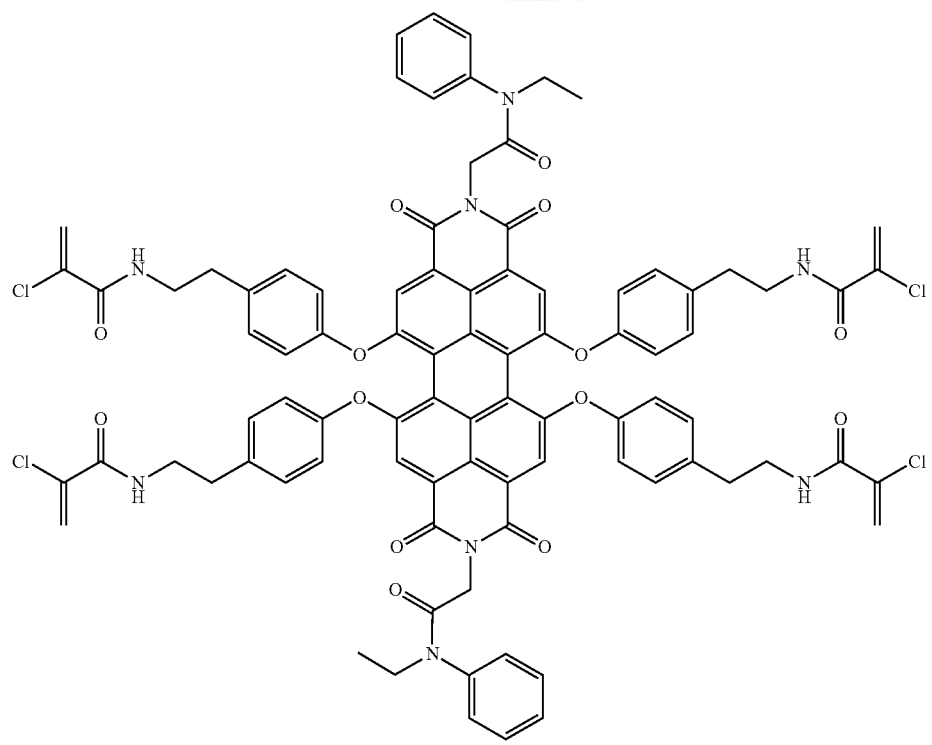
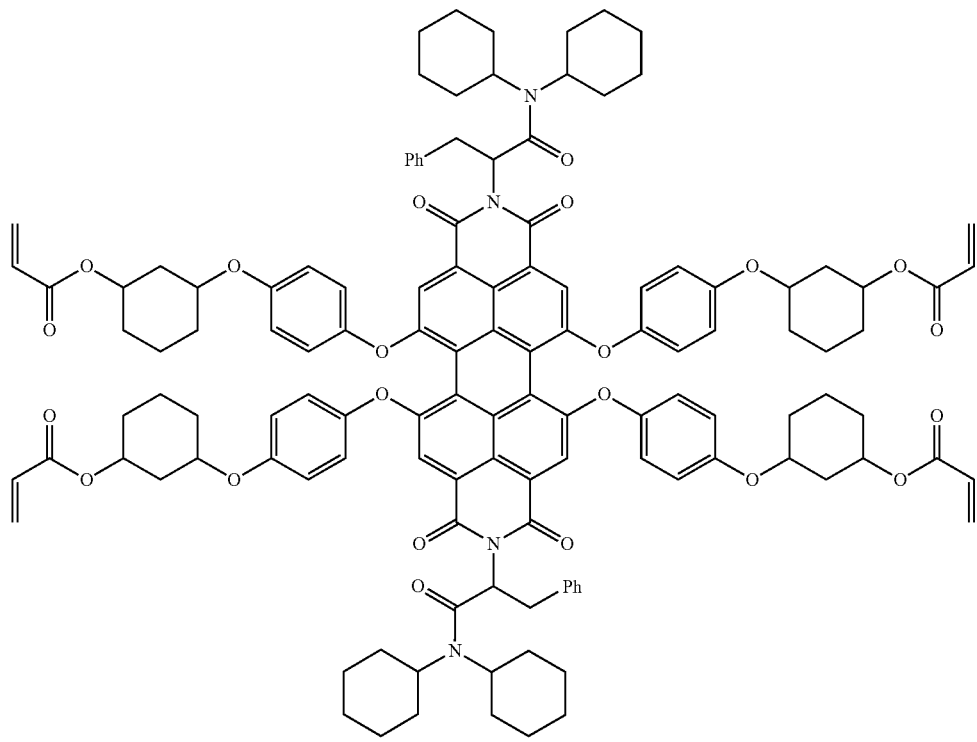 [SMILES: C=CC(=O)OC1CCCC(Oc2ccc(Oc3cc4c5c(cc(Oc6ccc(OC7CCCC(OC(=O)C=C)C7)cc6)c6c7c(Oc8ccc(OC9CCCC(OC(=O)C=C)C9)cc8)cc8c9c(cc(Oc%10ccc(OC%11CCCC(OC(=O)C=C)C%11)cc%10)c(c3c56)c97)C(=O)N(C(Cc3ccccc3)C(=O)N(C3CCCCC3)C3CCCCC3)C8=O)C(=O)N(C(Cc3ccccc3)C(=O)N(C3CCCCC3)C3CCCCC3)C4=O)cc2)C1]

-continued
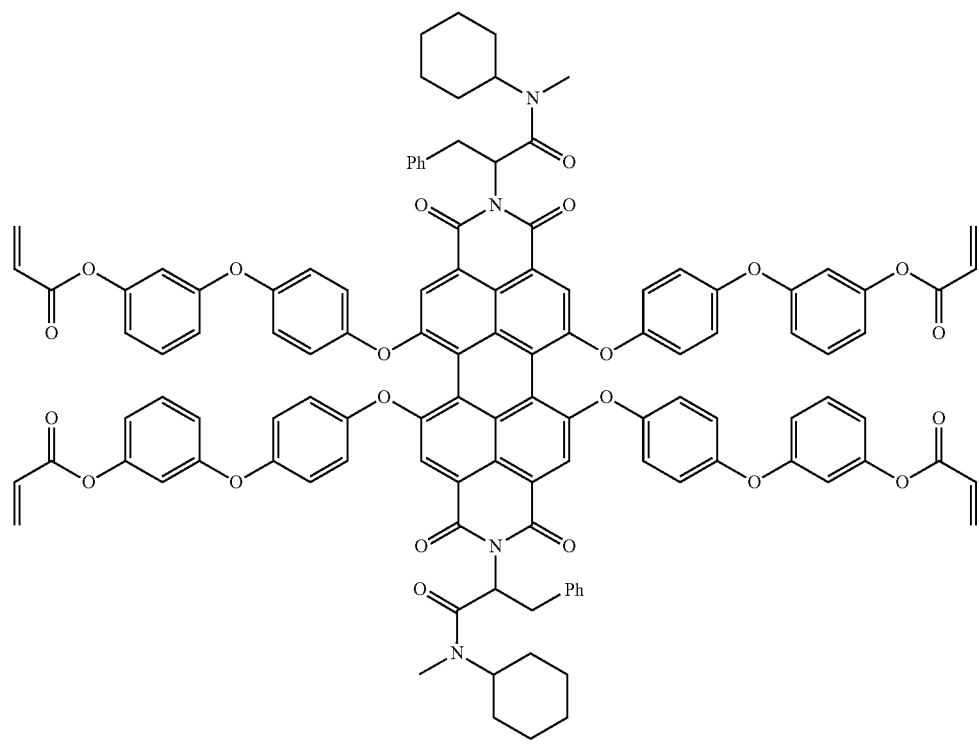
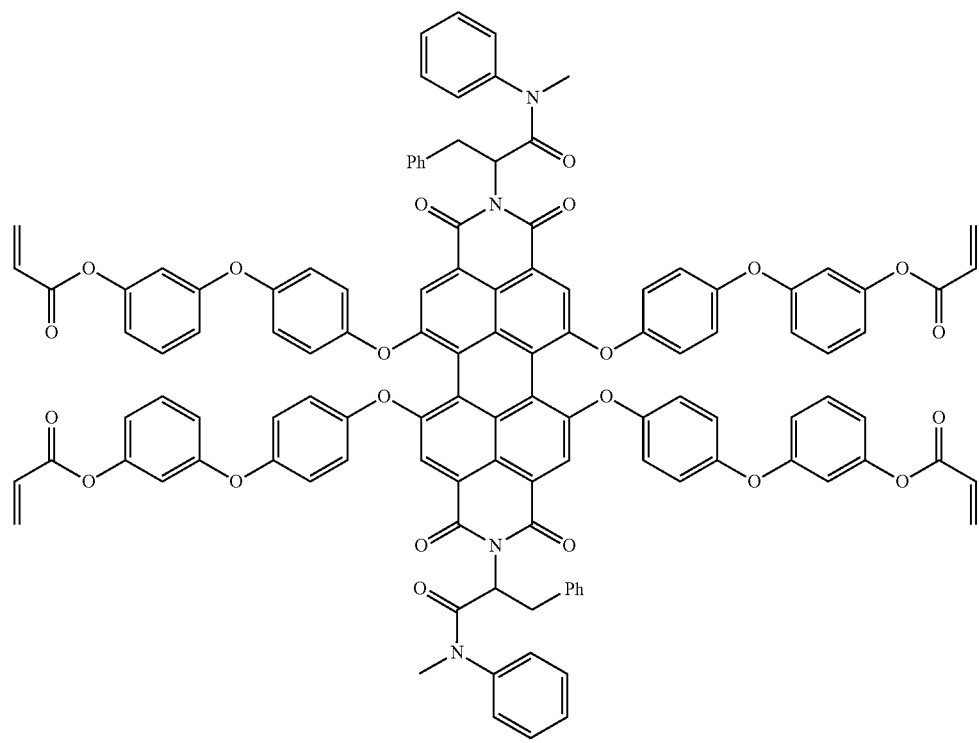 [SMILES: C=CC(=O)Oc1cccc(Oc2ccc(Oc3cc4c5c(cc(Oc6ccc(Oc7cccc(OC(=O)C=C)c7)cc6)c6c7c(Oc8ccc(Oc9cccc(OC(=O)C=C)c9)cc8)cc8c9c(cc(Oc%10ccc(Oc%11cccc(OC(=O)C=C)c%11)cc%10)c(c3c56)c97)C(=O)N(C(Cc3ccccc3)C(=O)N(C)c3ccccc3)C8=O)C(=O)N(C(Cc3ccccc3)C(=O)N(C)c3ccccc3)C4=O)cc2)c1]

593
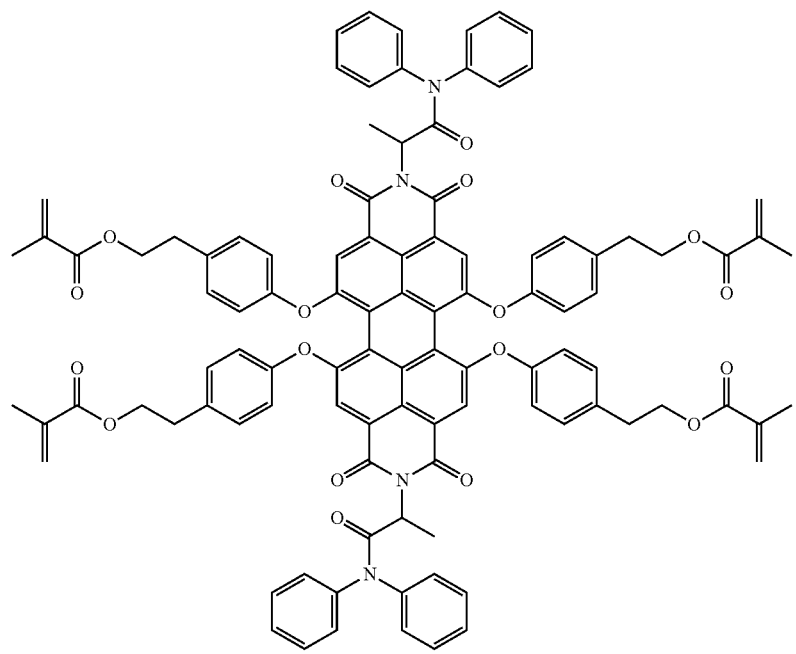
594
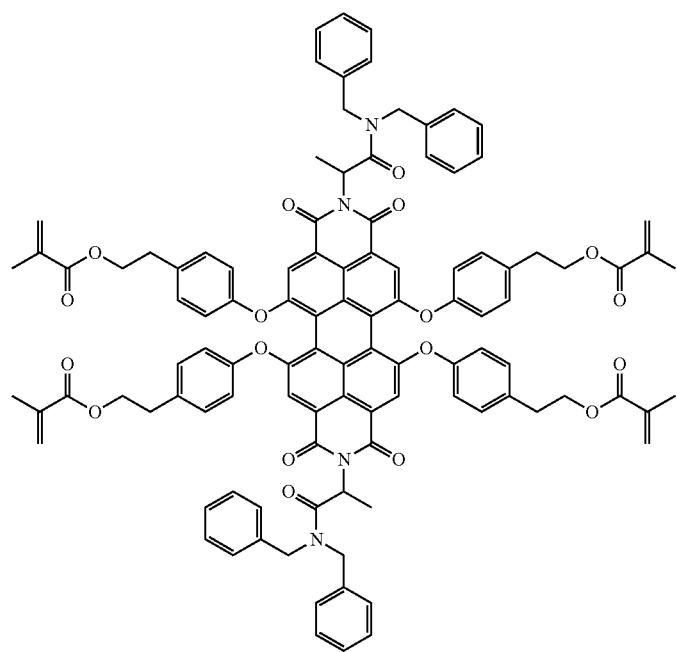

-continued
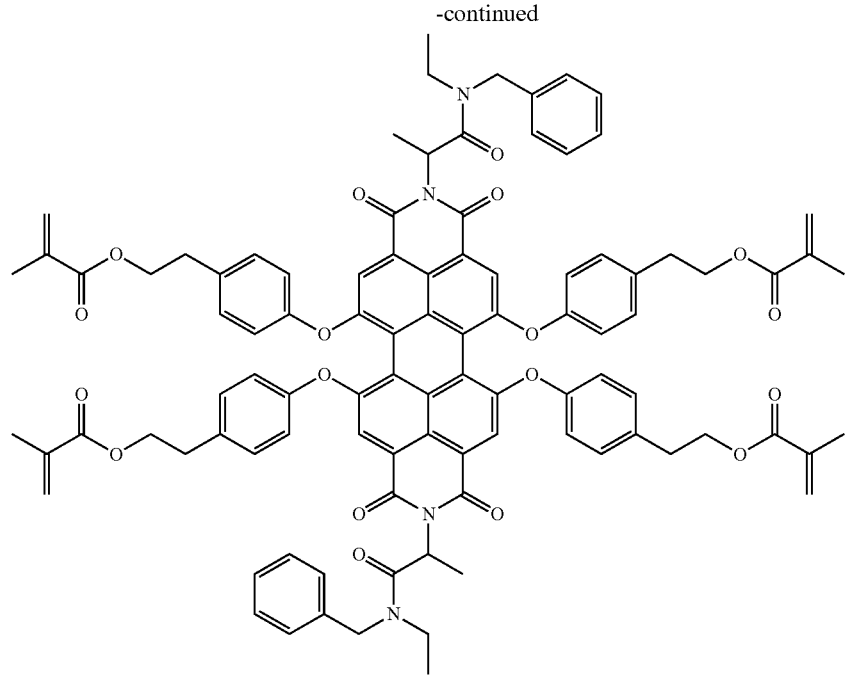
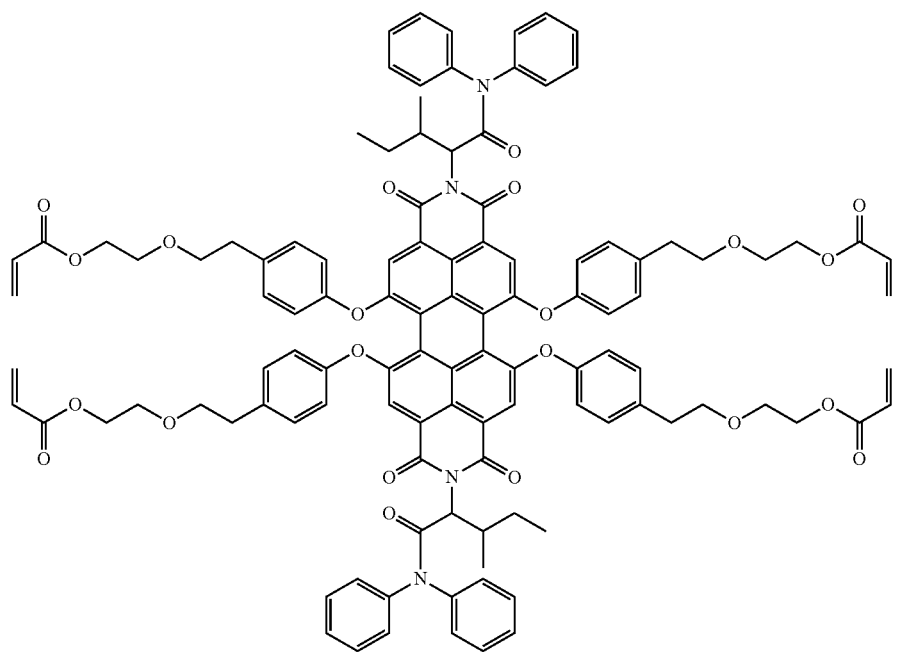

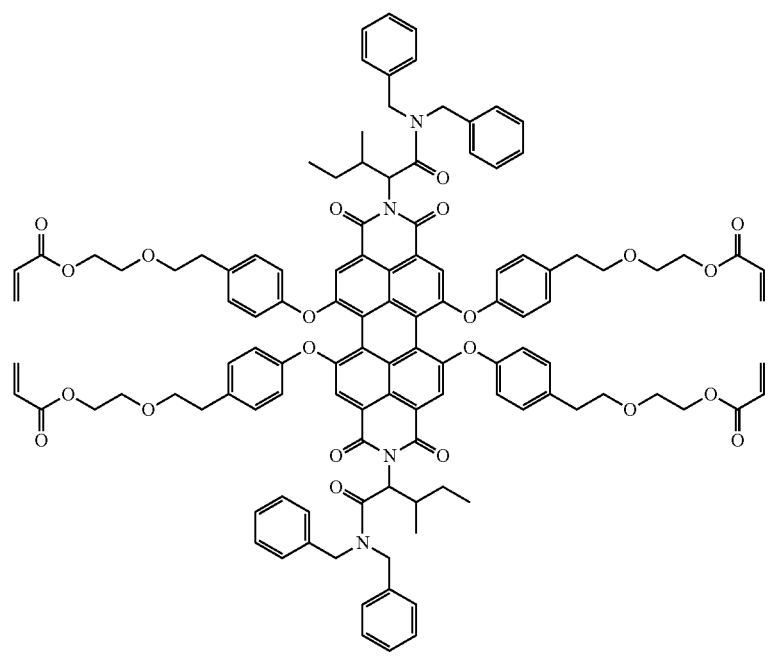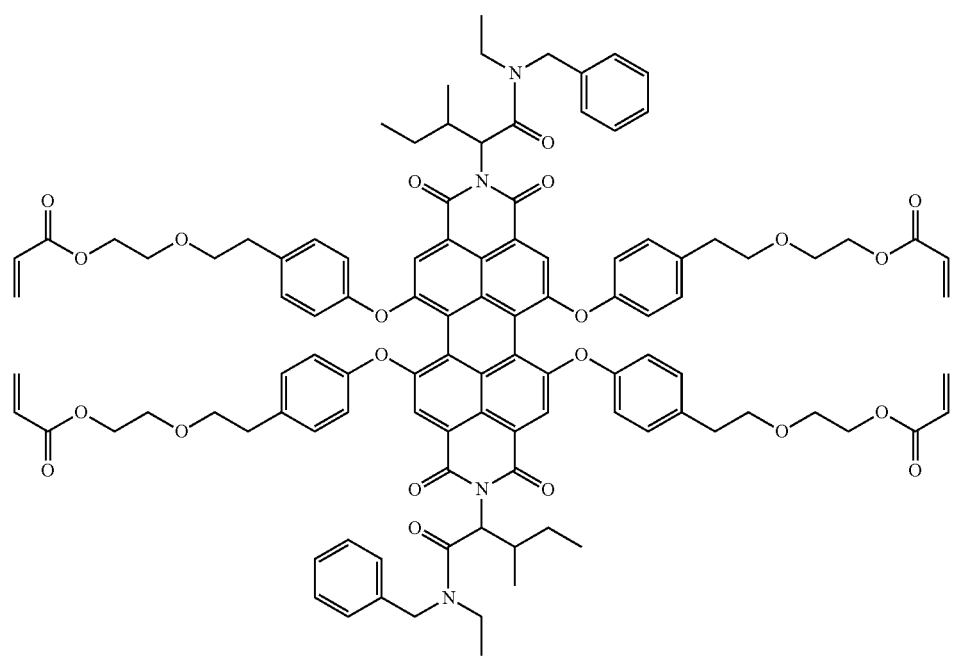

-continued
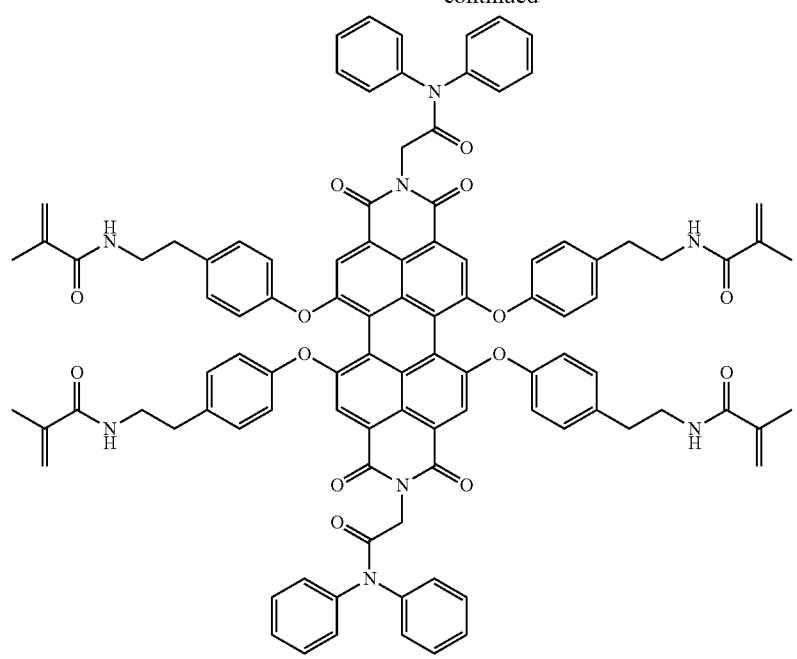
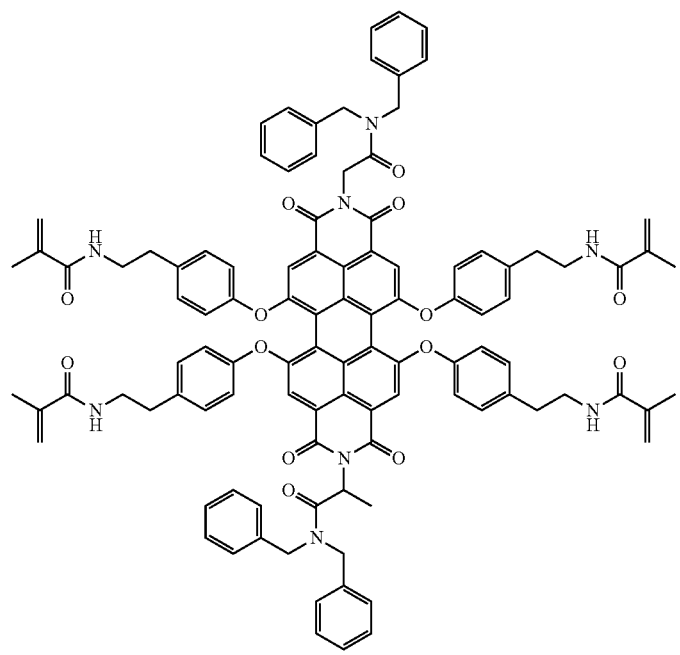

-continued
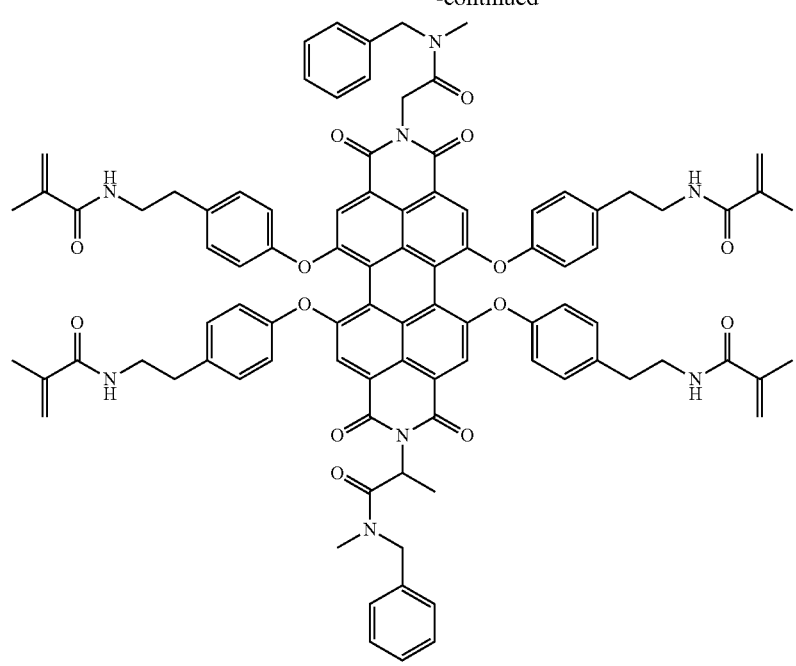
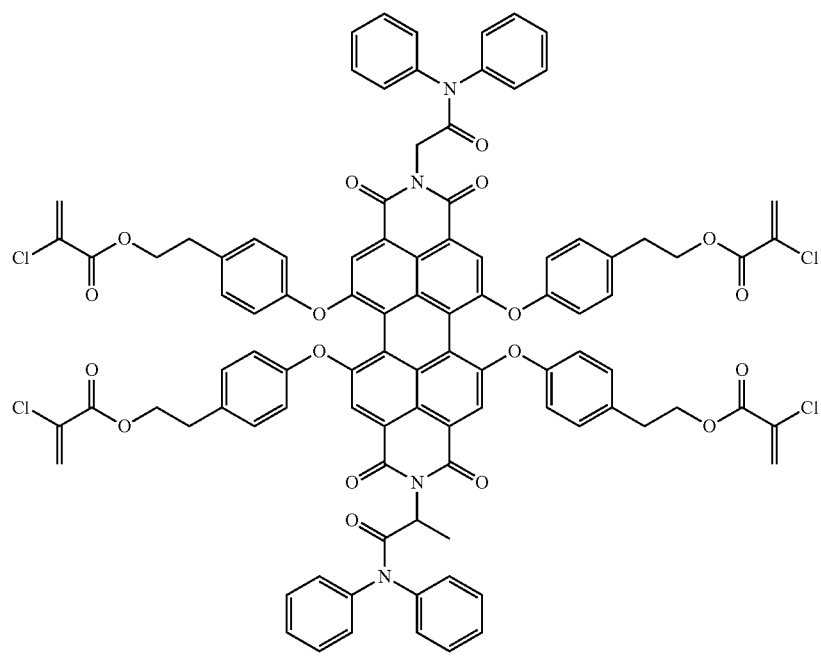

-continued
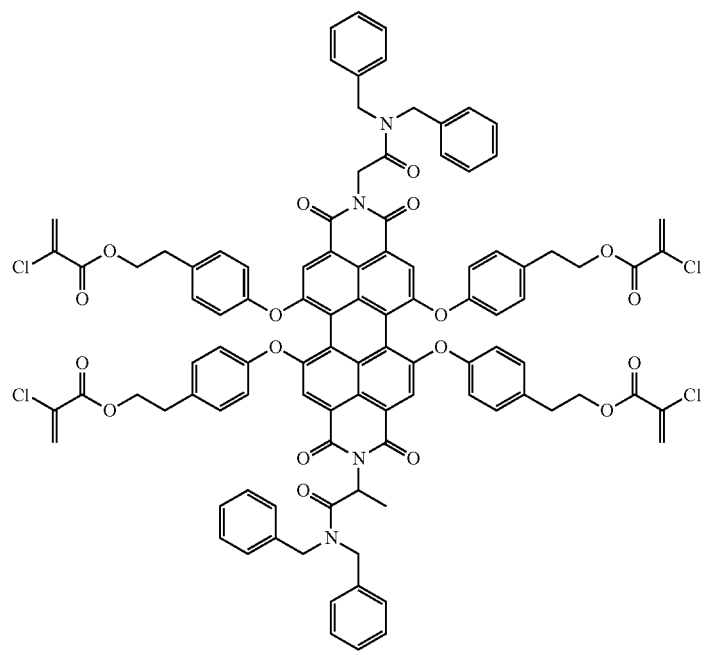
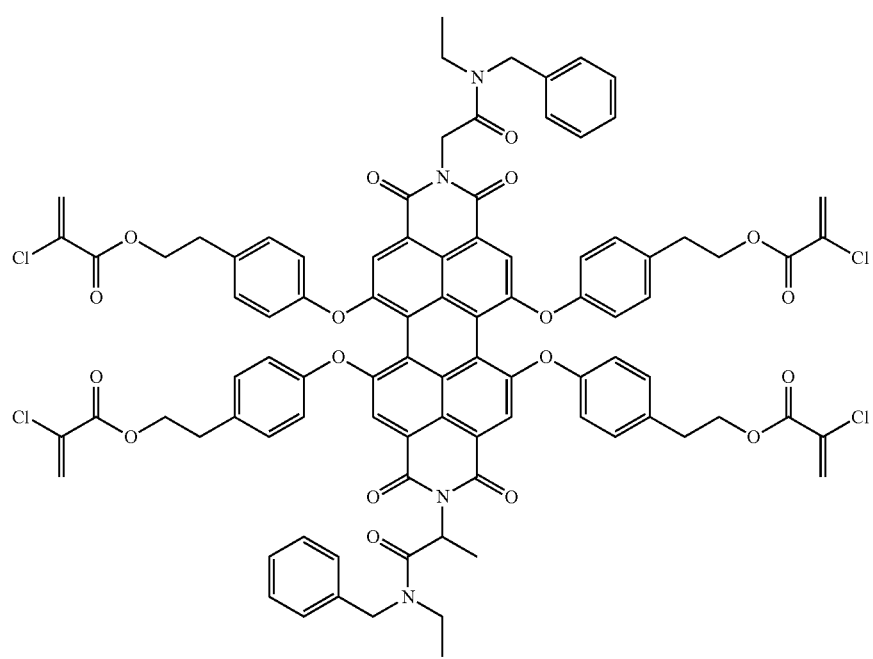

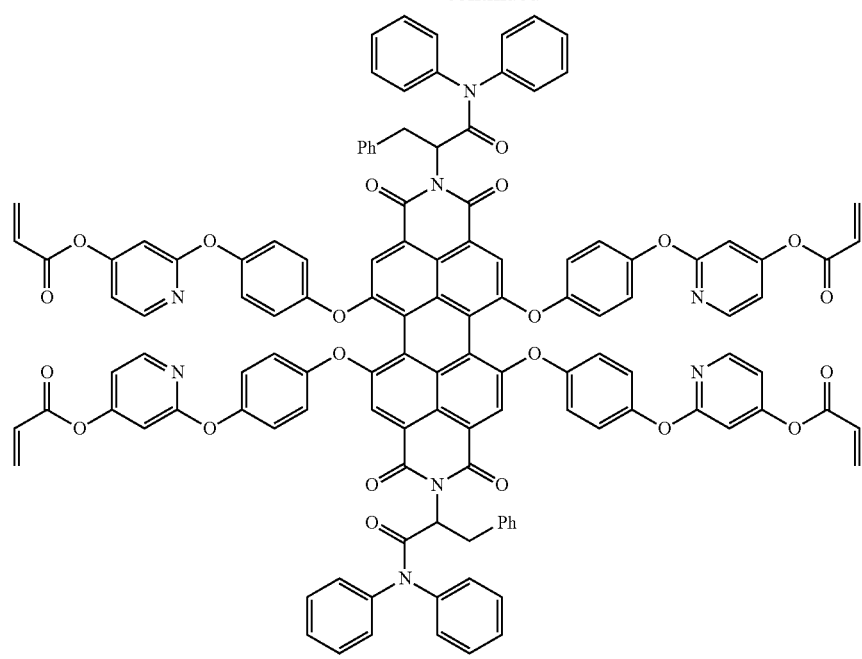
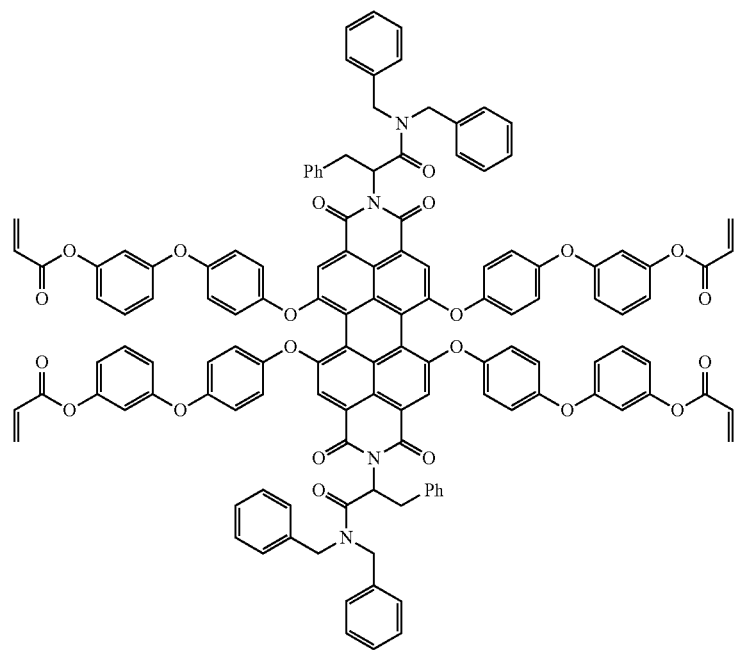

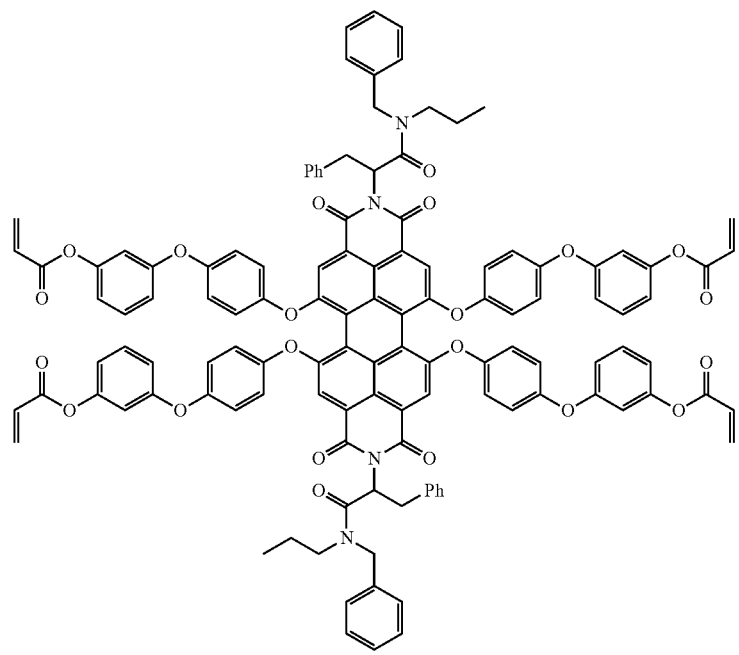
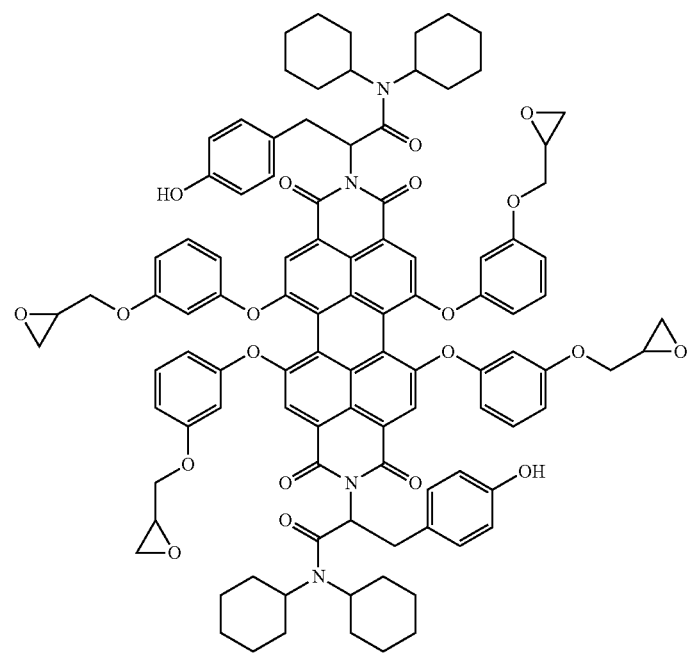

609
-continued
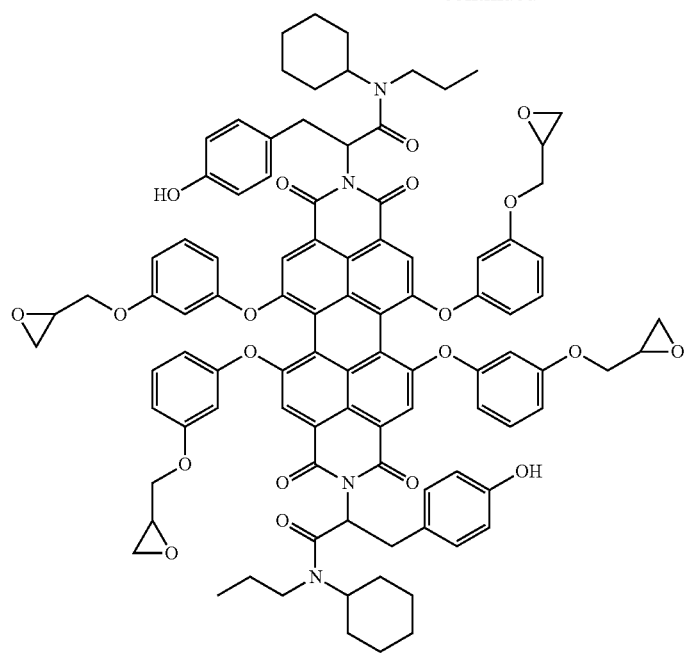
610
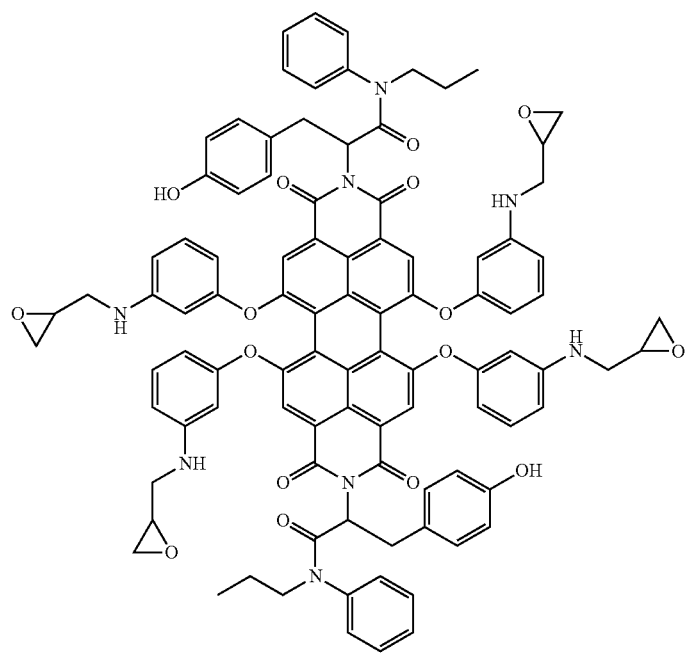

-continued
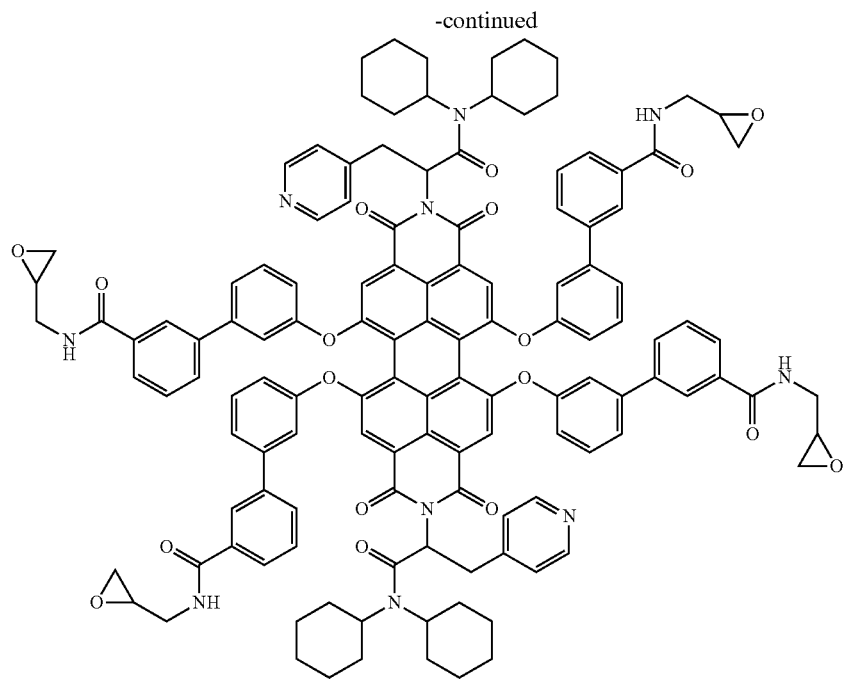
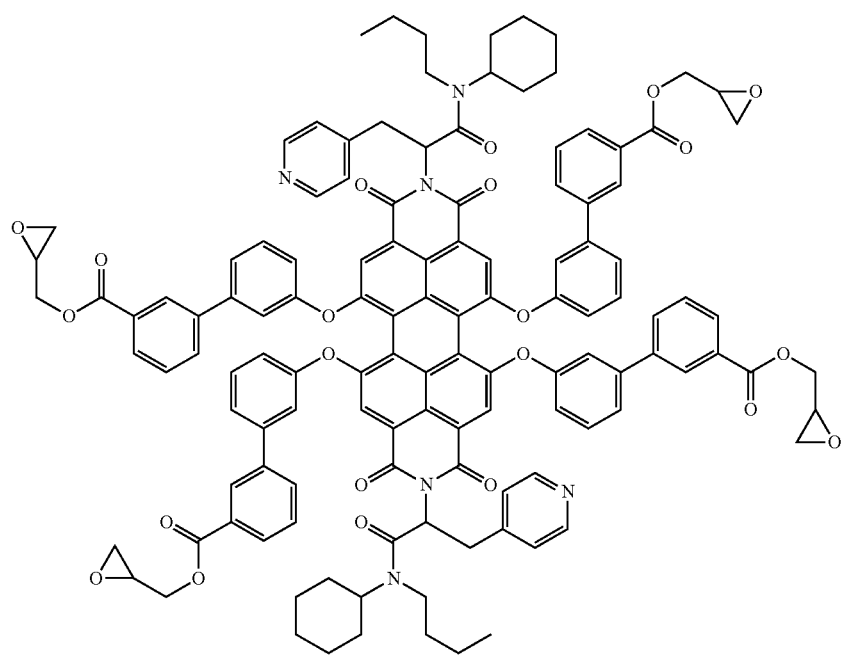

-continued
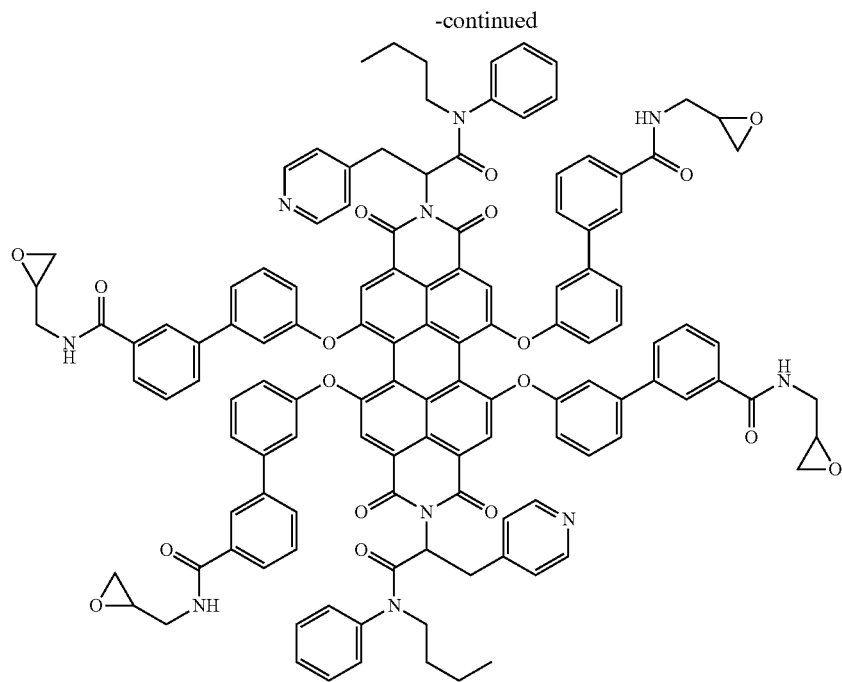
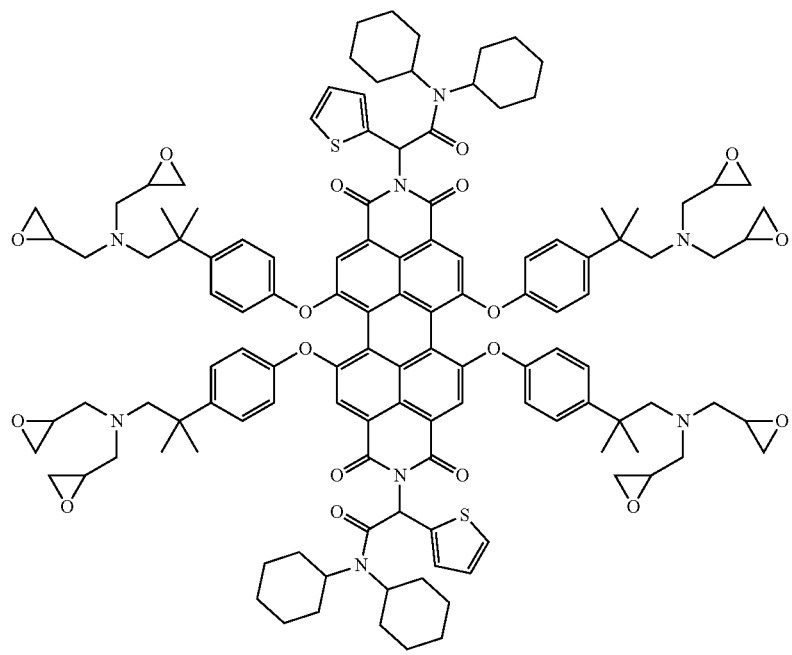

-continued
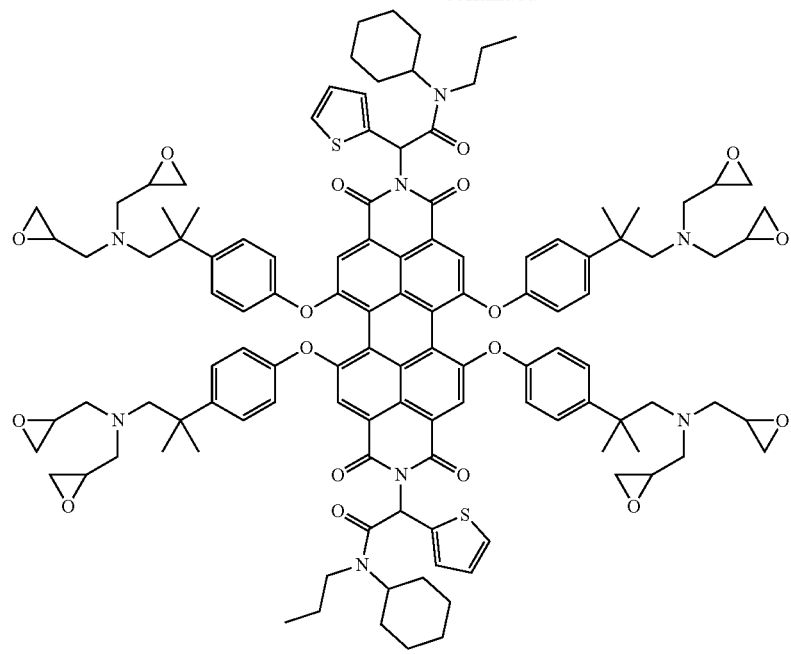
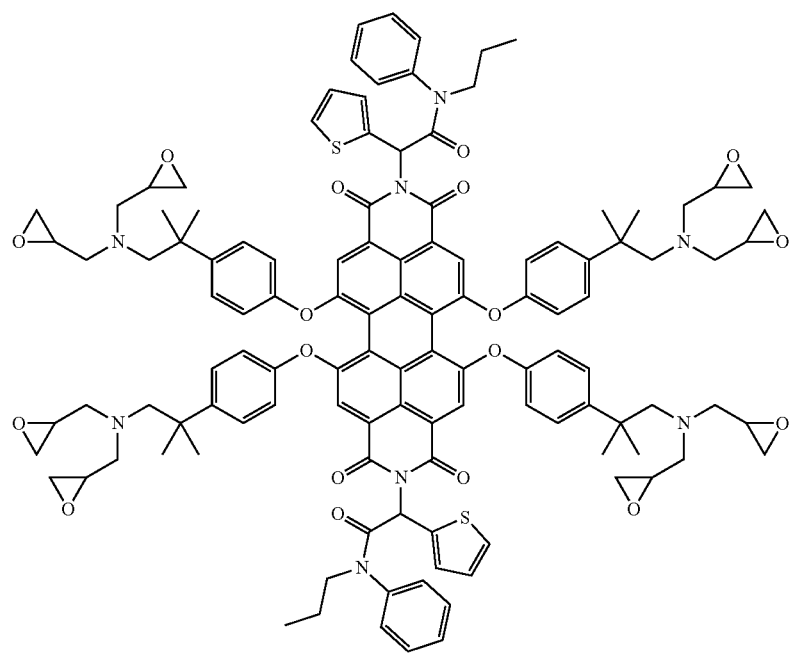

-continued
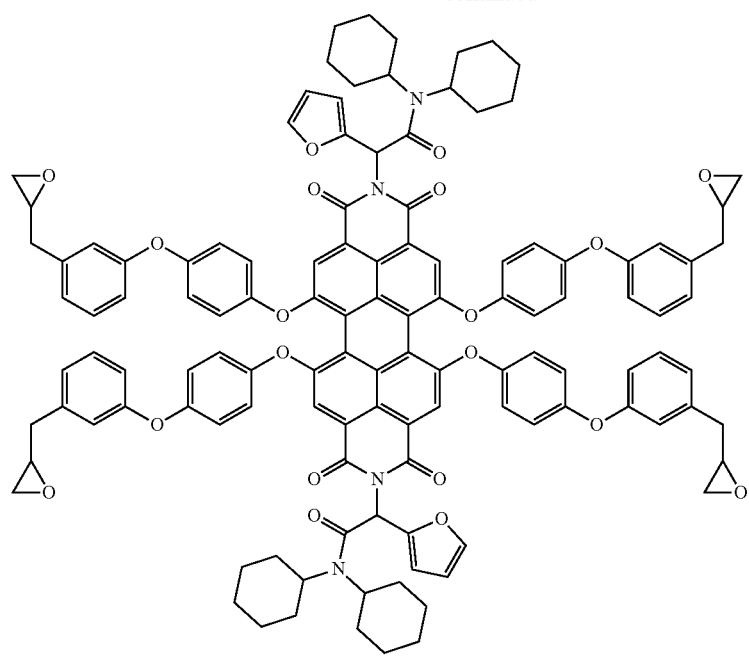
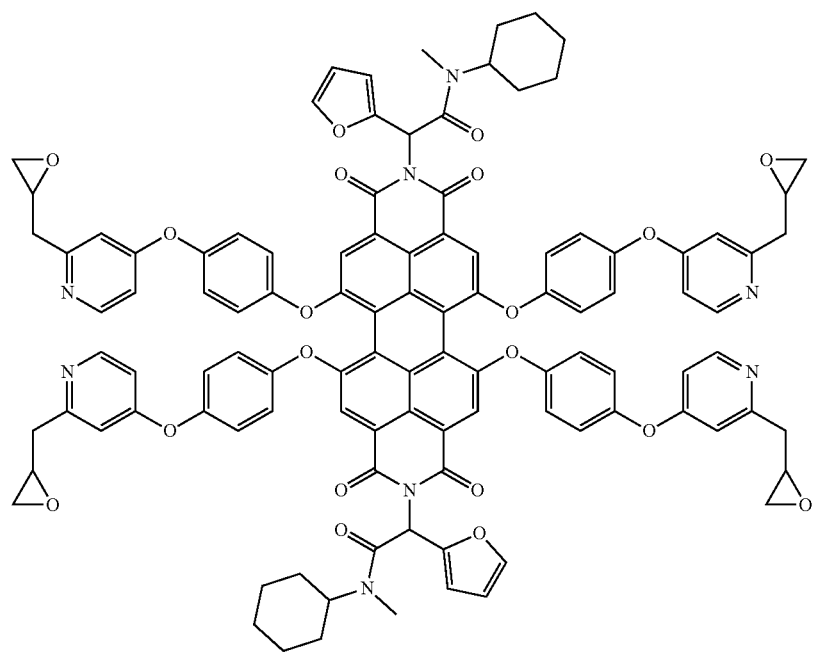

-continued
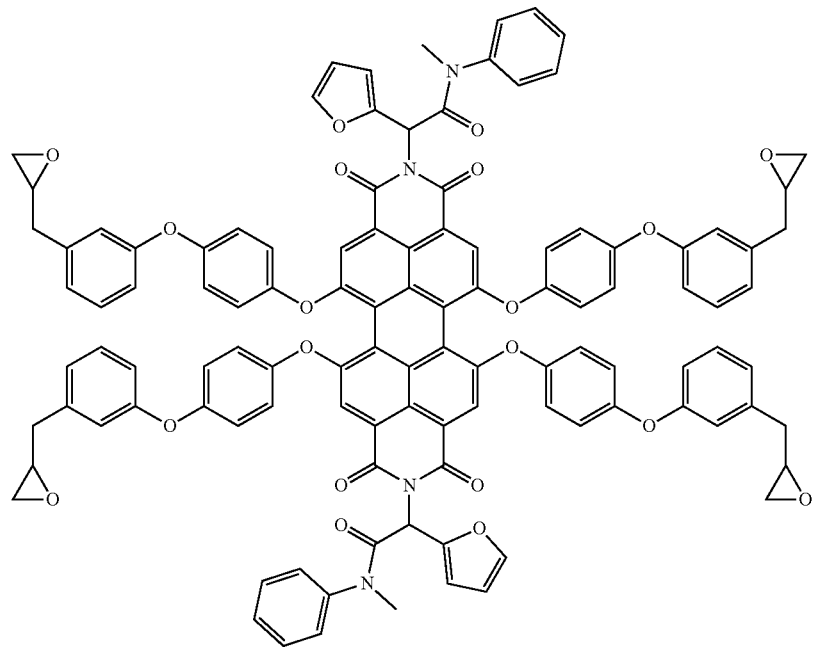
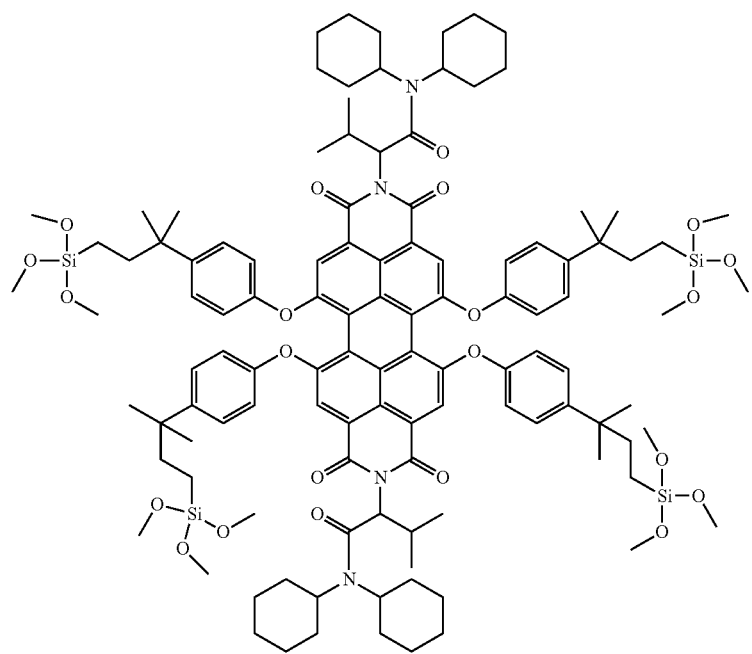

621
-continued
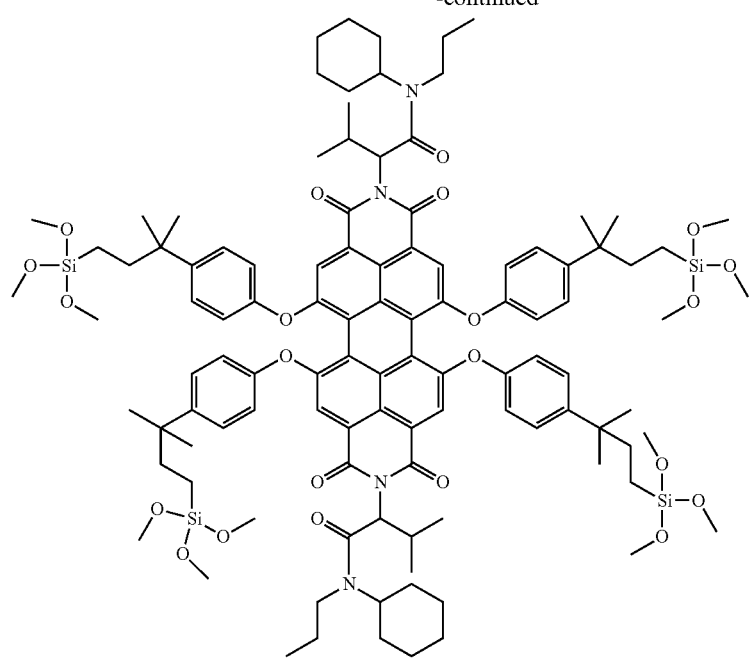
622
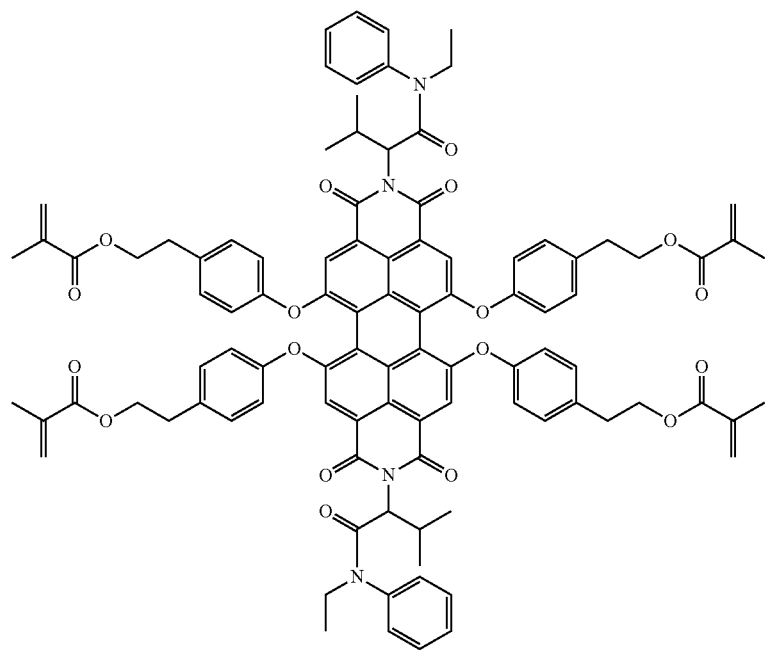

-continued
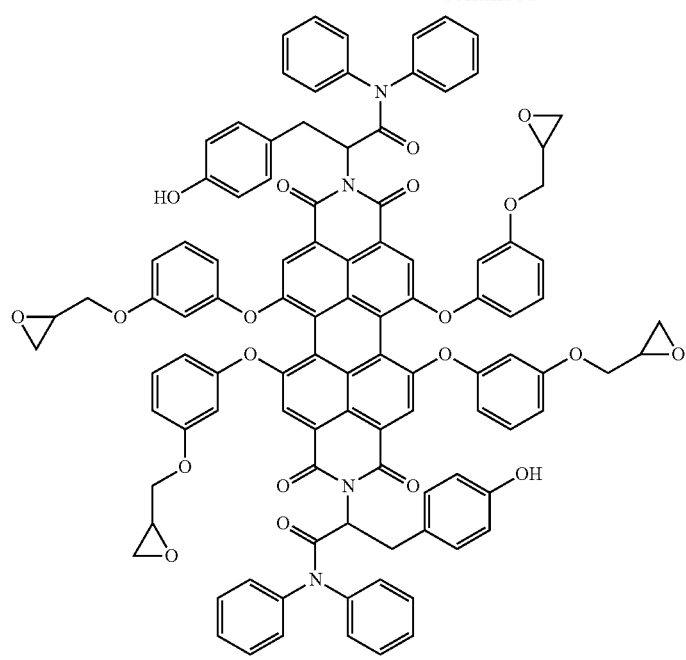
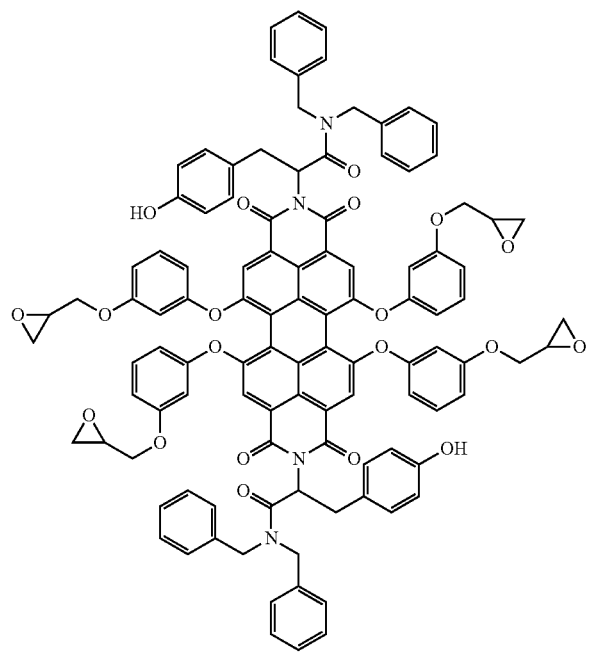

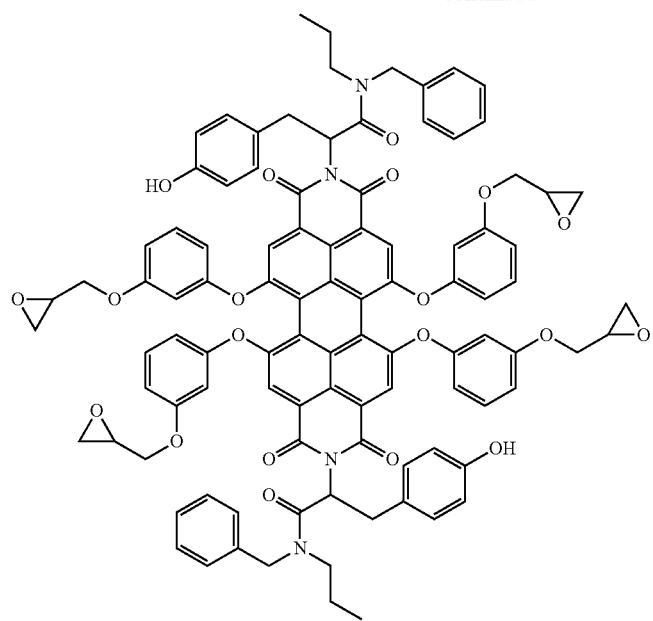
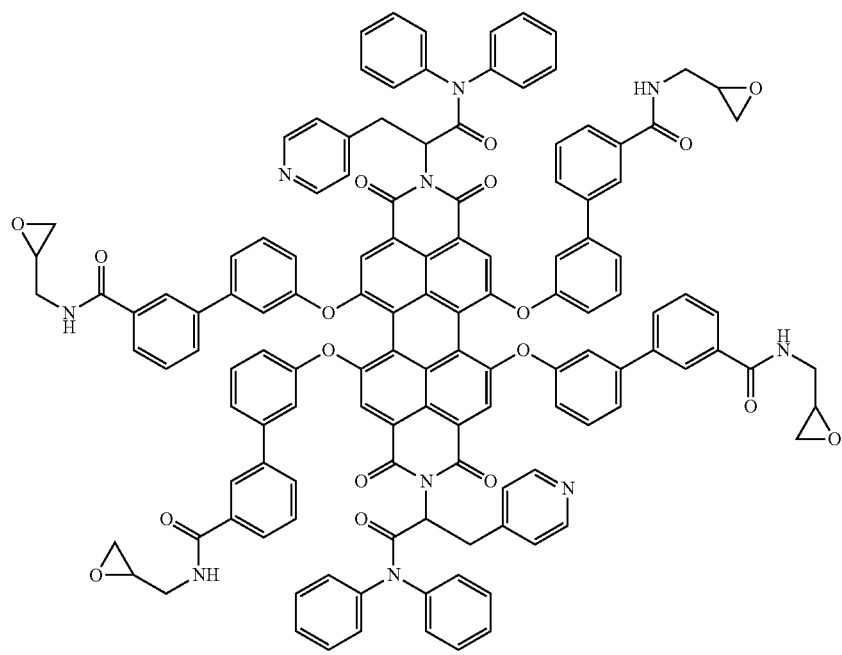

-continued
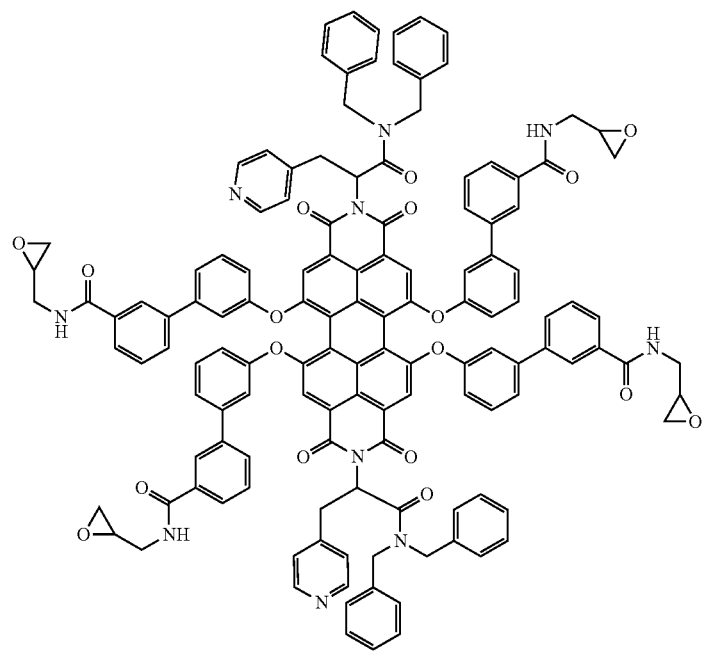
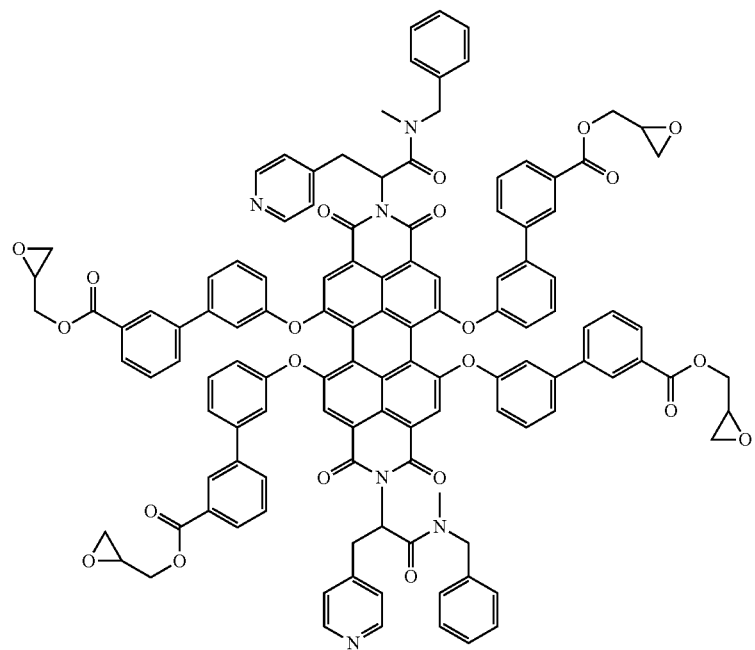

-continued
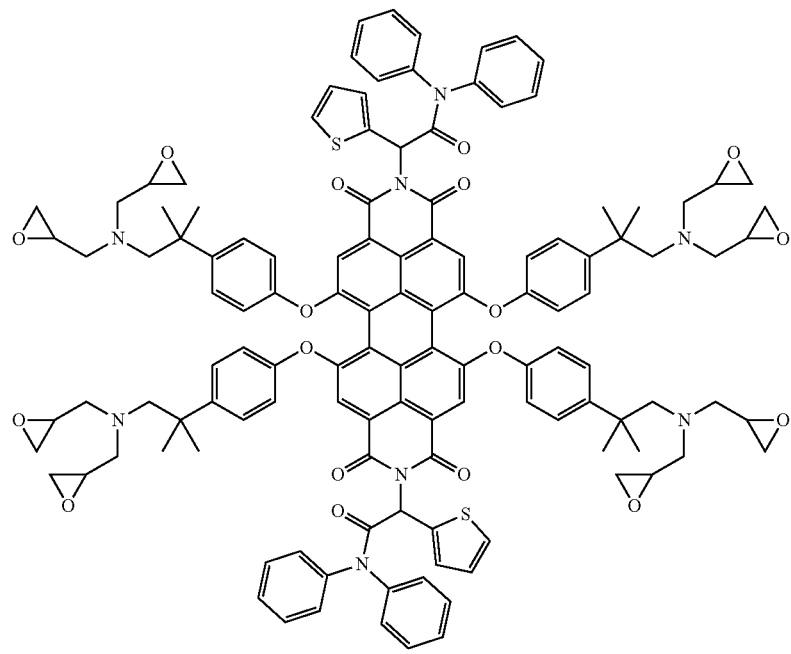
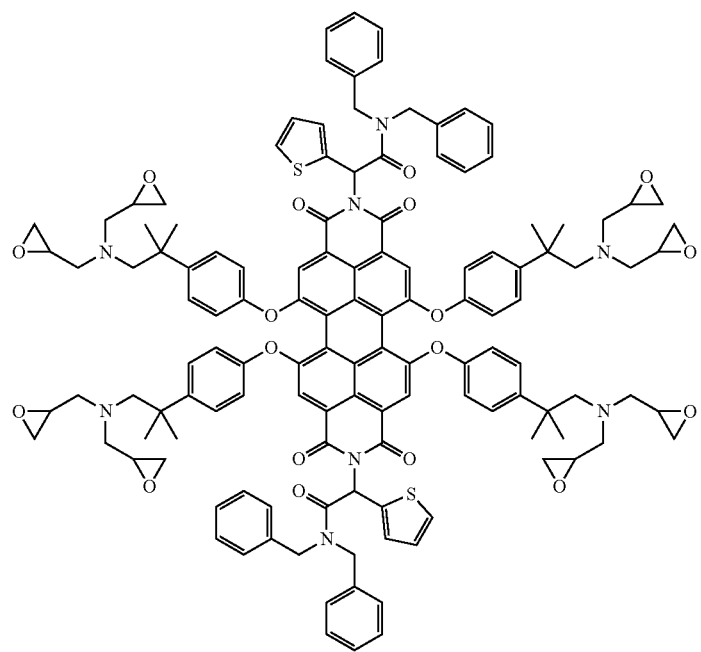

631
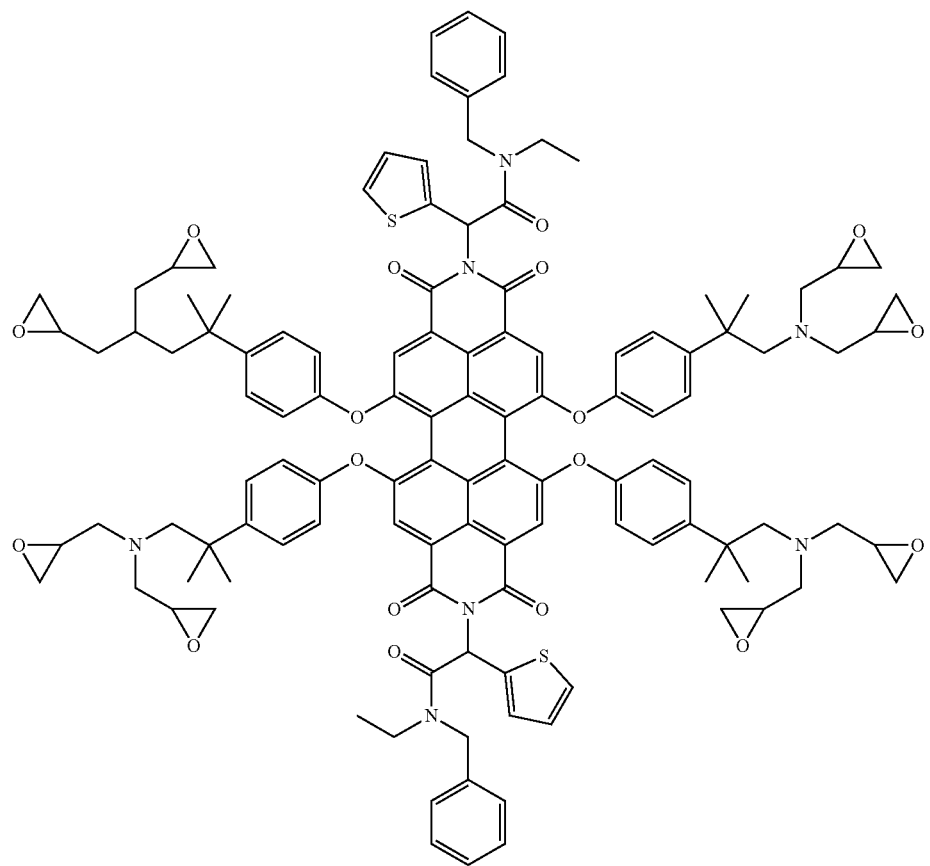
632
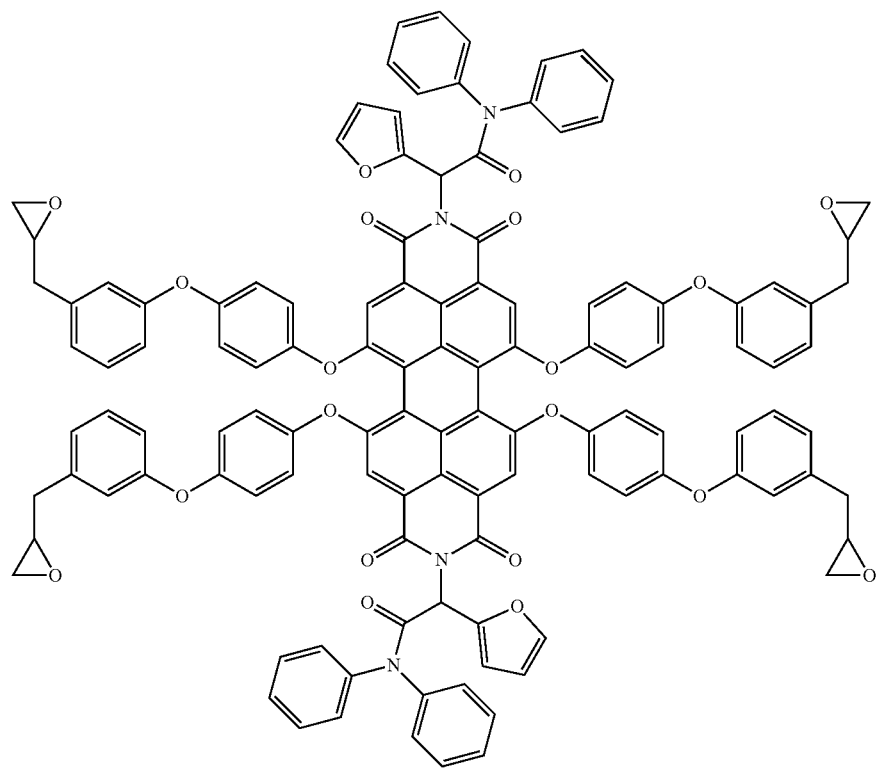

-continued
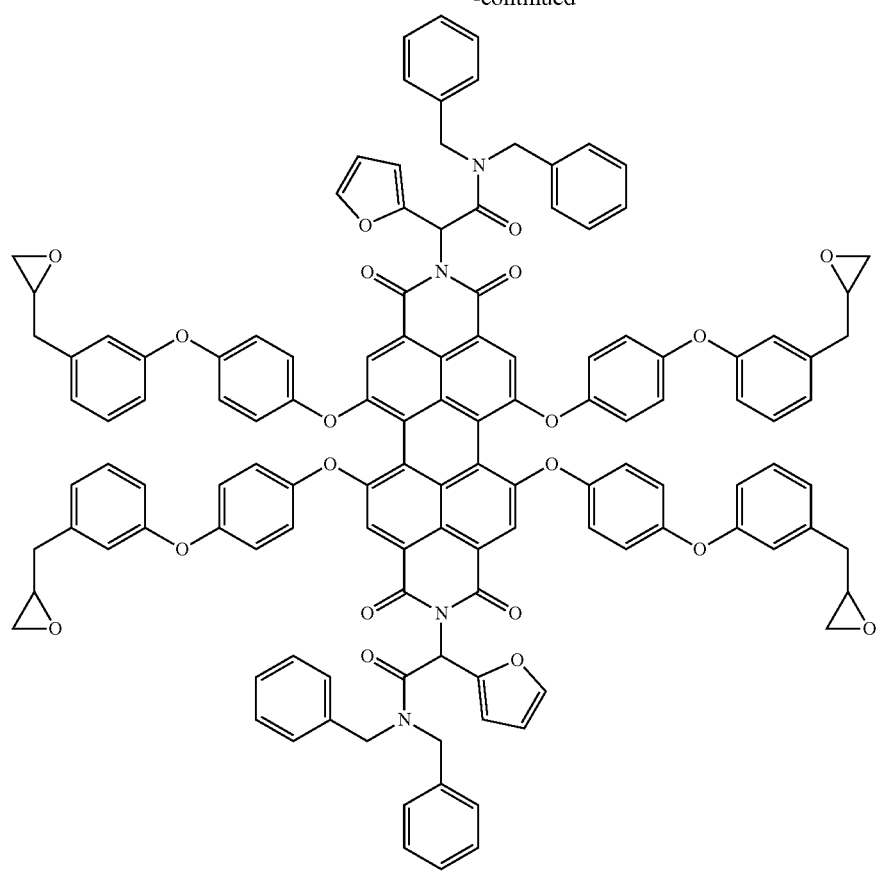
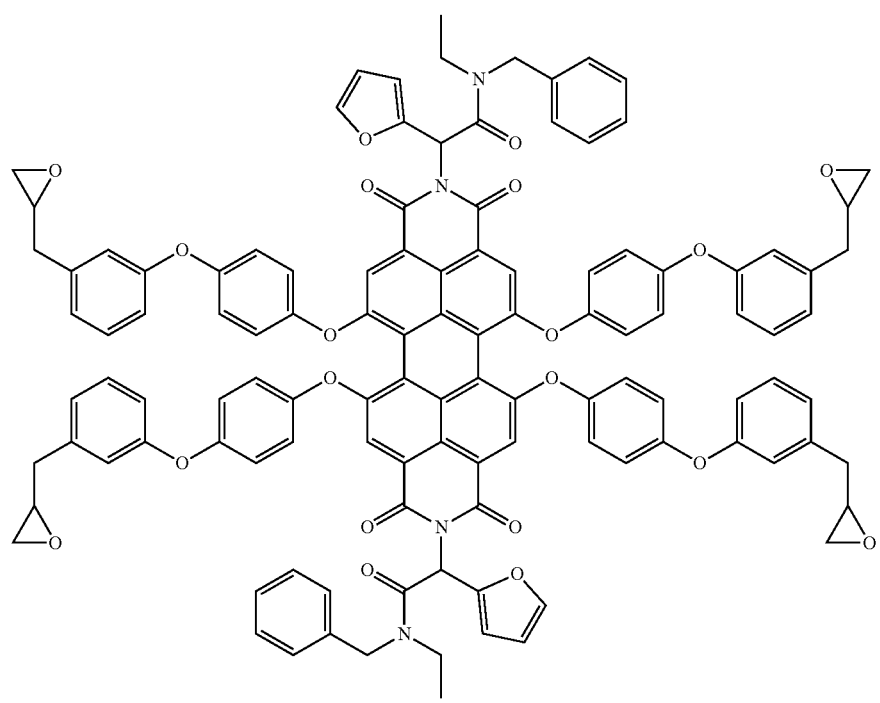

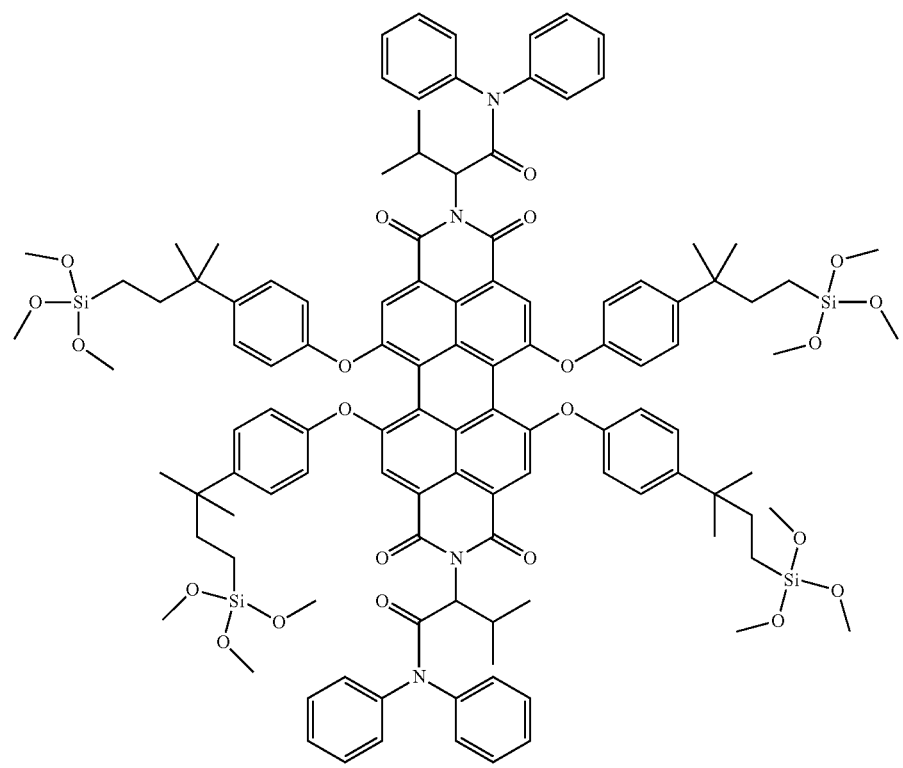
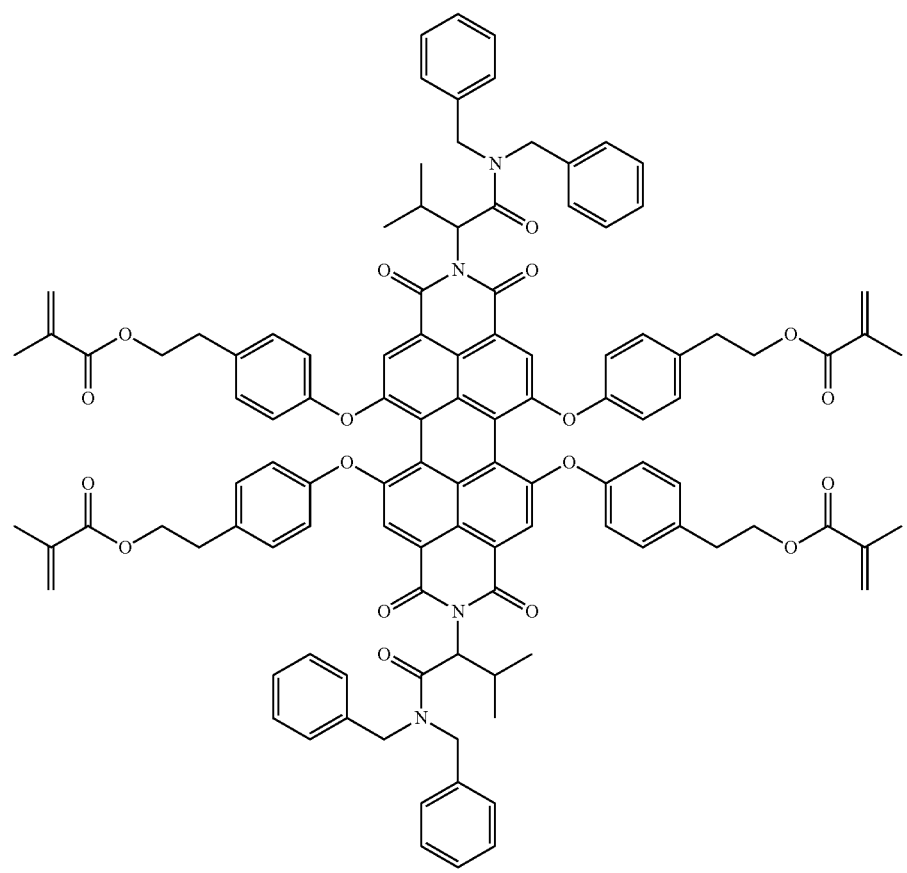

-continued
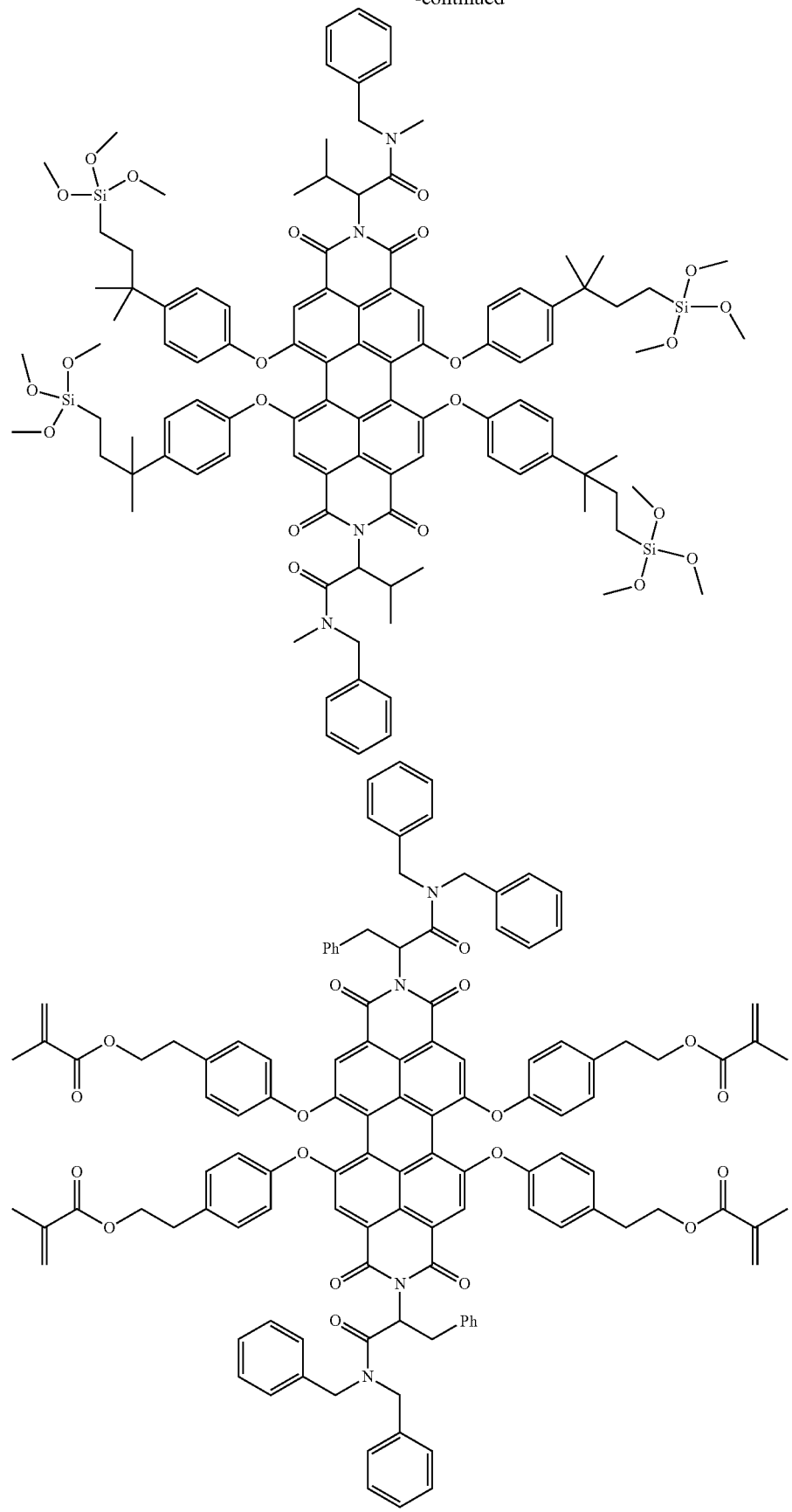

-continued
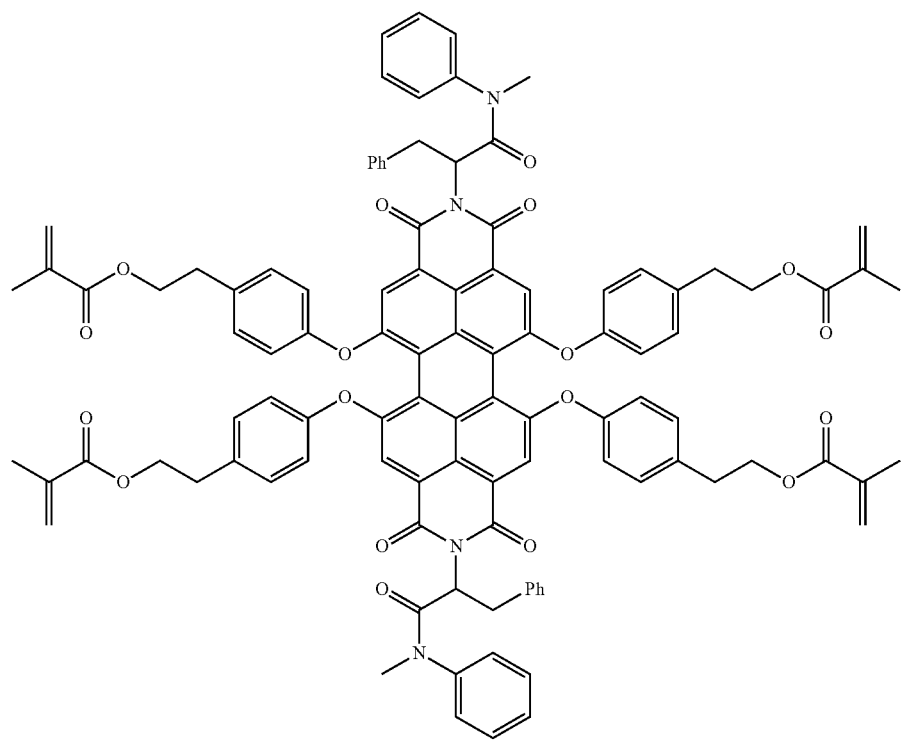
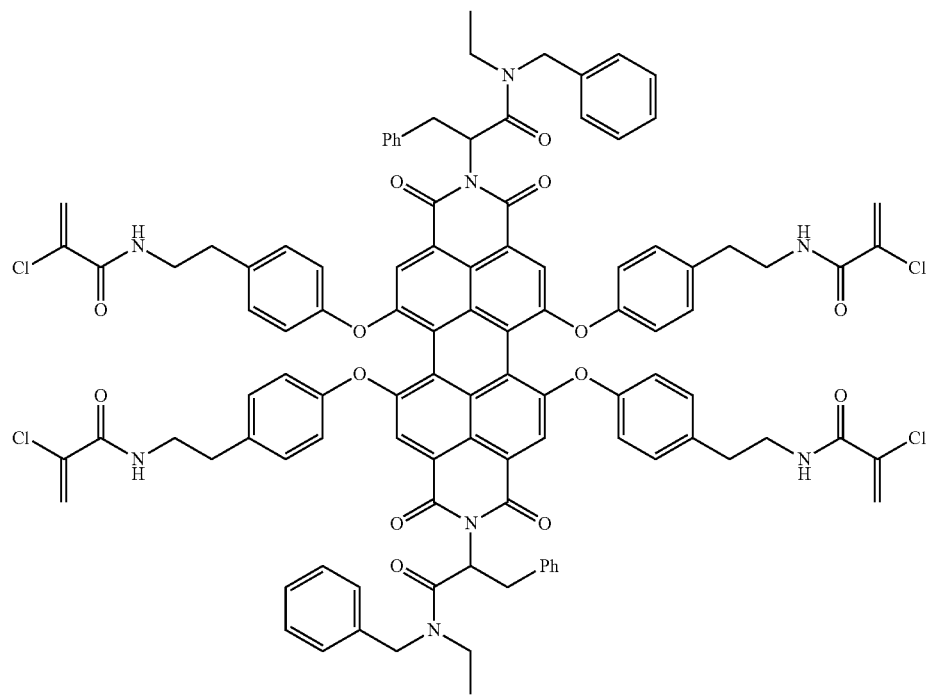

-continued
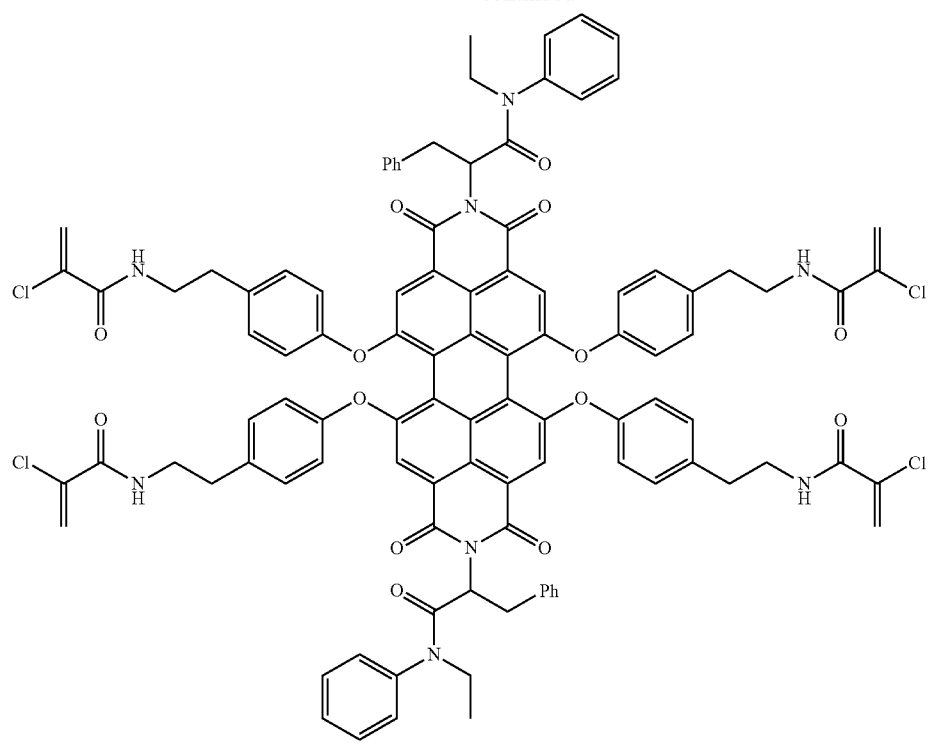
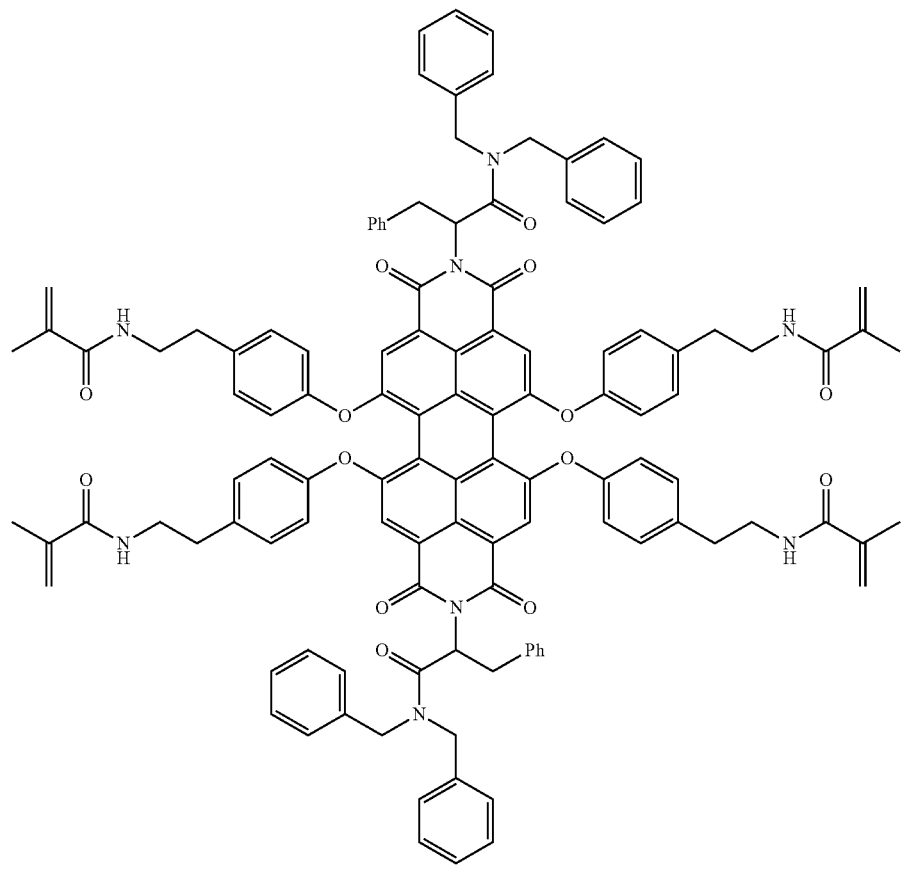

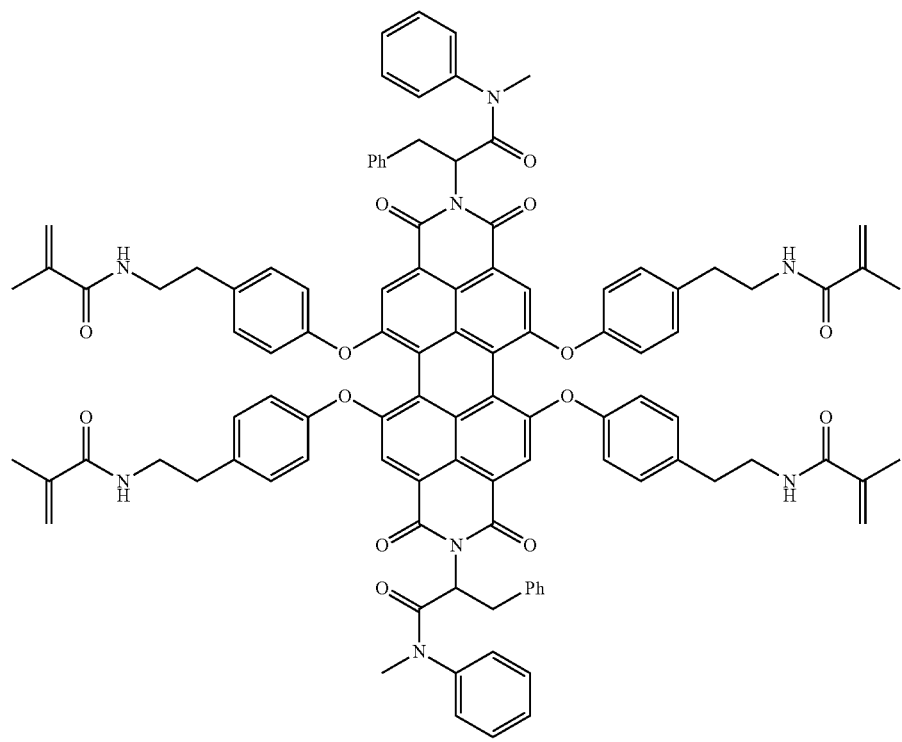
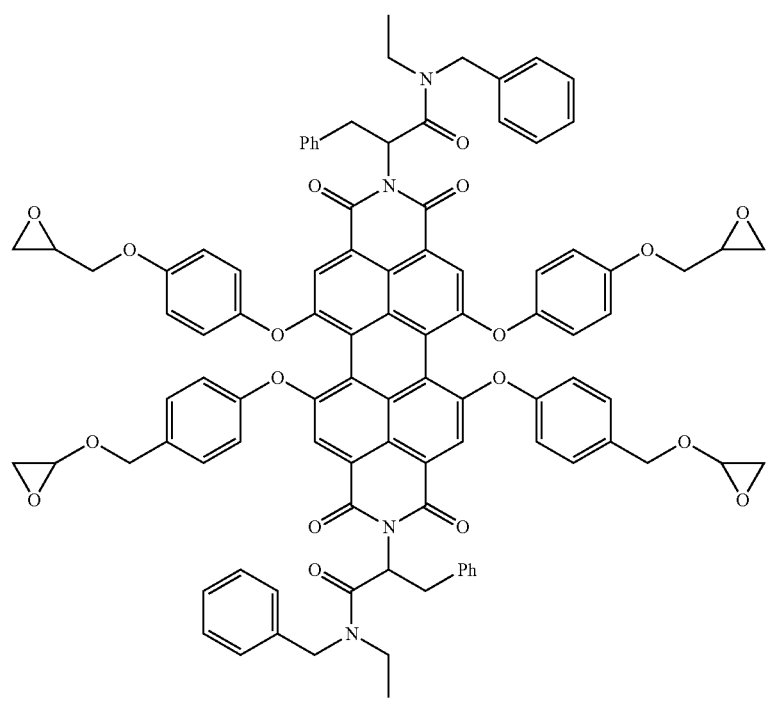

-continued
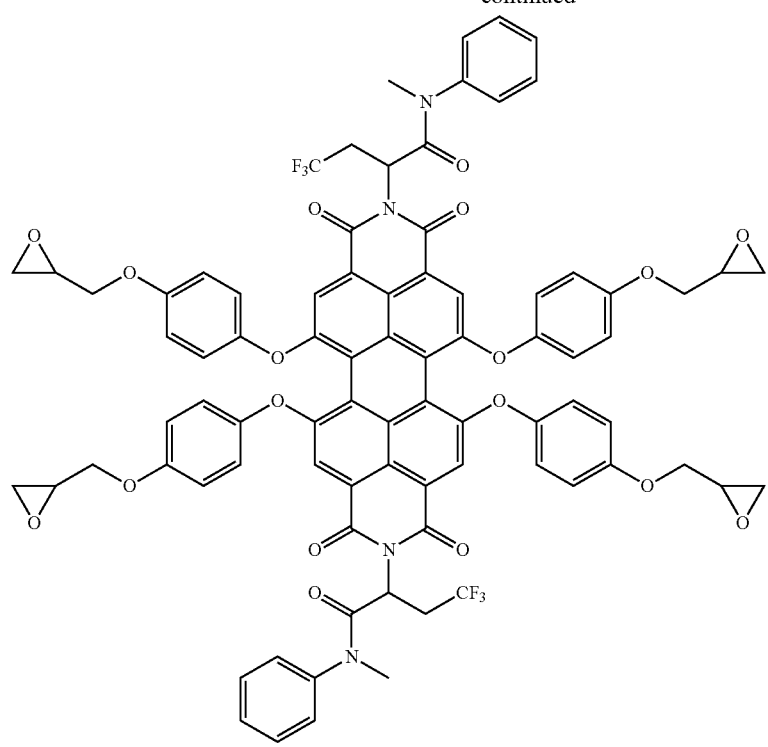
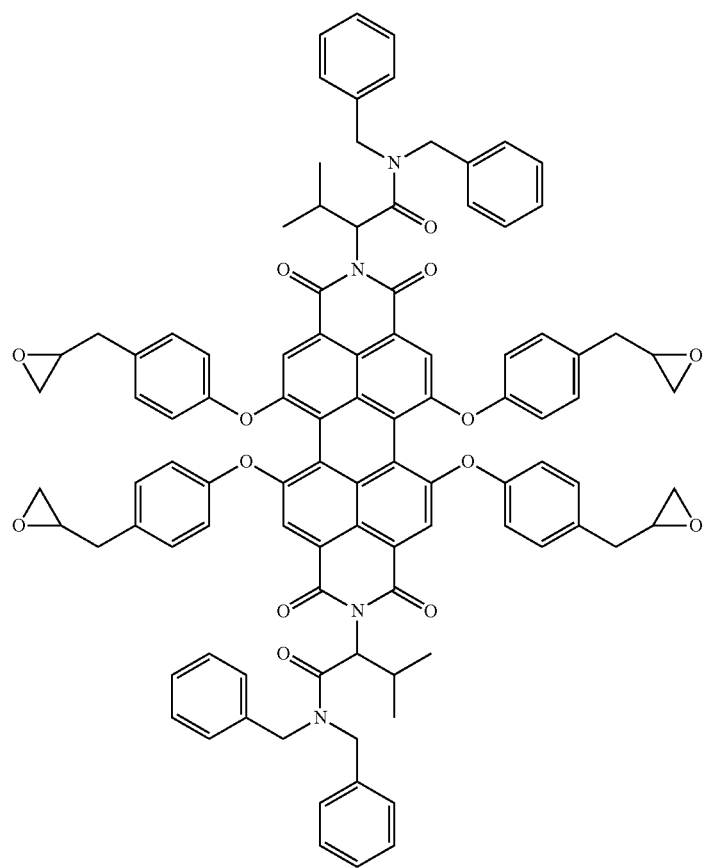

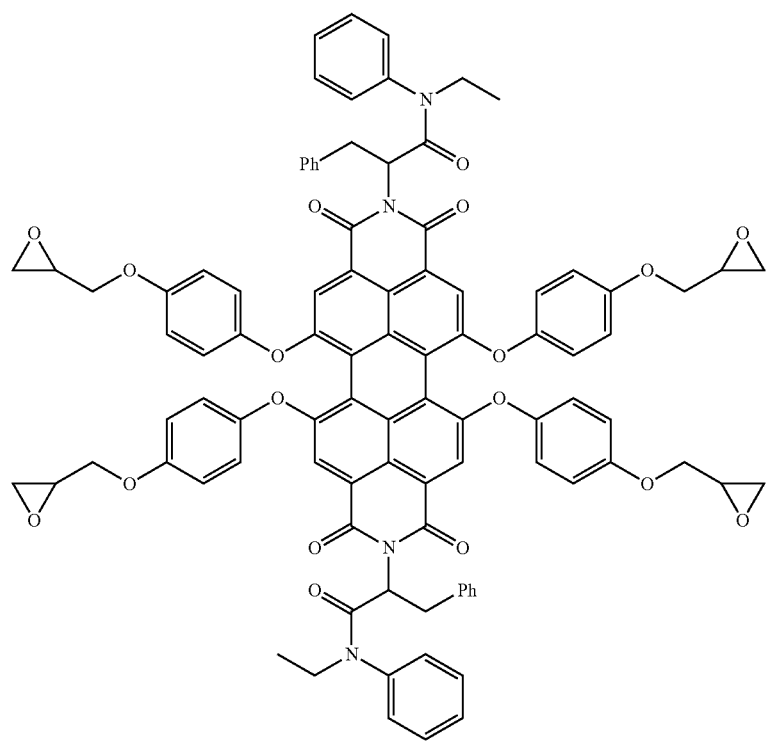
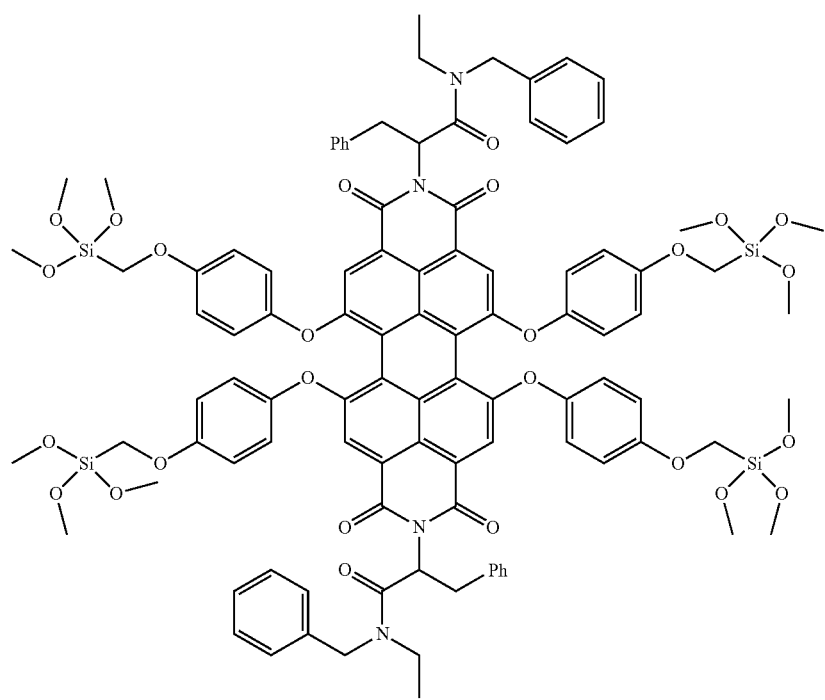

-continued
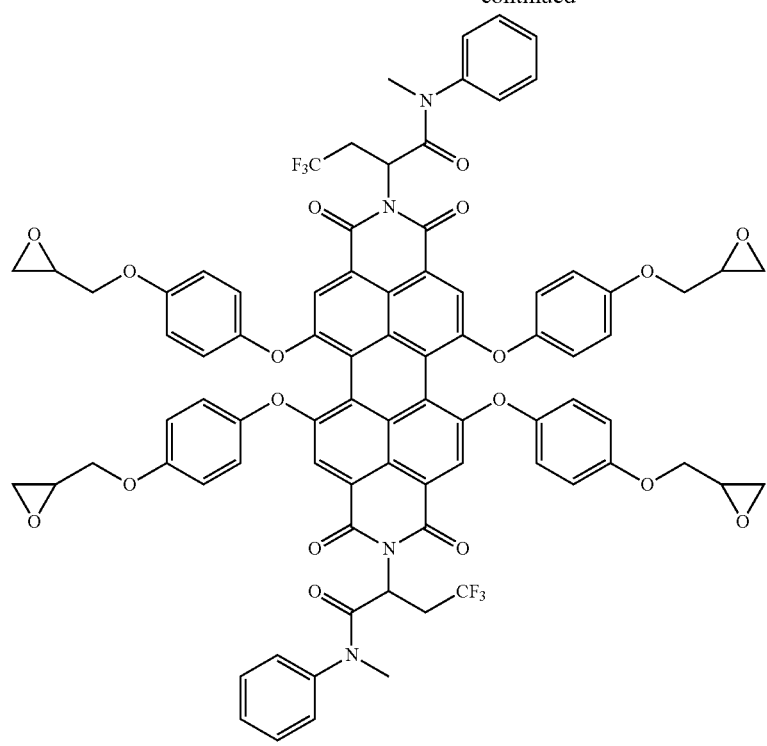
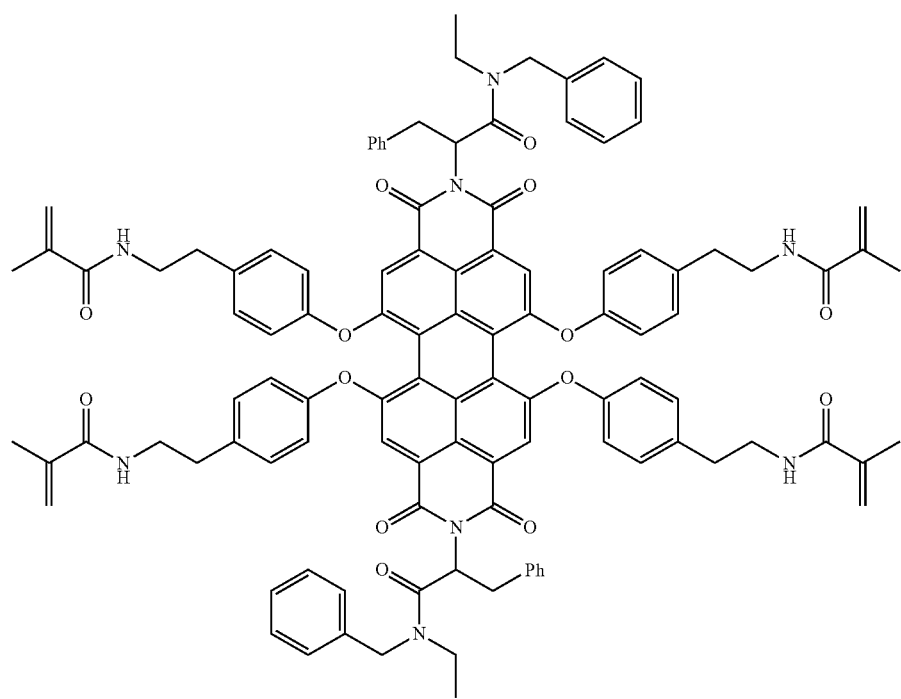

-continued
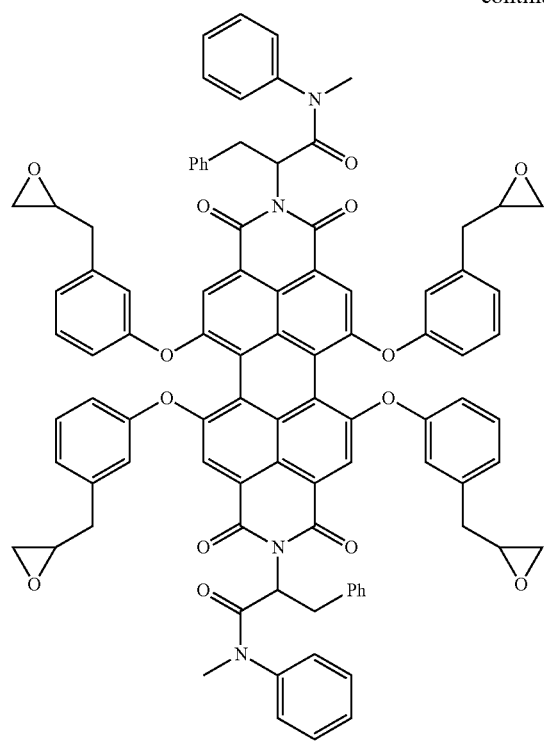
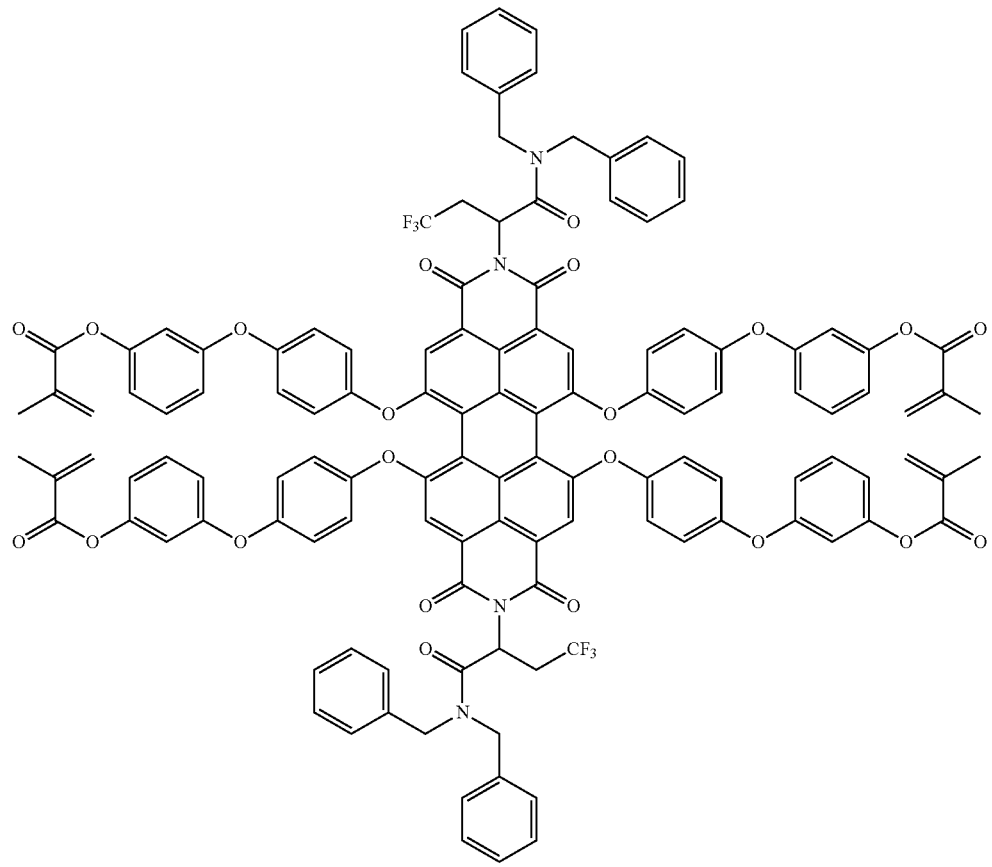

-continued
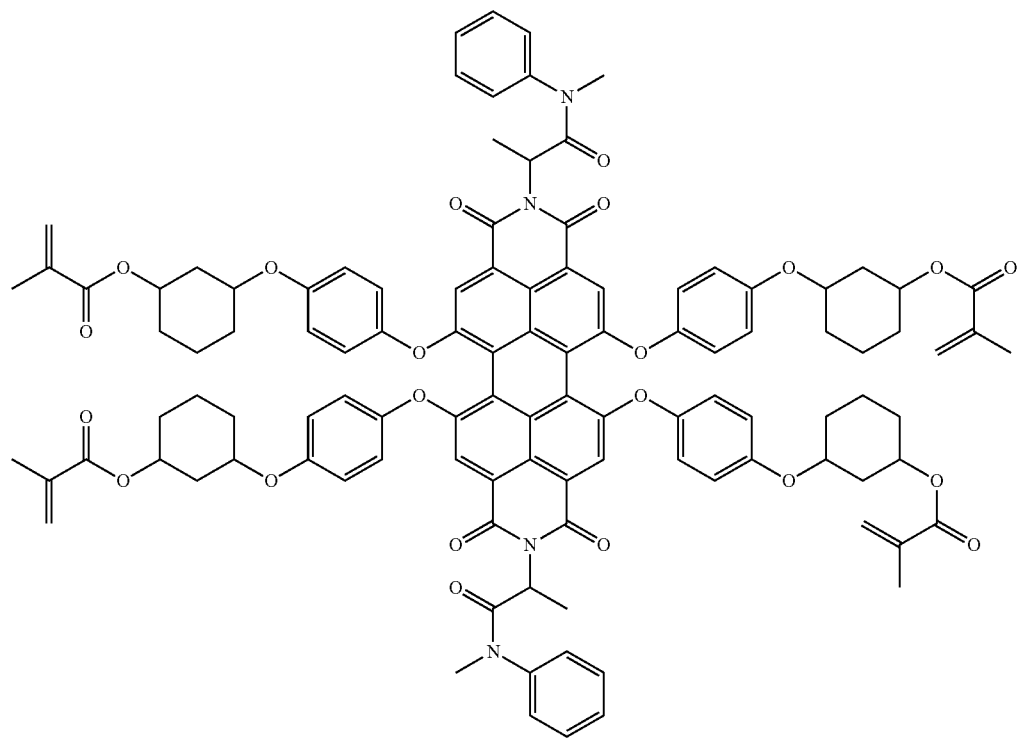
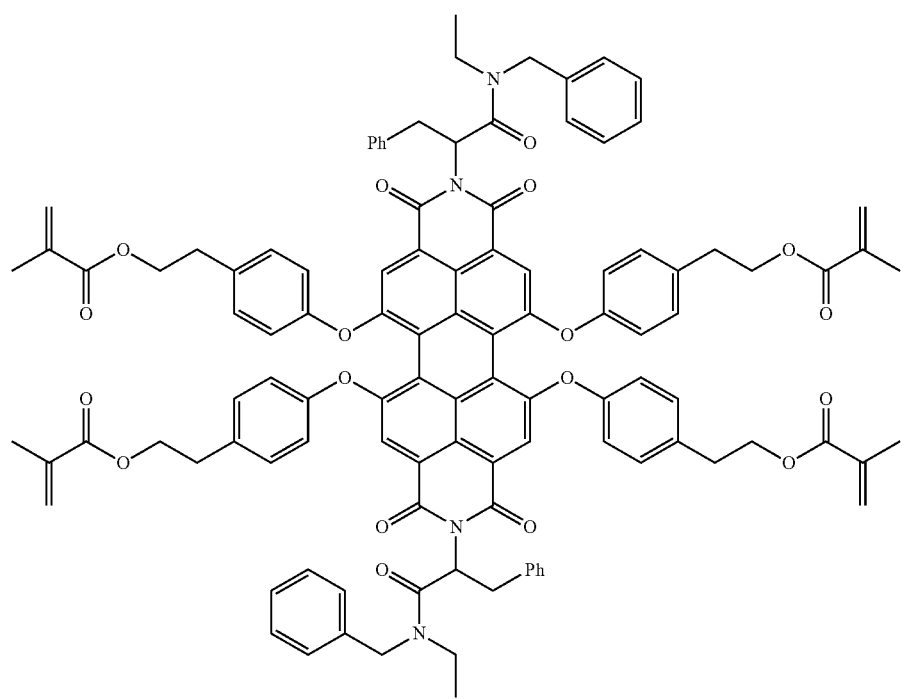

-continued
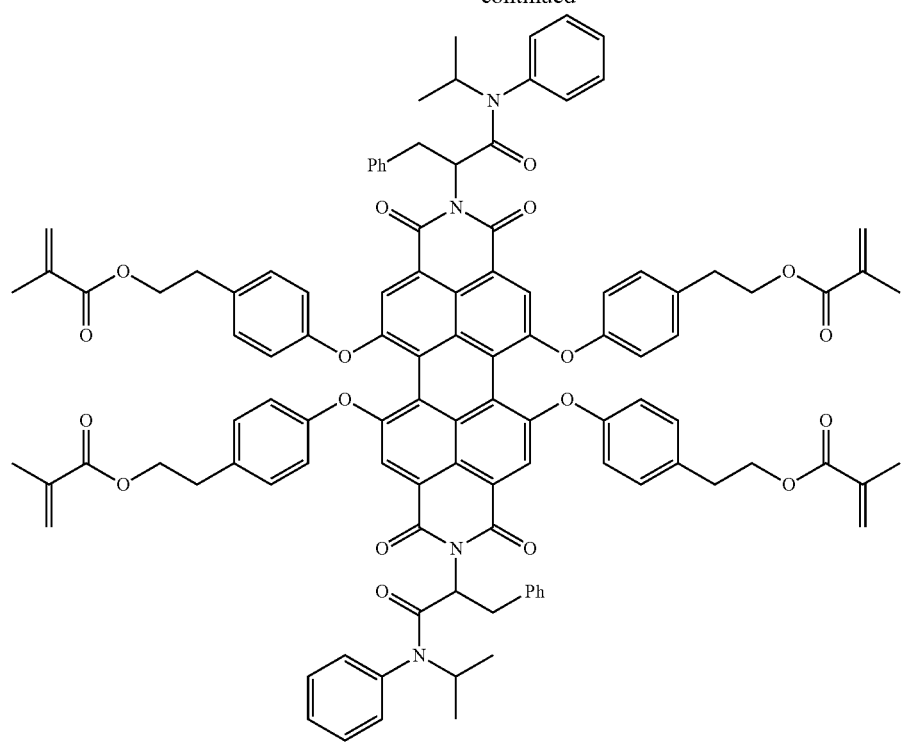
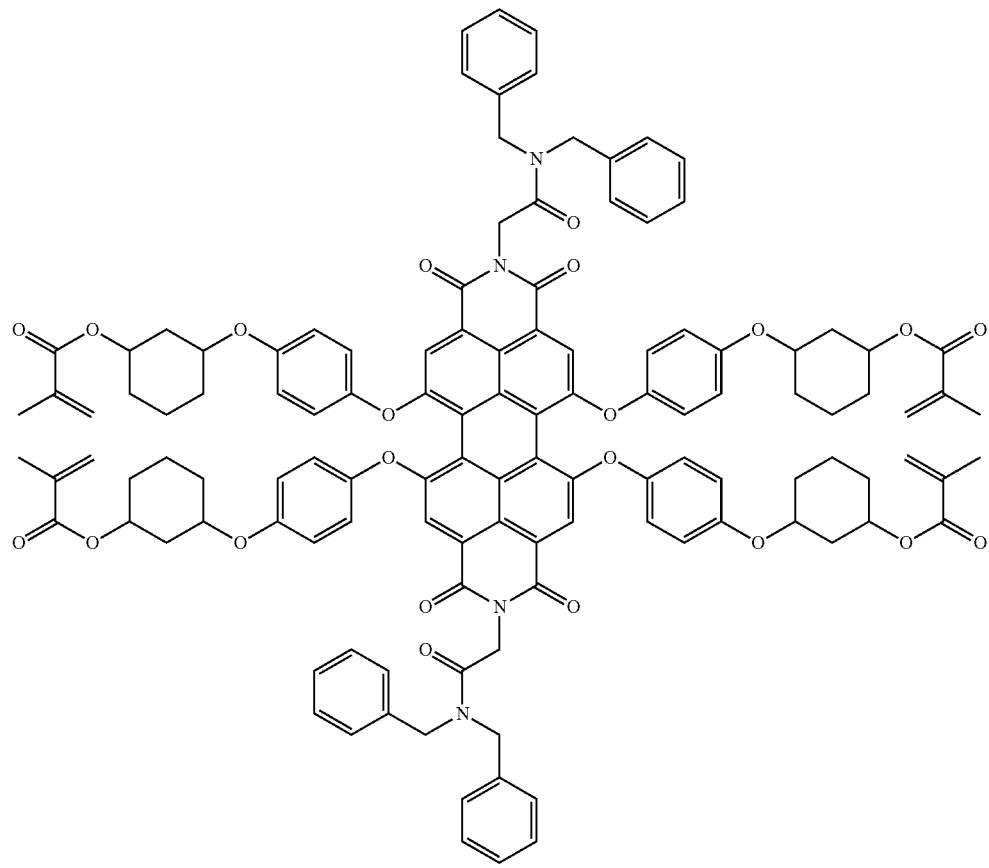

-continued
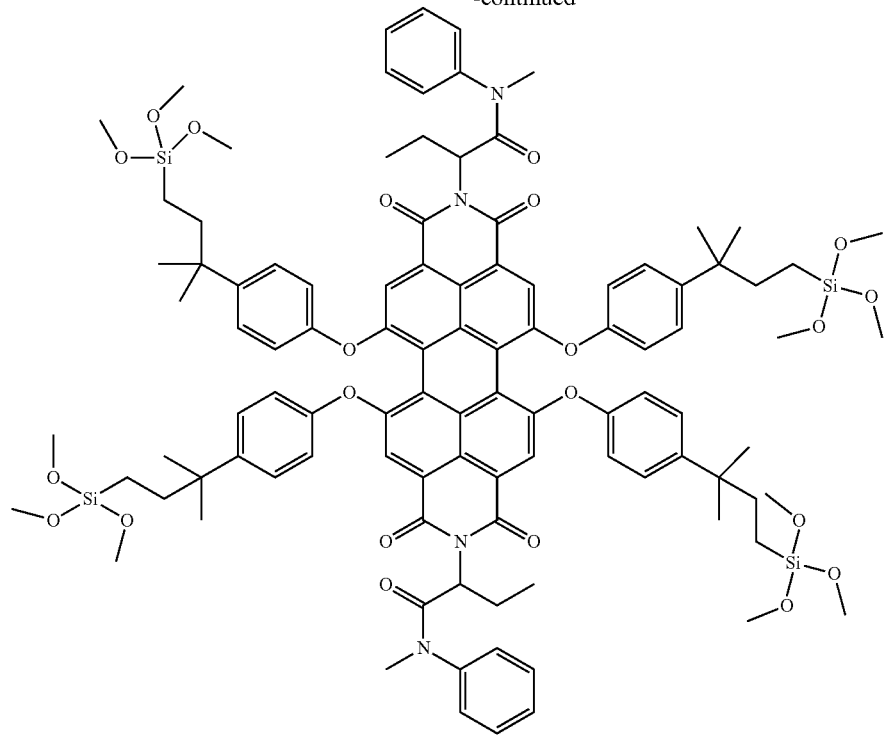
wherein, Ph is a phenyl group.
* * * * *